United States Patent
Chesworth et al.

(10) Patent No.: US 10,118,931 B2
(45) Date of Patent: Nov. 6, 2018

(54) CARM1 INHIBITORS AND USES THEREOF

(71) Applicant: Epizyme, Inc., Cambridge, MA (US)

(72) Inventors: Richard Chesworth, Concord, MA (US); Oscar Miguel Moradei, Burlington, MA (US); Gideon Shapiro, Gainesville, FL (US); Lei Jin, Wellesley, MA (US); Robert E. Babine, Carlsbad, CA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/835,758

(22) Filed: Dec. 8, 2017

(65) Prior Publication Data

US 2018/0282343 A1 Oct. 4, 2018

Related U.S. Application Data

(63) Continuation of application No. 15/648,701, filed on Jul. 13, 2017, now Pat. No. 9,856,267, which is a (Continued)

(51) Int. Cl.
| | | |
|---|---|---|
| C07D 471/04 | (2006.01) | |
| A61K 31/437 | (2006.01) | |
| C07D 487/10 | (2006.01) | |
| C07D 413/04 | (2006.01) | |
| C07D 487/04 | (2006.01) | |
| C07D 498/10 | (2006.01) | |
| C07D 498/04 | (2006.01) | |

(Continued)

(52) U.S. Cl.
CPC ......... *C07D 487/10* (2013.01); *C07D 239/42* (2013.01); *C07D 401/04* (2013.01); *C07D 403/04* (2013.01); *C07D 403/12* (2013.01); *C07D 405/04* (2013.01); *C07D 405/12* (2013.01); *C07D 405/14* (2013.01); *C07D 409/14* (2013.01); *C07D 413/04* (2013.01); *C07D 413/12* (2013.01); *C07D 413/14* (2013.01); *C07D 417/14* (2013.01); *C07D 471/04* (2013.01); *C07D 471/10* (2013.01); *C07D 487/04* (2013.01); *C07D 487/08* (2013.01); *C07D 493/04* (2013.01); *C07D 493/10* (2013.01); *C07D 495/04* (2013.01); *C07D 498/04* (2013.01); *C07D 498/10* (2013.01)

(58) Field of Classification Search
None
See application file for complete search history.

(56) References Cited

U.S. PATENT DOCUMENTS

| | | |
|---|---|---|
| 4,001,426 A | 1/1977 | Brenner et al. |
| 4,011,321 A | 3/1977 | Coates et al. |
| 4,728,651 A | 3/1988 | Ong et al. |
| 5,221,675 A | 6/1993 | Chung et al. |
| 6,710,052 B2 | 3/2004 | Pease et al. |
| 6,730,792 B2 | 5/2004 | Evers et al. |
| 6,864,267 B2 | 3/2005 | Bhatnagar et al. |
| 7,098,207 B2 | 8/2006 | Niewohner et al. |
| 7,485,722 B2 | 2/2009 | Egle et al. |
| 8,063,071 B2 | 11/2011 | Kerns et al. |
| 8,110,579 B2 | 2/2012 | Altenburger et al. |
| 8,338,437 B2 | 12/2012 | Wahhab et al. |
| 8,906,900 B2 | 12/2014 | Duncan et al. |
| 8,940,726 B2 | 1/2015 | Duncan et al. |
| 8,952,026 B2 | 2/2015 | Mitchell et al. |
| 8,993,555 B2 | 3/2015 | Duncan et al. |

(Continued)

FOREIGN PATENT DOCUMENTS

| | | |
|---|---|---|
| DE | 100 10 067 A1 | 9/2001 |
| GB | 1488330 A | 10/1977 |

(Continued)

OTHER PUBLICATIONS

International Search Report and Written Opinion for International Application No. PCT/US2014/028874 dated May 21, 2014.
(Continued)

*Primary Examiner* — Michael Barker
(74) *Attorney, Agent, or Firm* — Wolf, Greenfield & Sacks, P.C.

(57) ABSTRACT

Provided herein are compounds of Formula (I):

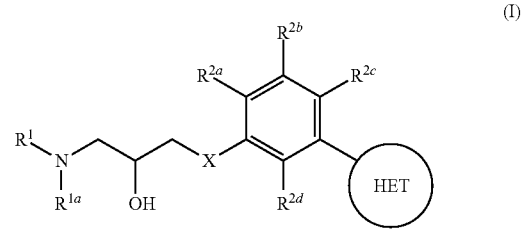

and pharmaceutically acceptable salts thereof, and pharmaceutical compositions thereof, wherein X, $R^1$, $R^{1a}$, $R^{2a}$, $R^{2b}$, $R^{2c}$, $R^{2d}$, are as defined herein, and Ring HET is a 6-membered monocyclic heteroaryl ring system of Formula:

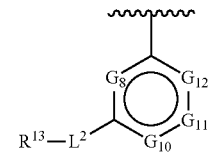

wherein $L^2$, $R^{13}$, $G_8$, $G_{10}$, $G_{11}$, and $G_{12}$ are as defined herein. Compounds of the present invention are useful for inhibiting CARM1 activity. Methods of using the compounds for treating CARM1-mediated disorders are also described.

4 Claims, 1 Drawing Sheet

Specification includes a Sequence Listing.

Related U.S. Application Data continuation of application No. 14/775,766, filed as application No. PCT/US2014/028463 on Mar. 14, 2014, now Pat. No. 9,738,651.

(60) Provisional application No. 61/937,333, filed on Feb. 7, 2014, provisional application No. 61/794,442, filed on Mar. 15, 2013.

(51) Int. Cl.

| | | |
|---|---|---|
| C07D 495/04 | (2006.01) | |
| C07D 493/10 | (2006.01) | |
| C07D 493/04 | (2006.01) | |
| C07D 487/08 | (2006.01) | |
| C07D 471/10 | (2006.01) | |
| C07D 417/14 | (2006.01) | |
| C07D 413/12 | (2006.01) | |
| C07D 409/14 | (2006.01) | |
| C07D 239/42 | (2006.01) | |
| C07D 405/12 | (2006.01) | |
| C07D 405/04 | (2006.01) | |
| C07D 403/04 | (2006.01) | |
| C07D 401/04 | (2006.01) | |
| C07D 413/14 | (2006.01) | |
| C07D 405/14 | (2006.01) | |
| C07D 403/12 | (2006.01) | |

(56) References Cited

U.S. PATENT DOCUMENTS

| | | |
|---|---|---|
| 9,023,883 B2 | 5/2015 | Kuntz et al. |
| 9,045,455 B2 | 6/2015 | Mitchell et al. |
| 9,120,757 B2 | 9/2015 | Chesworth et al. |
| 9,133,189 B2 | 9/2015 | Chesworth et al. |
| 9,221,794 B2 | 12/2015 | Duncan et al. |
| 9,266,836 B2 | 2/2016 | Duncan et al. |
| 9,346,761 B2 | 5/2016 | Chesworth et al. |
| 9,346,802 B2 | 5/2016 | Chesworth et al. |
| 9,365,519 B2 | 6/2016 | Duncan et al. |
| 9,365,527 B2 | 6/2016 | Chesworth et al. |
| 9,365,555 B2 | 6/2016 | Duncan et al. |
| 9,388,173 B2 | 7/2016 | Duncan et al. |
| 9,394,258 B2 | 7/2016 | Chesworth et al. |
| 9,440,950 B2 | 9/2016 | Mitchell et al. |
| 9,447,079 B2 | 9/2016 | Mitchell et al. |
| 9,475,776 B2 | 10/2016 | Kuntz et al. |
| 9,598,374 B2 | 3/2017 | Chesworth et al. |
| 9,604,930 B2 | 3/2017 | Duncan et al. |
| 9,611,257 B2 | 4/2017 | Duncan et al. |
| 9,630,961 B2 | 4/2017 | Chesworth et al. |
| 9,675,614 B2 | 6/2017 | Duncan et al. |
| 9,718,816 B2 | 8/2017 | Chesworth et al. |
| 9,724,332 B2 | 8/2017 | Chesworth et al. |
| 9,732,041 B2 | 8/2017 | Chesworth et al. |
| 9,732,072 B2 | 8/2017 | Duncan et al. |
| 9,738,651 B2 | 8/2017 | Chesworth et al. |
| 9,745,291 B2 | 8/2017 | Duncan et al. |
| 9,765,035 B2 | 9/2017 | Chesworth et al. |
| 9,765,068 B2 | 9/2017 | Duncan et al. |
| 9,776,972 B2 | 10/2017 | Chesworth et al. |
| 9,777,008 B2 | 10/2017 | Duncan et al. |
| 9,856,267 B2 | 1/2018 | Chesworth et al. |
| 9,868,703 B2 | 1/2018 | Kuntz et al. |
| 9,908,887 B2 | 3/2018 | Duncan et al. |
| 9,943,504 B2 | 4/2018 | Chesworth et al. |
| 2003/0055244 A1 | 3/2003 | Scarborough et al. |
| 2004/0242633 A1 | 12/2004 | Evers et al. |
| 2005/0124001 A1 | 6/2005 | Coats et al. |
| 2006/0235037 A1 | 10/2006 | Purandare et al. |
| 2009/0318473 A1 | 12/2009 | Altenburger et al. |
| 2010/0144722 A1 | 6/2010 | Alexander et al. |
| 2011/0065681 A1 | 3/2011 | Wei et al. |
| 2011/0098268 A1 | 4/2011 | Mampreian et al. |
| 2014/0163049 A1 | 6/2014 | Duffy et al. |
| 2014/0213582 A1 | 7/2014 | Duncan et al. |
| 2014/0221310 A1 | 8/2014 | Eccles et al. |
| 2014/0228360 A1 | 8/2014 | Duncan et al. |
| 2014/0288067 A1 | 9/2014 | Chesworth et al. |
| 2014/0288105 A1 | 9/2014 | Chesworth et al. |
| 2014/0288124 A1 | 9/2014 | Chesworth et al. |
| 2014/0288129 A1 | 9/2014 | Mitchell et al. |
| 2014/0315961 A1 | 10/2014 | Chesworth et al. |
| 2014/0323537 A1 | 10/2014 | Chesworth et al. |
| 2015/0133427 A1 | 5/2015 | Duncan et al. |
| 2015/0252031 A1 | 9/2015 | Duncan et al. |
| 2015/0284334 A1 | 10/2015 | Kuntz et al. |
| 2015/0344433 A1 | 12/2015 | Duncan et al. |
| 2015/0344434 A1 | 12/2015 | Duncan et al. |
| 2015/0344457 A1 | 12/2015 | Duncan et al. |
| 2015/0344463 A1 | 12/2015 | Duncan et al. |
| 2015/0361042 A1 | 12/2015 | Duncan et al. |
| 2016/0024016 A1 | 1/2016 | Chesworth et al. |
| 2016/0024017 A1 | 1/2016 | Chesworth et al. |
| 2016/0031839 A1 | 2/2016 | Chesworth et al. |
| 2016/0039767 A1 | 2/2016 | Mitchell et al. |
| 2016/0039834 A1 | 2/2016 | Chesworth et al. |
| 2016/0052922 A1 | 2/2016 | Chesworth et al. |
| 2016/0108018 A1 | 4/2016 | Mitchell et al. |
| 2016/0137609 A1 | 5/2016 | Chesworth et al. |
| 2016/0137631 A1 | 5/2016 | Duncan et al. |
| 2016/0184267 A1 | 6/2016 | Chesworth et al. |
| 2016/0185772 A1 | 6/2016 | Chesworth et al. |
| 2016/0214985 A1 | 7/2016 | Duncan et al. |
| 2016/0368907 A1 | 12/2016 | Duncan et al. |
| 2017/0027935 A1 | 2/2017 | Duncan et al. |
| 2017/0056409 A1 | 3/2017 | Chesworth et al. |
| 2017/0057926 A1 | 3/2017 | Chesworth et al. |
| 2017/0088529 A1 | 3/2017 | Chesworth et al. |
| 2017/0088541 A1 | 3/2017 | Duncan et al. |
| 2017/0119735 A1 | 5/2017 | Chesworth et al. |
| 2017/0182005 A1 | 6/2017 | Mitchell et al. |
| 2017/0198006 A1 | 7/2017 | Chesworth et al. |
| 2017/0210751 A1 | 7/2017 | Duncan et al. |
| 2017/0224685 A1 | 8/2017 | Duncan et al. |
| 2017/0240537 A1 | 8/2017 | Duncan et al. |
| 2017/0267642 A1 | 9/2017 | Chesworth et al. |
| 2017/0280720 A1 | 10/2017 | Chesworth et al. |
| 2017/0283400 A1 | 10/2017 | Mitchell et al. |
| 2017/0283440 A1 | 10/2017 | Chesworth et al. |
| 2017/0291905 A1 | 10/2017 | Chesworth et al. |
| 2017/0298073 A1 | 10/2017 | Olhava et al. |
| 2017/0305922 A1* | 10/2017 | Chesworth .......... C07D 487/10 |
| 2017/0334861 A1 | 11/2017 | Duncan et al. |
| 2018/0105497 A1 | 4/2018 | Chesworth et al. |

FOREIGN PATENT DOCUMENTS

| | | |
|---|---|---|
| GB | 1548601 A | 7/1979 |
| WO | WO 95/15952 A1 | 6/1995 |
| WO | WO 99/59959 A1 | 11/1999 |
| WO | WO 00/39101 A1 | 7/2000 |
| WO | WO 01/64653 A1 | 9/2001 |
| WO | WO 2004/078114 A2 | 9/2004 |
| WO | WO 2008/104077 A1 | 9/2008 |
| WO | WO 2011/115183 A1 | 9/2011 |
| WO | WO 2012/121939 A2 | 9/2012 |
| WO | WO 2012/173689 A2 | 12/2012 |
| WO | WO 2014/100695 A1 | 6/2014 |
| WO | WO 2014/100716 A1 | 6/2014 |
| WO | WO 2014/100719 A1 | 6/2014 |
| WO | WO 2014/100730 A1 | 6/2014 |
| WO | WO 2014/100734 A1 | 6/2014 |
| WO | WO 2014/100764 A1 | 6/2014 |
| WO | WO 2014/144169 A1 | 9/2014 |
| WO | WO 2014/144455 A1 | 9/2014 |
| WO | WO 2014/144659 A1 | 9/2014 |
| WO | WO 2014/153090 A1 | 9/2014 |
| WO | WO 2014/153100 A1 | 9/2014 |
| WO | WO 2014/153172 A1 | 9/2014 |
| WO | WO 2014/153208 A1 | 9/2014 |
| WO | WO 2014/153214 A1 | 9/2014 |

(56) References Cited

FOREIGN PATENT DOCUMENTS

| WO | WO 2014/153226 A1 | 9/2014 |
|---|---|---|
| WO | WO 2014/153235 A1 | 9/2014 |
| WO | WO 2014/178954 A1 | 11/2014 |
| WO | WO 2015/200677 A1 | 12/2015 |
| WO | WO 2015/200680 A1 | 12/2015 |
| WO | WO 2016/022605 A1 | 2/2016 |
| WO | WO 2016/044556 A2 | 3/2016 |
| WO | WO 2016/044560 A1 | 3/2016 |
| WO | WO 2016/044569 A1 | 3/2016 |
| WO | WO 2016/044576 A1 | 3/2016 |
| WO | WO 2016/044585 A1 | 3/2016 |
| WO | WO 2016/044604 A1 | 3/2016 |
| WO | WO 2016/044626 A1 | 3/2016 |
| WO | WO 2016/044641 A2 | 3/2016 |
| WO | WO 2016/044650 A1 | 3/2016 |

OTHER PUBLICATIONS

International Search Report and Written Opinion for International Application No. PCT/US2014/028463 dated Jun. 10, 2014.
International Search Report and Written Opinion for International Application No. PCT/US2015/050712 dated Dec. 15, 2015.
International Search Report and Written Opinion for International Application No. PCT/US2015/050776 dated Dec. 14, 2015.
International Search Report and Written Opinion for International Application No. PCT/US2015/050788 dated Dec. 17, 2015.
International Search Report and Written Opinion for International Application No. PCT/US2015/050675 dated Dec. 17, 2015.
International Search Report and Written Opinion for International Application No. PCT/US2015/050647 dated Dec. 14, 2015.
Al-Dhaheri et al., CARM1 is an important determinant of ERα-dependent breast cancer cell differentiation and proliferation in breast cancer cells. Cancer Res. Mar. 15, 2011;71(6):2118-28. doi: 10.1158/0008-5472.CAN-10-2426. Epub Jan. 31, 2011.
Copeland, Protein methyltransferase inhibitors as personalized cancer therapeutics. Drug Discovery Today. Therapeutic Strategies. 2012;9(2-3):e83-90.
Di Lorenzo et al., Castration-resistant prostate cancer: current and emerging treatment strategies. Drugs. May 28, 2010;70(8):983-1000. doi: 10.2165/10898600-000000000-00000.
Drew et al., Identification of a CARM1 Inhibitor with Potent In Vitro and In Vivo Activity in Preclinical Models of Multiple Myeloma. Sci Rep. Dec. 21, 2017;7(1):17993. doi: 10.1038/s41598-017-18446-z.
El Messaoudi et al., Coactivator-associated arginine methyltransferase 1 (CARM1) is a positive regulator of the Cyclin E1 gene. Proc Natl Acad Sci U S A. Sep. 5, 2006;103(36):13351-6. Epub Aug. 28, 2006.
Engelmann et al., The dark side of E2F1: in transit beyond apoptosis. Cancer Res. Feb. 1, 2012;72(3):571-5. doi: 10.1158/0008-5472.CAN-11-2575.
Eymin et al., Distinct pattern of E2F1 expression in human lung tumours: E2F1 is upregulated in small cell lung carcinoma. Oncogene. Mar. 29, 2001;20(14):1678-87.
Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.
Hong et al., Aberrant expression of CARM1, a transcriptional coactivator of androgen receptor, in the development of prostate carcinoma and androgen-independent status. Cancer. Jul. 1, 2004;101(1):83-9.
Kim et al., Differential CARM1 expression in prostate and colorectal cancers. BMC Cancer. May 13, 2010;10:197. doi: 10.1186/1471-2407-10-197.
Majumder et al., Involvement of arginine methyltransferase CARM1 in androgen receptor function and prostate cancer cell viability. Prostate. Sep. 1, 2006;66(12):1292-301.
Ou et al., A coactivator role of CARM1 in the dysregulation of β-catenin activity in colorectal cancer cell growth and gene expression. Mol Cancer Res. May 2011;9(5):660-70. doi: 10.1158/1541-7786.MCR-10-0223. Epub Apr. 8, 2011.
Pubchem Submission; NIH/NCBI, Compound Identifier 90425581. Feb 13, 2015. 9 pages.
Purandare et al., Pyrazole inhibitors of coactivator associated arginine methyltransferase 1 (CARM1). Bioorg Med Chem Lett. Aug. 1, 2008;18(15):4438-41. doi: 10.1016/j.bmcl.2008.06.026. Epub Jun. 12, 2008.
Sack et al., Structural basis for CARM1 inhibition by indole and pyrazole inhibitors. Biochem J. Jun. 1, 2011;436(2):331-9. doi: 10.1042/BJ20102161.
Teyssier et al., Protein arginine methylation in estrogen signaling and estrogen-related cancers. Trends Endocrinol Metab. Mar. 2010;21(3):181-9. doi: 10.1016/j.tem.2009.11.002. Epub Dec. 11, 2009.
Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.
Vu et al., PRMT4 blocks myeloid differentiation by assembling a methyl-RUNX1-dependent repressor complex. Cell Rep. Dec. 26, 2013;5(6):1625-38. doi: 10.1016/j.celrep.2013.11.025.
Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.
Wang et al., CARM1/PRMT4 is necessary for the glycogen gene expression programme in skeletal muscle cells. Biochem J. Jun. 1, 2012;444(2):323-31. doi: 10.1042/BJ20112033.
Zauli et al., miR-34a induces the downregulation of both E2F1 and B-Myb oncogenes in leukemic cells. Clin Cancer Res. May 1, 2011;17(9):2712-24. doi:10.1158/1078-0432.CCR-10-3244.

* cited by examiner

```
                              SEQUENCE LISTING

<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Pro Arg Lys Gln Leu Ala Thr Lys Ala Ala Arg Lys Ser Ala Pro
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Met Asp Tyr Lys Asp Asp Asp Asp Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Glu Gly His His His His His His
1               5

<210> SEQ ID NO 4
<211> LENGTH: 601
<212> TYPE: PRT
<213> ORGANISM: Artificial Sequence
<220> FEATURE:
<223> OTHER INFORMATION: Synthetic Polypeptide

<400> SEQUENCE: 4

Met Asp Tyr Lys Asp Asp Asp Asp Lys Ala Ala Ala Ala Ala Val
1               5                   10                  15

Gly Pro Gly Ala Gly Gly Ala Gly Ser Ala Val Pro Gly Gly Ala Gly
                20                  25                  30

Pro Cys Ala Thr Val Ser Val Phe Pro Gly Ala Arg Leu Leu Thr Ile
                35                  40                  45

Gly Asp Ala Asn Gly Glu Ile Gln Arg His Ala Glu Gln Gln Ala Leu
            50                  55                  60

Arg Leu Glu Val Arg Ala Gly Pro Asp Ser Ala Gly Ile Ala Leu Tyr
65                  70                  75                  80

Ser His Glu Asp Val Cys Val Phe Lys Cys Ser Val Ser Arg Glu Thr
                    85                  90                  95

Glu Cys Ser Arg Val Gly Lys Gln Ser Phe Ile Ile Thr Leu Gly Cys
                100                 105                 110
```

```
Asn Ser Val Leu Ile Gln Phe Ala Thr Pro Asn Asp Phe Cys Ser Phe
            115                 120                 125

Tyr Asn Ile Leu Lys Thr Cys Arg Gly His Thr Leu Glu Arg Ser Val
130                 135                 140

Phe Ser Glu Arg Thr Glu Glu Ser Ser Ala Val Gln Tyr Phe Gln Phe
145                 150                 155                 160

Tyr Gly Tyr Leu Ser Gln Gln Gln Asn Met Met Gln Asp Tyr Val Arg
                165                 170                 175

Thr Gly Thr Tyr Gln Arg Ala Ile Leu Gln Asn His Thr Asp Phe Lys
            180                 185                 190

Asp Lys Ile Val Leu Asp Val Gly Cys Gly Ser Gly Ile Leu Ser Phe
        195                 200                 205

Phe Ala Ala Gln Ala Gly Ala Arg Lys Ile Tyr Ala Val Glu Ala Ser
210                 215                 220

Thr Met Ala Gln His Ala Glu Val Leu Val Lys Ser Asn Asn Leu Thr
225                 230                 235                 240

Asp Arg Ile Val Val Ile Pro Gly Lys Val Glu Val Ser Leu Pro
                245                 250                 255

Glu Gln Val Asp Ile Ile Ile Ser Glu Pro Met Gly Tyr Met Leu Phe
            260                 265                 270

Asn Glu Arg Met Leu Glu Ser Tyr Leu His Ala Lys Lys Tyr Leu Lys
    275                 280                 285

Pro Ser Gly Asn Met Phe Pro Thr Ile Gly Asp Val His Leu Ala Pro
        290                 295                 300

Phe Thr Asp Glu Gln Leu Tyr Met Glu Gln Phe Thr Lys Ala Asn Phe
305                 310                 315                 320

Trp Tyr Gln Pro Ser Phe His Gly Val Asp Leu Ser Ala Leu Arg Gly
                325                 330                 335

Ala Ala Val Asp Glu Tyr Phe Arg Gln Pro Val Val Asp Thr Phe Asp
            340                 345                 350

Ile Arg Ile Leu Met Ala Lys Ser Val Lys Tyr Thr Val Asn Phe Leu
        355                 360                 365

Glu Ala Lys Glu Gly Asp Leu His Arg Ile Glu Ile Pro Phe Lys Phe
370                 375                 380

His Met Leu His Ser Gly Leu Val His Gly Leu Ala Phe Trp Phe Asp
385                 390                 395                 400

Val Ala Phe Ile Gly Ser Ile Met Thr Val Trp Leu Ser Thr Ala Pro
                405                 410                 415

Thr Glu Pro Leu Thr His Trp Tyr Gln Val Arg Cys Leu Phe Gln Ser
            420                 425                 430

Pro Leu Phe Ala Lys Ala Gly Asp Thr Leu Ser Gly Thr Cys Leu Leu
        435                 440                 445

Ile Ala Asn Lys Arg Gln Ser Tyr Asp Ile Ser Ile Val Ala Gln Val
    450                 455                 460

Asp Gln Thr Gly Ser Lys Ser Ser Asn Leu Leu Asp Leu Lys Asn Pro
465                 470                 475                 480

Phe Phe Arg Tyr Thr Gly Thr Thr Pro Ser Pro Pro Gly Ser His
                485                 490                 495

Tyr Thr Ser Pro Ser Glu Asn Met Trp Asn Thr Gly Ser Thr Tyr Asn
            500                 505                 510

Leu Ser Ser Gly Met Ala Val Ala Gly Met Pro Thr Ala Tyr Asp Leu
        515                 520                 525

Ser Ser Val Ile Ala Ser Gly Ser Ser Val Gly His Asn Asn Leu Ile
```

```
                            530                 535                 540
Pro Leu Gly Ser Ser Gly Ala Gln Gly Ser Gly Gly Gly Ser Thr Ser
545                 550                 555                 560

Ala His Tyr Ala Val Asn Ser Gln Phe Thr Met Gly Gly Pro Ala Ile
                565                 570                 575

Ser Met Ala Ser Pro Met Ser Ile Pro Thr Asn Thr Met His Tyr Gly
            580                 585                 590

Ser Glu Gly His His His His His
            595                 600
```

CARM1 INHIBITORS AND USES THEREOF

RELATED APPLICATIONS

This application is a Continuation Application of U.S. patent application Ser. No. 15/648,701, filed Jul. 13, 2017, allowed, which is a Continuation of U.S. patent application Ser. No. 14/775,766, now issued U.S. Pat. No. 9,738,651, which is a national stage filing under 35 U.S.C. § 371 of International PCT application PCT/US2014/028463, filed Mar. 14, 2014 which claims priority under 35 U.S.C. § 119(e) to U.S. provisional patent application, U.S. Ser. No. 61/794,442, filed Mar. 15, 2013, and to U.S. provisional patent application, U.S. Ser. No. 61/937,333, filed Feb. 7, 2014, the entire contents of each of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., CARM1 (co-activator-associated arginine methyltransferase 1; PRMT4)), many of which are associated with specific genetic alterations that can cause human disease.

Disease-associated chromatin-modifying enzymes play a role in diseases such as proliferative disorders, autoimmune disorders, muscular disorders, and neurological disorders. Thus, there is a need for the development of small molecules that are capable of inhibiting the activity of CARM1.

DETAILED DESCRIPTION OF CERTAIN EMBODIMENTS

Figure 1A:
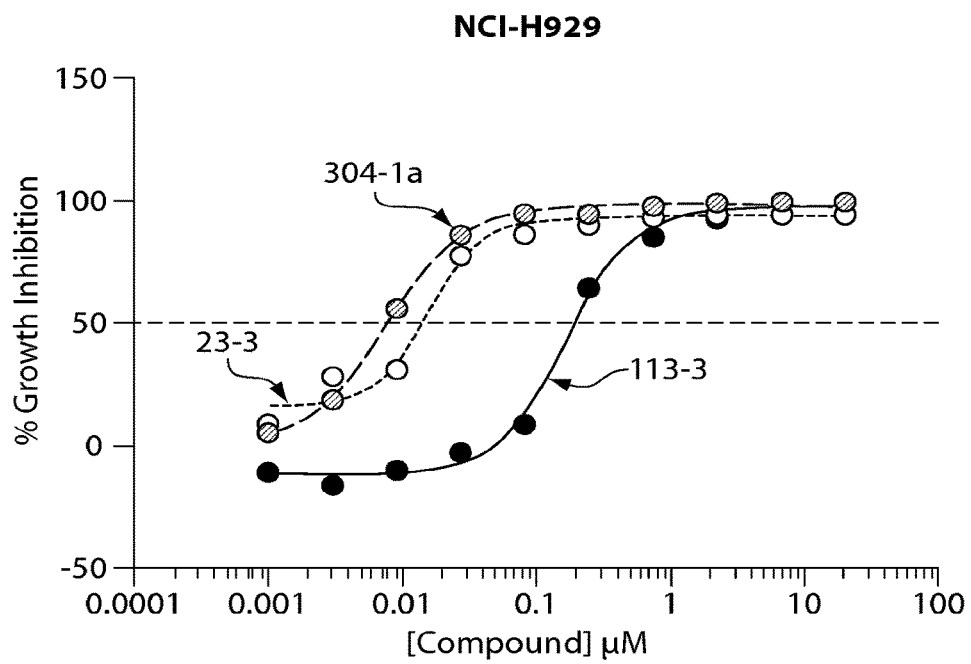
FIGS. 1A and 1B show cell proliferation in response to the presence of compounds of the current invention. Human Multiple Myeloma cell lines NCI-H929 (FIG. 1A) and U266B1 (FIG. 1B) were treated with varying doses of 304-1a (medium grey data points), 23-3 (light grey data points), and 113-3 (black data points) in a 14-day proliferation assay. At the end of the experiment, total cell number was determined for each cell line for different doses of 304-1a, 23-3, and 113-3. As shown below, all compounds tested decreased the proliferation of these cell lines, at potencies consistent with that seen for the biochemical and cell-based (PABP1me2a) ICW (In Cell Western) assays.

CARM1 is an attractive target for modulation given its role in the regulation of diverse biological processes. It has now been found that compounds described herein, and pharmaceutically acceptable salts and compositions thereof, are effective as inhibitors of CARM1. Such compounds have the general Formula (I):

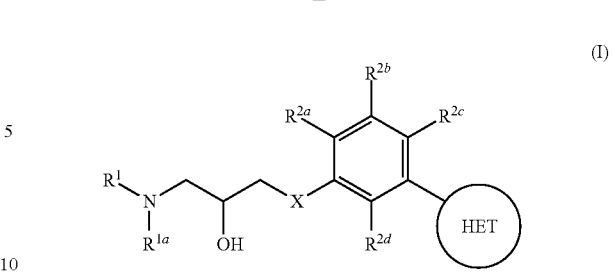

and pharmaceutically acceptable salts thereof, and pharmaceutical compositions thereof; wherein X, $R^1$, $R^{1a}$, $R^{2a}$, $R^{2b}$, $R^{2c}$, $R^{2d}$, are as defined herein, and wherein Ring HET is a 6-membered monocyclic heteroaryl ring system of Formula:

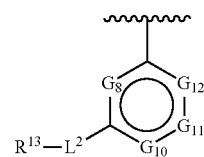

wherein $L^2$, $R^{13}$, $G_8$, $G_{10}$, $G_{11}$, and $G_{12}$ are as defined herein. In certain embodiments of Formula (I), $R^{1a}$ is hydrogen. In certain embodiments of Formula (I), $R^1$ is not hydrogen, and $R^{1a}$ is hydrogen. In certain embodiments of Formula (I), each of $R^1$ and $R^{1a}$ is not hydrogen. In certain embodiments of Formula (I), each of $R^1$ and $R^{1a}$ is hydrogen. A non-hydrogen group, as used herein, refers to any group recited as a possibility for that particular group but excluding hydrogen.

In some embodiments, pharmaceutical compositions are provided which comprise a compound described herein (e.g., a compound of Formula (I), or a pharmaceutically acceptable salt thereof) and optionally a pharmaceutically acceptable excipient.

In certain embodiments, compounds described herein inhibit the activity of CARM1. In certain embodiments, methods of inhibiting CARM1 are provided which comprise contacting CARM1 with an effective amount of a compound of Formula (I), or a pharmaceutically acceptable salt thereof. The CARM1 may be purified or crude, and may be present in a cell, tissue, or a subject. Thus, such methods encompass inhibition of CARM1 activity both in vitro and in vivo. In certain embodiments, the CARM1 is wild-type CARM1. In certain embodiments, the CARM1 is overexpressed. In certain embodiments, the CARM1 is a mutant. In certain embodiments, the CARM1 is in a cell. In certain embodiments, the CARM1 is in a tissue. In certain embodiments, the CARM1 is in a biological sample. In certain embodiments, the CARM1 is in an animal, e.g., a human. In some embodiments, the CARM1 is expressed at normal levels in a subject, but the subject would benefit from CARM1 inhibition (e.g., because the subject has one or more mutations in an CARM1 substrate that causes an increase in methylation of the substrate with normal levels of CARM1). In some embodiments, the CARM1 is in a subject known or identified as having abnormal CARM1 activity (e.g., overexpression). In some embodiments, the CARM1 is in a subject known or identified as having aberrant CARM1 activity. In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective relative to one or more other methyltransferases.

In certain embodiments, methods of modulating gene expression or activity in a cell are provided which comprise contacting a cell with an effective amount of a compound of Formula (I), or a pharmaceutically acceptable salt thereof, or a pharmaceutical composition thereof. In certain embodiments, the cell is cultured in vitro. In certain embodiments, cell is in an animal, e.g., a human.

In certain embodiments, methods of modulating transcription in a cell are provided which comprise contacting a cell with an effective amount of a compound of Formula (I), or a pharmaceutically acceptable salt thereof, or a pharmaceutical composition thereof. In certain embodiments, the cell is cultured in vitro. In certain embodiments, the cell is in an animal, e.g., a human.

In some embodiments, methods of treating a CARM1-mediated disorder are provided which comprise administering to a subject suffering from a CARM1-mediated disorder an effective amount of a compound described herein (e.g., a compound of Formula (I), or a pharmaceutically acceptable salt thereof), or a pharmaceutical composition thereof. In certain embodiments, the CARM1-mediated disorder is a proliferative disorder. In certain embodiments, compounds described herein are useful for treating cancer. In certain embodiments, compounds described herein are useful for treating breast cancer or prostate cancer. In certain embodiments, the CARM1-mediated disorder is a metabolic disorder.

Compounds described herein are also useful for the study of CARM1 in biological and pathological phenomena, the study of intracellular signal transduction pathways mediated by CARM1, and the comparative evaluation of new CARM1 inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Aliphatic" refers to alkyl, alkenyl, alkynyl, and carbocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —CH$_3$). In certain embodiments, the alkyl group is substituted $C_{1-10}$ alkyl.

"Haloalkyl" refers to an alkyl group substituted with one or more halogen atoms, e.g., 1, 2, 3, 4, 5, or 6 halogen atoms. Haloalkyl encompasses perhaloalkyl as defined herein.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl").

In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") or tricyclic system ("tricyclic carbocyclyl"), and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_5$ cycloalkyl groups include cyclopentyl ($C_5$) and cyclohexyl ($C_5$). Examples of $C_3$ 6 cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3-14 membered non-aromatic ring system having ring carbon atoms and 1 to 4 ring heteroatoms, wherein each heteroatom is independently selected from nitrogen, oxygen, and sulfur ("3-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl") or tricyclic system ("tricyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-14 membered monocyclic or polycyclic (e.g., bicyclic or tricyclic) 4n+2 aromatic ring system (e.g., having 6 or 10 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In some embodiments, heteroaryl refers to a radical of a 5-10 membered monocyclic or bicyclic 4n+2 aromatic ring system (e.g., having 6 or 10 It electrons shared in a cyclic array)

having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Fused" or "ortho-fused" are used interchangeably herein, and refer to two rings that have two atoms and one bond in common, e.g.,

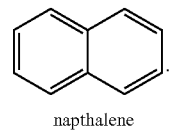

napthalene

"Bridged" refers to a ring system containing (1) a bridgehead atom or group of atoms which connect two or more non-adjacent positions of the same ring; or (2) a bridgehead atom or group of atoms which connect two or more positions of different rings of a ring system and does not thereby form an ortho-fused ring, e.g.,

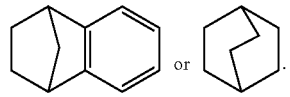

"Spiro" or "Spiro-fused" refers to a group of atoms which connect to the same atom of a carbocyclic or heterocyclic ring system (geminal attachment), thereby forming a ring, e.g.,

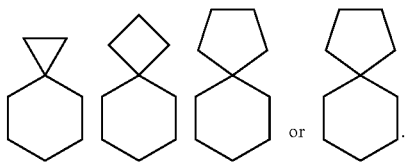

Spiro-fusion at a bridgehead atom is also contemplated.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_6$ 14 aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$COR$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-4}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —CO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC (=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si (C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$ (C$_{1-6}$ alkyl), —P(=O)(C$_{1-6}$ alkyl)$_2$, —OP(=O)(C$_1$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F, Cl, Br, I), NO$_3$, ClO$_4$, OH, H$_2$PO$_4$, HSO$_4$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Hydroxyl" or "hydroxy" refers to the group —OH. "Substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

"Thiol" or "thio" refers to the group —SH. "Substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

"Amino" refers to the group —NH$_2$. "Substituted amino," by extension, refers to a monosubstituted amino, a disubstituted amino, or a trisubstituted amino, as defined herein. In certain embodiments, the "substituted amino" is a monosubstituted amino or a disubstituted amino group.

"Monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

"Disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

"Trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

"Sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Sulfinyl" refers to the group —S(=O)R$^{aa}$, wherein R$^{aa}$ is as defined herein.

"Carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(l-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, t-butyl carbonate (Boc), 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methytransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as CARM1 inhibitors. In some embodiments, the present disclosure provides a compound of Formula (I):

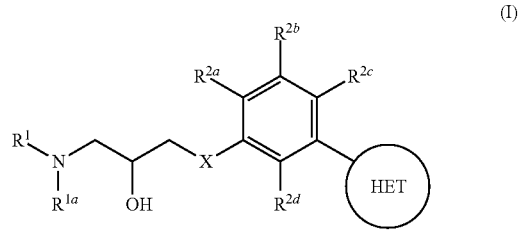

(I)

or a pharmaceutically acceptable salt thereof;
wherein:
X is —O—, —S—, or —CH$_2$—;
R$^1$ and R$^{1a}$ are each independently hydrogen or optionally substituted C$_{1-4}$ aliphatic, or R$^1$ and R$^{1a}$ may be joined to form a substituted or unsubstituted heterocyclic, or substituted or unsubstituted heteroaryl ring;
each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O) R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;
Ring HET is a 6-membered monocylic heteroaryl ring system of the Formula:

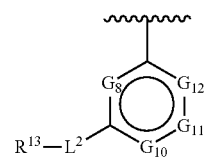

wherein:
G$_8$ is C—R$^8$ or N;
G$_{10}$ is C—R$^{10}$ or N;
G$_{11}$ is C—R$^{11}$ or N;
G$_{12}$ is C—R$^{12}$ or N;
provided at least one instance of G$_8$, G$^{10}$, G$_{11}$, or G$_{12}$ is N;
each instance of R$^8$, R$^{10}$, R$^{11}$, and R$^{12}$ is independently selected from the group consisting of hydrogen, halo, —CN, —NO$_2$, —C(=O)R', —C(=O)OR', —C(=O)N(R')$_2$, optionally substituted alkyl, optionally substituted C$_{3-4}$cycloalkyl, and -L$^1$-R$^3$;
each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each instance of $L^1$ and $L^2$ is independently a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —NR$^L$C(O)—, —NR$^L$C(O)N($R^L$)—, —NR$^L$C(O)N($R^L$)N($R^L$)—, —NR$^L$C(O)O—, —SC(O)—, —C(=NR$^L$)—, —C(=NNR$^L$)—, —C(=NOR$^L$)—, —C(=NR$^L$)N($R^L$)—, —NR$^L$C(=NR$^L$)—, —C(S)—, —C(S)N($R^L$)—, —NR$^L$C(S)—, —S(O)—, —OS(O)$_2$—, —S(O)$_2$O—, —SO$_2$—, —N($R^L$)SO$_2$—, —SO$_2$N($R^L$)—, —N($R^L$)SO$_2$N($R^L$)—, an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —NR$^L$C(O)—, —NR$^L$C(O)N($R^L$)—, —NR$^L$C(O)N($R^L$)N($R^L$)—, —NR C(O)O—, —SC(O)—, —C(=NR$^L$)—, —C(=NNR$^L$)—, —C(=NOR$^L$)—, —C(=NR$^L$)N($R^L$)—, —NR$^L$C(=NR$^L$)—, —C(S)—, —C(S)N($R^L$)—, —NR$^L$C(S)—, —S(O)—, —OS(O)$_2$—, —S(O)$_2$O—, —SO$_2$—, —N($R^L$)SO$_2$—, —SO$_2$N($R^L$), and —N($R^L$)SO$_2$N($R^L$) is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring;

$R^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when $R^3$ is hydrogen, then $L^1$ is not a bond; and $R^{13}$ is optionally substituted carbocyclyl, optionally substituted heterocyclyl, optionally substituted aryl, or optionally substituted heteroaryl.

In certain embodiments of Formula (I), $R^{1a}$ is hydrogen. In certain embodiments of Formula (I), $R^{1a}$ is not hydrogen. In certain embodiments of Formula (I), $R^1$ is not hydrogen (e.g., —CH$_3$), and $R^{1a}$ is hydrogen. In certain embodiments of Formula (I), each of $R^1$ and $R^{1a}$ is not hydrogen (e.g., each is —CH$_3$). In certain embodiments of Formula (I), each of $R^1$ and $R^{1a}$ is hydrogen.

It is generally understood that compounds of Formula (I), as described herein, comprises one or more asymmetric centers, and thus can exist in various isomeric forms, e.g., enantiomeric and/or diastereomeric forms. In certain embodiments, the compound of Formula (I) has the following stereochemistry (I-a) or (I-b):

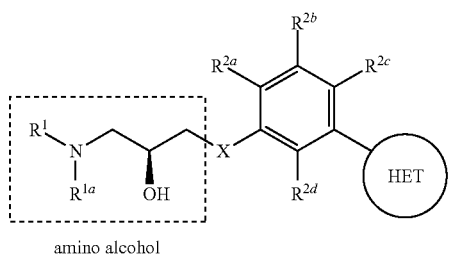

amino alcohol (I-a)

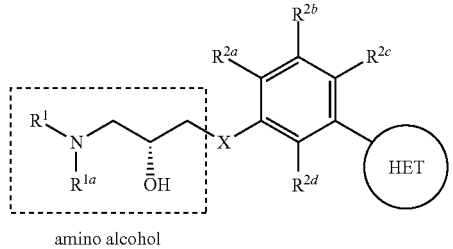

amino alcohol (I-b)

In certain embodiments of Formula (I-a) or (I-b), $R^{1a}$ is hydrogen. In certain embodiments of Formula (I-a) or (I-b), $R^{1a}$ is not hydrogen. In certain embodiments of Formula (I-a) or (I-b), $R^1$ is not hydrogen (e.g., —CH$_3$), and $R^{1a}$ is hydrogen. In certain embodiments of Formula (I-a) or (I-b), each of $R^1$ and $R^{1a}$ is not hydrogen (e.g., each is —CH$_3$). In certain embodiments of Formula (I-a) or (I-b), each of $R^1$ and $R^{1a}$ is hydrogen.

For example, in certain embodiments, the hydroxyl group of the amino alcohol moiety provided in any of the genera or compounds depicted herein has (S) stereochemistry. In certain embodiments the hydroxyl group of the amino alcohol moiety provided in any of the genera or compounds depicted herein has (R) stereochemistry.

As generally defined herein, X is —O—, —S—, or —CH$_2$—. In certain embodiments, X is —O—. In certain embodiments, X is —S—. In certain embodiments, X is —O—.

As generally defined herein, $R^1$ is hydrogen or optionally substituted $C_{1-4}$ aliphatic. In certain embodiments, $R^1$ is hydrogen. In certain embodiments, $R^1$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic. It is understood that aliphatic, as used herein, encompasses alkyl, alkenyl, alkynyl, and carbocyclic groups. In certain embodiments, $R^1$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_{1-2}$ alkyl, optionally substituted $C_{2-3}$ alkyl, optionally substituted $C_3$alkyl, or optionally substituted $C_4$alkyl. In certain embodiments, $R^1$ is unsubstituted $C_{1-4}$ alkyl, e.g., unsubstituted $C_{1-2}$alkyl, unsubstituted $C_{2-3}$alkyl, unsubstituted $C_{3-4}$alkyl, unsubstituted $C_1$alkyl, unsubstituted $C_2$alkyl, unsubstituted $C_3$alkyl, or unsubstituted $C_4$alkyl. Exemplary $C_{1-4}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), or iso-butyl ($C_4$), each of which may be substituted or unsubstituted. In certain embodiments, $R^1$ is optionally substituted $C_{2-4}$ alkenyl, e.g., optionally substituted $C_{2-3}$ alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^1$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^1$ is optionally substituted $C_3$carbocylyl, e.g., optionally substituted cyclopropyl. In certain embodiments, $R^1$ is hydrogen or an unsubstituted $C_{1-4}$ aliphatic group, e.g., for example, in certain embodiments, $R^1$ is hydrogen, methyl (—CH$_3$), ethyl (—CH$_2$CH$_3$), n-propyl (—CH$_2$CH$_2$CH$_3$), isopropyl (—CH(CH$_3$)$_2$), or cyclopropyl (—C$_3$H$_5$).

As generally defined herein, $R^{1a}$ is hydrogen or optionally substituted $C_{1-4}$ aliphatic. In certain embodiments, $R^{1a}$ is hydrogen. In certain embodiments, $R^{1a}$ is not hydrogen. In certain embodiments, $R^{1a}$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic. It is understood that aliphatic, as used herein, encompasses alkyl, alkenyl, alkynyl, and carbocyclic groups. In certain embodiments, $R^{1a}$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, $R^{1a}$ is unsubstituted $C_{1-4}$ alkyl, e.g., unsubstituted $C_{1-2}$alkyl, unsubstituted $C_{2-3}$alkyl, unsubstituted $C_{3-4}$alkyl, unsubstituted $C_1$alkyl, unsubstituted $C_2$alkyl, unsubstituted $C_3$alkyl, or unsubstituted $C_4$alkyl. Exemplary C-4alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), or iso-butyl ($C_4$), each of which may be substituted or unsubstituted. In certain embodiments, $R^{1a}$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^{1a}$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^{1a}$ is optionally substituted $C_3$carbocylyl, e.g., optionally substituted cyclopropyl. In certain embodiments, $R^{1a}$ is hydrogen or an unsubstituted $C_{1-4}$ aliphatic group, e.g., for example, in certain embodiments, $R^{1a}$ is hydrogen, methyl (—$CH_3$), ethyl (—$CH_2CH_3$), n-propyl (—$CH_2CH_2CH_3$), isopropyl (—$CH(CH_3)_2$), or cyclopropyl (—$C_3H_5$).

In certain embodiments, $R^1$ is hydrogen, and $R^{1a}$ is hydrogen.

In certain embodiments, $R^1$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic; and $R^{1a}$ is hydrogen. In certain embodiments, $R^1$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl; and $R^{1a}$ is hydrogen. In certain embodiments, $R^1$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl; and $R^{1a}$ is hydrogen. In certain embodiments, $R^1$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl; and $R^{1a}$ is hydrogen. In certain embodiments, $R^1$ is optionally substituted $C_3$carbocylyl, e.g., optionally substituted cyclopropyl; and $R^{1a}$ is hydrogen. In certain embodiments, $R^1$ is an unsubstituted $C_{1-4}$ aliphatic group, e.g., for example, in certain embodiments, $R^1$ is methyl (—$CH_3$), ethyl (—$CH_2CH_3$), n-propyl (—$CH_2CH_2CH_3$), isopropyl (—$CH(CH_3)_2$), or cyclopropyl (—$C_3H_5$); and $R^{1a}$ is hydrogen.

In certain embodiments, each of $R^1$ and $R^{1a}$ is independently a non-hydrogen group.

In certain embodiments, $R^1$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic; and $R^{1a}$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic. In certain embodiments, $R^1$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl; and $R^{1a}$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, $R^1$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl; and $R^{1a}$ is optionally substituted $C_{1-4}$ alkyl, e.g., optionally substituted $C_{1-2}$alkyl, optionally substituted $C_{2-3}$ alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, $R^1$ is optionally substituted $C_{2-4}$ alkynyl, e.g., optionally substituted $C_{2\ 3}$alkynyl, optionally substituted $C_{3\ 4}$alkynyl, optionally substituted $C_2$alkynyl, optionally substituted $C_3$alkynyl, or optionally substituted $C_4$alkynyl; and $R^{1a}$ is optionally substituted $C_{1-4}$ alkyl, e.g., optionally substituted $C_1$ 2alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, $R^1$ is optionally substituted $C_3$carbocylyl, e.g., optionally substituted cyclopropyl; and $R^{1a}$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, each of $R^1$ and $R^{1a}$ is independently an unsubstituted $C_{1-4}$ aliphatic group, e.g., for example, in certain embodiments, each of $R^1$ and $R^{1a}$ is independently methyl (—$CH_3$), ethyl (—$CH_2CH_3$), n-propyl (—$CH_2CH_2CH_3$), isopropyl (—$CH(CH_3)_2$), or cyclopropyl (—$C_3H_5$). In certain embodiments, each of $R^1$ and $R^{1a}$ is methyl (—$CH_3$).

Alternatively, as generally defined herein, $R^1$ and $R^{1a}$ may be joined to form a substituted or unsubstituted heterocyclic, or substituted or unsubstituted heteroaryl ring. In certain embodiments, $R^1$ and $R^{1a}$ are joined to form a 3-6 membered substituted or unsubstituted heterocyclic ring, e.g., 3-membered, 4-membered, 5-membered, or 6-membered, substituted or unsubstituted heterocyclic ring. In certain embodiments, $R^1$ and $R^{1a}$ are joined to form a 5-6 membered substituted or unsubstituted heteroaryl ring, e.g., 5-membered or 6-membered, substituted or unsubstituted heteroaryl ring. In certain embodiments, $R^1$ and $R^{1a}$ may be joined to form a substituted or unsubstituted azetidine. In certain embodiments, $R^1$ and $R^{1a}$ may be joined to form a substituted or unsubstituted pyrrolidine. In certain embodiments, $R^1$ and $R^{1a}$ may be joined to form a substituted or unsubstituted piperidine. In certain embodiments, $R^1$ and $R^{1a}$ may be joined to form a substituted or unsubstituted piperazine. In certain embodiments, $R^1$ and $R^{1a}$ may be joined to form a substituted or unsubstituted morpholine. In certain embodiments, $R^1$ and $R^{1a}$ may be joined to form a substituted or unsubstituted pyrrole. In certain embodiments, $R^1$ and $R^{1a}$ may be joined to form a substituted or unsubstituted imidazole. In certain embodiments, $R^1$ and $R^{1a}$ may be joined to form a substituted or unsubstituted pyrazole. In certain embodiments, $R^1$ and $R^{1a}$ may be joined to form a substituted or unsubstituted triazole. In certain embodiments, $R^1$ and $R^{1a}$ may be joined to form a substituted or unsubstituted tetrazole.

However, in certain embodiments, $R^1$ and $R^{1a}$ are not both methyl (—$CH_3$). In certain embodiments, $R^1$ and $R^{1a}$ are not joined to form a substituted or unsubstituted heterocyclic ring, e.g., a 3-membered, 4-membered, 5-membered, or 6-membered substituted or unsubstituted heterocyclic ring. In certain embodiments, $R^1$ and $R^{1a}$ are not joined to form a substituted or unsubstituted pyrrolidine ring. In certain embodiments, $R^1$ and $R^{1a}$ are not joined to form a substituted or unsubstituted heteroaryl ring, e.g., 5-membered or 6-membered substituted or unsubstituted heteroaryl ring.

As generally defined herein, each of $R^{2a}$, $R^{2b}$, $R^{2c}$, and $R^{2d}$ is independently hydrogen, halo, —CN, —$NO_2$, —C(=O)$R^{A2}$, —C(=O)O$R^{A2}$, —C(=O)N($R^{A2}$)$_2$, —O$R^{A2}$, —S$R^{A2}$, —N($R^{A2}$)$_2$, —S(=O)$R^{A2}$, —S(=O)$_2R^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring.

In certain embodiments, at least one of (e.g., one, two, three, each of) $R^{2a}$, $R^{2b}$, $R^{2c}$ and $R^{2d}$ is hydrogen. In certain embodiments, at least one of $R^{2a}$, $R^{2b}$, $R^{2c}$, and $R^{2d}$ is halo, e.g., fluoro, chloro, bromo, or iodo. In certain embodiments, at least one of $R^{2a}$, $R^{2b}$, $R^{2c}$, and $R^{2d}$ is chloro. However, in certain embodiments, neither of $R^{2a}$, $R^{2b}$, $R^{2c}$, and $R^{2d}$ are halo, e.g., fluoro, chloro, bromo, or iodo. In certain embodiments, $R^{2a}$ is not halo, e.g., fluoro, chloro, bromo, or iodo. In certain embodiments, $R^{2a}$ is not chloro. In certain embodiments, $R^{2d}$ is not halo, e.g., fluoro, chloro, bromo, or iodo. In certain embodiments, $R^{2d}$ is not fluoro. In certain embodiments, at least one of $R^{2a}$, $R^{2b}$, $R^{2c}$, and $R^{2d}$ is —CN. In certain embodiments, at least one of $R^{2a}$, $R^{2b}$, $R^{2c}$, and $R^{2d}$ is —$NO_2$. In certain embodiments, at least one of $R^{2a}$, $R^{2b}$, $R^{2c}$, and $R^{2d}$ is —C(=O)$R^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)O$R^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)N($R^{A2}$)$_2$, e.g., wherein each instance of $R^{A2}$ is hydrogen or optionally substituted alkyl (e.g., methyl), or two $R^{A2}$ groups attached to the same nitrogen atom are joined to form an optionally substituted heterocyclyl or optionally substituted heteroaryl ring. In certain embodiments, at least one of $R^{2a}$, $R^{2b}$, $R^{2c}$, and $R^{2d}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. Exemplary $R^{2a}$, $R^{2b}$, $R^{2c}$, and $R^{2d}$ $C_{1-4}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), and iso-butyl ($C_4$), each of which may be substituted or unsubstituted. In certain embodiments, at least one of $R^{2a}$, $R^{2b}$, $R^{2c}$, and $R^{2d}$ is alkyl substituted with hydroxy or substituted hydroxy, e.g., —($CH_2$)$_a$OH or —($CH_2$)$_a$O$CH_3$, wherein a is 1, 2, 3, 4, 5, or 6. In certain embodiments, at least one of $R^{2a}$, $R^2$, $R^{2c}$, and $R^{2d}$ is alkyl substituted with halogen (e.g., fluoro), e.g., at least one of $R^{2a}$, $R^{2b}$, $R^{2c}$, and $R^{2d}$ is —$CF_3$. In certain embodiments, at least one of $R^{2a}$, $R^{2b}$, $R^{2c}$, and $R^{2d}$ is optionally substituted alkenyl, e.g., optionally substituted $C_{2-4}$ alkenyl, optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, at least one of $R^{2a}$, $R^{2b}$, $R^{2c}$, and $R^{2d}$ is optionally substituted $C_2$alkenyl or optionally substituted $C_3$alkenyl, e.g., vinyl or allyl. In certain embodiments, at least one of $R^{2a}$, $R^{2b}$, $R^{2c}$, and $R^{2d}$ is optionally substituted alkynyl, e.g., optionally substituted $C_{2-4}$ alkynyl, optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, at least one of $R^{2a}$, $R^{2b}$, $R^{2c}$, and $R^{2d}$ is optionally substituted $C_2$alkynyl, e.g., acetylene. In certain embodiments, at least one of $R^{2a}$, $R^{2b}$, $R^{2c}$, and $R^{2d}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one of $R^{2a}$, $R^{2b}$, $R^{2c}$, and $R^{2d}$ is optionally substituted $C_3$carbocyclyl, e.g., cyclopropyl. In certain embodiments, at least one of $R^{2a}$, $R^{2b}$, $R^{2c}$, and $R^{2d}$ is optionally substituted heterocyclyl, e.g., optionally substituted 3-to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{2a}$, $R^{2b}$, $R^{2c}$, and $R^{2d}$ is —O$R^{A2}$, —S$R^{A2}$, or —N($R^{A2}$)$_2$, wherein $R^{A2}$ is as defined herein. In certain embodiments, at least one of $R^{2a}$, $R^{2b}$, $R^{2c}$, and $R^{2d}$ is —S(=O)$R^{A2}$ or —S(=O)$_2R^{A2}$, wherein $R^{A2}$ is as defined herein. In certain embodiments, at least one $R^{A2}$ is hydrogen, e.g., for example, to provide at least one of $R^{2a}$, $R^{2b}$, $R^{2c}$, and $R^{2d}$ as —OH, —SH, —$NH_2$, or —NH$R^{A2}$. In certain embodiments, at least one of $R^{A2}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl, e.g., for example, at least one of $R^{A2}$ is methyl to provide a group $R^{2a}$, $R^{2b}$, $R^{2c}$, and $R^{2d}$ of formula —O$CH_3$, —S$CH_3$, —NH$CH_3$, —N($CH_3$)$_2$, or —N$CH_3R^{A2}$. In certain embodiments, at least one of $R^{A2}$ is alkyl substituted with halogen (e.g., fluoro), e.g., to provide a group $R^{2a}$, $R^{2b}$, $R^{2c}$, and $R^{2d}$ of formula —O$CF_3$, —S$CF_3$, —NH$CF_3$, —N($CF_3$)$_2$, or —N$CF_3R^{A2}$. In certain embodiments, at least one of $R^{A2}$ is a group of formula —$CH_2$CH(OH)$CH_2$NH$R^1$, wherein $R^1$ is as defined herein, e.g., to provide a group $R^{2a}$, $R^{2b}$, $R^{2c}$, and $R^{2d}$ of formula —O$CH_2$CH(OH)$CH_2$NH$R^1$, —S$CH_2$CH(OH)$CH_2$NH$R^1$, —NH$CH_2$CH(OH)$CH_2$NH$R^1$, or —N($R^{A2}$)$CH_2$CH(OH)$CH_2$NH$R^1$. In certain embodiments, at least one of $R^{A2}$ is alkyl substituted with an optionally substituted aryl (e.g., optionally substituted phenyl) or optionally substituted heteroaryl (e.g., optionally substituted pyridinyl), e.g., to provide a group $R^{2a}$, $R^{2b}$, $R^{2c}$, and $R^{2d}$ of formula —O(CH$_2$)$_a$Ar, —S(CH$_2$)$_a$Ar, —NH(CH$_2$)$_a$Ar, or —N(R$^{A2}$)(CH$_2$)$_a$Ar, wherein a is 1, 2, 3, 4, 5, or 6, and Ar is optionally substituted aryl (e.g., optionally substituted phenyl) or optionally substituted heteroaryl (e.g., optionally substituted pyridinyl). In certain embodiments, at least one of $R^{A2}$ is optionally substituted alkenyl, e.g., optionally substituted C$_{2-4}$ alkenyl, optionally substituted C$_{2-3}$ alkenyl, optionally substituted C$_{3-4}$alkenyl, optionally substituted C$_2$alkenyl, optionally substituted C$_3$alkenyl, or optionally substituted C$_4$alkenyl. In certain embodiments, at least one of $R^{A2}$ is optionally substituted alkynyl, e.g., optionally substituted C$_{2-4}$ alkynyl, optionally substituted C$_{2-3}$alkynyl, optionally substituted C$_{3-4}$alkynyl, optionally substituted C$_2$alkynyl, optionally substituted C$_3$alkynyl, or optionally substituted C$_4$alkynyl. In certain embodiments, at least one of $R^{A2}$ is optionally substituted carbocyclyl, e.g., optionally substituted C$_{3-5}$carbocyclyl, optionally substituted C$_{3-4}$carbocyclyl, optionally substituted C$_{4-5}$carbocyclyl, optionally substituted C$_3$carbocyclyl, optionally substituted C$_4$carbocyclyl, or optionally substituted C$_5$carbocyclyl. In certain embodiments, at least one of $R^{A2}$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{A2}$ is optionally substituted aryl (e.g., optionally substituted phenyl) or optionally substituted heteroaryl (e.g., optionally substituted pyridinyl). In certain embodiments, two $R^{A2}$ groups, e.g., of —N(R$^{A2}$)$_2$, are joined to form an optionally substituted heterocyclyl or optionally substituted heteroaryl ring.

In certain embodiments, at least one of $R^{2a}$, $R^{2b}$, $R^{2c}$, and $R^{2d}$ is hydrogen. In certain embodiments, at least two of $R^{2a}$, $R^{2b}$, $R^{2c}$, and $R^{2d}$ is hydrogen. In certain embodiments, at least three of $R^{2a}$, $R^{2b}$, $R^{2c}$, and $R^{2d}$ are hydrogen. In certain embodiments, each of $R^{2a}$, $R^{2b}$, $R^{2c}$, and $R^{2d}$ is hydrogen, e.g., to provide a compound of Formula (I-c):

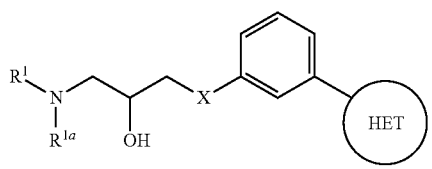

(I-c)

or a pharmaceutically acceptable salt thereof. In certain embodiments, $R^1$ is hydrogen or optionally substituted C$_{1-2}$ alkyl, e.g., methyl or ethyl. In certain embodiments of Formula (I-c), $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

However, in certain embodiments, at least one of $R^{2a}$, $R^{2b}$, $R^{2c}$, and $R^{2d}$ is a non-hydrogen group. For example, in certain embodiments, $R^{2a}$ is a non-hydrogen group. In certain embodiments, $R^{2a}$ is a non-hydrogen group, and each of $R^{2b}$, $R^{2c}$, and $R^{2d}$ is hydrogen, e.g., to provide a compound of Formula (I-d):

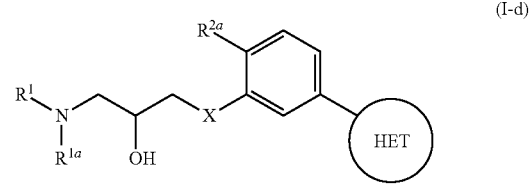

(I-d)

or a pharmaceutically acceptable salt thereof. In certain embodiments, $R^{2a}$ is a non-hydrogen group selected from the group consisting of halogen (e.g., chloro), —CN, —C(=O)R$^{A2}$, —OR$^2$, —SR$^{A2}$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein $R^{A2}$ is hydrogen, optionally substituted alkyl, or two $R^{A2}$ groups, e.g., of —N(R$^{A2}$)$_2$, are joined to form an optionally substituted heterocyclyl or optionally substituted heteroaryl ring. In certain embodiments, $R^1$ is hydrogen or optionally substituted C$_{1-2}$ alkyl, e.g., methyl or ethyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

In certain embodiments, $R^{2b}$ is a non-hydrogen group. In certain embodiments, $R^{2b}$ is a non-hydrogen group, and each of $R^{2a}$, $R^{2c}$, and $R^{2d}$ is hydrogen, e.g., to provide a compound of Formula (I-e):

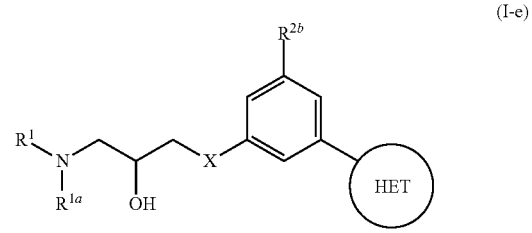

(I-e)

or a pharmaceutically acceptable salt thereof. In certain embodiments, $R^{2b}$ is a non-hydrogen group selected from the group consisting of halogen (e.g., chloro), —CN, —C(=O)R$^{A2}$, —OR$^{A2}$, —SR$^2$, —N(R$^{A2}$)$_2$, optionally substituted cyclopropyl, optionally substituted C$_{1-4}$alkyl, optionally substituted C$_{2-4}$alkenyl, and optionally substituted C$_{2-4}$alkynyl, wherein $R^{A2}$ is hydrogen, optionally substituted alkyl, or two $R^{A2}$ groups, e.g., of —N(R$^{A2}$)$_2$, are joined to form an optionally substituted heterocyclyl or optionally substituted heteroaryl ring. In certain embodiments, $R^1$ is hydrogen or optionally substituted C$_{1-2}$ alkyl, e.g., methyl or ethyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

In certain embodiments, $R^{2c}$ is a non-hydrogen group. In certain embodiments, $R^{2c}$ is a non-hydrogen group, and each of $R^{2a}$, $R^{2b}$, and $R^{2d}$ is hydrogen, e.g., to provide a compound of Formula (I-f):

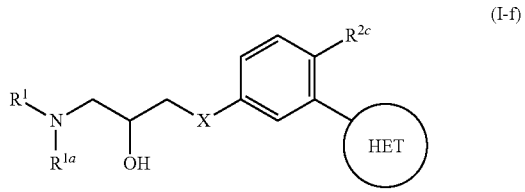

(I-f)

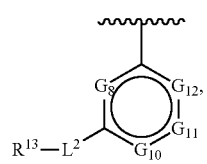

or a pharmaceutically acceptable salt thereof. In certain embodiments, $R^{2c}$ is a non-hydrogen group selected from the group consisting of halogen (e.g., chloro), —CN, —C(=O)$R^{A2}$, —O$R^2$, —SR, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$ is hydrogen, optionally substituted alkyl, or two $R^{A2}$ groups, e.g., of —N($R^{A2}$)$_2$, are joined to form an optionally substituted heterocyclyl or optionally substituted heteroaryl ring. In certain embodiments, $R^1$ is hydrogen or optionally substituted $C_{1-2}$ alkyl, e.g., methyl or ethyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

In certain embodiments, $R^{2d}$ is a non-hydrogen group. In certain embodiments, $R^{2d}$ is a non-hydrogen group, and each of $R^{2a}$, $R^{2b}$, and $R^{2c}$ is hydrogen, e.g., to provide a compound of Formula (I-g):

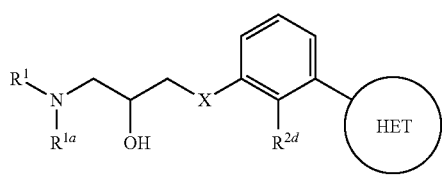

(I-g)

or a pharmaceutically acceptable salt thereof. In certain embodiments, $R^{2d}$ is a non-hydrogen group selected from the group consisting of halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$, is hydrogen, optionally substituted alkyl, or two $R^{A2}$ groups, e.g., of —N($R^{A2}$)$_2$, are joined to form an optionally substituted heterocyclyl or optionally substituted heteroaryl ring. In certain embodiments, $R^{2d}$ is not halogen, e.g., fluoro. In certain embodiments, $R^1$ is hydrogen or optionally substituted $C_{1-2}$ alkyl, e.g., methyl or ethyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

As generally understood from the present disclosure, Ring HET is a 6-membered monocyclic heteroaryl ring system of Formula:

i.e., to provide a compound of Formula (I-h):

(I-h)

or pharmaceutically acceptable salt thereof, wherein at least one instance of $G_8$, $G_{10}$, $G_{11}$, or $G_{12}$ is N, e.g., at least one, two, or three instances of $G_8$, $G_{10}$, $G_{11}$, or $G_{12}$ are N. In certain embodiments, $G_8$ is N. In certain embodiments, $G_{10}$ is N. In certain embodiments, $G_{11}$ is N. In certain embodiments, $G_{12}$ is N. In certain embodiments, two instances of $G_8$, $G_{10}$, $G_{11}$, or $G_{12}$ are N. In certain embodiments, $G_8$ and $G_{10}$ are both N. In certain embodiments, $G_8$ and $G_{11}$ are both N. However, in certain embodiments, $G_8$ and $G_{11}$ are not both N. In certain embodiments, $G_8$ and $G_{12}$ are both N. In certain embodiments, $G_{10}$ and $G_{12}$ are both N. In certain embodiments, three instances of $G_8$, $G_{10}$, $G_{11}$, or $G_{12}$ are N. In certain embodiments, $G_8$, $G_{10}$, and $G_{12}$ are each N. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, X is —O—.

Exemplary Ring HET groups of the formula (i), (ii), or (iii), include, but are not limited to, any one of the following ring systems, wherein one, two, or three instances of $G_8$, $G_{10}$, $G_{11}$, and $G_{12}$ are N:

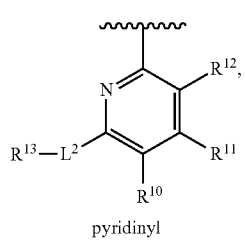

(i-a)

pyridinyl

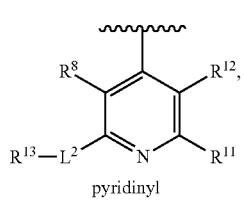

(i-b)

pyridinyl

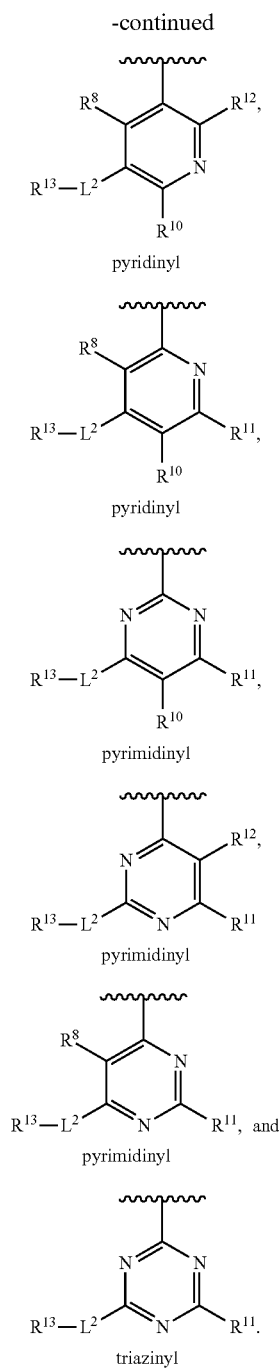

pyridinyl pyridinyl pyrimidinyl pyrimidinyl pyrimidinyl triazinyl

Furthermore, as generally defined above, each instance of $R^8$, $R^{10}$, $R^{11}$, and $R^{12}$ is independently selected from the group consisting of hydrogen, halo, —CN, —NO$_2$, —C(=O)R', —C(=O)OR', —C(=O)N(R')$_2$, optionally substituted alkyl, optionally substituted $C_{3-4}$cycloalkyl, or -L$^1$-R$^3$; wherein L$^1$, R$^3$, and R$^1$ are as defined herein.

In certain embodiments, one of $R^8$, $R^{10}$, $R^{11}$, and $R^{12}$ is -L$^1$-R$^3$. Alternatively, neither $R^8$, $R^{10}$, $R^{11}$, and $R^{12}$ is -L$^1$-R$^3$. In certain embodiments, $R^8$ is -L$^1$-R$^3$. In certain embodiments, $R^{10}$ is -L$^1$-R$^3$. In certain embodiments, $R^{11}$ is -L$^1$-R$^3$. In certain embodiments, $R^{12}$ is -L$^1$-R$^3$. In certain embodiments, one instance of $R^8$, $R^{10}$, $R^{11}$, and $R^{12}$ is a -L$^1$-R$^3$, and the other instances (i.e., one or two instances) are hydrogen or a non-hydrogen moiety selected from the group consisting of halo, —CN, —NO$_2$, —C(=O)R', —C(=O)OR', —C(=O)N(R')$_2$, or optionally substituted alkyl. For example, in certain embodiments, at least one instance of $R^8$, $R^{10}$, $R^{11}$, and $R^{12}$ is halo, e.g., fluoro, chloro, bromo, or iodo. In certain embodiments, at least one instance of $R^8$, $R^{10}$, $R^{11}$, and $R^{12}$ is —CN. In certain embodiments, at least one instance of $R^8$, $R^{10}$, $R^{11}$, and $R^{12}$ is NO$_2$. In certain embodiments, at least one instance of $R^8$, $R^{10}$, $R^{11}$, and $R^{12}$ is —C(=O)R', —C(=O)OR', or —C(=O)N(R')$_2$, wherein R$^1$ is as defined herein. In certain embodiments, at least one instance of $R^8$, $R^{10}$, $R^{11}$, and $R^{12}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. In certain embodiments, at least one instance of $R^8$, $R^{10}$, $R^{11}$, and $R^{12}$ is haloalkyl, e.g., alkyl substituted with 1 or more halogen atoms, e.g., 1, 2, 3, 4, 5, or 6 halogen atoms as valency permits. In certain embodiments, at least one instance of $R^8$, $R^{10}$, $R^{11}$, and $R^{12}$ is fluoro alkyl, in which the alkyl chain is substituted with one, two, or three fluoro groups. In certain embodiments, at least one instance of $R^8$, $R^{10}$, $R^{11}$, and $R^{12}$ is trifluoromethyl (—CF$_3$). In certain embodiments, at least one instance of $R^8$, $R^{10}$, $R^{11}$, and $R^{12}$ is difluoromethyl (—CHF$_2$). In certain embodiments, at least one instance of $R^8$, $R^{10}$, $R^{11}$, and $R^{12}$ is fluoromethyl (—CH$_2$F). In certain embodiments, at least one instance of $R^8$, $R^{10}$, $R^{11}$, and $R^{12}$ is alkyl substituted by hydroxyl or substituted hydroxyl, e.g., in certain embodiments, at least one instance of $R^8$, $R^{10}$, $R^{11}$, and $R^{12}$ is —CH$_2$OH. In certain embodiments, at least one instance of $R^8$, $R^{10}$, $R^{11}$, and $R^{12}$ is methyl. In certain embodiments, at least one instance of $R^8$, $R^{10}$, $R^{11}$, and $R^{12}$ is optionally substituted $C_{3-4}$cycloalkyl; e.g., optionally substituted cyclopropyl or optionally substituted cyclobutyl. In certain embodiments, each instance of $R^8$, $R^{10}$, $R^{11}$, and $R^{12}$ is hydrogen. In certain embodiments, at least one instance of $R^8$, $R^{10}$, $R^{11}$, and $R^{12}$ is hydrogen or methyl.

As understood from the present disclosure, Ring HET optionally comprises a group -L$^1$-R$^3$ attached thereto. In certain embodiments, Ring HET does not comprise a group of formula -L$^1$-R$^3$ attached thereto, but in other embodiments, Ring HET does comprise a group of formula -L$^1$-R$^3$ attached thereto. In certain embodiments, -L$^1$-R$^3$ is meta to the point of attachment of Ring HET to the parent moiety. In certain embodiments, -L$^1$-R$^3$ is meta to-L$^2$-R$^{13}$. In certain embodiments, R$^3$ is an acyclic moiety selected from the group consisting of hydrogen, optionally substituted alkyl, optionally substituted alkenyl, or optionally substituted alkynyl. In certain embodiments, R$^3$ is a cyclic moiety selected from the group consisting of optionally substituted carbocyclyl, optionally substituted heterocyclyl, optionally substituted aryl, and optionally substituted heteroaryl. In certain embodiments, R$^3$ is directly attached to the Ring HET, i.e., wherein L$^1$ is a bond, provided that R$^3$ is not also hydrogen. In other embodiments, R$^3$ is indirectly attached to Ring HET, i.e., wherein L$^1$ is a linking group.

As generally defined herein, L$^1$ is a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^1$)— is optionally and independently present between two carbon atoms of the hydrocarbon chain, and optionally and independently present at one or both ends of the hydrocarbon chain. It is understood that the linker joining R$^3$ to Ring HET may comprise one or more of the above recited moieties in combination to form the group L$^1$.

In certain embodiments, L$^1$ is a bond. In certain embodiments, L$^1$ is a bond, and R$^3$ is optionally substituted alkyl, optionally substituted alkenyl, or optionally substituted alkynyl. In certain embodiments, L$^1$ is a bond, and R$^3$ is optionally substituted carbocyclyl, optionally substituted heterocyclyl, optionally substituted aryl, and optionally substituted heteroaryl. However, in certain embodiments, when L$^1$ is a bond, R$^3$ is not optionally substituted phenyl.

In certain embodiments, L$^1$ is —O—. In certain embodiments, L$^1$ is —N(R$^L$)—. However, in certain embodiments, L$^1$ is not —N(R$^L$)— wherein R$^L$ and R$^3$ are each hydrogen. In certain embodiments, L$^1$ is —S—. In certain embodiments, L$^1$ is —C(O)—. In certain embodiments, L$^1$ is —C(O)O—. In certain embodiments, L$^1$ is —C(O)S—. In certain embodiments, L$^1$ is —C(O)N(R$^L$)—. In certain embodiments, L$^1$ is —C(O)N(R$^L$)N(R$^L$)—. In certain embodiments, L$^1$ is —OC(O)—. In certain embodiments, L$^1$ is —OC(O)N(R$^L$)—. In certain embodiments, L$^1$ is —NR$^L$C(O)—. In certain embodiments, L$^1$ is —NR$^L$C(O)N(R$^L$). In certain embodiments, L$^1$ is —NR$^L$C(O)N(R$^L$)N(R$^L$)—. In certain embodiments, L$^1$ is —NR$^L$C(O)O—. In certain embodiments, L$^1$ is —SC(O)—. In certain embodiments, L$^1$ is C(=NR$^L$). In certain embodiments, L$^1$ is C(=NNR$^L$). In certain embodiments, L$^1$ is C(=NOR$^L$)—. In certain embodiments, L$^1$ is —C(=N R$^L$)N(R$^L$)—. In certain embodiments, L$^1$ is —NR$^L$C(=NR$^L$)—. In certain embodiments, L$^1$ is —C(S)—. In certain embodiments, L$^1$ is —C(S)N(R$^L$)—. In certain embodiments, L$^1$ is —NR$^L$C(S)—. In certain embodiments, L$^1$ is —S(O)—. In certain embodiments, L$^1$ is —OS(O)$_2$—. In certain embodiments, L$^1$ is —S(O)$_2$O—. In certain embodiments, L$^1$ is —SO$_2$—. In certain embodiments, L$^1$ is —N(R$^L$)SO$_2$—. In certain embodiments, L$^1$ is —SO$_2$N(R$^L$)—. In certain embodiments, L$^1$ is —N(R$^L$)SO$_2$N(R$^L$)—.

In certain embodiments, L$^1$ is an optionally substituted C$_{1-10}$ saturated or unsaturated hydrocarbon chain, e.g., in certain embodiments, L$^1$ is an optionally substituted C$_{1-10}$ alkyl chain, L$^1$ is an optionally substituted C$_{2-10}$ alkenyl chain, or L$^1$ is an optionally substituted C$_{2-10}$ alkynyl chain. In certain embodiments, L$^1$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain. In certain embodiments, L$^1$ is an unsubstituted C$_{1-10}$ n-alkyl chain of the formula —(CH$_2$)$_x$, wherein x is 1, 2, 3, 4, 5, 6, 7, 8, 9, or 10. In certain embodiments, L$^1$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain. In certain embodiments, L$^1$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain.

In certain embodiments, L$^1$ is an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, or —N(R$^L$)SO$_2$N(R$^L$)— independently present between two carbon atoms of the hydrocarbon chain, or present at one or both ends of the hydrocarbon chain. In this instance, in certain embodiments, L$^1$ is a chain of at least 2 atoms, e.g., L$^1$ is a chain comprising 1 to 10 carbon atoms (e.g., 1, 2, 3, 4, 5, 6, 7, 8, 9, or 10 carbon atoms), and 1 or more of the above recited moieties (e.g., 1, 2, 3, or more), to provide a chain of between 2 and 20 atoms, inclusive, e.g., 2, 3, 4, 5, 6, 7, 8, 9, 10, 11, 12, 13, 14, 15, 16, 17, 18, 19, or 20 chain atoms. In certain embodiments, a moiety is present between two carbon atoms of the hydrocarbon chain. In certain embodiments, a moiety is present at one end of the hydrocarbon chain. In certain embodiments, a moiety is independently present at each end of the hydrocarbon chain. In certain embodiments, L$^1$ is an optionally substituted C$_{1-10}$ alkyl chain, L$^1$ is an optionally substituted C$_{2-10}$ alkenyl chain, or L$^1$ is an optionally substituted C$_{2-10}$ alkynyl chain comprising one or more of the above recited moieties independently present between two carbon atoms of the hydrocarbon chain, or present at one or both ends of the hydrocarbon chain. In certain embodiments, L$^1$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain, comprising one or more of the above recited moieties independently present between two carbon atoms of the hydrocarbon chain, or present at one or both ends of the hydrocarbon chain. In certain embodiments, L$^1$ is an unsubstituted C$_{1-10}$ n-alkyl chain of the formula —(CH$_2$)$_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, L$^1$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain, comprising one or more of the above recited moieties independently present between two carbon atoms of the hydrocarbon chain, or present at one or both ends of the hydrocarbon chain. In certain embodiments, L$^1$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain, comprising one or more of the above recited moieties independently present between two carbon atoms of the hydrocarbon chain, or present at one or both ends of the hydrocarbon chain.

As described above, in certain embodiments, $L^1$ is an unsubstituted $C_{1-10}$n-alkyl chain of the formula —$(CH_2)_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^1$ is —O—$(CH_2)_x$—, —$(CH_2)_x$—O—, or —O—$(CH_2)_x$—O—. In certain embodiments, $L^1$ is —N($R^L$)—$(CH_2)_x$—, —$(CH_2)_x$—N($R^L$)—, —N($R^L$)—$(CH_2)_x$—N($R^L$)—, —O—$(CH_2)_x$—N($R^L$)—, —N($R^L$)—$(CH_2)_x$—O—, —$NR^L$—$(CH_2)_x$—C(O)O—, or —OC(O)—$(CH_2)_x$—N($R^L$)—. In certain embodiments, $L^1$ is —S—$(CH_2)_x$— or —$(CH_2)_x$—S—. In certain embodiments, $L^1$ is —C(O)—$(CH_2)_x$— or —$(CH_2)_x$—C(O)—. In certain embodiments, $L^1$ is —C(O)O—$(CH_2)_x$— or —$(CH_2)_x$—C(O)O—. In certain embodiments, $L^1$ is —C(O)S—$(CH_2)_x$— or —$(CH_2)_x$—C(O)S—. In certain embodiments, $L^1$ is —C(O)N($R^L$)—$(CH_2)_x$— or —$(CH_2)_x$—C(O)N($R^L$)—. In certain embodiments, $L^1$ is —C(O)N($R^L$)N($R^L$)—$(CH_2)_x$— or —$(CH_2)_x$—C(O)N($R^L$)N($R^L$)—. In certain embodiments, $L^1$ is —OC(O)—$(CH_2)_x$— or —$(CH_2)_x$—OC(O)—. In certain embodiments, $L^1$ is —OC(O)N($R^L$)—$(CH_2)_x$— or —$(CH_2)_x$—OC(O)N($R^L$)—. In certain embodiments, $L^1$ is —$NR^LC(O)$—$(CH_2)_x$— or —$(CH_2)_x$—$NR^LC(O)$—. In certain embodiments, $L^1$ is —$NR^LC(O)N(R^L)$—$(CH_2)_x$— or —$(CH_2)_x$—$NR^LC(O)N(R^L)$—. In certain embodiments, $L^1$ is —$NR^LC(O)N(R^L)N(R^L)$—$(CH_2)_x$— or —$(CH_2)_x$—$NR^LC(O)N(R^L)N(R^L)$—. In certain embodiments, $L^1$ is —$NR^LC(O)O$—$(CH_2)_x$— or —$(CH_2)_x$—$NR^LC(O)O$—. In certain embodiments, $L^1$ is —SC(O)—$(CH_2)_x$— or —$(CH_2)_x$—SC(O)—. In certain embodiments, $L^1$ is —C(=$NR^L$)—$(CH_2)_x$— or —$(CH_2)_x$—C(=$NR^L$)—. In certain embodiments, $L^1$ is —C(=$NNR^L$)—$(CH_2)_x$— or —$(CH_2)_x$—C(=$NNR^L$)—. In certain embodiments, $L^1$ is —C(=$NOR^L$)—$(CH_2)_x$— or —$(CH_2)_x$—C(=$NOR^L$)—. In certain embodiments, $L^1$ is —C(=N $R^L$)N($R^L$)—$(CH_2)_x$— or —$(CH_2)_x$—C(=N $R^L$)N($R^L$)—. In certain embodiments, $L^1$ is —NR C(=$NR^1$)—$(CH_2)_x$— or —$(CH_2)_x$—$NR^LC$(=$NR^L$)—. In certain embodiments, $L^1$ is —C(S)—$(CH_2)_x$— or —$(CH_2)_x$—C(S)—. In certain embodiments, $L^1$ is —C(S)N($R^L$)—$(CH_2)_x$— or —$(CH_2)_x$—C(S)N($R^L$)—. In certain embodiments, $L^1$ is —$NR^LC(S)$—$(CH_2)_x$— or —$(CH_2)_x$—$NR^LC(S)$—. In certain embodiments, $L^1$ is —S(O)—$(CH_2)_x$— or —$(CH_2)_x$—S(O)—. In certain embodiments, $L^1$ is —OS(O)$_2$—$(CH_2)_x$— or —$(CH_2)_x$—OS(O)$_2$—. In certain embodiments, $L^1$ is —S(O)$_2$O—$(CH_2)_x$— or —$(CH_2)_x$—S(O)$_2$O—. In certain embodiments, $L^1$ is —SO$_2$—$(CH_2)_x$— or —$(CH_2)_x$—SO$_2$—. In certain embodiments, $L^1$ is —N($R^L$)SO$_2$—$(CH_2)_x$— or —$(CH_2)_x$—N($R^L$)SO$_2$—. In certain embodiments, $L^1$ is —SO$_2$N($R^L$)—$(CH_2)_x$— or —$(CH_2)$—SO$_2$N($R^L$)—. In certain embodiments, $L^1$ is —N($R^L$)SO$_2$N($R^L$)—$(CH_2)_x$— or —$(CH_2)_x$—N($R^L$)SO$_2$N($R^L$)—. In certain embodiments, $L^1$ is a bond, —N($R^L$)—, —$NR^LC(O)O$—, —$NR^LC(O)N(R^L)$—, —N($R^L$)—, —N($R^L$)SO$_2$N($R^L$)—, —$NR^L$—$(CH_2)_x$—C(O)O—, —$NR^L$—$(CH_2)_x$—O—, —$NR^LC(O)N(R^L)$—, —$NR^L$—$(CH_2)_x$—, —$(CH_2)_x$—$NR^L$—, —$NR^LC(O)O(CH_2)_x$—, —$NR^LC(O)NR^L(CH_2)_x$—, or —$NR^L(CH_2)_xN$-$R^LC(O)$—.

In certain embodiments, $R^3$ is an acyclic moiety selected from the group consisting of hydrogen, optionally substituted alkyl, optionally substituted alkenyl, and optionally substituted alkynyl. In certain embodiments, $R^3$ is hydrogen, e.g., for example, when $L^1$ is —N($R^L$)— or —$NR^L$—$(CH_2)_x$—$NR^L$—. In certain embodiments, $R^3$ is optionally substituted alkyl, e.g., for example, when $L^1$ is —$NR^LC(O)$O—, —$NR^LC(O)N(R^L)$—, —N($R^L$)—, —N($R^L$)SO$_2$N($R^L$)—, —$NR^L$—$(CH_2)_x$—C(O)O—, or —$NR^L$—$(CH_2)_x$—O—. In certain embodiments, $R^3$ is optionally substituted $C_{1-6}$ alkyl, e.g., optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^3$ $C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, $R^3$ is alkyl substituted with —CN, e.g., —$(CH_2)_y$CN, wherein y is 1, 2, 3, 4, 5, or 6. In certain embodiments, $R^3$ is alkyl substituted with hydroxy or substituted hydroxy, e.g., —$(CH_2)_y$OCH$_3$, wherein y is 1, 2, 3, 4, 5, or 6. In certain embodiments, $R^3$ is alkyl substituted with amino or substituted substituted amino, e.g., —$(CH_2)_y$NH$_2$, wherein y is 1, 2, 3, 4, 5, or 6. In certain embodiments, $R^3$ is optionally substituted alkenyl, e.g., for example, when $L^1$ is a bond. In certain embodiments, $R^3$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^3$ is optionally substituted $C_2$alkenyl or $C_3$alkenyl, e.g., optionally substituted vinyl or optionally substituted allyl. In certain embodiments, $R^3$ is optionally substituted alkynyl, e.g., for example, when $L^1$ is a bond. In certain embodiments, $R^3$ is optionally substituted $C_{2-4}$ alkynyl, e.g., optionally substituted $C_{2-3}$ alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^3$ is optionally substituted $C_2$alkynyl, e.g., optionally substituted acetylene.

Alternatively, in certain embodiments, $R^3$ is a cyclic moiety selected from the group consisting of optionally substituted carbocyclyl, optionally substituted heterocyclyl, optionally substituted aryl, and optionally substituted heteroaryl. It is understood that the $R^3$ cyclic moiety may be monocyclic or polycyclic (e.g., bicyclic or tricyclic). In certain embodiments, $R^3$ is a monocyclic optionally substituted carbocyclyl, monocyclic optionally substituted heterocyclyl, monocyclic optionally substituted aryl, or monocylic optionally substituted heteroaryl. In certain embodiments, $R^3$ is a bicyclic optionally substituted carbocyclyl, bicyclic optionally substituted heterocyclyl, bicyclic optionally substituted aryl, or bicyclic optionally substituted heteroaryl.

In certain embodiments, $R^3$ is an optionally substituted monocyclic or bicyclic carbocyclyl, e.g., an optionally substituted $C_{3-10}$ carbocyclyl, optionally substituted $C_{3-9}$ carbocyclyl, optionally substituted $C_{3-8}$ carbocyclyl, optionally substituted $C_{3-7}$ carbocyclyl, optionally substituted $C_{3-6}$ carbocyclyl, optionally substituted $C_{3-4}$carbocyclyl, optionally substituted $C_{5-10}$ carbocyclyl, optionally substituted $C_3$ carbocyclyl, optionally substituted $C_4$ carbocyclyl, optionally substituted $C_5$ carbocyclyl, optionally substituted $C_6$ carbocyclyl, optionally substituted $C_7$ carbocyclyl, optionally substituted $C_8$ carbocyclyl, optionally substituted $C_9$ carbocyclyl, or optionally substituted $C_{10}$ carbocyclyl. In certain embodiments, $R^3$ is an optionally substituted cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), or spiro[4.5]decanyl ($C_{10}$) ring.

In certain embodiments, $R^3$ is an optionally substituted monocyclic or bicyclic heterocyclyl, e.g., an optionally substituted 3- to 10-membered heterocyclyl, 3- to 8-membered heterocyclyl, 3- to 6-membered heterocyclyl, 3- to 5-membered heterocyclyl, 3-to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl. In certain embodiments, $R^3$ is an optionally substituted aziridinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolidin-2-one, pyrrolyl-2,5-dione, dioxolanyl, oxasulfuranyl, disulfuranyl, oxazolidin-2-one, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, benzoxazolinonyl, tetrahydroquinolinyl, tetrahydroisoquinolinyl, furo[2,3-b]furanyl, 2,3-dihydro-1,4-dioxinyl, 3-oxa-8-azabicyclo[3.2.1]octanyl, or 8-oxa-3-azabicyclo[3.2.1]octanyl ring.

In certain embodiments, $R^3$ is an optionally substituted monocyclic or bicyclic aryl, e.g., an optionally substituted phenyl, or optionally substituted naphthyl ring.

In certain embodiments, $R^3$ is an optionally substituted monocyclic or bicyclic heteroaryl, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, $R^3$ is an optionally substituted pyrrolyl, furanyl, thiophenyl, imidazolyl, pyrazolyl, oxazolyl, isoxazolyl, thiazolyl, isothiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, or quinazolinyl ring.

In certain embodiments, $R^3$ is an optionally substituted spiro-fused heterocyclic ring system, e.g., comprising an optionally substituted heterocyclic ring spiro fused to an optionally substituted carbocyclic or optionally substituted heterocyclic ring, wherein the point of attachment is either on the heterocylic or carbocyclic ring. In certain embodiments, $R^3$ is an optionally substituted 3,4-spiro-fused heterocyclic ring system, e.g., wherein the point of attachment is either on the 3- or 4-membered ring. In certain embodiments, $R^3$ is an optionally substituted 3,5-spiro-fused heterocyclic ring system, e.g., wherein the point of attachment is either on the 3- or 5-membered ring. In certain embodiments, $R^3$ is an optionally substituted 3,6-spiro-fused heterocyclic ring system, e.g., wherein the point of attachment is either on the 3- or 6-membered ring. In certain embodiments, $R^3$ is an optionally substituted 4,4-spiro-fused heterocyclic ring system. In certain embodiments, $R^3$ is an optionally substituted 4,5-spiro-fused heterocyclic ring system, e.g., wherein the point of attachment is either on the 4- or 5-membered ring. In certain embodiments, $R^3$ is an optionally substituted 4,6-spiro-fused heterocyclic ring system, e.g., wherein the point of attachment is either on the 4- or 6-membered ring. In certain embodiments, $R^3$ is an optionally substituted 5,5-spiro-fused heterocyclic ring system. In certain embodiments, $R^3$ is an optionally substituted 5,6-spiro-fused heterocyclic ring system, e.g., wherein the point of attachment is either on the 5- or 6-membered ring. In certain embodiments, $R^3$ is an optionally substituted 6,6-spiro-fused heterocyclic ring system. In any of the above embodiments, $R^3$ is an N-linked, optionally substituted spiro-fused heterocyclic ring system, i.e., wherein the point of attachment is on a nitrogen atom. Alternatively, in any of the above embodiments, $R^3$ is an C-linked, optionally substituted spiro-fused heterocyclic ring system, i.e., wherein the point of attachment is on a carbon atom.

In certain embodiments, $R^3$ is an optionally substituted ortho-fused heterocyclic ring system, e.g., comprising an optionally substituted heterocyclic ring ortho fused to an optionally substituted carbocyclic or optionally substituted heterocyclic ring wherein the point of attachment is either on the heterocylic or carbocyclic ring or comprising an optionally substituted heterocyclic ring ortho fused to an optionally substituted aryl or optionally substituted heteroaryl ring, wherein the point of attachment is on the heterocylic ring. In certain embodiments, $R^3$ is an optionally substituted 3,4-ortho-fused heterocyclic ring system, e.g., wherein the point of attachment is either on the 3- or 4-membered ring. In certain embodiments, $R^3$ is an optionally substituted 3,5-ortho-fused heterocyclic ring system, e.g., wherein the point of attachment is either on the 3- or 5-membered ring. In certain embodiments, $R^3$ is an optionally substituted 3,6-ortho-fused heterocyclic ring system, e.g., wherein the point of attachment is either on the 3- or 6-membered ring. In certain embodiments, $R^3$ is an optionally substituted 4,4-ortho-fused heterocyclic ring system. In certain embodiments, $R^3$ is an optionally substituted 4,5-ortho-fused heterocyclic ring system, e.g., wherein the point of attachment is either on the 4- or 5-membered ring. In certain embodiments, $R^3$ is an optionally substituted 4,6-ortho-fused heterocyclic ring system, e.g., wherein the point of attachment is either on the 4- or 6-membered ring. In certain embodiments, $R^3$ is an optionally substituted 5,5-ortho-fused heterocyclic ring system. In certain embodiments, $R^3$ is an optionally substituted 5,6-ortho-fused heterocyclic ring system, e.g., wherein the point of attachment is either on the 5- or 6-membered ring. In certain embodiments, $R^3$ is an optionally substituted 6,6-ortho-fused heterocyclic ring system. In any of the above embodiments, $R^3$ is an N-linked, optionally substituted ortho-fused heterocyclic ring system, i.e., wherein the point of attachment is on a nitrogen atom. Alternatively, in any of the above embodiments, $R^3$ is an C-linked, optionally substituted ortho-fused heterocyclic ring system, i.e., wherein the point of attachment is on a carbon atom.

In certain embodiments, $R^3$ is an optionally substituted ortho-fused heteroaryl ring system, e.g., comprising an optionally substituted heteroaryl ring ortho fused to an optionally substituted carbocyclic or optionally substituted heterocyclic ring wherein the point of attachment is on the heteroaryl ring or comprising an optionally substituted heteroaryl ring ortho fused to an optionally substituted aryl or optionally substituted heteroaryl ring, wherein the point of attachment is either on the aryl ring or heteroaryl ring. In certain embodiments, the $R^3$ heteroaryl ring ortho fused to an optionally substituted carbocyclic or optionally substituted heterocyclic ring is a 5-membered heteroaryl ring, e.g., to provide a 3,5-, 4,5-, 5,5-, or 6,5-ortho fused ring system. In certain embodiments, the $R^3$ heteroaryl ring ortho fused to an optionally substituted carbocyclic or optionally substituted heterocyclic ring is a 6-membered heteroaryl ring, e.g., to provide a 3,6-, 4,6-, 5,6-, or 6,6-ortho fused ring system. In certain embodiments, the $R^3$ optionally substituted heteroaryl ring ortho fused to an optionally substituted aryl ring is a 5-membered heteroaryl ring, e.g., to provide a 5,6-ortho fused ring system. In certain embodiments, the $R^3$ optionally substituted heteroaryl ring ortho fused to an optionally substituted aryl ring is a 6-membered heteroaryl ring, e.g., to provide a 6,6-fused ring system. In certain embodiments, the $R^3$ optionally substituted heteroaryl ring ortho fused to an optionally heteroaryl ring is a 5-membered heteroaryl ring, e.g., to provide a 6,5- or 5,5-fused ring system. In certain embodiments, the $R^3$ optionally substituted heteroaryl ring ortho fused to an optionally heteroaryl ring is a 6-membered heteroaryl ring, e.g., to provide a 6,5- or 5,5-fused ring system. In any of the above embodiments, $R^3$ is an N-linked, optionally substituted ortho-fused heteroaryl ring system, i.e., wherein the point of attachment is on a nitrogen atom. Alternatively, in any of the above embodiments, $R^3$ is an C-linked, optionally substituted ortho-fused heteroaryl ring system, i.e., wherein the point of attachment is on a carbon atom.

In certain embodiments, $R^3$ is an optionally substituted ortho-fused aryl ring system, e.g., comprising an optionally substituted 6-membered aryl ring ortho fused to an optionally substituted carbocyclic or optionally substituted heterocyclic ring wherein the point of attachment is on the aryl ring, e.g., to provide a 3,6-, 4,6-, 5,6-, or 6,6-ortho fused ring system. In certain embodiments, $R^3$ is an optionally substituted ortho-fused aryl ring system, e.g., comprising an optionally substituted 6-membered aryl ring ortho fused to an optionally substituted 6-membered aryl ring.

In certain embodiments, $R^3$ is a cyclic moiety selected from the group consisting of

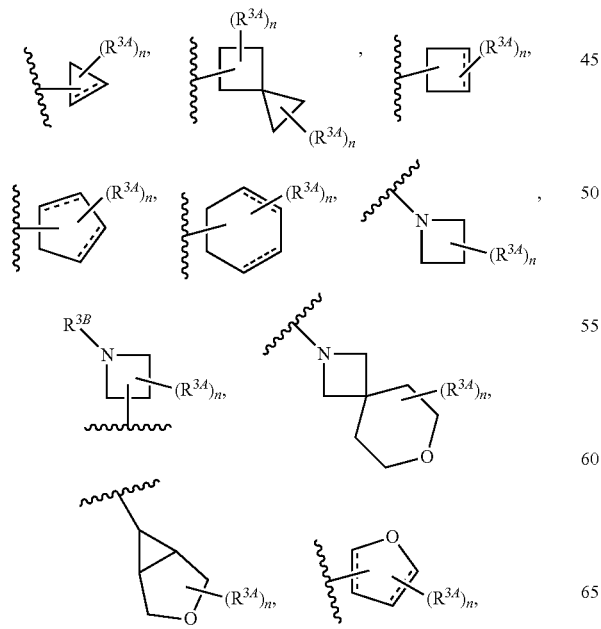

-continued

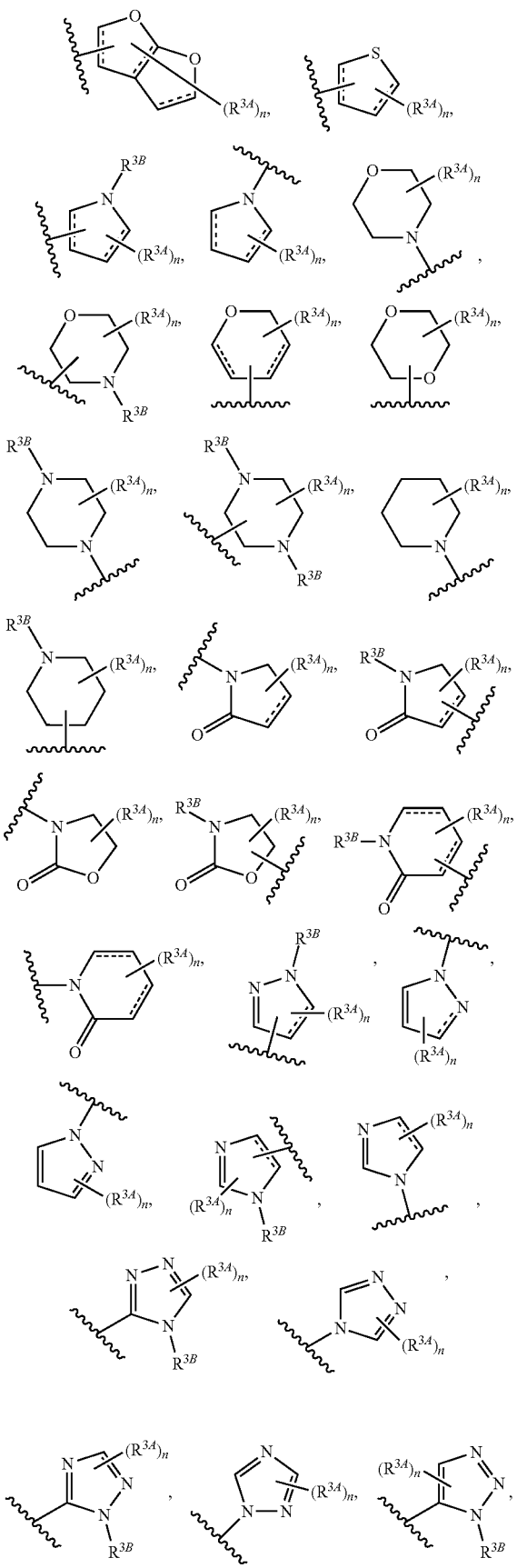

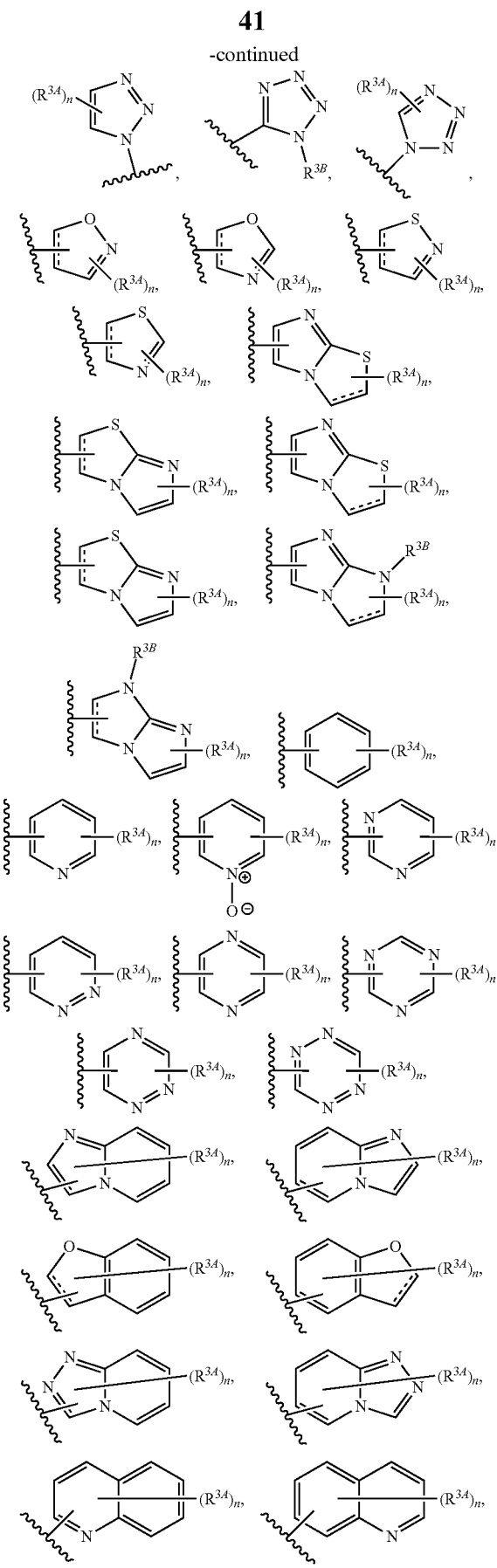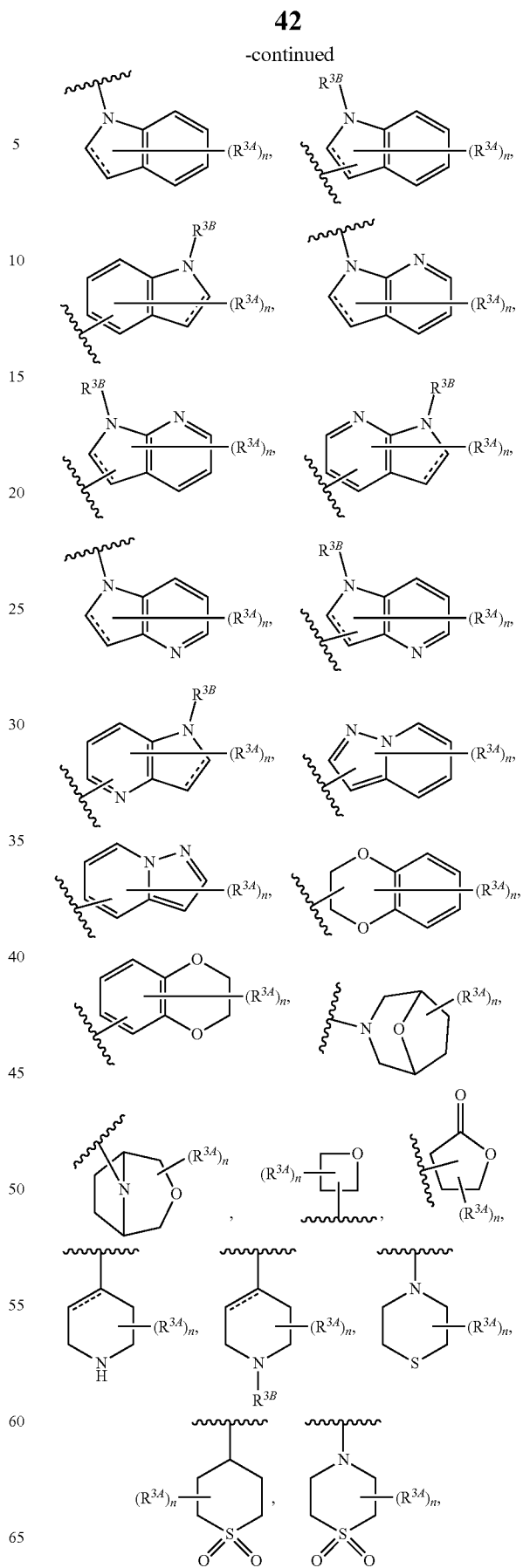

-continued
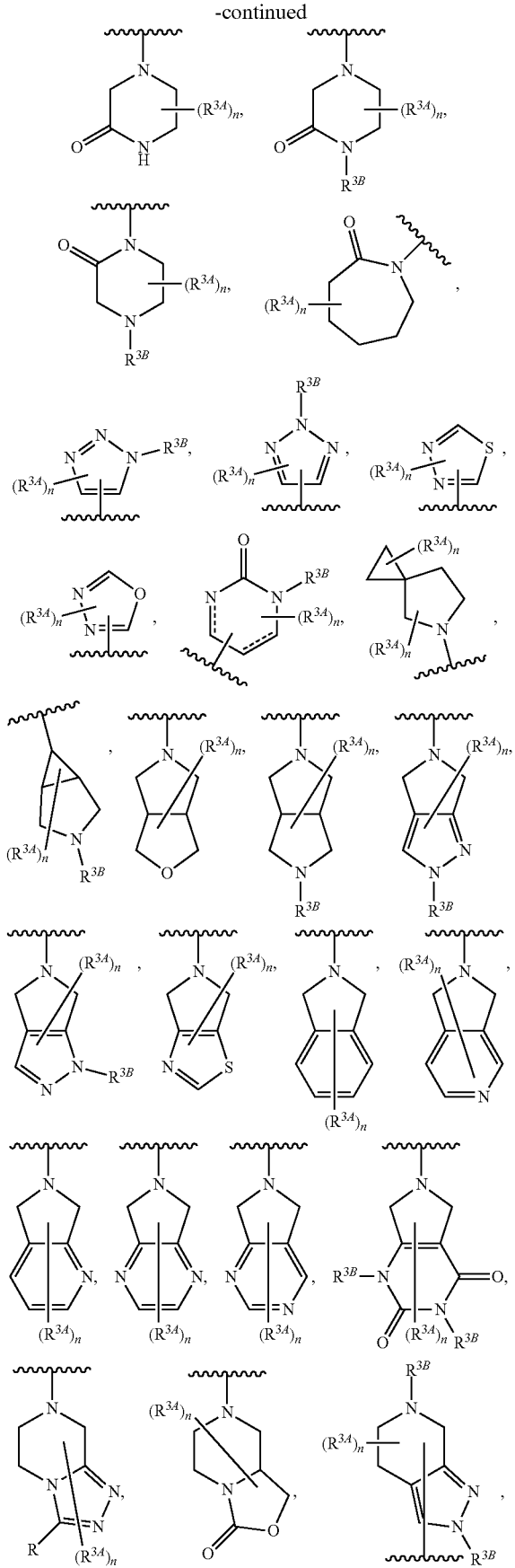
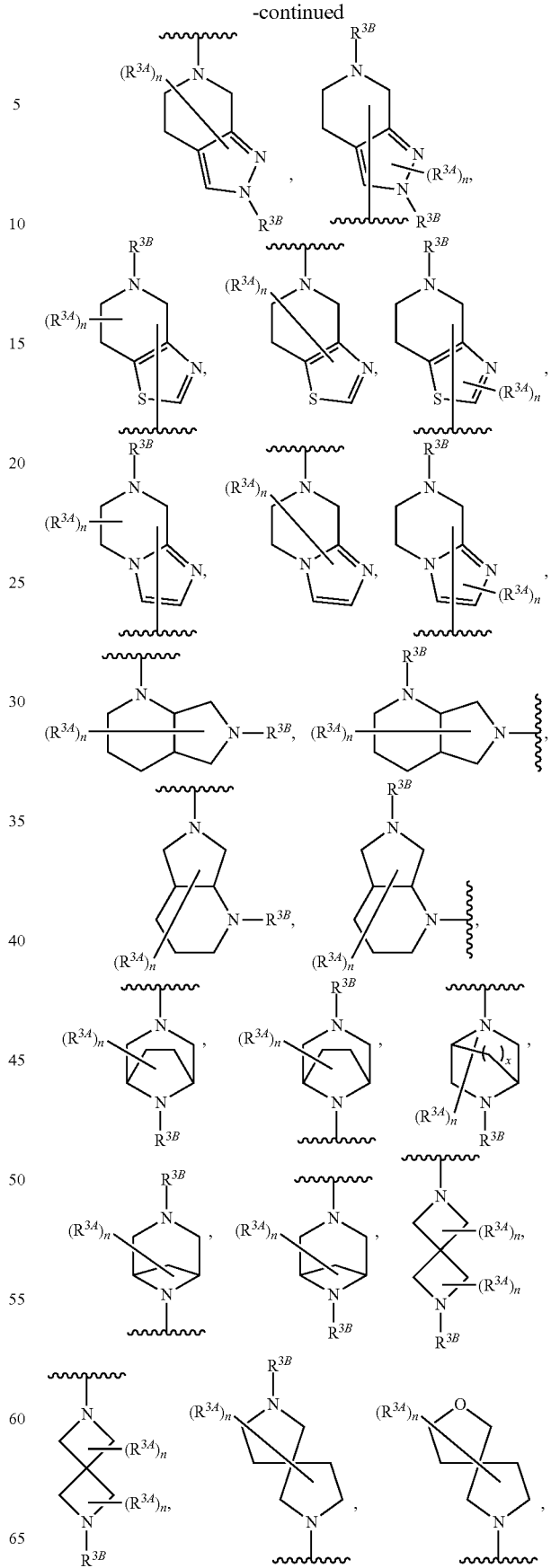

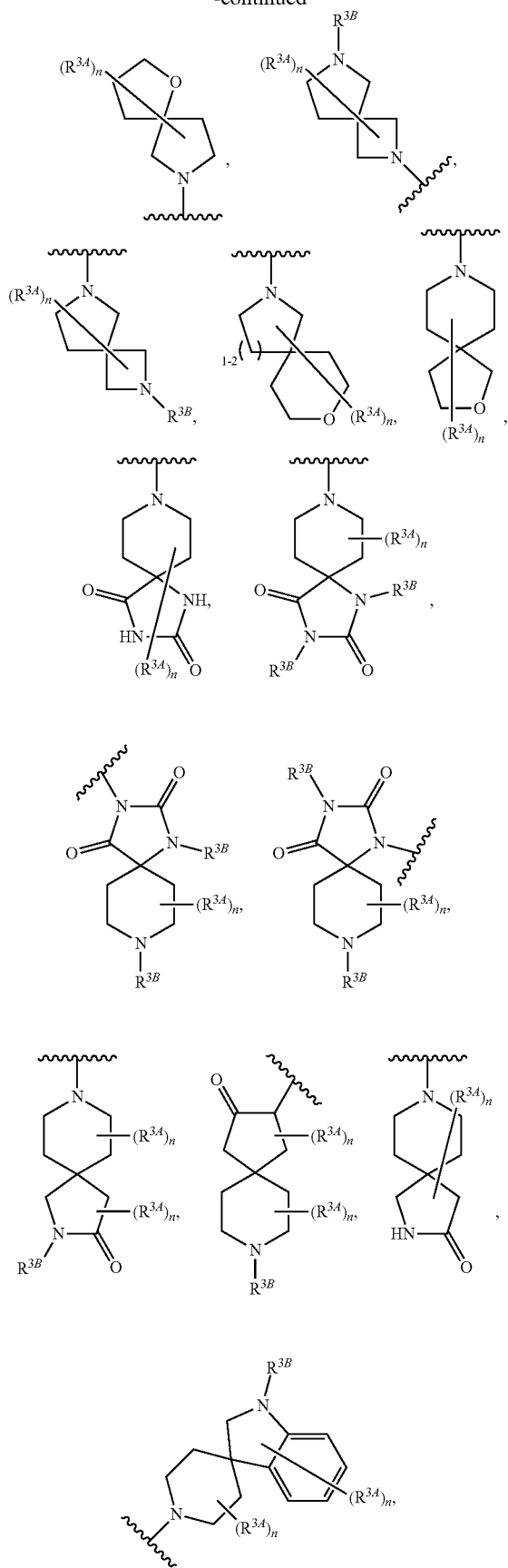
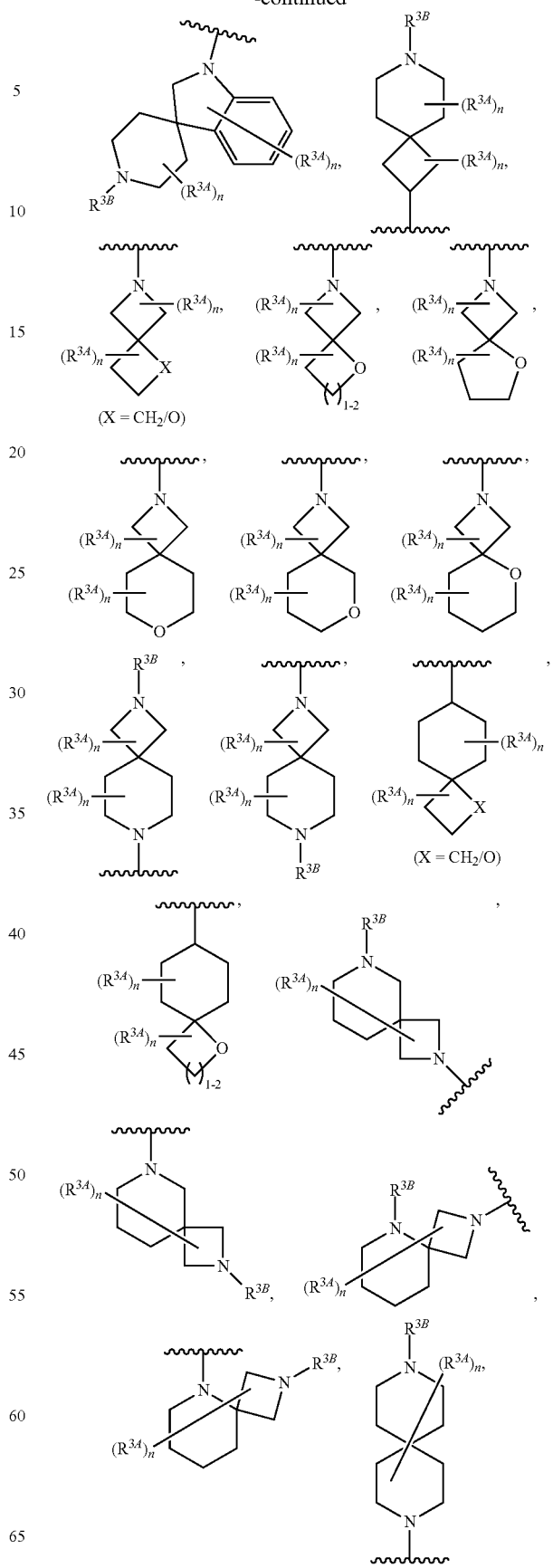

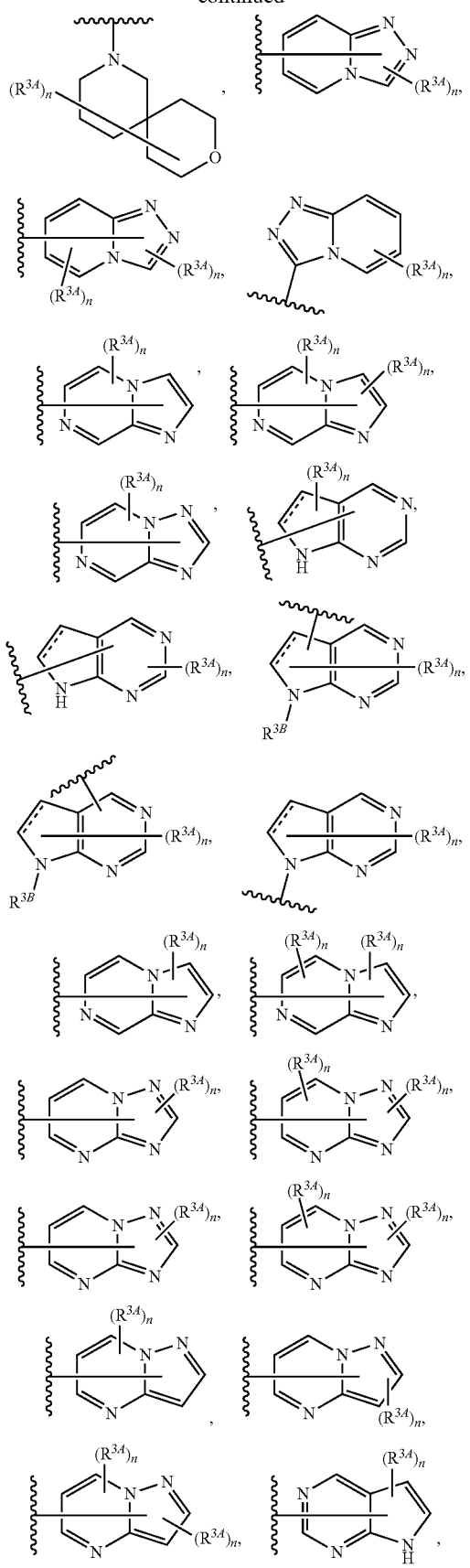
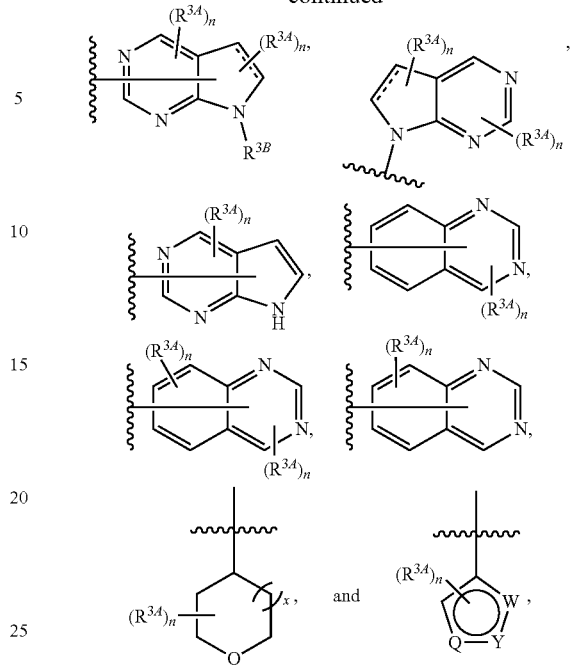

wherein:
each instance of ═ independently represents a single or double bond;
n is 0, 1, 2, or 3;
x is 0 or 1;
Y is O, S, N, or $NR^{3B}$ and each instance of Q and W is independently CH, $CR^{3A}$, N, or $NR^{3B}$, as valency permits;
each instance of $R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, optionally substituted alkenyl, optionally substituted alkynyl, optionally substituted carbocyclic, optionally substituted heterocyclic, optionally substituted aryl, or optionally substituted heteroaryl, or two $R^{3A}$ groups are joined to form an optionally substituted carbocyclic, optionally substituted heterocyclic, optionally substituted aryl, optionally substituted heteroaryl, or oxo (═O) group, or $R^{3A}$ and $R^{3B}$ groups are joined to form an optionally substituted carbocyclic, optionally substituted heterocyclic, optionally substituted aryl, or optionally substituted heteroaryl ring; and
$R^{3B}$ is hydrogen, optionally substituted alkyl, hydroxyl, substituted hydroxyl, amino, substituted amino, carbonyl, sulfonyl, optionally substituted carbocyclic, optionally substituted heterocyclic, optionally substituted aryl, optionally substituted heteroaryl, or a nitrogen protecting group.

In certain embodiments, n is 0. In certain embodiments, n is 1. In certain embodiments, n is 2. In certain embodiments, n is 3. In certain embodiments, each instance of $R^{3A}$ is independently hydroxyl, —OCH$_3$, optionally substituted $C_{1-4}$alkyl (e.g., methyl, trifluoromethyl, ethyl, propyl, isopropyl, butyl, isobutyl, secbutyl, tertbutyl), —CN, or sulfonyl (e.g., —S(O)$_2$CH$_3$).

As generally defined herein, $L^2$ is a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(═$NR^L$)—, —C(═$NNR^L$)—, —C(═$NOR^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and optionally and independently present at one or both ends of the hydrocarbon chain. It is understood that the linker joining R$^{13}$ to Ring HET may comprise one or more of the above recited moieties in combination to form the group L$^2$.

In certain embodiments, L$^2$ is a bond. In certain embodiments, L$^2$ is —O—. In certain embodiments, L$^2$ is —N(R$^L$)—. In certain embodiments, L$^2$ is —S—. In certain embodiments, L$^2$ is —C(O)—. In certain embodiments, L$^2$ is —C(O)O—. In certain embodiments, L$^2$ is —C(O)S—. In certain embodiments, L$^2$ is —C(O)N(R$^L$)—. However, in certain embodiments, L$^2$ is not C(O)N(R$^L$) wherein R$^{13}$ is optionally substituted carbocyclyl, e.g., optionally substituted adamantanyl. In certain embodiments, L$^2$ is —C(O)N(R$^L$)N(R$^L$)—. In certain embodiments, L$^2$ is —OC(O)—. In certain embodiments, L$^2$ is —OC(O)N(R$^L$)—. In certain embodiments, L$^2$ is —NR$^L$C(O)—. In certain embodiments, L$^2$ is —NR$^L$C(O)N(R$^L$)—. In certain embodiments, L$^2$ is —NR$^L$C(O)N(R$^L$)N(R$^L$)—. In certain embodiments, L$^2$ is —NR$^L$C(O)O—. In certain embodiments, L$^2$ is —SC(O)—. In certain embodiments, L$^2$ is —C(=NR$^L$)—. In certain embodiments, L$^2$ is —C(=NNR$^L$)—. In certain embodiments, L$^2$ is —C(=NOR$^L$)—. In certain embodiments, L$^2$ is —C(=N R$^L$)N(R$^L$)—. In certain embodiments, L$^2$ is —NR$^L$C(=NR$^L$)—. In certain embodiments, L$^2$ is —C(S)—. In certain embodiments, L$^2$ is —C(S)N(R$^L$)—. In certain embodiments, L$^2$ is —NR$^L$C(S)—. In certain embodiments, L$^2$ is —S(O)—. In certain embodiments, L$^2$ is —OS(O)$_2$—. In certain embodiments, L$^2$ is —S(O)$_2$O—. In certain embodiments, L$^2$ is —SO$_2$—. In certain embodiments, L$^2$ is —N(R$^L$)SO$_2$—. In certain embodiments, L$^2$ is —SO$_2$N(R$^L$)—. In certain embodiments, L$^2$ is —N(R$^L$)SO$_2$N(R$^L$)—.

In certain embodiments, L$^2$ is an optionally substituted C$_{1-10}$ saturated or unsaturated hydrocarbon chain, e.g., in certain embodiments, L$^2$ is an optionally substituted C$_{1-10}$ alkyl chain, L$^2$ is an optionally substituted C$_{2-10}$ alkenyl chain, or L$^2$ is an optionally substituted C$_{2-10}$ alkynyl chain. In certain embodiments, L$^2$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain. In certain embodiments, L$^2$ is an unsubstituted C$_{1-10}$ n-alkyl chain of the formula —(CH$_2$)$_x$—, wherein x is 1, 2, 3, 4, 5, 6, 7, 8, 9, or 10. In certain embodiments, L$^2$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain. In certain embodiments, L$^2$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain.

In certain embodiments, L$^2$ is an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$), —C(S)—, —C(S)N(R$^L$)—, —NR$^L$C(S), —S(O)—, —OS(O)$_2$—, —S(O)$_2$O—, —SO$_2$—, —N(R$^L$)SO$_2$—, —SO$_2$N(R$^L$)—, or —N(R$^L$)SO$_2$N(R$^L$) independently present between two carbon atoms of the hydrocarbon chain, or present at one or both ends of the hydrocarbon chain. In this instance, in certain embodiments, L$^2$ is a chain of at least 2 atoms, e.g., L$^2$ is a chain comprising 1 to 10 carbon atoms (e.g., 1, 2, 3, 4, 5, 6, 7, 8, 9, or 10 carbon atoms), and 1 or more of the above recited moieties (e.g., 1, 2, 3, or more), to provide a chain of between 2 and 20 atoms, inclusive, e.g., 2, 3, 4, 5, 6, 7, 8, 9, 10, 11, 12, 13, 14, 15, 16, 17, 18, 19, or 20 chain atoms. In certain embodiments, a moiety is present between two carbon atoms of the hydrocarbon chain. In certain embodiments, a moiety is present at one end of the hydrocarbon chain. In certain embodiments, a moiety is independently present at each end of the hydrocarbon chain. In certain embodiments, L$^2$ is an optionally substituted C$_{1-10}$ alkyl chain, L$^2$ is an optionally substituted C$_{2-10}$ alkenyl chain, or L$^2$ is an optionally substituted C$_{2-10}$ alkynyl chain comprising one or more of the above recited moieties independently present between two carbon atoms of the hydrocarbon chain, or present at one or both ends of the hydrocarbon chain. In certain embodiments, L$^2$ is an optionally substituted C$_{1-10}$ alkyl chain, e.g., an optionally substituted C$_{1-8}$ alkyl chain, optionally substituted C$_{1-6}$ alkyl chain, optionally substituted C$_{1-4}$ alkyl chain, optionally substituted C$_{1-3}$ alkyl chain, or optionally substituted C$_{1-2}$ alkyl chain, comprising one or more of the above recited moieties independently present between two carbon atoms of the hydrocarbon chain, or present at one or both ends of the hydrocarbon chain. In certain embodiments, L$^2$ is an unsubstituted C$_{1-10}$ n-alkyl chain of the formula —(CH$_2$)$_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, L$^2$ is an optionally substituted C$_{2-10}$ alkenyl chain, e.g., an optionally substituted C$_{2-8}$ alkenyl chain, optionally substituted C$_{2-6}$ alkenyl chain, optionally substituted C$_{2-4}$ alkenyl chain, optionally substituted C$_{2-3}$ alkenyl chain, or optionally substituted C$_2$ alkenyl chain, comprising one or more of the above recited moieties independently present between two carbon atoms of the hydrocarbon chain, or present at one or both ends of the hydrocarbon chain. In certain embodiments, L$^2$ is an optionally substituted C$_{2-10}$ alkynyl chain, e.g., an optionally substituted C$_{2-8}$ alkynyl chain, optionally substituted C$_{2-6}$ alkynyl chain, optionally substituted C$_{2-4}$ alkynyl chain, optionally substituted C$_{2-3}$ alkynyl chain, or optionally substituted C$_2$ alkynyl chain, comprising one or more of the above recited moieties independently present between two carbon atoms of the hydrocarbon chain, or present at one or both ends of the hydrocarbon chain.

As described above, in certain embodiments, $L^2$ is an unsubstituted $C_{1-10}$ n-alkyl chain of the formula —$(CH_2)_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^2$ is —O—$(CH_2)_x$—, —$(CH_2)_x$—O—, or —O—$(CH_2)_x$—O—. In certain embodiments, $L^2$ is —$N(R^L)$—$(CH_2)_x$—, —$(CH_2)_x$—$N(R^L)$—, —$N(R^L)$—$(CH_2)_x$—$N(R^L)$—, —O—$(CH_2)_x$—$N(R^L)$—, —$N(R^L)$—$(CH_2)_x$—O—, —$NR^L$—$(CH_2)_x$—C(O)O—, or —OC(O)—$(CH_2)_x$—$N(R^L)$—. In certain embodiments, $L^2$ is —S—$(CH_2)_x$— or —$(CH_2)_x$—S—. In certain embodiments, $L^2$ is —C(O)—$(CH_2)_x$— or —$(CH_2)_x$—C(O)—. In certain embodiments, $L^2$ is —C(O)O—$(CH_2)_x$— or —$(CH_2)_x$—C(O)O—. In certain embodiments, $L^2$ is —C(O)S—$(CH_2)_x$— or —$(CH_2)_x$—C(O)S—. In certain embodiments, $L^2$ is —$C(O)N(R^L)$—$(CH_2)_x$— or —$(CH_2)_x$—$C(O)N(R^L)$—. In certain embodiments, $L^2$ is —$C(O)N(R^L)N(R^L)$—$(CH_2)_x$— or —$(CH_2)_x$—$C(O)N(R^L)N(R^L)$—. In certain embodiments, $L^2$ is —OC(O)—$(CH_2)_x$— or —$(CH_2)_x$—OC(O)—. In certain embodiments, $L^2$ is —$OC(O)N(R^L)$—$(CH_2)_x$— or —$(CH_2)_x$—$OC(O)N(R^L)$—. In certain embodiments, $L^2$ is —$NR^LC(O)$—$(CH_2)_x$— or —$(CH_2)_x$—$NR^LC(O)$—. In certain embodiments, $L^2$ is —$NR^LC(O)N(R^L)$—$(CH_2)_x$— or —$(CH_2)_x$—$NR^LC(O)N(R^L)$—. In certain embodiments, $L^2$ is $NR^LC(O)N(R^L)N(R^L)(CH_2)_x$ or $(CH_2)_x NR^LC(O)N(R^L)N(R^L)$—. In certain embodiments, $L^2$ is $NR^LC(O)O$—$(CH_2)_x$ or $(CH_2)_x$—$NR^LC(O)O$—. In certain embodiments, $L^2$ is —SC(O)—$(CH_2)_x$— or —$(CH_2)_x$—SC(O)—. In certain embodiments, $L^2$ is —$C(=NR^L)$—$(CH_2)_x$— or —$(CH_2)$—$C(=NR^L)$—. In certain embodiments, $L^2$ is —$C(=NNR^L)$—$(CH_2)_x$— or —$(CH_2)_x$—$C(=NNR^L)$—. In certain embodiments, $L^2$ is —$C(=NOR^L)$—$(CH_2)_x$— or —$(CH_2)_x$—$C(=NOR^L)$—. In certain embodiments, $L^2$ is —$C(=NR^L)N(R^L)$—$(CH_2)_x$— or —$(CH_2)_x$—$C(=NR^L)N(R^L)$—. In certain embodiments, $L^2$ is —$NR^LC(=NR^L)$—$(CH_2)_x$— or —$(CH_2)_x$—$NR^LC(=NR^L)$—. In certain embodiments, $L^2$ is —C(S)—$(CH_2)_x$— or —$(CH_2)_x$—C(S)—. In certain embodiments, $L^2$ is —$C(S)N(R^L)$—$(CH_2)_x$— or —$(CH_2)_x$—$C(S)N(R^L)$—. In certain embodiments, $L^2$ is —$NR^LC(S)$—$(CH_2)_x$— or —$(CH_2)_x$—$NR^LC(S)$—. In certain embodiments, $L^2$ is —S(O)—$(CH_2)_x$— or —$(CH_2)_x$—S(O)—. In certain embodiments, $L^2$ is —$OS(O)_2$—$(CH_2)_x$— or —$(CH_2)_x$—$OS(O)_2$—. In certain embodiments, $L^2$ is —$S(O)_2O$—$(CH_2)_x$— or —$(CH_2)_x$—$S(O)_2O$—. In certain embodiments, $L^2$ is —$SO_2$—$(CH_2)_x$— or —$(CH_2)_x$—$SO_2$—. In certain embodiments, $L^2$ is —$N(R^L)SO_2$—$(CH_2)_x$— or —$(CH_2)_x$—$N(R^L)SO_2$—. In certain embodiments, $L^2$ is —$SO_2N(R^L)$—$(CH_2)_x$— or —$(CH_2)_x$—$SO_2N(R^L)$—. In certain embodiments, $L^2$ is —$N(R^L)SO_2N(R^L)$—$(CH_2)_x$— or —$(CH_2)_x$—$N(R^L)SO_2N(R^L)$—. In certain embodiments, $L^2$ is a bond, —$N(R^L)$—, —$NR^LC(O)O$—, —$NR^LC(O)N(R^L)$—, —$N(R^L)$—, —$N(R^L)SO_2N(R^L)$—, —$NR^L$—$(CH_2)_x$—C(O)O—, —$NR^L$—$(CH_2)_x$—O—, —$NR^LC(O)N(R^L)$—, —$NR^L$—$(CH_2)_x$—, —$(CH_2)_x$—$NR^L$—, —$NR^LC(O)O(CH_2)$, —$NR^LC(O)NR^L(CH_2)_x$—, or —$NR^L(CH_2)_xNR^LC(O)$—.

As generally defined herein, $R^{13}$ attached directly (wherein $L^2$ is a bond) or indirectly (wherein $L^2$ is a linking group) to Ring HET is a cyclic moiety selected from the group consisting of optionally substituted carbocyclyl, optionally substituted heterocyclyl, optionally substituted aryl, and optionally substituted heteroaryl. It is understood that the $R^{13}$ cyclic moiety may be monocyclic or polycyclic (e.g., bicyclic or tricyclic). In certain embodiments, $R^{13}$ is a monocyclic optionally substituted carbocyclyl, monocyclic optionally substituted heterocyclyl, monocylic optionally substituted aryl, or monocylic optionally substituted heteroaryl. In certain embodiments, $R^{13}$ is a bicyclic optionally substituted carbocyclyl, bicyclic optionally substituted heterocyclyl, bicyclic optionally substituted aryl, or bicyclic optionally substituted heteroaryl.

In certain embodiments, $R^{13}$ is an optionally substituted monocyclic or bicyclic carbocyclyl, e.g., an optionally substituted $C_{3-10}$ carbocyclyl, optionally substituted $C_{3-9}$ carbocyclyl, optionally substituted $C_{3-8}$ carbocyclyl, optionally substituted $C_{3-7}$ carbocyclyl, optionally substituted $C_{3-6}$ carbocyclyl, optionally substituted $C_{3-4}$ carbocyclyl, optionally substituted $C_{5-10}$ carbocyclyl, optionally substituted $C_3$ carbocyclyl, optionally substituted $C_4$ carbocyclyl, optionally substituted $C_5$ carbocyclyl, optionally substituted $C_6$ carbocyclyl, optionally substituted $C_7$ carbocyclyl, optionally substituted $C_8$ carbocyclyl, optionally substituted $C_9$ carbocyclyl, or optionally substituted $C_{10}$ carbocyclyl. In certain embodiments, $R^{13}$ is an optionally substituted cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), or spiro[4.5]decanyl ($C_{10}$) ring.

In certain embodiments, $R^{13}$ is an optionally substituted monocyclic or bicyclic heterocyclyl, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl. In certain embodiments, $R^3$ is an optionally substituted azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolidin-2-one, pyrrolyl-2,5-dione, dioxolanyl, oxasulfuranyl, disulfuranyl, oxazolidin-2-one, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, benzoxazolinonyl, tetrahydroquinolinyl, tetrahydroisoquinolinyl, furo[2,3-b]furanyl, 2,3-dihydro-1,4-dioxinyl, 3-oxa-8-azabicyclo[3.2.1]octanyl, or 8-oxa-3-azabicyclo[3.2.1]octanyl ring.

In certain embodiments, $R^{13}$ is an optionally substituted spiro-fused heterocyclic ring system, e.g., comprising an optionally substituted heterocyclic ring spiro fused to an optionally substituted carbocyclic or optionally substituted heterocyclic ring, wherein the point of attachment is either on the heterocyclic or carbocyclic ring. In certain embodiments, $R^{13}$ is an optionally substituted 3,4-spiro-fused heterocyclic ring system, e.g., wherein the point of attachment is either on the 3- or 4-membered ring. In certain embodiments, $R^{13}$ is an optionally substituted 3,5-spiro-fused heterocyclic ring system, e.g., wherein the point of attachment is either on the 3- or 5-membered ring. In certain embodiments, $R^{13}$ is an optionally substituted 3,6-spiro-fused heterocyclic ring system, e.g., wherein the point of attachment is either on the 3- or 6-membered ring. In certain embodiments, $R^{13}$ is an optionally substituted 4,4-spiro-fused heterocyclic ring system. In certain embodiments, $R^{13}$ is an optionally substituted 4,5-spiro-fused heterocyclic ring system, e.g., wherein the point of attachment is either on the 4- or 5-membered ring. In certain embodiments, $R^{13}$ is an optionally substituted 4,6-spiro-fused heterocyclic ring system, e.g., wherein the point of attachment is either on the 4- or 6-membered ring. In certain embodiments, $R^{13}$ is an optionally substituted 5,5-spiro-fused heterocyclic ring system. In certain embodiments, $R^{13}$ is an optionally substituted 5,6-spiro-fused heterocyclic ring system, e.g., wherein the point of attachment is either on the 5- or 6-membered ring. In certain embodiments, $R^{13}$ is an optionally substituted 6,6-spiro-fused heterocyclic ring system. In any of the above embodiments, $R^{13}$ is an N-linked, optionally substituted spiro-fused heterocyclic ring system, i.e., wherein the point of attachment is on a nitrogen atom. Alternatively, in any of the above embodiments, $R^{13}$ is an C-linked, optionally substituted spiro-fused heterocyclic ring system, i.e., wherein the point of attachment is on a carbon atom.

In certain embodiments, $R^{13}$ is an optionally substituted ortho-fused heterocyclic ring system, e.g., comprising an optionally substituted heterocyclic ring ortho fused to an optionally substituted carbocyclic or optionally substituted heterocyclic ring wherein the point of attachment is either on the heterocylic or carbocyclic ring or comprising an optionally substituted heterocyclic ring ortho fused to an optionally substituted aryl or optionally substituted heteroaryl ring, wherein the point of attachment is on the heterocylic ring. In certain embodiments, $R^{13}$ is an optionally substituted 3,4-ortho-fused heterocyclic ring system, e.g., wherein the point of attachment is either on the 3- or 4-membered ring. In certain embodiments, $R^{13}$ is an optionally substituted 3,5-ortho-fused heterocyclic ring system, e.g., wherein the point of attachment is either on the 3- or 5-membered ring. In certain embodiments, $R^{13}$ is an optionally substituted 3,6-ortho-fused heterocyclic ring system, e.g., wherein the point of attachment is either on the 3- or 6-membered ring. In certain embodiments, $R^{13}$ is an optionally substituted 4,4-ortho-fused heterocyclic ring system. In certain embodiments, $R^{13}$ is an optionally substituted 4,5-ortho-fused heterocyclic ring system, e.g., wherein the point of attachment is either on the 4- or 5-membered ring. In certain embodiments, $R^{13}$ is an optionally substituted 4,6-ortho-fused heterocyclic ring system, e.g., wherein the point of attachment is either on the 4- or 6-membered ring. In certain embodiments, $R^{13}$ is an optionally substituted 5,5-ortho-fused heterocyclic ring system. In certain embodiments, $R^{13}$ is an optionally substituted 5,6-ortho-fused heterocyclic ring system, e.g., wherein the point of attachment is either on the 5- or 6-membered ring. In certain embodiments, $R^{13}$ is an optionally substituted 6,6-ortho-fused heterocyclic ring system. In any of the above embodiments, $R^{13}$ is an N-linked, optionally substituted ortho-fused heterocyclic ring system, i.e., wherein the point of attachment is on a nitrogen atom. Alternatively, in any of the above embodiments, $R^{13}$ is an C-linked, optionally substituted ortho-fused heterocyclic ring system, i.e., wherein the point of attachment is on a carbon atom.

In certain embodiments, $R^{13}$ is an optionally substituted ortho-fused heteroaryl ring system, e.g., comprising an optionally substituted heteroaryl ring ortho fused to an optionally substituted carbocyclic or optionally substituted heterocyclic ring wherein the point of attachment is on the heteroaryl ring or comprising an optionally substituted heteroaryl ring ortho fused to an optionally substituted aryl or optionally substituted heteroaryl ring, wherein the point of attachment is either on the aryl ring or heteroaryl ring. In certain embodiments, the heteroaryl ring ortho fused to an optionally substituted carbocyclic or optionally substituted heterocyclic ring is a 5-membered heteroaryl ring, e.g., to provide a 3,5-, 4,5-, 5,5-, or 6,5-ortho fused ring system. In certain embodiments, the heteroaryl ring ortho fused to an optionally substituted carbocyclic or optionally substituted heterocyclic ring is a 6-membered heteroaryl ring, e.g., to provide a 3,6-, 4,6-, 5,6-, or 6,6-ortho fused ring system. In certain embodiments, the optionally substituted heteroaryl ring ortho fused to an optionally substituted aryl ring is a 5-membered heteroaryl ring, e.g., to provide a 5,6-ortho fused ring system. In certain embodiments, the optionally substituted heteroaryl ring ortho fused to an optionally substituted aryl ring is a 6-membered heteroaryl ring, e.g., to provide a 6,6-fused ring system. In certain embodiments, the optionally substituted heteroaryl ring ortho fused to an optionally heteroaryl ring is a 5-membered heteroaryl ring, e.g., to provide a 6,5- or 5,5-fused ring system. In certain embodiments, the optionally substituted heteroaryl ring ortho fused to an optionally heteroaryl ring is a 6-membered heteroaryl ring, e.g., to provide a 6,5- or 5,5-fused ring system. In any of the above embodiments, $R^{13}$ is an N-linked, optionally substituted ortho-fused heteroaryl ring system, i.e., wherein the point of attachment is on a nitrogen atom. Alternatively, in any of the above embodiments, $R^{13}$ is an C-linked, optionally substituted ortho-fused heteroaryl ring system, i.e., wherein the point of attachment is on a carbon atom.

In certain embodiments, $R^{13}$ is an optionally substituted monocyclic or bicyclic aryl, e.g., an optionally substituted phenyl, or optionally substituted naphthyl ring. However, in certain embodiments, $R^{13}$ is not optionally substituted monocyclic or bicyclic aryl. In certain embodiments, $R^{13}$ is not optionally substituted phenyl. In certain embodiments, $R^{13}$ is not substituted phenyl.

In certain embodiments, $R^{13}$ is an optionally substituted ortho-fused aryl ring system, e.g., comprising an optionally substituted 6-membered aryl ring ortho fused to an optionally substituted carbocyclic or an optionally substituted heterocyclic ring wherein the point of attachment is on the aryl ring, e.g., to provide a 3,6-, 4,6-, 5,6-, or 6,6-ortho fused ring system. In certain embodiments, $R^{13}$ is an optionally substituted ortho-fused aryl ring system, e.g., comprising an optionally substituted 6-membered aryl ring ortho fused to an optionally substituted 6-membered aryl ring.

In certain embodiments, $R^{13}$ is an optionally substituted monocyclic or bicyclic heteroaryl, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, $R^{13}$ is an optionally substituted pyrrolyl, furanyl, thiophenyl, imidazolyl, pyrazolyl, oxazolyl, isoxazolyl, thiazolyl, isothiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, or quinazolinyl ring.

In certain embodiments, $R^{13}$ is a cyclic moiety selected from the group consisting of:

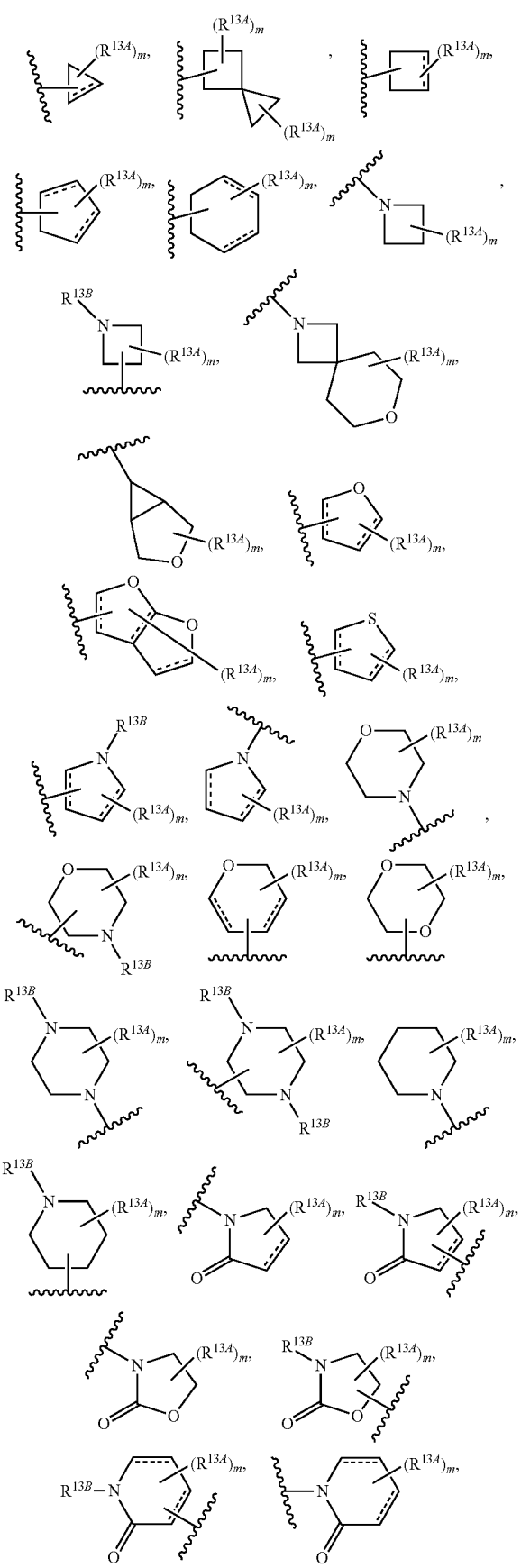
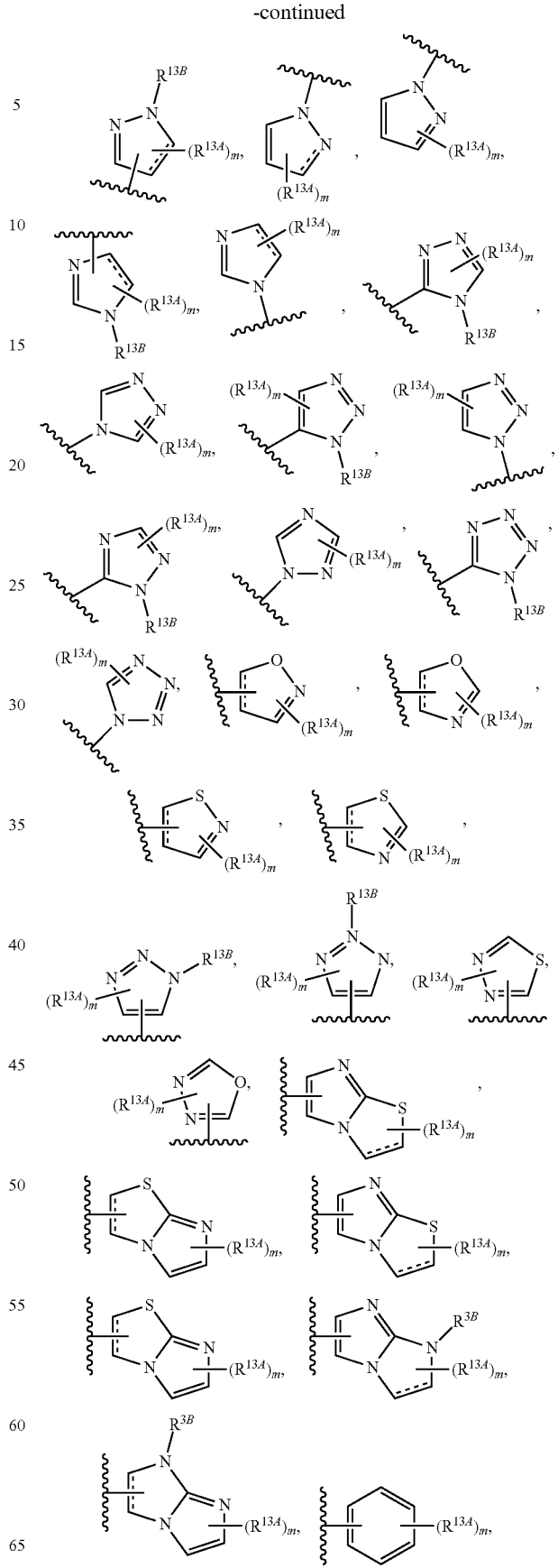

-continued
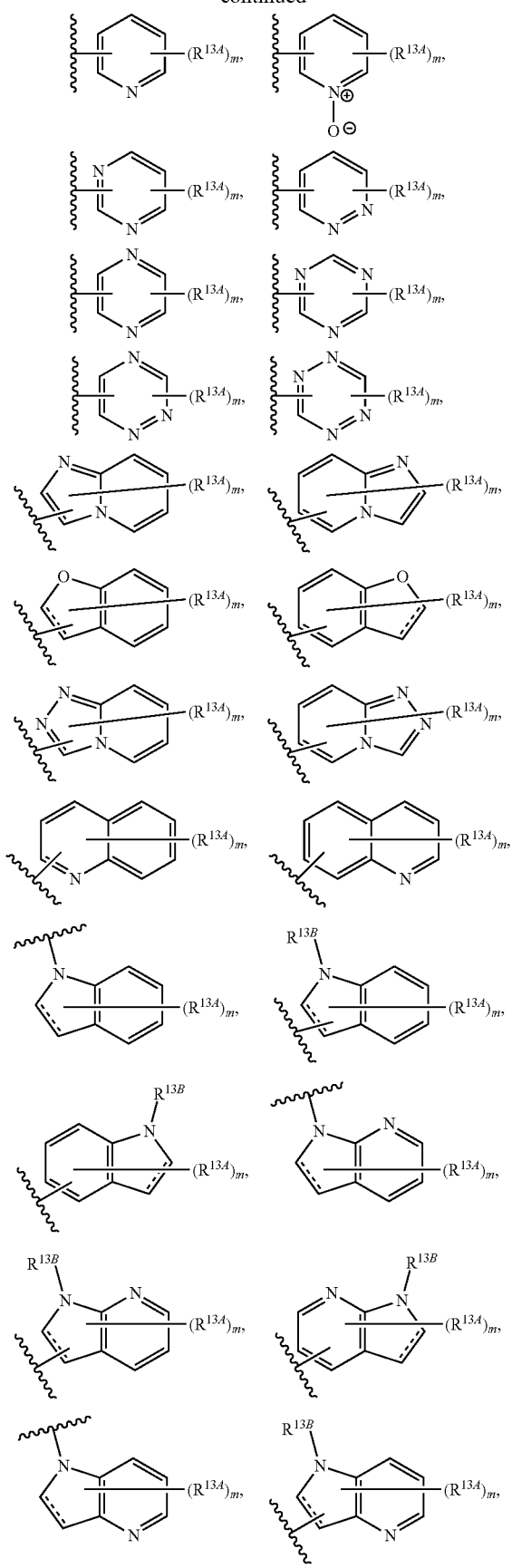
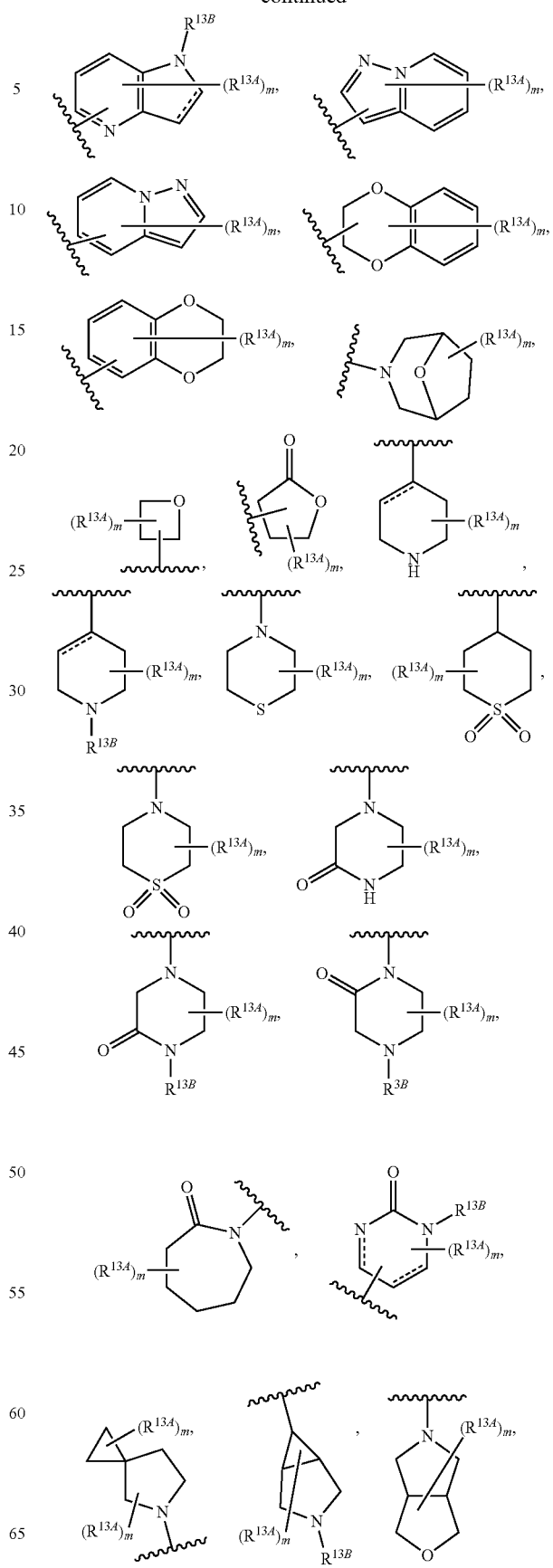

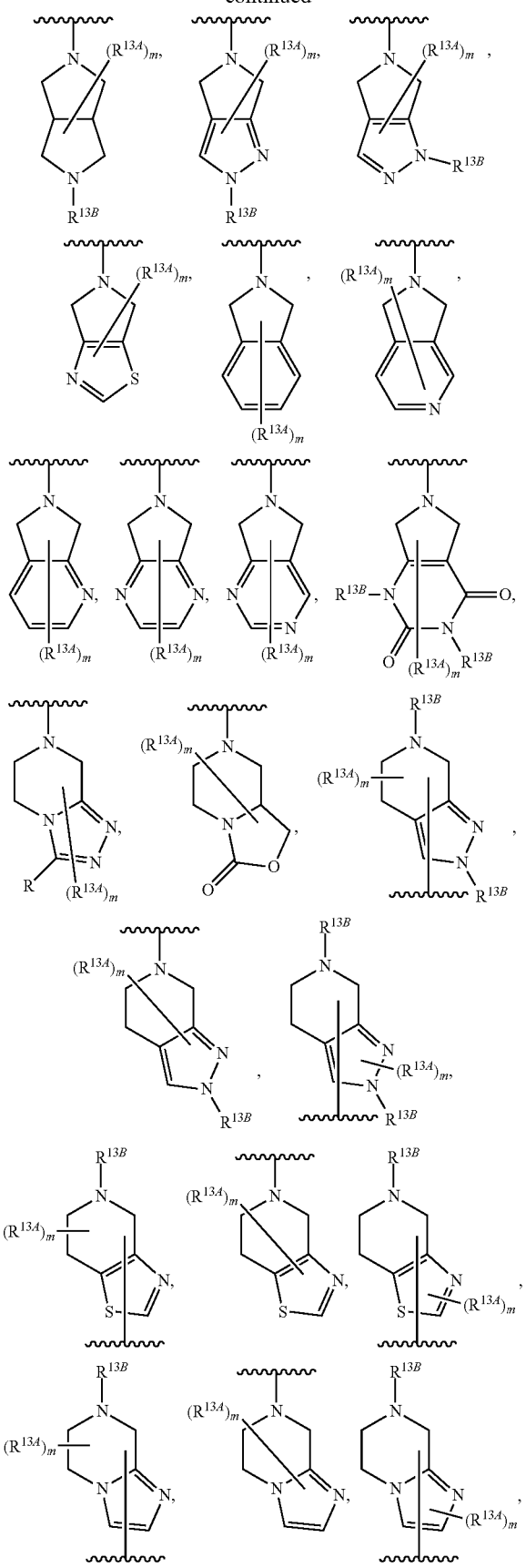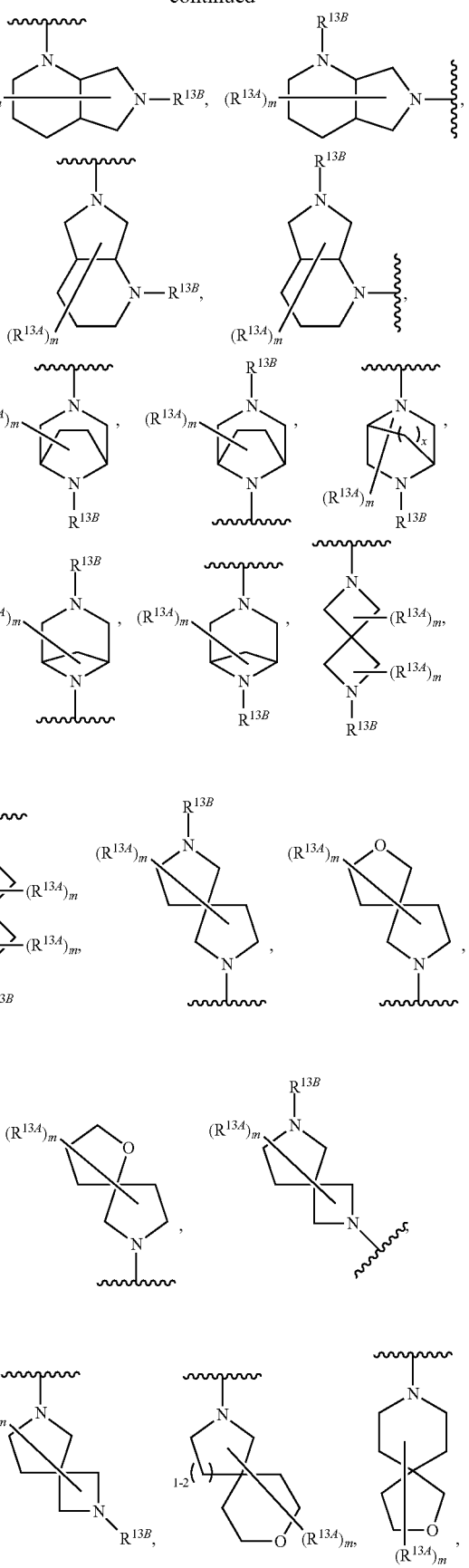

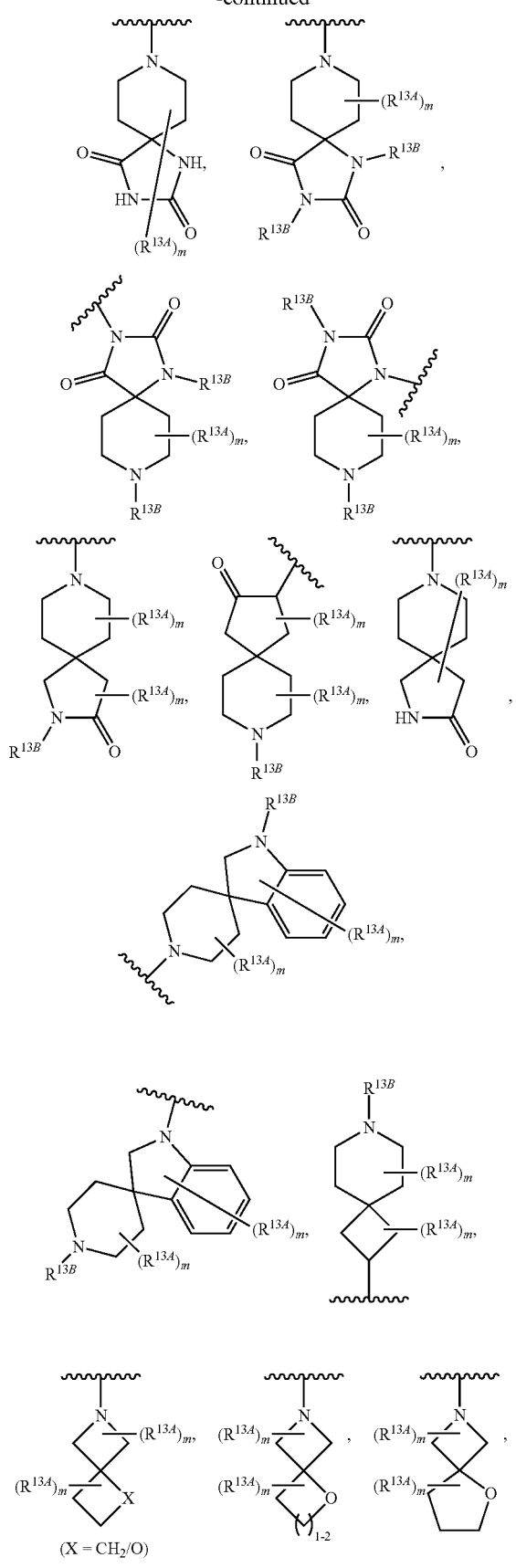
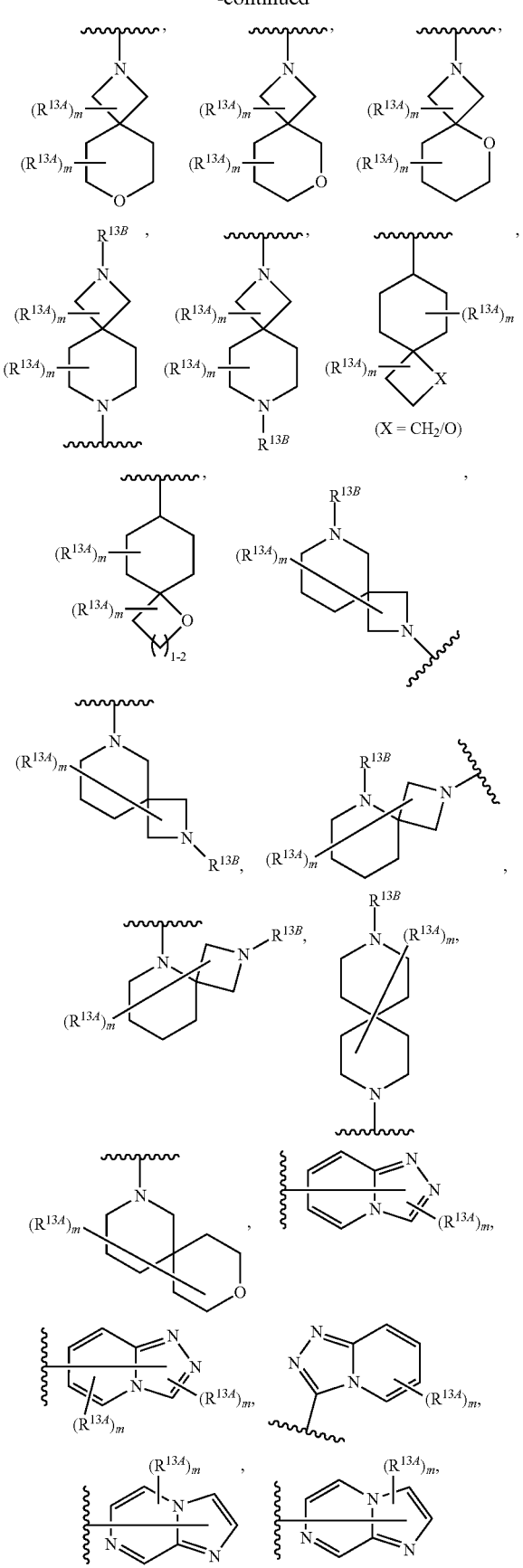

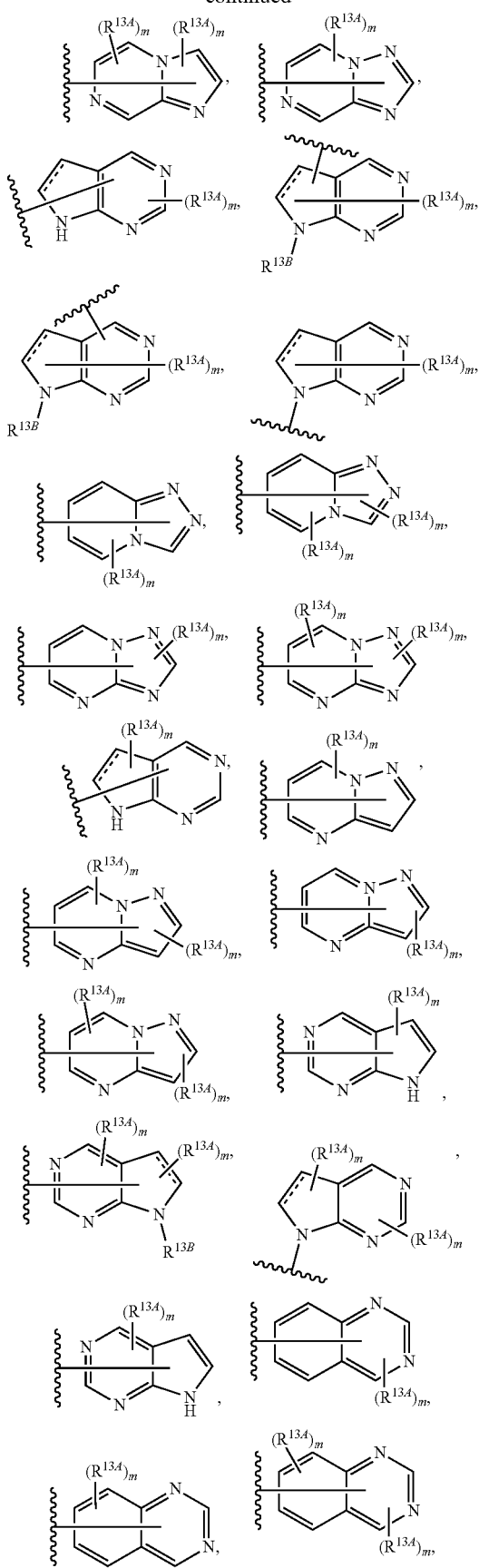

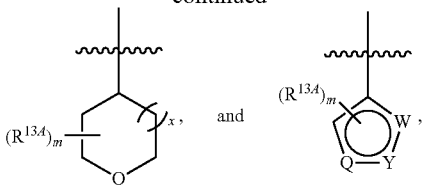

wherein:
each instance of ═══ independently represents a single or double bond;
x is 0 or 1;
m is 0, 1, 2, or 3;
Y is O, S, N, or $NR^{13B}$ and each instance of Q and W is independently CH, $CR^{13A}$, N, or $NR^{13B}$, as valency permits;
each instance of $R^{13A}$ is independently hydroxyl, substituted hydroxyl, thiol, substituted thiol, amino, substituted amino, carbonyl, sulfonyl, sulfinyl, —CN, —NO₂, halogen, optionally substituted alkyl, optionally substituted alkenyl, optionally substituted alkynyl, optionally substituted carbocyclic, optionally substituted heterocyclic, optionally substituted aryl, or optionally substituted heteroaryl, or two $R^{13A}$ groups are joined to form an optionally substituted carbocyclic, optionally substituted heterocyclic, optionally substituted aryl, optionally substituted heteroaryl, or oxo (═O) group, or $R^{13A}$ and $R^{13B}$ groups are joined to form an optionally substituted carbocyclic, optionally substituted heterocyclic, optionally substituted aryl, or optionally substituted heteroaryl ring; and
$R^{13B}$ is hydrogen, optionally substituted alkyl, hydroxyl, substituted hydroxyl, amino, substituted amino, carbonyl, sulfonyl, optionally substituted carbocyclic, optionally substituted heterocyclic, optionally substituted aryl, optionally substituted heteroaryl, or a nitrogen protecting group.

In certain embodiments, m is 0. In certain embodiments, m is 1. In certain embodiments, m is 2. In certain embodiments, m is 3. In certain embodiments, each instance of $R^{13A}$ is independently hydroxyl, —OCH₃, optionally substituted $C_{1-4}$alkyl (e.g., methyl, trifluoromethyl, ethyl, propyl, isopropyl, butyl, isobutyl, secbutyl, tertbutyl), —CN, or sulfonyl (e.g., —S(O)₂CH₃).

As generally defined herein, each $R^L$ provided in $L^1$ and $L^2$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring. In certain embodiments, at least one instance of $R^L$ is hydrogen. In certain embodiments, each instance of $R^L$ is hydrogen. In certain embodiments, at least one instance of $R^L$ is optionally substituted alkyl, e.g., optionally substituted $C_{1-6}$ alkyl, optionally substituted $C_{1-5}$alkyl, optionally substituted $C_{1-4}$alkyl, optionally substituted $C_{1-2}$alkyl, optionally substituted $C_{2-3}$alkyl, optionally substituted $C_3$-alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^L$ $C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, $R^L$ is alkyl substituted with —CN, e.g., —(CH₂)$_z$CN, wherein z is 1, 2, 3, 4, 5, or 6. In certain embodiments, $R^L$ is alkyl substituted with hydroxy or substituted hydroxy, e.g., —$(CH_2)_zOCH_3$, wherein z is 1, 2, 3, 4, 5, or 6. In certain embodiments, $R^L$ is alkyl substituted with amino or substituted substituted amino, e.g., —$(CH_2)_zNH_2$, wherein z is 1, 2, 3, 4, 5, or 6. In certain embodiments, at least one instance of $R^L$ is a nitrogen protecting group. In certain embodiments, $R^L$ and $R^3$ taken together form an optionally substituted heterocyclyl ring, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl ring. In certain embodiments, $R^L$ and $R^3$ taken together form an optionally substituted heteroaryl ring, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl. In certain embodiments, $R^L$ and $R^{13}$ taken together form an optionally substituted heterocyclyl ring, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl ring. However, in certain embodiments, when $L^2$ is —$N(R^L)$—, $R^L$ and $R^{13}$ taken together do not form an optionally substituted heterocyclyl ring, e.g., a 6-membered heterocyclyl, e.g., an optionally substituted piperidinyl ring. In certain embodiments, $R^L$ and $R^{13}$ taken together form an optionally substituted heteroaryl ring, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl.

In certain embodiments, compounds wherein $R^{2d}$ is hydrogen or fluoro, each of $R^{2b}$, $R^{2c}$, and $R^{2a}$ is hydrogen, $L^2$ is a bond and $R^{13}$ is substituted phenyl, or $L^2$ is —$N(R^L)$— and $R^L$ and $R^{13}$ taken together do not form an optionally substituted piperidinyl ring, $G_8$ and $G_{11}$ are both N, $G_{10}$ is $L^1$-$R^3$, wherein $L^1$ is —$N(R^L)$— and $R^L$ and $R^3$ are each hydrogen, and $G_{12}$ is not N, are specifically excluded. In certain embodiments, the following compounds are specifically excluded:

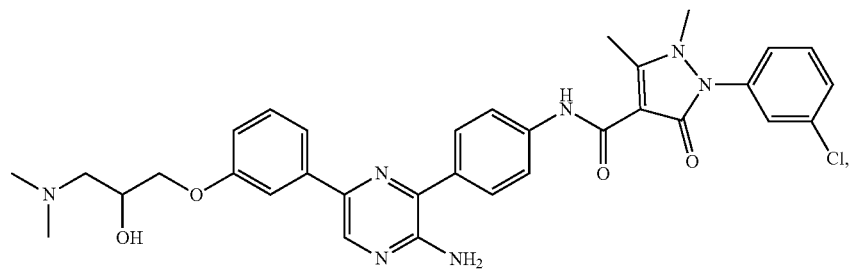

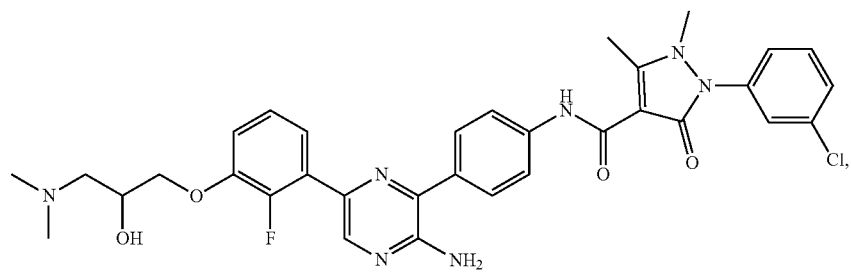

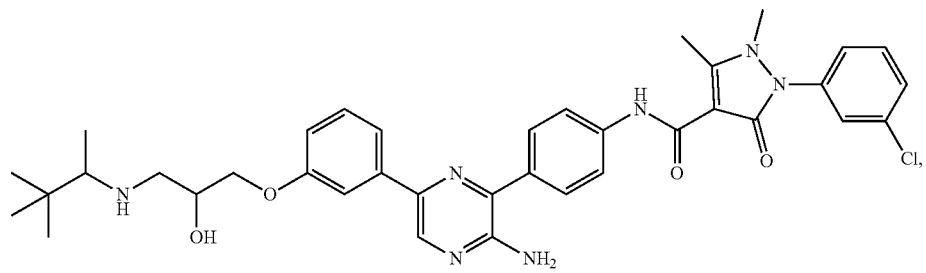

-continued

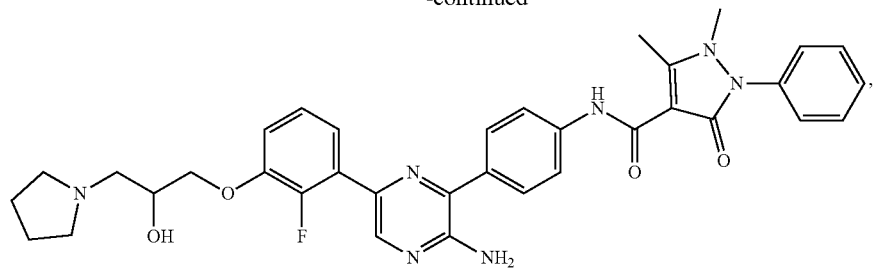

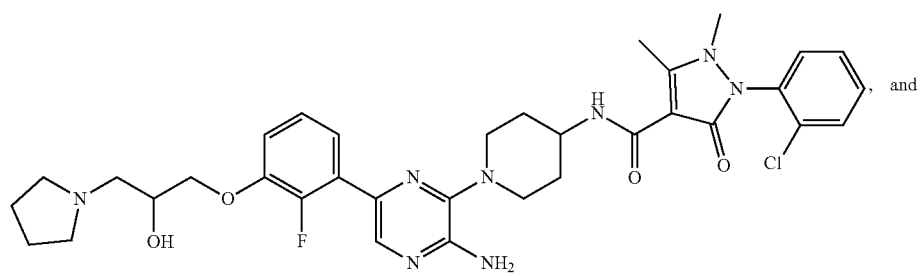

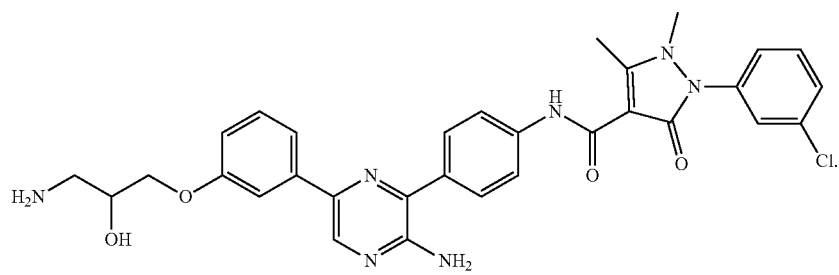

In certain embodiments, compounds wherein $R^1$ and $R^{1a}$ are each methyl, $R^{2a}$ is chloro, each of $R^{2b}$, $R^{2c}$, and $R^{2d}$ is hydrogen, $G_8$ is N and $G_{10}$ and $G_{11}$ are not N, $G^{12}$ is $L^1$-$R^3$, wherein $L^1$ is a bond and $R^3$ is optionally substituted phenyl, $L^2$ is —C(O)N($R^L$)—, and $R^{13}$ is optionally substituted adamantanyl, is specifically excluded. In certain embodiments, the following compounds are specifically excluded:

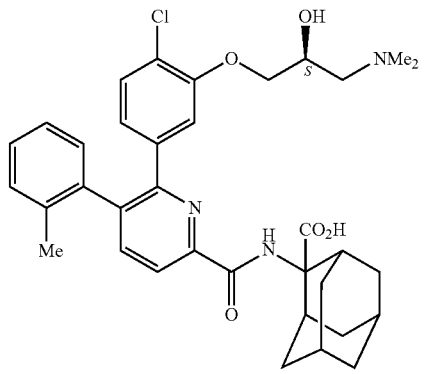

and

-continued

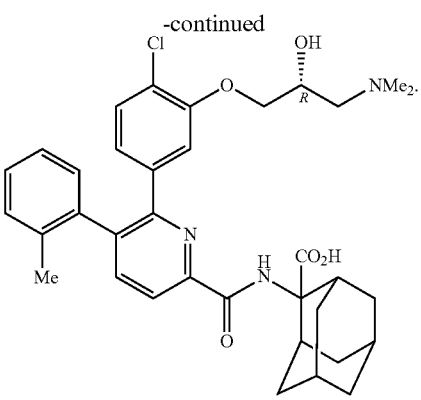

Various combination of the above described embodiments are further contemplated herein. For example, in certain embodiments of Formula (I-h), wherein $G_8$ and $G_{12}$ are both N, provided is a compound of Formula (I-i):

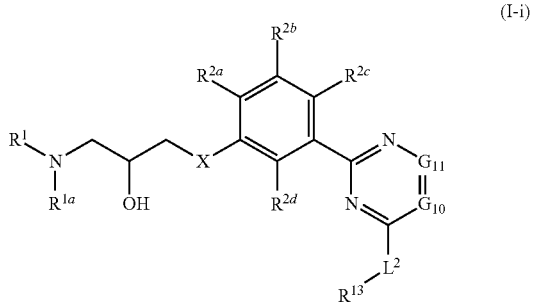

(I-i)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —NR$^L$C(O)O—, —NR$^L$C(O)N($R^L$)—, —N($R^L$)—, —N($R^L$)SO$_2$N($R^L$)—, —NR$^L$—(CH$_2$)$_x$—C(O)O—, —NR$^L$, —(CH$_2$)$_x$—O—, —NR$^L$C(O)N($R^L$)—, —NR$^L$—(CH$_2$)$_x$—, —(CH$_2$)$_x$—NR$^L$—, —NR$^L$C(O)O(CH$_2$)$_x$—, —NR$^L$C(O)NR$^L$(CH$_2$)$_x$—, or —NR$^L$(CH$_2$)NR$^L$C(O)—. In certain embodiments, $R^{13}$ is optionally substituted heterocylyl or optionally substituted heteroaryl.

In certain embodiments of Formula (I-h), wherein $G_8$ and $G_{12}$ are both N, and $G_{11}$ is a group of formula C—$R^{11}$, provided is a compound of Formula (I-j):

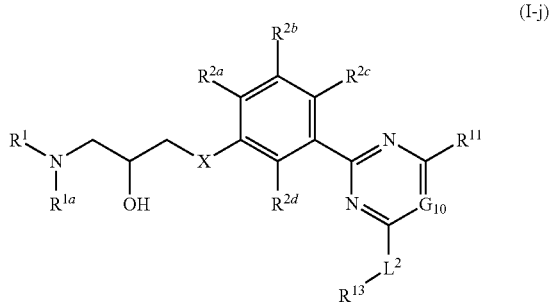

(I-j)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —NR$^L$C(O)O—, —NR$^L$C(O)N($R^L$)—, —N($R^L$)—, —N($R^L$)SO$_2$N($R^L$)—, —NR$^L$—(CH$_2$)$_x$—C(O)O—, —NR$^L$, —(CH$_2$)$_x$—O—, —NR$^L$C(O)N($R^L$)—, —NR$^L$—(CH$_2$)$_x$—, —(CH$_2$)$_x$—NR$^L$—, —NR$^L$C(O)O(CH$_2$)$_x$—, —NR$^L$C(O)NR$^L$ (CH$_2$)$_x$—, or —NR$^L$ (CH$_2$)$_x$NR$^L$C(O)—. In certain embodiments, $R^{13}$ is optionally substituted heterocylyl or optionally substituted heteroaryl. In certain embodiments, $R^{11}$ is hydrogen or a group -L$^1$-R$^3$.

In certain embodiments of Formula (I-h), wherein $G_8$ and $G_{12}$ are both N, $G_{11}$ is C—$R^{11}$, and $G_{10}$ is C—$R^{10}$, provided is a compound of Formula (I-k):

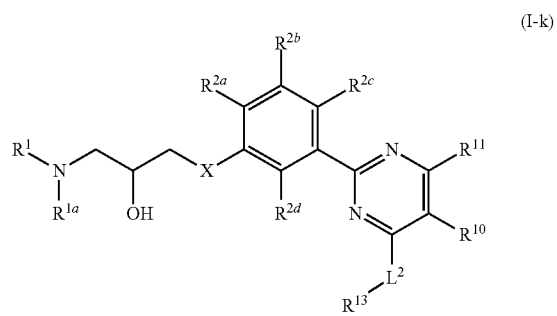

(I-k)

or a pharmaceutically acceptable salt thereof. In certain embodiments, X is —O—. In certain embodiments, $R^1$ is hydrogen, methyl, or ethyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —NR$^L$C(O) O—, —NR$^L$C(O)N($R^L$)—, —N($R^L$)—, —N($R^L$)SO$_2$N ($R^L$)—, —NR$^L$—(CH$_2$)$_x$—C(O)O—, —NR$^L$—(CH$_2$)$_x$—O—, —NR$^L$C(O)N($R^L$)—, —NR$^L$—(CH$_2$)$_x$—, —(CH$_2$)$_x$—NR$^L$—, —NR$^L$C(O)O(CH$_2$)$_x$—, —NR$^L$C(O)NR$^L$(CH$_2$)$_x$—, or —NR$^L$(CH$_2$)$_x$NR$^L$C(O)—. In certain embodiments, $R^{13}$ is optionally substituted heterocylyl or optionally substituted heteroaryl. In certain embodiments, $R^{11}$ is hydrogen or a group -L $R^3$. In certain embodiments, $R^{10}$ is hydrogen, optionally substituted alkyl (e.g., methyl, ethyl, —CH$_2$OH, CHF$_2$), optionally substituted C$_3$ 4cycloalkyl (e.g., cyclopropyl, cyclobutyl), or halo (e.g., fluoro, chloro, bromo, iodo). In certain embodiments, $R^{10}$ is hydrogen, methyl, or halogen (e.g., chloro).

In certain embodiments of Formula (I-h), wherein $G_8$ and $G_{12}$ are both N, $G_{11}$ is C—$R^{11}$, $R^{11}$ is -L$^1$-R$^3$, and $G_{10}$ is C—$R^{10}$, provided is a compound of Formula (I-i):

(I-l)

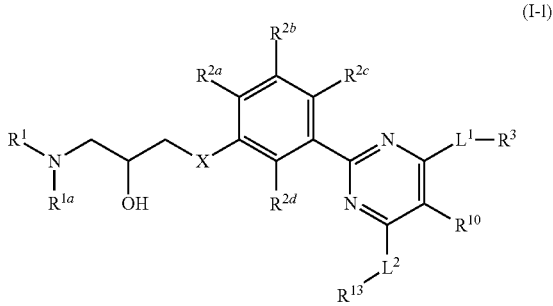

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$, —(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is an acyclic moiety. In certain embodiments, $R^3$ is a cyclic moiety. In certain embodiments, $R^{10}$ is hydrogen, optionally substituted alkyl (e.g., methyl, ethyl, —CH$_2$OH, CHF$_2$), optionally substituted C$_{3-4}$cycloalkyl (e.g., cyclopropyl, cyclobutyl), or halo (e.g., fluoro, chloro, bromo, iodo). In certain embodiments, $R^{10}$ is hydrogen, methyl, or halogen (e.g., chloro).

In other embodiments of Formula (I-h), wherein $G_8$ and $G_{10}$ are both N, provided is a compound of Formula (I-m):

(I-m)

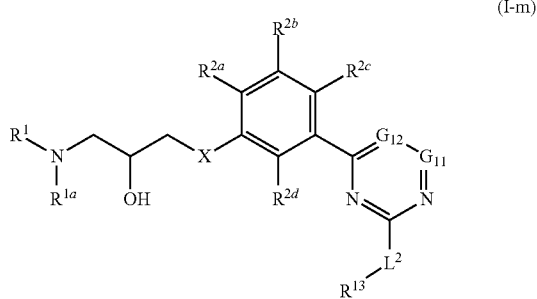

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^2$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$, —(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)NR$^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl.

In certain embodiments of Formula (I-h), wherein $G_8$ and $G_{12}$ are both N, and $G_{11}$ is C—$R^{11}$, provided is a compound of Formula (I-n):

(I-n)

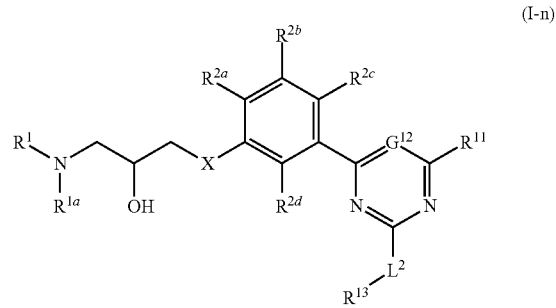

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$), —C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $R^{11}$ is hydrogen or a group -$L^1$-$R^3$.

In certain embodiments of Formula (I-h), wherein $G_8$ and $G_{12}$ are both N, $G_{11}$ is C—$R^{11}$, and $G_{12}$ is C—$R^{12}$, provided is a compound of Formula (I-o):

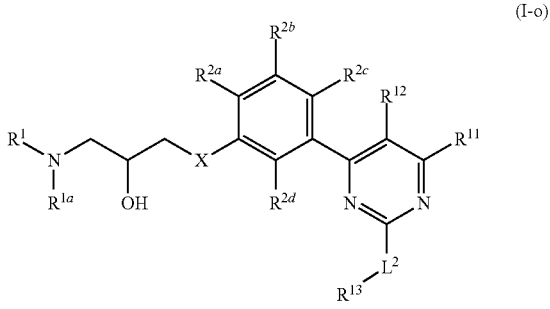

(I-o)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, L is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$)—, —(CH$_2$)$_x$—O—, —NR C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $R^{11}$ is hydrogen or a group -$L^1$-$R^3$. In certain embodiments, $R^{12}$ is hydrogen or methyl.

In certain embodiments of Formula (I-h), wherein G$_8$ and G$_{12}$ are both N, G$_{11}$ is C—$R^{11}$, $R^{11}$ is a group of formula -$L^1$-$R^3$, and G$_{12}$ is C—$R^{12}$, provided is a compound of Formula (I-p):

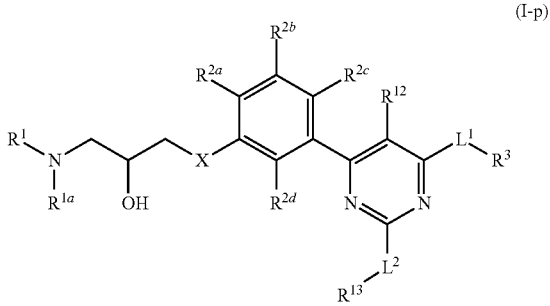

(I-p)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted C$_{1-4}$alkyl, optionally substituted C$_{2-4}$alkenyl, optionally substituted C$_{2-4}$alkynyl, wherein $R^{A2}$ is optionally substituted alkyl. In certain embodiments, $L^2$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$, —(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^{13}$ is optionally substituted heterocylyl or optionally substituted heteroaryl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$, —(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is an acyclic moiety. In certain embodiments, $R^3$ is a cyclic moiety. In certain embodiments, $R^{12}$ is hydrogen or methyl.

In any of the above embodiments, as recited herein, in certain embodiments, $R^{13}$ is an optionally substituted heteroaryl, e.g., an optionally substituted 5-membered heteroaryl. For example, in any of the above embodiments, as recited herein, $R^{13}$ is a group of Formula:

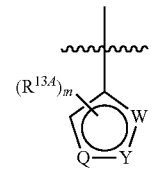

wherein Y is O, S, N, or NR$^{13B}$ and each instance of Q and W is independently CH, CR$^{13A}$, N, or NR$^{13B}$, as valency permits, m is 0 or 1, and R$^{13A}$ and R$^{13B}$ are as defined herein. In certain embodiments, Y is O. In certain embodiments, Y is S. In certain embodiments, Y is NR$^{13B}$ In certain embodiments, Q is N, Y is O, and W is CH or CR$^{13A}$. In certain embodiments, Q is N, Y is S, and W is CH or CR$^{13A}$. In certain embodiments, Q is N, Y is NR$^{13B}$, and W is CH or CR$^{13A}$. In certain embodiments, Q is N, Y is O, and W is N. In certain embodiments, Q is N, Y is S, and W is N. In certain embodiments, Q is N, Y is NR$^{13B}$, and W is N. In certain embodiments, Q is N, Y is N, and W is NR$^{13B}$. In certain embodiments, if Q is NR$^{13A}$, then neither Y nor W is O. In certain embodiments, if Q is NR$^{13A}$, then neither Y nor W is S. In certain embodiments, if Y is NR$^{13A}$, then neither Q nor W is O. In certain embodiments, if Y is NR$^{13A}$, then neither Q nor W is S. In certain embodiments, if W is NR$^{13A}$, then neither Y nor Q is O. In certain embodiments, if W is NR$^{13A}$, then neither Y nor Q is S. In certain embodiments, only one of Q, Y, and W is NR$^{13A}$. In any of these instances, in certain embodiments, $L^2$ is a bond.

For example, in certain embodiments of Formula (I-1), provided is a compound of Formula (I-1-A) or (I-1-A'):

(I-1-A)

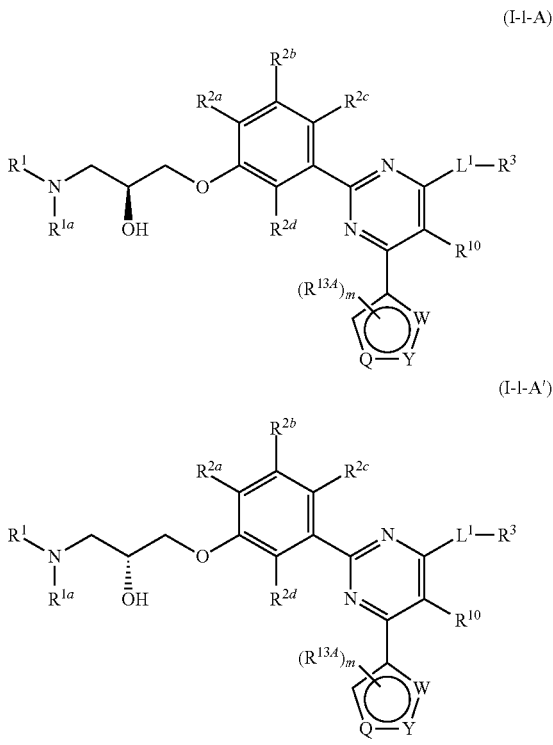

(I-1-A')

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $R^{2b}$ is hydrogen or halogen (e.g., chloro, fluoro), and $R^{2a}$, $R^{2c}$, and $R^{2d}$ is hydrogen. In certain embodiments, $R^{2a}$ $R^{2b}$, and $R^{2d}$ are hydrogen. In certain embodiments, $R^{2c}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $R^{2c}$ is hydrogen or halogen (e.g., chloro, fluoro), and $R^{2a}$, $R^{2b}$, and $R^{2d}$ is hydrogen. In certain embodiments, L is a bond, —N($R^L$)—, —N$R^L$C(O)O—, —N$R^L$C(O)N($R^L$)—, —N($R^L$)—, —N($R^L$)SO$_2$N($R^L$)—, —N$R^L$, —(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$, or —N$R^L$(CH$_2$)$_x$N$R^L$C(O)—. In certain embodiments, $R^3$ is an acyclic moiety. In certain embodiments, $R^3$ is a cyclic moiety. In certain embodiments, $R^{10}$ is hydrogen, optionally substituted alkyl (e.g., methyl, ethyl, —CH$_2$OH, CHF$_2$), optionally substituted $C_{3-4}$cycloalkyl (e.g., cyclopropyl, cyclobutyl), or halo (e.g., fluoro, chloro, bromo, iodo). In certain embodiments, $R^{10}$ is hydrogen, methyl, or halogen (e.g., chloro). In certain embodiments, Y is O. In certain embodiments, Y is S. In certain embodiments, Y is N$R^{13B}$. In certain embodiments, Q is N, Y is O, and W is CH or C$R^{13A}$. In certain embodiments, Q is N, Y is S, and W is CH or C$R^{13A}$. In certain embodiments, Q is N, Y is N$R^{13B}$, and W is CH or C$R^{13A}$. In certain embodiments, Q is N, Y is O, and W is N. In certain embodiments, Q is N, Y is S, and W is N. In certain embodiments, Q is N, Y is N$R^{13B}$, and W is N. In certain embodiments, Q is N, Y is N, and W is N$R^{13B}$. In certain embodiments, m is 0. In certain embodiments, m is 1, and $R^{13A}$ is optionally substituted alkyl (e.g., methyl)

In certain embodiments of Formula (I-1-A) or (I-1-A'), wherein Q is N, provided is a compound of Formula (I-1-Aa) or (I-1-Aa'):

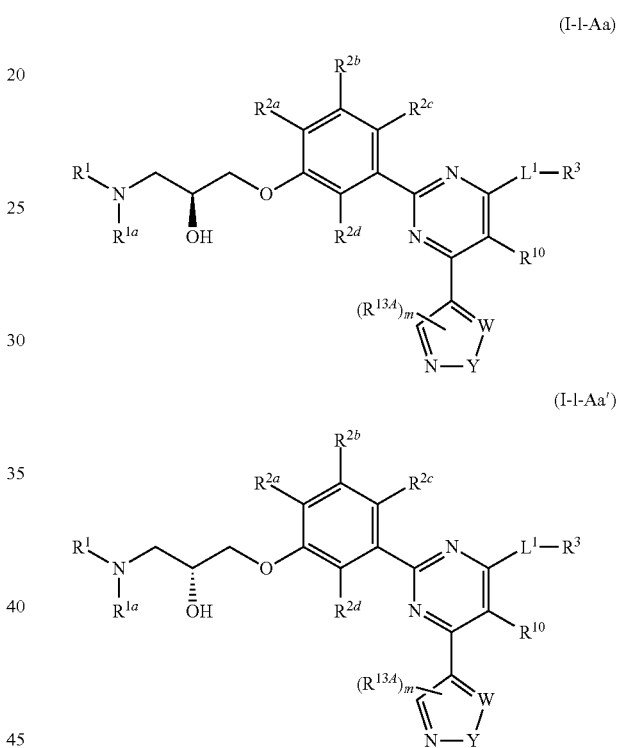

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $L^1$ is a bond or —N($R^L$)—. In certain embodiments, $R^3$ is a cyclic moiety. In certain embodiments, $R^{10}$ is hydrogen, methyl, or chloro. In certain embodiments, W is CH or C$R^{13A}$. In certain embodiments, W is N. In certain embodiments, m is 0. In certain embodiments, m is 1, and $R^{13A}$ is optionally substituted alkyl (e.g., methyl).

In certain embodiments of Formula (I-1-Aa) or (I-1-Aa'), wherein $L^1$ is —N($R^L$)—, provided is a compound of Formula (I-1-Aa1) or (I-1-Aa1'):

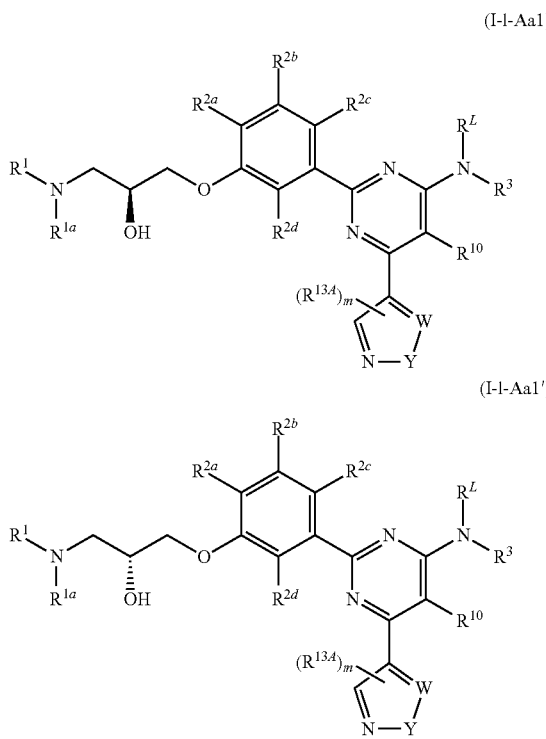

(I-1-Aa1)

(I-1-Aa1')

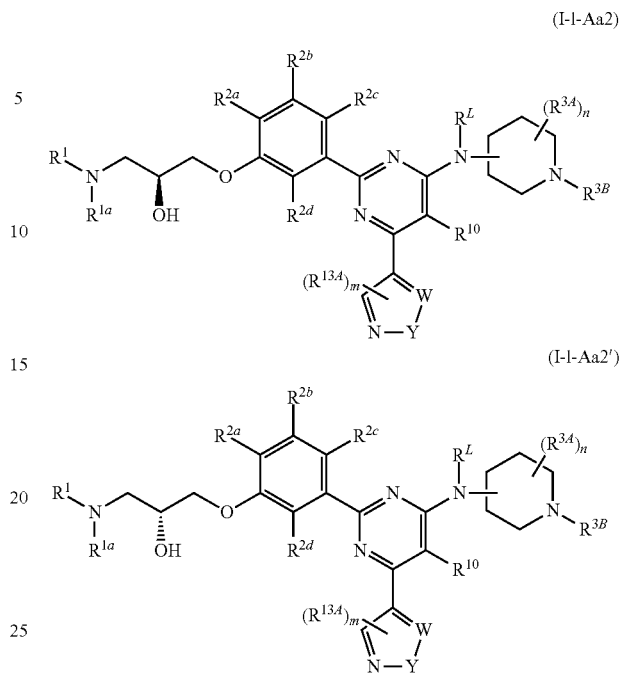

(I-1-Aa2)

(I-1-Aa2')

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^L$ is hydrogen. In certain embodiments, $R^3$ is a cyclic moiety. In certain embodiments, $R^{10}$ is hydrogen, methyl, or chloro. In certain embodiments, W is CH or $CR^{13A}$. In certain embodiments, W is N. In certain embodiments, m is 0. In certain embodiments, m is 1, and $R^{13A}$ is optionally substituted alkyl (e.g., methyl). In certain embodiments, $R^L$ and $R^3$ are taken together to form an optionally substituted heterocyclic ring. In certain embodiments, $R^L$ and $R^3$ are taken together to form an optionally substituted heterocyclic ring which is fused to an optionally substituted aromatic ring. In certain embodiments, $R^L$ and $R^3$ are taken together to form an optionally substituted heterocyclic ring which is fused to an optionally substituted heteroaromatic ring. In certain embodiments, $R^L$ and $R^3$ are taken together to form an optionally substituted bicyclic heterocyclic ring system. In certain embodiments, $R^L$ and $R^3$ are taken together to form an optionally substituted ortho-fused heterocyclic ring system. In certain embodiments, $R^L$ and $R^3$ are taken together to form an optionally substituted spiro-fused heterocyclic ring system. In certain embodiments, $R^1$ and $R^3$ are taken together to form an optionally substituted bridged heterocyclic ring system.

In certain embodiments of Formula (I-1-Aa) or (I-1-Aa'), wherein $L^1$ is —N($R^L$)—, provided is a compound of Formula (I-1-Aa2) or (I-1-Aa2'):

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$), and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^L$ is hydrogen. In certain embodiments, $R^{3B}$ is —CO$_2R^{aa}$. In certain embodiments, $R^{aa}$ is $C_{1-10}$ alkyl. In certain embodiments, $R^{3B}$ is —CO$_2$Me. In certain embodiments, $R^{3B}$ is —CO$_2$Et. In certain embodiments, $R^{3B}$ is a nitrogen protecting group. In certain embodiments, $R^{10}$ is hydrogen, methyl, or chloro. In certain embodiments, W is CH or $CR^{13}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted $C_{1-6}$ alkyl. In certain embodiments, $R^{3A}$ is methyl.

In certain embodiments of Formula (I-1-Aa) or (I-1-Aa'), wherein $L^1$ is —N($R^L$)—, provided is a compound of Formula (I-1-Aa3) or (I-1-Aa3'):

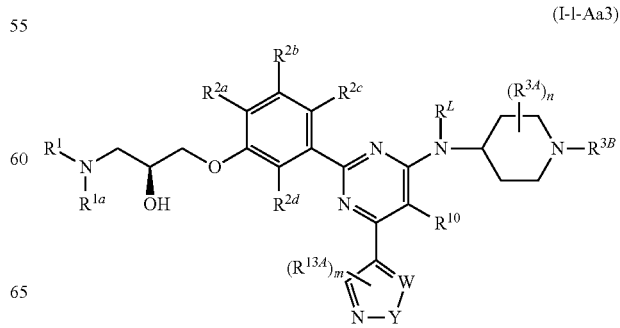

(I-1-Aa3)

-continued (I-1-Aa3')

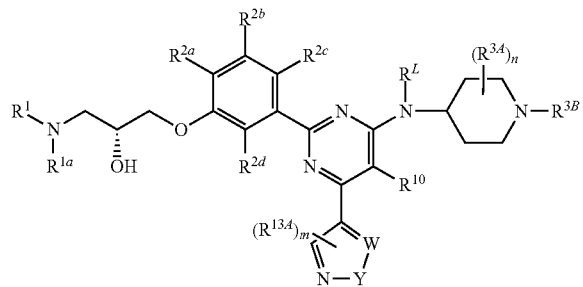

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^L$ is hydrogen. In certain embodiments, $R^{3B}$ is —CO$_2$R$^{aa}$. In certain embodiments, $R^{aa}$ is C$_{1-10}$ alkyl. In certain embodiments, $R^{3B}$ is —CO$_2$Me. In certain embodiments, $R^{3B}$ is —CO$_2$Et. In certain embodiments, $R^{3B}$ is a nitrogen protecting group. In certain embodiments, $R^{10}$ is hydrogen, methyl, or chloro. In certain embodiments, W is CH or CR$^{13}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted C$_{1-6}$ alkyl. In certain embodiments, $R^{3A}$ is methyl.

In certain embodiments of Formula (I-1-Aa) or (I-1-Aa'), wherein $L^1$ is —N(R$^L$)—, provided is a compound of Formula (I-1-Aa4) or (I-1-Aa4'):

(I-1-Aa4)

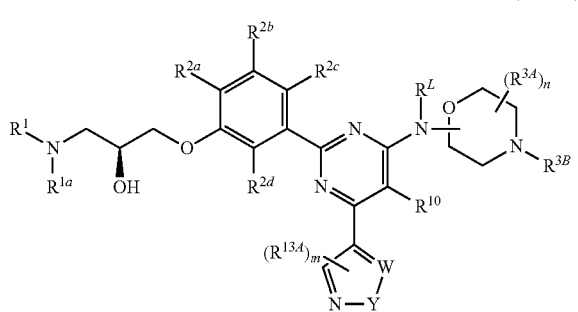

(I-1-Aa4')

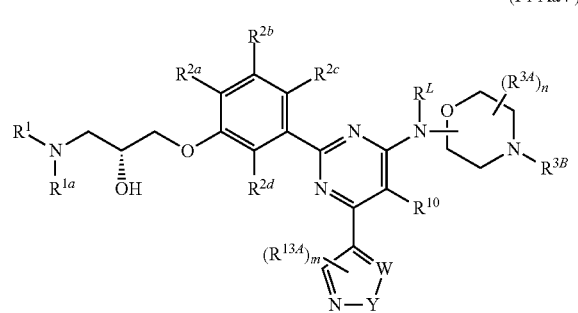

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^L$ is hydrogen. In certain embodiments, $R^{3B}$ is —CO$_2$R$^{aa}$. In certain embodiments, $R^{aa}$ is C$_{1-10}$ alkyl. In certain embodiments, $R^{3B}$ is —CO$_2$Me. In certain embodiments, $R^{3B}$ is —CO$_2$Et. In certain embodiments, $R^{3B}$ is a nitrogen protecting group. In certain embodiments, $R^{10}$ is hydrogen, methyl, or chloro. In certain embodiments, W is CH or CR$^{13A}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted C$_{1-6}$ alkyl. In certain embodiments, $R^{3A}$ is methyl.

In certain embodiments of Formula (I-1-Aa) or (I-1-Aa'), wherein $L^1$ is —N(R$^L$)—, provided is a compound of Formula (I-1-Aa5) or (I-1-Aa5'):

(I-1-Aa5)

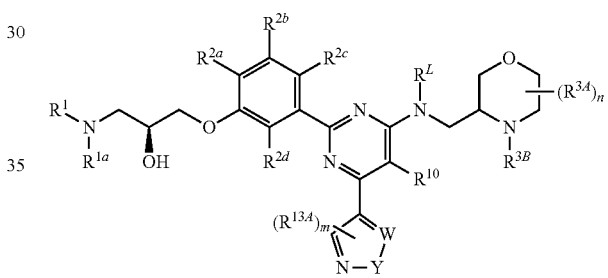

(I-1-Aa5')

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —CH$_3$) and $R^{1a}$ is hydrogen. In certain embodiments, each of $R^1$ and $R^{1a}$ is non-hydrogen (e.g., each is —CH$_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^L$ is hydrogen. In certain embodiments, $R^{3B}$ is —CO$_2$R$^{aa}$. In certain embodiments, $R^{aa}$ is C$_{1-10}$ alkyl. In certain embodiments, $R^{3B}$ is —CO$_2$Me. In certain embodiments, $R^{3B}$ is —CO$_2$Et. In certain embodiments, $R^{3B}$ is a nitrogen protecting group. In certain embodiments, $R^{10}$ is hydrogen, methyl, or chloro. In certain embodiments, W is CH or $CR^{13}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted $C_{1-6}$ alkyl. In certain embodiments, $R^{3A}$ is methyl. In certain embodiments, the stereochemistry at the morpholine sidechain is

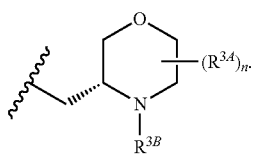

In certain embodiments, the stereochemistry at the morpholine sidechain is

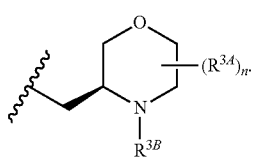

In certain embodiments of Formula (I-1-Aa) or (I-1-Aa'), wherein $L^1$ is a bond, provided is a compound of Formula (I-1-Aa6) or (I-1-Aa6'):

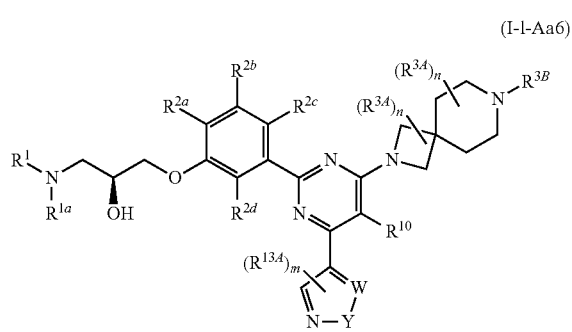

(I-l-Aa6)

(I-l-Aa6')

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —$CH_3$) and $R^{1a}$ is hydrogen. In certain embodiments, each of $R^1$ and $R^{1a}$ is non-hydrogen (e.g., each is —$CH_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^{3B}$ is $CO_2R^{aa}$. In certain embodiments, $R^{1a}$ is $C_{1-10}$ alkyl. In certain embodiments, $R^{3B}$ is $CO_2Me$. In certain embodiments, $R^{3B}$ is $CO_2Et$. In certain embodiments, $R^{3B}$ is a nitrogen protecting group. In certain embodiments, $R^{10}$ is hydrogen, methyl, or chloro. In certain embodiments, W is CH or $CR^{13A}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted $C_{1-6}$ alkyl. In certain embodiments, $R^{3A}$ is methyl.

In certain embodiments of Formula (I-1-Aa) or (I-1-Aa'), wherein $L^1$ is a bond, provided is a compound of Formula (I-1-Aa7) or (I-1-Aa7'):

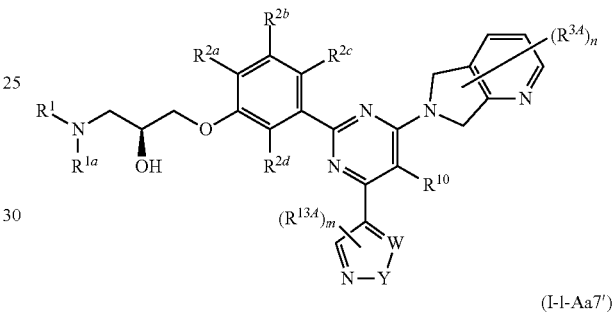

(I-l-Aa7)

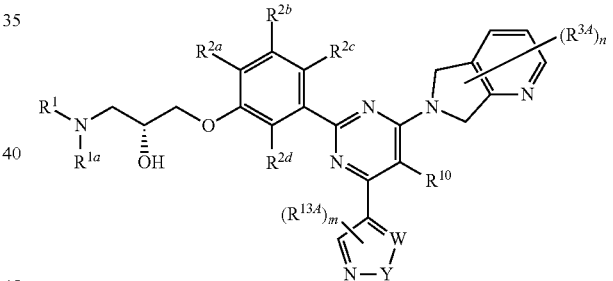

(I-l-Aa7')

or a pharmaceutically acceptable salt thereof. In certain embodiments, X is —O—. In certain embodiments, $R^1$ is hydrogen or methyl. In certain embodiments, $R^{1a}$ is hydrogen. In certain embodiments, $R^1$ is non-hydrogen (e.g., —$CH_3$) and $R^{1a}$ is hydrogen. In certain embodiments, each of $R^1$ and $R^{1a}$ is non-hydrogen (e.g., each is —$CH_3$). In certain embodiments, each of $R^1$ and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $R^{10}$ is hydrogen, methyl, or chloro. In certain embodiments, W is CH or $CR^{13A}$. In certain embodiments, W is N. In certain embodiments, m is 0. In certain embodiments, m is 1, and $R^{13A}$ is optionally substituted alkyl (e.g., methyl). In certain embodiments, n is 0. In certain embodiments, n is 1. In certain embodiments, $R^{3A}$ is a optionally substituted $C_{1-6}$ alkyl. In certain embodiments, $R^{3A}$ is methyl. In certain embodiments of Formula (I-1-Aa) or (I-1-Aa'), wherein Y is O and W is $CR^{13A}$, provided is a compound of Formula (I-1-Ab) or (I-1-Ab'):

(I-l-Ab)

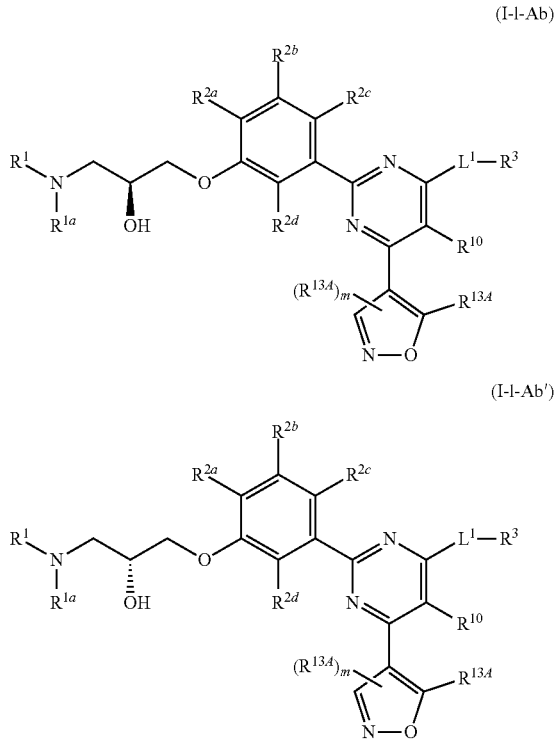

(I-l-Ab')

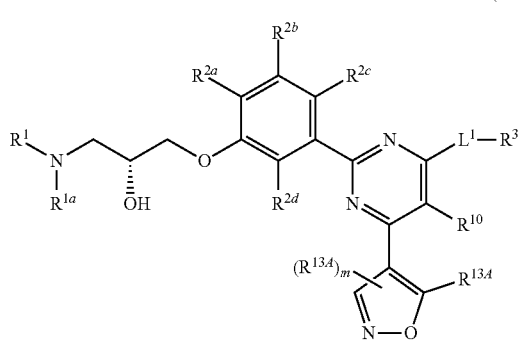

or a pharmaceutically acceptable salt thereof. In certain embodiments, X is —O—. In certain embodiments, R¹ is hydrogen or methyl. In certain embodiments, $R^{1a}$ is hydrogen or methyl. In certain embodiments, $R^{1a}$ is hydrogen. In certain embodiments, both $R^1$ and $R^{1a}$ are hydrogen or methyl. In certain embodiments, both $R^1$ and $R^{1a}$ are methyl. In certain embodiments, $R^1$ is methyl; and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $L^1$ is a bond or —N($R^L$)—. In certain embodiments, $R^3$ is a cyclic moiety. In certain embodiments, $R^{10}$ is hydrogen, methyl, or chloro. In certain embodiments, m is 0. In certain embodiments, m is 1, and $R^{13A}$ is optionally substituted alkyl (e.g., methyl).

In certain embodiments of Formula (I-1-A) or (I-1-A'), wherein Q is N, Y is N, and W is $NR^{13B}$, provided is a compound of Formula (I-1-Ac) or (I-1-Ac'):

(I-l-Ac)

(I-l-Ac')

or a pharmaceutically acceptable salt thereof. In certain embodiments, X is —O—. In certain embodiments, R¹ is hydrogen or methyl. In certain embodiments, $R^{1a}$ is hydrogen or methyl. In certain embodiments, $R^{1a}$ is hydrogen. In certain embodiments, $R^{1a}$ is hydrogen. In certain embodiments, both $R^1$ and $R^{1a}$ are hydrogen or methyl. In certain embodiments, both $R^1$ and $R^{1a}$ are methyl. In certain embodiments, $R^1$ is methyl; and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $L^1$ is a bond or —N($R^L$)—. In certain embodiments, $R^3$ is a cyclic moiety. In certain embodiments, $R^{10}$ is hydrogen, methyl, or chloro. In certain embodiments, m is 0. In certain embodiments, m is 1, and $R^{13A}$ is optionally substituted alkyl (e.g., methyl).

In any of the above embodiments, as recited herein, in certain embodiments $R^{13}$ is an optionally substituted heterocyclyl, e.g., an optionally substituted 5- to 6-membered heterocylyl. For example, in any of the above embodiments, as recited herein, in certain embodiments $R^{13}$ is a group of formula:

wherein x is 0 or 1, m is 0, 1, 2, or 3, and $R^{13A}$ is as defined herein. In this instance, in certain embodiments, $L^2$ is —N($R^L$)—.

For example, in certain embodiments of Formula (I-1), provided is a compound of Formula (I-1-B) or (I-1-B'):

(I-l-B)

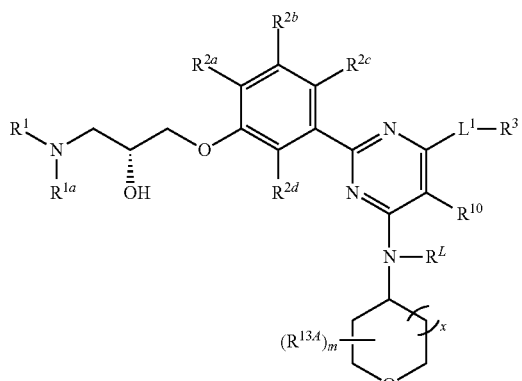

(I-1-B')

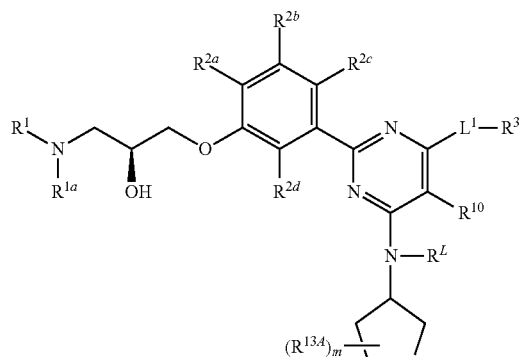

(I-1-Ba)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{1a}$ is hydrogen, methyl, ethyl, n-propyl, isopropyl, or cyclopropyl. In certain embodiments, $R^{1a}$ is hydrogen. In certain embodiments, both $R^1$ and $R^{1a}$ are hydrogen, methyl, ethyl, n-propyl, isopropyl, or cyclopropyl. In certain embodiments, both $R^1$ and $R^{1a}$ are methyl. In certain embodiments, $R^1$ is methyl; and $R^{1a}$ is hydrogen. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $R^{2b}$ is hydrogen or halogen (e.g., chloro, fluoro), and $R^{2}$, $R^{2c}$, and $R^{2d}$ is hydrogen. In certain embodiments, $R^{2a}$, $R^{2b}$, and $R^{2d}$ are hydrogen. In certain embodiments, $R^{2c}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $R^{2c}$ is hydrogen or halogen (e.g., chloro, fluoro), and $R^{2a}$, $R^{2b}$, and $R^{2d}$ is hydrogen. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)—N$R^L$—, —N$R^L$C(O)O(CH$_2$)$_x$—, —N$R^L$C(O)N$R^L$(CH$_2$)—, or —N$R^L$(CH$_2$)$_x$N$R^L$C(O)—. In certain embodiments, $R^3$ is an acyclic moiety. In certain embodiments, $R^3$ is a cyclic moiety. In certain embodiments, $R^{10}$ is hydrogen, optionally substituted alkyl (e.g., methyl, ethyl, —CH$_2$OH, CHF$_2$), optionally substituted $C_{3-4}$cycloalkyl (e.g., cyclopropyl, cyclobutyl), or halo (e.g., fluoro, chloro, bromo, iodo). In certain embodiments, $R^{10}$ is hydrogen, methyl, or halogen (e.g., chloro). In certain embodiments, $R^{10}$ is methyl. In certain embodiments, x is 0. In certain embodiments, x is 1. In certain embodiments, m is 0 or 1. In certain embodiments, $R^L$ is hydrogen or optionally substituted alkyl (e.g., methyl).

In certain embodiments of Formula (I-1-B) or (I-1-B'), wherein x is 0 or 1, provided is a compound of Formula (I-1-Ba) or (I-1-Ba') or Formula (I-1-Bb) or (I-1-Bb'):

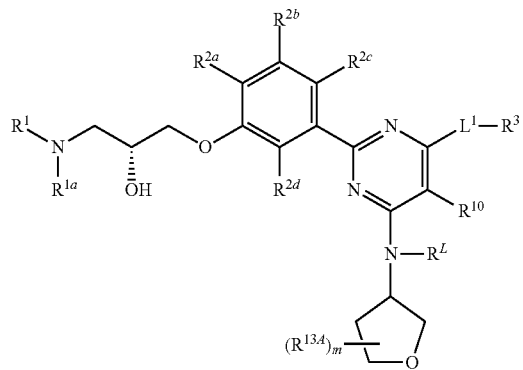

(I-1-Ba')

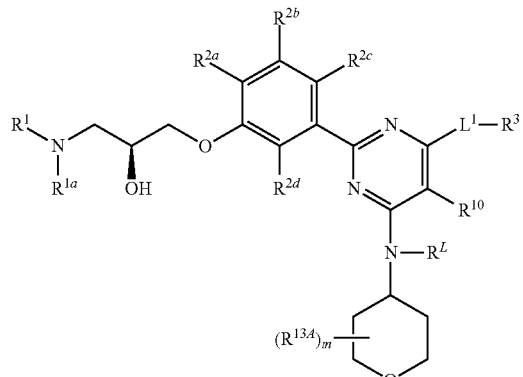

(I-1-Bb)

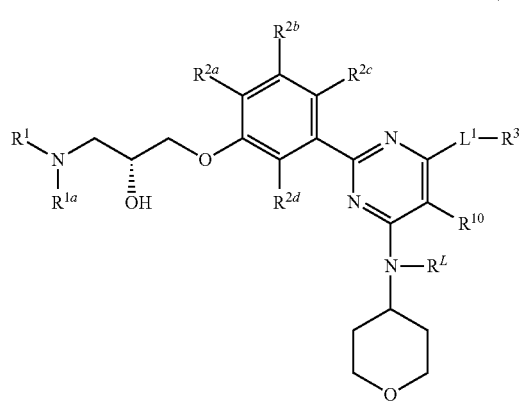

(I-1-Bb')

or a pharmaceutically acceptable salt thereof. In certain embodiments, X is —O—. In certain embodiments, $R^1$ is hydrogen or methyl. In certain embodiments, $R^{1a}$ is hydrogen or methyl. In certain embodiments, $R^{1a}$ is hydrogen. In certain embodiments, both $R^1$ and $R^{1a}$ are hydrogen or methyl. In certain embodiments, both $R^1$ and $R^{1a}$ are methyl. In certain embodiments, $R^1$ is methyl; and $R^{1a}$ is hydrogen. In certain embodiments, $R^{2a}$, $R^{2b}$, and $R^{2d}$ are hydrogen. In certain embodiments, $R^{2c}$ is hydrogen, chloro, or fluoro, and $R^{2a}$, $R^{2b}$, and $R^{2d}$ is hydrogen. In certain embodiments, $L^1$ is a bond or —N($R^L$)—. In certain embodiments, $R^3$ is a cyclic moiety. In certain embodiments, $R^{10}$ is hydrogen, methyl, or chloro. In certain embodiments, m is 0 or 1. In certain embodiments, $R^L$ is hydrogen or methyl.

In certain embodiments, a compound of Formula (I) is selected from any one of the compounds provided in Tables 1A, 1B, 1C, and 2, and pharmaceutically acceptable salts thereof.

TABLE 1A

Exemplary Compounds

| # | Structure | LC-MS m/z (M + H) |
|---|-----------|-------------------|
| 1-1 | 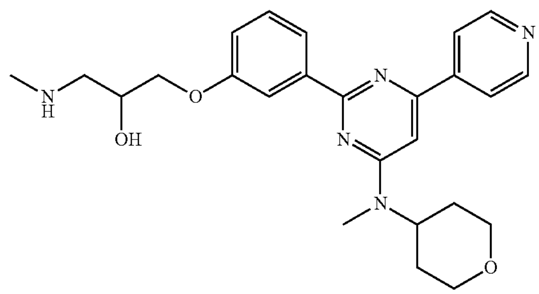 [SMILES: CNCC(O)COc1cccc(-c2nc(-c3ccncc3)cc(N(C)C3CCOCC3)n2)c1] | 450.3 |
| 3-1 | 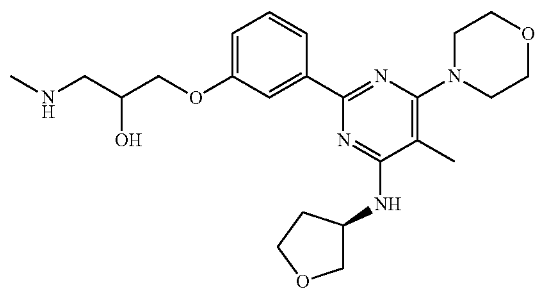 [SMILES: CNCC(O)COc1cccc(-c2nc(N[C@@H]3CCOC3)c(C)c(N3CCOCC3)n2)c1] | 444.3 |
| 4-1 | 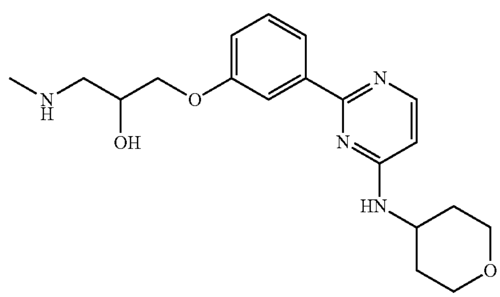 [SMILES: CNCC(O)COc1cccc(-c2nccc(NC3CCOCC3)n2)c1] | 359.2 |
| 5-1 | 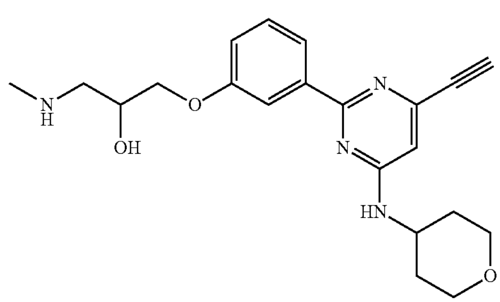 [SMILES: C#Cc1cc(NC2CCOCC2)nc(-c2cccc(OCC(O)CNC)c2)n1] | 383.2 |

TABLE 1A-continued

Exemplary Compounds

| # | Structure | LC-MS m/z (M + H) |
|---|---|---|
| 6-1 | 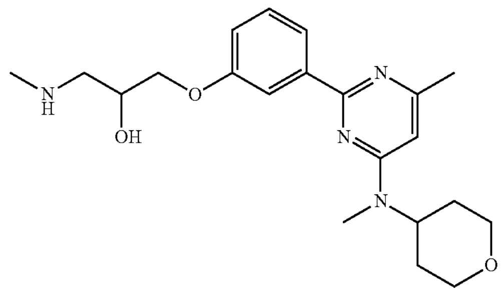 [SMILES: CNCC(O)COc1cccc(-c2nc(C)cc(N(C)C3CCOCC3)n2)c1] | 387.2 |
| 7-1 | 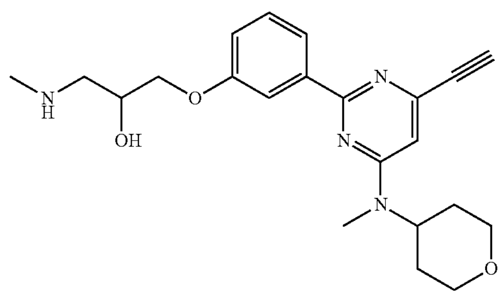 [SMILES: C#Cc1cc(N(C)C2CCOCC2)nc(-c2cccc(OCC(O)CNC)c2)n1] | 397.2 |
| 8-1 | 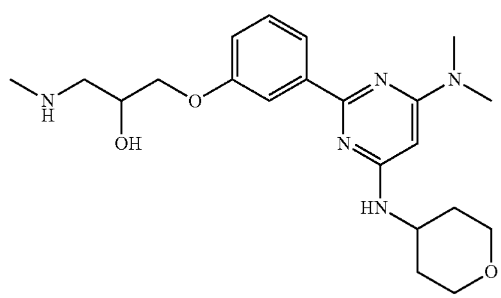 | 403.3 |
| 9-1 | 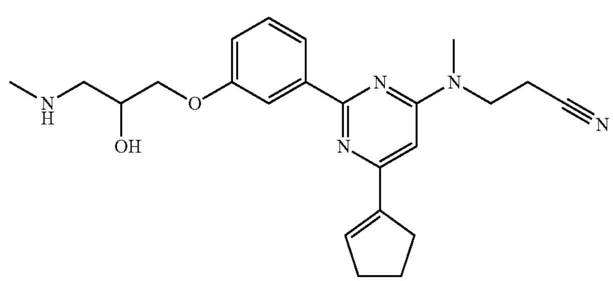 [SMILES: CNCC(O)COc1cccc(-c2nc(C3=CCCC3)cc(N(C)CCC#N)n2)c1] | 408.1 |
| 10-1 | 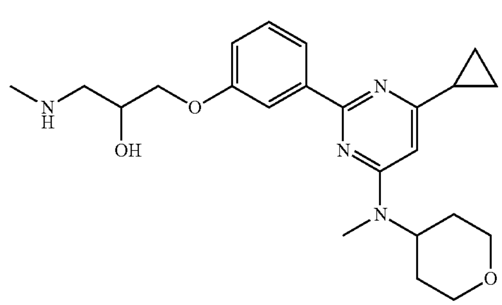 [SMILES: CNCC(O)COc1cccc(-c2nc(C3CC3)cc(N(C)C3CCOCC3)n2)c1] | 413.3 |

TABLE 1A-continued

Exemplary Compounds

| # | Structure | LC-MS m/z (M + H) |
|---|---|---|
| 11-1 | 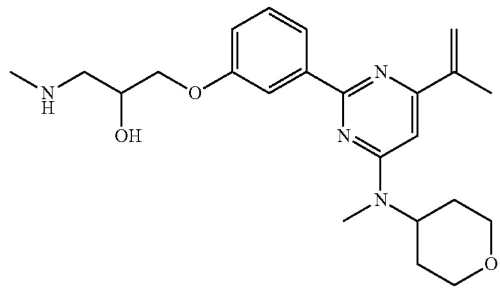 | 413.3 |
| 12-1 | 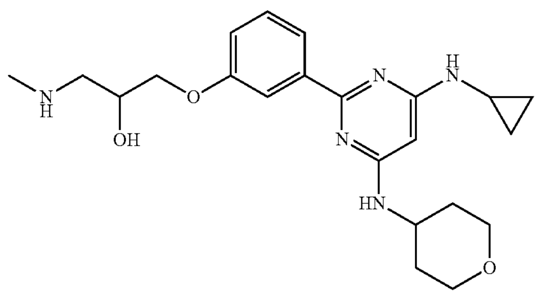 [SMILES: CNCC(O)COc1cccc(-c2nc(NC3CCOCC3)cc(NC3CC3)n2)c1] | 414.2 |
| 13-1 | 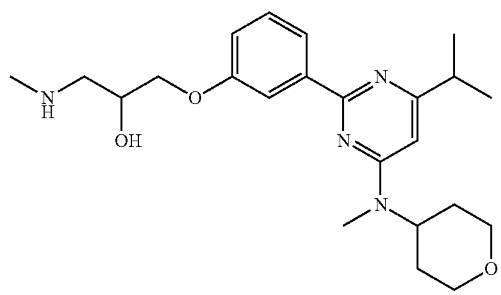 [SMILES: CNCC(O)COc1cccc(-c2nc(C(C)C)cc(N(C)C3CCOCC3)n2)c1] | 415.3 |
| 14-1 | 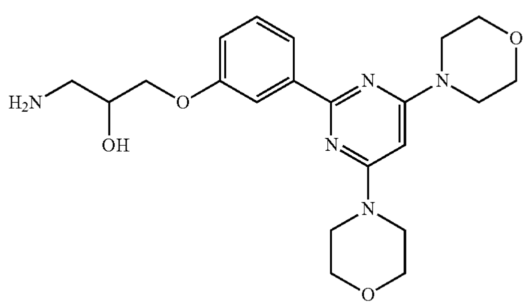 [SMILES: NCC(O)COc1cccc(-c2nc(N3CCOCC3)cc(N3CCOCC3)n2)c1] | 416.3 |
| 15-1 | 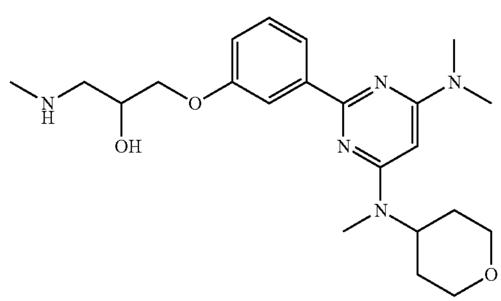 | 416.3 |

TABLE 1A-continued

Exemplary Compounds

| # | Structure | LC-MS m/z (M + H) |
|---|-----------|-------------------|
| 16-1 | 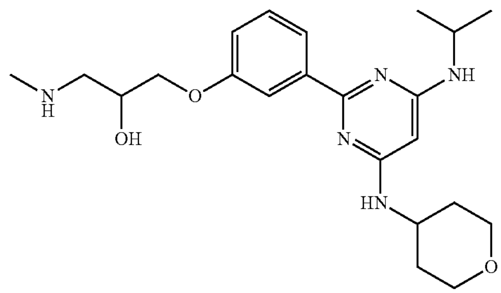 [SMILES: CNCC(O)COc1cccc(-c2nc(NC(C)C)cc(NC3CCOCC3)n2)c1] | 416.3 |
| 17-1 | 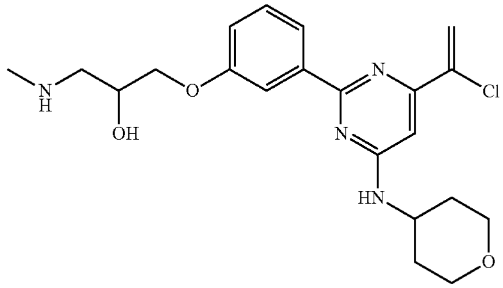 [SMILES: C=C(Cl)c1cc(NC2CCOCC2)nc(-c2cccc(OCC(O)CNC)c2)n1] | 419.2 |
| 18-1 | 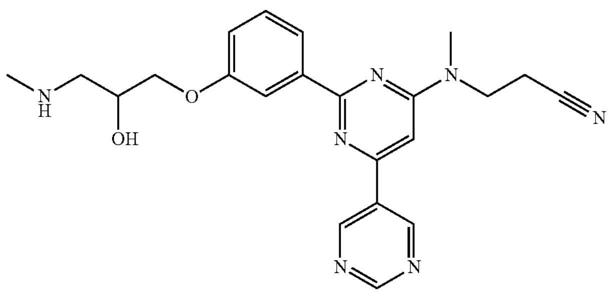 [SMILES: CNCC(O)COc1cccc(-c2nc(-c3cncnc3)cc(N(C)CCC#N)n2)c1] | 420.1 |
| 19-1 | 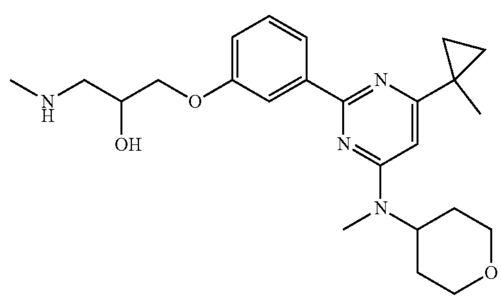 [SMILES: CNCC(O)COc1cccc(-c2nc(N(C)C3CCOCC3)cc(C3(C)CC3)n2)c1] | 427.2 |
| 20-1 | 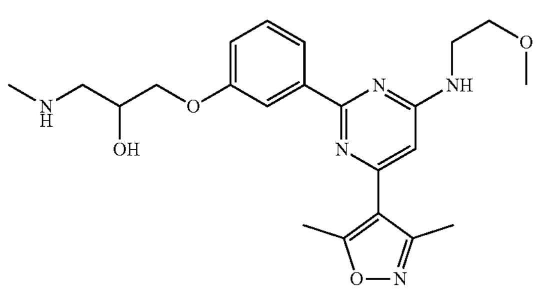 | 428.3 |

TABLE 1A-continued

Exemplary Compounds

| # | Structure | LC-MS m/z (M + H) |
|---|-----------|-------------------|
| 21-1 | 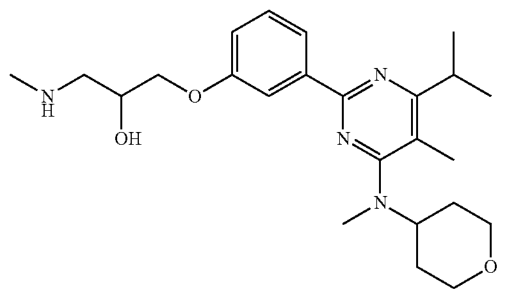 [SMILES: CNCC(O)COc1cccc(-c2nc(C(C)C)c(C)c(N(C)C3CCOCC3)n2)c1] | 429.3 |
| 22-1 | 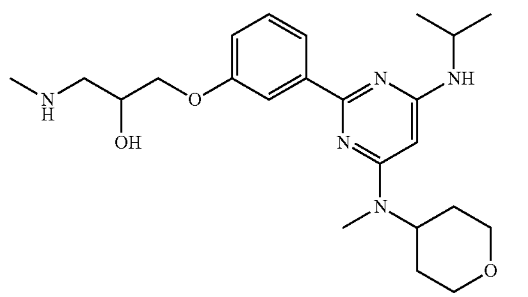 [SMILES: CNCC(O)COc1cccc(-c2nc(NC(C)C)cc(N(C)C3CCOCC3)n2)c1] | 430.3 |
| 23-1 | 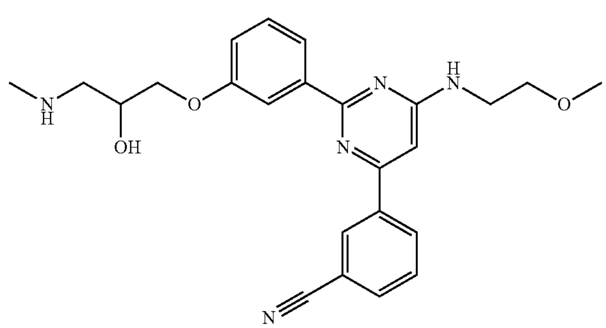 | 434.2 |
| 24-1 | 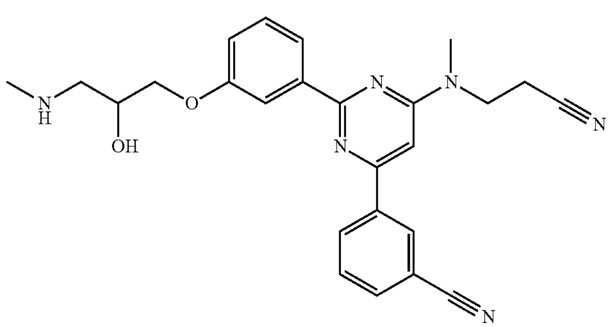 [SMILES: CNCC(O)COc1cccc(-c2nc(-c3cccc(C#N)c3)cc(N(C)CCC#N)n2)c1] | 443.2 |

TABLE 1A-continued

Exemplary Compounds

| # | Structure | LC-MS m/z (M + H) |
|---|---|---|
| 25-1 | 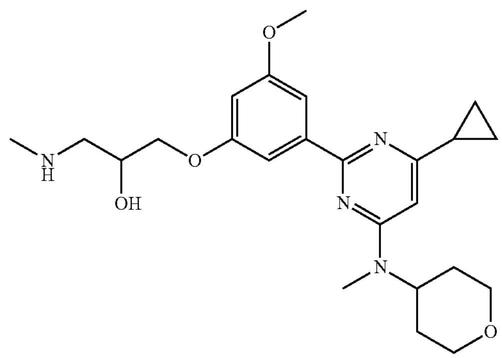 [SMILES: CNCC(O)COc1cc(OC)cc(-c2nc(C3CC3)cc(N(C)C3CCOCC3)n2)c1] | 443.3 |
| 26-1 | 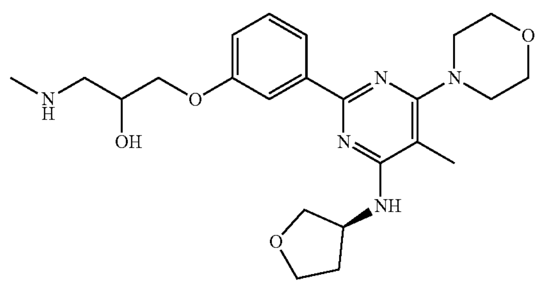 [SMILES: CNCC(O)COc1cccc(-c2nc(N[C@H]3CCOC3)c(C)c(N3CCOCC3)n2)c1] | 444.3 |
| 27-1 | 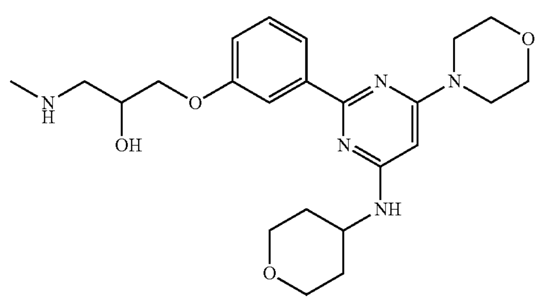 [SMILES: CNCC(O)COc1cccc(-c2nc(NC3CCOCC3)cc(N3CCOCC3)n2)c1] | 444.4 |
| 28-1 | 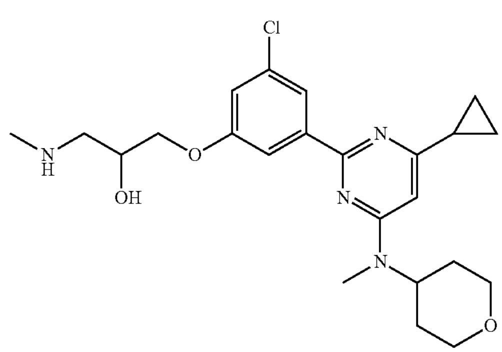 [SMILES: CNCC(O)COc1cc(Cl)cc(-c2nc(C3CC3)cc(N(C)C3CCOCC3)n2)c1] | 447.3 |

TABLE 1A-continued

Exemplary Compounds

| # | Structure | LC-MS m/z (M + H) |
|---|---|---|
| 29-1 | 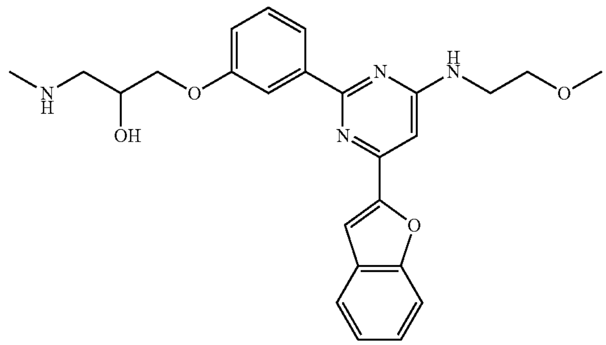 | 449.2 |
| 30-1 | 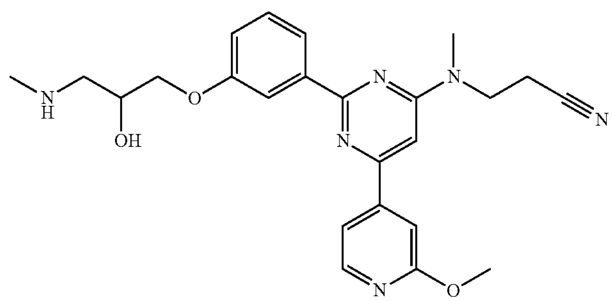 [SMILES: CNCC(O)COc1cccc(-c2nc(-c3ccnc(OC)c3)cc(N(C)CCC#N)n2)c1] | 449.2 |
| 31-1 | 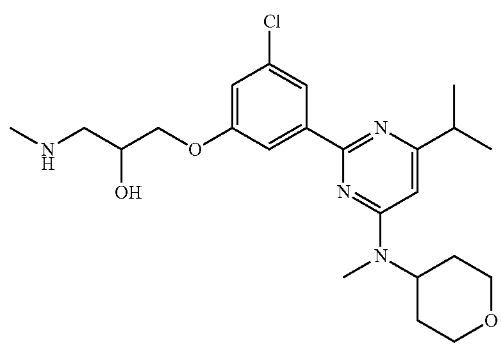 [SMILES: CNCC(O)COc1cc(Cl)cc(-c2nc(C(C)C)cc(N(C)C3CCOCC3)n2)c1] | 449.2 |
| 32-1 | 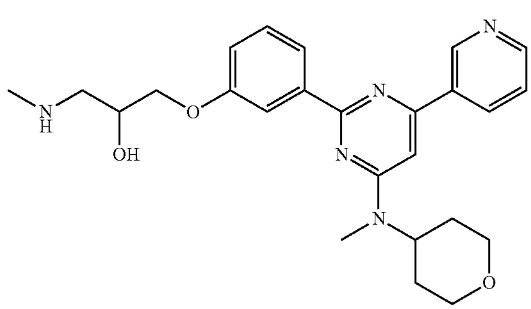 [SMILES: CNCC(O)COc1cccc(-c2nc(-c3cccnc3)cc(N(C)C3CCOCC3)n2)c1] | 450.2 |

TABLE 1A-continued
Exemplary Compounds
| # | Structure | LC-MS m/z (M + H) |
|---|---|---|
| 33-1 | 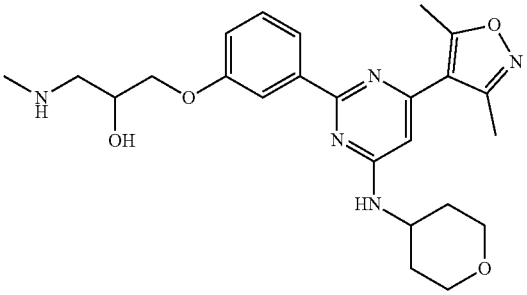 [SMILES: CNCC(O)COc1cccc(-c2nc(NC3CCOCC3)cc(-c3c(C)noc3C)n2)c1] | 454.3 |
| 34-1 | 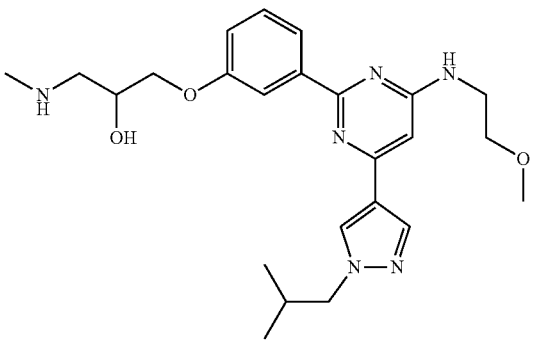 | 455.3 |
| 35-1 | 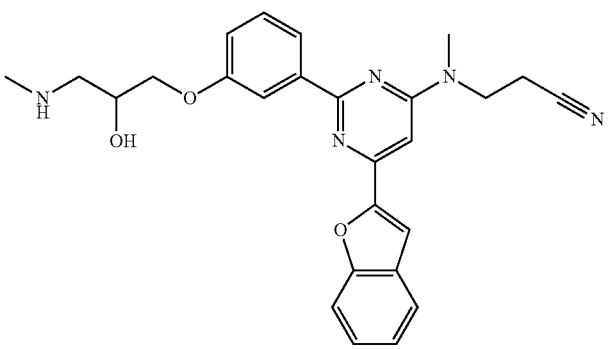 [SMILES: CNCC(O)COc1cccc(-c2nc(-c3cc4ccccc4o3)cc(N(C)CCC#N)n2)c1] | 458.2 |
| 36-1 | 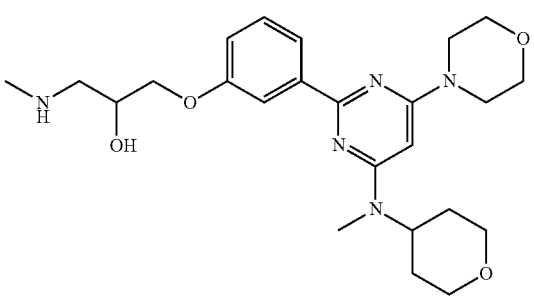 [SMILES: CNCC(O)COc1cccc(-c2nc(N3CCOCC3)cc(N(C)C3CCOCC3)n2)c1] | 458.4 |
| 37-1 | 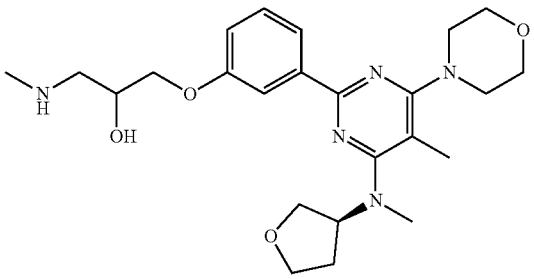 [SMILES: CNCC(O)COc1cccc(-c2nc(N3CCOCC3)c(C)c(N(C)[C@H]3CCOC3)n2)c1] | 458.3 |

TABLE 1A-continued

Exemplary Compounds

| # | Structure | LC-MS m/z (M + H) |
|---|-----------|-------------------|
| 38-1 | 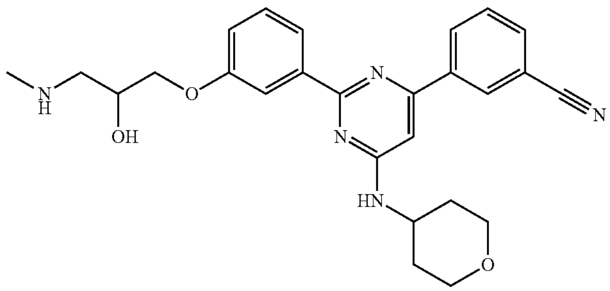 [SMILES: CNCC(O)COc1cccc(-c2nc(NC3CCOCC3)cc(-c3cccc(C#N)c3)n2)c1] | 460.2 |
| 39-1 | 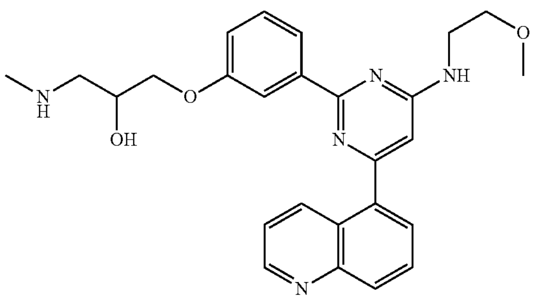 | 460.2 |
| 40-1 | 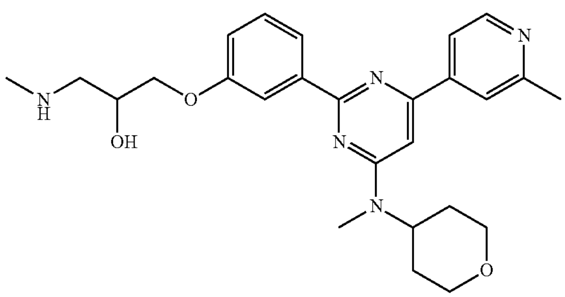 | 464.3 |
| 41-1 | 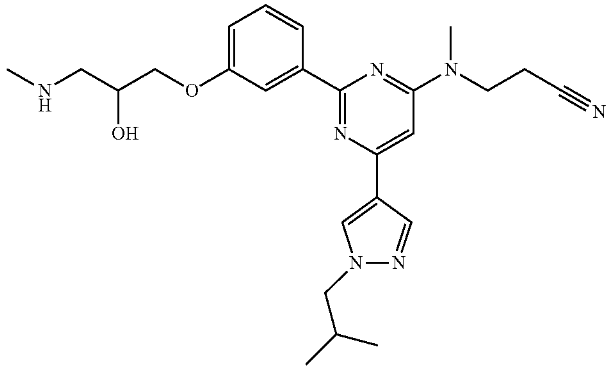 [SMILES: CNCC(O)COc1cccc(-c2nc(-c3cnn(CC(C)C)c3)cc(N(C)CCC#N)n2)c1] | 464.2 |

TABLE 1A-continued

Exemplary Compounds

| # | Structure | LC-MS m/z (M + H) |
|---|---|---|
| 42-1 | 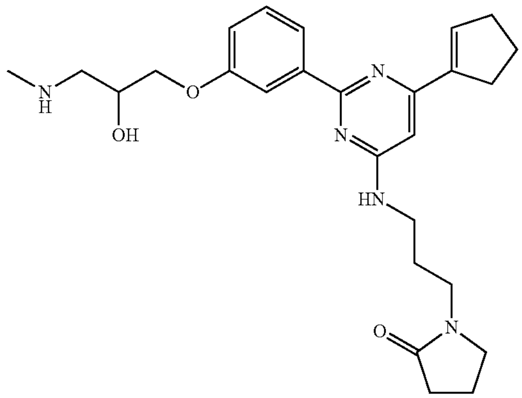 [SMILES: CNCC(O)COc1cccc(-c2nc(NCCCN3CCCC3=O)cc(C3=CCCC3)n2)c1] | 466.1 |
| 43-1 | 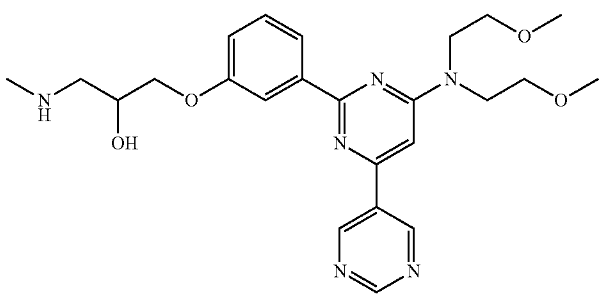 | 469.0 |
| 44-1 | 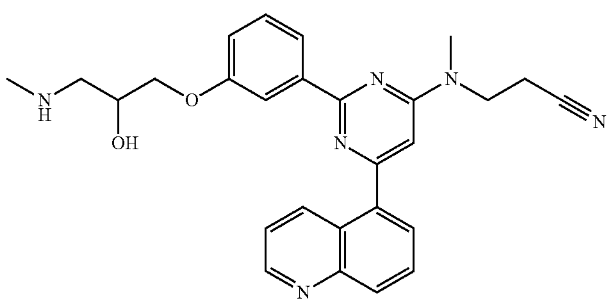 [SMILES: CNCC(O)COc1cccc(-c2nc(-c3cccc4ncccc34)cc(N(C)CCC#N)n2)c1] | 469.2 |
| 45-1 | 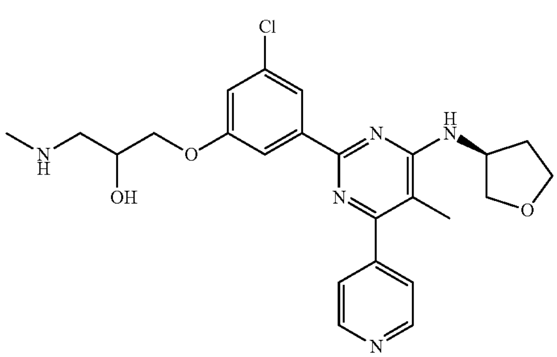 [SMILES: CNCC(O)COc1cc(Cl)cc(-c2nc(N[C@H]3CCOC3)c(C)c(-c3ccncc3)n2)c1] | 470.3 |

TABLE 1A-continued
Exemplary Compounds
| # | Structure | LC-MS m/z (M + H) |
|---|---|---|
| 46-1 | 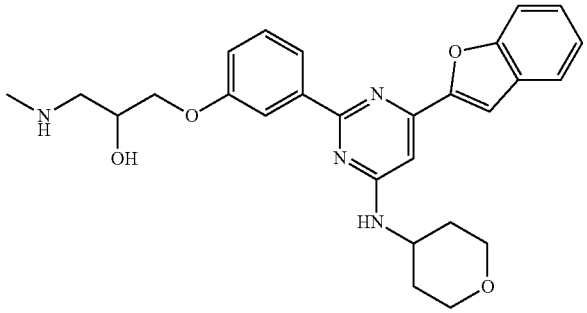 [SMILES: CNCC(O)COc1cccc(-c2nc(NC3CCOCC3)cc(-c3cc4ccccc4o3)n2)c1] | 475.2 |
| 47-1 | 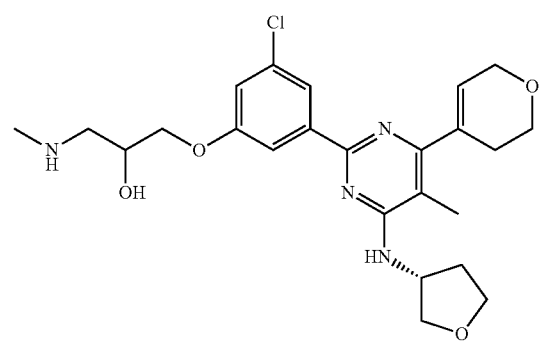 [SMILES: CNCC(O)COc1cc(Cl)cc(-c2nc(N[C@@H]3CCOC3)c(C)c(C3=CCOCC3)n2)c1] | 475.2 |
| 48-1 | 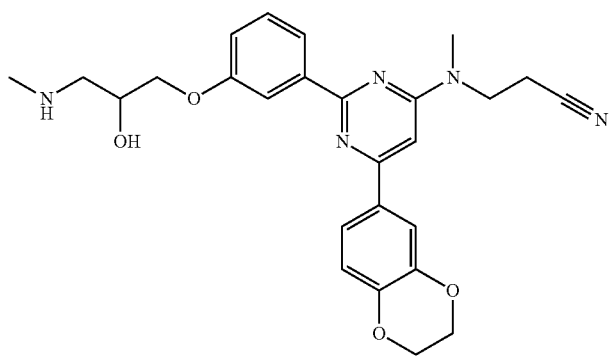 [SMILES: CNCC(O)COc1cccc(-c2nc(-c3ccc4c(c3)OCCO4)cc(N(C)CCC#N)n2)c1] | 476.0 |
| 49-1 | 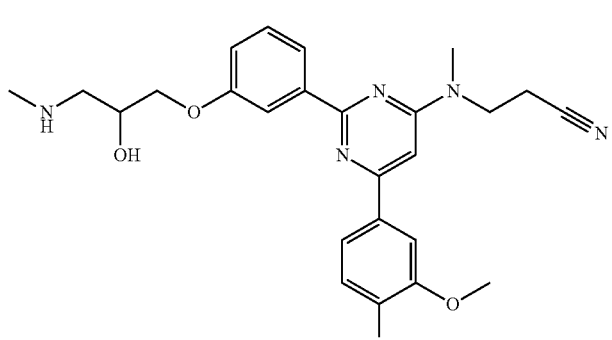 | 478.2 |

TABLE 1A-continued

Exemplary Compounds

| # | Structure | LC-MS m/z (M + H) |
|---|-----------|-------------------|
| 50-1 | 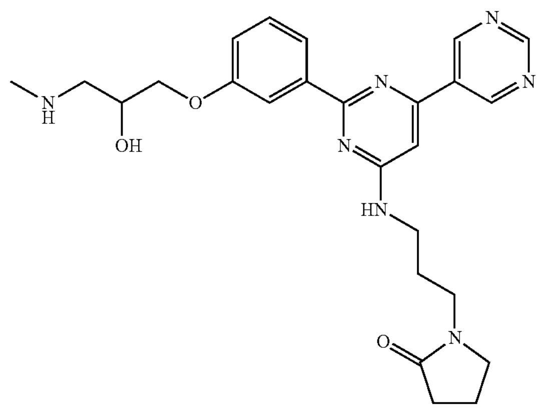 [SMILES: CNCC(O)COc1cccc(-c2nc(NCCCN3CCCC3=O)cc(-c3cncnc3)n2)c1] | 478.1 |
| 51-1 | 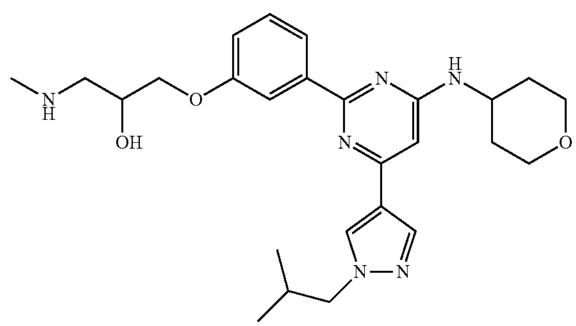 [SMILES: CNCC(O)COc1cccc(-c2nc(NC3CCOCC3)cc(-c3cnn(CC(C)C)c3)n2)c1] | 481.3 |
| 52-1 | 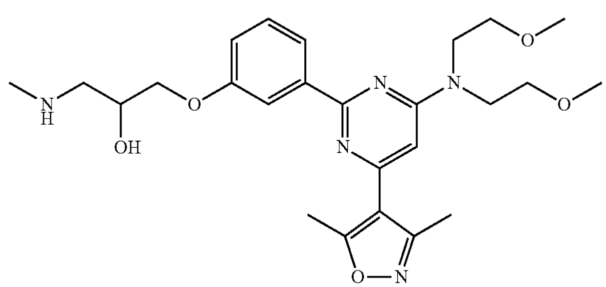 | 486.3 |
| 53-1 | 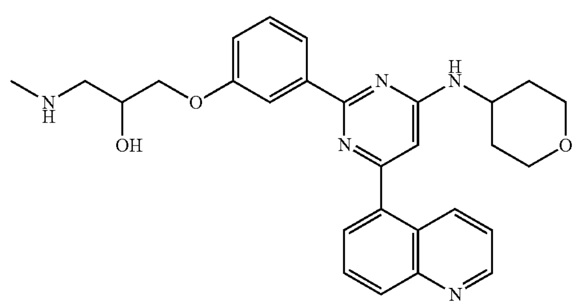 [SMILES: CNCC(O)COc1cccc(-c2nc(NC3CCOCC3)cc(-c3cccc4ncccc34)n2)c1] | 486.2 |

TABLE 1A-continued

Exemplary Compounds

| # | Structure | LC-MS m/z (M + H) |
|---|---|---|
| 54-1 | 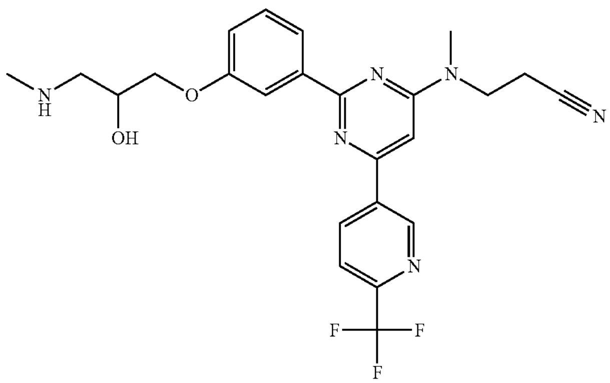 [SMILES: CNCC(O)COc1cccc(-c2nc(-c3ccc(C(F)(F)F)nc3)cc(N(C)CCC#N)n2)c1] | 487.1 |
| 55-1 | 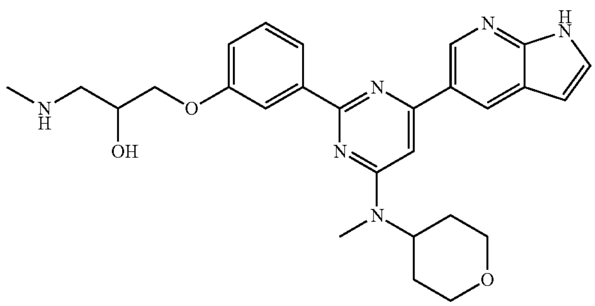 [SMILES: CNCC(O)COc1cccc(-c2nc(-c3cnc4[nH]ccc4c3)cc(N(C)C3CCOCC3)n2)c1] | 489.3 |
| 56-1 | 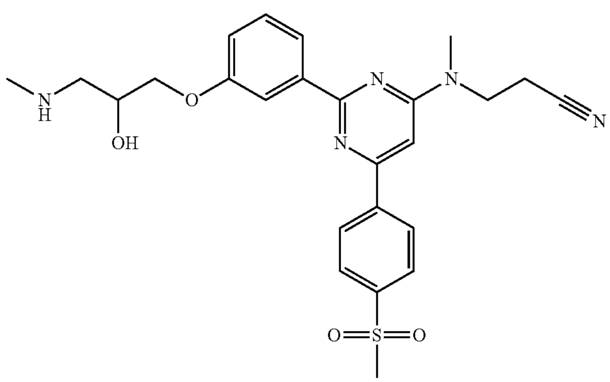 [SMILES: CNCC(O)COc1cccc(-c2nc(-c3ccc(S(C)(=O)=O)cc3)cc(N(C)CCC#N)n2)c1] | 496.3 |
| 57-1 | 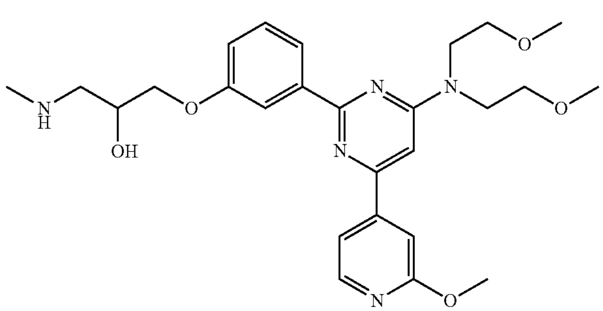 | 498.1 |

TABLE 1A-continued

Exemplary Compounds

| # | Structure | LC-MS m/z (M + H) |
|---|---|---|
| 58-1 | 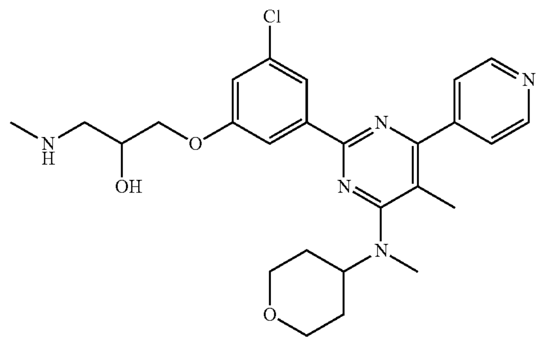 [SMILES: CNCC(O)COc1cc(Cl)cc(-c2nc(-c3ccncc3)c(C)c(N(C)C3CCOCC3)n2)c1] | 498.2 |
| 59-1 | 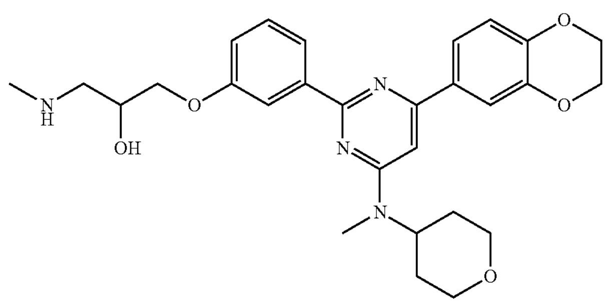 [SMILES: CNCC(O)COc1cccc(-c2nc(-c3ccc4c(c3)OCCO4)cc(N(C)C3CCOCC3)n2)c1] | 507.1 |
| 60-1 | 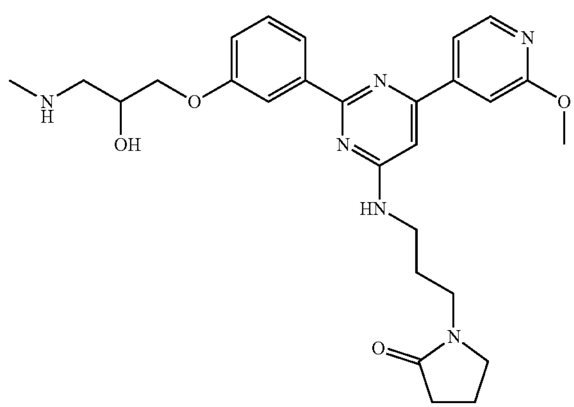 | 507.2 |
| 61-1 | 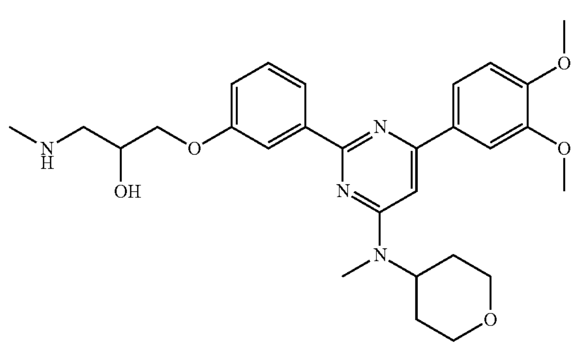 | 509.2 |

TABLE 1A-continued
Exemplary Compounds
| # | Structure | LC-MS m/z (M + H) |
|---|---|---|
| 62-1 | 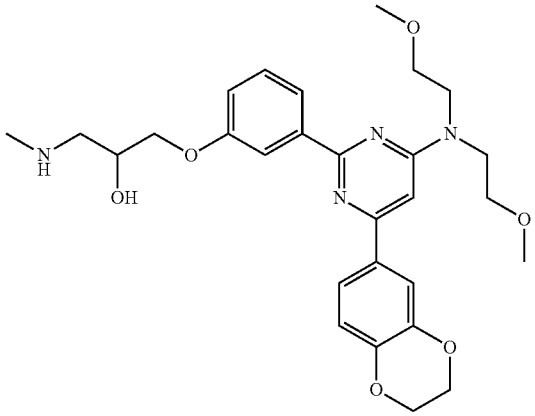 | 525.0 |
| 63-1 | 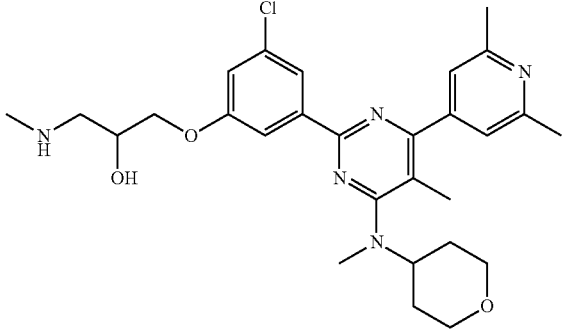 | 526.2 |
| 64-1 | 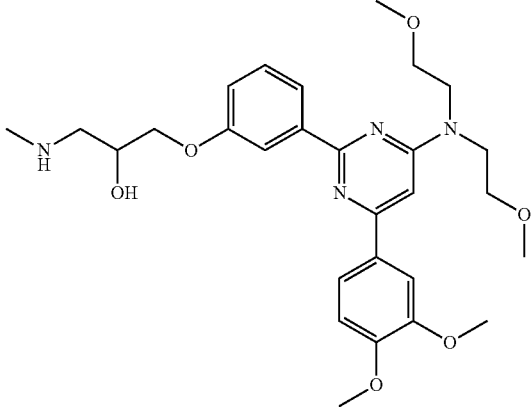 | 527.2 |
| 65-1 | 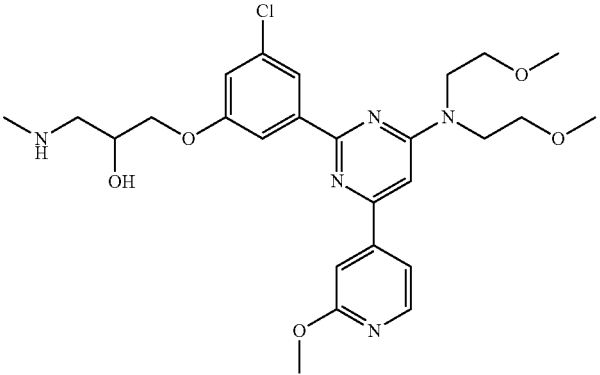 | 532.2 |

TABLE 1A-continued
Exemplary Compounds
| # | Structure | LC-MS m/z (M + H) |
|---|---|---|
| 66-1 | 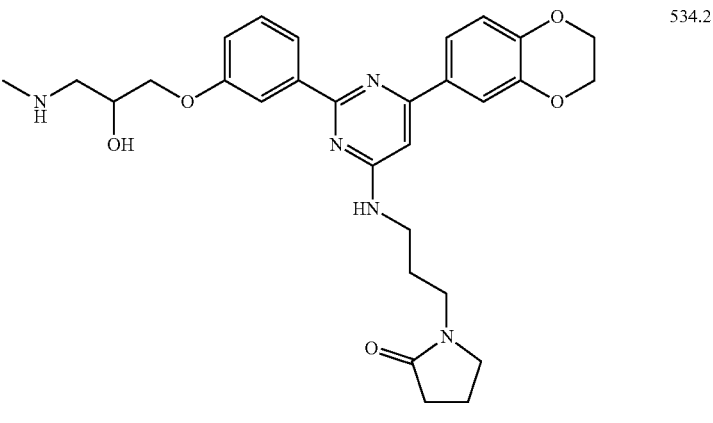 | 534.2 |
| 67-1 | 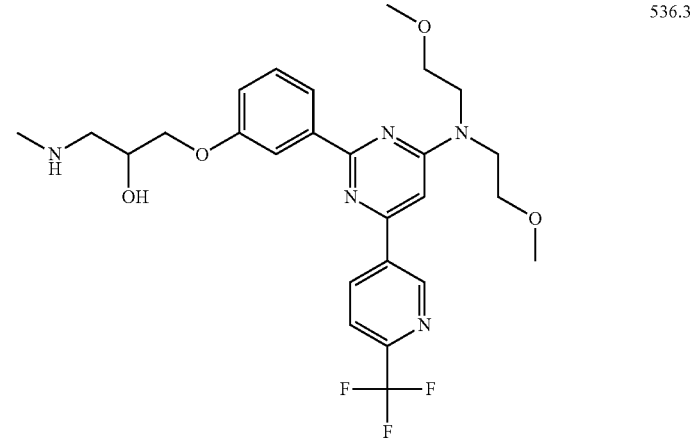 | 536.3 |
| 68-1 | 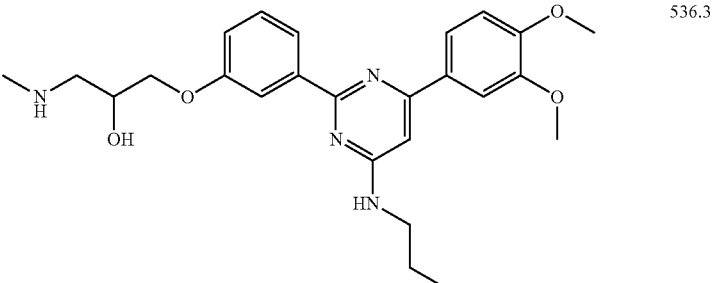 | 536.3 |

TABLE 1A-continued
Exemplary Compounds
| # | Structure | LC-MS m/z (M + H) |
|---|---|---|
| 69-1 | 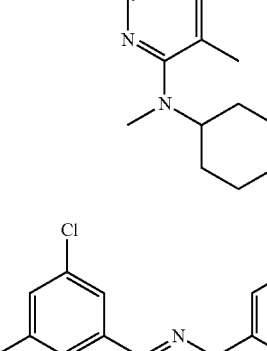 | 537.3 |
| 70-1 | 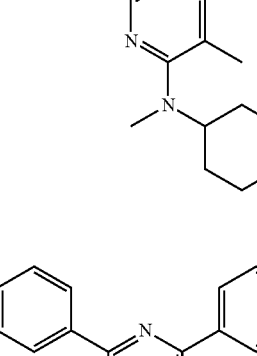 | 538.3 |
| 71-1 | 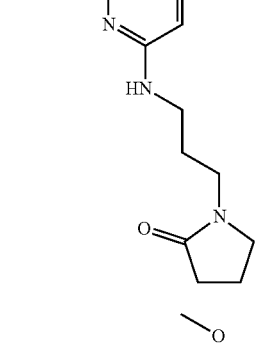 | 545.2 |
| 72-1 | 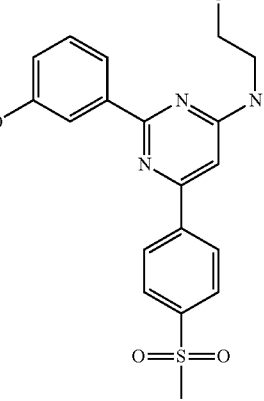 | 545.2 |

TABLE 1A-continued

| Exemplary Compounds | | |
|---|---|---|
| # | Structure | LC-MS m/z (M + H) |
| 73-1 | | 554.2 |
| 74-1 | | 559.2 |
| 75-1 | | 561.0 |

TABLE 1B

Exemplary Compounds

| # | Structure | LC-MS m/z (M + H) |
|---|---|---|
| 1-1a | 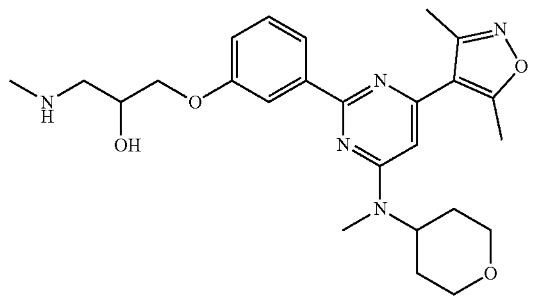 [SMILES: CNCC(O)COc1cccc(-c2nc(-c3c(C)noc3C)cc(N(C)C3CCOCC3)n2)c1] | 468.2 |
| 2-1a | 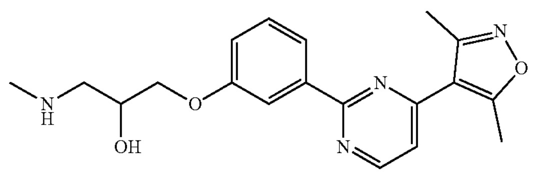 [SMILES: CNCC(O)COc1cccc(-c2nccc(-c3c(C)noc3C)n2)c1] | 355.2 |
| 3-1a | 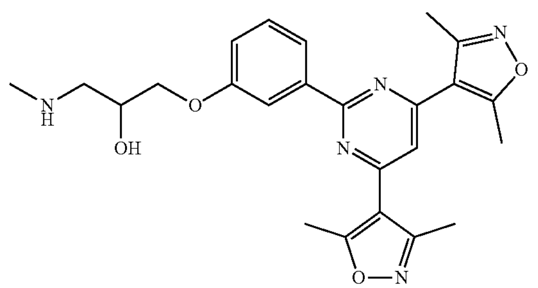 [SMILES: CNCC(O)COc1cccc(-c2nc(-c3c(C)noc3C)cc(-c3c(C)noc3C)n2)c1] | 450.2 |
| 4-1a | 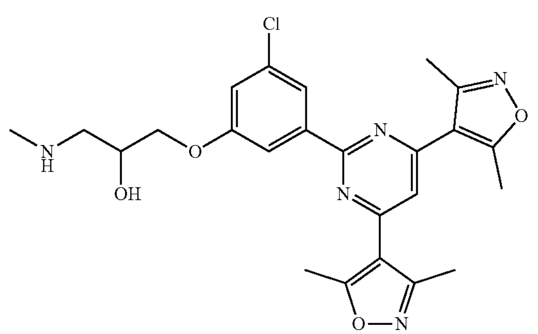 [SMILES: CNCC(O)COc1cc(Cl)cc(-c2nc(-c3c(C)noc3C)cc(-c3c(C)noc3C)n2)c1] | 484.2 |
| 5-1a | 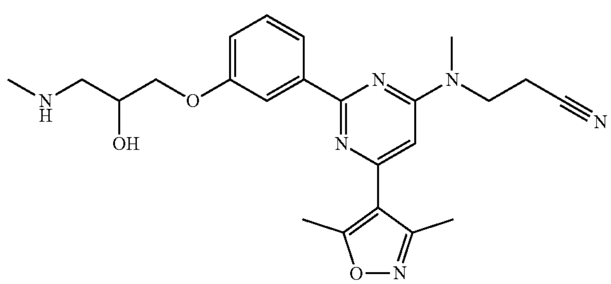 [SMILES: CNCC(O)COc1cccc(-c2nc(-c3c(C)noc3C)cc(N(C)CCC#N)n2)c1] | 437.1 |

TABLE 1B-continued

Exemplary Compounds

| # | Structure | LC-MS m/z (M + H) |
|---|---|---|
| 6-1a | 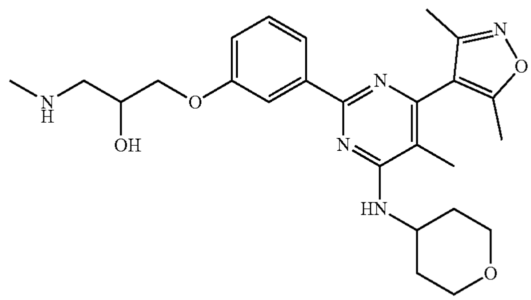 [SMILES: CNCC(O)COc1cccc(-c2nc(NC3CCOCC3)c(C)c(-c3c(C)noc3C)n2)c1] | 468.3 |
| 7-1a | 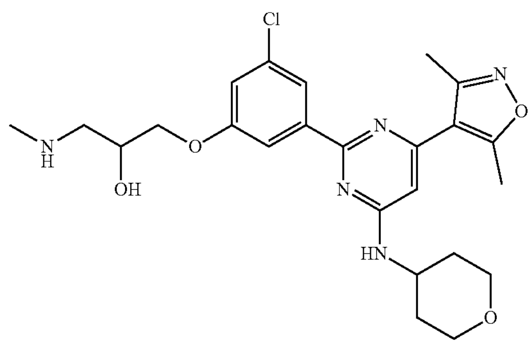 [SMILES: CNCC(O)COc1cc(Cl)cc(-c2nc(NC3CCOCC3)cc(-c3c(C)noc3C)n2)c1] | 488.2 |
| 8-1a | 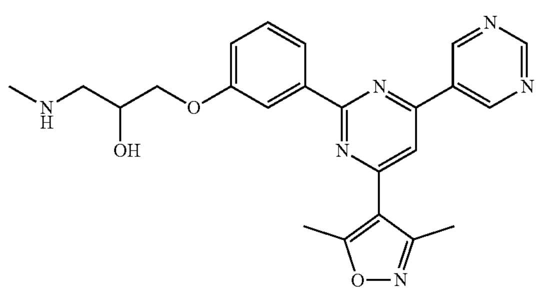 [SMILES: CNCC(O)COc1cccc(-c2nc(-c3cncnc3)cc(-c3c(C)noc3C)n2)c1] | 433.1 |
| 9-1a | 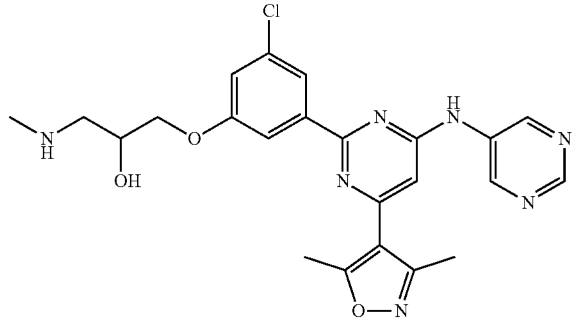 [SMILES: CNCC(O)COc1cc(Cl)cc(-c2nc(Nc3cncnc3)cc(-c3c(C)noc3C)n2)c1] | 482.1 |

TABLE 1B-continued
Exemplary Compounds
| # | Structure | LC-MS m/z (M + H) |
|---|-----------|-------------------|
| 10-1a | 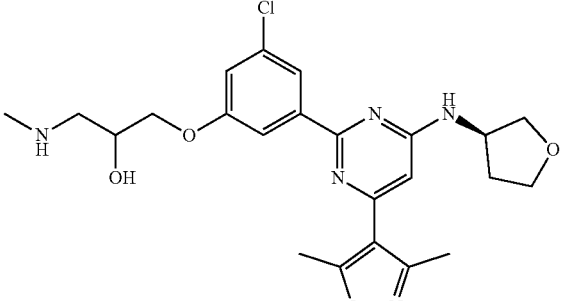 | 474.3 |
| 11-1a | 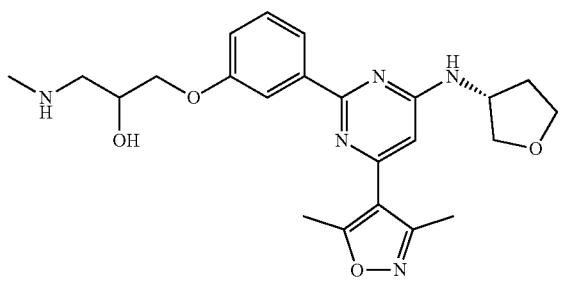 [SMILES: CNCC(O)COc1cccc(-c2nc(N[C@@H]3CCOC3)cc(-c3c(C)noc3C)n2)c1] | 440.2 |
| 12-1a | 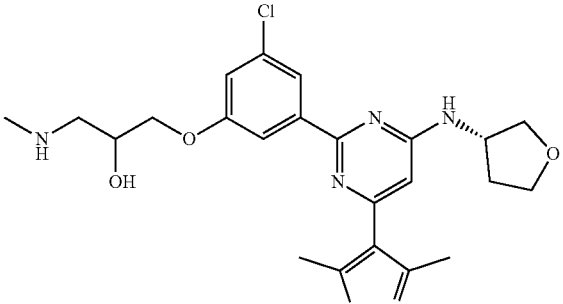 | 474.2 |
| 13-1a | 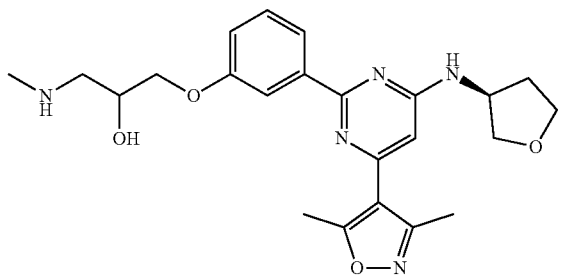 [SMILES: CNCC(O)COc1cccc(-c2nc(N[C@H]3CCOC3)cc(-c3c(C)noc3C)n2)c1] | 440.2 |
| 14-1a | 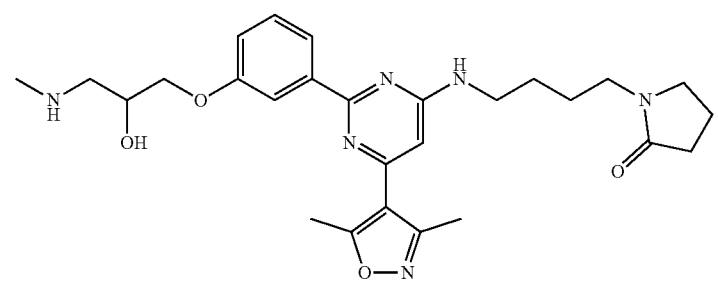 [SMILES: CNCC(O)COc1cccc(-c2nc(NCCCCN3CCCC3=O)cc(-c3c(C)noc3C)n2)c1] | 495.1 |

TABLE 1B-continued

Exemplary Compounds

| # | Structure | LC-MS m/z (M + H) |
|---|---|---|
| 15-1a | 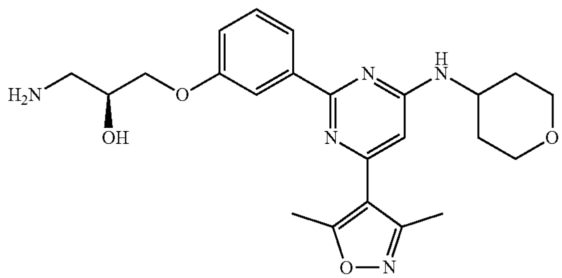 [SMILES: Cc1noc(C)c1-c1cc(NC2CCOCC2)nc(-c2cccc(OC[C@@H](O)CN)c2)n1] | 440.2 |
| 16-1a | 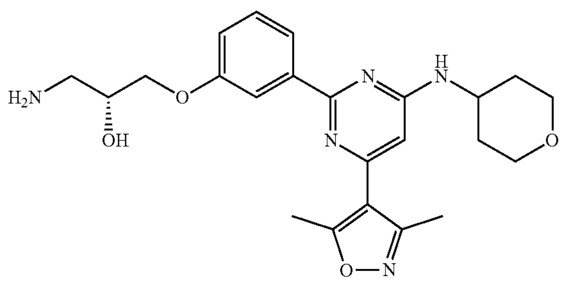 [SMILES: Cc1noc(C)c1-c1cc(NC2CCOCC2)nc(-c2cccc(OC[C@H](O)CN)c2)n1] | 440.2 |
| 17-1a | 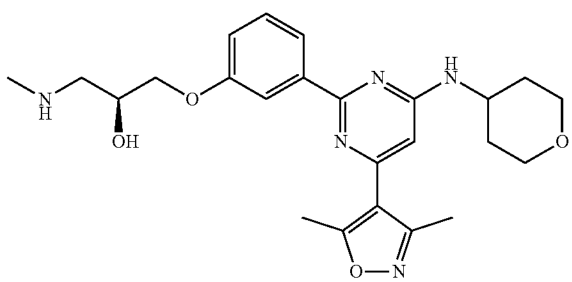 [SMILES: CNC[C@H](O)COc1cccc(-c2nc(NC3CCOCC3)cc(-c3c(C)noc3C)n2)c1] | 454.2 |
| 18-1a | 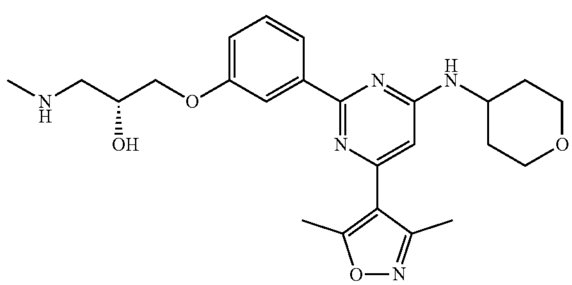 [SMILES: CNC[C@@H](O)COc1cccc(-c2nc(NC3CCOCC3)cc(-c3c(C)noc3C)n2)c1] | 454.2 |
| 19-1a | 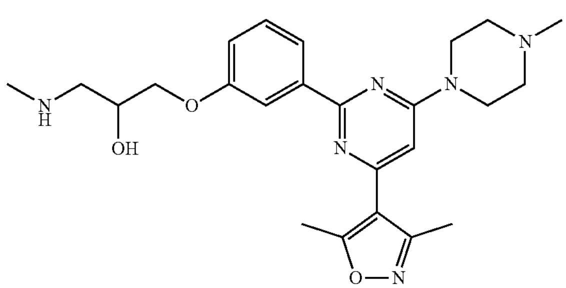 | 452.9 |

TABLE 1B-continued
Exemplary Compounds
| # | Structure | LC-MS m/z (M + H) |
|---|---|---|
| 20-1a | 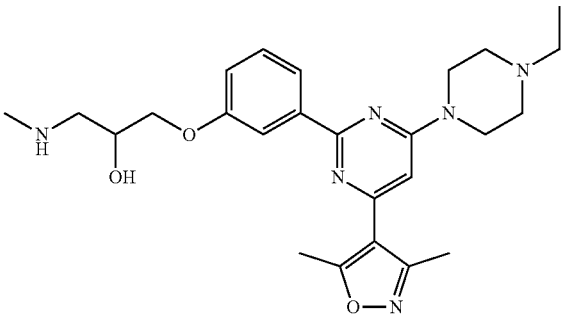 [SMILES: CCN1CCN(c2cc(-c3c(C)noc3C)nc(-c3cccc(OCC(O)CNC)c3)n2)CC1] | 467.3 |
| 21-1a | 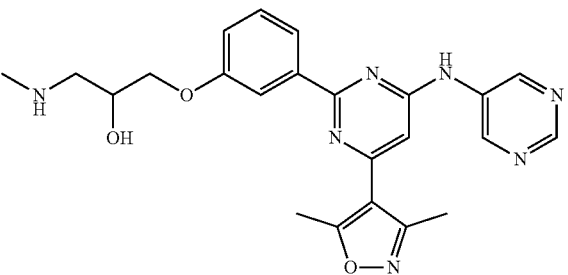 [SMILES: CNCC(O)COc1cccc(-c2nc(Nc3cncnc3)cc(-c3c(C)noc3C)n2)c1] | 448.3 |
| 22-1a | 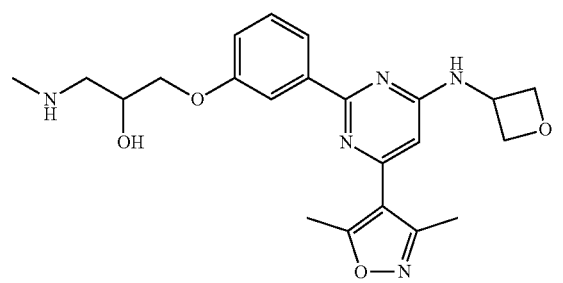 [SMILES: CNCC(O)COc1cccc(-c2nc(NC3COC3)cc(-c3c(C)noc3C)n2)c1] | 426.2 |
| 23-1a | 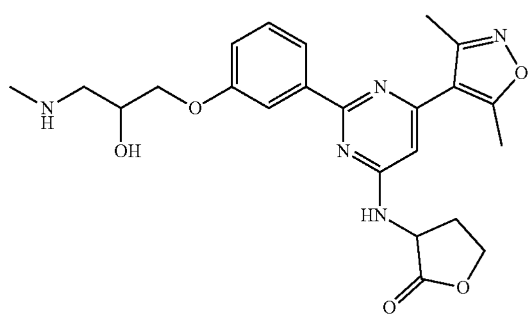 [SMILES: CNCC(O)COc1cccc(-c2nc(NC3CCOC3=O)cc(-c3c(C)noc3C)n2)c1] | 454.3 |
| 24-1a | 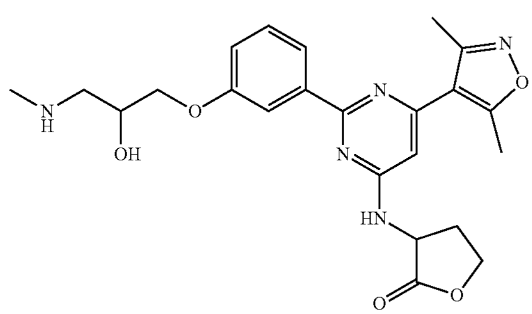 [SMILES: CNCC(O)COc1cccc(-c2nc(NC3CCOC3=O)cc(-c3c(C)noc3C)n2)c1] | 454.3 |

TABLE 1B-continued

Exemplary Compounds

| # | Structure | LC-MS m/z (M + H) |
|---|---|---|
| 25-1a | 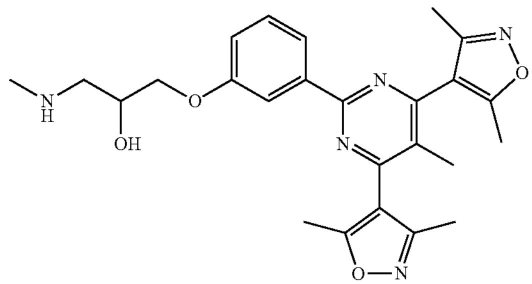 [SMILES: CNCC(O)COc1cccc(-c2nc(-c3c(C)noc3C)c(C)c(-c3c(C)noc3C)n2)c1] | 463.3 |
| 26-1a | 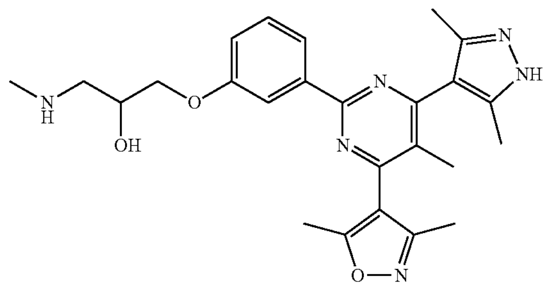 [SMILES: CNCC(O)COc1cccc(-c2nc(-c3c(C)n[nH]c3C)c(C)c(-c3c(C)noc3C)n2)c1] | 463.3 |
| 27-1a | 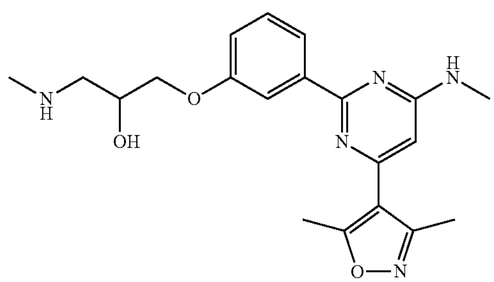 | 384.2 |
| 28-1a | 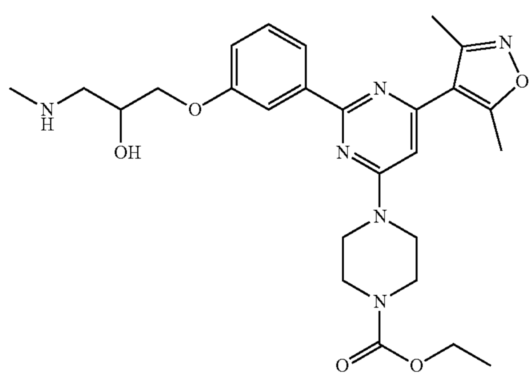 [SMILES: CCOC(=O)N1CCN(c2cc(-c3c(C)noc3C)nc(-c3cccc(OCC(O)CNC)c3)n2)CC1] | 511.0 |
| 29-1a | 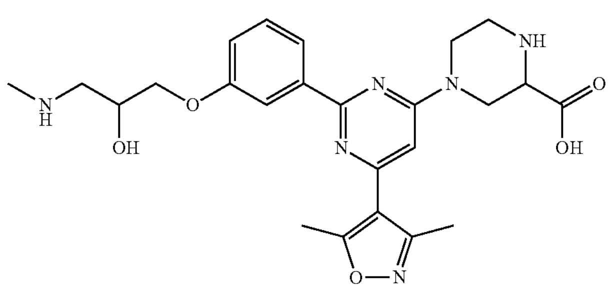 [SMILES: CNCC(O)COc1cccc(-c2nc(-c3c(C)noc3C)cc(N3CCNC(C(=O)O)C3)n2)c1] | 482.9 |

TABLE 1B-continued
Exemplary Compounds
| # | Structure | LC-MS m/z (M + H) |
|---|---|---|
| 30-1a | 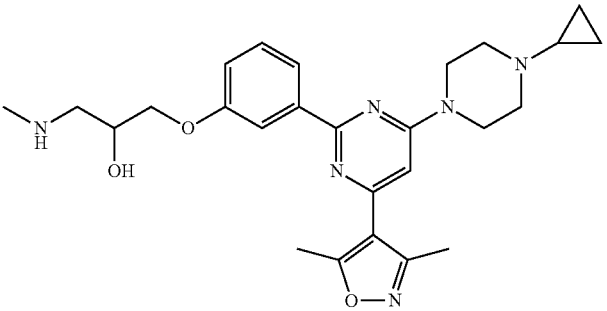 [SMILES: CNCC(O)COc1cccc(-c2nc(-c3c(C)noc3C)cc(N3CCN(C4CC4)CC3)n2)c1] | 479.2 |
| 31-1a | 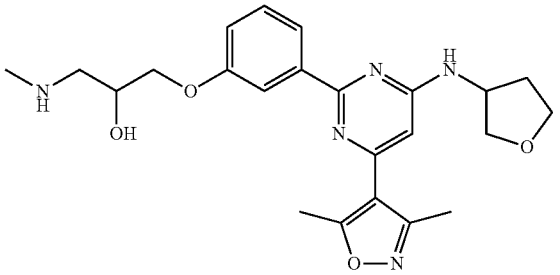 [SMILES: CNCC(O)COc1cccc(-c2nc(NC3CCOC3)cc(-c3c(C)noc3C)n2)c1] | 440.0 |
| 32-1a | 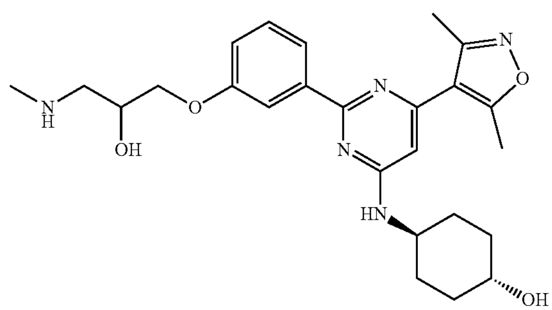 [SMILES: CNCC(O)COc1cccc(-c2nc(N[C@H]3CC[C@H](O)CC3)cc(-c3c(C)noc3C)n2)c1] | 467.9 |
| 33-1a | 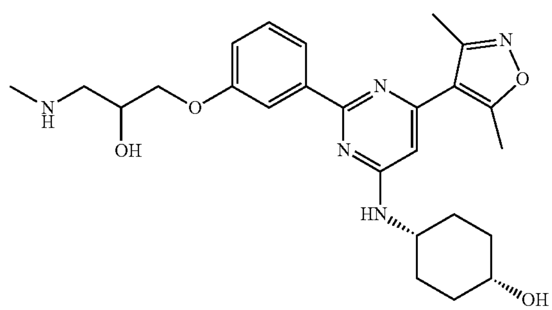 [SMILES: CNCC(O)COc1cccc(-c2nc(N[C@H]3CC[C@@H](O)CC3)cc(-c3c(C)noc3C)n2)c1] | 467.9 |
| 34-1a | 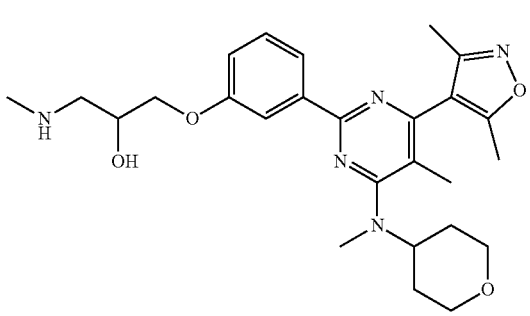 [SMILES: CNCC(O)COc1cccc(-c2nc(-c3c(C)noc3C)c(C)c(N(C)C3CCOCC3)n2)c1] | 482.3 |

TABLE 1B-continued

Exemplary Compounds

| # | Structure | LC-MS m/z (M + H) |
|---|---|---|
| 35-1a | 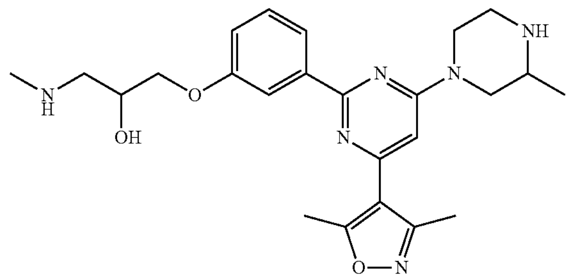 | 453.0 |
| 36-1a | 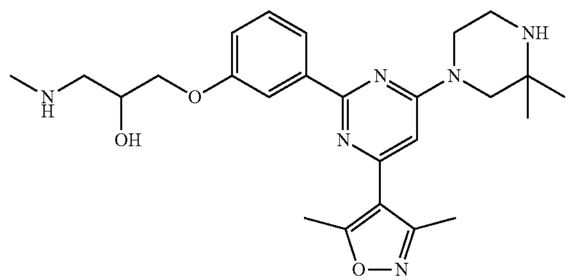 | 467.0 |
| 37-1a | 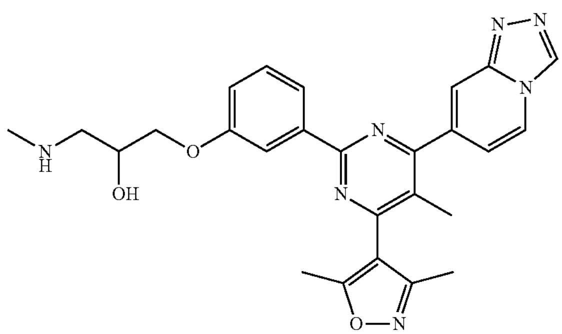 [SMILES: CNCC(O)COc1cccc(-c2nc(-c3ccn4cnnc4c3)c(C)c(-c3c(C)noc3C)n2)c1] | 486.2 |
| 38-1a | 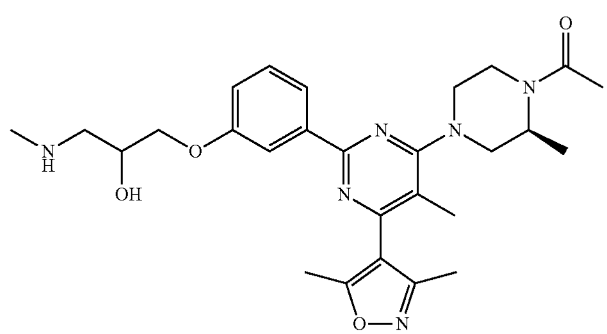 [SMILES: CNCC(O)COc1cccc(-c2nc(-c3c(C)noc3C)c(C)c(N3CCN(C(C)=O)[C@@H](C)C3)n2)c1] | 495.0 |
| 39-1a | 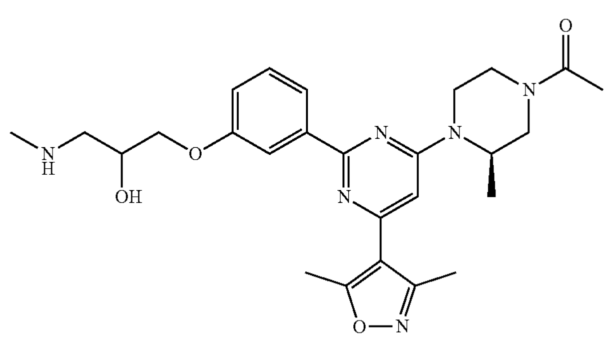 [SMILES: CNCC(O)COc1cccc(-c2nc(-c3c(C)noc3C)cc(N3CCN(C(C)=O)C[C@H]3C)n2)c1] | 495.3 |

TABLE 1B-continued

Exemplary Compounds

| # | Structure | LC-MS m/z (M + H) |
|---|---|---|
| 40-1a | 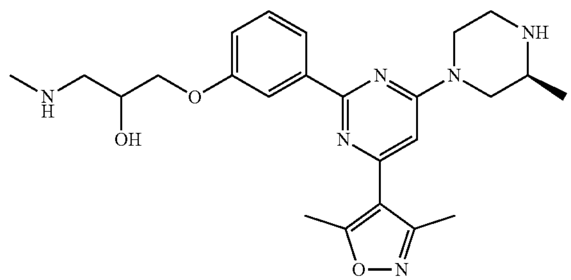 | 452.9 |
| 41-1a | 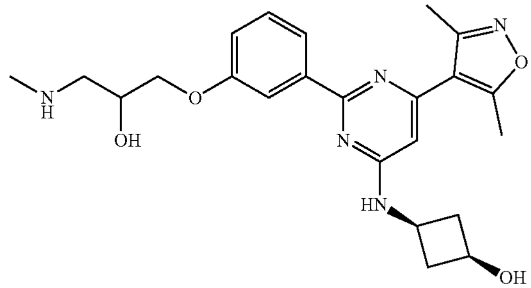 [SMILES: CNCC(O)COc1cccc(-c2nc(N[C@H]3C[C@@H](O)C3)cc(-c3c(C)noc3C)n2)c1] | 440.2 |
| 42-1a | 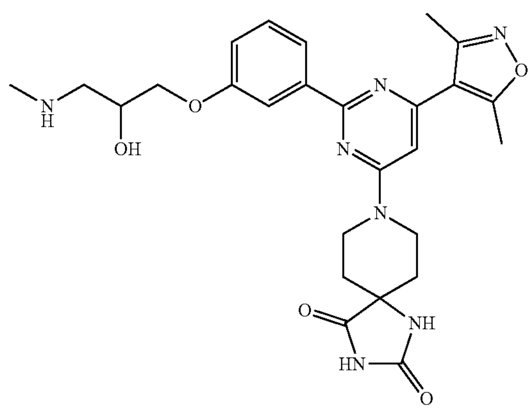 [SMILES: CNCC(O)COc1cccc(-c2nc(-c3c(C)noc3C)cc(N3CCC4(CC3)NC(=O)NC4=O)n2)c1] | 521.9 |
| 43-1a | 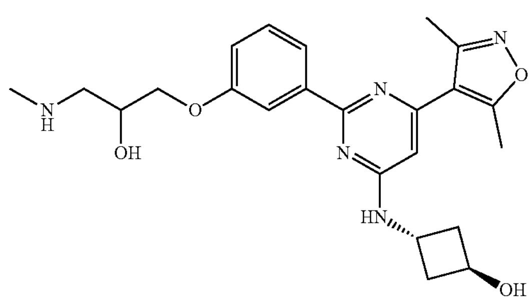 [SMILES: CNCC(O)COc1cccc(-c2nc(N[C@H]3C[C@H](O)C3)cc(-c3c(C)noc3C)n2)c1] | 440.2 |

TABLE 1B-continued
Exemplary Compounds
| # | Structure | LC-MS m/z (M + H) |
|---|---|---|
| 44-1a | 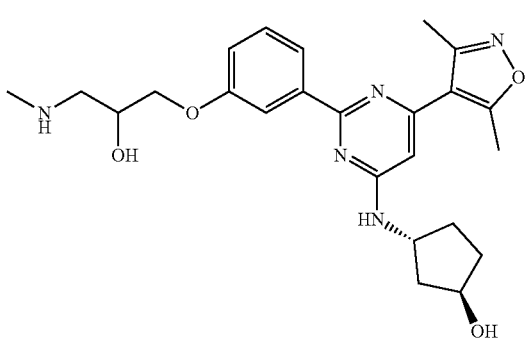 [SMILES: CNCC(O)COc1cccc(-c2nc(N[C@@H]3CC[C@@H](O)C3)cc(-c3c(C)noc3C)n2)c1] | 454.0 |
| 45-1a | 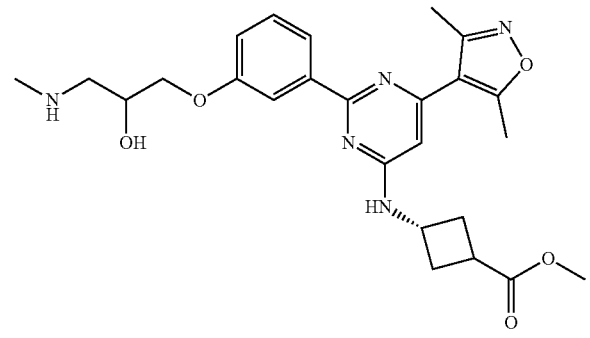 | 481.9 |
| 46-1a | 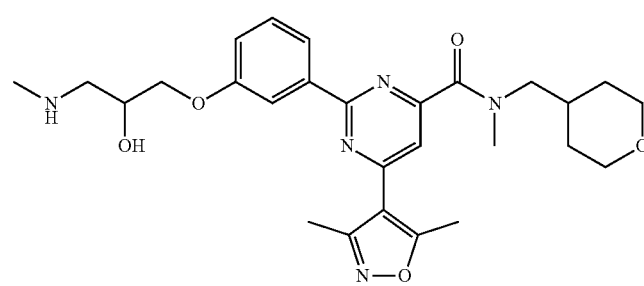 [SMILES: CNCC(O)COc1cccc(-c2nc(C(=O)N(C)CC3CCOCC3)cc(-c3c(C)noc3C)n2)c1] | 510.2 |
| 47-1a | 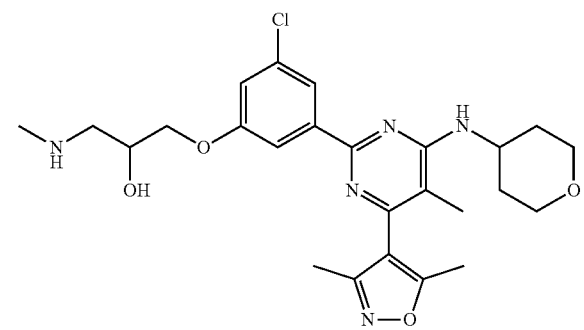 [SMILES: CNCC(O)COc1cc(Cl)cc(-c2nc(NC3CCOCC3)c(C)c(-c3c(C)noc3C)n2)c1] | 502.3 |

TABLE 1B-continued
Exemplary Compounds
| # | Structure | LC-MS m/z (M + H) |
|---|---|---|
| 48-1a | 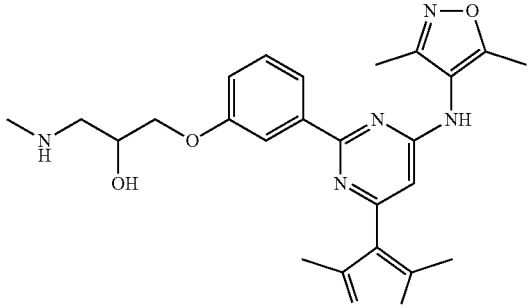 | 465.3 |
| 49-1a | 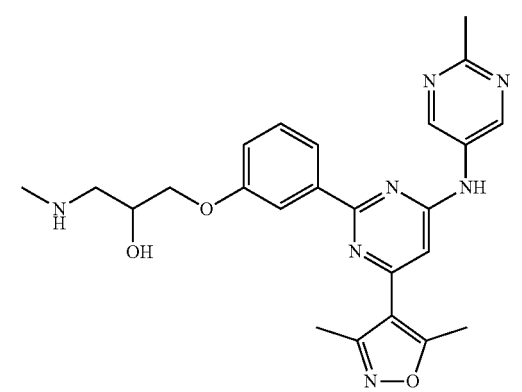 [SMILES: CNCC(O)COc1cccc(-c2nc(Nc3cnc(C)nc3)cc(-c3c(C)noc3C)n2)c1] | 462.3 |
| 50-1a | 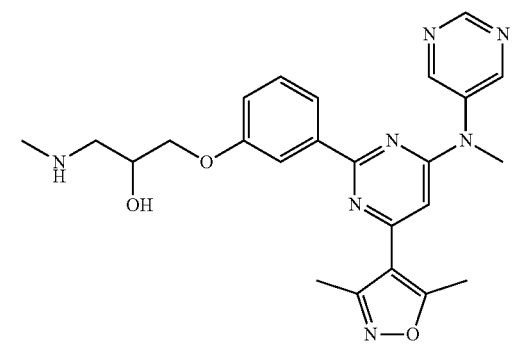 [SMILES: CNCC(O)COc1cccc(-c2nc(-c3c(C)noc3C)cc(N(C)c3cncnc3)n2)c1] | 462.3 |
| 51-1a | 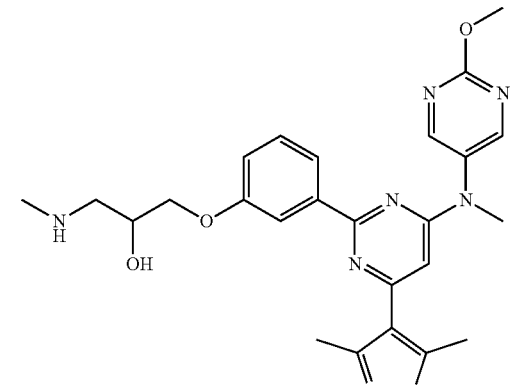 | 492.3 |

TABLE 1B-continued
Exemplary Compounds
| # | Structure | LC-MS m/z (M + H) |
|---|---|---|
| 52-1a | 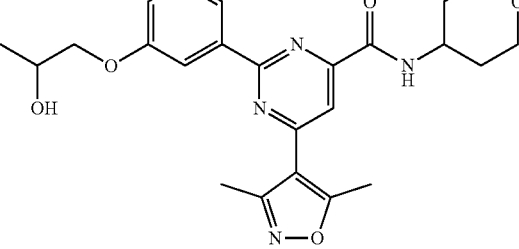 | 482.2 |
| 53-1a | 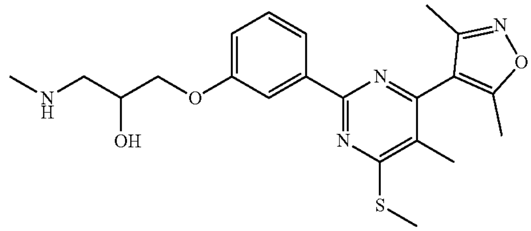 [SMILES: CNCC(O)COc1cccc(-c2nc(SC)c(C)c(-c3c(C)noc3C)n2)c1] | 415.3 |
| 54-1a | 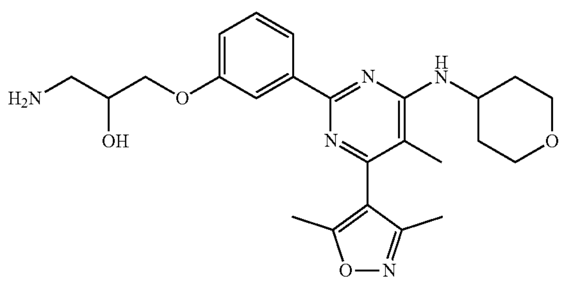 [SMILES: Cc1noc(C)c1-c1nc(-c2cccc(OCC(O)CN)c2)nc(NC2CCOCC2)c1C] | 454.3 |
| 55-1a | 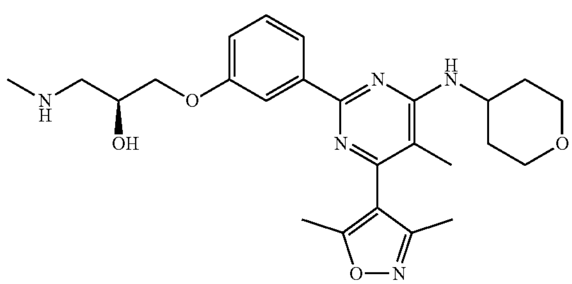 [SMILES: CNC[C@H](O)COc1cccc(-c2nc(NC3CCOCC3)c(C)c(-c3c(C)noc3C)n2)c1] | 468.3 |
| 56-1a | 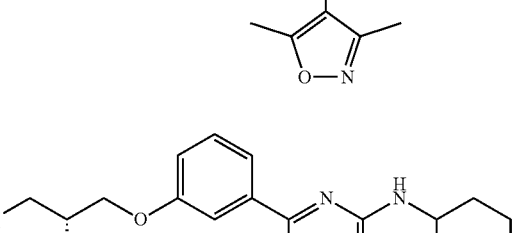 | 468.3 |

TABLE 1B-continued
Exemplary Compounds
| # | Structure | LC-MS m/z (M + H) |
|---|---|---|
| 57-1a | 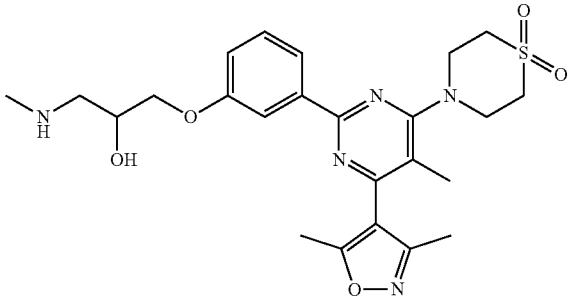 [SMILES: CNCC(O)COc1cccc(-c2nc(-c3c(C)noc3C)c(C)c(N3CCS(=O)(=O)CC3)n2)c1] | 502.2 |
| 58-1a | 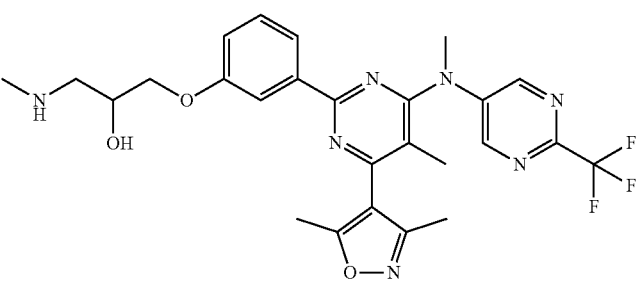 [SMILES: CNCC(O)COc1cccc(-c2nc(-c3c(C)noc3C)c(C)c(N(C)c3cnc(C(F)(F)F)nc3)n2)c1] | 530.2 |
| 59-1a | 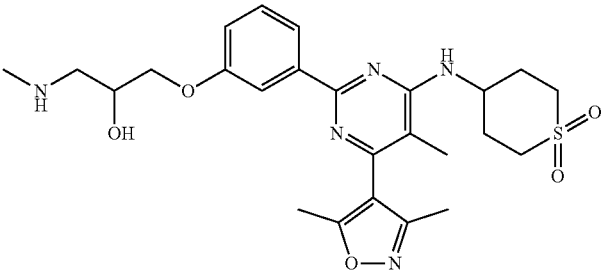 [SMILES: CNCC(O)COc1cccc(-c2nc(NC3CCS(=O)(=O)CC3)c(C)c(-c3c(C)noc3C)n2)c1] | 516.2 |
| 60-1a | 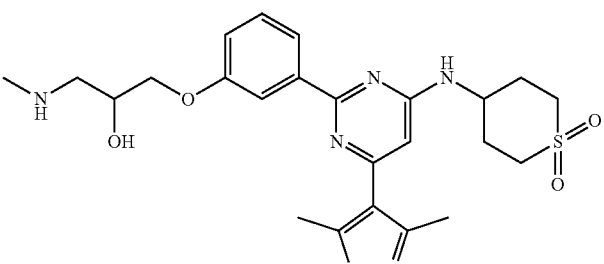 | 502.1 |
| 61-1a | 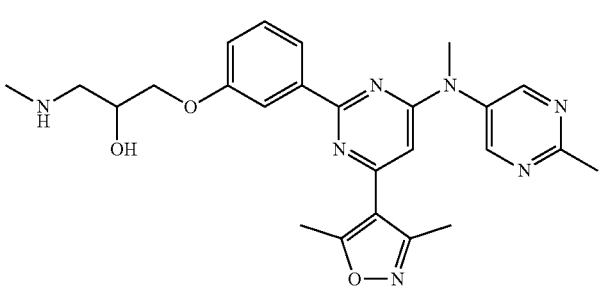 | 476.1 |

TABLE 1B-continued
Exemplary Compounds
| # | Structure | LC-MS m/z (M + H) |
|---|---|---|
| 62-1a | 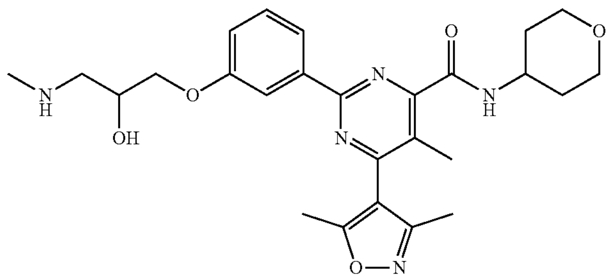 [SMILES: CNCC(O)COc1cccc(-c2nc(C(=O)NC3CCOCC3)c(C)c(-c3c(C)noc3C)n2)c1] | 496.3 |
| 63-1a | 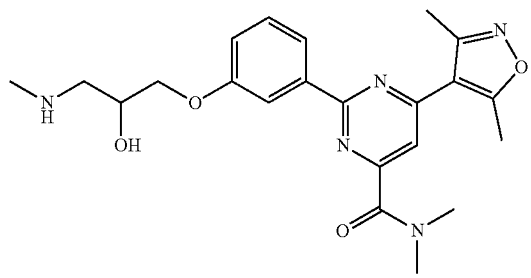 [SMILES: CNCC(O)COc1cccc(-c2nc(C(=O)N(C)C)cc(-c3c(C)noc3C)n2)c1] | 426.2 |
| 64-1a | 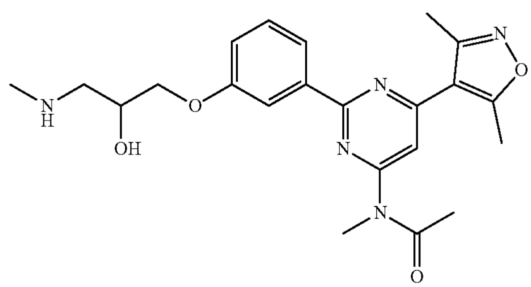 [SMILES: CNCC(O)COc1cccc(-c2nc(-c3c(C)noc3C)cc(N(C)C(C)=O)n2)c1] | 426.2 |
| 65-1a | 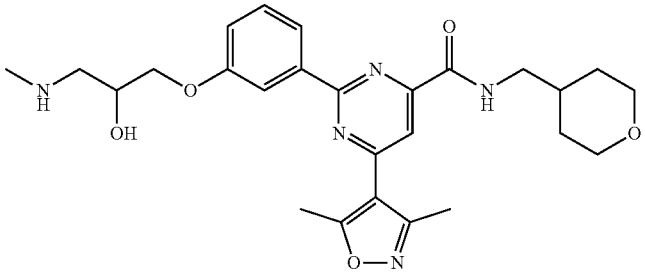 [SMILES: CNCC(O)COc1cccc(-c2nc(C(=O)NCC3CCOCC3)cc(-c3c(C)noc3C)n2)c1] | 496.3 |
| 66-1a | 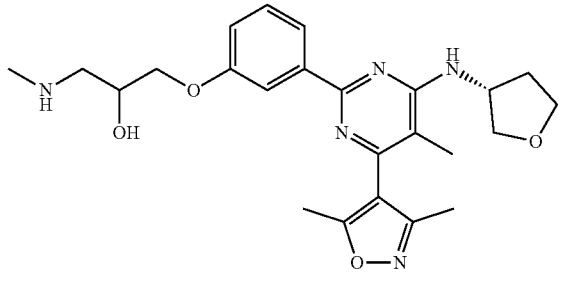 [SMILES: CNCC(O)COc1cccc(-c2nc(N[C@@H]3CCOC3)c(C)c(-c3c(C)noc3C)n2)c1] | 454.2 |

TABLE 1B-continued
Exemplary Compounds
| # | Structure | LC-MS m/z (M + H) |
|---|---|---|
| 67-1a | 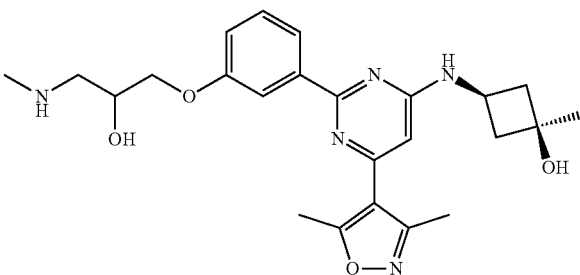 | 454.0 |
| 68-1a | 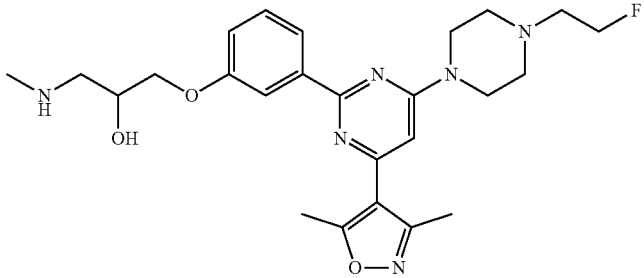 [SMILES: CNCC(O)COc1cccc(-c2nc(-c3c(C)noc3C)cc(N3CCN(CCF)CC3)n2)c1] | 485.0 |
| 69-1a | 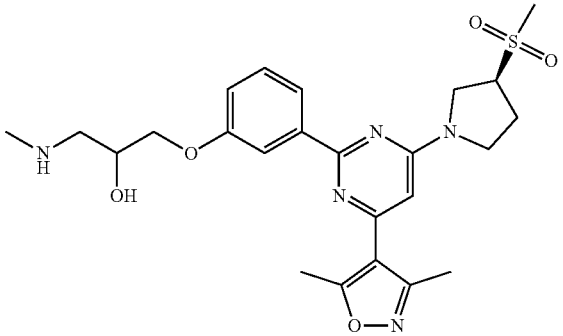 [SMILES: CNCC(O)COc1cccc(-c2nc(-c3c(C)noc3C)cc(N3CC[C@H](S(C)(=O)=O)C3)n2)c1] | 502.0 |
| 70-1a | 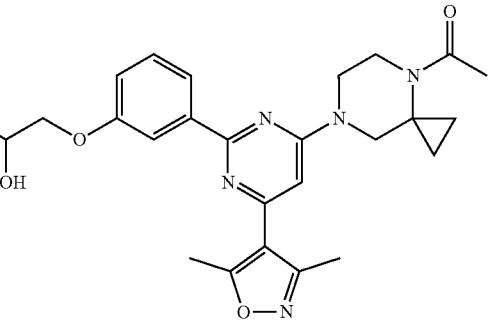 | 507.0 |
| 71-1a | 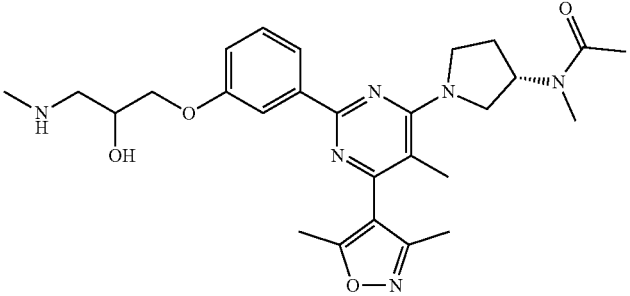 [SMILES: CNCC(O)COc1cccc(-c2nc(-c3c(C)noc3C)c(C)c(N3CC[C@H](N(C)C(C)=O)C3)n2)c1] | 509.3 |

TABLE 1B-continued
Exemplary Compounds
| # | Structure | LC-MS m/z (M + H) |
|---|---|---|
| 72-1a | 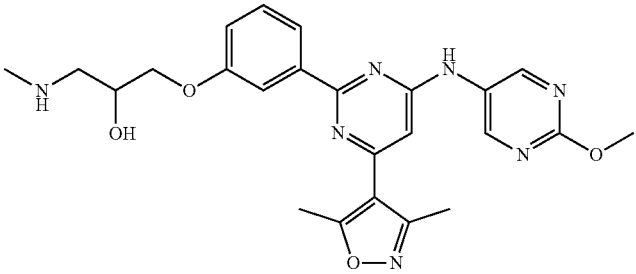 | 478.2 |
| 73-1a | 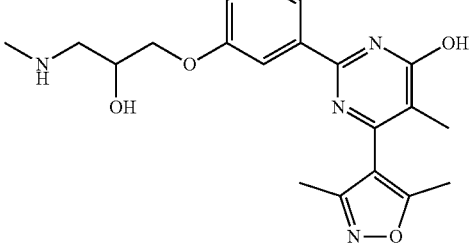 | 385.2 |
| 74-1a | 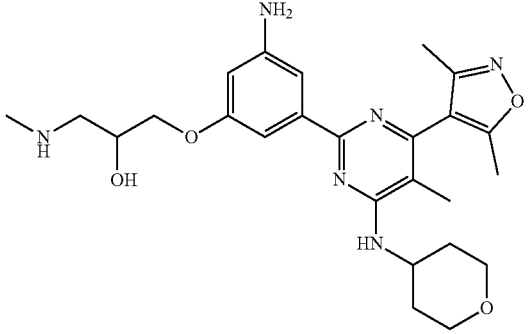 [SMILES: CNCC(O)COc1cc(N)cc(-c2nc(NC3CCOCC3)c(C)c(-c3c(C)noc3C)n2)c1] | 483.2 |
| 75-1a | 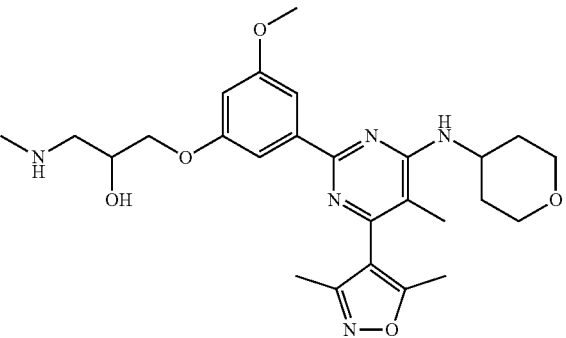 [SMILES: CNCC(O)COc1cc(OC)cc(-c2nc(NC3CCOCC3)c(C)c(-c3c(C)noc3C)n2)c1] | 498.3 |
| 76-1a | 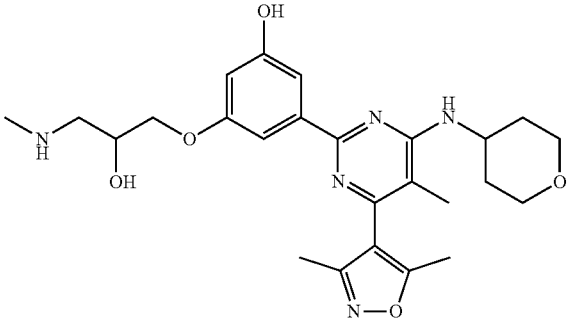 [SMILES: CNCC(O)COc1cc(O)cc(-c2nc(NC3CCOCC3)c(C)c(-c3c(C)noc3C)n2)c1] | 484.2 |

TABLE 1B-continued

Exemplary Compounds

| # | Structure | LC-MS m/z (M + H) |
|---|---|---|
| 77-1a | 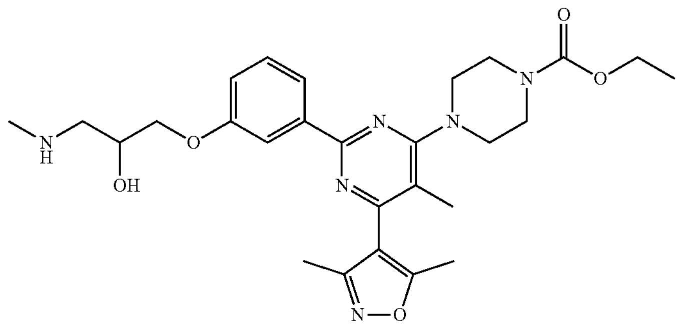 [SMILES: CCOC(=O)N1CCN(c2nc(-c3cccc(OCC(O)CNC)c3)nc(-c3c(C)noc3C)c2C)CC1] | 525.0 |
| 78-1a | 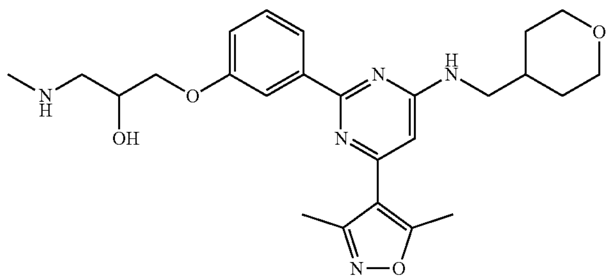 [SMILES: CNCC(O)COc1cccc(-c2nc(NCC3CCOCC3)cc(-c3c(C)noc3C)n2)c1] | 468.2 |
| 79-1a | 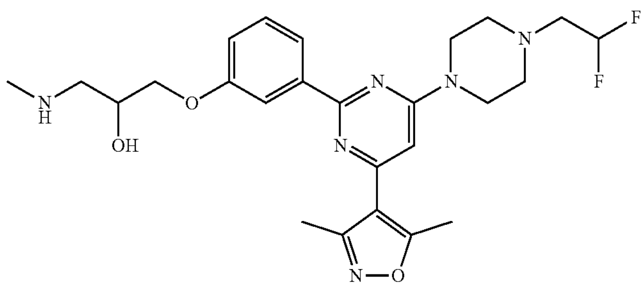 [SMILES: CNCC(O)COc1cccc(-c2nc(-c3c(C)noc3C)cc(N3CCN(CC(F)F)CC3)n2)c1] | 503.0 |
| 80-1a | 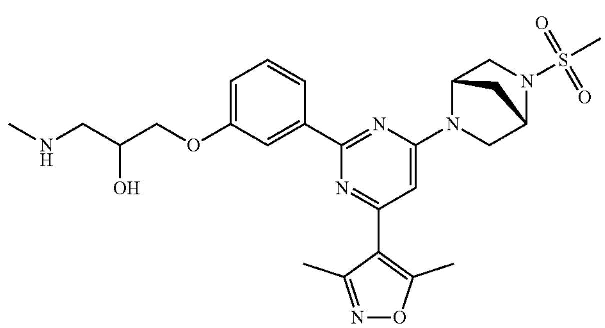 | 529.2 |
| 81-1a | 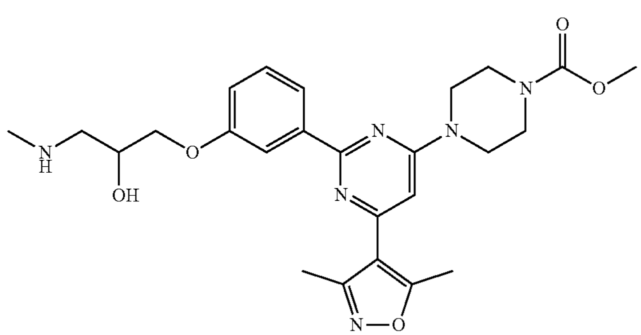 | 497.0 |

TABLE 1B-continued

Exemplary Compounds

| # | Structure | LC-MS m/z (M + H) |
|---|-----------|-------------------|
| 82-1a | 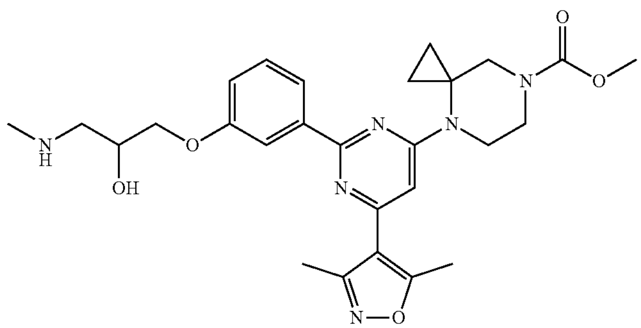 | 507.0 |
| 83-1a | 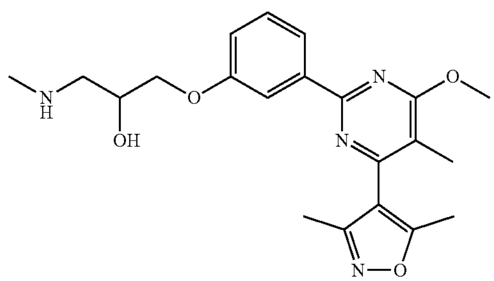 | 399.2 |
| 84-1a | 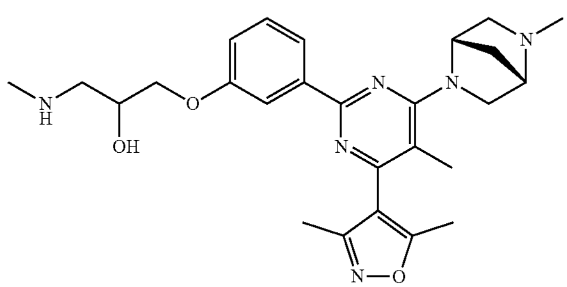 | 479.3 |
| 85-1a | 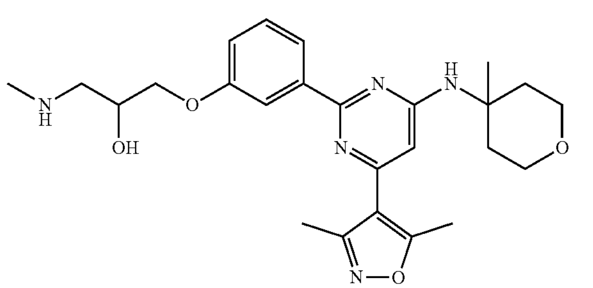 [SMILES: CNCC(O)COc1cccc(-c2nc(NC3(C)CCOCC3)cc(-c3c(C)noc3C)n2)c1] | 468.0 |
| 86-1a | 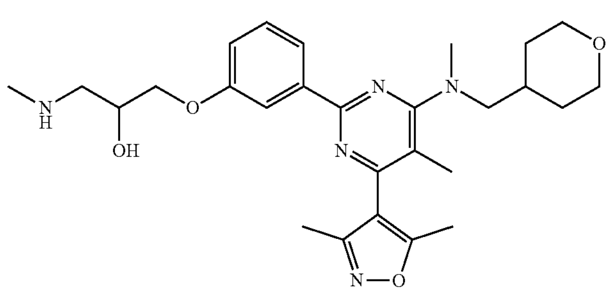 [SMILES: CNCC(O)COc1cccc(-c2nc(-c3c(C)noc3C)c(C)c(N(C)CC3CCOCC3)n2)c1] | 496.3 |

TABLE 1B-continued

Exemplary Compounds

| # | Structure | LC-MS m/z (M + H) |
|---|---|---|
| 87-1a | 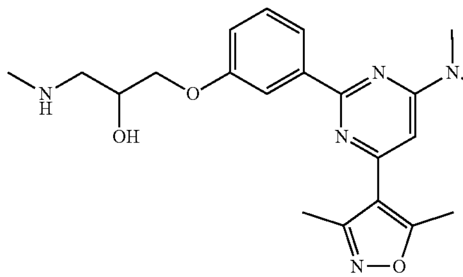 | 482.3 |
| 88-1a | 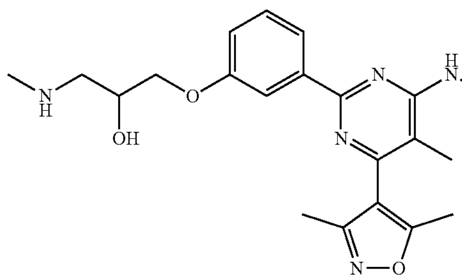 | 482.3 |
| 89-1a | 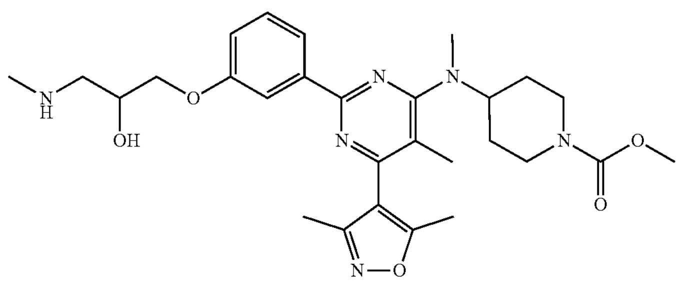 | 539.0 |
| 90-1a | 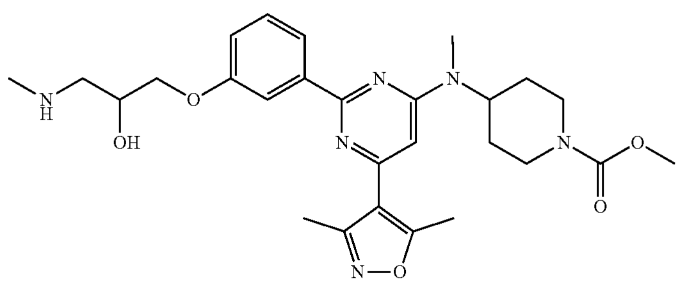 | 525.0 |
| 91-1a | 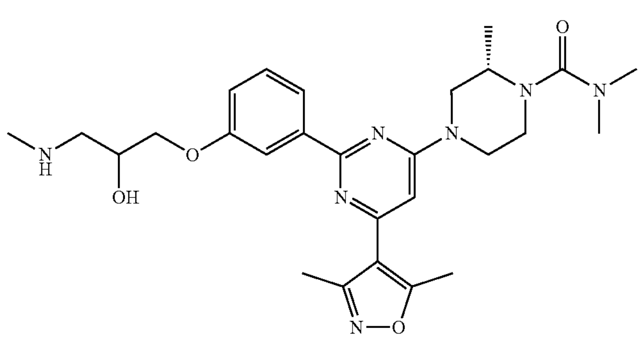 | 524.3 |

TABLE 1B-continued
Exemplary Compounds
| # | Structure | LC-MS m/z (M + H) |
|---|---|---|
| 92-1a | 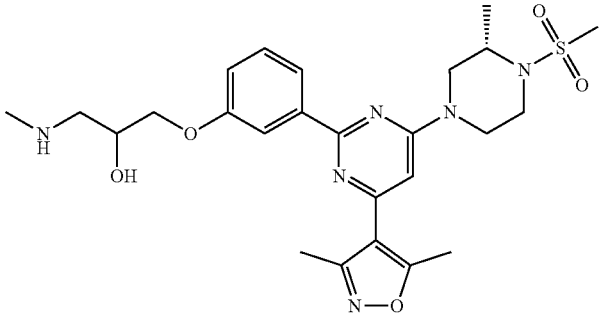 | 531.2 |
| 93-1a | 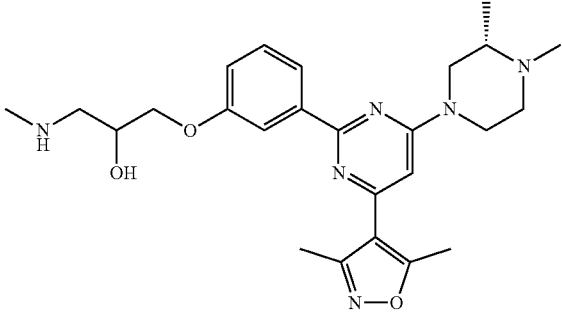 | 467.3 |
| 94-1a | 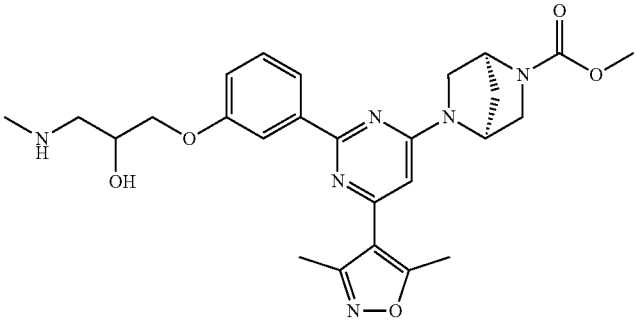 | 509.0 |
| 95-1a | 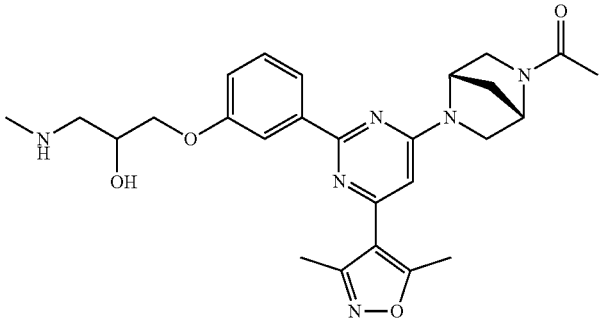 [SMILES: CNCC(O)COc1cccc(-c2nc(-c3c(C)noc3C)cc(N3C[C@@H]4C[C@H]3CN4C(C)=O)n2)c1] | 493.0 |

TABLE 1B-continued

Exemplary Compounds

| # | Structure | LC-MS m/z (M + H) |
|---|---|---|
| 96-1a | 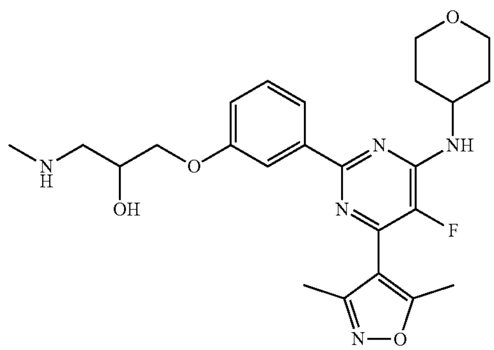 [SMILES: CNCC(O)COc1cccc(-c2nc(NC3CCOCC3)c(F)c(-c3c(C)noc3C)n2)c1] | 472.0 |
| 97-1a | 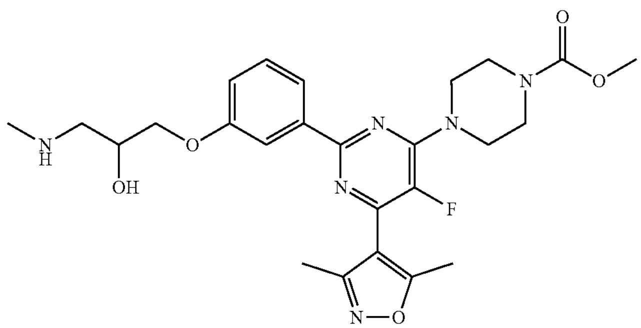 | 515.0 |
| 98-1a | 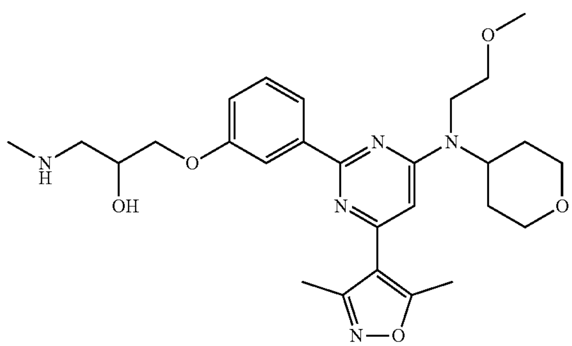 [SMILES: CNCC(O)COc1cccc(-c2nc(-c3c(C)noc3C)cc(N(CCOC)C3CCOCC3)n2)c1] | 512.0 |
| 99-1a | 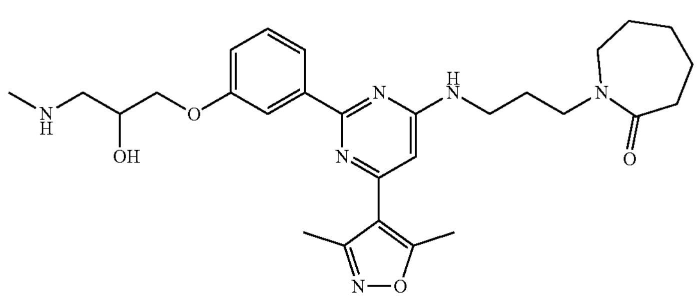 [SMILES: CNCC(O)COc1cccc(-c2nc(NCCCN3CCCCCC3=O)cc(-c3c(C)noc3C)n2)c1] | 523.2 |

TABLE 1B-continued

Exemplary Compounds

| # | Structure | LC-MS m/z (M + H) |
|---|---|---|
| 100-1a | 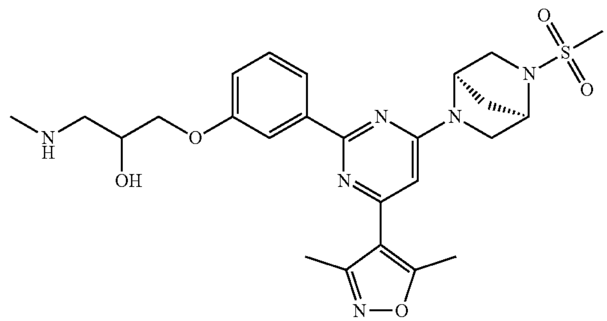 | 529.0 |
| 101-1a | 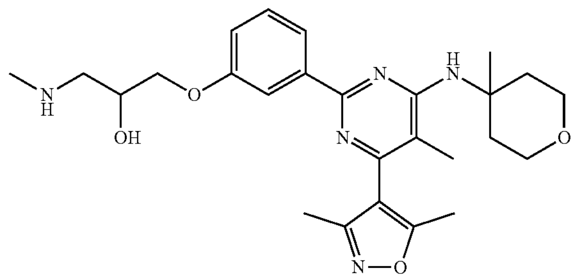 [SMILES: CNCC(O)COc1cccc(-c2nc(NC3(C)CCOCC3)c(C)c(-c3c(C)noc3C)n2)c1] | 482.0 |
| 102-1a | 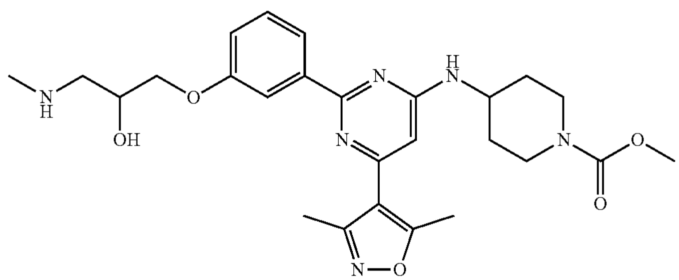 | 511.0 |
| 103-1a | 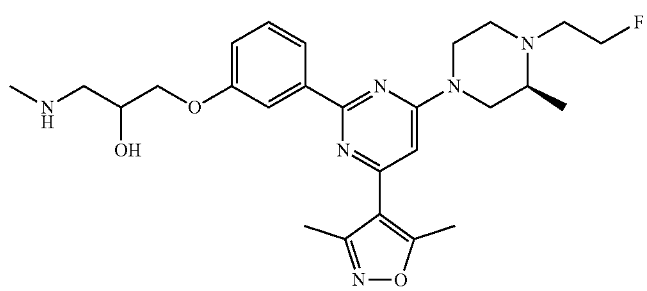 [SMILES: CNCC(O)COc1cccc(-c2nc(-c3c(C)noc3C)cc(N3CCN(CCF)[C@@H](C)C3)n2)c1] | 499.2 |
| 104-1a | 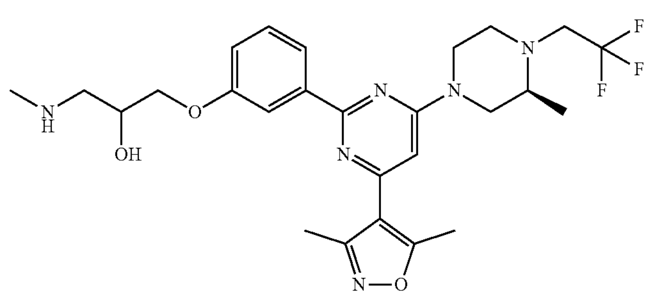 [SMILES: CNCC(O)COc1cccc(-c2nc(-c3c(C)noc3C)cc(N3CCN(CC(F)(F)F)[C@@H](C)C3)n2)c1] | 535.3 |

TABLE 1B-continued
Exemplary Compounds
| # | Structure | LC-MS m/z (M + H) |
|---|---|---|
| 105-1a | 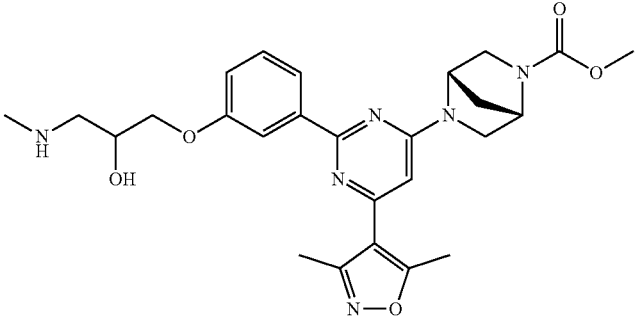 | 509.1 |
| 106-1a | 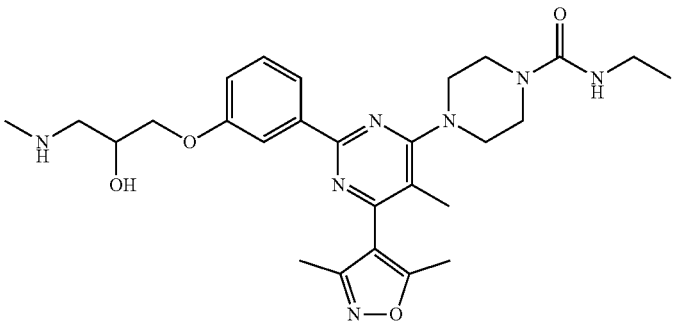 | 524.2 |
| 107-1a | 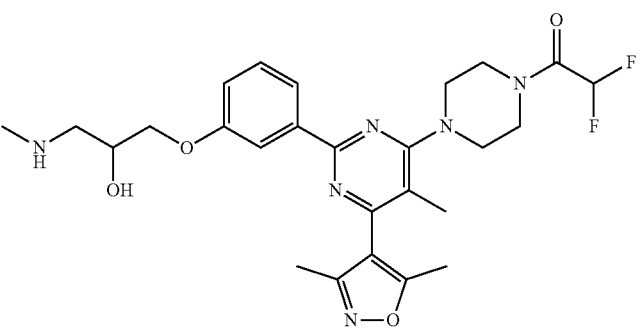 [SMILES: CNCC(O)COc1cccc(-c2nc(-c3c(C)noc3C)c(C)c(N3CCN(C(=O)C(F)F)CC3)n2)c1] | 531.1 |
| 108-1a | 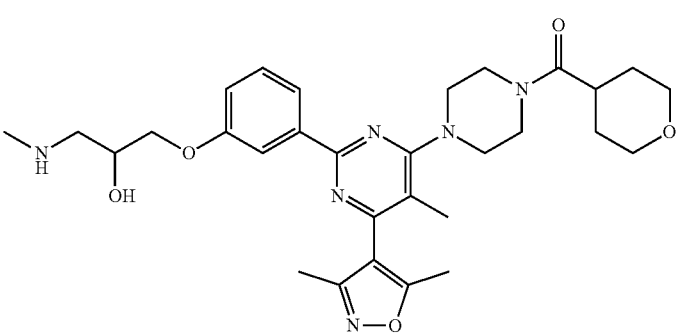 [SMILES: CNCC(O)COc1cccc(-c2nc(-c3c(C)noc3C)c(C)c(N3CCN(C(=O)C4CCOCC4)CC3)n2)c1] | 565.2 |

US 10,118,931 B2
TABLE 1B-continued
Exemplary Compounds
| # | Structure | LC-MS m/z (M + H) |
|---|---|---|
| 109-1a | 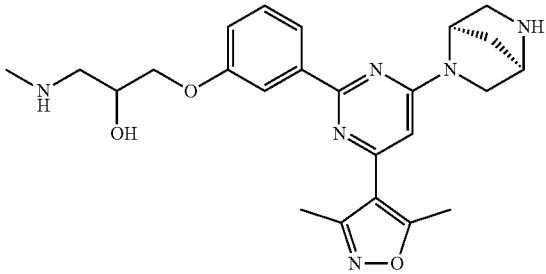 [SMILES: CNCC(O)COc1cccc(-c2nc(-c3c(C)noc3C)cc(N3C[C@H]4C[C@@H]3CN4)n2)c1] | 451.0 |
| 110-1a | 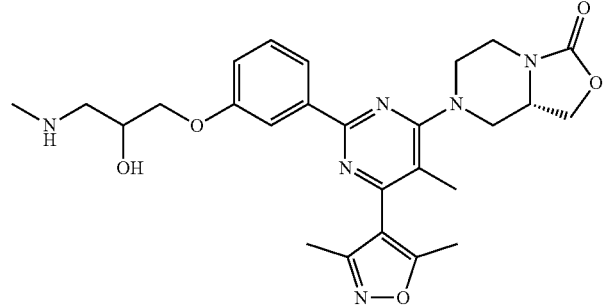 [SMILES: CNCC(O)COc1cccc(-c2nc(-c3c(C)noc3C)c(C)c(N3CCN4C(=O)OC[C@@H]4C3)n2)c1] | 509.1 |
| 111-1a | 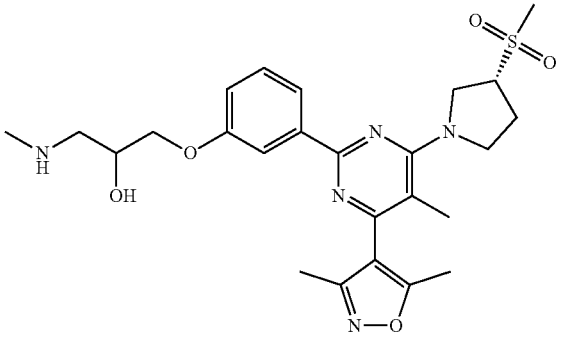 [SMILES: CNCC(O)COc1cccc(-c2nc(-c3c(C)noc3C)c(C)c(N3CC[C@@H](S(C)(=O)=O)C3)n2)c1] | 516.2 |
| 112-1a | 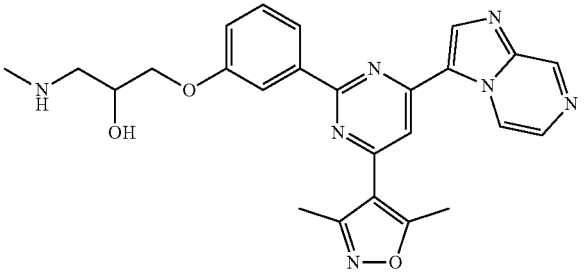 [SMILES: CNCC(O)COc1cccc(-c2nc(-c3c(C)noc3C)cc(-c3cnc4cnccn34)n2)c1] | 472.0 |
| 113-1a | 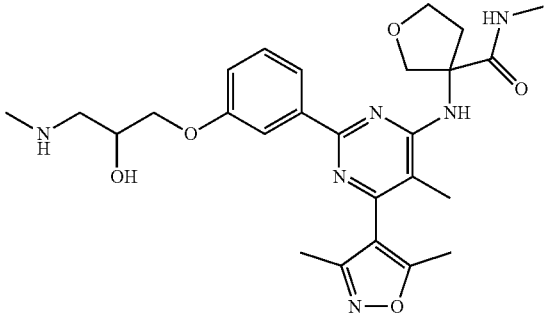 | 511.3 |

TABLE 1B-continued

Exemplary Compounds

| # | Structure | LC-MS m/z (M + H) |
|---|---|---|
| 114-1a | 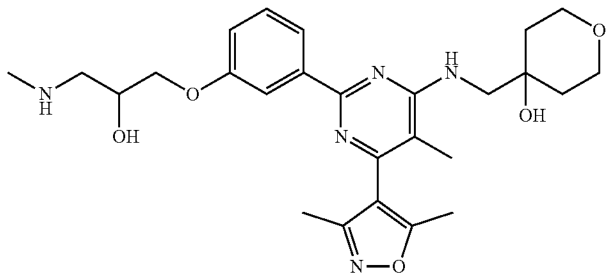 [SMILES: CNCC(O)COc1cccc(-c2nc(NCC3(O)CCOCC3)c(C)c(-c3c(C)noc3C)n2)c1] | 498.2 |
| 115-1a | 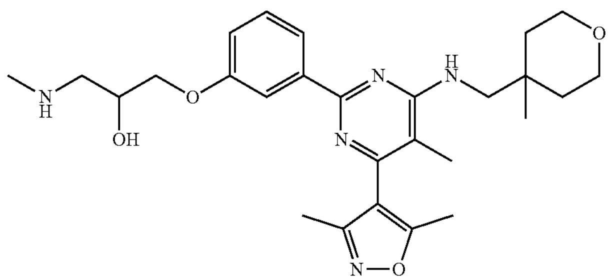 [SMILES: CNCC(O)COc1cccc(-c2nc(NCC3(C)CCOCC3)c(C)c(-c3c(C)noc3C)n2)c1] | 496.2 |
| 116-1a | 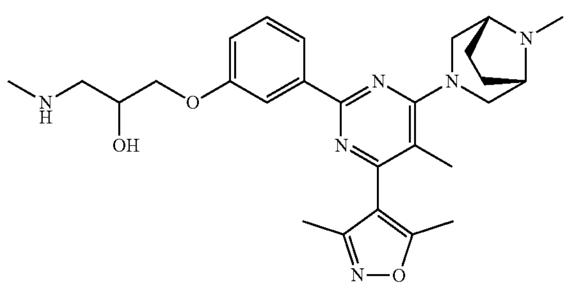 | 493.3 |
| 117-1a | 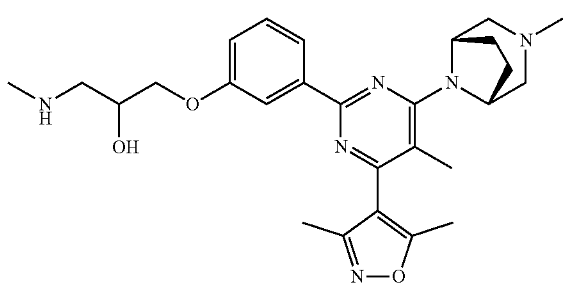 | 493.0 |
| 118-1a | 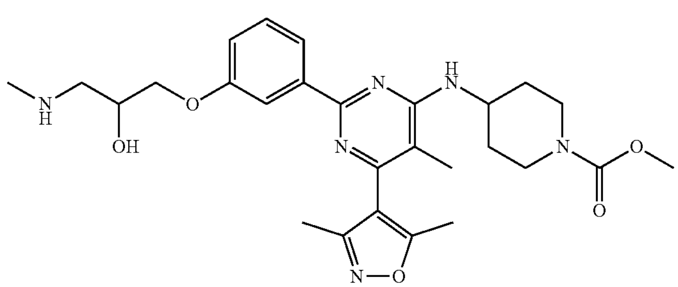 | 525.0 |

TABLE 1B-continued
Exemplary Compounds
| # | Structure | LC-MS m/z (M + H) |
|---|---|---|
| 119-1a | 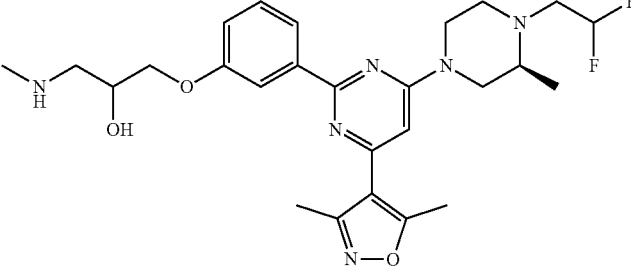 | 517.3 |
| 120-1a | 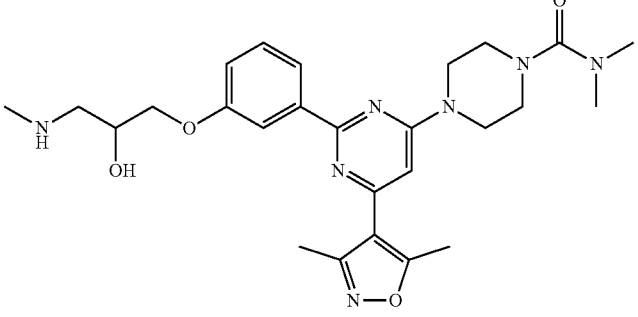 | 510.0 |
| 121-1a | 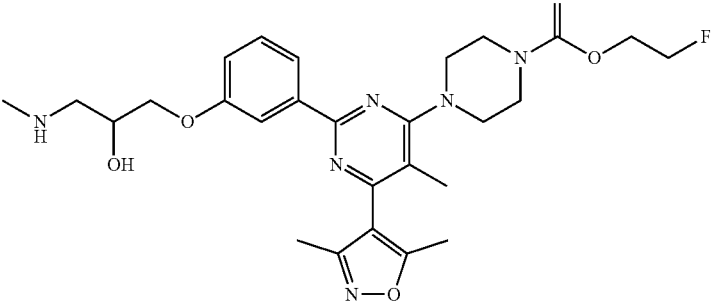 | 543.2 |
| 122-1a | 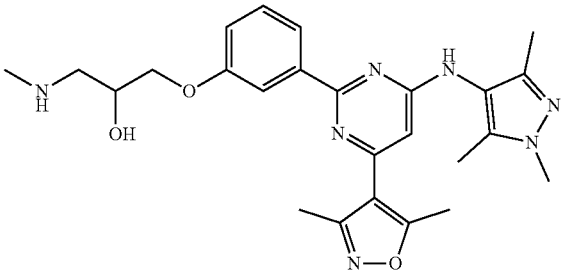 [SMILES: CNCC(O)COc1cccc(-c2nc(Nc3c(C)nn(C)c3C)cc(-c3c(C)noc3C)n2)c1] | 478.1 |
| 123-1a | 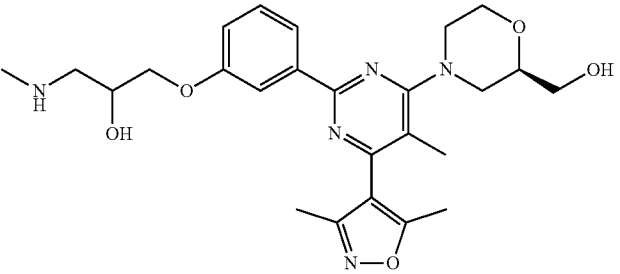 [SMILES: CNCC(O)COc1cccc(-c2nc(-c3c(C)noc3C)c(C)c(N3CCO[C@@H](CO)C3)n2)c1] | 484.2 |

TABLE 1B-continued

Exemplary Compounds

| # | Structure | LC-MS m/z (M + H) |
|---|-----------|-------------------|
| 124-1a | 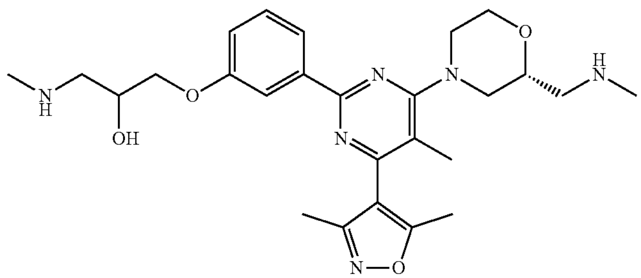 | 497.3 |
| 125-1a | 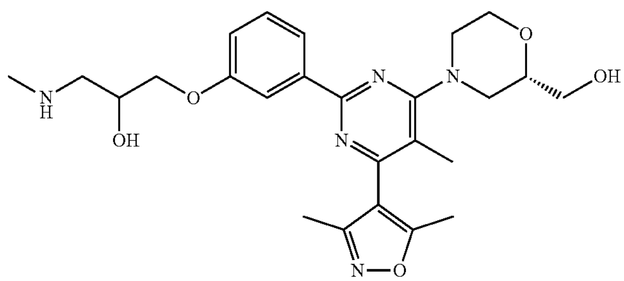 [SMILES: CNCC(O)COc1cccc(-c2nc(-c3c(C)noc3C)c(C)c(N3CCO[C@H](CO)C3)n2)c1] | 484.2 |
| 126-1a | 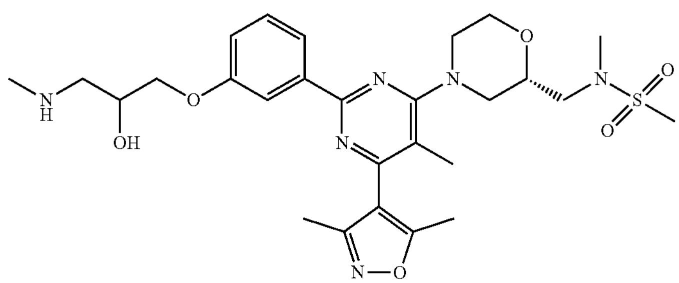 | 575.2 |
| 127-1a | 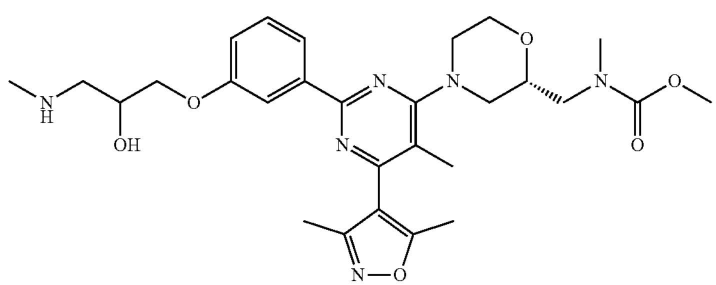 | 555.3 |
| 128-1a | 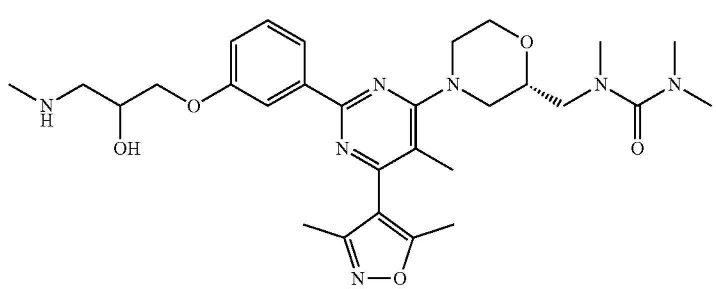 | 568.3 |

TABLE 1B-continued

Exemplary Compounds

| # | Structure | LC-MS m/z (M + H) |
|---|---|---|
| 129-1a | 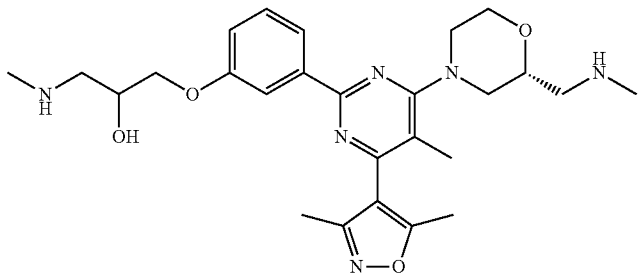 | 497.3 |
| 130-1a | 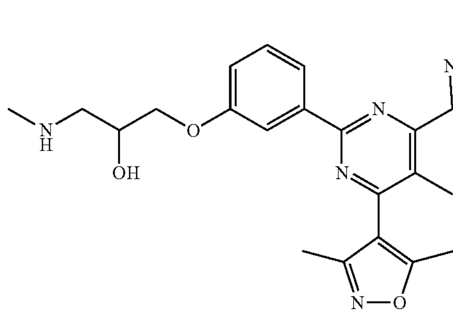 | 463.3 |
| 131-1a | 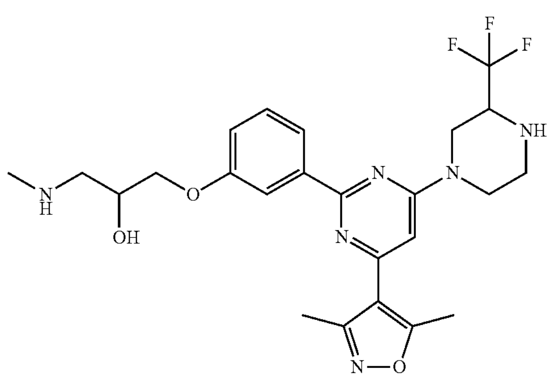 [SMILES: CNCC(O)COc1cccc(-c2nc(-c3c(C)noc3C)cc(N3CCNC(C(F)(F)F)C3)n2)c1] | 506.9 |
| 132-1a | 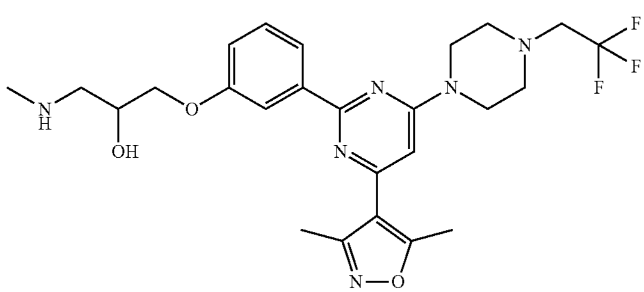 [SMILES: CNCC(O)COc1cccc(-c2nc(-c3c(C)noc3C)cc(N3CCN(CC(F)(F)F)CC3)n2)c1] | 521.0 |

TABLE 1B-continued

Exemplary Compounds

| # | Structure | LC-MS m/z (M + H) |
|---|---|---|
| 133-1a | 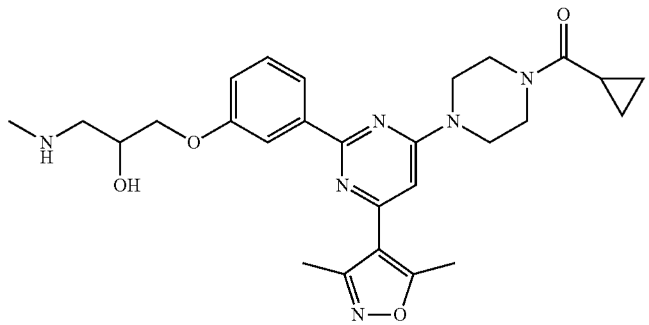 [SMILES: CNCC(O)COc1cccc(-c2nc(-c3c(C)noc3C)cc(N3CCN(C(=O)C4CC4)CC3)n2)c1] | 507.0 |
| 134-1a | 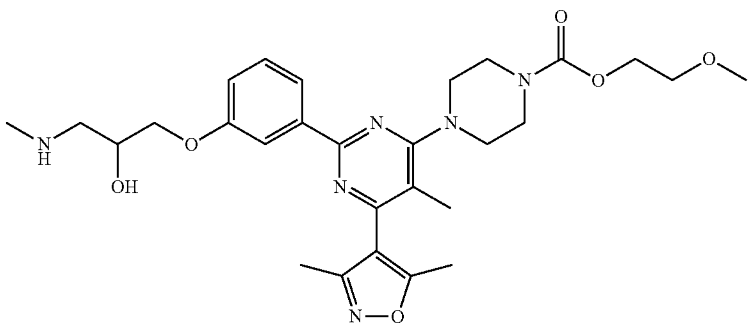 | 555.3 |
| 135-1a | 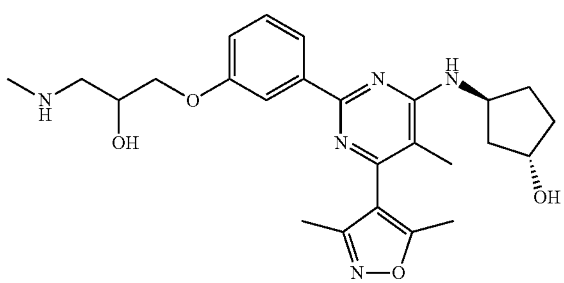 [SMILES: CNCC(O)COc1cccc(-c2nc(N[C@H]3CC[C@H](O)C3)c(C)c(-c3c(C)noc3C)n2)c1] | 468.1 |
| 136-1a | 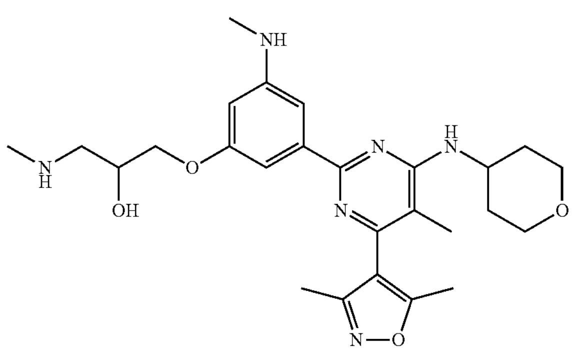 [SMILES: CNCC(O)COc1cc(NC)cc(-c2nc(NC3CCOCC3)c(C)c(-c3c(C)noc3C)n2)c1] | 497.3 |
| 137-1a | 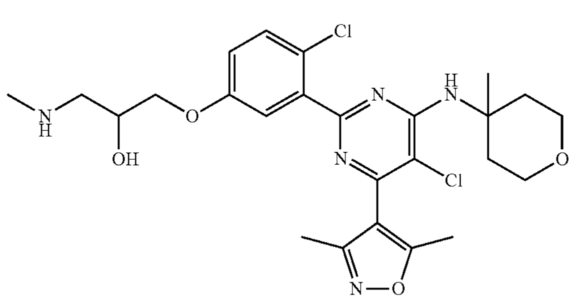 [SMILES: CNCC(O)COc1ccc(Cl)c(-c2nc(NC3(C)CCOCC3)c(Cl)c(-c3c(C)noc3C)n2)c1] | 536.2 |

TABLE 1B-continued

Exemplary Compounds

| # | Structure | LC-MS m/z (M + H) |
|---|---|---|
| 139-1a | 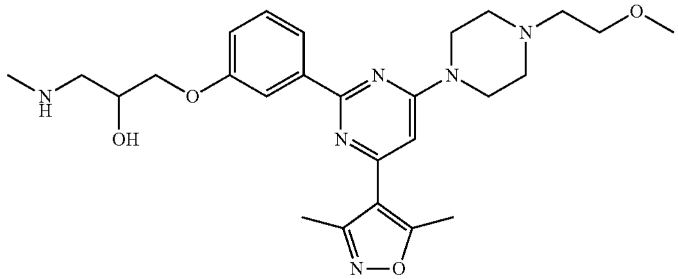 | 497.0 |
| 140-1a | 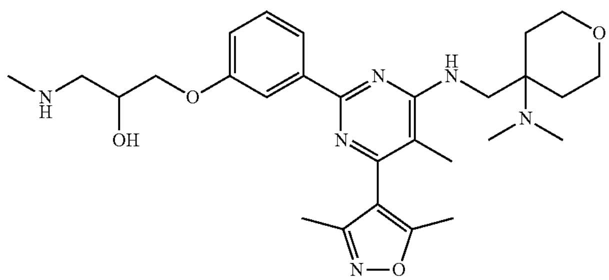 [SMILES: CNCC(O)COc1cccc(-c2nc(NCC3(N(C)C)CCOCC3)c(C)c(-c3c(C)noc3C)n2)c1] | 525.3 |
| 141-1a | 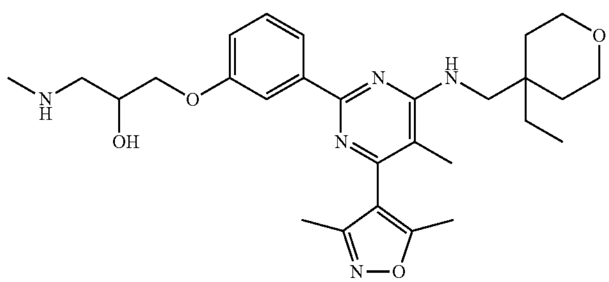 [SMILES: CCC1(CNc2nc(-c3cccc(OCC(O)CNC)c3)nc(-c3c(C)noc3C)c2C)CCOCC1] | 510.3 |
| 142-1a | 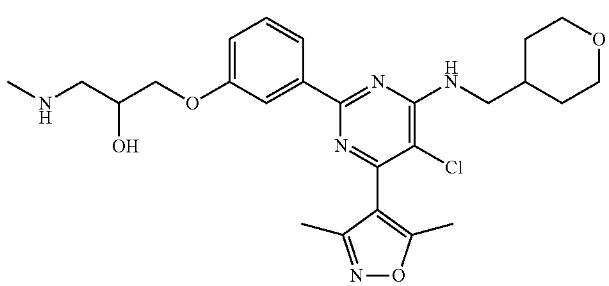 [SMILES: CNCC(O)COc1cccc(-c2nc(NCC3CCOCC3)c(Cl)c(-c3c(C)noc3C)n2)c1] | 502.2 |
| 143-1a | 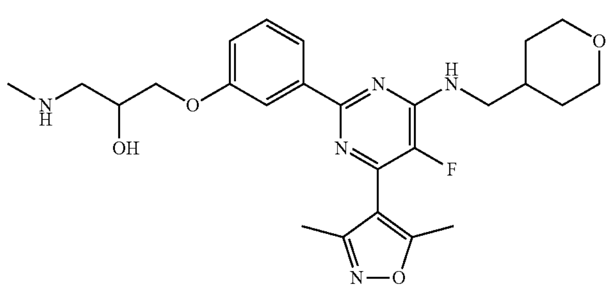 [SMILES: CNCC(O)COc1cccc(-c2nc(NCC3CCOCC3)c(F)c(-c3c(C)noc3C)n2)c1] | 486.3 |

TABLE 1B-continued

Exemplary Compounds

| # | Structure | LC-MS m/z (M + H) |
|---|---|---|
| 144-1a | 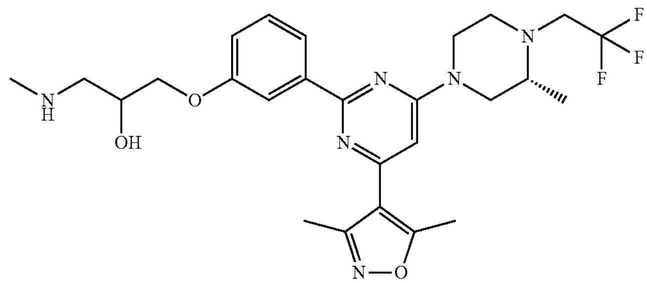 [SMILES: CNCC(O)COc1cccc(-c2nc(-c3c(C)noc3C)cc(N3CCN(CC(F)(F)F)[C@H](C)C3)n2)c1] | 535.3 |
| 145-1a | 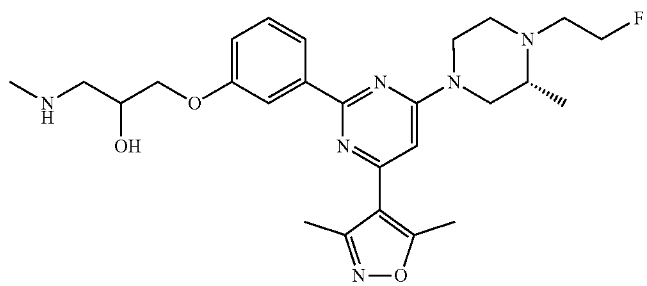 [SMILES: CNCC(O)COc1cccc(-c2nc(-c3c(C)noc3C)cc(N3CCN(CCF)[C@H](C)C3)n2)c1] | 499.3 |
| 146-1a | 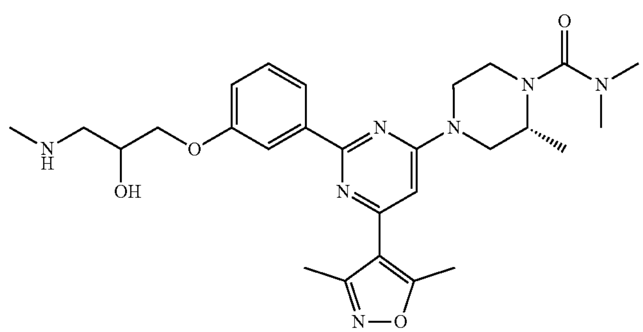 | 524.3 |
| 147-1a | 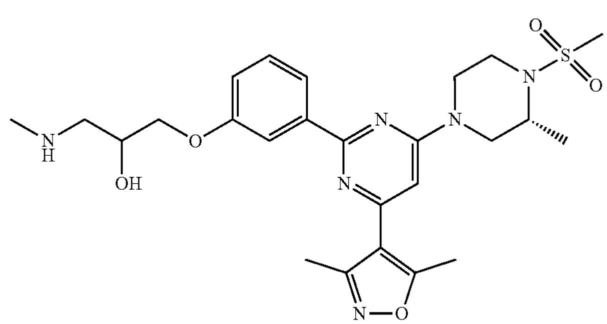 | 531.2 |
| 148-1a | 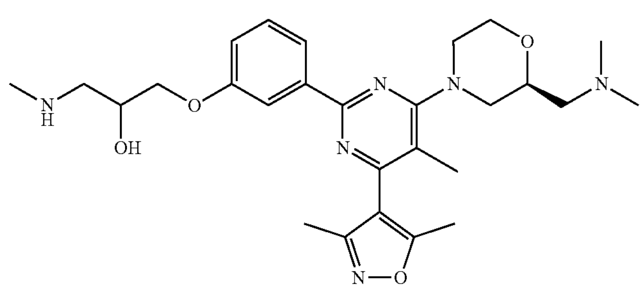 | 511.4 |

TABLE 1B-continued

Exemplary Compounds

| # | Structure | LC-MS m/z (M + H) |
|---|---|---|
| 149-1a | 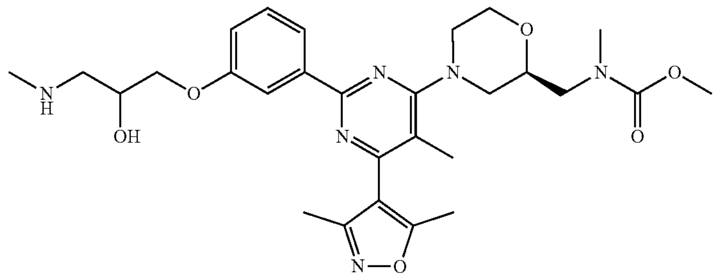 | 555.3 |
| 150-1a | 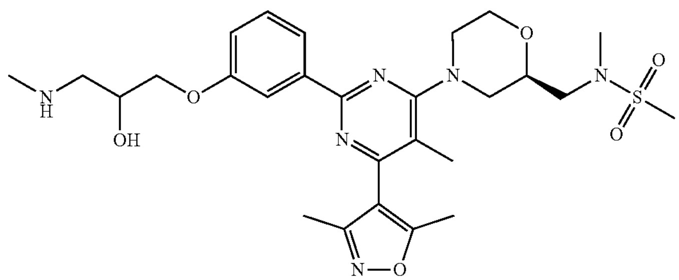 | 575.3 |
| 151-1a | 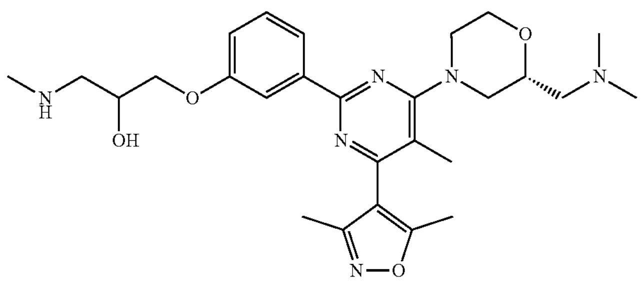 | 511.3 |
| 152-1a | 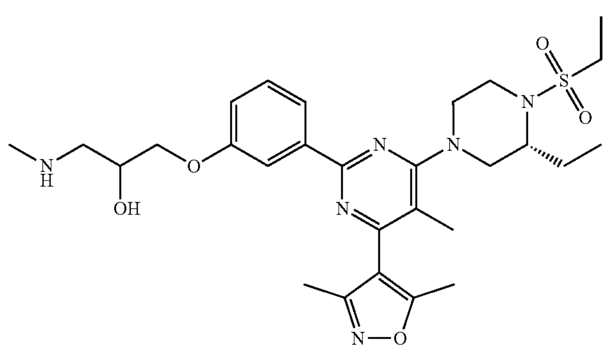 [SMILES: CC[C@@H]1CN(c2nc(-c3cccc(OCC(O)CNC)c3)nc(-c3c(C)noc3C)c2C)CCN1S(=O)(=O)CC] | 573.3 |
| 153-1a | 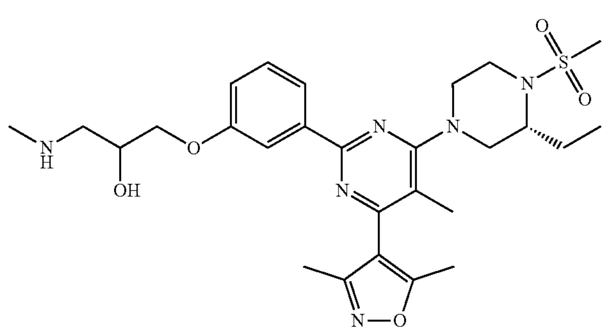 | 559.3 |

TABLE 1B-continued

Exemplary Compounds

| # | Structure | LC-MS m/z (M + H) |
|---|---|---|
| 154-1a | 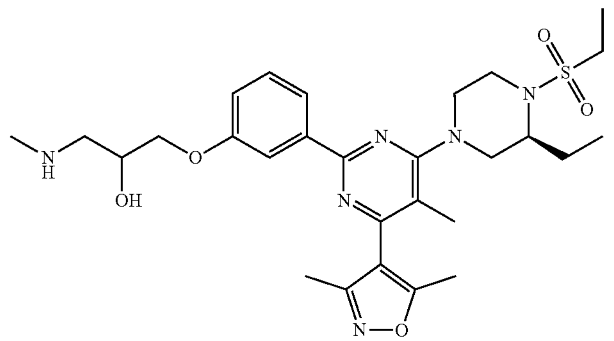 [SMILES: CC[C@H]1CN(c2nc(-c3cccc(OCC(O)CNC)c3)nc(-c3c(C)noc3C)c2C)CCN1S(=O)(=O)CC] | 573.3 |
| 155-1a | 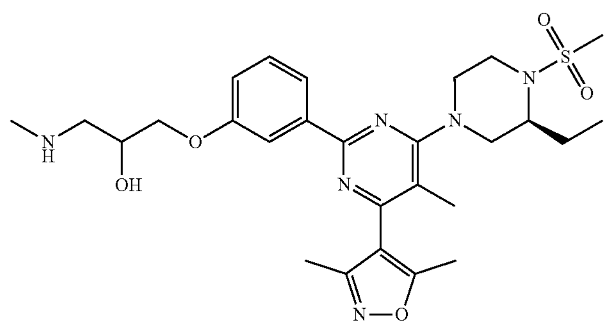 | 559.2 |
| 156-1a | 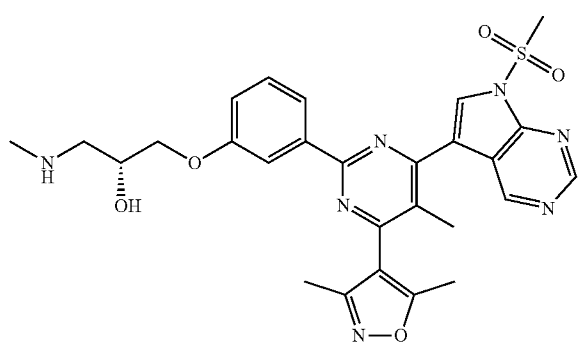 [SMILES: CNC[C@@H](O)COc1cccc(-c2nc(-c3c(C)noc3C)c(C)c(-c3cn(S(C)(=O)=O)c4ncncc34)n2)c1] | 563.8 |
| 157-1a | 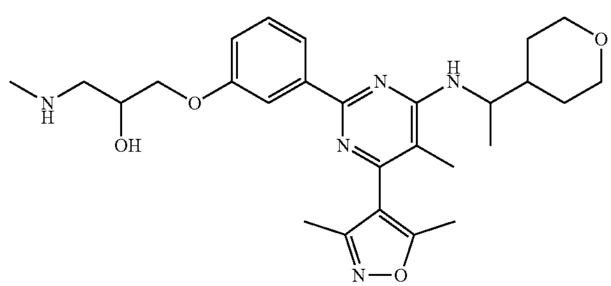 [SMILES: CNCC(O)COc1cccc(-c2nc(NC(C)C3CCOCC3)c(C)c(-c3c(C)noc3C)n2)c1] | 496.4 |
| 158-1a | 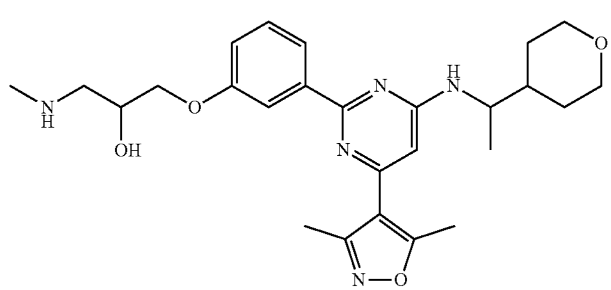 [SMILES: CNCC(O)COc1cccc(-c2nc(NC(C)C3CCOCC3)cc(-c3c(C)noc3C)n2)c1] | 482.3 |

TABLE 1B-continued

Exemplary Compounds

| # | Structure | LC-MS m/z (M + H) |
|---|---|---|
| 159-1a | 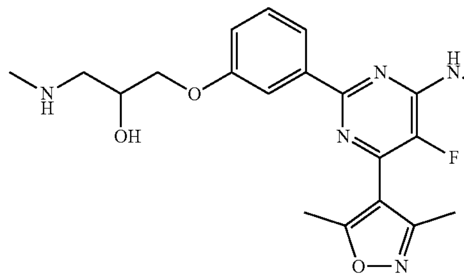 | 486.3 |
| 160-1a | 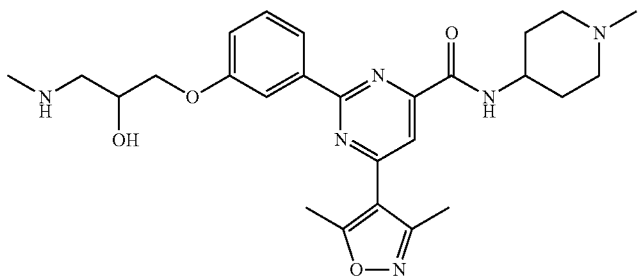 | 495.3 |
| 161-1a | 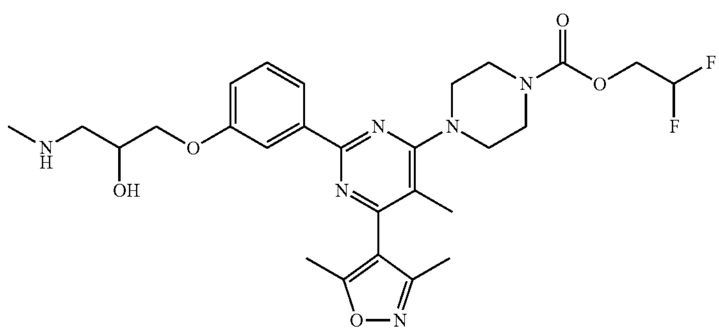 [SMILES: CNCC(O)COc1cccc(-c2nc(-c3c(C)noc3C)c(C)c(N3CCN(C(=O)OCC(F)F)CC3)n2)c1] | 561.3 |
| 162-1a | 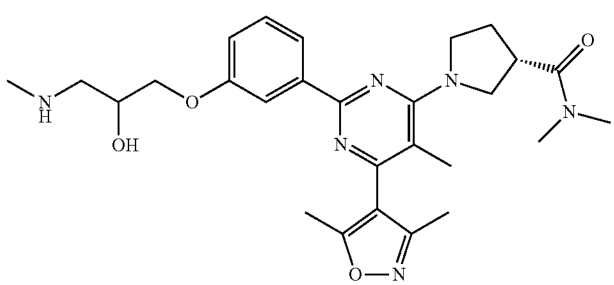 | 509.0 |
| 163-1a | 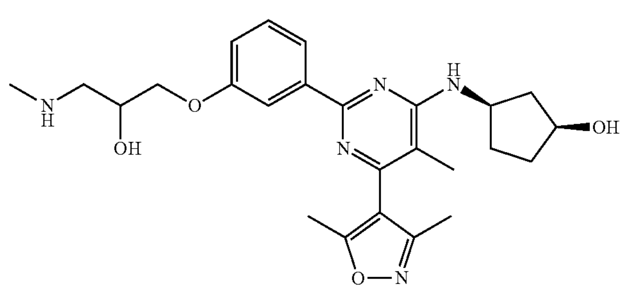 [SMILES: CNCC(O)COc1cccc(-c2nc(N[C@@H]3CC[C@H](O)C3)c(C)c(-c3c(C)noc3C)n2)c1] | 468.3 |

TABLE 1B-continued

Exemplary Compounds

| # | Structure | LC-MS m/z (M + H) |
|---|---|---|
| 164-1a | 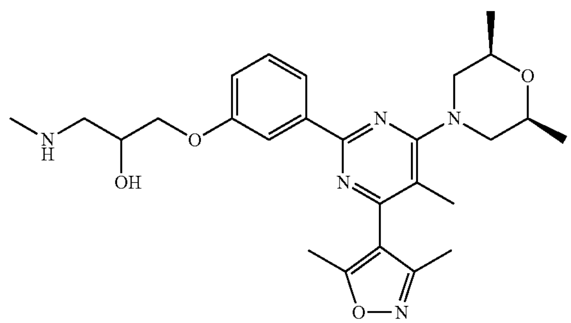 | 482.0 |
| 165-1a | 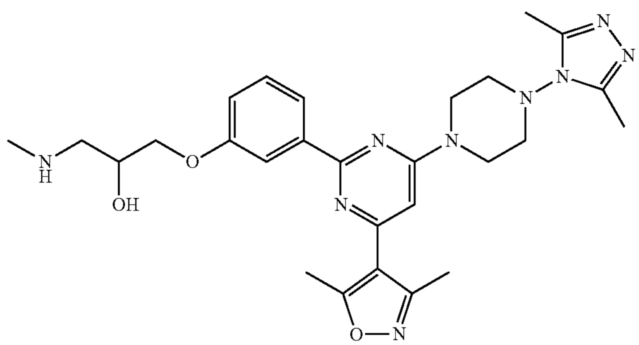 [SMILES: CNCC(O)COc1cccc(-c2nc(-c3c(C)noc3C)cc(N3CCN(n4c(C)nnc4C)CC3)n2)c1] | 534.0 |
| 166-1a | 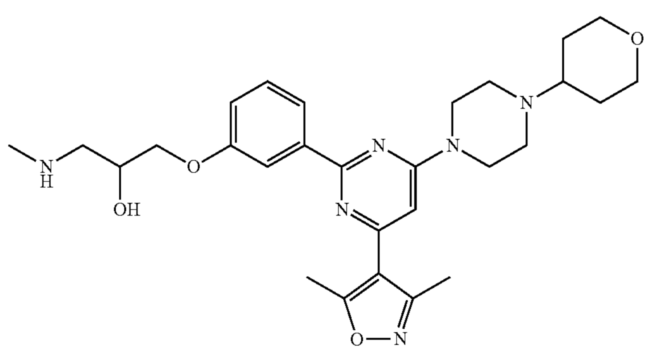 [SMILES: CNCC(O)COc1cccc(-c2nc(-c3c(C)noc3C)cc(N3CCN(C4CCOCC4)CC3)n2)c1] | 523.0 |
| 167-1a | 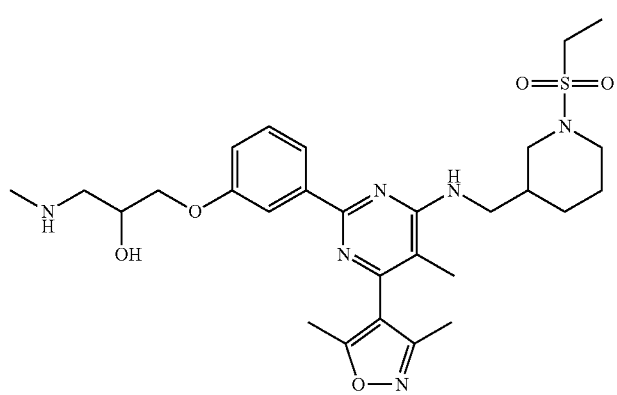 [SMILES: CCS(=O)(=O)N1CCCC(CNc2nc(-c3cccc(OCC(O)CNC)c3)nc(-c3c(C)noc3C)c2C)C1] | 573.3 |

TABLE 1B-continued

Exemplary Compounds

| # | Structure | LC-MS m/z (M + H) |
|---|---|---|
| 168-1a | 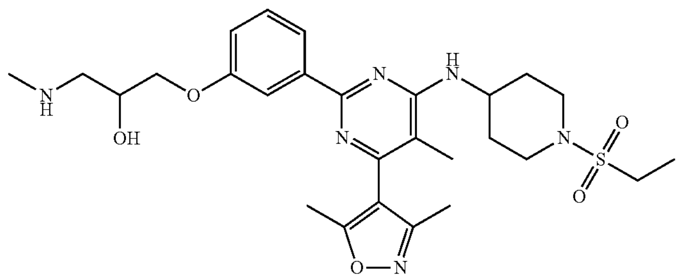 [SMILES: CCS(=O)(=O)N1CCC(Nc2nc(-c3cccc(OCC(O)CNC)c3)nc(-c3c(C)noc3C)c2C)CC1] | 559.2 |
| 169-1a | 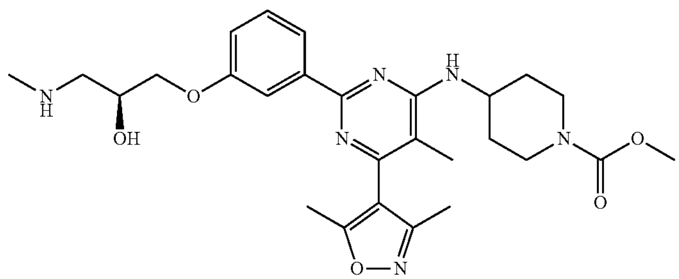 | 525.3 |
| 170-1a | 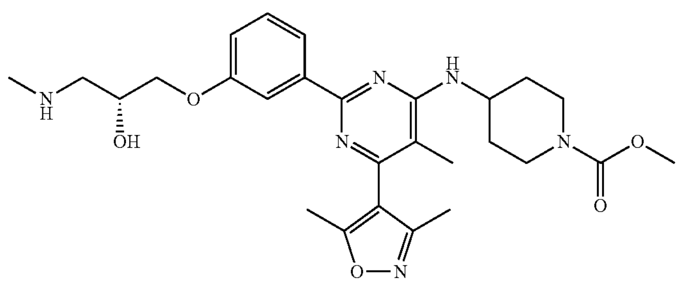 | 525.3 |
| 171-1a | 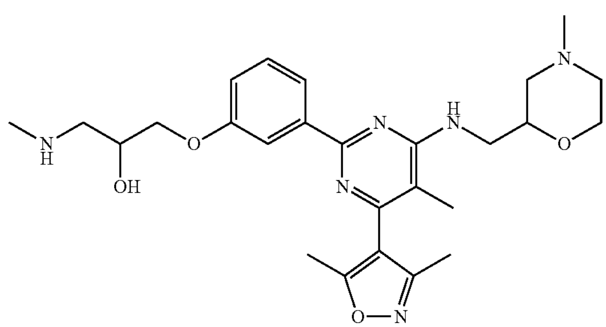 [SMILES: CNCC(O)COc1cccc(-c2nc(NCC3CN(C)CCO3)c(C)c(-c3c(C)noc3C)n2)c1] | 497.0 |
| 172-1a | 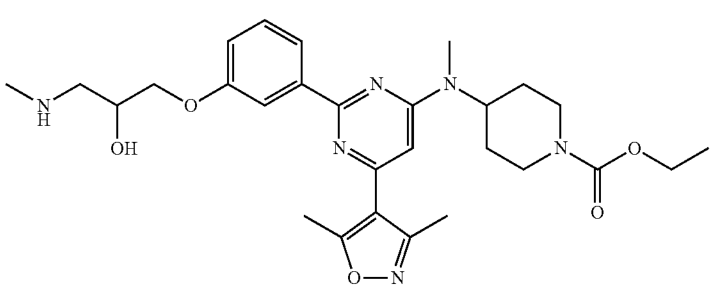 [SMILES: CCOC(=O)N1CCC(N(C)c2cc(-c3c(C)noc3C)nc(-c3cccc(OCC(O)CNC)c3)n2)CC1] | 539.3 |

TABLE 1B-continued
Exemplary Compounds
| # | Structure | LC-MS m/z (M + H) |
|---|---|---|
| 173-1a | 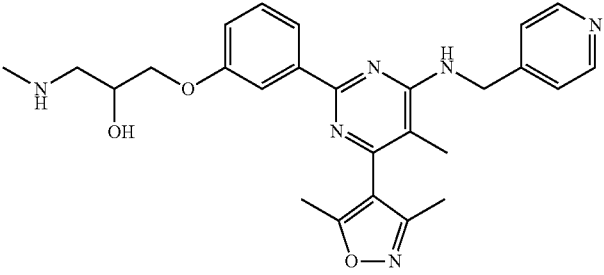 [SMILES: CNCC(O)COc1cccc(-c2nc(NCc3ccncc3)c(C)c(-c3c(C)noc3C)n2)c1] | 575.0 |
| 174-1a | 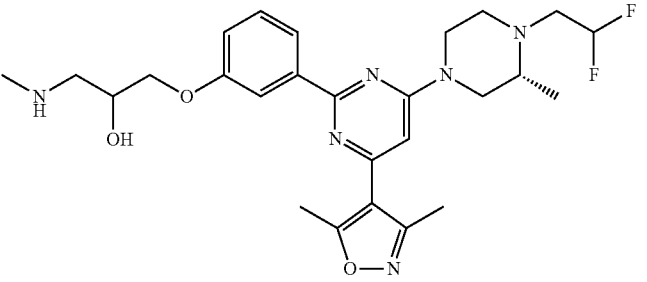 [SMILES: CNCC(O)COc1cccc(-c2nc(-c3c(C)noc3C)cc(N3CCN(CC(F)F)[C@H](C)C3)n2)c1] | 517.3 |
| 175-1a | 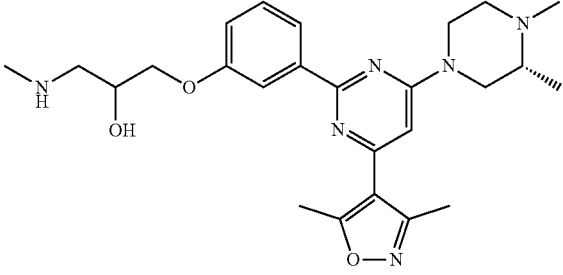 | 467.3 |
| 176-1a | 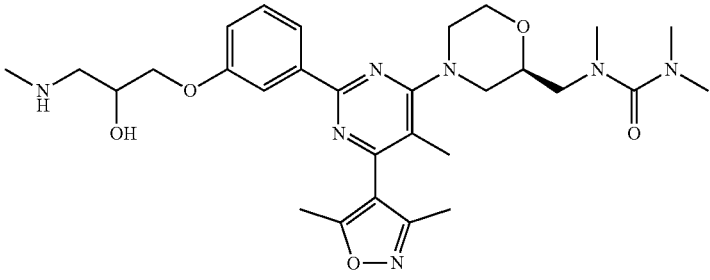 | 568.3 |
| 177-1a | 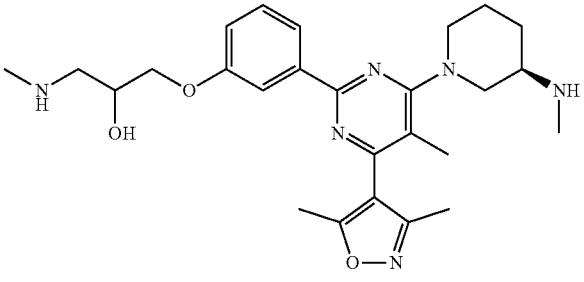 | 481.4 |

TABLE 1B-continued
Exemplary Compounds
| # | Structure | LC-MS m/z (M + H) |
|---|---|---|
| 178-1a | 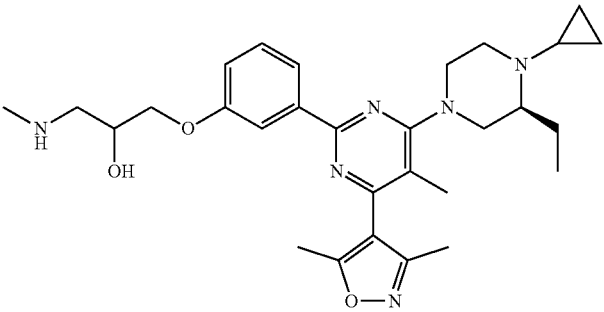 [SMILES: CC[C@H]1CN(c2nc(-c3cccc(OCC(O)CNC)c3)nc(-c3c(C)noc3C)c2C)CCN1C1CC1] | 521.4 |
| 179-1a | 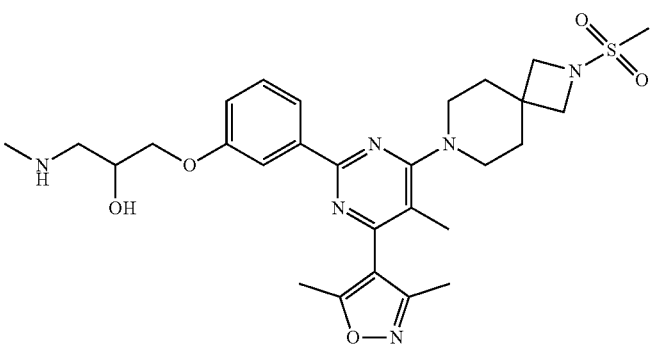 | 571.3 |
| 180-1a | 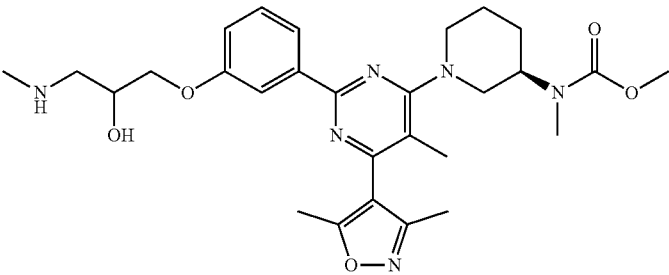 | 539.3 |
| 181-1a | 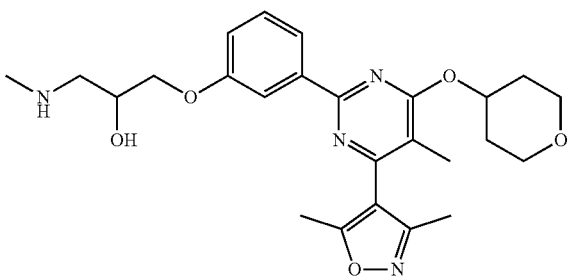 [SMILES: CNCC(O)COc1cccc(-c2nc(OC3CCOCC3)c(C)c(-c3c(C)noc3C)n2)c1] | 469.0 |
| 182-1a | 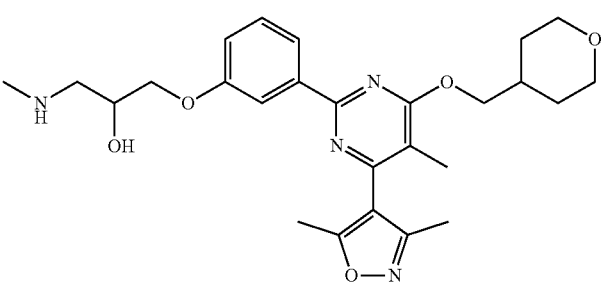 [SMILES: CNCC(O)COc1cccc(-c2nc(OCC3CCOCC3)c(C)c(-c3c(C)noc3C)n2)c1] | 483.0 |

TABLE 1B-continued

Exemplary Compounds

| # | Structure | LC-MS m/z (M + H) |
|---|---|---|
| 183-1a | 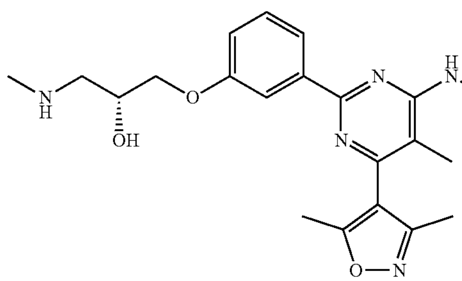 | 482.3 |
| 184-1a | 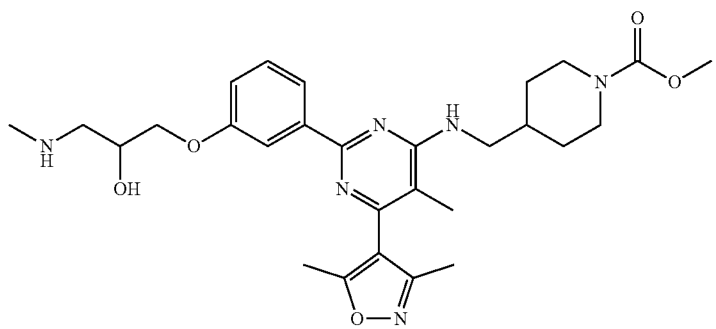 | 539.3 |
| 185-1a | 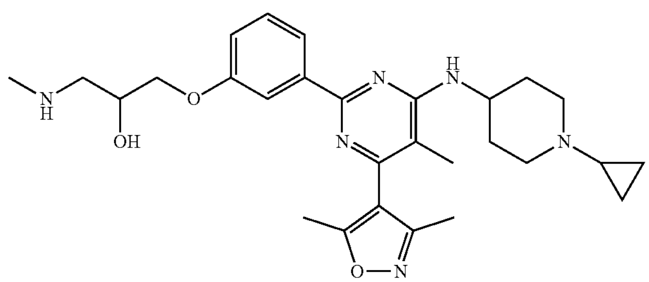 [SMILES: CNCC(O)COc1cccc(-c2nc(NC3CCN(C4CC4)CC3)c(C)c(-c3c(C)noc3C)n2)c1] | 507.3 |
| 186-1a | 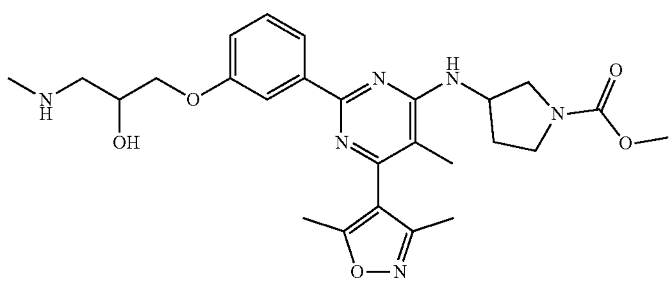 | 511.3 |
| 187-1a | 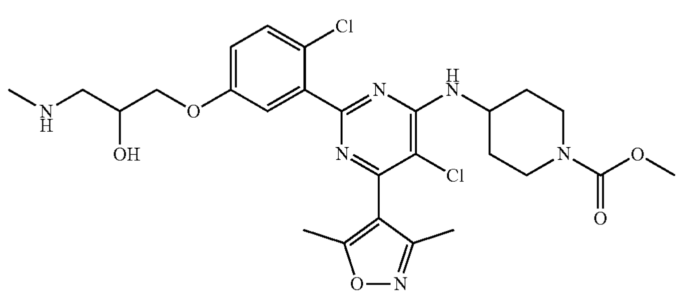 | 579.2 |

TABLE 1B-continued

Exemplary Compounds

| # | Structure | LC-MS m/z (M + H) |
|---|---|---|
| 188-1a | 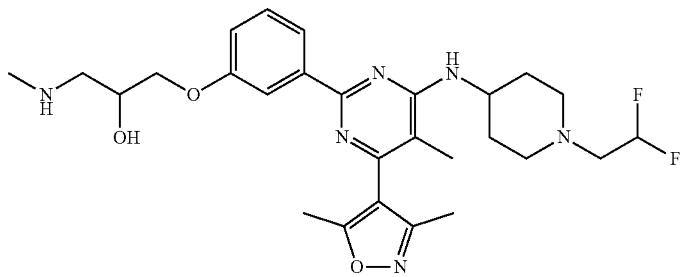 [SMILES: CNCC(O)COc1cccc(-c2nc(NC3CCN(CC(F)F)CC3)c(C)c(-c3c(C)noc3C)n2)c1] | 531.0 |
| 189-1a | 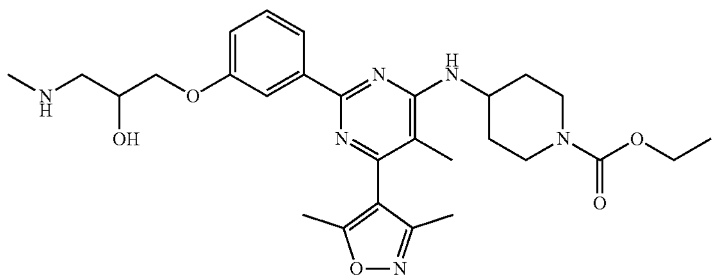 [SMILES: CCOC(=O)N1CCC(Nc2nc(-c3cccc(OCC(O)CNC)c3)nc(-c3c(C)noc3C)c2C)CC1] | 539.3 |
| 190-1a | 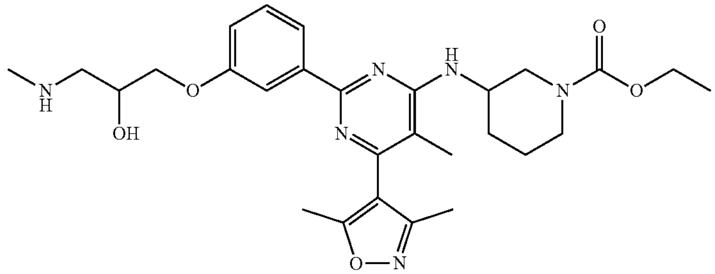 [SMILES: CCOC(=O)N1CCCC(Nc2nc(-c3cccc(OCC(O)CNC)c3)nc(-c3c(C)noc3C)c2C)C1] | 539.3 |
| 191-1a | 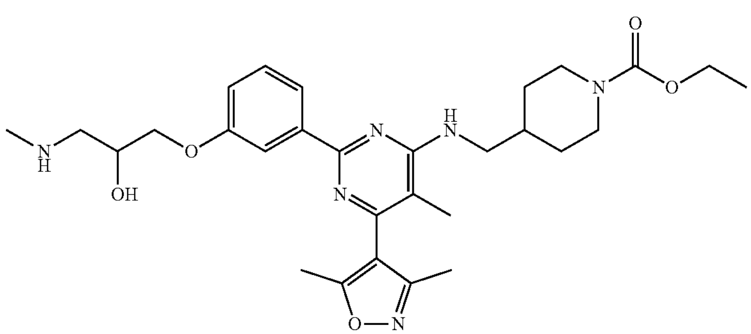 [SMILES: CCOC(=O)N1CCC(CNc2nc(-c3cccc(OCC(O)CNC)c3)nc(-c3c(C)noc3C)c2C)CC1] | 553.3 |
| 192-1a | 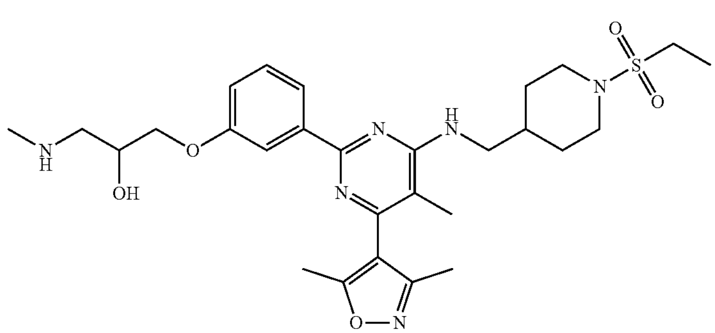 [SMILES: CCS(=O)(=O)N1CCC(CNc2nc(-c3cccc(OCC(O)CNC)c3)nc(-c3c(C)noc3C)c2C)CC1] | 573.3 |

TABLE 1B-continued
Exemplary Compounds
| # | Structure | LC-MS m/z (M + H) |
|---|---|---|
| 193-1a | 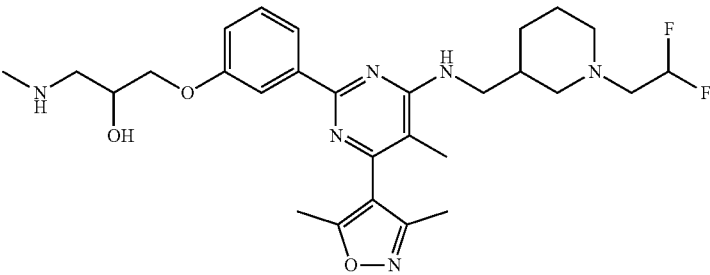 [SMILES: CNCC(O)COc1cccc(-c2nc(NCC3CCCN(CC(F)F)C3)c(C)c(-c3c(C)noc3C)n2)c1] | 545.3 |
| 194-1a | 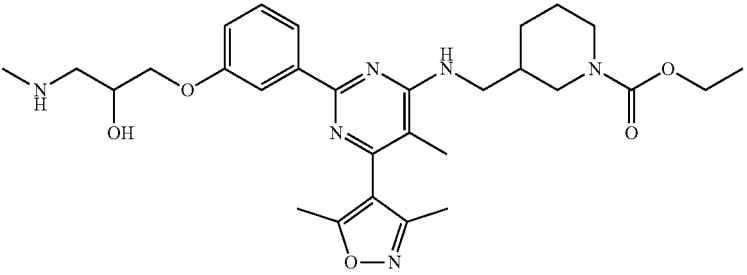 [SMILES: CCOC(=O)N1CCCC(CNc2nc(-c3cccc(OCC(O)CNC)c3)nc(-c3c(C)noc3C)c2C)C1] | 553.3 |
| 195-1a | 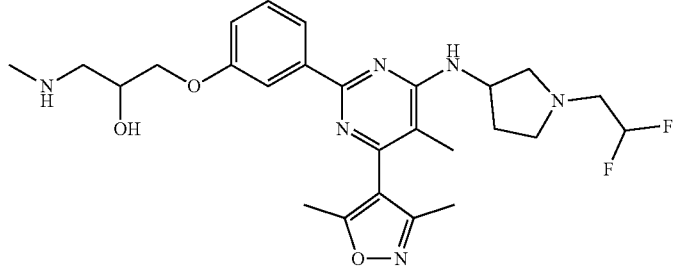 [SMILES: CNCC(O)COc1cccc(-c2nc(NC3CCN(CC(F)F)C3)c(C)c(-c3c(C)noc3C)n2)c1] | 517.3 |
| 196-1a | 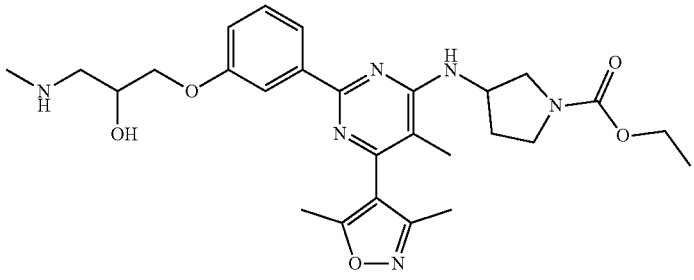 [SMILES: CCOC(=O)N1CCC(Nc2nc(-c3cccc(OCC(O)CNC)c3)nc(-c3c(C)noc3C)c2C)C1] | 525.3 |
| 197-1a | 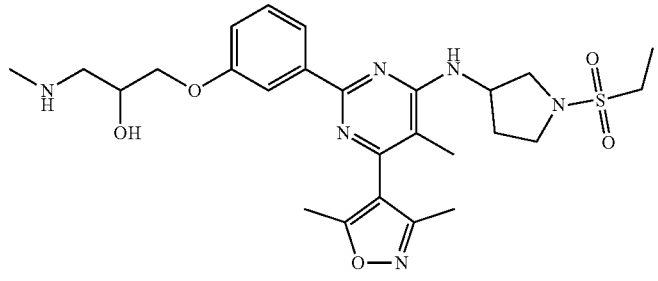 [SMILES: CCS(=O)(=O)N1CCC(Nc2nc(-c3cccc(OCC(O)CNC)c3)nc(-c3c(C)noc3C)c2C)C1] | 545.3 |

TABLE 1B-continued

Exemplary Compounds

| # | Structure | LC-MS m/z (M + H) |
|---|---|---|
| 198-1a | 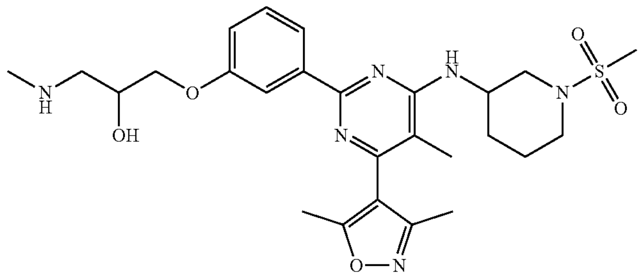 | 545.3 |
| 199-1a | 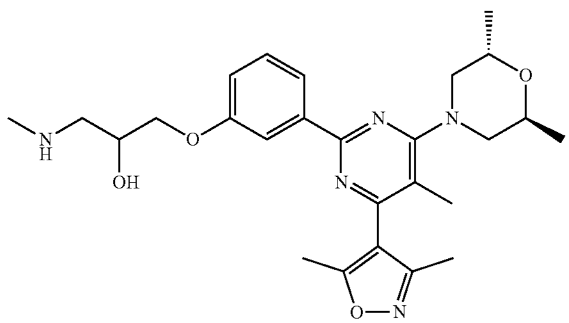 | 482.0 |
| 200-1a | 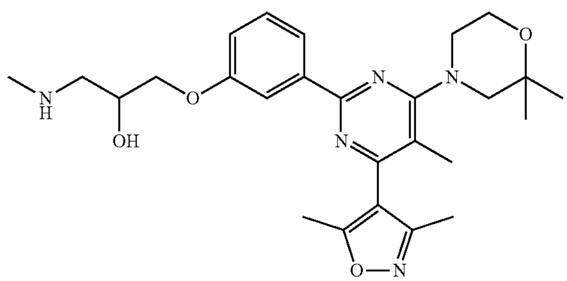 | 482.0 |
| 201-1a | 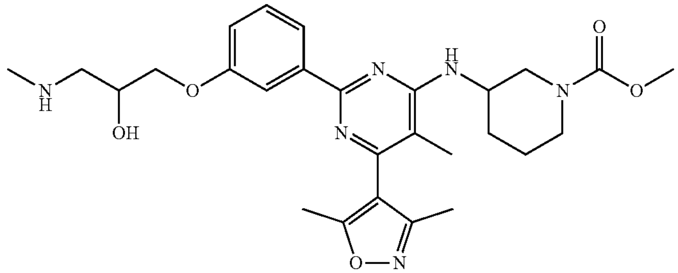 | 525.3 |
| 202-1a | 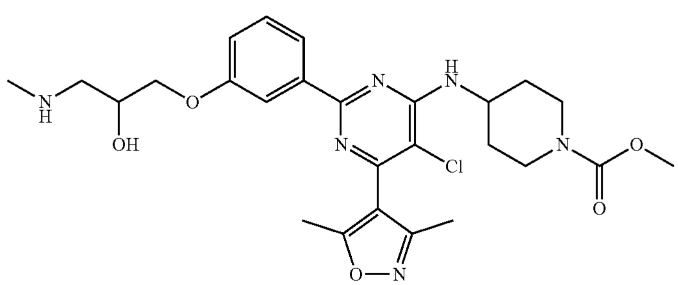 | 544.8 |

TABLE 1B-continued

Exemplary Compounds

| # | Structure | LC-MS m/z (M + H) |
|---|---|---|
| 203-1a | 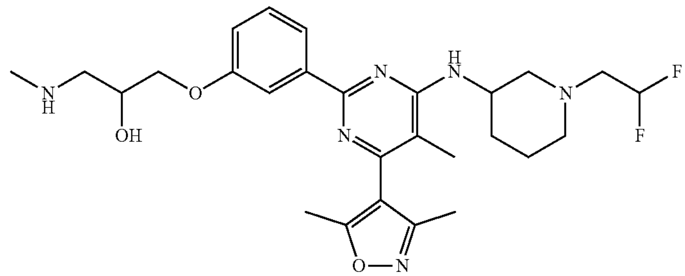 [SMILES: CNCC(O)COc1cccc(-c2nc(NC3CCCN(CC(F)F)C3)c(C)c(-c3c(C)noc3C)n2)c1] | 531.3 |
| 204-1a | 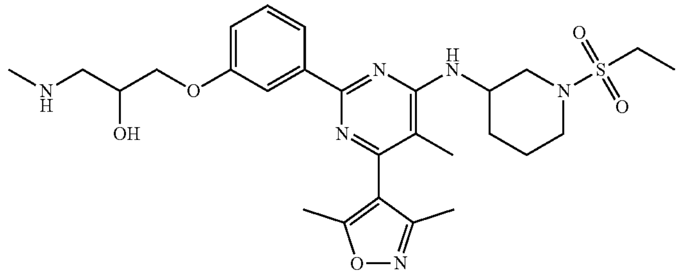 [SMILES: CCS(=O)(=O)N1CCCC(Nc2nc(-c3cccc(OCC(O)CNC)c3)nc(-c3c(C)noc3C)c2C)C1] | 559.3 |
| 205-1a | 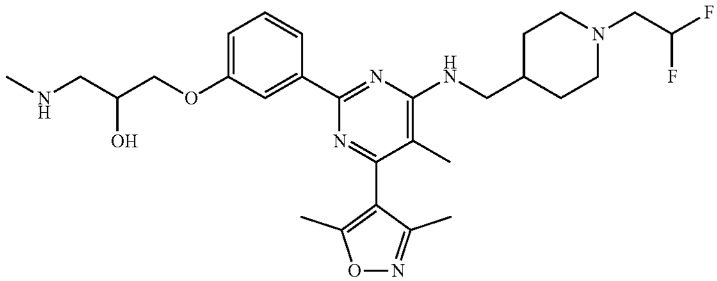 [SMILES: CNCC(O)COc1cccc(-c2nc(NCC3CCN(CC(F)F)CC3)c(C)c(-c3c(C)noc3C)n2)c1] | 545.3 |
| 206-1a | 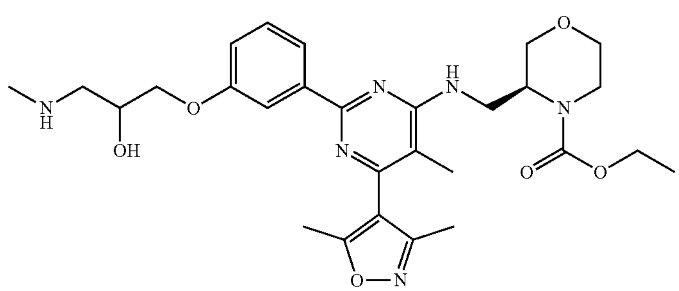 | 555.4 |
| 207-1a | 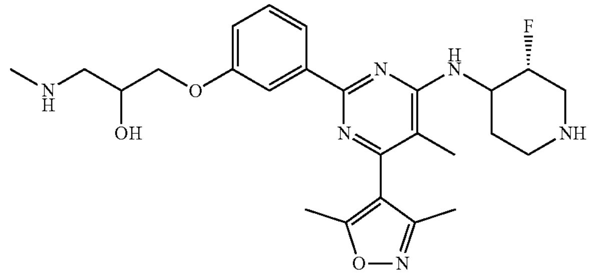 [SMILES: CNCC(O)COc1cccc(-c2nc(NC3CCNC[C@H]3F)c(C)c(-c3c(C)noc3C)n2)c1] | 485.3 |

US 10,118,931 B2
TABLE 1B-continued
Exemplary Compounds
| # | Structure | LC-MS m/z (M + H) |
|---|---|---|
| 208-1a | 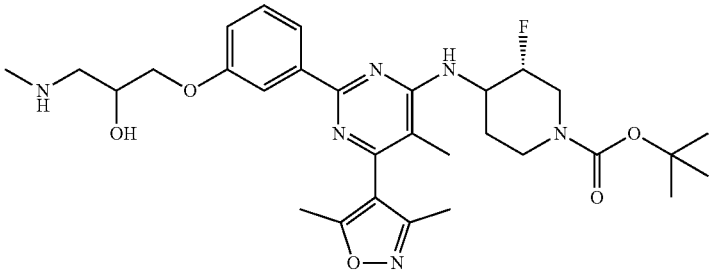 [SMILES: CNCC(O)COc1cccc(-c2nc(NC3CCN(C(=O)OC(C)(C)C)C[C@H]3F)c(C)c(-c3c(C)noc3C)n2)c1] | 585.4 |
| 209-1a | 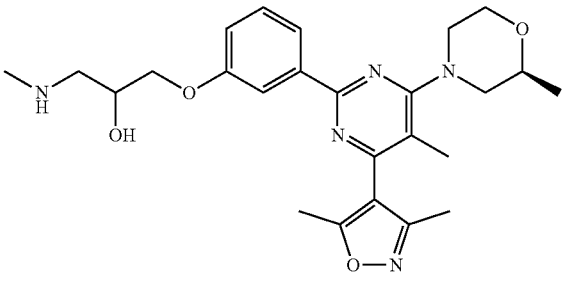 | 468.0 |
| 210-1a | 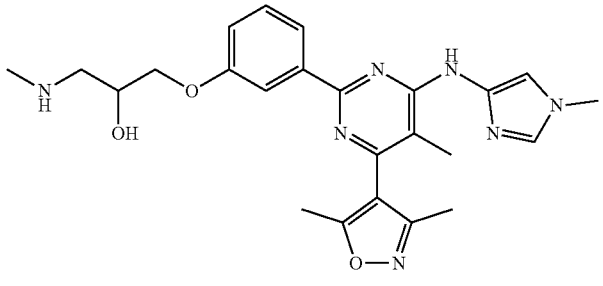 | 464.3 |
| 211-1a | 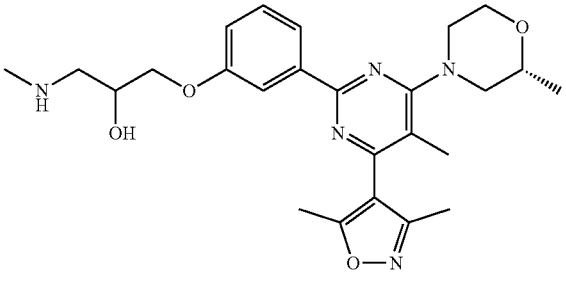 | 468.0 |
| 212-1a | 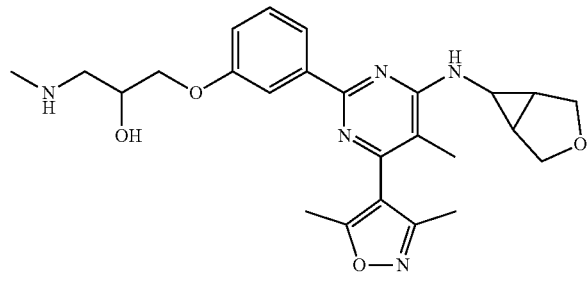 [SMILES: CNCC(O)COc1cccc(-c2nc(NC3C4COCC43)c(C)c(-c3c(C)noc3C)n2)c1] | 466.0 |

TABLE 1B-continued
Exemplary Compounds
| # | Structure | LC-MS m/z (M + H) |
|---|-----------|-------------------|
| 213-1a | 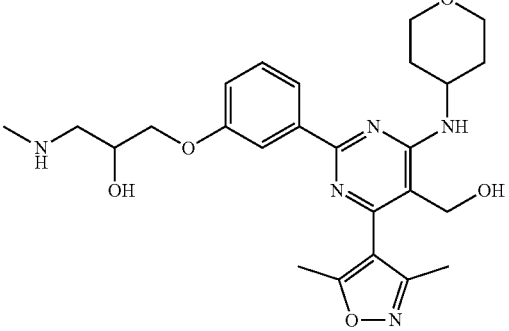 | 484.0 |
| 214-1a | 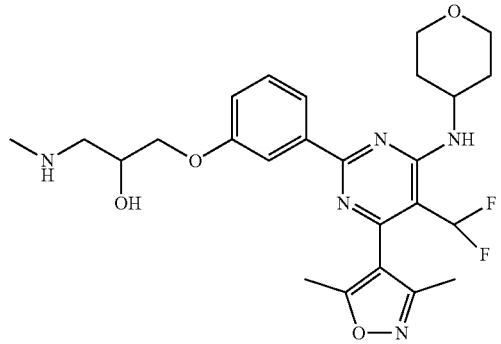 [SMILES: CNCC(O)COc1cccc(-c2nc(NC3CCOCC3)c(C(F)F)c(-c3c(C)noc3C)n2)c1] | 504.0 |
| 215-1a | 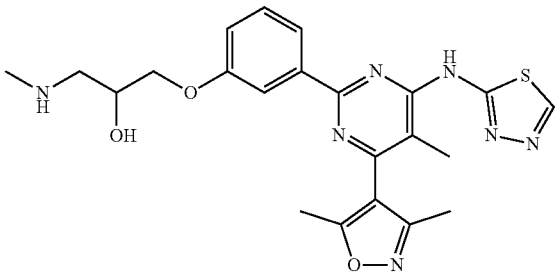 [SMILES: CNCC(O)COc1cccc(-c2nc(Nc3nncs3)c(C)c(-c3c(C)noc3C)n2)c1] | 468.2 |
| 216-1a | 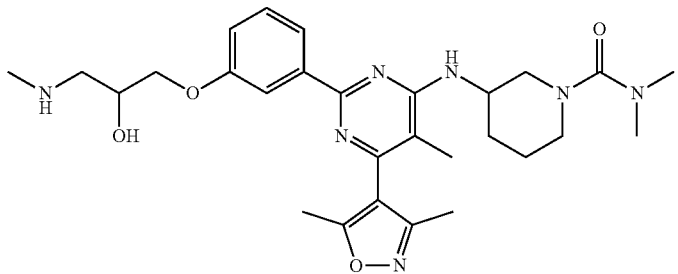 | 538.3 |
| 217-1a | 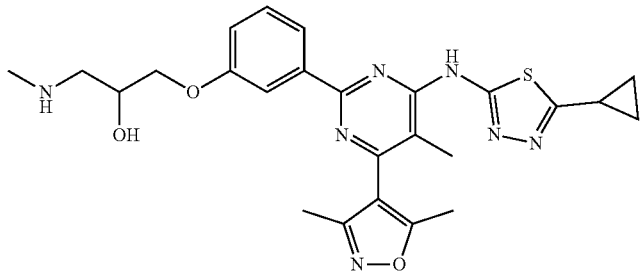 [SMILES: CNCC(O)COc1cccc(-c2nc(Nc3nnc(C4CC4)s3)c(C)c(-c3c(C)noc3C)n2)c1] | 508.1 |

TABLE 1B-continued

Exemplary Compounds

| # | Structure | LC-MS m/z (M + H) |
|---|---|---|
| 218-1a | 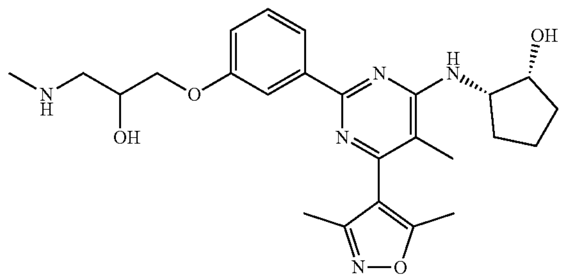 [SMILES: CNCC(O)COc1cccc(-c2nc(N[C@H]3CCC[C@H]3O)c(C)c(-c3c(C)noc3C)n2)c1] | 468.0 |
| 219-1a | 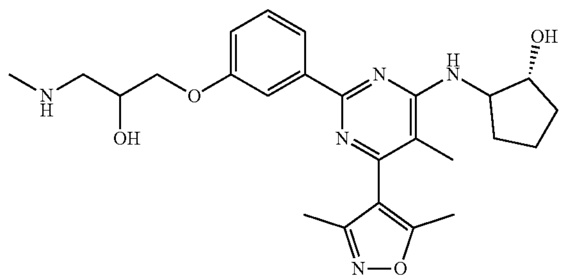 [SMILES: CNCC(O)COc1cccc(-c2nc(NC3CCC[C@H]3O)c(C)c(-c3c(C)noc3C)n2)c1] | 468.0 |
| 220-1a | 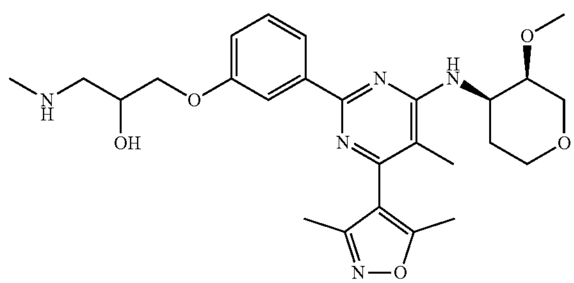 | 498.0 |
| 221-1a | 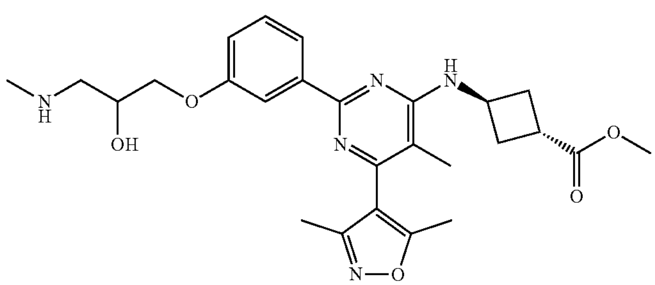 | 496.2 |
| 222-1a | 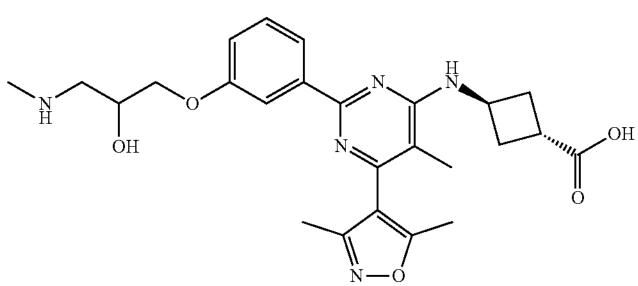 [SMILES: CNCC(O)COc1cccc(-c2nc(N[C@H]3C[C@H](C(=O)O)C3)c(C)c(-c3c(C)noc3C)n2)c1] | 482.3 |

US 10,118,931 B2
215 216
TABLE 1B-continued
Exemplary Compounds
| # | Structure | LC-MS m/z (M + H) |
|---|---|---|
| 223-1a | 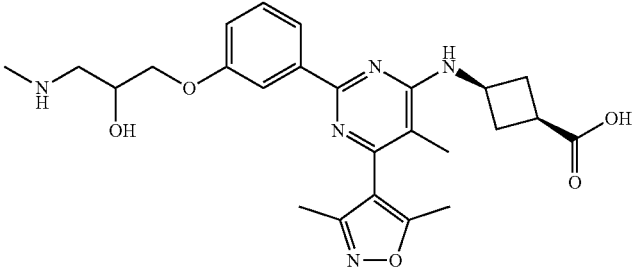 [SMILES: CNCC(O)COc1cccc(-c2nc(N[C@H]3C[C@@H](C(=O)O)C3)c(C)c(-c3c(C)noc3C)n2)c1] | 482.1 |
| 224-1a | 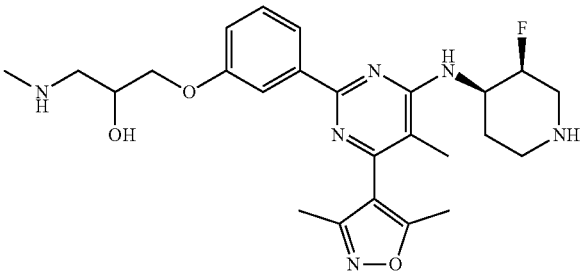 [SMILES: CNCC(O)COc1cccc(-c2nc(N[C@@H]3CCNC[C@@H]3F)c(C)c(-c3c(C)noc3C)n2)c1] | 485.3 |
| 225-1a | 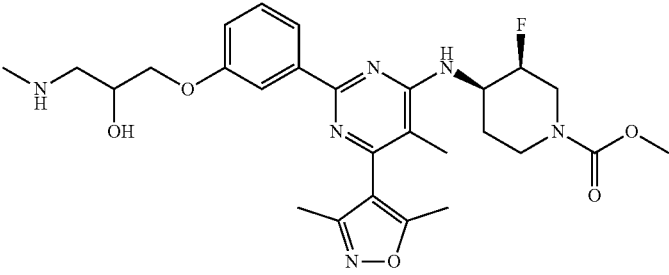 | 543.3 |
| 226-1a | 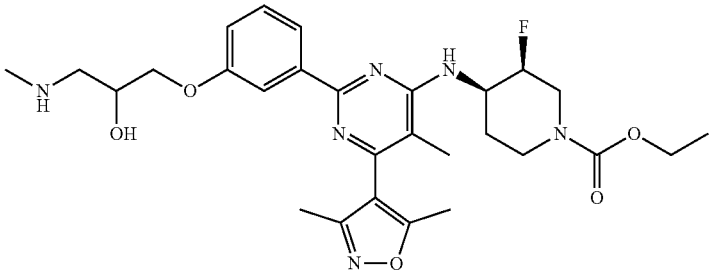 [SMILES: CCOC(=O)N1CC[C@@H](Nc2nc(-c3cccc(OCC(O)CNC)c3)nc(-c3c(C)noc3C)c2C)[C@@H](F)C1] | 557.3 |
| 227-1a | 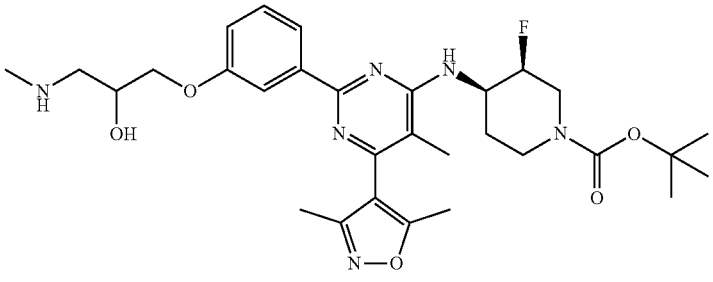 [SMILES: CNCC(O)COc1cccc(-c2nc(N[C@@H]3CCN(C(=O)OC(C)(C)C)C[C@@H]3F)c(C)c(-c3c(C)noc3C)n2)c1] | 585.3 |

TABLE 1B-continued

Exemplary Compounds

| # | Structure | LC-MS m/z (M + H) |
|---|---|---|
| 228-1a | 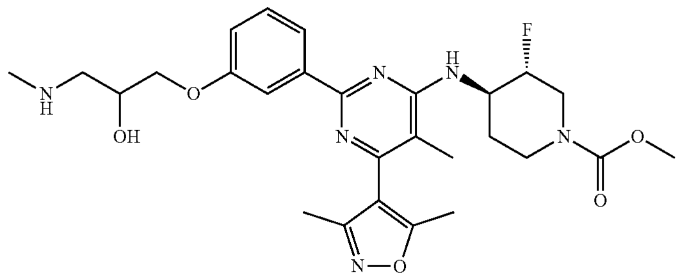 | 543.3 |
| 229-1a | 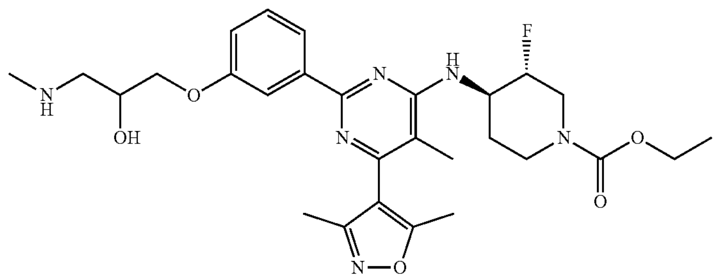 [SMILES: CCOC(=O)N1CC[C@@H](Nc2nc(-c3cccc(OCC(O)CNC)c3)nc(-c3c(C)noc3C)c2C)[C@H](F)C1] | 557.2 |
| 230-1a | 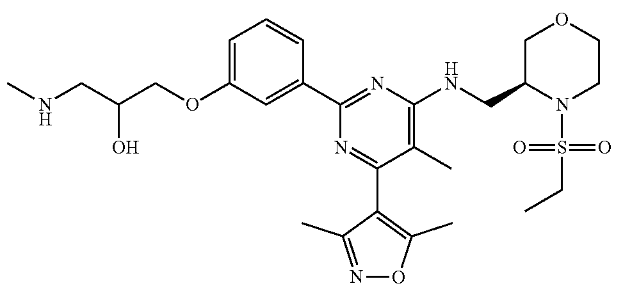 [SMILES: CCS(=O)(=O)N1CCOC[C@@H]1CNc1nc(-c2cccc(OCC(O)CNC)c2)nc(-c2c(C)noc2C)c1C] | 575.3 |
| 231-1a | 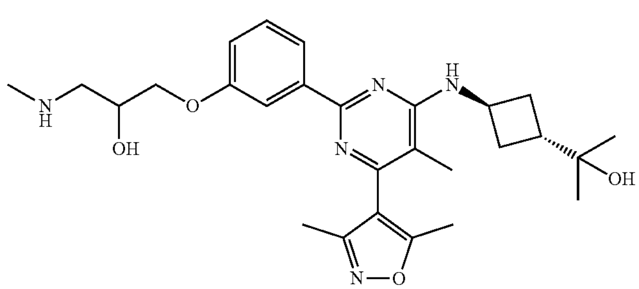 [SMILES: CNCC(O)COc1cccc(-c2nc(N[C@H]3C[C@H](C(C)(C)O)C3)c(C)c(-c3c(C)noc3C)n2)c1] | 496.3 |
| 232-1a | 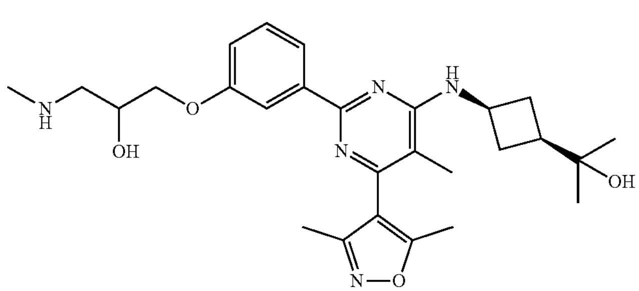 [SMILES: CNCC(O)COc1cccc(-c2nc(N[C@H]3C[C@@H](C(C)(C)O)C3)c(C)c(-c3c(C)noc3C)n2)c1] | 496.3 |

TABLE 1B-continued
Exemplary Compounds
| # | Structure | LC-MS m/z (M + H) |
|---|---|---|
| 233-1a | 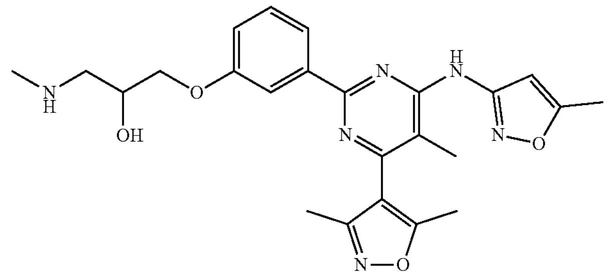 | 465.2 |
| 234-1a | 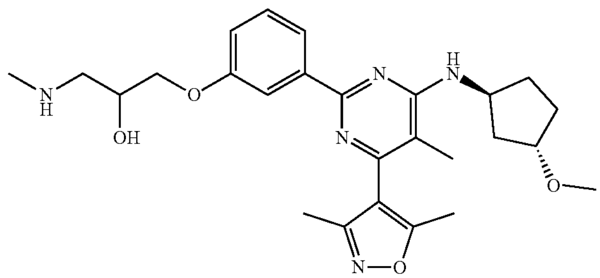 | 482.4 |
| 235-1a | 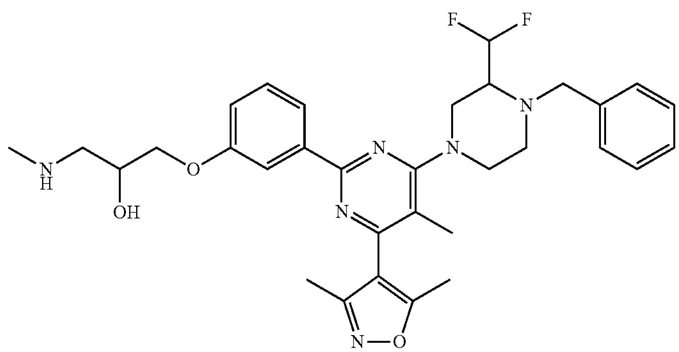 [SMILES: CNCC(O)COc1cccc(-c2nc(-c3c(C)noc3C)c(C)c(N3CCN(Cc4ccccc4)C(C(F)F)C3)n2)c1] | 593.9 |
| 236-1a | 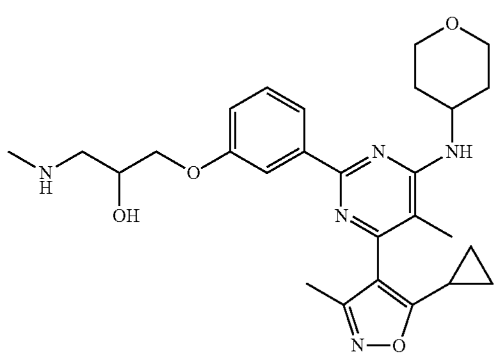 [SMILES: CNCC(O)COc1cccc(-c2nc(NC3CCOCC3)c(C)c(-c3c(C)noc3C3CC3)n2)c1] | 494.3 |
| 237-1a | 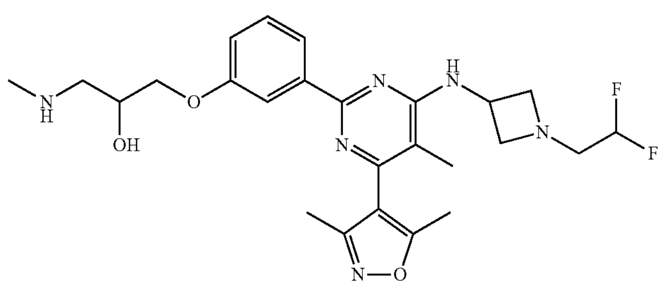 [SMILES: CNCC(O)COc1cccc(-c2nc(NC3CN(CC(F)F)C3)c(C)c(-c3c(C)noc3C)n2)c1] | 503.2 |

TABLE 1B-continued

Exemplary Compounds

| # | Structure | LC-MS m/z (M + H) |
|---|---|---|
| 238-1a | 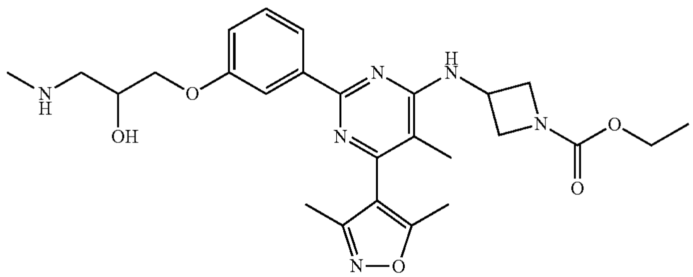 [SMILES: CCOC(=O)N1CC(Nc2nc(-c3cccc(OCC(O)CNC)c3)nc(-c3c(C)noc3C)c2C)C1] | 511.3 |
| 239-1a | 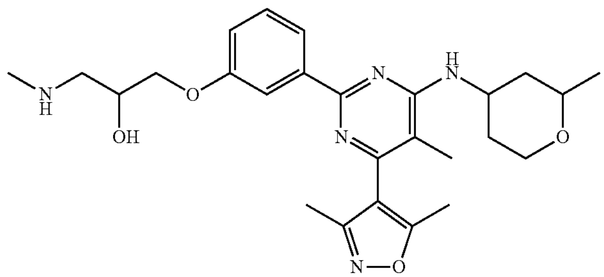 | 482.0 |
| 240-1a | 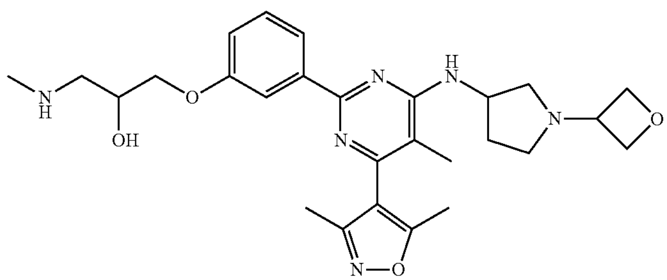 [SMILES: CNCC(O)COc1cccc(-c2nc(NC3CCN(C4COC4)C3)c(C)c(-c3c(C)noc3C)n2)c1] | 509.3 |
| 241-1a | 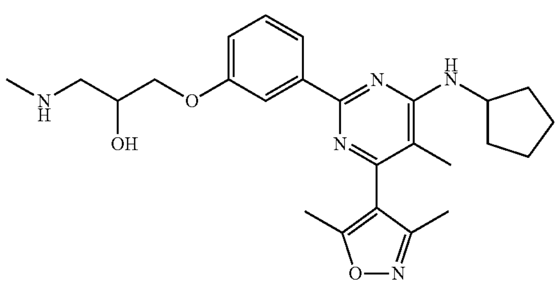 [SMILES: CNCC(O)COc1cccc(-c2nc(NC3CCCC3)c(C)c(-c3c(C)noc3C)n2)c1] | 452.0 |
| 242-1a | 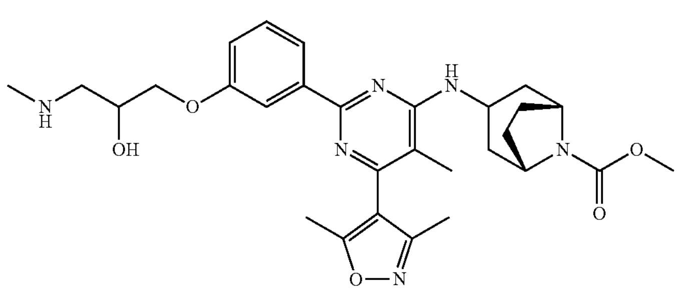 | 551.3 |

TABLE 1B-continued
Exemplary Compounds
| # | Structure | LC-MS m/z (M + H) |
|---|---|---|
| 243-1a | 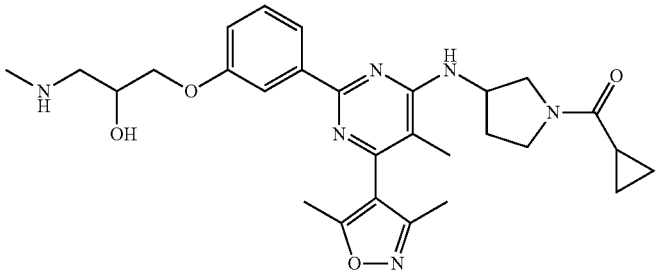 [SMILES: CNCC(O)COc1cccc(-c2nc(NC3CCN(C(=O)C4CC4)C3)c(C)c(-c3c(C)noc3C)n2)c1] | 521.3 |
| 244-1a | 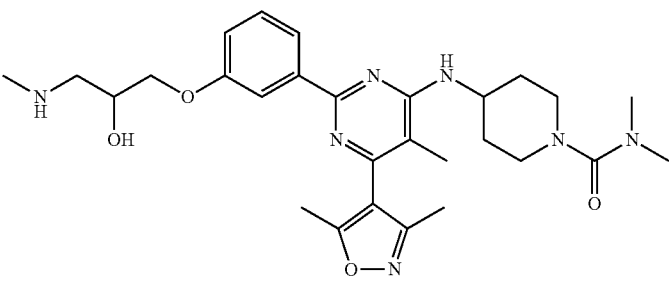 | 538.3 |
| 245-1a | 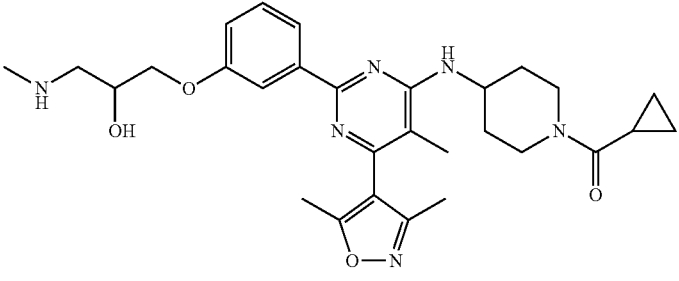 [SMILES: CNCC(O)COc1cccc(-c2nc(NC3CCN(C(=O)C4CC4)CC3)c(C)c(-c3c(C)noc3C)n2)c1] | 535.3 |
| 246-1a | 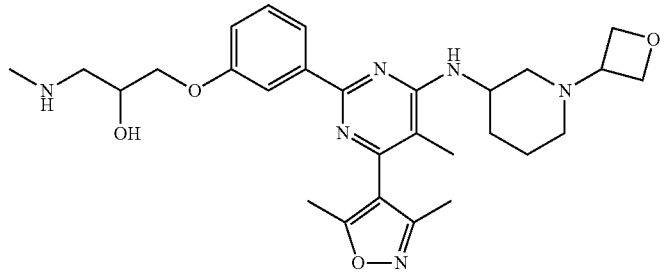 [SMILES: CNCC(O)COc1cccc(-c2nc(NC3CCCN(C4COC4)C3)c(C)c(-c3c(C)noc3C)n2)c1] | 523.3 |
| 247-1a | 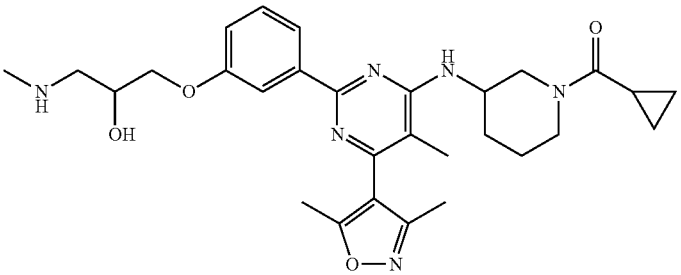 [SMILES: CNCC(O)COc1cccc(-c2nc(NC3CCCN(C(=O)C4CC4)C3)c(C)c(-c3c(C)noc3C)n2)c1] | 535.3 |

TABLE 1B-continued

Exemplary Compounds

| # | Structure | LC-MS m/z (M + H) |
|---|---|---|
| 248-1a | 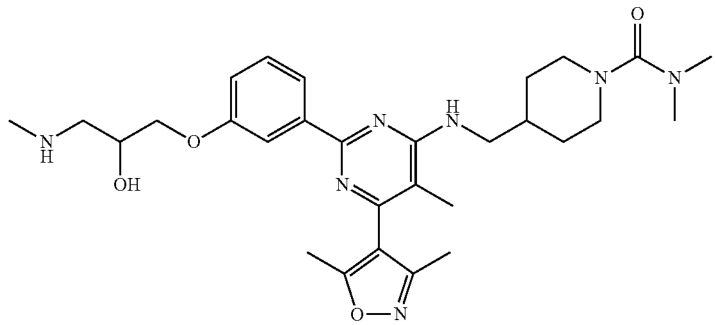 | 552.3 |
| 249-1a | 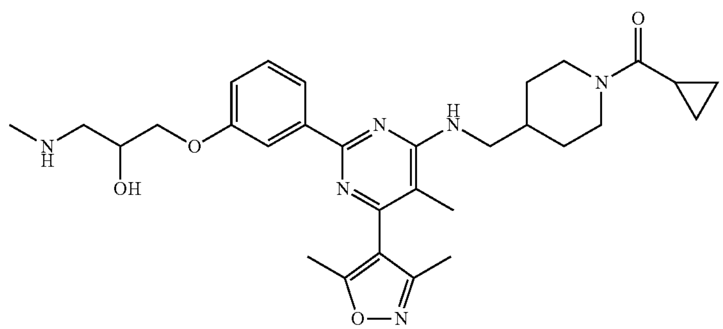 [SMILES: CNCC(O)COc1cccc(-c2nc(NCC3CCN(C(=O)C4CC4)CC3)c(C)c(-c3c(C)noc3C)n2)c1] | 549.3 |
| 250-1a | 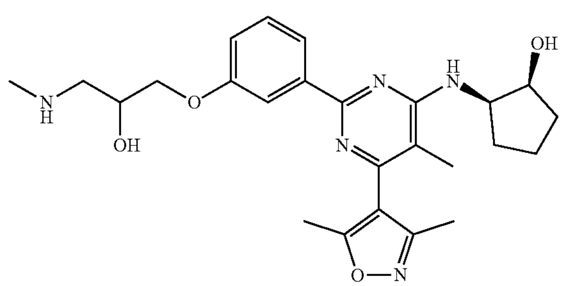 [SMILES: CNCC(O)COc1cccc(-c2nc(N[C@@H]3CCC[C@@H]3O)c(C)c(-c3c(C)noc3C)n2)c1] | 468.0 |
| 251-1a | 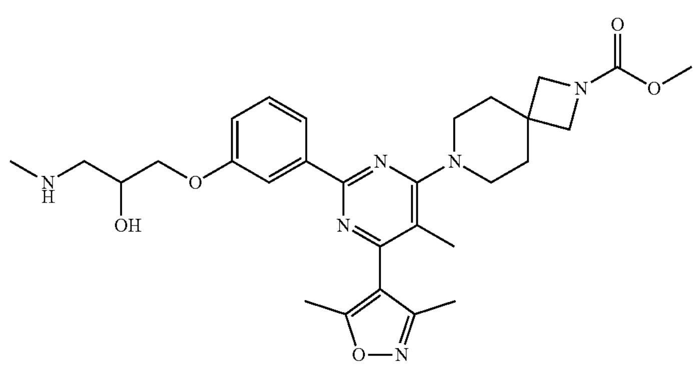 | 551.3 |

TABLE 1B-continued

Exemplary Compounds

| # | Structure | LC-MS m/z (M + H) |
|---|-----------|-------------------|
| 252-1a | 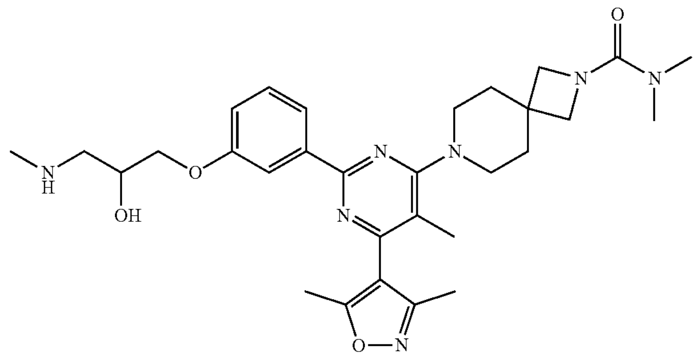 | 564.4 |
| 253-1a | 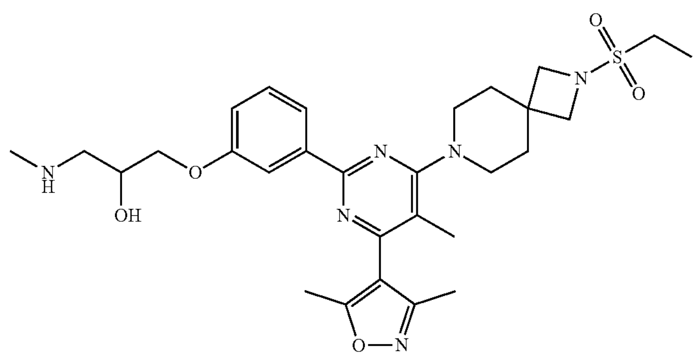 [SMILES: CCS(=O)(=O)N1CC2(CCN(c3nc(-c4cccc(OCC(O)CNC)c4)nc(-c4c(C)noc4C)c3C)CC2)C1] | 585.3 |
| 254-1a | 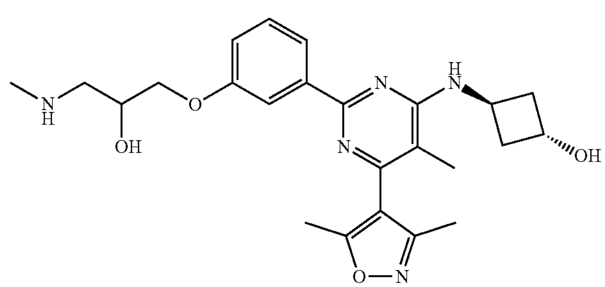 [SMILES: CNCC(O)COc1cccc(-c2nc(N[C@H]3C[C@H](O)C3)c(C)c(-c3c(C)noc3C)n2)c1] | 454.0 |
| 255-1a | 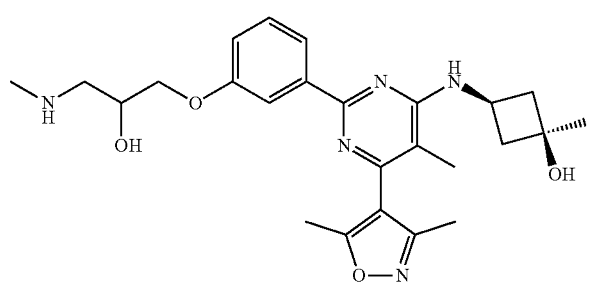 | 468.0 |
| 256-1a | 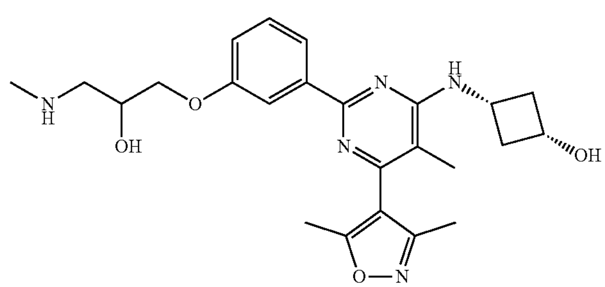 [SMILES: CNCC(O)COc1cccc(-c2nc(N[C@H]3C[C@@H](O)C3)c(C)c(-c3c(C)noc3C)n2)c1] | 454.0 |

TABLE 1B-continued

Exemplary Compounds

| # | Structure | LC-MS m/z (M + H) |
|---|---|---|
| 257-1a | 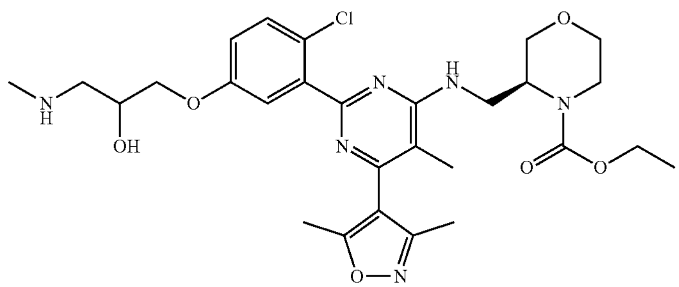 [SMILES: CCOC(=O)N1CCOC[C@@H]1CNc1nc(-c2cc(OCC(O)CNC)ccc2Cl)nc(-c2c(C)noc2C)c1C] | 488.9 |
| 258-1a | 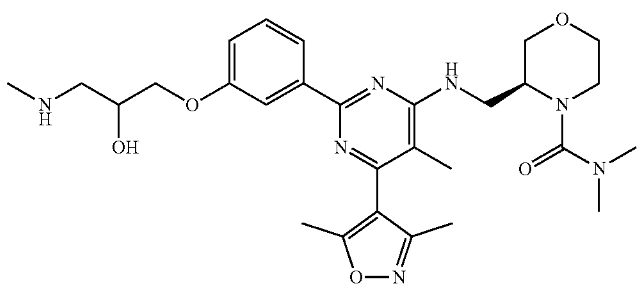 | 554.3 |
| 259-1a | 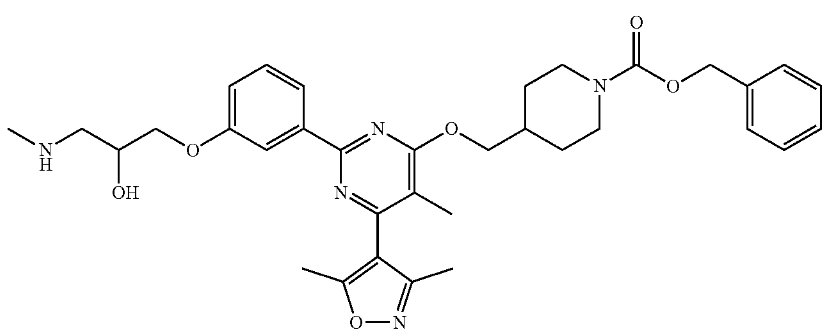 [SMILES: CNCC(O)COc1cccc(-c2nc(OCC3CCN(C(=O)OCc4ccccc4)CC3)c(C)c(-c3c(C)noc3C)n2)c1] | 615.9 |
| 260-1a | 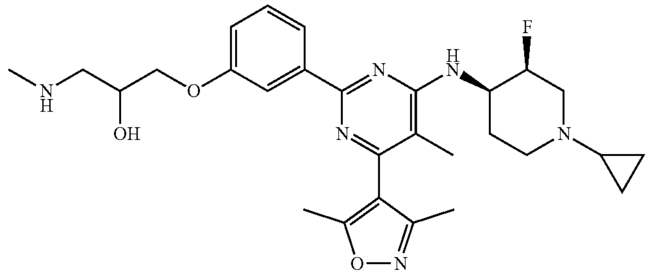 [SMILES: CNCC(O)COc1cccc(-c2nc(N[C@@H]3CCN(C4CC4)C[C@@H]3F)c(C)c(-c3c(C)noc3C)n2)c1] | 525.3 |
| 261-1a | 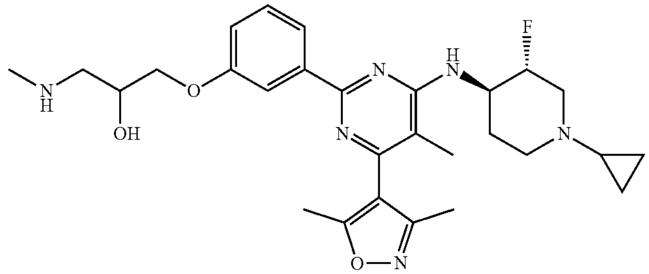 [SMILES: CNCC(O)COc1cccc(-c2nc(N[C@@H]3CCN(C4CC4)C[C@H]3F)c(C)c(-c3c(C)noc3C)n2)c1] | 525.3 |

TABLE 1B-continued
Exemplary Compounds
| # | Structure | LC-MS m/z (M + H) |
|---|---|---|
| 262-1a | 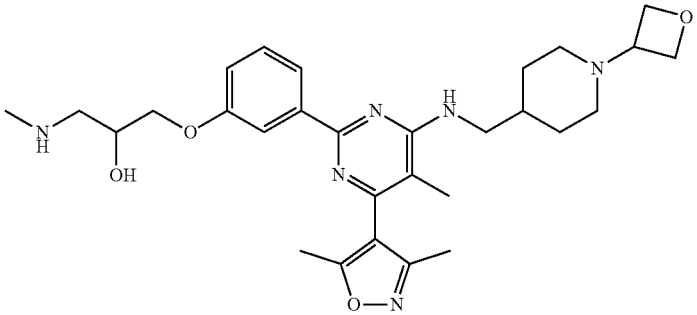 [SMILES: CNCC(O)COc1cccc(-c2nc(NCC3CCN(C4COC4)CC3)c(C)c(-c3c(C)noc3C)n2)c1] | 537.3 |
| 263-1a | 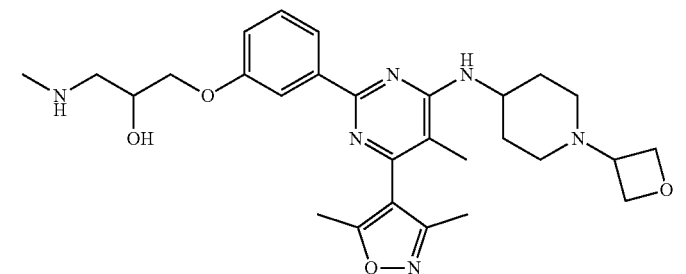 [SMILES: CNCC(O)COc1cccc(-c2nc(NC3CCN(C4COC4)CC3)c(C)c(-c3c(C)noc3C)n2)c1] | 523.3 |
| 264-1a | 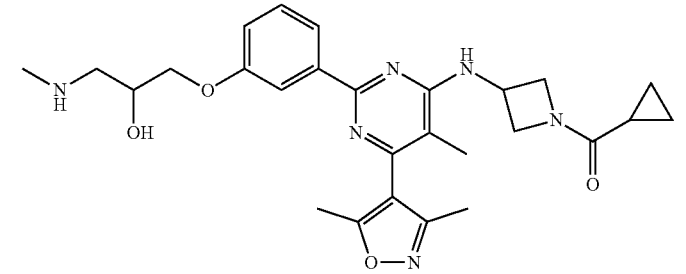 [SMILES: CNCC(O)COc1cccc(-c2nc(NC3CN(C(=O)C4CC4)C3)c(C)c(-c3c(C)noc3C)n2)c1] | 507.3 |
| 265-1a | 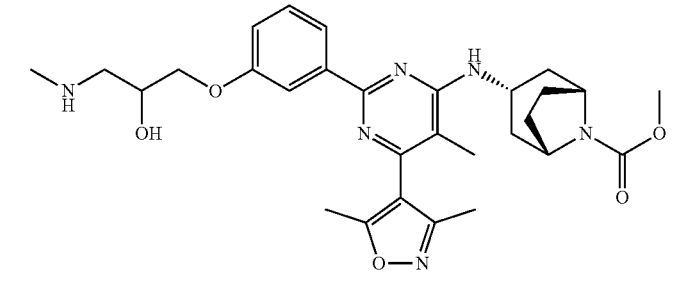 | 551.0 |
| 266-1a | 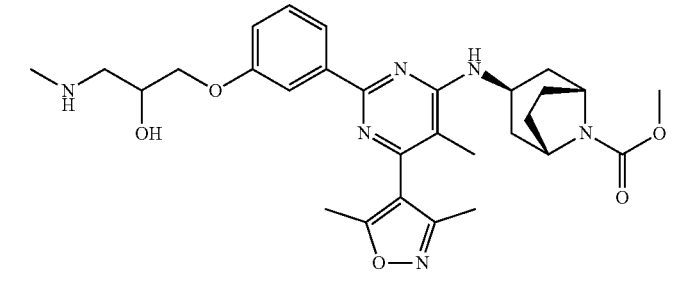 | 551.0 |

TABLE 1B-continued

Exemplary Compounds

| # | Structure | LC-MS m/z (M + H) |
|---|---|---|
| 267-1a | 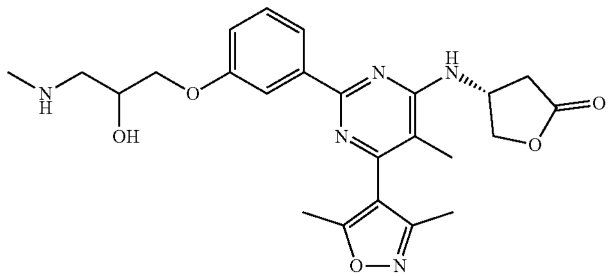 [SMILES: CNCC(O)COc1cccc(-c2nc(N[C@H]3COC(=O)C3)c(C)c(-c3c(C)noc3C)n2)c1] | 467.9 |
| 268-1a | 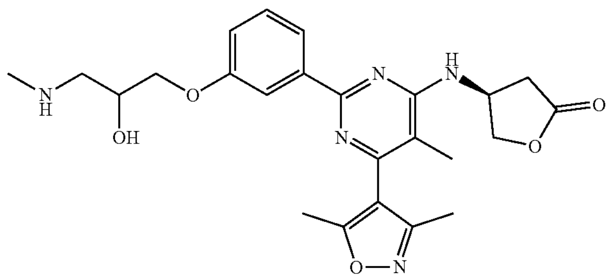 [SMILES: CNCC(O)COc1cccc(-c2nc(N[C@@H]3COC(=O)C3)c(C)c(-c3c(C)noc3C)n2)c1] | 468.0 |
| 269-1a | 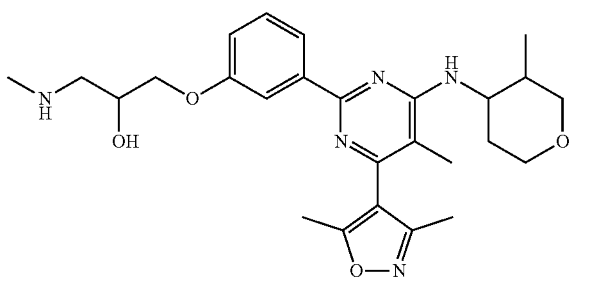 | 482.0 |
| 270-1a | 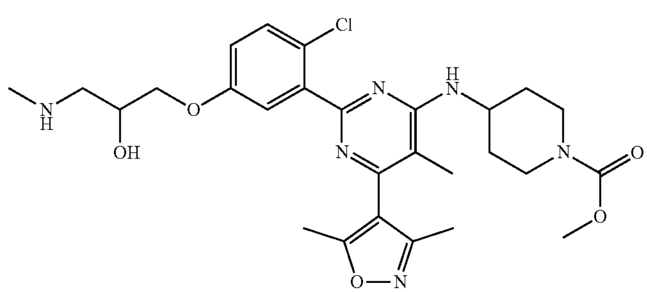 [SMILES: CNCC(O)COc1ccc(Cl)c(-c2nc(NC3CCN(C(=O)OC)CC3)c(C)c(-c3c(C)noc3C)n2)c1] | 558.9 |
| 271-1a | 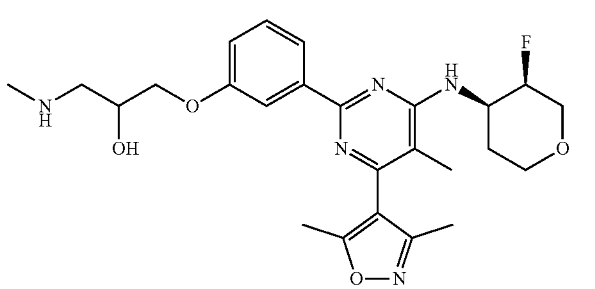 [SMILES: CNCC(O)COc1cccc(-c2nc(N[C@@H]3CCOC[C@@H]3F)c(C)c(-c3c(C)noc3C)n2)c1] | 486.2 |

TABLE 1B-continued

Exemplary Compounds

| # | Structure | LC-MS m/z (M + H) |
|---|---|---|
| 273-1a | 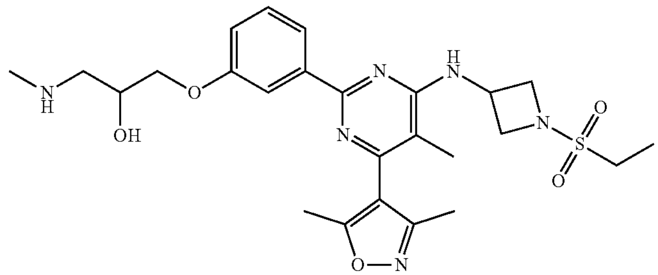 [SMILES: CCS(=O)(=O)N1CC(Nc2nc(-c3cccc(OCC(O)CNC)c3)nc(-c3c(C)noc3C)c2C)C1] | 531.2 |
| 274-1a | 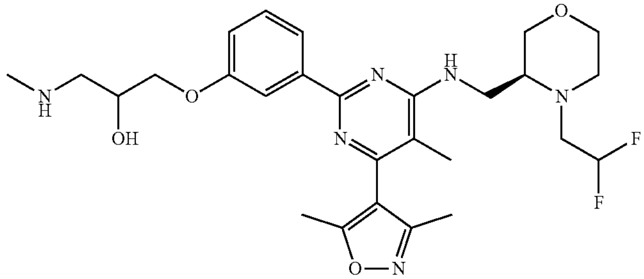 [SMILES: CNCC(O)COc1cccc(-c2nc(NC[C@H]3COCCN3CC(F)F)c(C)c(-c3c(C)noc3C)n2)c1] | 547.3 |
| 275-1a | 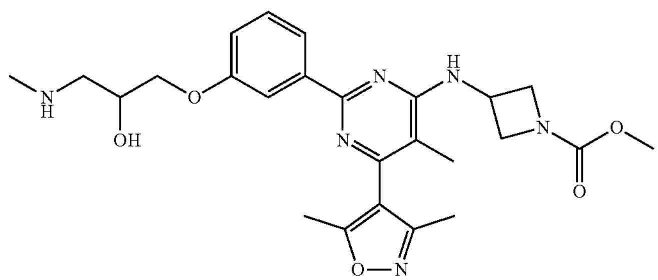 | 497.2 |
| 276-1a | 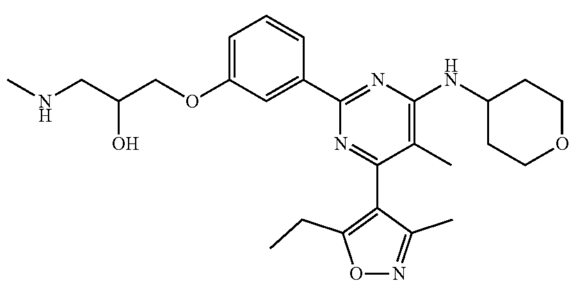 [SMILES: CCc1onc(C)c1-c1nc(-c2cccc(OCC(O)CNC)c2)nc(NC2CCOCC2)c1C] | 482.3 |
| 277-1a | 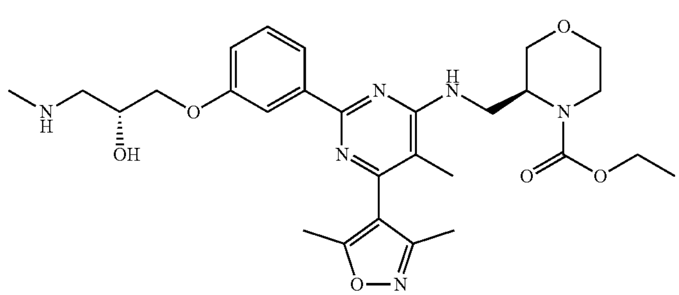 [SMILES: CCOC(=O)N1CCOC[C@@H]1CNc1nc(-c2cccc(OC[C@H](O)CNC)c2)nc(-c2c(C)noc2C)c1C] | 555.3 |

TABLE 1B-continued

Exemplary Compounds

| # | Structure | LC-MS m/z (M + H) |
|---|---|---|
| 278-1a | 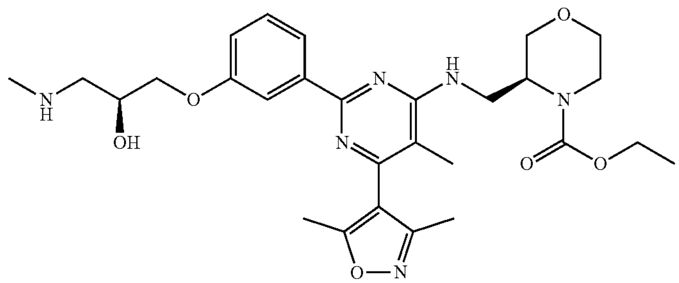 [SMILES: CCOC(=O)N1CCOC[C@@H]1CNc1nc(-c2cccc(OC[C@@H](O)CNC)c2)nc(-c2c(C)noc2C)c1C] | 555.3 |
| 279-1a | 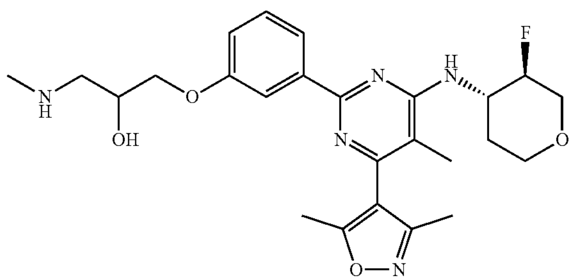 [SMILES: CNCC(O)COc1cccc(-c2nc(N[C@H]3CCOC[C@@H]3F)c(C)c(-c3c(C)noc3C)n2)c1] | 486.3 |
| 280-1a | 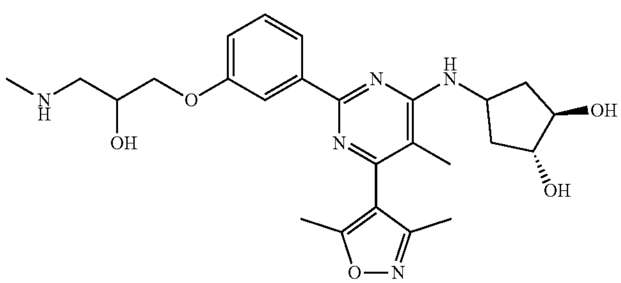 [SMILES: CNCC(O)COc1cccc(-c2nc(NC3C[C@@H](O)[C@H](O)C3)c(C)c(-c3c(C)noc3C)n2)c1] | 484.2 |
| 281-1a | 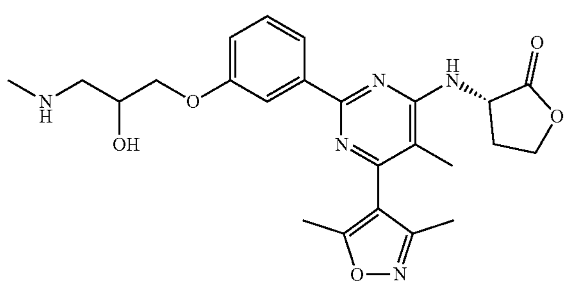 [SMILES: CNCC(O)COc1cccc(-c2nc(N[C@H]3CCOC3=O)c(C)c(-c3c(C)noc3C)n2)c1] | 468.0 |
| 282-1a | 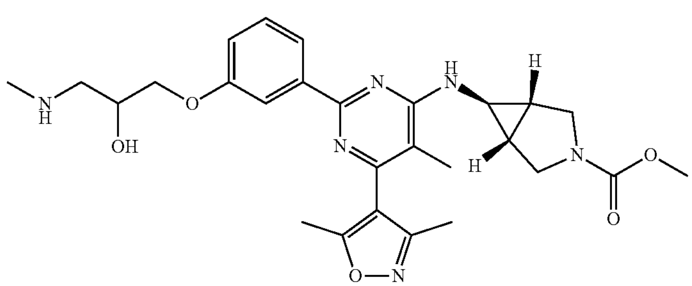 | 523.3 |

TABLE 1B-continued
Exemplary Compounds
| # | Structure | LC-MS m/z (M + H) |
|---|---|---|
| 283-1a | 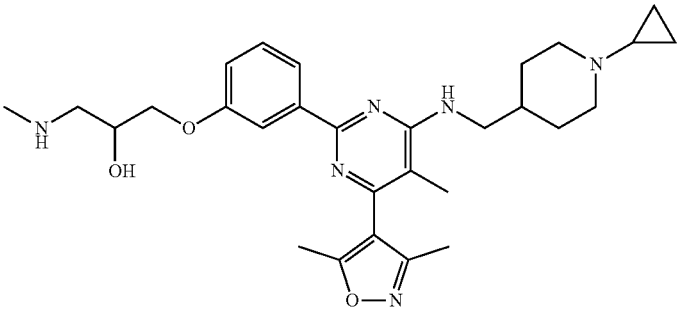 | 521.3 |
| 284-1a | 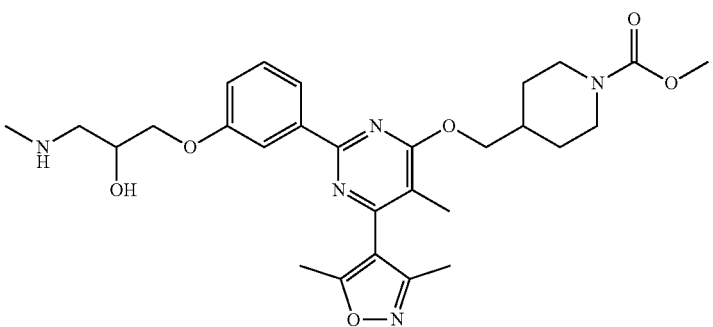 | 540.0 |
| 285-1a | 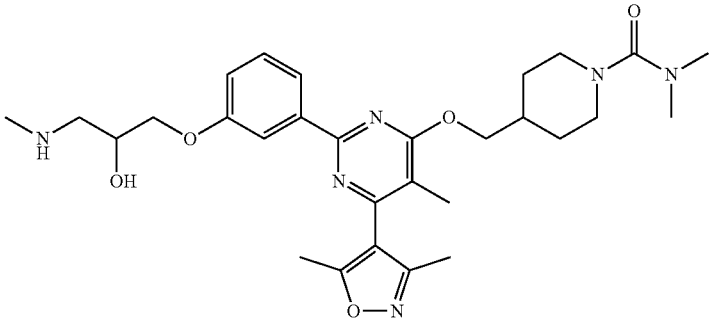 | 553.0 |
| 286-1a | 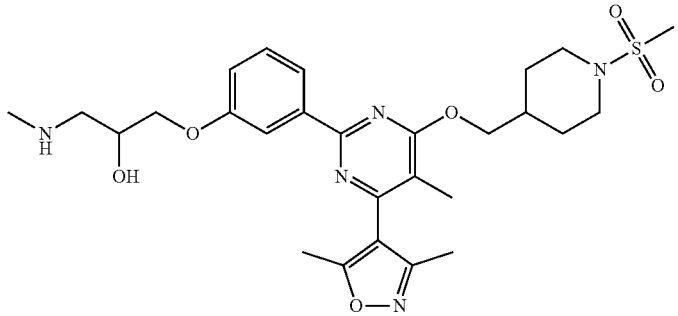 | 559.9 |

TABLE 1B-continued

Exemplary Compounds

| # | Structure | LC-MS m/z (M + H) |
|---|---|---|
| 287-1a | 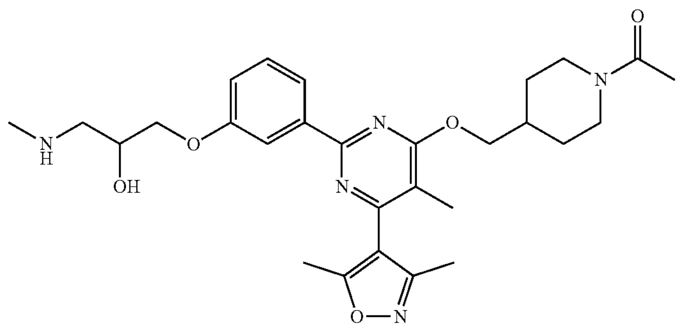 [SMILES: CNCC(O)COc1cccc(-c2nc(OCC3CCN(C(C)=O)CC3)c(C)c(-c3c(C)noc3C)n2)c1] | 524.0 |
| 288-1a | 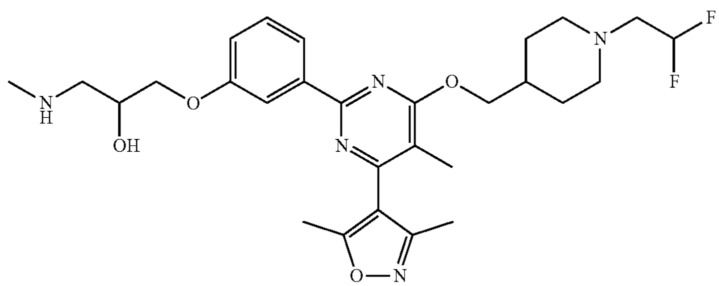 [SMILES: CNCC(O)COc1cccc(-c2nc(OCC3CCN(CC(F)F)CC3)c(C)c(-c3c(C)noc3C)n2)c1] | 546.0 |
| 289-1a | 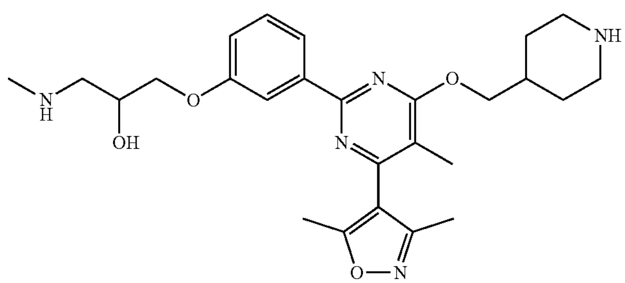 [SMILES: CNCC(O)COc1cccc(-c2nc(OCC3CCNCC3)c(C)c(-c3c(C)noc3C)n2)c1] | 482.3 |
| 290-1a | 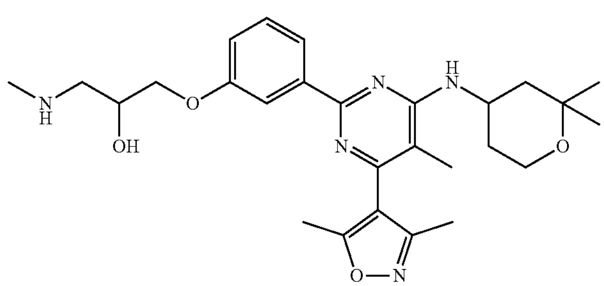 | 496.0 |
| 291-1a | 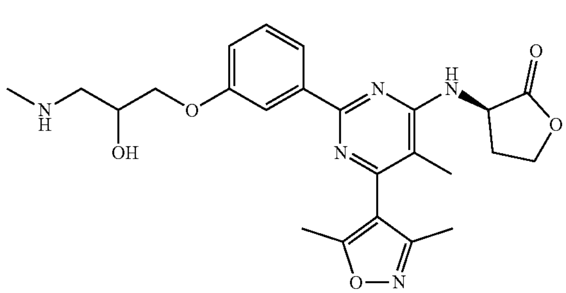 [SMILES: CNCC(O)COc1cccc(-c2nc(N[C@@H]3CCOC3=O)c(C)c(-c3c(C)noc3C)n2)c1] | 468.0 |

TABLE 1B-continued

Exemplary Compounds

| # | Structure | LC-MS m/z (M + H) |
|---|---|---|
| 292-1a | 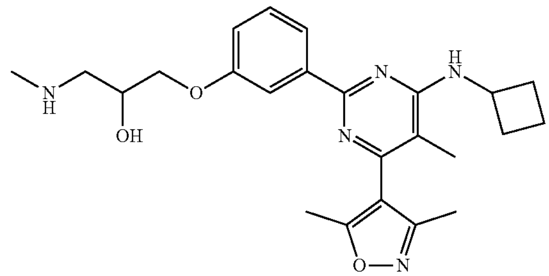 [SMILES: CNCC(O)COc1cccc(-c2nc(NC3CCC3)c(C)c(-c3c(C)noc3C)n2)c1] | 438.3 |
| 293-1a | 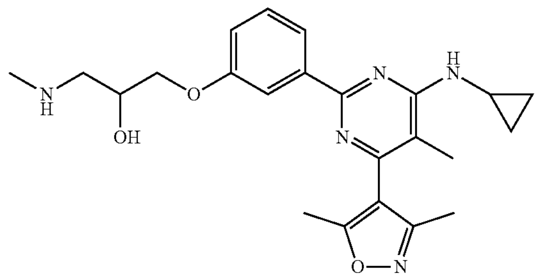 [SMILES: CNCC(O)COc1cccc(-c2nc(NC3CC3)c(C)c(-c3c(C)noc3C)n2)c1] | 424.2 |
| 294-1a | 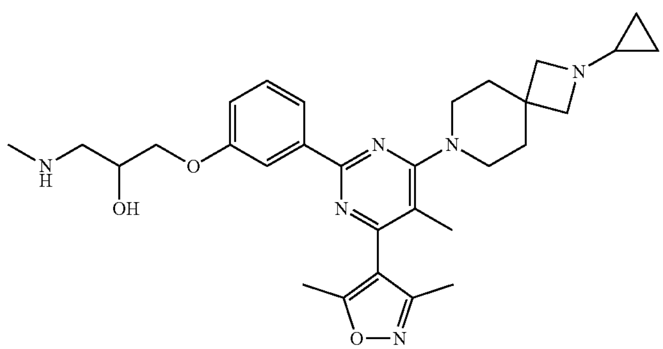 [SMILES: CNCC(O)COc1cccc(-c2nc(-c3c(C)noc3C)c(C)c(N3CCC4(CC3)CN(C3CC3)C4)n2)c1] | 533.3 |
| 295-1a | 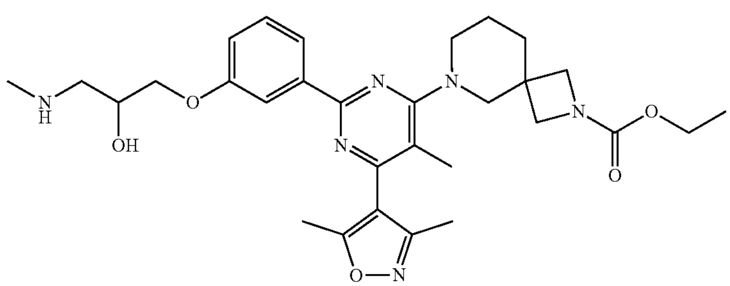 [SMILES: CCOC(=O)N1CC2(CCCN(c3nc(-c4cccc(OCC(O)CNC)c4)nc(-c4c(C)noc4C)c3C)C2)C1] | 565.2 |
| 296-1a | 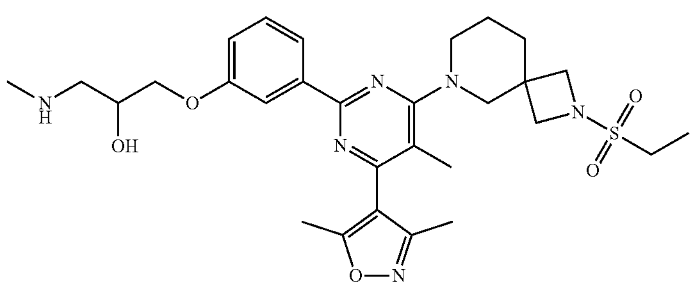 [SMILES: CCS(=O)(=O)N1CC2(CCCN(c3nc(-c4cccc(OCC(O)CNC)c4)nc(-c4c(C)noc4C)c3C)C2)C1] | 585.2 |

TABLE 1B-continued
Exemplary Compounds
| # | Structure | LC-MS m/z (M + H) |
|---|---|---|
| 297-1a | 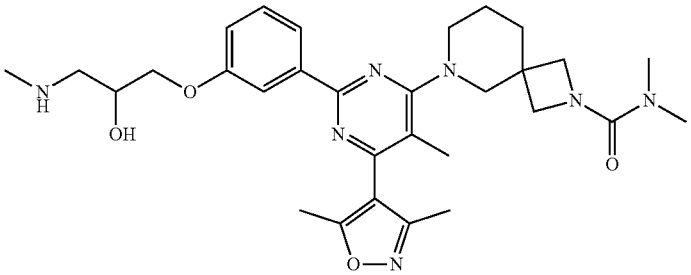 | 564.3 |
| 298-1a | 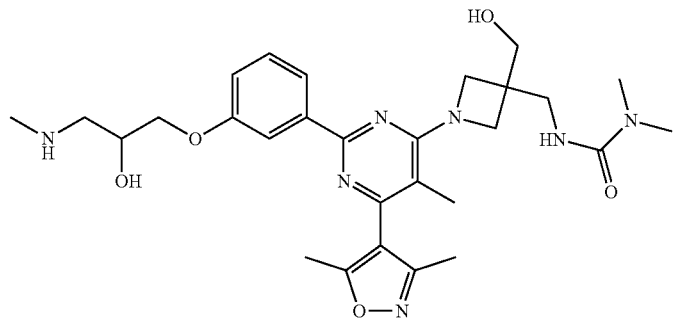 | 554.3 |
| 299-1a | 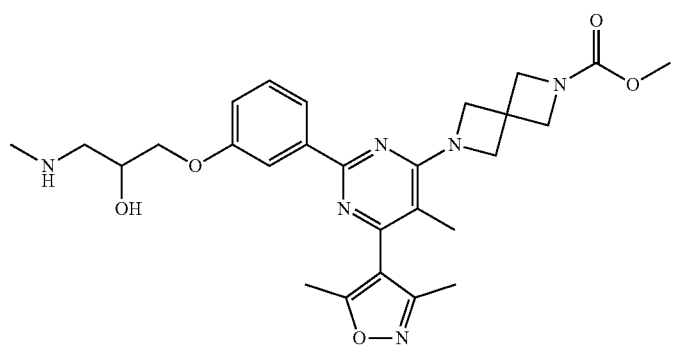 | 523.3 |
| 300-1a | 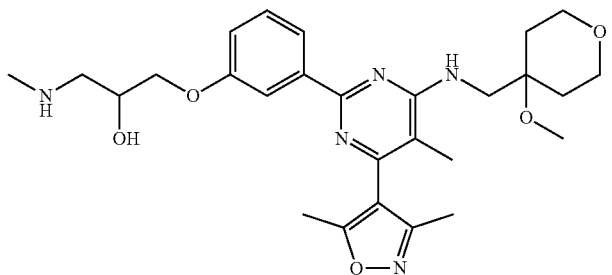 [SMILES: CNCC(O)COc1cccc(-c2nc(NCC3(OC)CCOCC3)c(C)c(-c3c(C)noc3C)n2)c1] | 512.3 |
| 301-1a | 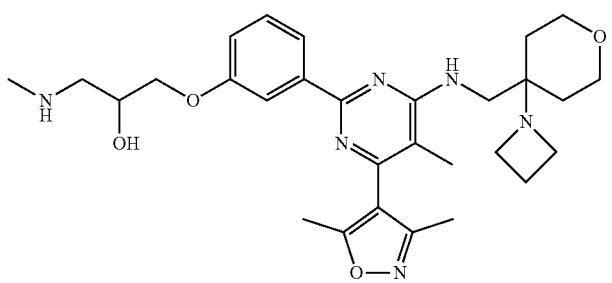 [SMILES: CNCC(O)COc1cccc(-c2nc(NCC3(N4CCC4)CCOCC3)c(C)c(-c3c(C)noc3C)n2)c1] | 537.3 |

US 10,118,931 B2
TABLE 1B-continued
Exemplary Compounds
| # | Structure | LC-MS m/z (M + H) |
|---|---|---|
| 302-1a | 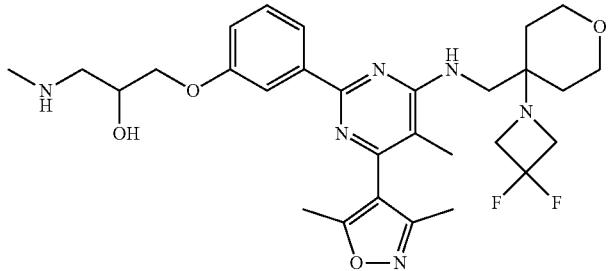 [SMILES: CNCC(O)COc1cccc(-c2nc(NCC3(N4CC(F)(F)C4)CCOCC3)c(C)c(-c3c(C)noc3C)n2)c1] | 573.3 |
| 303-1a | 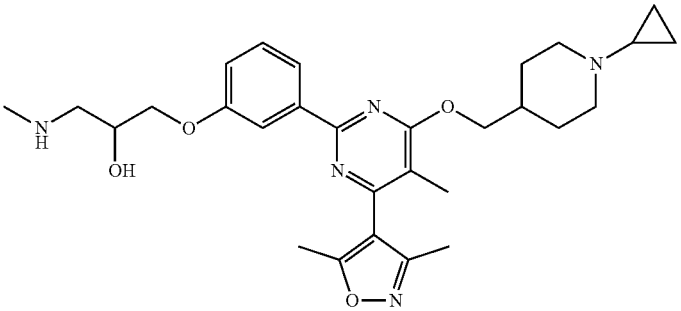 [SMILES: CNCC(O)COc1cccc(-c2nc(OCC3CCN(C4CC4)CC3)c(C)c(-c3c(C)noc3C)n2)c1] | 522.0 |
| 304-1a | 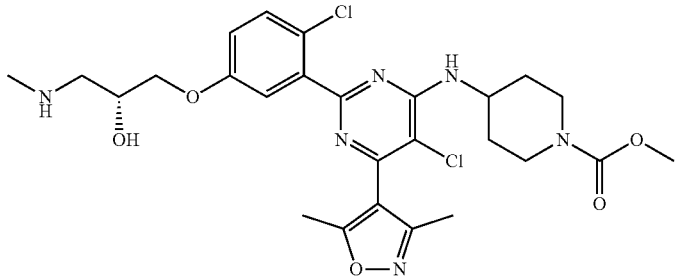 | 579.2 |
| 305-1a | 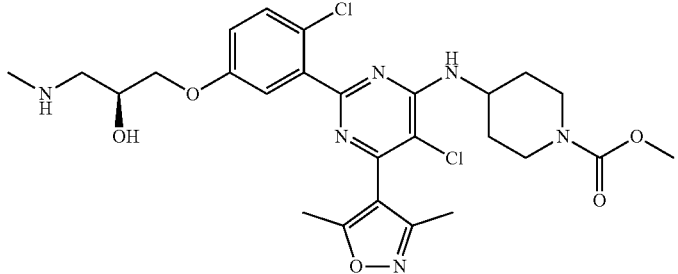 | 579.2 |
| 306-1a | 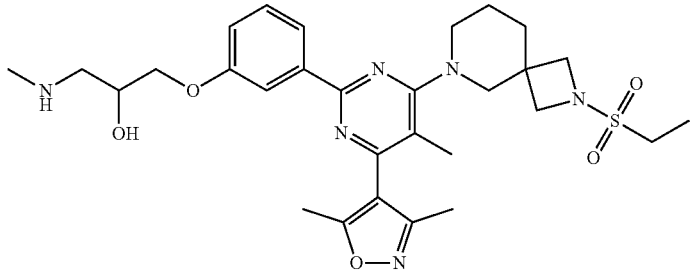 [SMILES: CCS(=O)(=O)N1CC2(CCCN(c3nc(-c4cccc(OCC(O)CNC)c4)nc(-c4c(C)noc4C)c3C)C2)C1] | 541.3 |

TABLE 1B-continued

Exemplary Compounds

| # | Structure | LC-MS m/z (M + H) |
|---|-----------|-------------------|
| 307-1a | 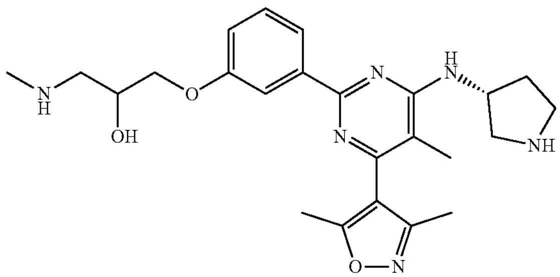 | 453.0 |
| 308-1a | 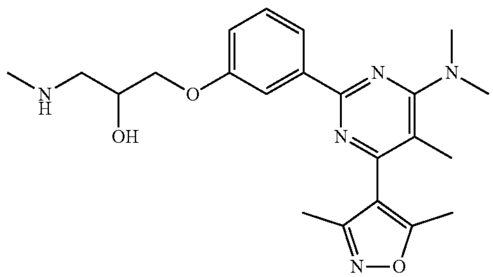 | 412.3 |
| 309-1a | 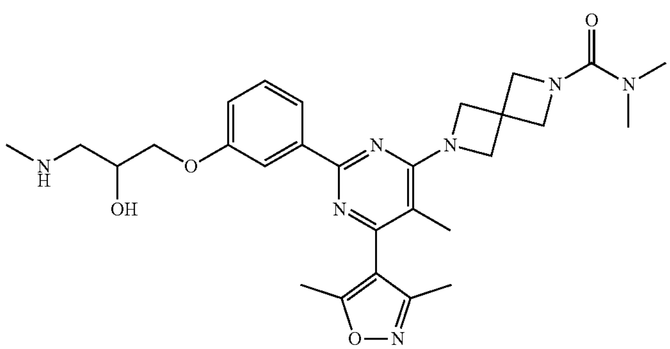 | 536.3 |
| 310-1a | 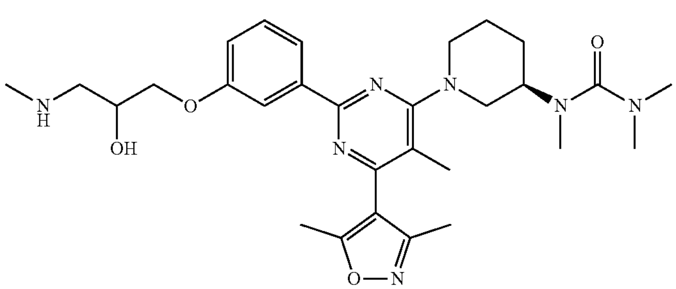 | 552.4 |
| 311-1a | 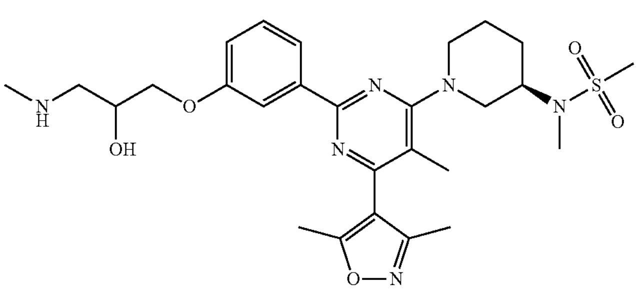 | 559.3 |

TABLE 1B-continued

Exemplary Compounds

| # | Structure | LC-MS m/z (M + H) |
|---|-----------|-------------------|
| 312-1a | 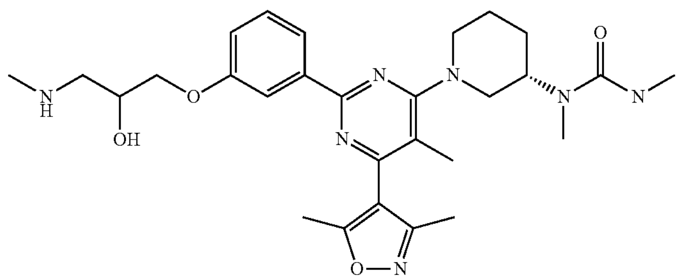 | 552.4 |
| 313-1a | 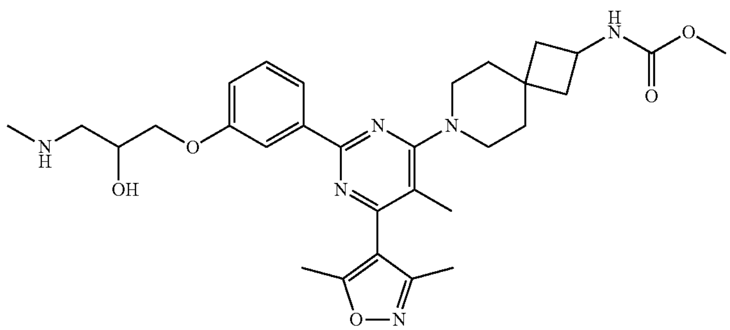 | 565.0 |
| 314-1a | 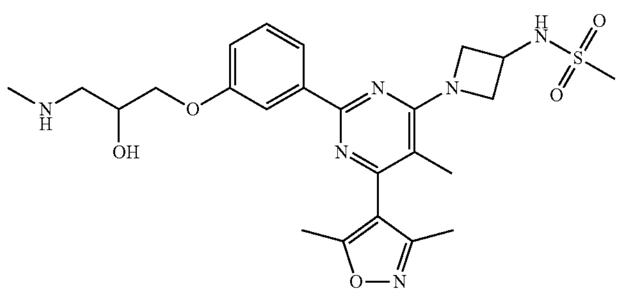 | 517.2 |
| 315-1a | 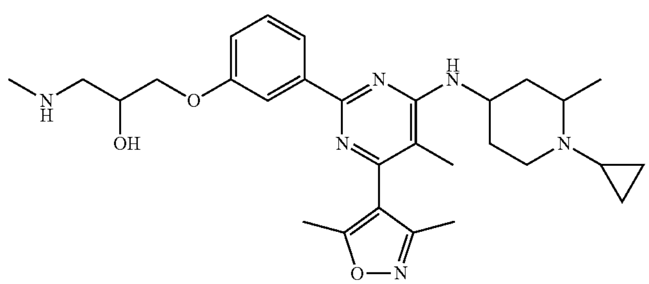 [SMILES: CNCC(O)COc1cccc(-c2nc(NC3CCN(C4CC4)C(C)C3)c(C)c(-c3c(C)noc3C)n2)c1] | 521.3 |
| 316-1a | 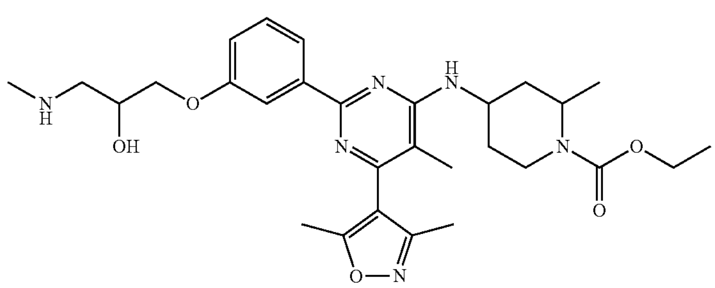 [SMILES: CCOC(=O)N1CCC(Nc2nc(-c3cccc(OCC(O)CNC)c3)nc(-c3c(C)noc3C)c2C)CC1C] | 553.3 |

TABLE 1B-continued

Exemplary Compounds

| # | Structure | LC-MS m/z (M + H) |
|---|---|---|
| 317-1a | 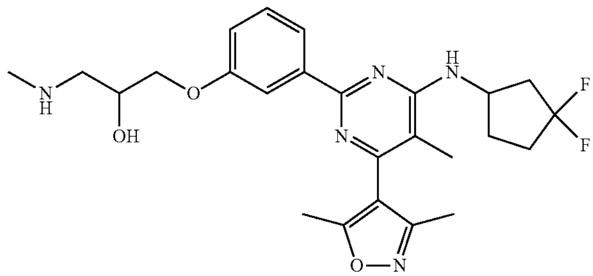 [SMILES: CNCC(O)COc1cccc(-c2nc(NC3CCC(F)(F)C3)c(C)c(-c3c(C)noc3C)n2)c1] | 488.0 |
| 318-1a | 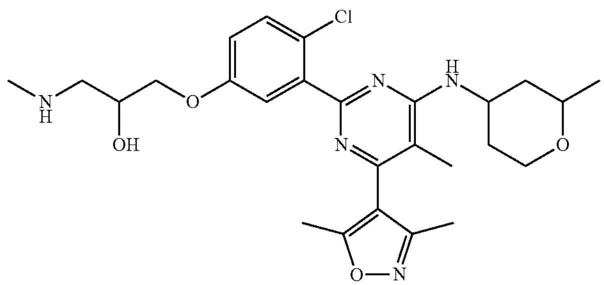 | 515.9 |
| 319-1a | 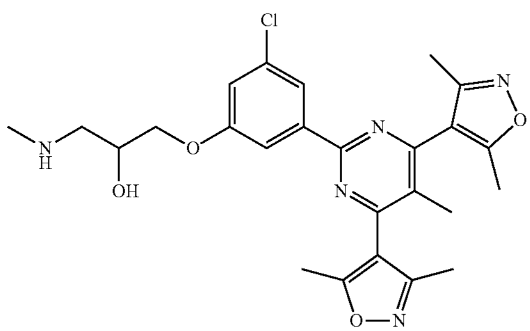 [SMILES: CNCC(O)COc1cc(Cl)cc(-c2nc(-c3c(C)noc3C)c(C)c(-c3c(C)noc3C)n2)c1] | 498.2 |
| 320-1a | 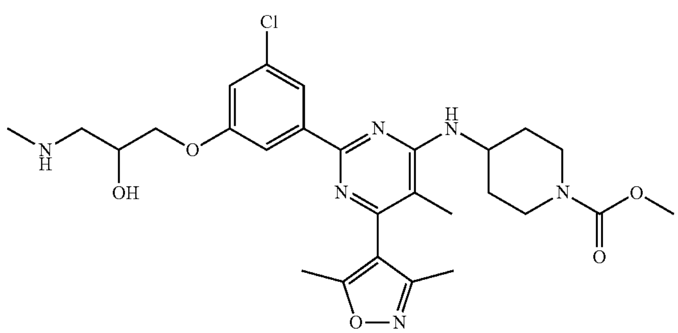 | 559.3 |
| 321-1a | 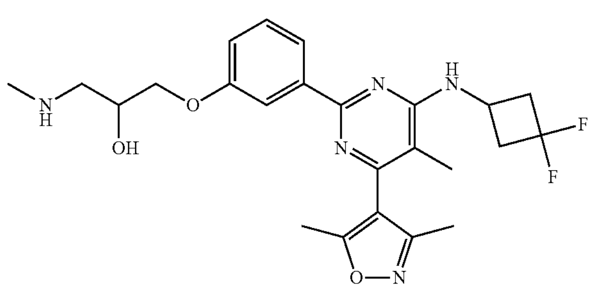 [SMILES: CNCC(O)COc1cccc(-c2nc(NC3CC(F)(F)C3)c(C)c(-c3c(C)noc3C)n2)c1] | 474.0 |

TABLE 1B-continued

Exemplary Compounds

| # | Structure | LC-MS m/z (M + H) |
|---|---|---|
| 322-1a | 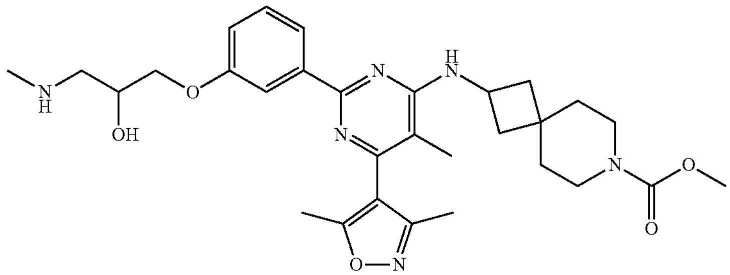 | 565.0 |
| 323-1a | 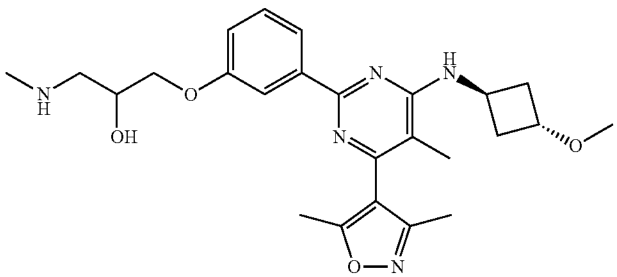 | 468.0 |
| 324-1a | 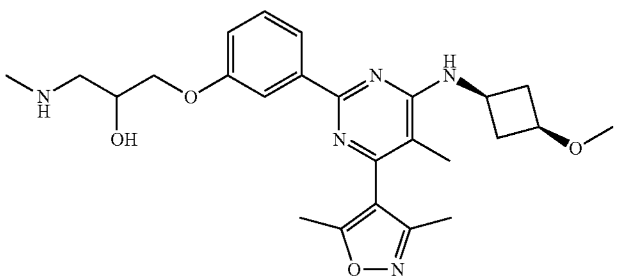 | 468.0 |
| 325-1a | 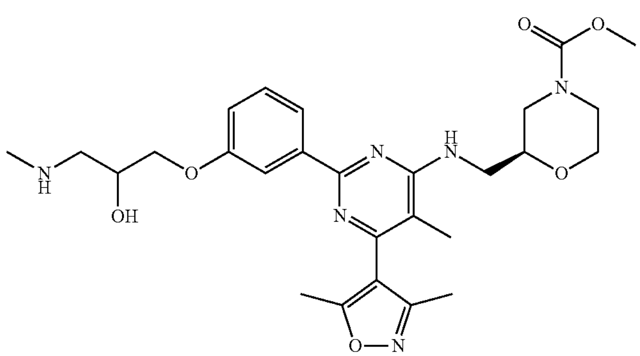 | 541.3 |
| 326-1a | 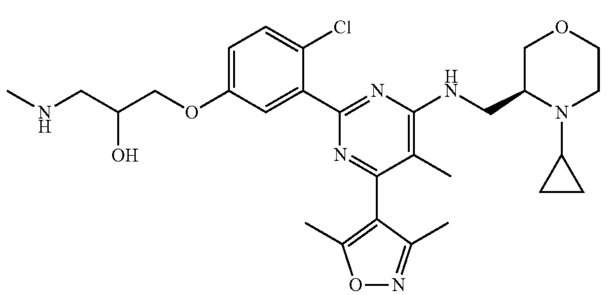 [SMILES: CNCC(O)COc1ccc(Cl)c(-c2nc(NC[C@H]3COCCN3C3CC3)c(C)c(-c3c(C)noc3C)n2)c1] | 557.3 |

TABLE 1B-continued
Exemplary Compounds
| # | Structure | LC-MS m/z (M + H) |
|---|---|---|
| 327-1a | 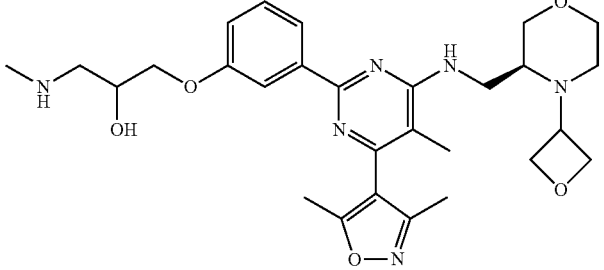 | 539.3 |
| 328-1a | 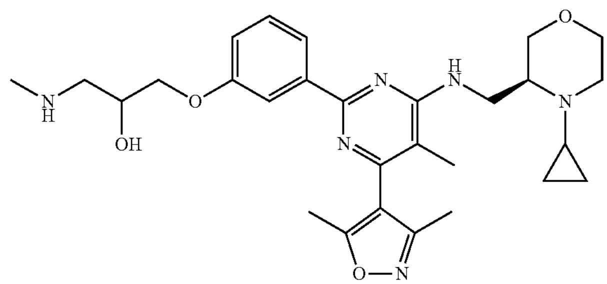 [SMILES: CNCC(O)COc1cccc(-c2nc(NC[C@H]3COCCN3C3CC3)c(C)c(-c3c(C)noc3C)n2)c1] | 523.3 |
| 329-1a | 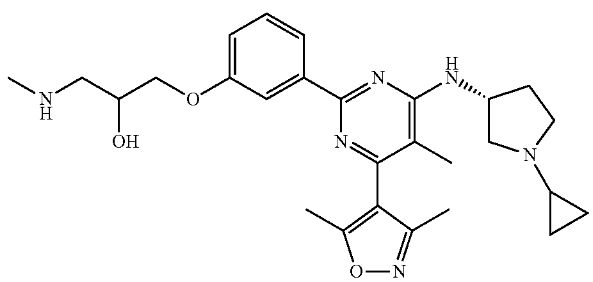 [SMILES: CNCC(O)COc1cccc(-c2nc(N[C@@H]3CCN(C4CC4)C3)c(C)c(-c3c(C)noc3C)n2)c1] | 493.2 |
| 330-1a | 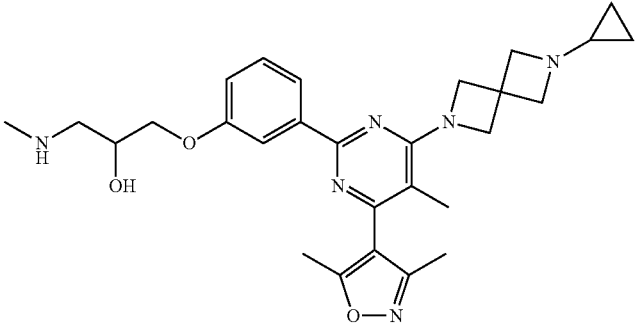 [SMILES: CNCC(O)COc1cccc(-c2nc(-c3c(C)noc3C)c(C)c(N3CC4(C3)CN(C3CC3)C4)n2)c1] | 505.3 |
| 331-1a | 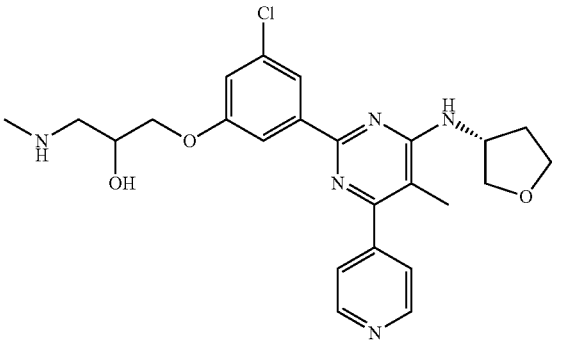 [SMILES: CNCC(O)COc1cc(Cl)cc(-c2nc(N[C@@H]3CCOC3)c(C)c(-c3ccncc3)n2)c1] | 470.7 |

TABLE 1B-continued

Exemplary Compounds

| # | Structure | LC-MS m/z (M + H) |
|---|---|---|
| 332-1a | 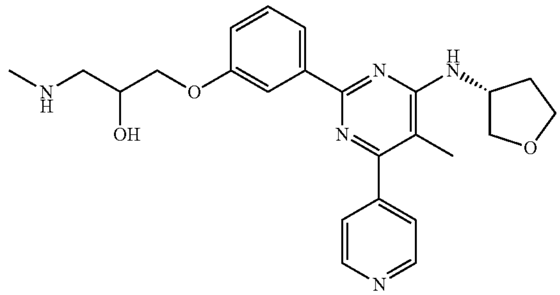 [SMILES: CNCC(O)COc1cccc(-c2nc(N[C@@H]3CCOC3)c(C)c(-c3ccncc3)n2)c1] | 436.3 |
| 333-1a | 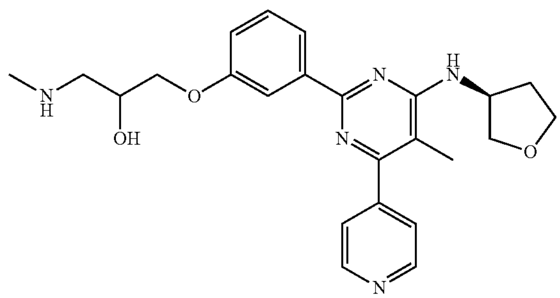 [SMILES: CNCC(O)COc1cccc(-c2nc(N[C@H]3CCOC3)c(C)c(-c3ccncc3)n2)c1] | 436.3 |
| 334-1a | 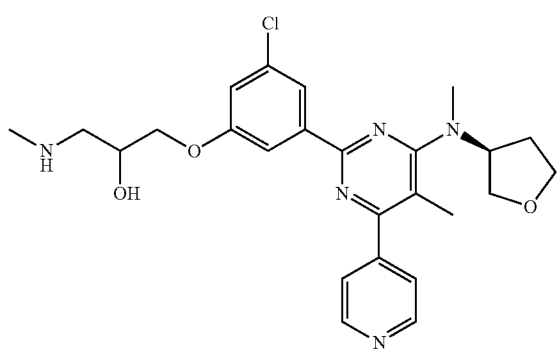 [SMILES: CNCC(O)COc1cc(Cl)cc(-c2nc(-c3ccncc3)c(C)c(N(C)[C@H]3CCOC3)n2)c1] | 484.3 |
| 335-1a | 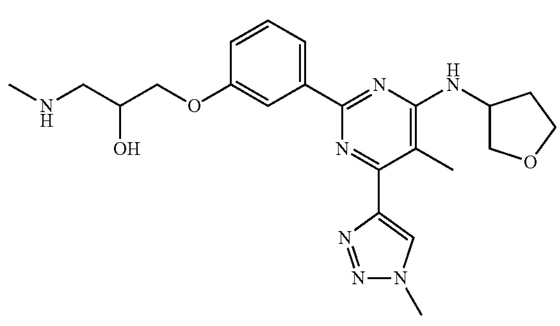 [SMILES: CNCC(O)COc1cccc(-c2nc(NC3CCOC3)c(C)c(-c3cn(C)nn3)n2)c1] | 440.2 |

TABLE 1B-continued
Exemplary Compounds
| # | Structure | LC-MS m/z (M + H) |
|---|---|---|
| 336-1a | 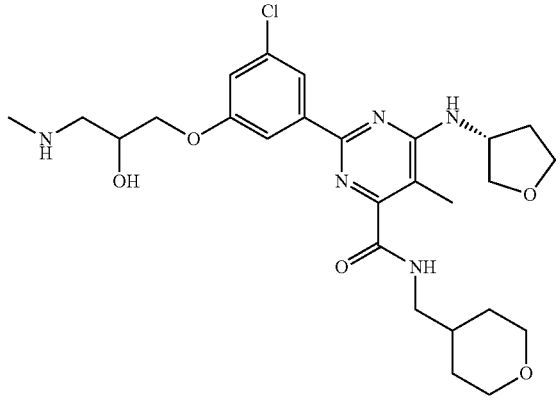 [SMILES: CNCC(O)COc1cc(Cl)cc(-c2nc(N[C@@H]3CCOC3)c(C)c(C(=O)NCC3CCOCC3)n2)c1] | 534.3 |
| 337-1a | 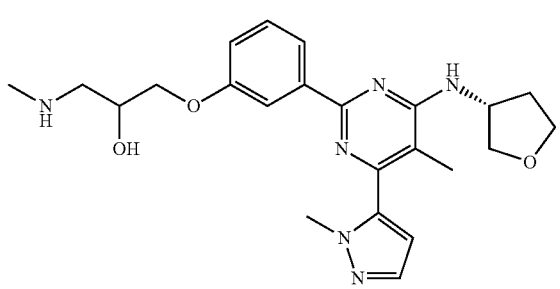 [SMILES: CNCC(O)COc1cccc(-c2nc(N[C@@H]3CCOC3)c(C)c(-c3ccnn3C)n2)c1] | 438.9 |
| 338-1a | 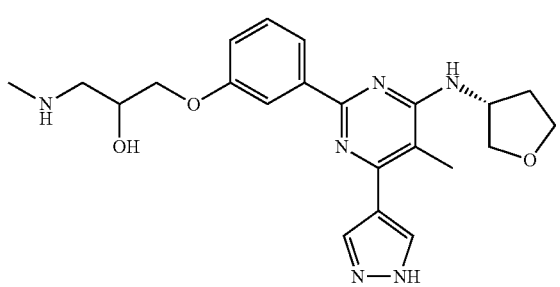 [SMILES: CNCC(O)COc1cccc(-c2nc(N[C@@H]3CCOC3)c(C)c(-c3cn[nH]c3)n2)c1] | 425.2 |
| 339-1a | 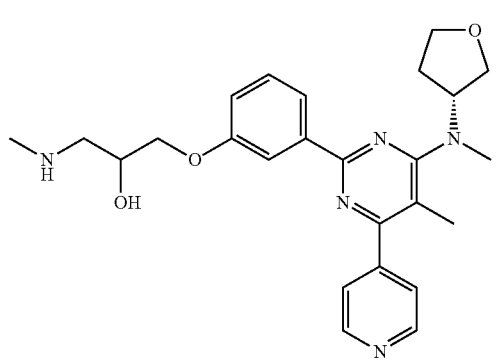 | 450.3 |

TABLE 1B-continued

Exemplary Compounds

| # | Structure | LC-MS m/z (M + H) |
|---|---|---|
| 340-1a | 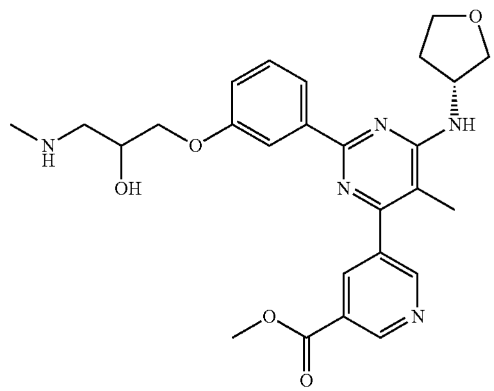 [SMILES: CNCC(O)COc1cccc(-c2nc(N[C@@H]3CCOC3)c(C)c(-c3cncc(C(=O)OC)c3)n2)c1] | 494.1 |
| 341-1a | 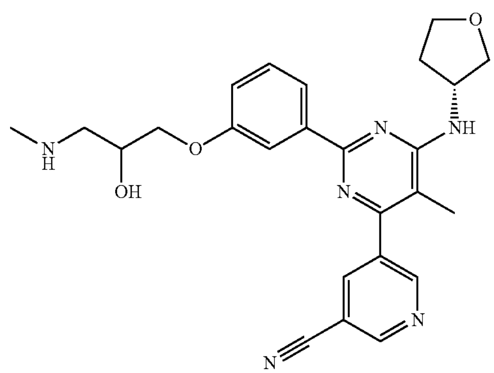 [SMILES: CNCC(O)COc1cccc(-c2nc(N[C@@H]3CCOC3)c(C)c(-c3cncc(C#N)c3)n2)c1] | 461.2 |
| 346-1a | 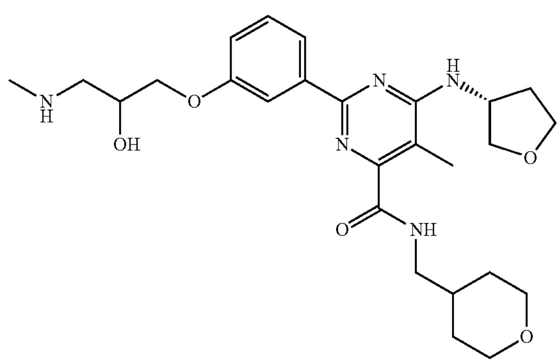 [SMILES: CNCC(O)COc1cccc(-c2nc(N[C@@H]3CCOC3)c(C)c(C(=O)NCC3CCOCC3)n2)c1] | 500.4 |
| 347-1a | 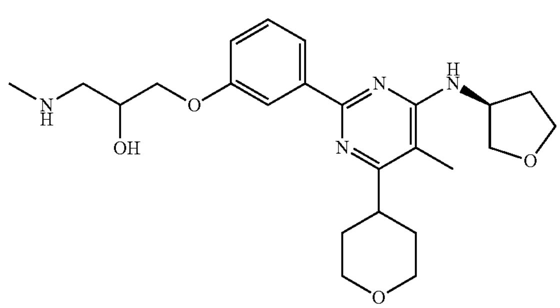 [SMILES: CNCC(O)COc1cccc(-c2nc(N[C@H]3CCOC3)c(C)c(C3CCOCC3)n2)c1] | 443.3 |

TABLE 1B-continued

Exemplary Compounds

| # | Structure | LC-MS m/z (M + H) |
|---|-----------|-------------------|
| 348-1a | 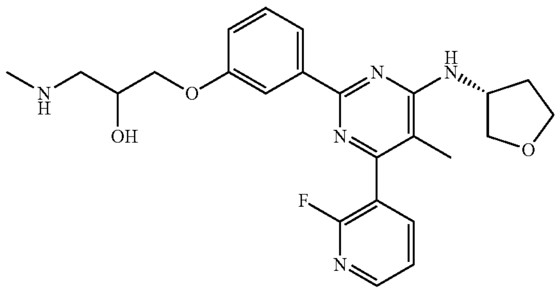 [SMILES: CNCC(O)COc1cccc(-c2nc(N[C@@H]3CCOC3)c(C)c(-c3cccnc3F)n2)c1] | 454.1 |
| 349-1a | 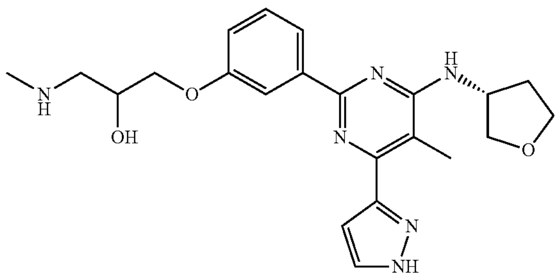 [SMILES: CNCC(O)COc1cccc(-c2nc(N[C@@H]3CCOC3)c(C)c(-c3cc[nH]n3)n2)c1] | 424.9 |
| 350-1a | 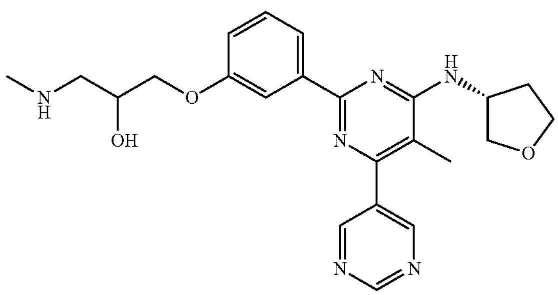 [SMILES: CNCC(O)COc1cccc(-c2nc(N[C@@H]3CCOC3)c(C)c(-c3cncnc3)n2)c1] | 437.1 |
| 351-1a | 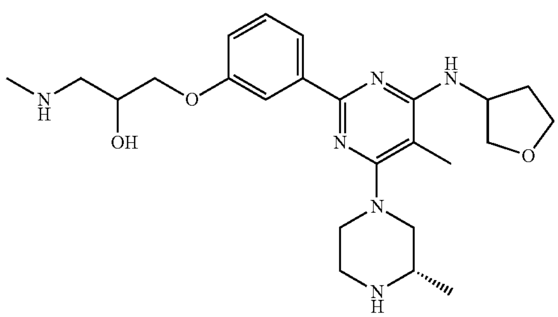 [SMILES: CNCC(O)COc1cccc(-c2nc(NC3CCOC3)c(C)c(N3CCN[C@@H](C)C3)n2)c1] | 457.0 |
| 352-1a | 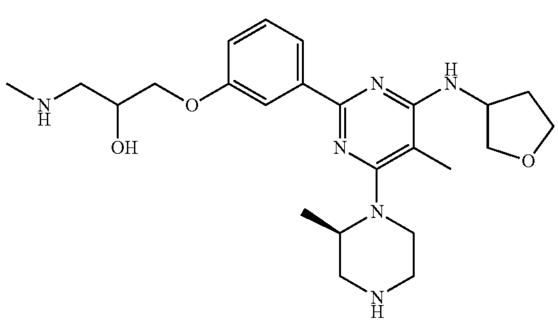 [SMILES: CNCC(O)COc1cccc(-c2nc(NC3CCOC3)c(C)c(N3CCNC[C@H]3C)n2)c1] | 457.0 |

TABLE 1B-continued
Exemplary Compounds
| # | Structure | LC-MS m/z (M + H) |
|---|---|---|
| 353-1a | 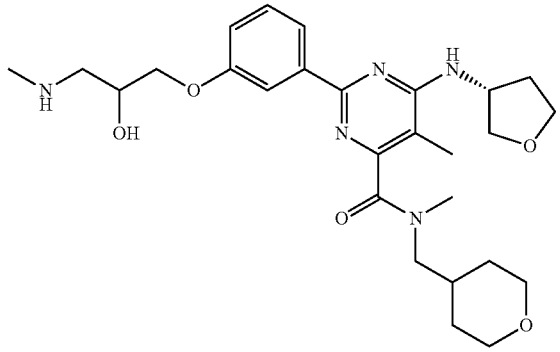 [SMILES: CNCC(O)COc1cccc(-c2nc(N[C@@H]3CCOC3)c(C)c(C(=O)N(C)CC3CCOCC3)n2)c1] | 547.8 |
| 354-1a | 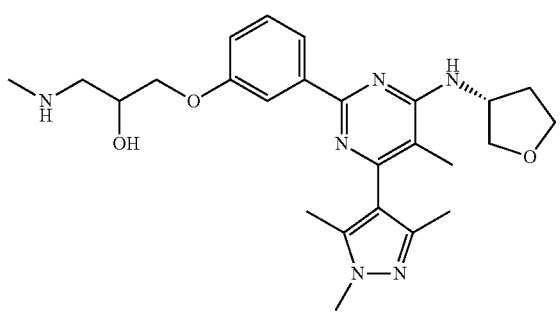 [SMILES: CNCC(O)COc1cccc(-c2nc(N[C@@H]3CCOC3)c(C)c(-c3c(C)nn(C)c3C)n2)c1] | 466.9 |
| 355-1a | 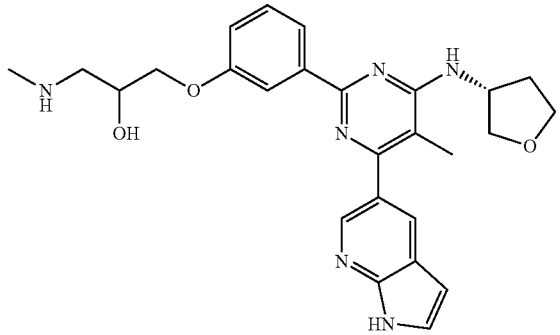 [SMILES: CNCC(O)COc1cccc(-c2nc(N[C@@H]3CCOC3)c(C)c(-c3cnc4[nH]ccc4c3)n2)c1] | 475.1 |
| 356-1a | 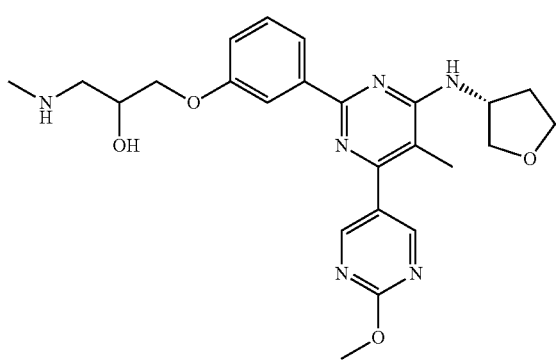 [SMILES: CNCC(O)COc1cccc(-c2nc(N[C@@H]3CCOC3)c(C)c(-c3cnc(OC)nc3)n2)c1] | 467.1 |

TABLE 1B-continued
Exemplary Compounds
| # | Structure | LC-MS m/z (M + H) |
|---|---|---|
| 357-1a | 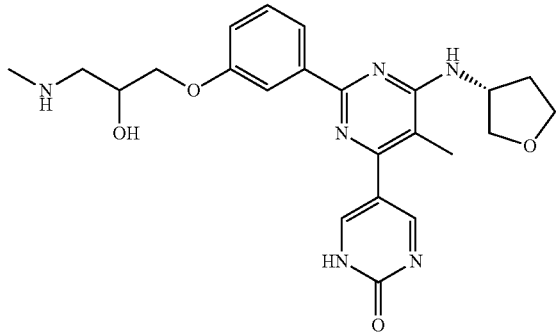 [SMILES: CNCC(O)COc1cccc(-c2nc(N[C@@H]3CCOC3)c(C)c(-c3cnc(=O)[nH]c3)n2)c1] | 453.1 |
| 358-1a | 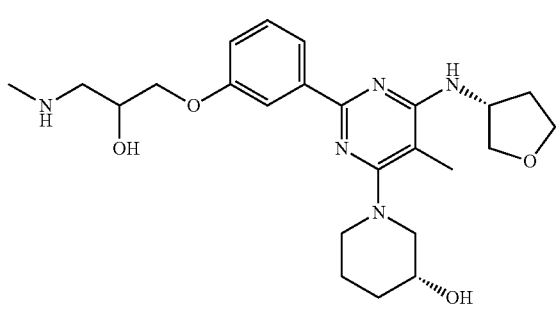 [SMILES: CNCC(O)COc1cccc(-c2nc(N[C@@H]3CCOC3)c(C)c(N3CCC[C@@H](O)C3)n2)c1] | 457.9 |
| 359-1a | 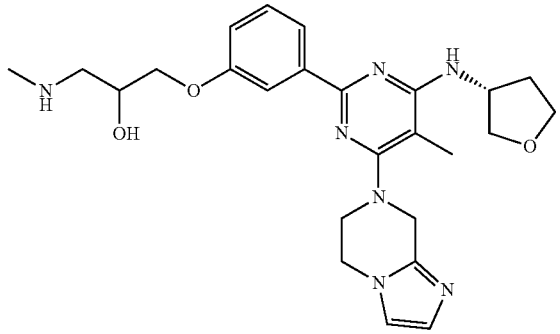 [SMILES: CNCC(O)COc1cccc(-c2nc(N[C@@H]3CCOC3)c(C)c(N3CCn4ccnc4C3)n2)c1] | 479.8 |
| 360-1a | 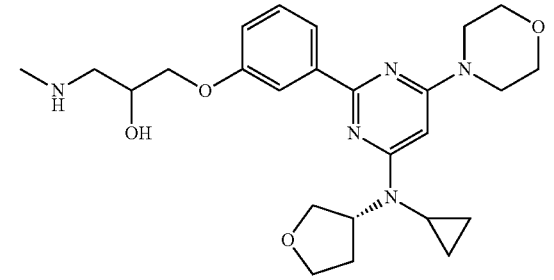 [SMILES: CNCC(O)COc1cccc(-c2nc(N3CCOCC3)cc(N(C3CC3)[C@@H]3CCOC3)n2)c1] | 470.4 |

TABLE 1B-continued

Exemplary Compounds

| # | Structure | LC-MS m/z (M + H) |
|---|---|---|
| 361-1a | 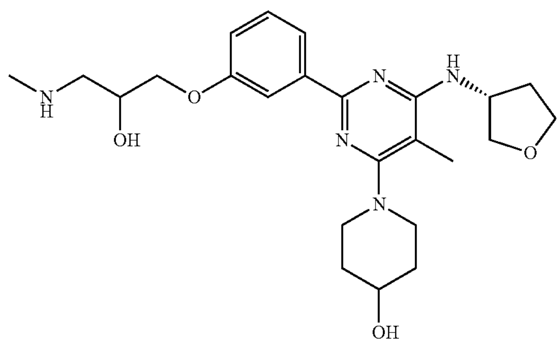 [SMILES: CNCC(O)COc1cccc(-c2nc(N[C@@H]3CCOC3)c(C)c(N3CCC(O)CC3)n2)c1] | 458.3 |
| 364-1a | 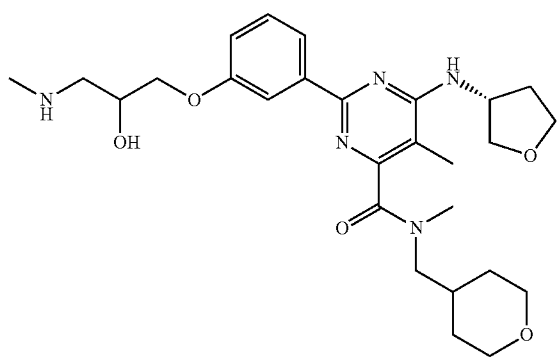 [SMILES: CNCC(O)COc1cccc(-c2nc(N[C@@H]3CCOC3)c(C)c(C(=O)N(C)CC3CCOCC3)n2)c1] | 514.2 |
| 365-1a | 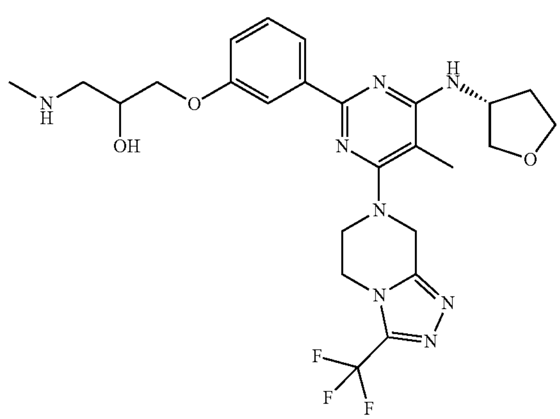 [SMILES: CNCC(O)COc1cccc(-c2nc(N[C@@H]3CCOC3)c(C)c(N3CCn4c(nnc4C(F)(F)F)C3)n2)c1] | 548.8 |
| 366-1a | 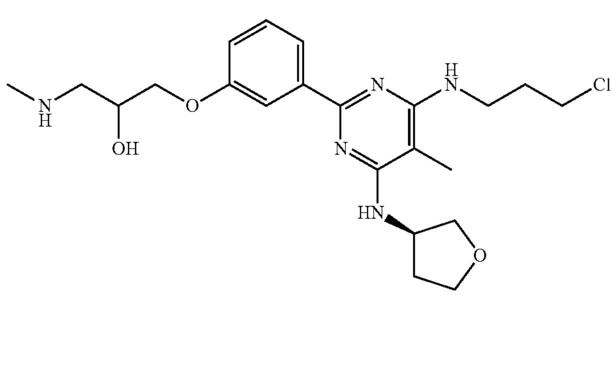 [SMILES: CNCC(O)COc1cccc(-c2nc(NCCCCl)c(C)c(N[C@@H]3CCOC3)n2)c1] | 450.2 |

TABLE 1B-continued

Exemplary Compounds

| # | Structure | LC-MS m/z (M + H) |
|---|-----------|-------------------|
| 367-1a | 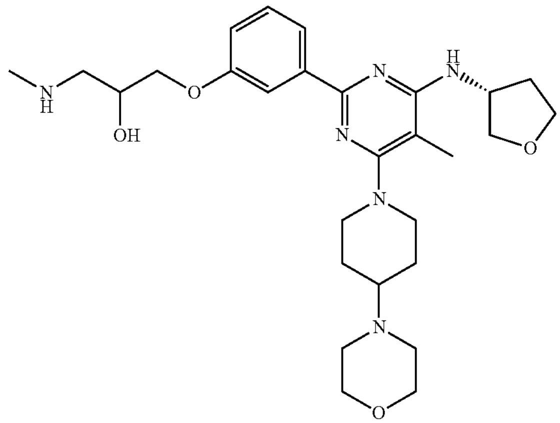 [SMILES: CNCC(O)COc1cccc(-c2nc(N[C@@H]3CCOC3)c(C)c(N3CCC(N4CCOCC4)CC3)n2)c1] | 527.2 |
| 368-1a | 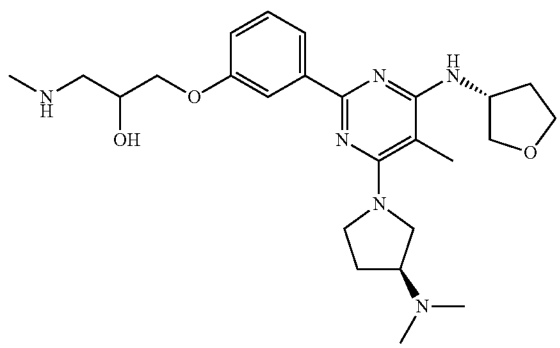 [SMILES: CNCC(O)COc1cccc(-c2nc(N[C@@H]3CCOC3)c(C)c(N3CC[C@H](N(C)C)C3)n2)c1] | 471.3 |
| 369-1a | 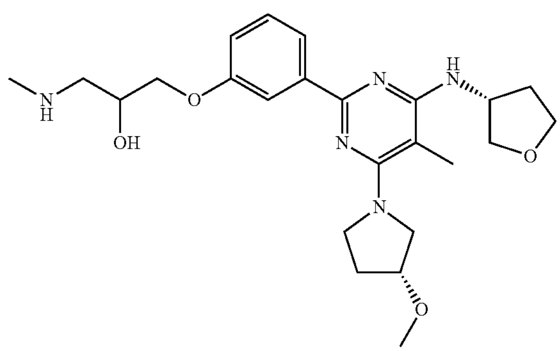 [SMILES: CNCC(O)COc1cccc(-c2nc(N[C@@H]3CCOC3)c(C)c(N3CC[C@@H](OC)C3)n2)c1] | 457.9 |
| 370-1a | 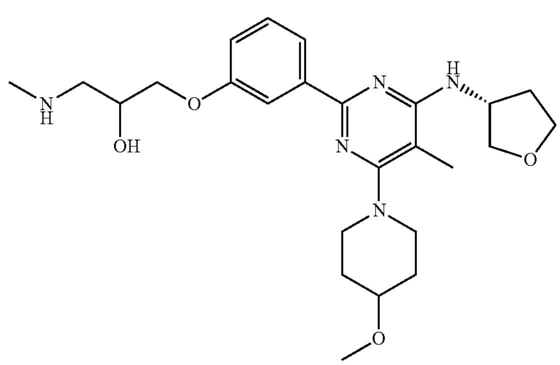 [SMILES: CNCC(O)COc1cccc(-c2nc(N[C@@H]3CCOC3)c(C)c(N3CCC(OC)CC3)n2)c1] | 472.1 |

TABLE 1B-continued

Exemplary Compounds

| # | Structure | LC-MS m/z (M + H) |
|---|---|---|
| 371-1a | 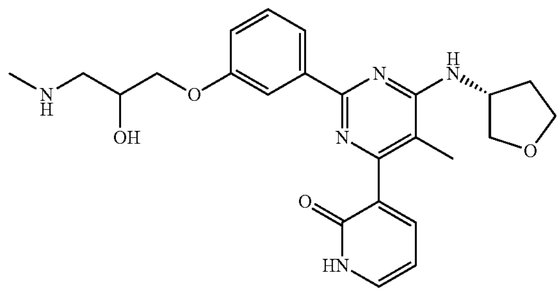 [SMILES: CNCC(O)COc1cccc(-c2nc(N[C@@H]3CCOC3)c(C)c(-c3ccc[nH]c3=O)n2)c1] | 451.7 |
| 372-1a | 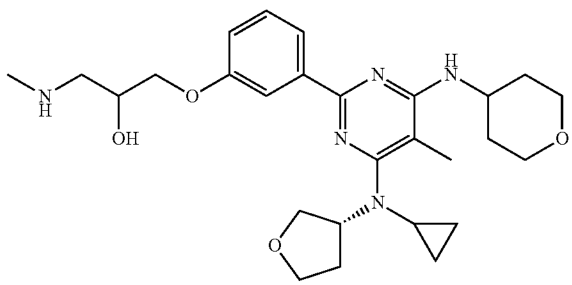 [SMILES: CNCC(O)COc1cccc(-c2nc(NC3CCOCC3)c(C)c(N(C3CC3)[C@@H]3CCOC3)n2)c1] | 484.3 |
| 373-1a | 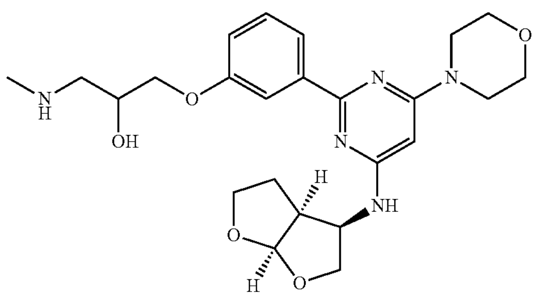 [SMILES: CNCC(O)COc1cccc(-c2nc(N[C@H]3CO[C@H]4OCC[C@H]43)cc(N3CCOCC3)n2)c1] | 472.3 |
| 374-1a | 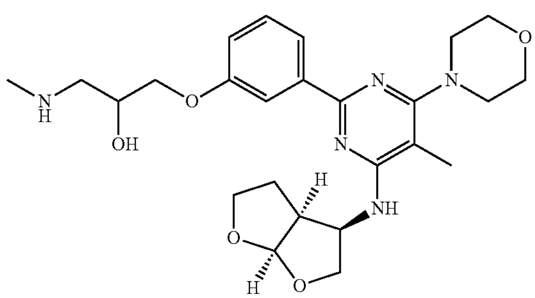 [SMILES: CNCC(O)COc1cccc(-c2nc(N[C@H]3CO[C@H]4OCC[C@H]43)c(C)c(N3CCOCC3)n2)c1] | 486.3 |
| 375-1a | 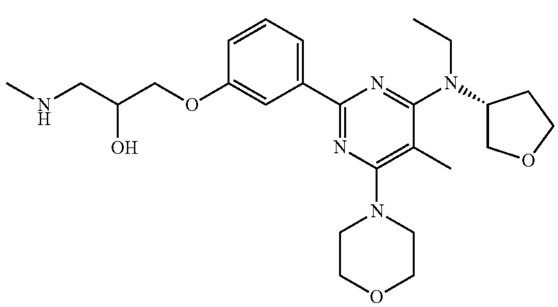 [SMILES: CCN(c1nc(-c2cccc(OCC(O)CNC)c2)nc(N2CCOCC2)c1C)[C@@H]1CCOC1] | 472.4 |

TABLE 1B-continued

Exemplary Compounds

| # | Structure | LC-MS m/z (M + H) |
|---|---|---|
| 376-1a | 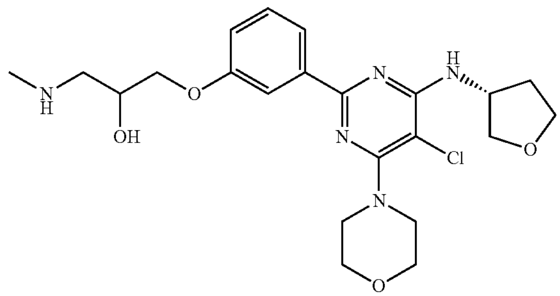 [SMILES: CNCC(O)COc1cccc(-c2nc(N[C@@H]3CCOC3)c(Cl)c(N3CCOCC3)n2)c1] | 464.3 |
| 377-1a | 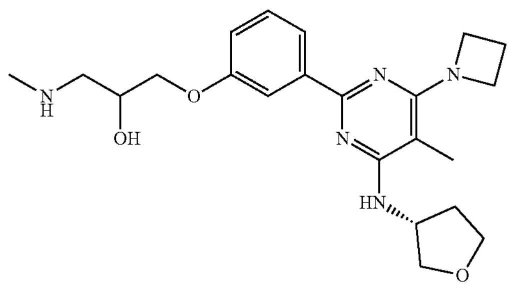 [SMILES: CNCC(O)COc1cccc(-c2nc(N[C@@H]3CCOC3)c(C)c(N3CCC3)n2)c1] | 413.9 |
| 378-1a | 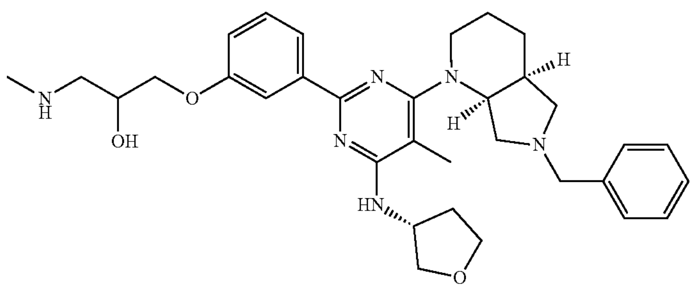 [SMILES: CNCC(O)COc1cccc(-c2nc(N[C@@H]3CCOC3)c(C)c(N3CCC[C@H]4CN(Cc5ccccc5)C[C@H]43)n2)c1] | 572.8 |
| 379-1a | 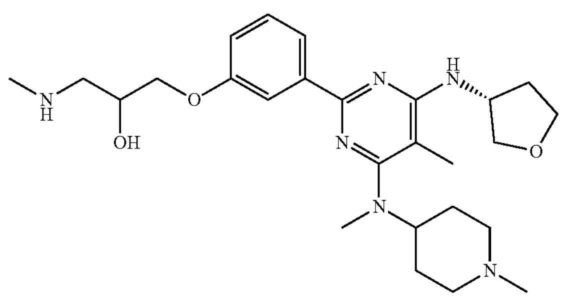 [SMILES: CNCC(O)COc1cccc(-c2nc(N[C@@H]3CCOC3)c(C)c(N(C)C3CCN(C)CC3)n2)c1] | 485.2 |
| 380-1a | 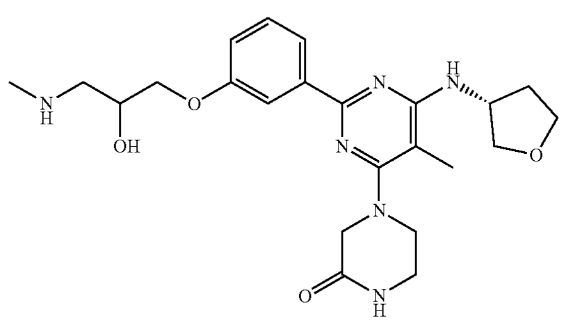 [SMILES: CNCC(O)COc1cccc(-c2nc(N[C@@H]3CCOC3)c(C)c(N3CCNC(=O)C3)n2)c1] | 456.9 |

TABLE 1B-continued

Exemplary Compounds

| # | Structure | LC-MS m/z (M + H) |
|---|---|---|
| 382-1a | 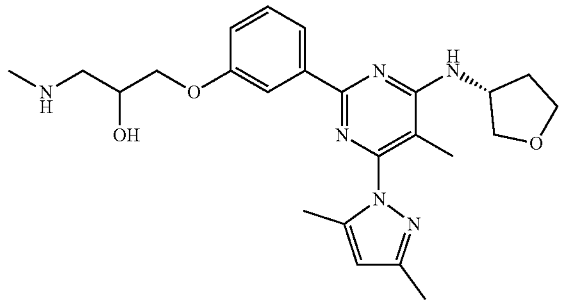 [SMILES: CNCC(O)COc1cccc(-c2nc(N[C@@H]3CCOC3)c(C)c(-n3nc(C)cc3C)n2)c1] | 453.3 |
| 383-1a | 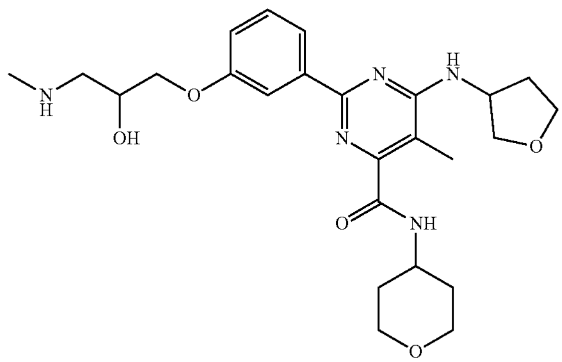 [SMILES: CNCC(O)COc1cccc(-c2nc(NC3CCOC3)c(C)c(C(=O)NC3CCOCC3)n2)c1] | 486.3 |
| 384-1a | 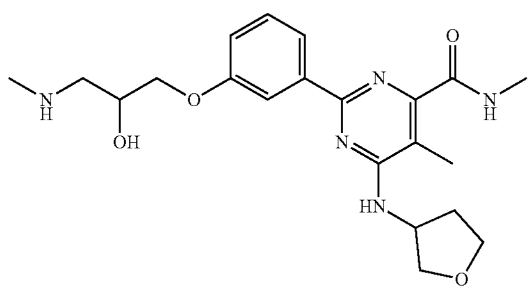 | 416.3 |
| 385-1a | 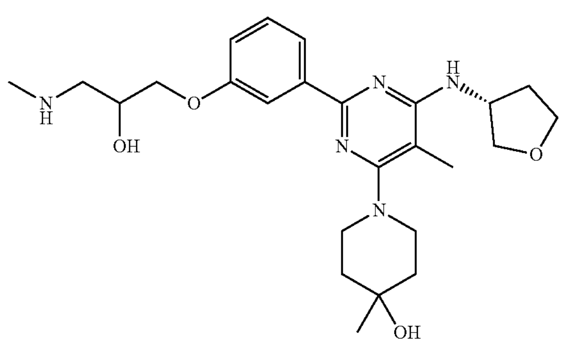 [SMILES: CNCC(O)COc1cccc(-c2nc(N[C@@H]3CCOC3)c(C)c(N3CCC(C)(O)CC3)n2)c1] | 472.3 |

TABLE 1B-continued

Exemplary Compounds

| # | Structure | LC-MS m/z (M + H) |
|---|-----------|-------------------|
| 386-1a | 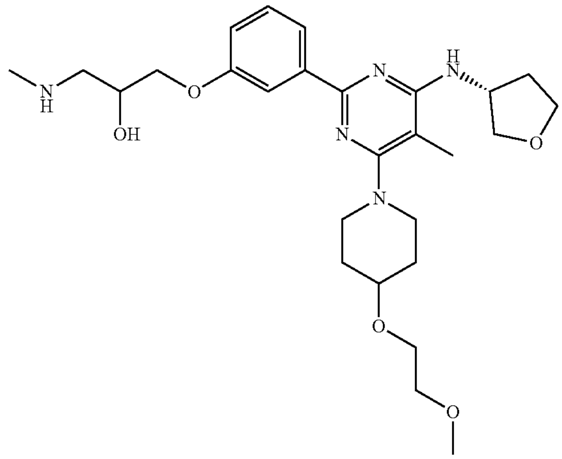 [SMILES: CNCC(O)COc1cccc(-c2nc(N[C@@H]3CCOC3)c(C)c(N3CCC(OCCOC)CC3)n2)c1] | 516.3 |
| 387-1a | 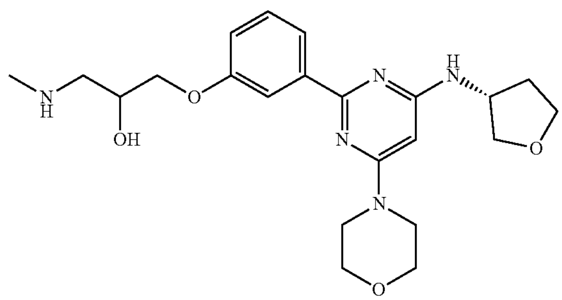 [SMILES: CNCC(O)COc1cccc(-c2nc(N[C@@H]3CCOC3)cc(N3CCOCC3)n2)c1] | 430.4 |
| 388-1a | 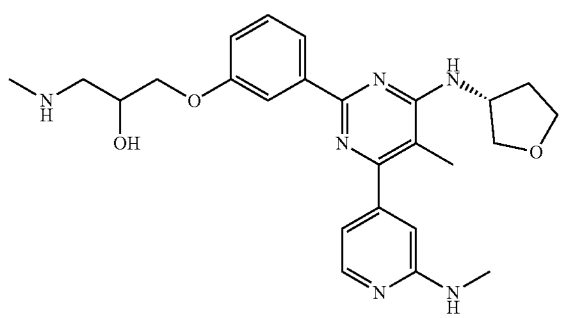 [SMILES: CNCC(O)COc1cccc(-c2nc(N[C@@H]3CCOC3)c(C)c(-c3ccnc(NC)c3)n2)c1] | 465.2 |
| 389-1a | 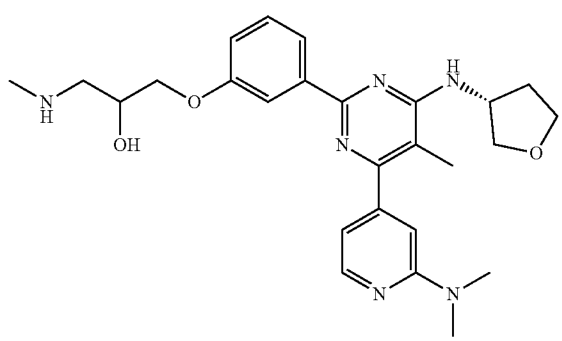 [SMILES: CNCC(O)COc1cccc(-c2nc(N[C@@H]3CCOC3)c(C)c(-c3ccnc(N(C)C)c3)n2)c1] | 479.2 |

TABLE 1B-continued
Exemplary Compounds
| # | Structure | LC-MS m/z (M + H) |
|---|---|---|
| 390-1a | 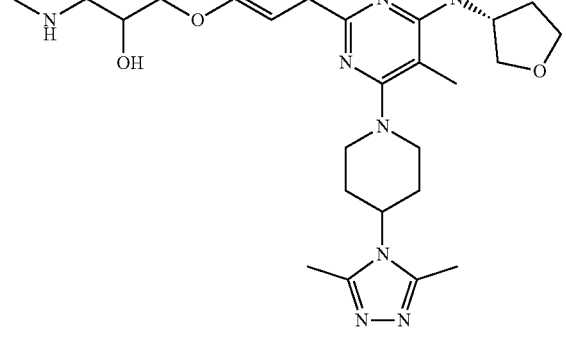 | 538.3 |
| 391-1a | 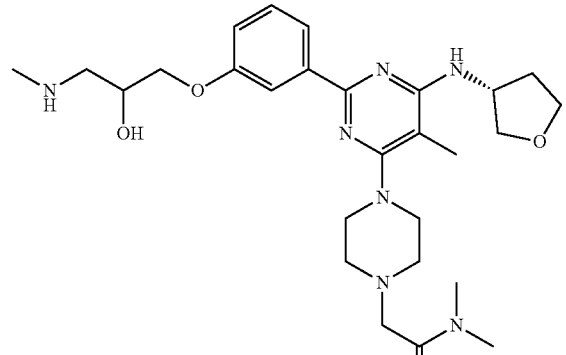 | 527.9 |
| 392-1a | 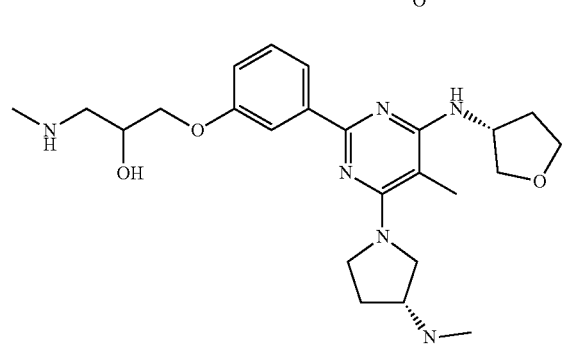 | 471.3 |
| 393-1a | 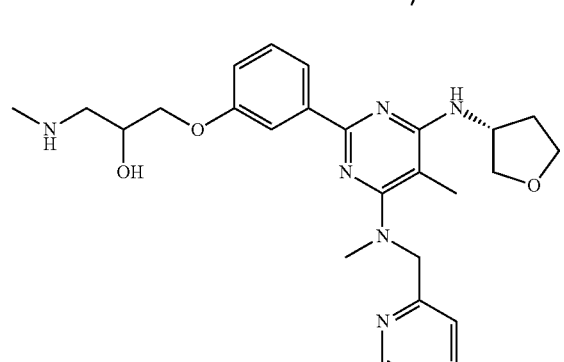 | 478.9 |

TABLE 1B-continued

Exemplary Compounds

| # | Structure | LC-MS m/z (M + H) |
|---|---|---|
| 394-1a | 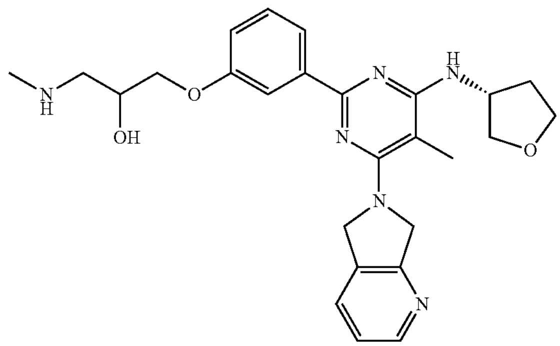 [SMILES: CNCC(O)COc1cccc(-c2nc(N[C@@H]3CCOC3)c(C)c(N3Cc4cccnc4C3)n2)c1] | 476.8 |
| 395-1a | 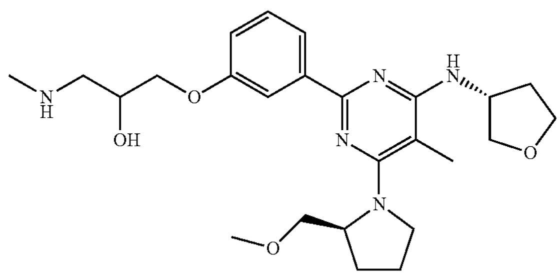 [SMILES: CNCC(O)COc1cccc(-c2nc(N[C@@H]3CCOC3)c(C)c(N3CCC[C@H]3COC)n2)c1] | 471.9 |
| 396-1a | 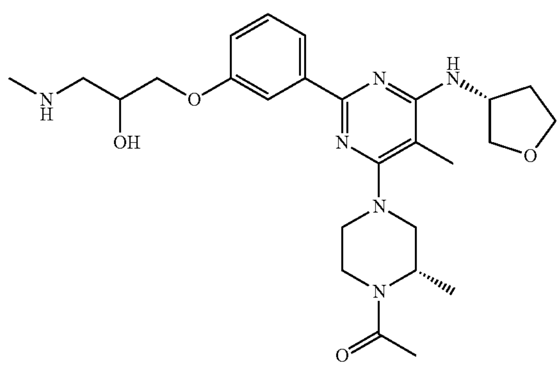 [SMILES: CNCC(O)COc1cccc(-c2nc(N[C@@H]3CCOC3)c(C)c(N3CCN(C(C)=O)[C@@H](C)C3)n2)c1] | 499.3 |
| 397-1a | 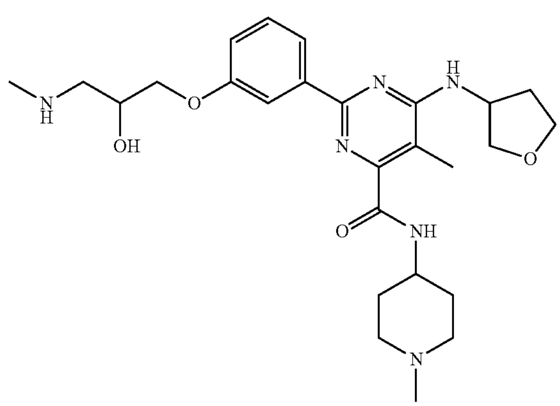 [SMILES: CNCC(O)COc1cccc(-c2nc(NC3CCOC3)c(C)c(C(=O)NC3CCN(C)CC3)n2)c1] | 499.2 |

TABLE 1B-continued
Exemplary Compounds
| # | Structure | LC-MS m/z (M + H) |
|---|---|---|
| 398-1a | 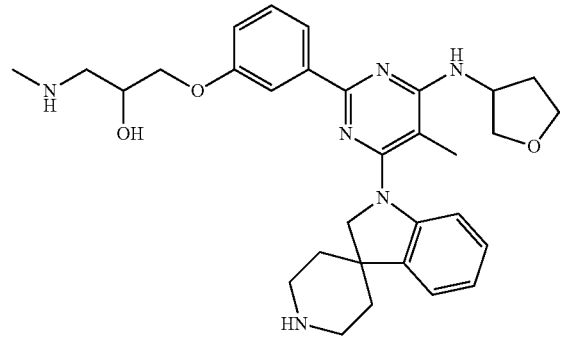 [SMILES: CNCC(O)COc1cccc(-c2nc(NC3CCOC3)c(C)c(N3CC4(CCNCC4)c4ccccc43)n2)c1] | 544.9 |
| 399-1a | 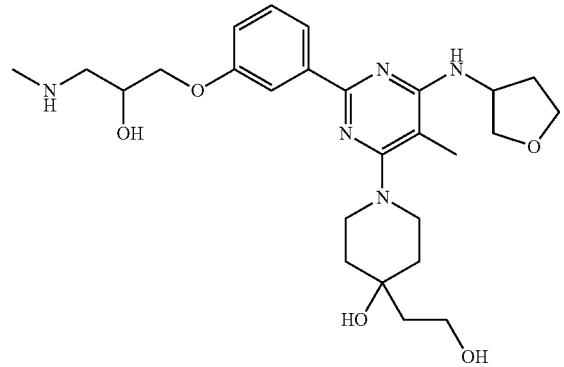 [SMILES: CNCC(O)COc1cccc(-c2nc(NC3CCOC3)c(C)c(N3CCC(O)(CCO)CC3)n2)c1] | 502.0 |
| 400-1a | 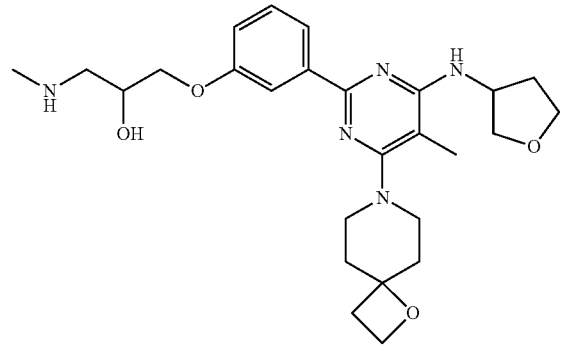 [SMILES: CNCC(O)COc1cccc(-c2nc(NC3CCOC3)c(C)c(N3CCC4(CCO4)CC3)n2)c1] | 484.0 |
| 401-1a | 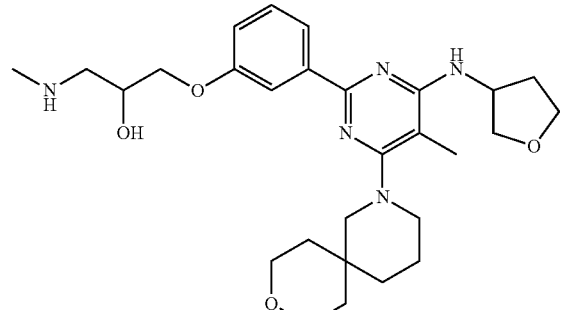 | 512.0 |

TABLE 1B-continued

Exemplary Compounds

| # | Structure | LC-MS m/z (M + H) |
|---|---|---|
| 402-1a | 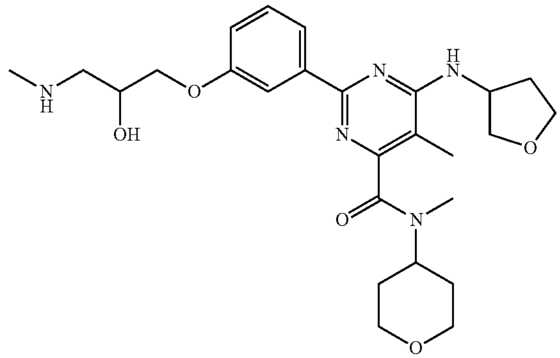 [SMILES: CNCC(O)COc1cccc(-c2nc(NC3CCOC3)c(C)c(C(=O)N(C)C3CCOCC3)n2)c1] | 500.4 |
| 403-1a | 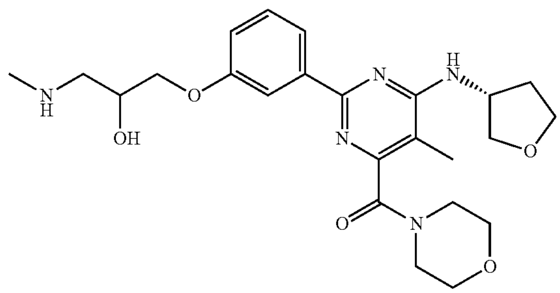 [SMILES: CNCC(O)COc1cccc(-c2nc(N[C@@H]3CCOC3)c(C)c(C(=O)N3CCOCC3)n2)c1] | 472.3 |
| 404-1a | 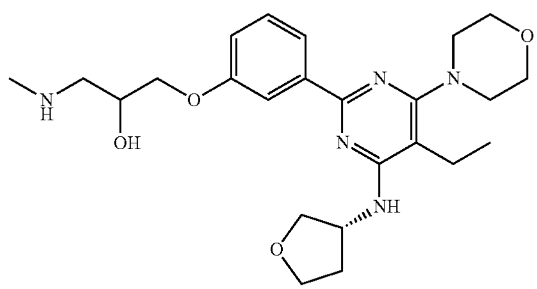 [SMILES: CCc1c(N[C@@H]2CCOC2)nc(-c2cccc(OCC(O)CNC)c2)nc1N1CCOCC1] | 458.4 |
| 405-1a | 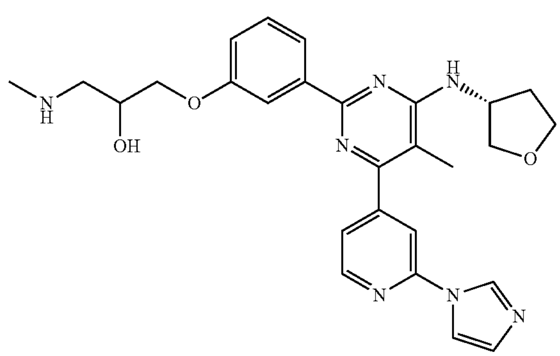 [SMILES: CNCC(O)COc1cccc(-c2nc(N[C@@H]3CCOC3)c(C)c(-c3ccnc(-n4ccnc4)c3)n2)c1] | 502.8 |

TABLE 1B-continued

Exemplary Compounds

| # | Structure | LC-MS m/z (M + H) |
|---|---|---|
| 406-1a | 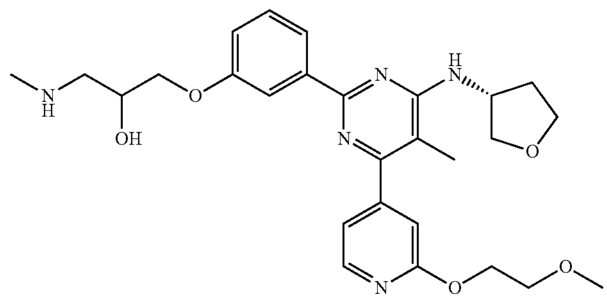 | 509.8 |
| 407-1a | 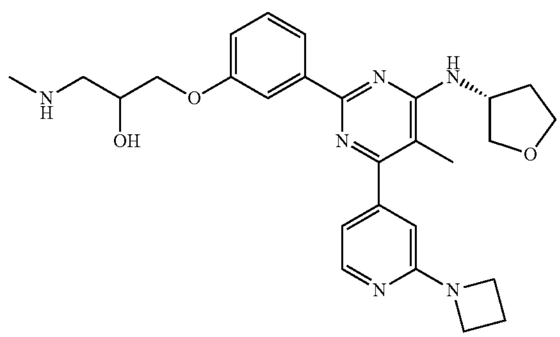 [SMILES: CNCC(O)COc1cccc(-c2nc(N[C@@H]3CCOC3)c(C)c(-c3ccnc(N4CCC4)c3)n2)c1] | 490.9 |
| 408-1a | 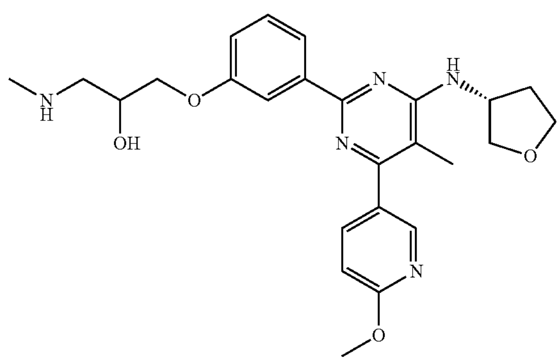 [SMILES: CNCC(O)COc1cccc(-c2nc(N[C@@H]3CCOC3)c(C)c(-c3ccc(OC)nc3)n2)c1] | 466.1 |
| 409-1a | 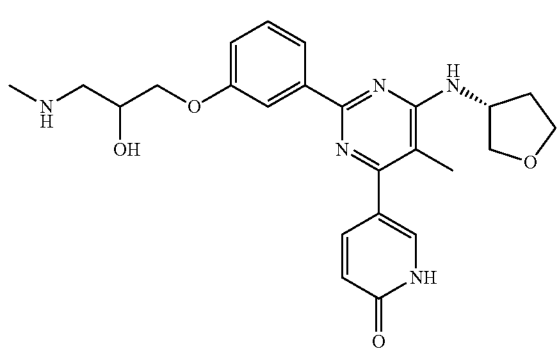 [SMILES: CNCC(O)COc1cccc(-c2nc(N[C@@H]3CCOC3)c(C)c(-c3ccc(=O)[nH]c3)n2)c1] | 452.2 |

TABLE 1B-continued

Exemplary Compounds

| # | Structure | LC-MS m/z (M + H) |
|---|---|---|
| 410-1a | 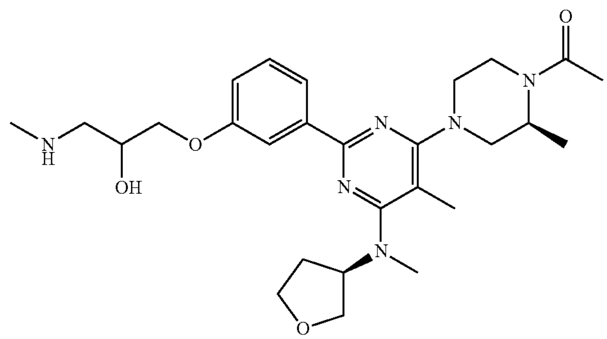 [SMILES: CNCC(O)COc1cccc(-c2nc(N3CCN(C(C)=O)[C@@H](C)C3)c(C)c(N(C)[C@@H]3CCOC3)n2)c1] | 513.3 |
| 412-1a | 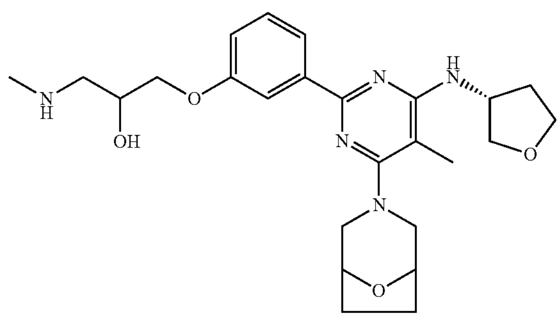 [SMILES: CNCC(O)COc1cccc(-c2nc(N[C@@H]3CCOC3)c(C)c(N3CC4CCC(C3)O4)n2)c1] | 470.3 |
| 413-1a | 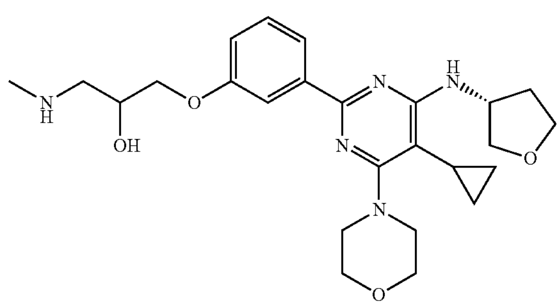 [SMILES: CNCC(O)COc1cccc(-c2nc(N[C@@H]3CCOC3)c(C3CC3)c(N3CCOCC3)n2)c1] | 470.0 |
| 414-1a | 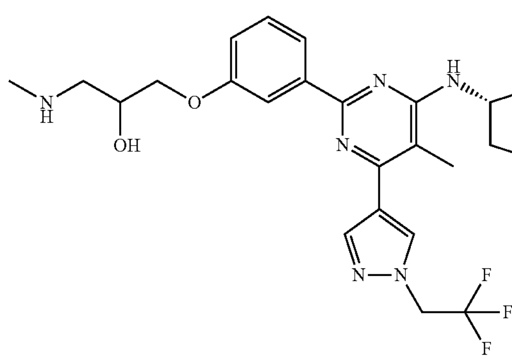 | 506.8 |

TABLE 1B-continued
Exemplary Compounds
| # | Structure | LC-MS m/z (M + H) |
|---|---|---|
| 415-1a | 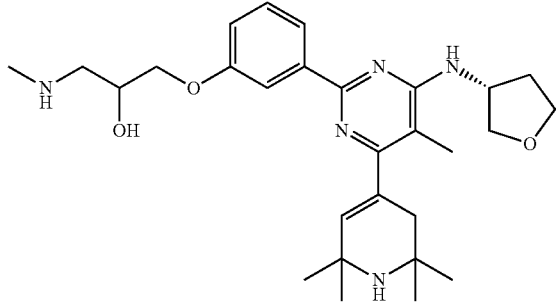 [SMILES: CNCC(O)COc1cccc(-c2nc(N[C@@H]3CCOC3)c(C)c(C3=CC(C)(C)NC(C)(C)C3)n2)c1] | 495.9 |
| 416-1a | 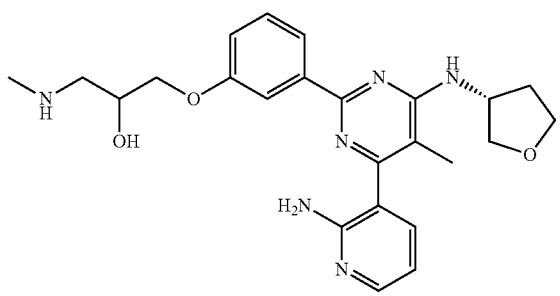 [SMILES: CNCC(O)COc1cccc(-c2nc(N[C@@H]3CCOC3)c(C)c(-c3cccnc3N)n2)c1] | 451.2 |
| 418-1a | 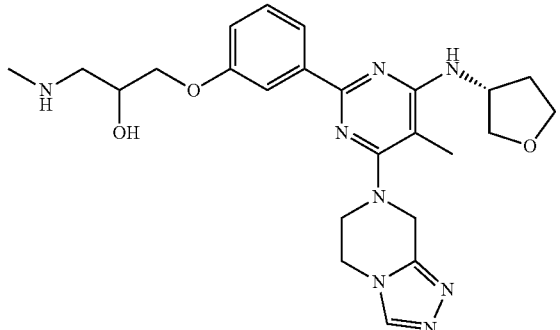 [SMILES: CNCC(O)COc1cccc(-c2nc(N[C@@H]3CCOC3)c(C)c(N3CCn4cnnc4C3)n2)c1] | 480.9 |
| 419-1a | 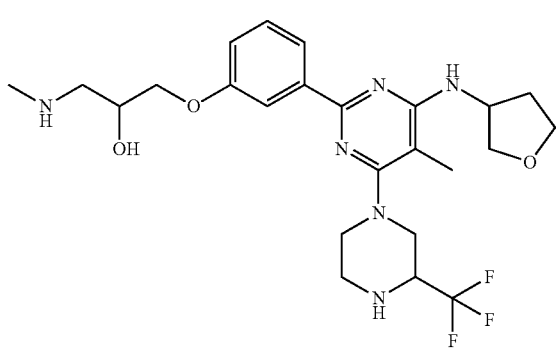 [SMILES: CNCC(O)COc1cccc(-c2nc(NC3CCOC3)c(C)c(N3CCNC(C(F)(F)F)C3)n2)c1] | 511.0 |

TABLE 1B-continued

Exemplary Compounds

| # | Structure | LC-MS m/z (M + H) |
|---|---|---|
| 420-1a | 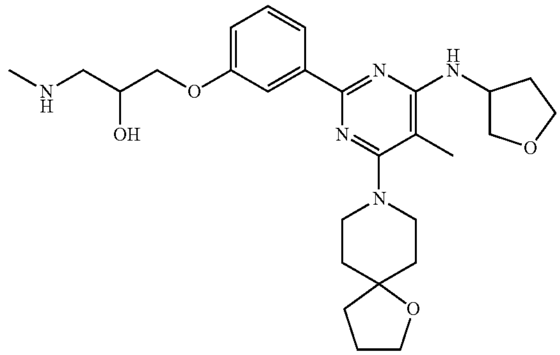 [SMILES: CNCC(O)COc1cccc(-c2nc(NC3CCOC3)c(C)c(N3CCC4(CCCO4)CC3)n2)c1] | 498.3 |
| 421-1a | 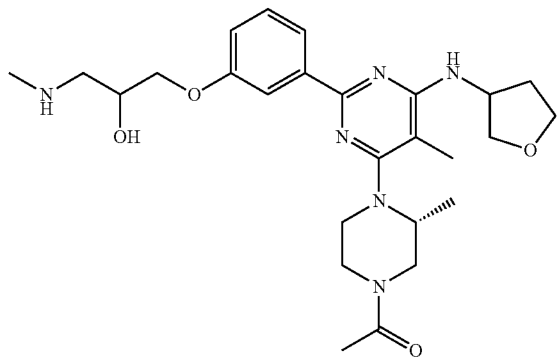 [SMILES: CNCC(O)COc1cccc(-c2nc(NC3CCOC3)c(C)c(N3CCN(C(C)=O)C[C@H]3C)n2)c1] | 499.3 |
| 422-1a | 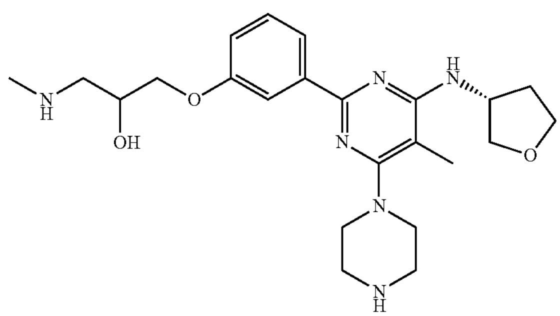 [SMILES: CNCC(O)COc1cccc(-c2nc(N[C@@H]3CCOC3)c(C)c(N3CCNCC3)n2)c1] | 443.3 |
| 423-1a | 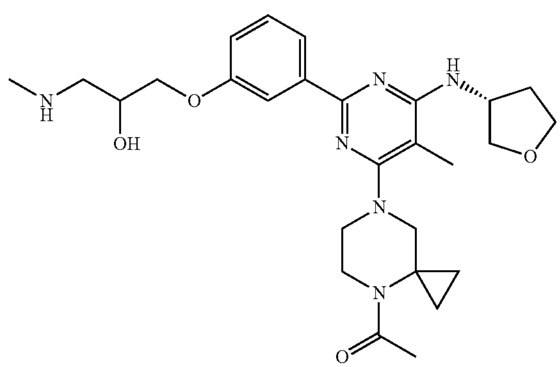 [SMILES: CNCC(O)COc1cccc(-c2nc(N[C@@H]3CCOC3)c(C)c(N3CCN(C(C)=O)C4(CC4)C3)n2)c1] | 511.0 |

TABLE 1B-continued

Exemplary Compounds

| # | Structure | LC-MS m/z (M + H) |
|---|---|---|
| 424-1a | 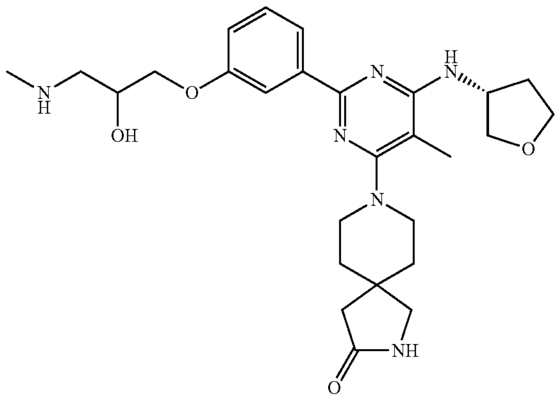 [SMILES: CNCC(O)COc1cccc(-c2nc(N[C@@H]3CCOC3)c(C)c(N3CCC4(CC3)CNC(=O)C4)n2)c1] | 511.3 |
| 425-1a | 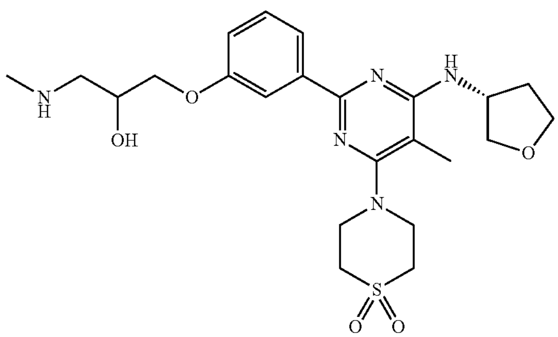 [SMILES: CNCC(O)COc1cccc(-c2nc(N[C@@H]3CCOC3)c(C)c(N3CCS(=O)(=O)CC3)n2)c1] | 492.2 |
| 426-1a | 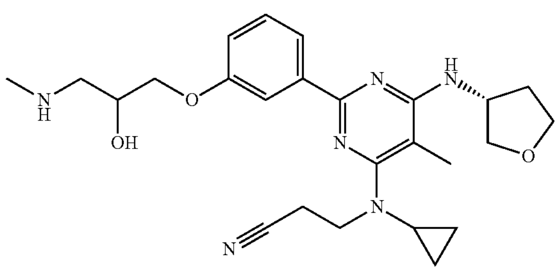 [SMILES: CNCC(O)COc1cccc(-c2nc(N[C@@H]3CCOC3)c(C)c(N(CCC#N)C3CC3)n2)c1] | 466.7 |
| 427-1a | 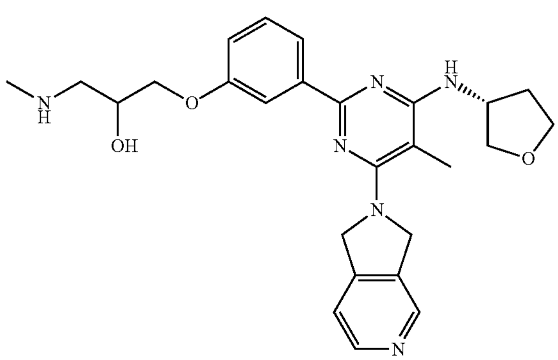 [SMILES: CNCC(O)COc1cccc(-c2nc(N[C@@H]3CCOC3)c(C)c(N3Cc4ccncc4C3)n2)c1] | 477.8 |

TABLE 1B-continued

Exemplary Compounds

| # | Structure | LC-MS m/z (M + H) |
|---|-----------|-------------------|
| 428-1a | 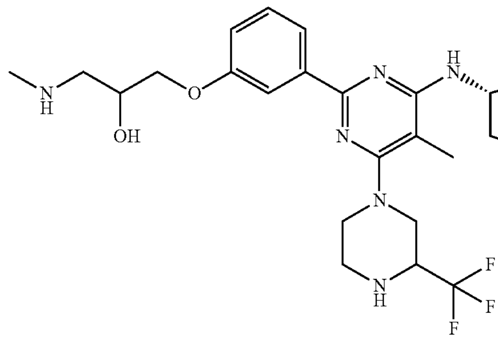 | 511.2 |
| 429-1a | 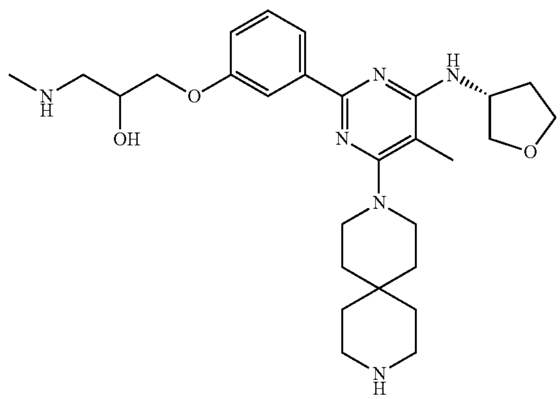 [SMILES: CNCC(O)COc1cccc(-c2nc(N[C@@H]3CCOC3)c(C)c(N3CCC4(CCNCC4)CC3)n2)c1] | 511.3 |
| 430-1a | 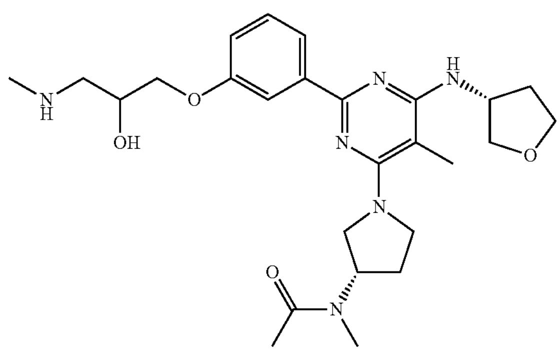 [SMILES: CNCC(O)COc1cccc(-c2nc(N[C@@H]3CCOC3)c(C)c(N3CC[C@H](N(C)C(C)=O)C3)n2)c1] | 499.3 |
| 431-1a | 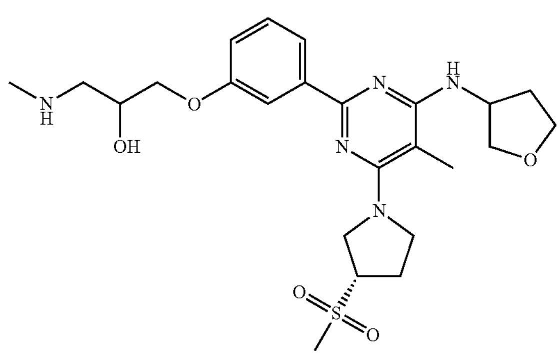 [SMILES: CNCC(O)COc1cccc(-c2nc(NC3CCOC3)c(C)c(N3CC[C@H](S(C)(=O)=O)C3)n2)c1] | 506.2 |

TABLE 1B-continued

Exemplary Compounds

| # | Structure | LC-MS m/z (M + H) |
|---|-----------|-------------------|
| 432-1a | 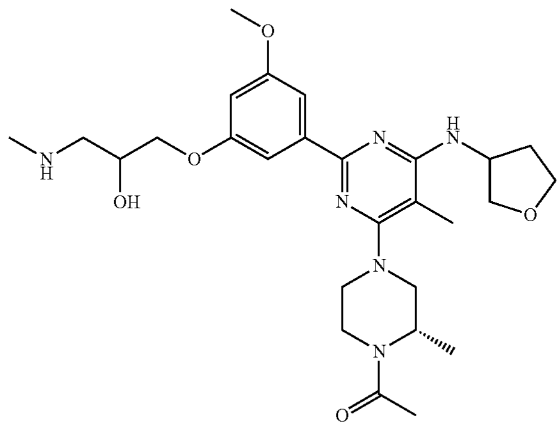 [SMILES: CNCC(O)COc1cc(OC)cc(-c2nc(NC3CCOC3)c(C)c(N3CCN(C(C)=O)[C@@H](C)C3)n2)c1] | 529.3 |
| 433-1a | 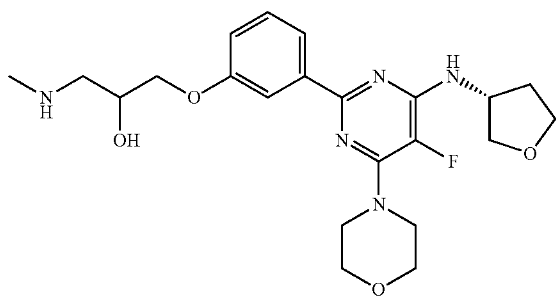 [SMILES: CNCC(O)COc1cccc(-c2nc(N[C@@H]3CCOC3)c(F)c(N3CCOCC3)n2)c1] | 448.1 |
| 434-1a | 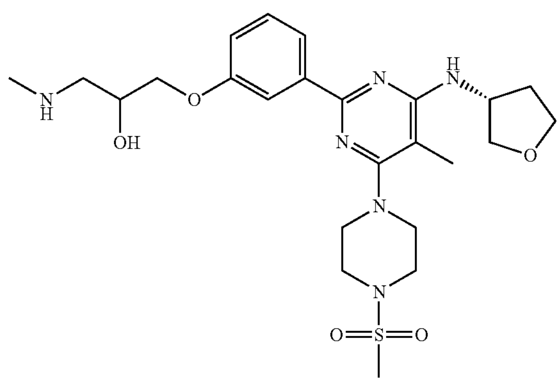 [SMILES: CNCC(O)COc1cccc(-c2nc(N[C@@H]3CCOC3)c(C)c(N3CCN(S(C)(=O)=O)CC3)n2)c1] | 521.0 |
| 435-1a | 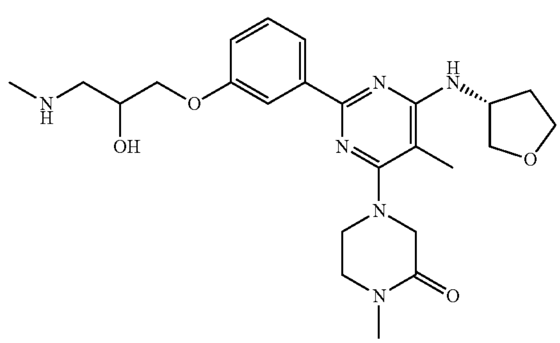 [SMILES: CNCC(O)COc1cccc(-c2nc(N[C@@H]3CCOC3)c(C)c(N3CCN(C)C(=O)C3)n2)c1] | 470.8 |

TABLE 1B-continued

Exemplary Compounds

| # | Structure | LC-MS m/z (M + H) |
|---|---|---|
| 436-1a | 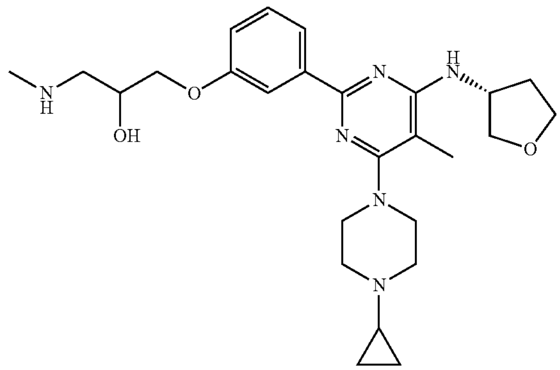 [SMILES: CNCC(O)COc1cccc(-c2nc(N[C@@H]3CCOC3)c(C)c(N3CCN(C4CC4)CC3)n2)c1] | 482.8 |
| 437-1a | 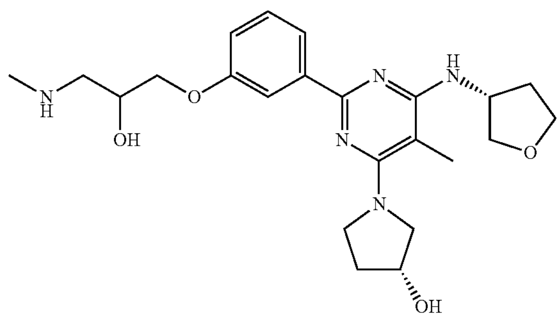 [SMILES: CNCC(O)COc1cccc(-c2nc(N[C@@H]3CCOC3)c(C)c(N3CC[C@@H](O)C3)n2)c1] | 443.8 |
| 438-1a | 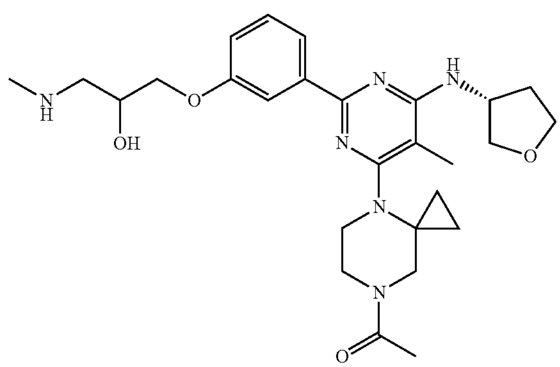 [SMILES: CNCC(O)COc1cccc(-c2nc(N[C@@H]3CCOC3)c(C)c(N3CCN(C(C)=O)CC34CC4)n2)c1] | 511.1 |
| 439-1a | 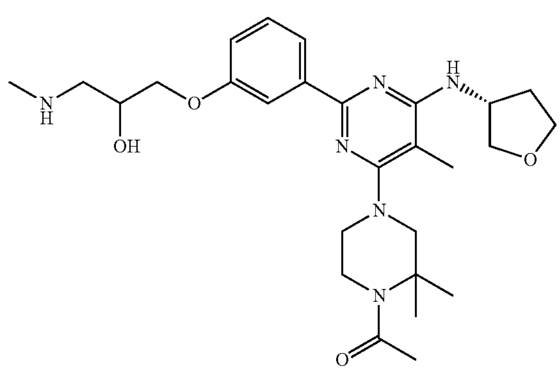 [SMILES: CNCC(O)COc1cccc(-c2nc(N[C@@H]3CCOC3)c(C)c(N3CCN(C(C)=O)C(C)(C)C3)n2)c1] | 513.3 |

TABLE 1B-continued

Exemplary Compounds

| # | Structure | LC-MS m/z (M + H) |
|---|---|---|
| 440-1a | 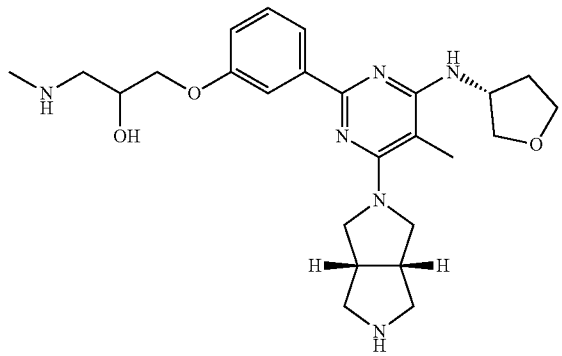 [SMILES: CNCC(O)COc1cccc(-c2nc(N[C@@H]3CCOC3)c(C)c(N3C[C@H]4CNC[C@H]4C3)n2)c1] | 469.2 |
| 441-1a | 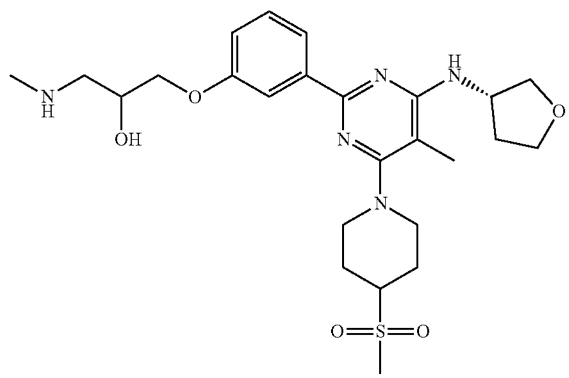 [SMILES: CNCC(O)COc1cccc(-c2nc(N[C@H]3CCOC3)c(C)c(N3CCC(S(C)(=O)=O)CC3)n2)c1] | 519.8 |
| 442-1a | 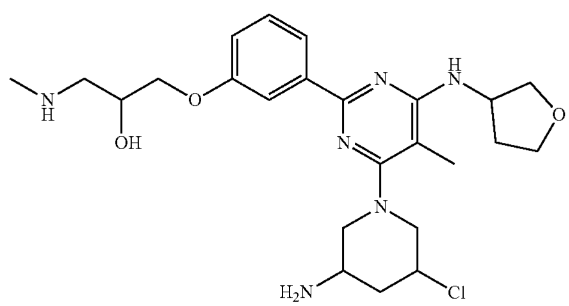 [SMILES: CNCC(O)COc1cccc(-c2nc(NC3CCOC3)c(C)c(N3CC(N)CC(Cl)C3)n2)c1] | 491.3 |
| 443-1a | 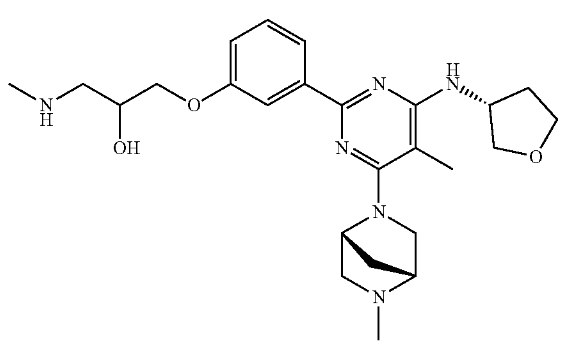 [SMILES: CNCC(O)COc1cccc(-c2nc(N[C@@H]3CCOC3)c(C)c(N3C[C@H]4C[C@@H]3CN4C)n2)c1] | 469.3 |

TABLE 1B-continued

Exemplary Compounds

| # | Structure | LC-MS m/z (M + H) |
|---|---|---|
| 445-1a | 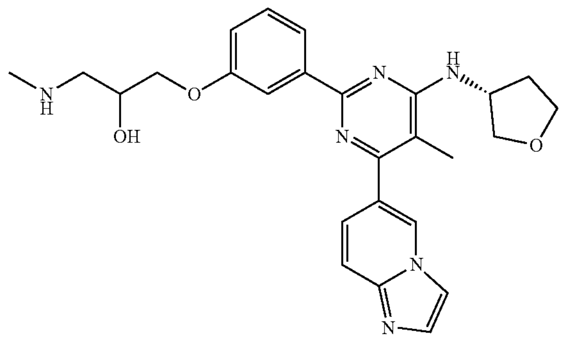 [SMILES: CNCC(O)COc1cccc(-c2nc(N[C@@H]3CCOC3)c(C)c(-c3ccc4nccn4c3)n2)c1] | 476.0 |
| 446-1a | 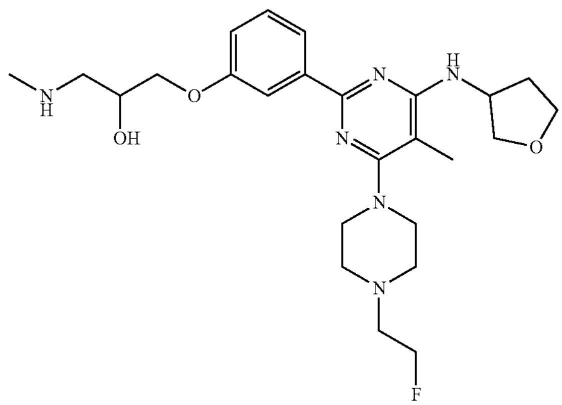 [SMILES: CNCC(O)COc1cccc(-c2nc(NC3CCOC3)c(C)c(N3CCN(CCF)CC3)n2)c1] | 489.3 |
| 447-1a | 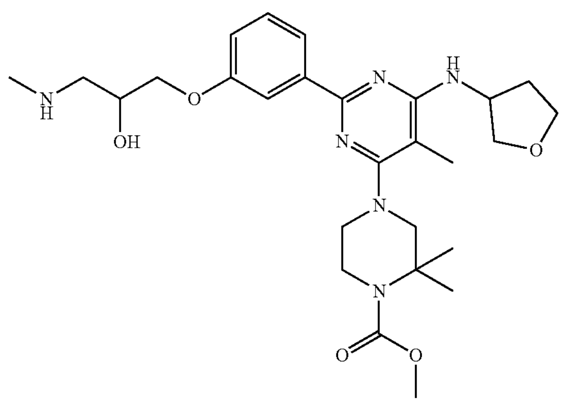 [SMILES: CNCC(O)COc1cccc(-c2nc(NC3CCOC3)c(C)c(N3CCN(C(=O)OC)C(C)(C)C3)n2)c1] | 529.3 |
| 448-1a | 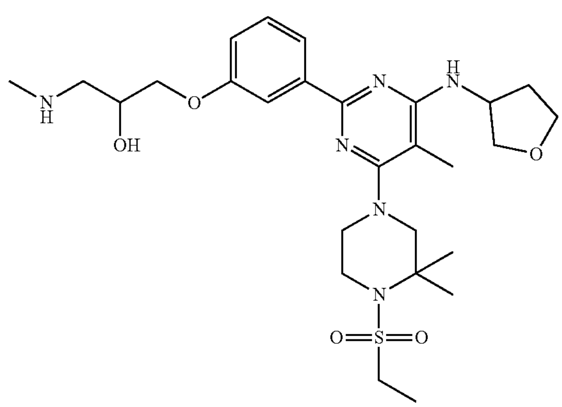 [SMILES: CCS(=O)(=O)N1CCN(c2nc(-c3cccc(OCC(O)CNC)c3)nc(NC3CCOC3)c2C)CC1(C)C] | 563.3 |

TABLE 1B-continued
Exemplary Compounds
| # | Structure | LC-MS m/z (M + H) |
|---|---|---|
| 449-1a | 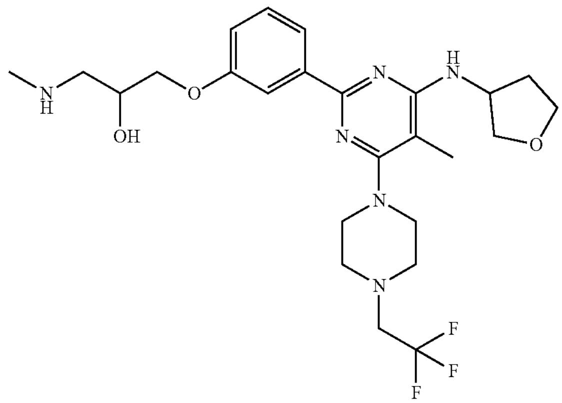 [SMILES: CNCC(O)COc1cccc(-c2nc(NC3CCOC3)c(C)c(N3CCN(CC(F)(F)F)CC3)n2)c1] | 525.3 |
| 450-1a | 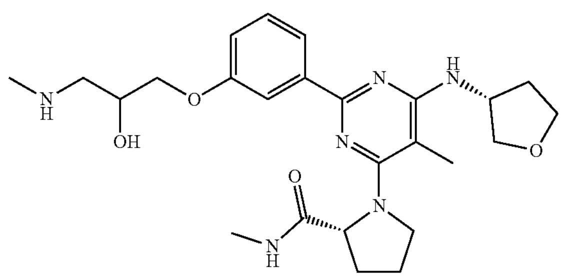 [SMILES: CNCC(O)COc1cccc(-c2nc(N[C@@H]3CCOC3)c(C)c(N3CCC[C@@H]3C(=O)NC)n2)c1] | 485.2 |
| 451-1a | 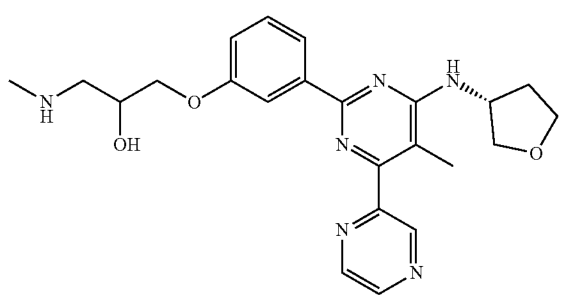 [SMILES: CNCC(O)COc1cccc(-c2nc(N[C@@H]3CCOC3)c(C)c(-c3cnccn3)n2)c1] | 436.7 |
| 452-1a | 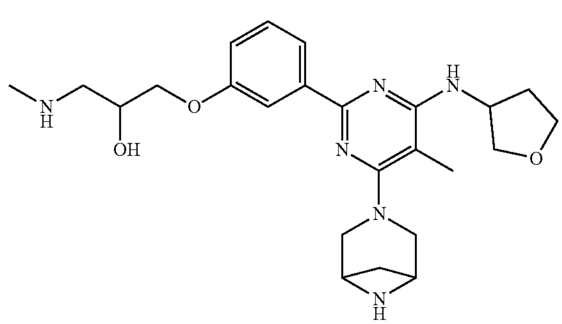 [SMILES: CNCC(O)COc1cccc(-c2nc(NC3CCOC3)c(C)c(N3CC4CC(C3)N4)n2)c1] | 455.3 |

TABLE 1B-continued
Exemplary Compounds
| # | Structure | LC-MS m/z (M + H) |
|---|---|---|
| 453-1a | 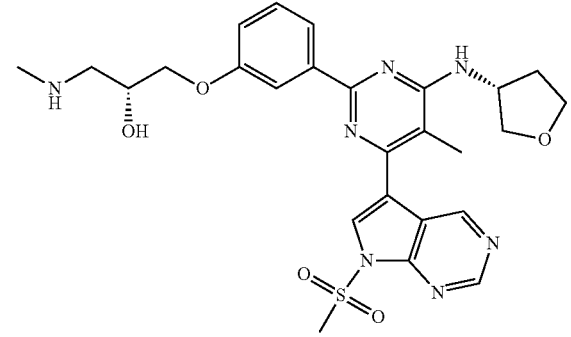 [SMILES: CNC[C@@H](O)COc1cccc(-c2nc(N[C@@H]3CCOC3)c(C)c(-c3cn(S(C)(=O)=O)c4ncncc34)n2)c1] | 554.2 |
| 454-1a | 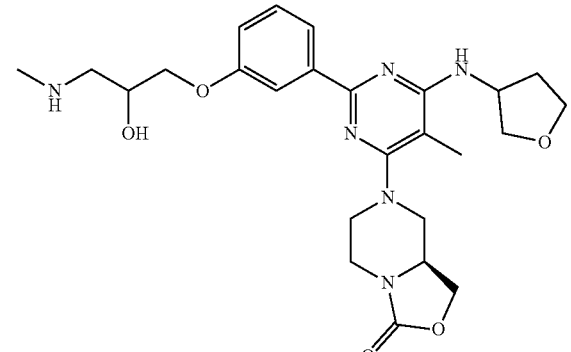 | 499.3 |
| 455-1a | 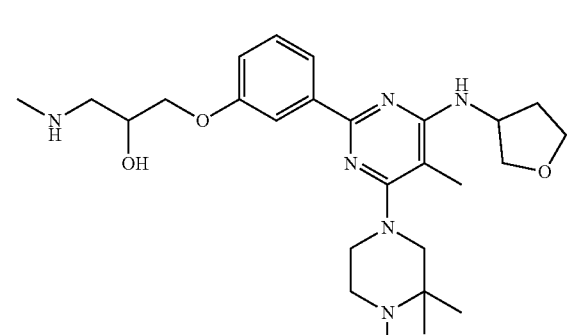 | 485.4 |
| 456-1a | 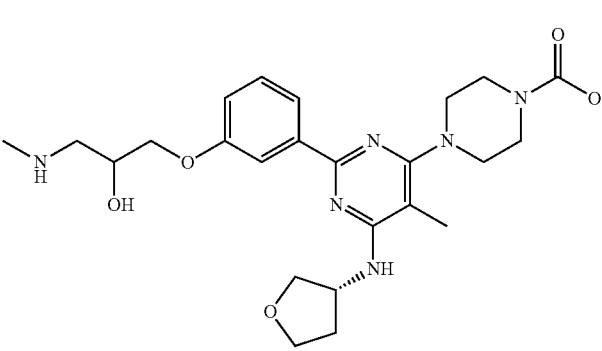 | 515.2 |

TABLE 1B-continued
Exemplary Compounds
| # | Structure | LC-MS m/z (M + H) |
|---|---|---|
| 457-1a | 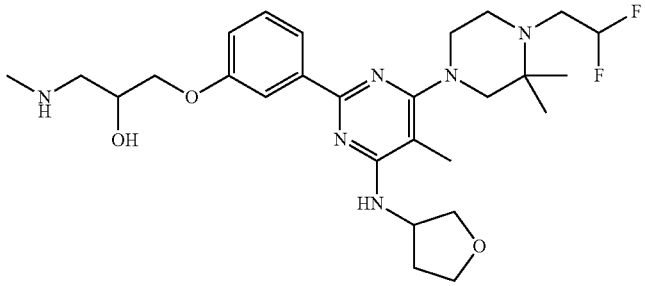 [SMILES: CNCC(O)COc1cccc(-c2nc(NC3CCOC3)c(C)c(N3CCN(CC(F)F)C(C)(C)C3)n2)c1] | 535.3 |
| 458-1a | 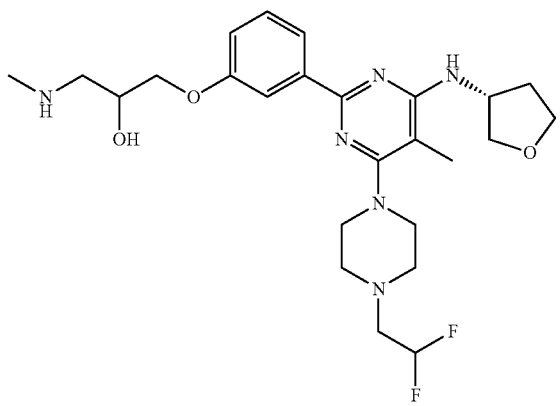 [SMILES: CNCC(O)COc1cccc(-c2nc(N[C@@H]3CCOC3)c(C)c(N3CCN(CC(F)F)CC3)n2)c1] | 507.3 |
| 459-1a | 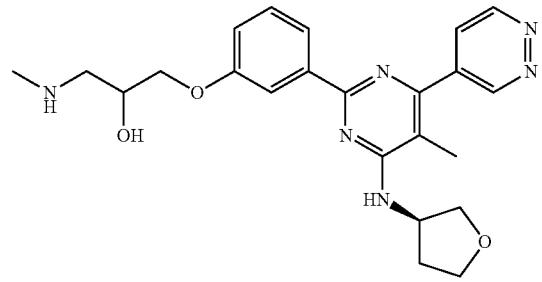 [SMILES: CNCC(O)COc1cccc(-c2nc(N[C@@H]3CCOC3)c(C)c(-c3ccnnc3)n2)c1] | 437.1 |
| 460-1a | 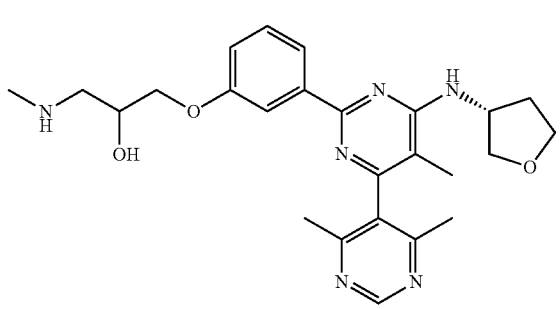 [SMILES: CNCC(O)COc1cccc(-c2nc(N[C@@H]3CCOC3)c(C)c(-c3c(C)ncnc3C)n2)c1] | 465.3 |

TABLE 1B-continued

Exemplary Compounds

| # | Structure | LC-MS m/z (M + H) |
|---|---|---|
| 461-1a | 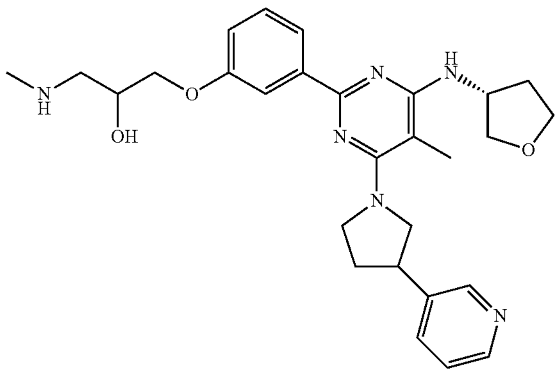 [SMILES: CNCC(O)COc1cccc(-c2nc(N[C@@H]3CCOC3)c(C)c(N3CCC(c4cccnc4)C3)n2)c1] | 505.3 |
| 462-1a | 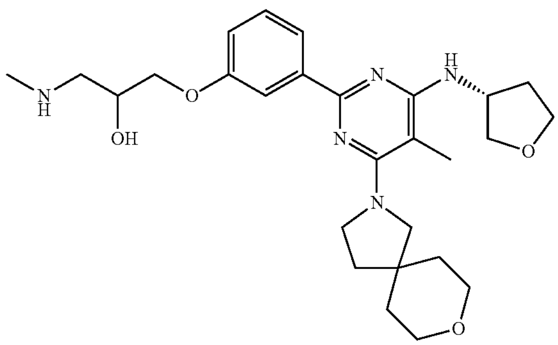 [SMILES: CNCC(O)COc1cccc(-c2nc(N[C@@H]3CCOC3)c(C)c(N3CCC4(CCOCC4)C3)n2)c1] | 498.3 |
| 463-1a | 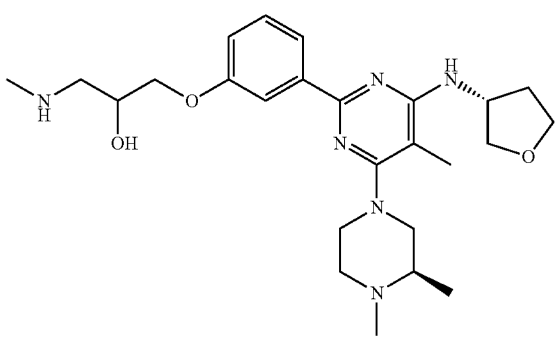 [SMILES: CNCC(O)COc1cccc(-c2nc(N[C@@H]3CCOC3)c(C)c(N3CCN(C)[C@H](C)C3)n2)c1] | 471.2 |
| 464-1a | 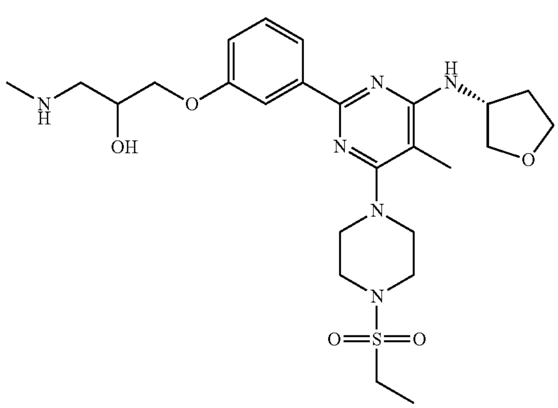 [SMILES: CCS(=O)(=O)N1CCN(c2nc(-c3cccc(OCC(O)CNC)c3)nc(N[C@@H]3CCOC3)c2C)CC1] | 535.3 |

TABLE 1B-continued

Exemplary Compounds

| # | Structure | LC-MS m/z (M + H) |
|---|---|---|
| 465-1a | 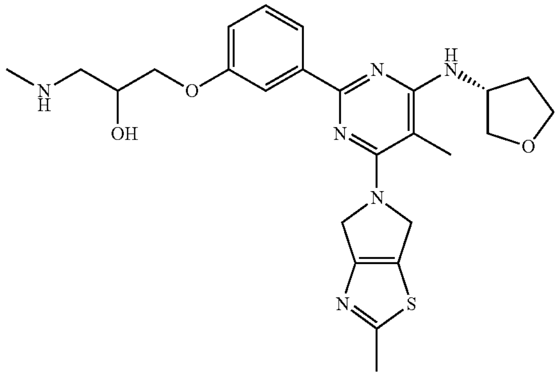 [SMILES: CNCC(O)COc1cccc(-c2nc(N[C@@H]3CCOC3)c(C)c(N3Cc4nc(C)sc4C3)n2)c1] | 497.2 |
| 466-1a | 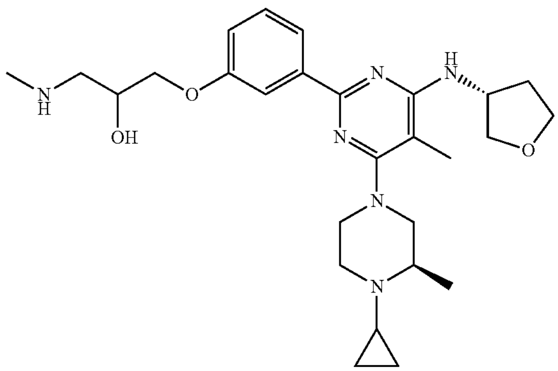 [SMILES: CNCC(O)COc1cccc(-c2nc(N[C@@H]3CCOC3)c(C)c(N3CCN(C4CC4)[C@H](C)C3)n2)c1] | 497.2 |
| 467-1a | 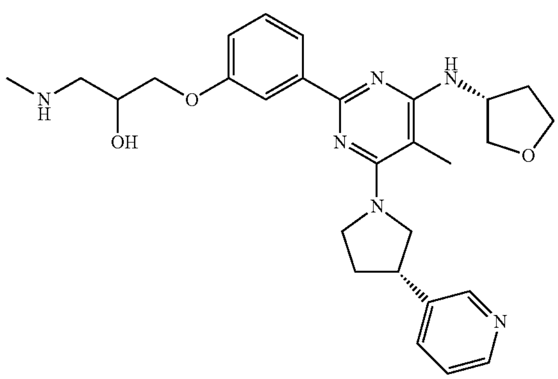 [SMILES: CNCC(O)COc1cccc(-c2nc(N[C@@H]3CCOC3)c(C)c(N3CC[C@@H](c4cccnc4)C3)n2)c1] | 505.4 |
| 468-1a | 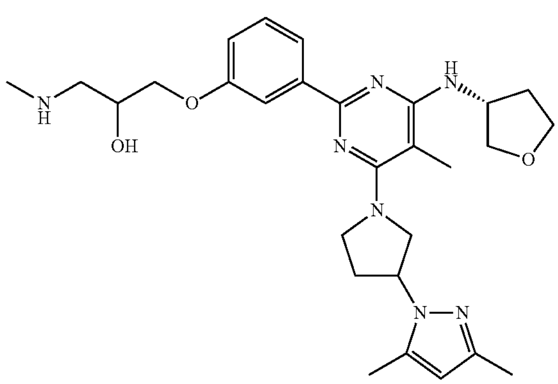 [SMILES: CNCC(O)COc1cccc(-c2nc(N[C@@H]3CCOC3)c(C)c(N3CCC(n4nc(C)cc4C)C3)n2)c1] | 522.3 |

TABLE 1B-continued

Exemplary Compounds

| # | Structure | LC-MS m/z (M + H) |
|---|-----------|-------------------|
| 469-1a | 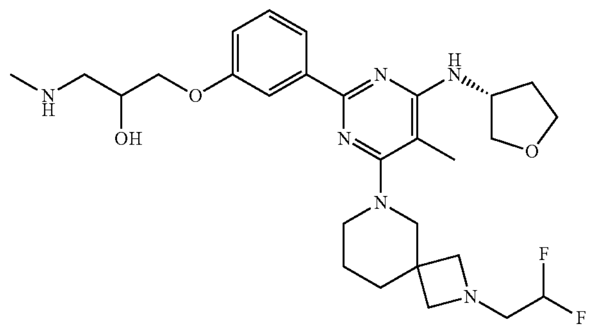 [SMILES: CNCC(O)COc1cccc(-c2nc(N[C@@H]3CCOC3)c(C)c(N3CCCC4(CN(CC(F)F)C4)C3)n2)c1] | 547.2 |
| 470-1a | 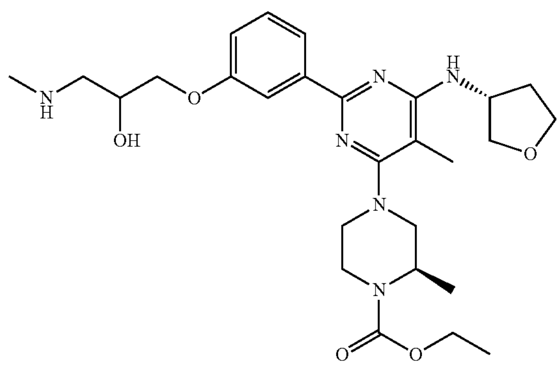 [SMILES: CCOC(=O)N1CCN(c2nc(-c3cccc(OCC(O)CNC)c3)nc(N[C@@H]3CCOC3)c2C)C[C@H]1C] | 529.1 |
| 471-1a | 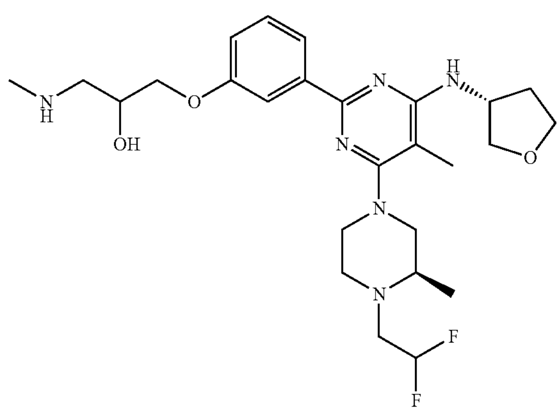 [SMILES: CNCC(O)COc1cccc(-c2nc(N[C@@H]3CCOC3)c(C)c(N3CCN(CC(F)F)[C@H](C)C3)n2)c1] | 521.3 |
| 472-1a | 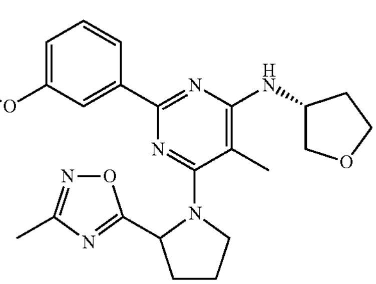 | 510.3 |

TABLE 1B-continued

Exemplary Compounds

| # | Structure | LC-MS m/z (M + H) |
|---|-----------|-------------------|
| 475-1a | 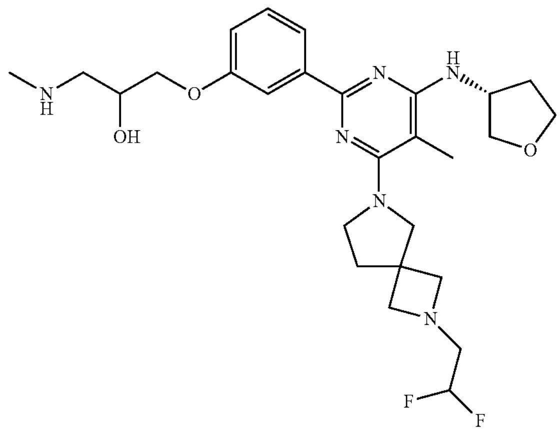 [SMILES: CNCC(O)COc1cccc(-c2nc(N[C@@H]3CCOC3)c(C)c(N3CCC4(CN(CC(F)F)C4)C3)n2)c1] | 533.2 |
| 478-1a | 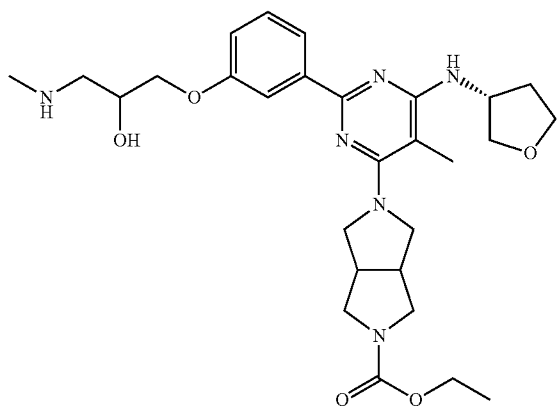 [SMILES: CCOC(=O)N1CC2CN(c3nc(-c4cccc(OCC(O)CNC)c4)nc(N[C@@H]4CCOC4)c3C)CC2C1] | 541.3 |
| 479-1a | 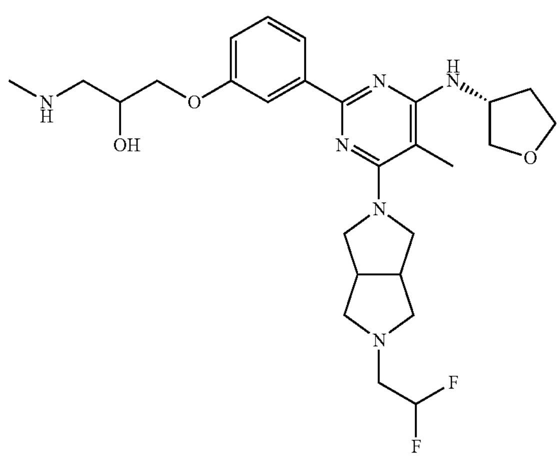 [SMILES: CNCC(O)COc1cccc(-c2nc(N[C@@H]3CCOC3)c(C)c(N3CC4CN(CC(F)F)CC4C3)n2)c1] | 533.3 |

TABLE 1B-continued
Exemplary Compounds
| # | Structure | LC-MS m/z (M + H) |
|---|-----------|-------------------|
| 480-1a | 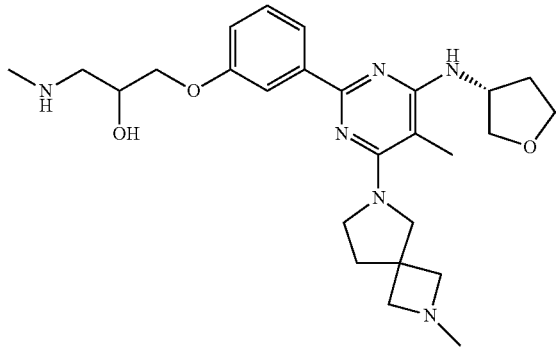 [SMILES: CNCC(O)COc1cccc(-c2nc(N[C@@H]3CCOC3)c(C)c(N3CCC4(CN(C)C4)C3)n2)c1] | 483.3 |
| 481-1a | 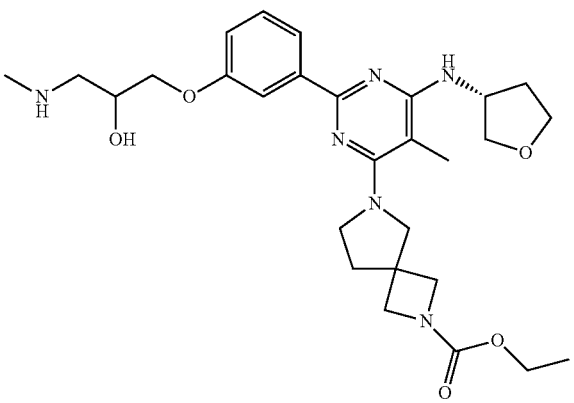 [SMILES: CCOC(=O)N1CC2(CCN(c3nc(-c4cccc(OCC(O)CNC)c4)nc(N[C@@H]4CCOC4)c3C)C2)C1] | 541.2 |
| 482-1a | 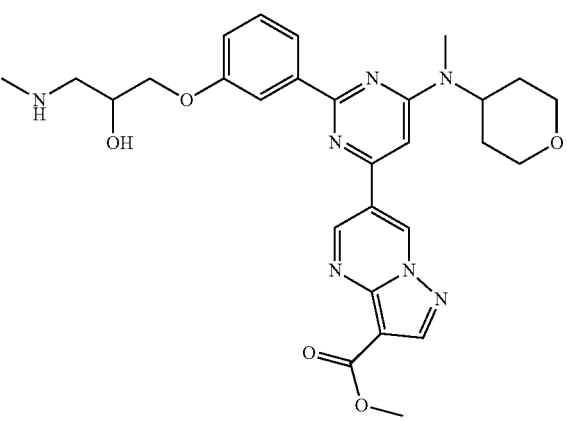 [SMILES: CNCC(O)COc1cccc(-c2nc(-c3cnc4c(C(=O)OC)cnn4c3)cc(N(C)C3CCOCC3)n2)c1] | 548.3 |
| 483-1a | 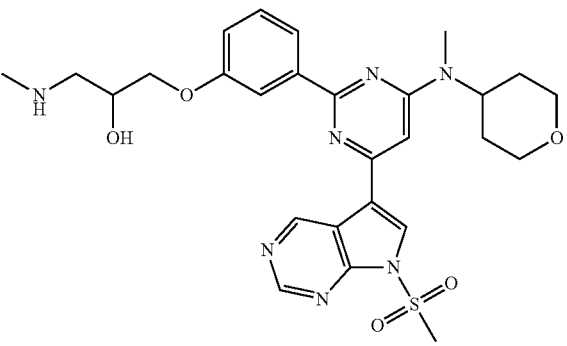 [SMILES: CNCC(O)COc1cccc(-c2nc(-c3cn(S(C)(=O)=O)c4ncncc34)cc(N(C)C3CCOCC3)n2)c1] | 568.3 |

TABLE 1B-continued
Exemplary Compounds
| # | Structure | LC-MS m/z (M + H) |
|---|---|---|
| 484-1a | 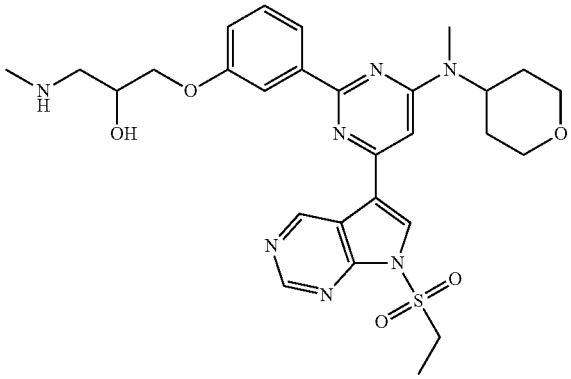 [SMILES: CCS(=O)(=O)n1cc(-c2cc(N(C)C3CCOCC3)nc(-c3cccc(OCC(O)CNC)c3)n2)c2cncnc21] | 583.3 |
| 485-1a | 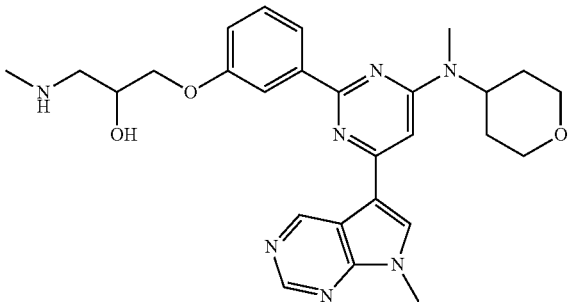 [SMILES: CNCC(O)COc1cccc(-c2nc(-c3cn(C)c4ncncc34)cc(N(C)C3CCOCC3)n2)c1] | 504.1 |
| 486-1a | 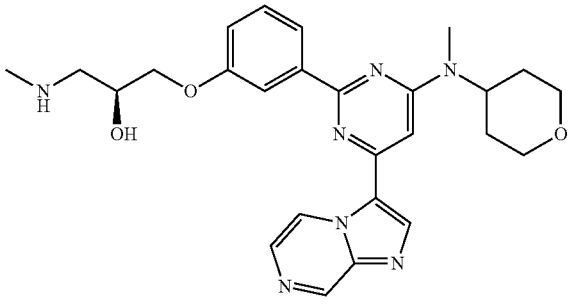 [SMILES: CNC[C@H](O)COc1cccc(-c2nc(-c3cnc4cnccn34)cc(N(C)C3CCOCC3)n2)c1] | 490.0 |
| 487-1a | 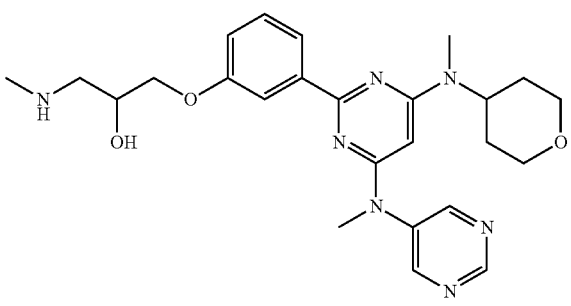 [SMILES: CNCC(O)COc1cccc(-c2nc(N(C)c3cncnc3)cc(N(C)C3CCOCC3)n2)c1] | 480.3 |

TABLE 1B-continued

Exemplary Compounds

| # | Structure | LC-MS m/z (M + H) |
|---|---|---|
| 488-1a | 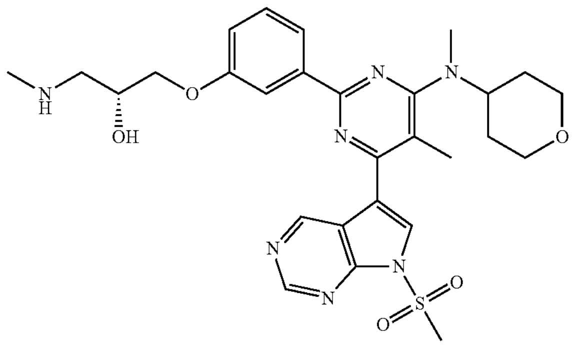 [SMILES: CNC[C@@H](O)COc1cccc(-c2nc(-c3cn(S(C)(=O)=O)c4ncncc34)c(C)c(N(C)C3CCOCC3)n2)c1] | 582.0 |
| 489-1a | 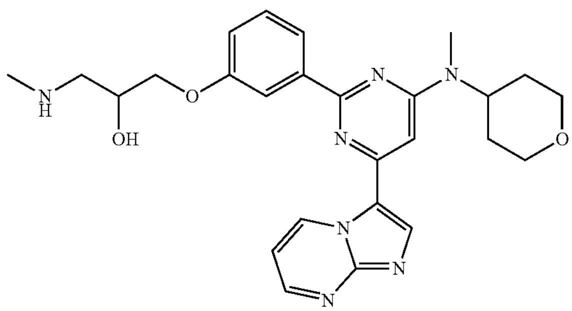 [SMILES: CNCC(O)COc1cccc(-c2nc(-c3cnc4ncccn34)cc(N(C)C3CCOCC3)n2)c1] | 490.3 |
| 490-1a | 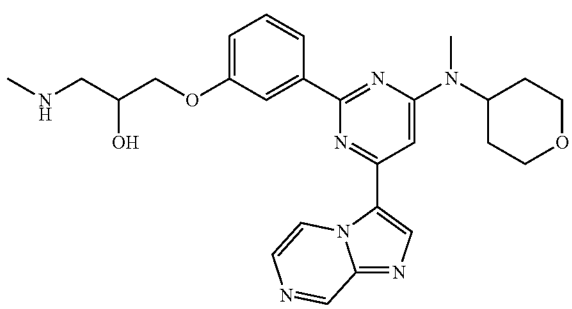 [SMILES: CNCC(O)COc1cccc(-c2nc(-c3cnc4cnccn34)cc(N(C)C3CCOCC3)n2)c1] | 490.3 |
| 491-1a | 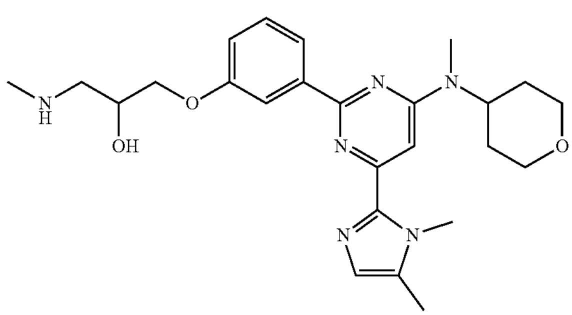 [SMILES: CNCC(O)COc1cccc(-c2nc(-c3ncc(C)n3C)cc(N(C)C3CCOCC3)n2)c1] | 467.4 |

TABLE 1B-continued

Exemplary Compounds

| # | Structure | LC-MS m/z (M + H) |
|---|-----------|-------------------|
| 492-1a | 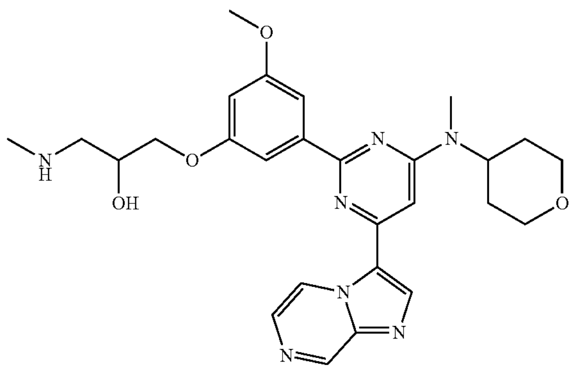 [SMILES: CNCC(O)COc1cc(OC)cc(-c2nc(-c3cnc4cnccn34)cc(N(C)C3CCOCC3)n2)c1] | 520.3 |
| 493-1a | 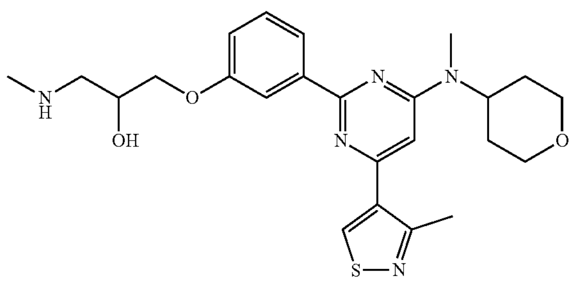 [SMILES: CNCC(O)COc1cccc(-c2nc(-c3csnc3C)cc(N(C)C3CCOCC3)n2)c1] | 470.0 |
| 494-1a | 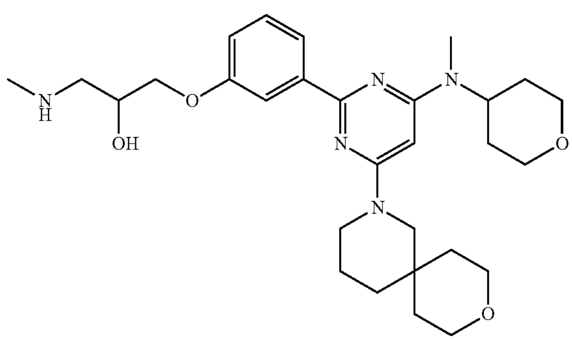 [SMILES: CNCC(O)COc1cccc(-c2nc(N3CCCC4(CCOCC4)C3)cc(N(C)C3CCOCC3)n2)c1] | 526.0 |
| 495-1a | 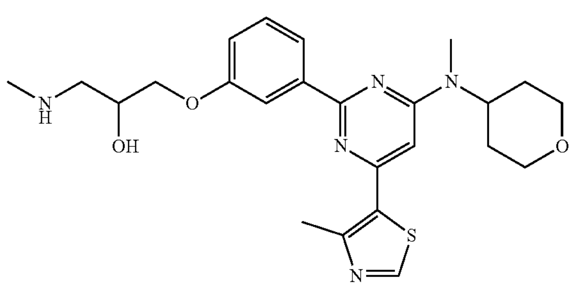 [SMILES: CNCC(O)COc1cccc(-c2nc(-c3scnc3C)cc(N(C)C3CCOCC3)n2)c1] | 470.0 |

TABLE 1B-continued

Exemplary Compounds

| # | Structure | LC-MS m/z (M + H) |
|---|---|---|
| 496-1a | 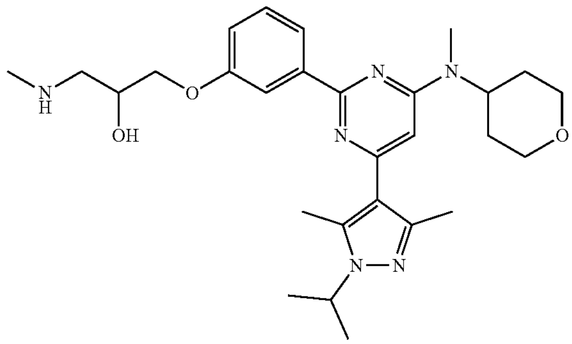 [SMILES: CNCC(O)COc1cccc(-c2nc(-c3c(C)nn(C(C)C)c3C)cc(N(C)C3CCOCC3)n2)c1] | 509.3 |
| 497-1a | 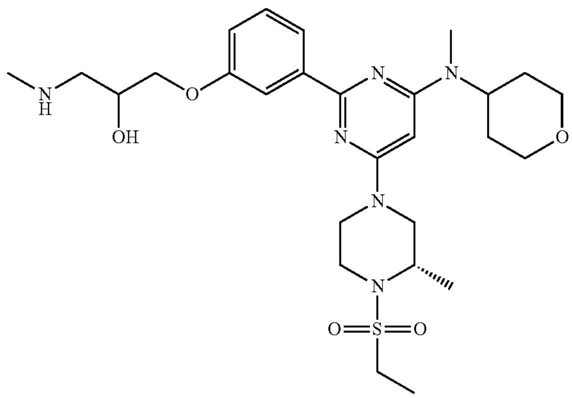 [SMILES: CCS(=O)(=O)N1CCN(c2cc(N(C)C3CCOCC3)nc(-c3cccc(OCC(O)CNC)c3)n2)C[C@@H]1C] | 563.3 |
| 498-1a | 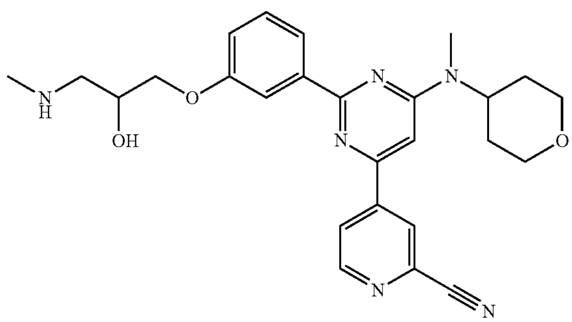 [SMILES: CNCC(O)COc1cccc(-c2nc(-c3ccnc(C#N)c3)cc(N(C)C3CCOCC3)n2)c1] | 475.3 |
| 499-1a | 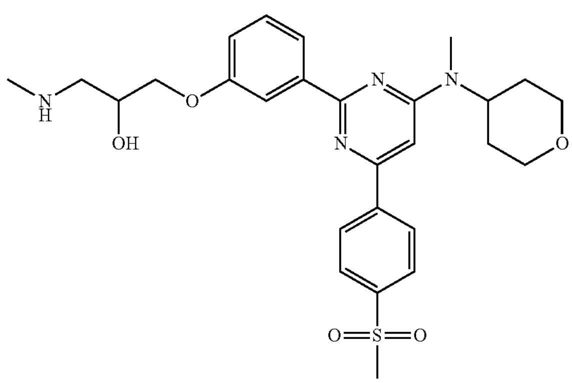 [SMILES: CNCC(O)COc1cccc(-c2nc(-c3ccc(S(C)(=O)=O)cc3)cc(N(C)C3CCOCC3)n2)c1] | 527.2 |

TABLE 1B-continued

Exemplary Compounds

| # | Structure | LC-MS m/z (M + H) |
|---|---|---|
| 500-1a | 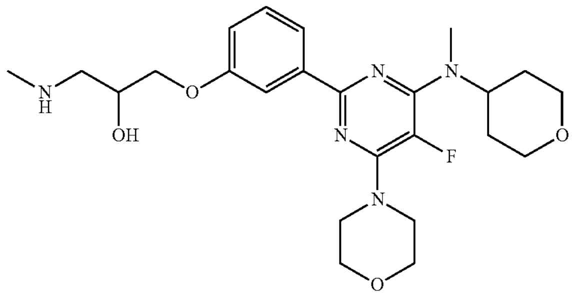 [SMILES: CNCC(O)COc1cccc(-c2nc(N3CCOCC3)c(F)c(N(C)C3CCOCC3)n2)c1] | 476.0 |
| 501-1a | 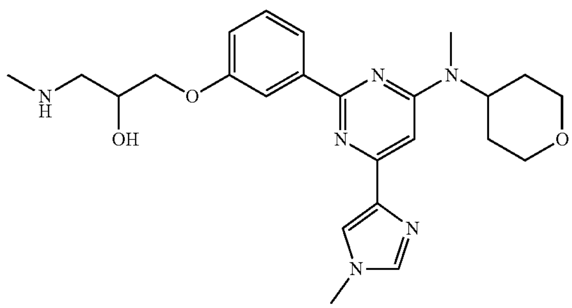 [SMILES: CNCC(O)COc1cccc(-c2nc(-c3cn(C)cn3)cc(N(C)C3CCOCC3)n2)c1] | 453.3 |
| 502-1a | 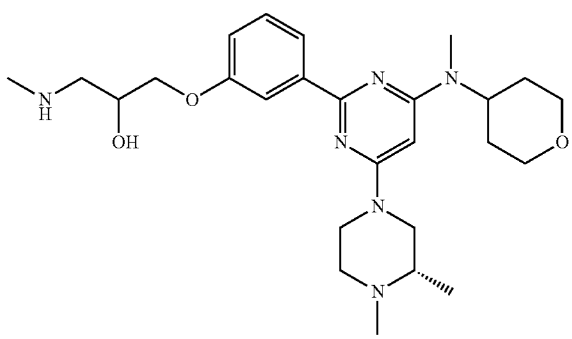 [SMILES: CNCC(O)COc1cccc(-c2nc(N3CCN(C)[C@@H](C)C3)cc(N(C)C3CCOCC3)n2)c1] | 485.3 |
| 503-1a | 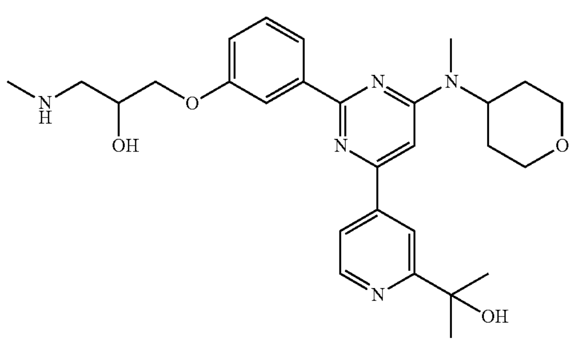 [SMILES: CNCC(O)COc1cccc(-c2nc(-c3ccnc(C(C)(C)O)c3)cc(N(C)C3CCOCC3)n2)c1] | 508.3 |

TABLE 1B-continued

Exemplary Compounds

| # | Structure | LC-MS m/z (M + H) |
|---|---|---|
| 504-1a | 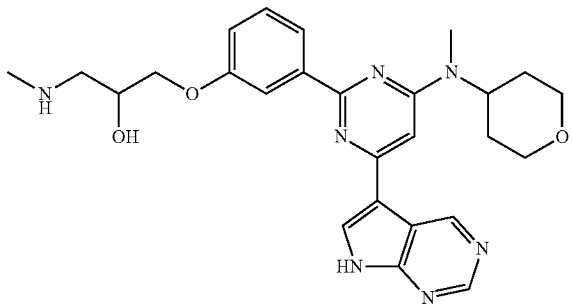 [SMILES: CNCC(O)COc1cccc(-c2nc(-c3c[nH]c4ncncc34)cc(N(C)C3CCOCC3)n2)c1] | 490.2 |
| 505-1a | 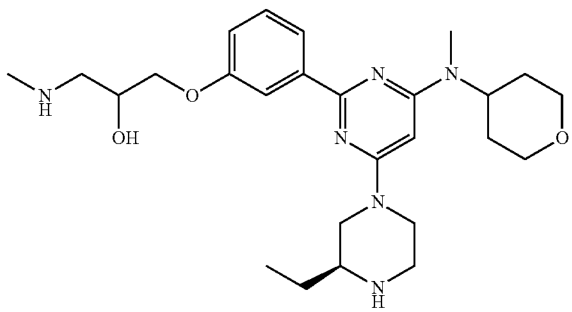 [SMILES: CC[C@H]1CN(c2cc(N(C)C3CCOCC3)nc(-c3cccc(OCC(O)CNC)c3)n2)CCN1] | 485.4 |
| 506-1a | 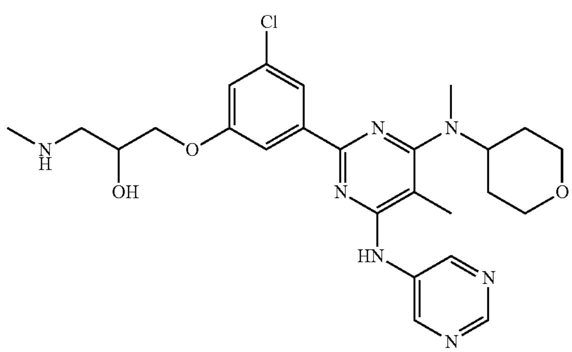 [SMILES: CNCC(O)COc1cc(Cl)cc(-c2nc(Nc3cncnc3)c(C)c(N(C)C3CCOCC3)n2)c1] | 514.2 |
| 507-1a | 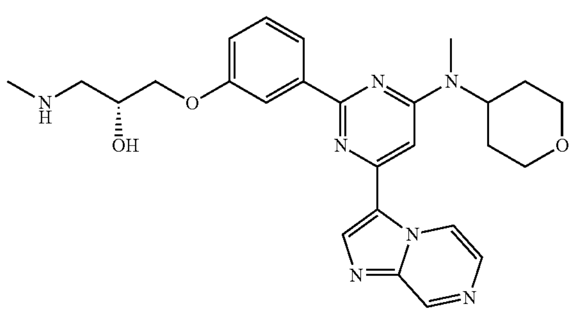 [SMILES: CNC[C@@H](O)COc1cccc(-c2nc(-c3cnc4cnccn34)cc(N(C)C3CCOCC3)n2)c1] | 490.4 |

US 10,118,931 B2
339                                                                                                  340
TABLE 1B-continued
Exemplary Compounds
| # | Structure | LC-MS m/z (M + H) |
|---|-----------|-------------------|
| 508-1a | 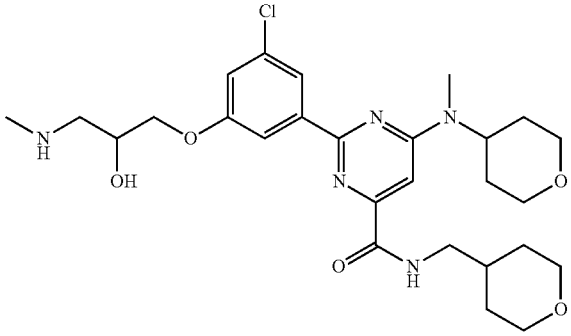 | 548.2 |
| 509-1a | 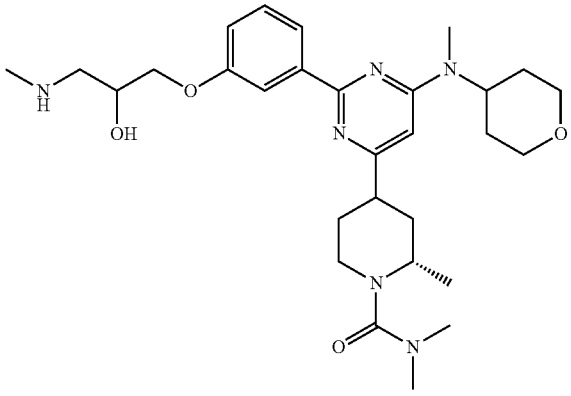 [SMILES: CNCC(O)COc1cccc(-c2nc(C3CCN(C(=O)N(C)C)[C@@H](C)C3)cc(N(C)C3CCOCC3)n2)c1] | 542.3 |
| 510-1a | 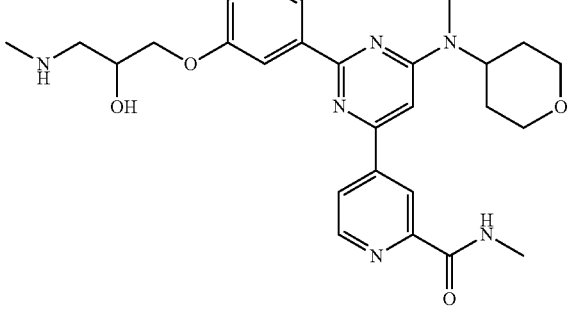 | 507.3 |
| 511-1a | 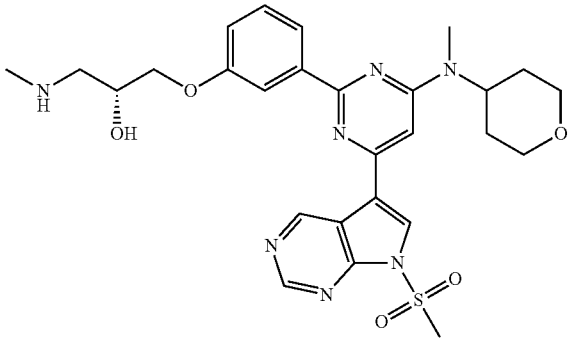 [SMILES: CNC[C@@H](O)COc1cccc(-c2nc(-c3cn(S(C)(=O)=O)c4ncncc34)cc(N(C)C3CCOCC3)n2)c1] | 567.9 |

TABLE 1B-continued
Exemplary Compounds
| # | Structure | LC-MS m/z (M + H) |
|---|---|---|
| 512-1a | 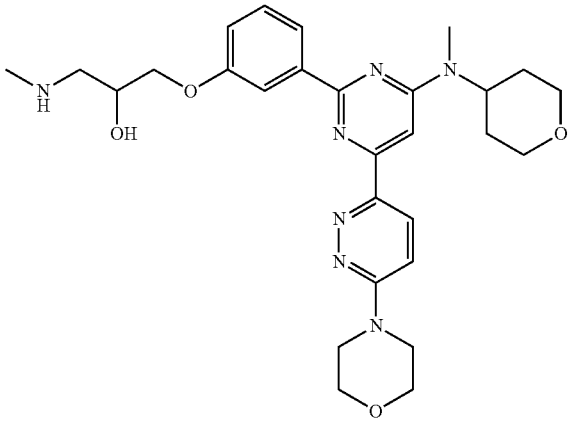 [SMILES: CNCC(O)COc1cccc(-c2nc(-c3ccc(N4CCOCC4)nn3)cc(N(C)C3CCOCC3)n2)c1] | 536.4 |
| 513-1a | 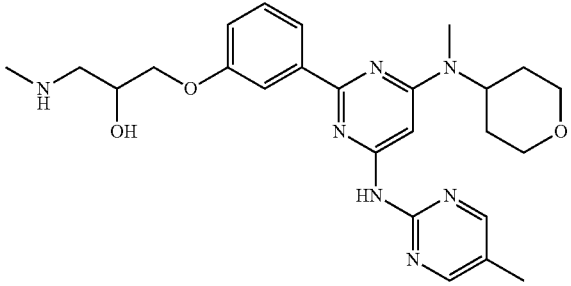 [SMILES: CNCC(O)COc1cccc(-c2nc(Nc3ncc(C)cn3)cc(N(C)C3CCOCC3)n2)c1] | 480.4 |
| 514-1a | 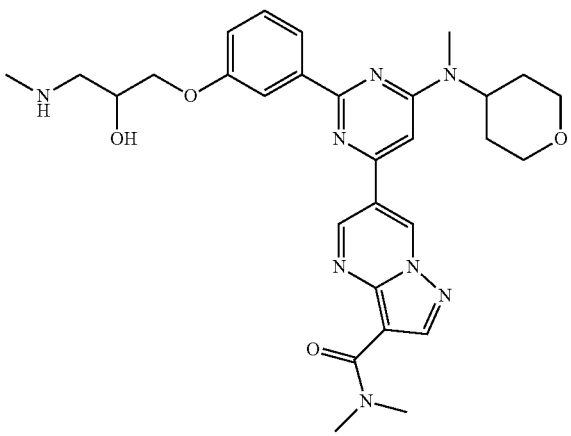 [SMILES: CNCC(O)COc1cccc(-c2nc(-c3cnc4c(C(=O)N(C)C)cnn4c3)cc(N(C)C3CCOCC3)n2)c1] | 561.0 |
| 515-1a | 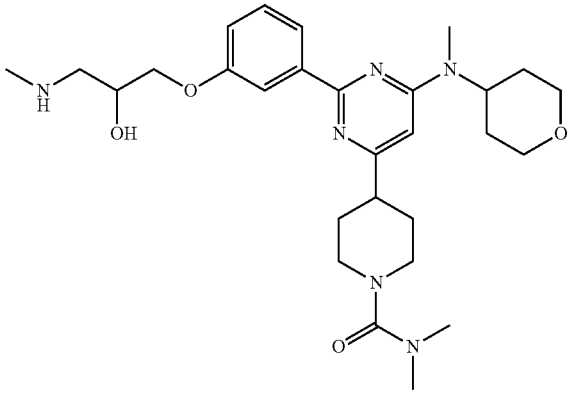 [SMILES: CNCC(O)COc1cccc(-c2nc(C3CCN(C(=O)N(C)C)CC3)cc(N(C)C3CCOCC3)n2)c1] | 527.4 |

TABLE 1B-continued
Exemplary Compounds
| # | Structure | LC-MS m/z (M + H) |
|---|---|---|
| 516-1a | 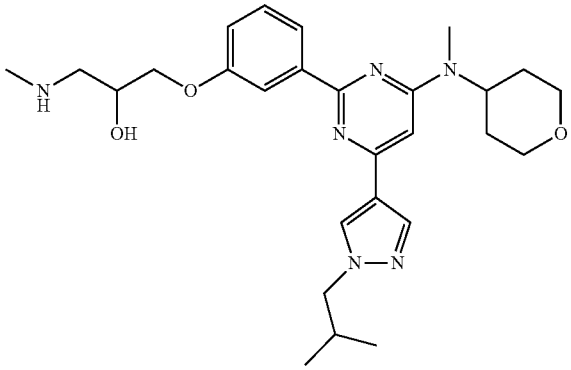 [SMILES: CNCC(O)COc1cccc(-c2nc(-c3cnn(CC(C)C)c3)cc(N(C)C3CCOCC3)n2)c1] | 495.2 |
| 517-1a | 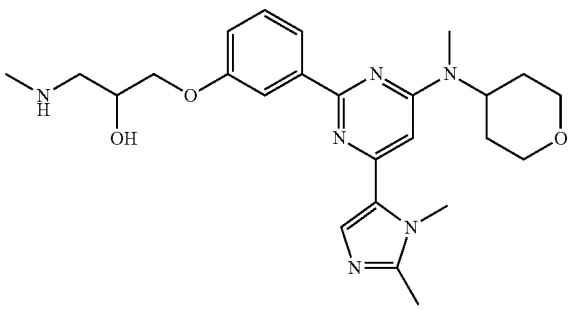 [SMILES: CNCC(O)COc1cccc(-c2nc(-c3cnc(C)n3C)cc(N(C)C3CCOCC3)n2)c1] | 467.3 |
| 518-1a | 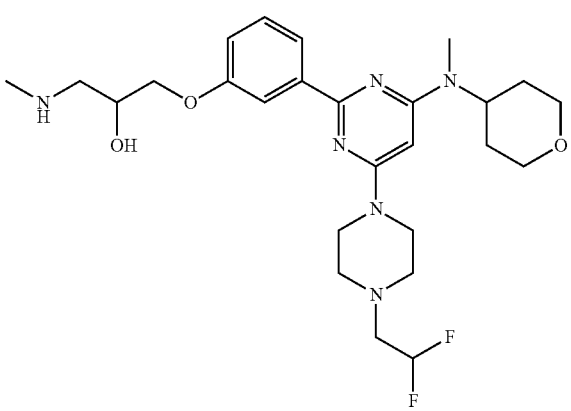 [SMILES: CNCC(O)COc1cccc(-c2nc(N3CCN(CC(F)F)CC3)cc(N(C)C3CCOCC3)n2)c1] | 521.2 |
| 519-1a | 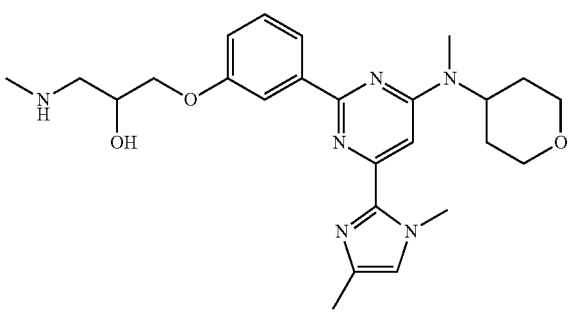 [SMILES: CNCC(O)COc1cccc(-c2nc(-c3nc(C)cn3C)cc(N(C)C3CCOCC3)n2)c1] | 467.4 |

TABLE 1B-continued
Exemplary Compounds
| # | Structure | LC-MS m/z (M + H) |
|---|---|---|
| 520-1a | 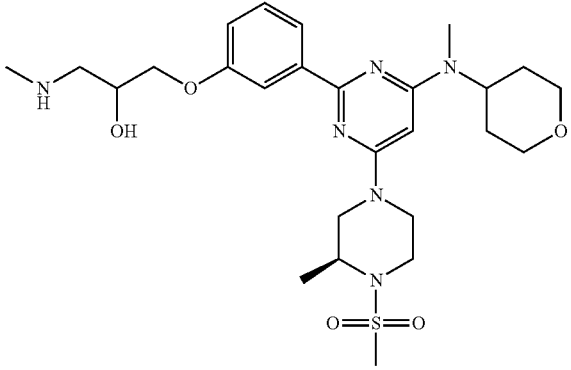 [SMILES: CNCC(O)COc1cccc(-c2nc(N3CCN(S(C)(=O)=O)[C@@H](C)C3)cc(N(C)C3CCOCC3)n2)c1] | 549.3 |
| 521-1a | 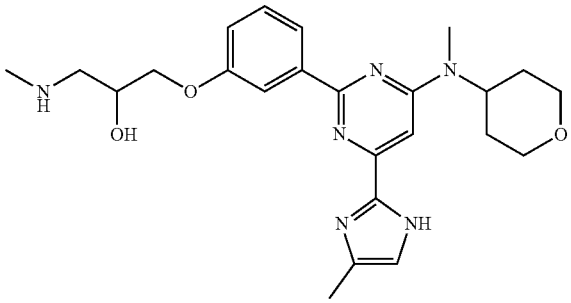 [SMILES: CNCC(O)COc1cccc(-c2nc(-c3nc(C)c[nH]3)cc(N(C)C3CCOCC3)n2)c1] | 453.3 |
| 522-1a | 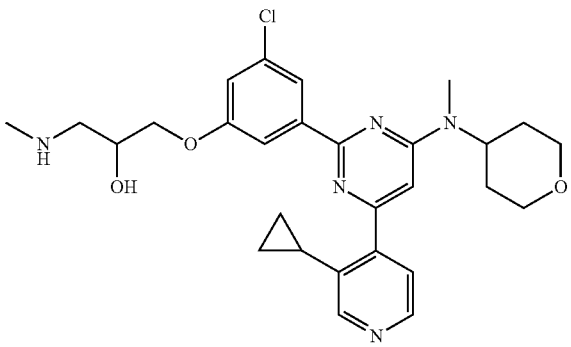 [SMILES: CNCC(O)COc1cc(Cl)cc(-c2nc(-c3ccncc3C3CC3)cc(N(C)C3CCOCC3)n2)c1] | 524.3 |
| 523-1a | 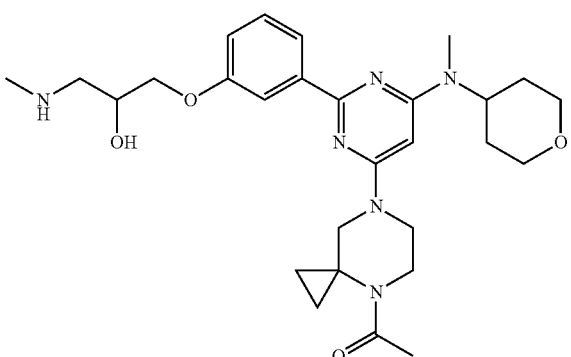 | 525.0 |

TABLE 1B-continued
Exemplary Compounds
| # | Structure | LC-MS m/z (M + H) |
|---|---|---|
| 524-1a | 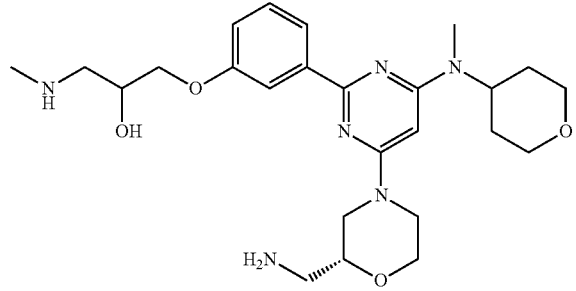 [SMILES: CNCC(O)COc1cccc(-c2nc(N3CCO[C@H](CN)C3)cc(N(C)C3CCOCC3)n2)c1] | 487.0 |
| 525-1a | 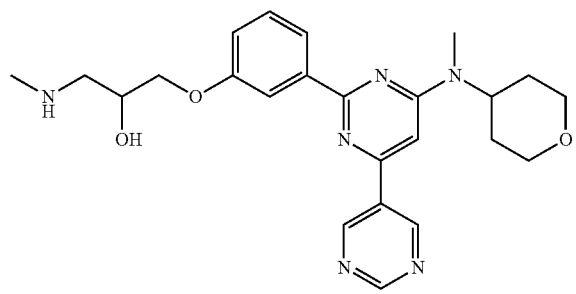 [SMILES: CNCC(O)COc1cccc(-c2nc(-c3cncnc3)cc(N(C)C3CCOCC3)n2)c1] | 451.1 |
| 526-1a | 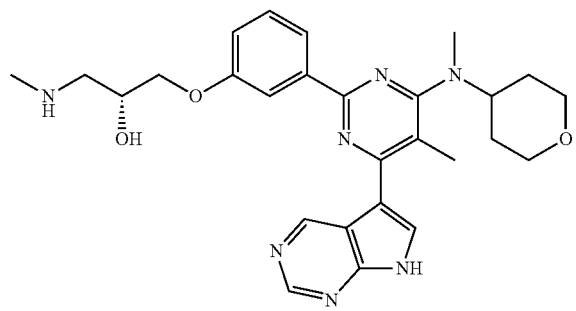 [SMILES: CNC[C@@H](O)COc1cccc(-c2nc(-c3c[nH]c4ncncc34)c(C)c(N(C)C3CCOCC3)n2)c1] | 504.3 |
| 527-1a | 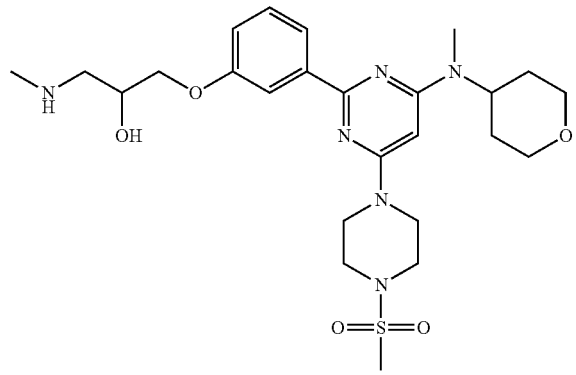 [SMILES: CNCC(O)COc1cccc(-c2nc(N3CCN(S(C)(=O)=O)CC3)cc(N(C)C3CCOCC3)n2)c1] | 534.3 |

TABLE 1B-continued
Exemplary Compounds
| # | Structure | LC-MS m/z (M + H) |
|---|---|---|
| 528-1a | 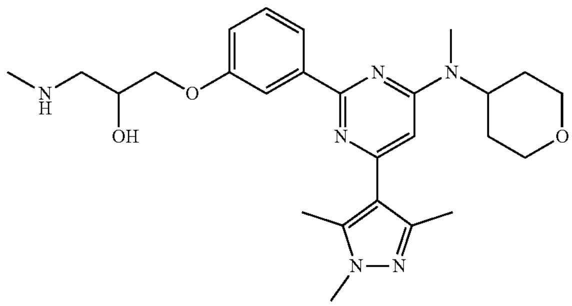 [SMILES: CNCC(O)COc1cccc(-c2nc(-c3c(C)nn(C)c3C)cc(N(C)C3CCOCC3)n2)c1] | 481.4 |
| 529-1a | 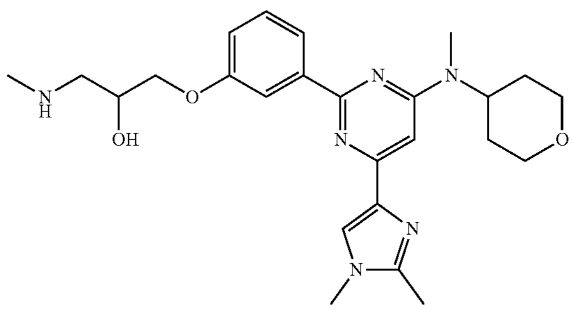 [SMILES: CNCC(O)COc1cccc(-c2nc(-c3cn(C)c(C)n3)cc(N(C)C3CCOCC3)n2)c1] | 467.4 |
| 530-1a | 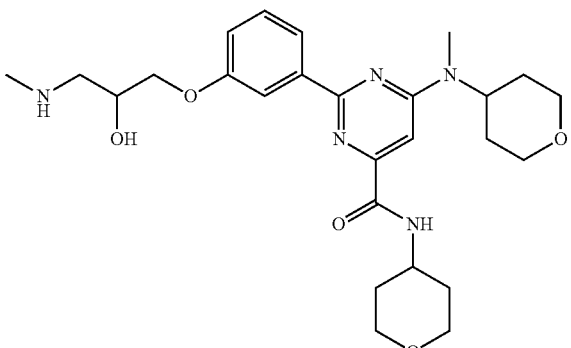 | 500.4 |
| 531-1a | 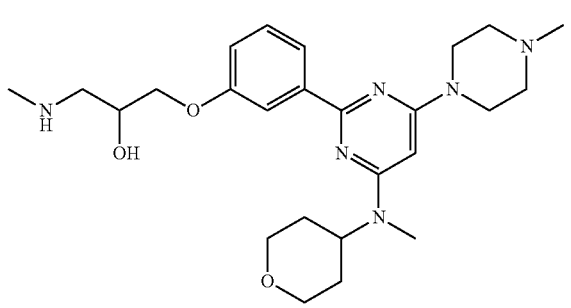 | 471.4 |

TABLE 1B-continued
Exemplary Compounds
| # | Structure | LC-MS m/z (M + H) |
|---|---|---|
| 532-1a | 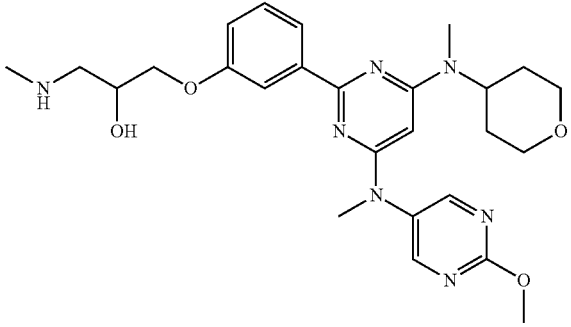 [SMILES: CNCC(O)COc1cccc(-c2nc(N(C)c3cnc(OC)nc3)cc(N(C)C3CCOCC3)n2)c1] | 510.3 |
| 533-1a | 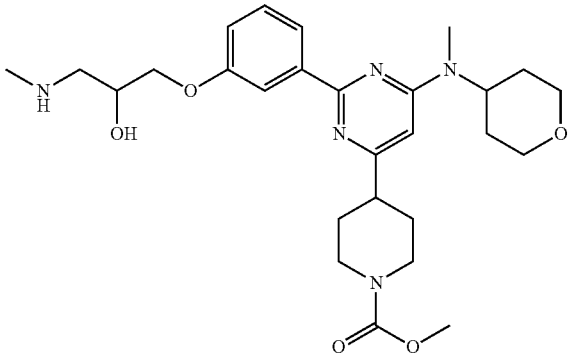 [SMILES: CNCC(O)COc1cccc(-c2nc(C3CCN(C(=O)OC)CC3)cc(N(C)C3CCOCC3)n2)c1] | 514.3 |
| 534-1a | 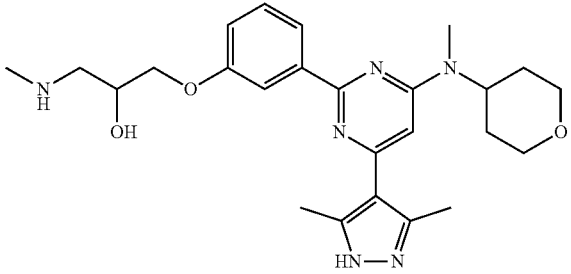 [SMILES: CNCC(O)COc1cccc(-c2nc(-c3c(C)n[nH]c3C)cc(N(C)C3CCOCC3)n2)c1] | 467.4 |
| 535-1a | 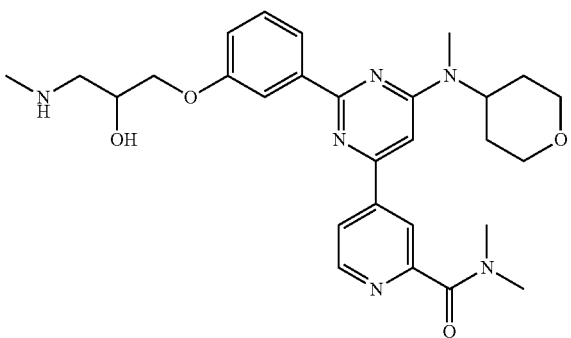 [SMILES: CNCC(O)COc1cccc(-c2nc(-c3ccnc(C(=O)N(C)C)c3)cc(N(C)C3CCOCC3)n2)c1] | 521.3 |

TABLE 1B-continued

Exemplary Compounds

| # | Structure | LC-MS m/z (M + H) |
|---|---|---|
| 536-1a | 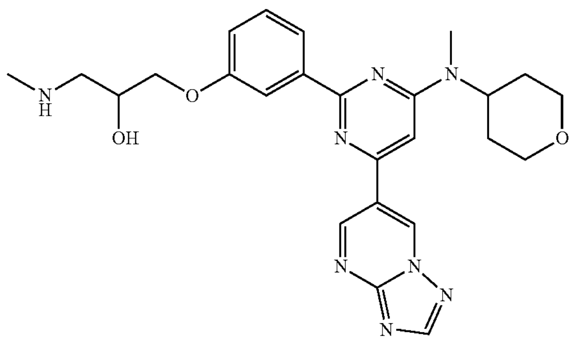 [SMILES: CNCC(O)COc1cccc(-c2nc(-c3cnc4ncnn4c3)cc(N(C)C3CCOCC3)n2)c1] | 491.1 |
| 537-1a | 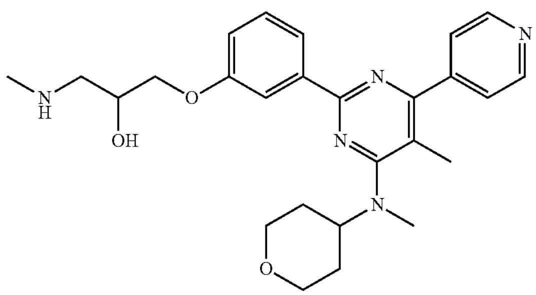 [SMILES: CNCC(O)COc1cccc(-c2nc(-c3ccncc3)c(C)c(N(C)C3CCOCC3)n2)c1] | 464.3 |
| 538-1a | 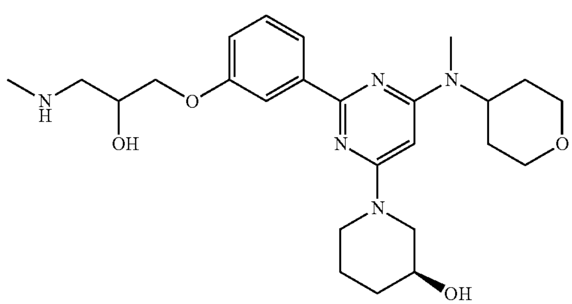 [SMILES: CNCC(O)COc1cccc(-c2nc(N3CCC[C@H](O)C3)cc(N(C)C3CCOCC3)n2)c1] | 472.4 |
| 539-1a | 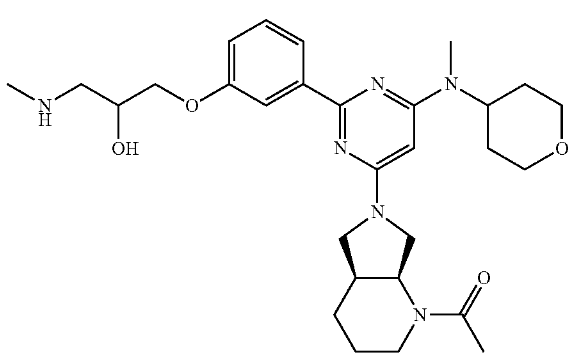 [SMILES: CNCC(O)COc1cccc(-c2nc(N3C[C@@H]4CCCN(C(C)=O)[C@@H]4C3)cc(N(C)C3CCOCC3)n2)c1] | 539.3 |

TABLE 1B-continued

Exemplary Compounds

| # | Structure | LC-MS m/z (M + H) |
|---|---|---|
| 540-1a | 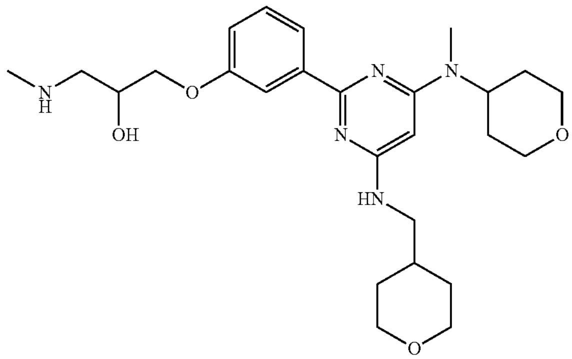 [SMILES: CNCC(O)COc1cccc(-c2nc(NCC3CCOCC3)cc(N(C)C3CCOCC3)n2)c1] | 486.4 |
| 541-1a | 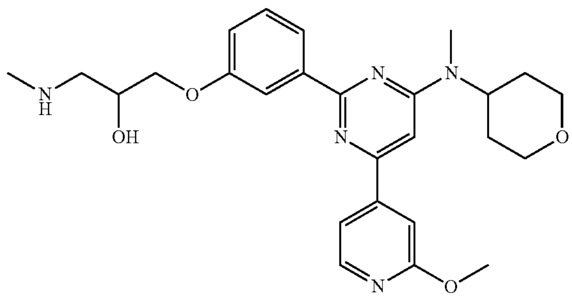 [SMILES: CNCC(O)COc1cccc(-c2nc(-c3ccnc(OC)c3)cc(N(C)C3CCOCC3)n2)c1] | 480.2 |
| 542-1a | 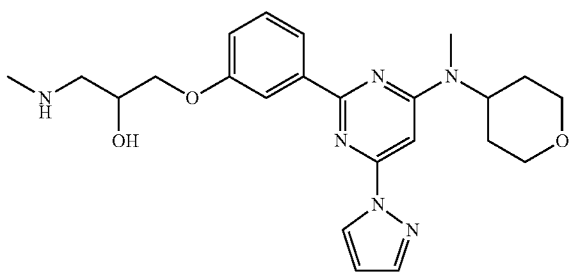 [SMILES: CNCC(O)COc1cccc(-c2nc(N(C)C3CCOCC3)cc(-n3cccn3)n2)c1] | 439.2 |
| 543-1a | 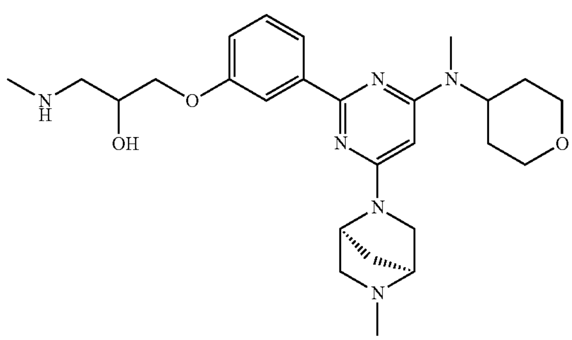 [SMILES: CNCC(O)COc1cccc(-c2nc(N(C)C3CCOCC3)cc(N3C[C@@H]4C[C@H]3CN4C)n2)c1] | 483.0 |
| 544-1a | 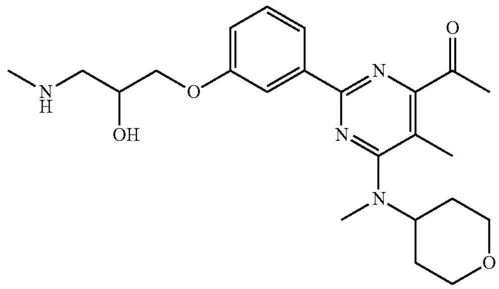 | 429.3 |

TABLE 1B-continued
Exemplary Compounds
| # | Structure | LC-MS m/z (M + H) |
|---|---|---|
| 545-1a | 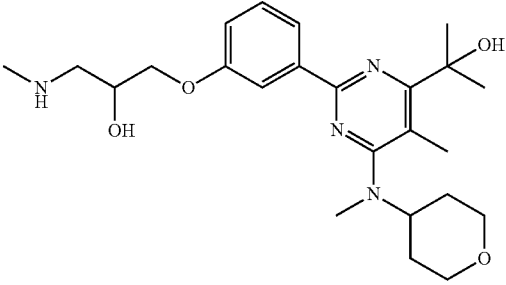 [SMILES: CNCC(O)COc1cccc(-c2nc(N(C)C3CCOCC3)c(C)c(C(C)(C)O)n2)c1] | 445.3 |
| 546-1a | 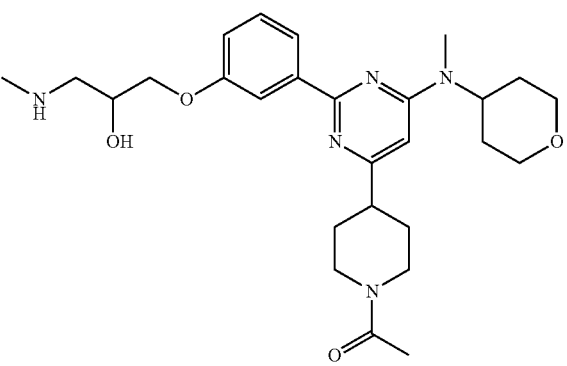 [SMILES: CNCC(O)COc1cccc(-c2nc(C3CCN(C(C)=O)CC3)cc(N(C)C3CCOCC3)n2)c1] | 498.4 |
| 547-1a | 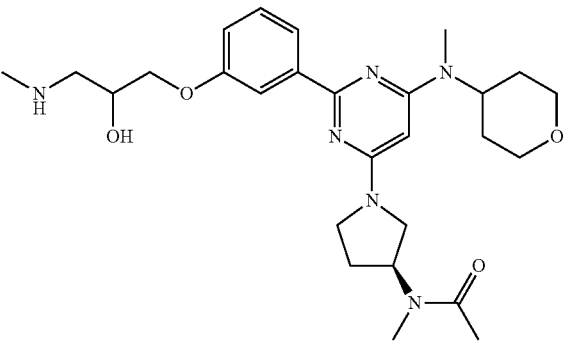 [SMILES: CNCC(O)COc1cccc(-c2nc(N3CC[C@H](N(C)C(C)=O)C3)cc(N(C)C3CCOCC3)n2)c1] | 513.3 |
| 548-1a | 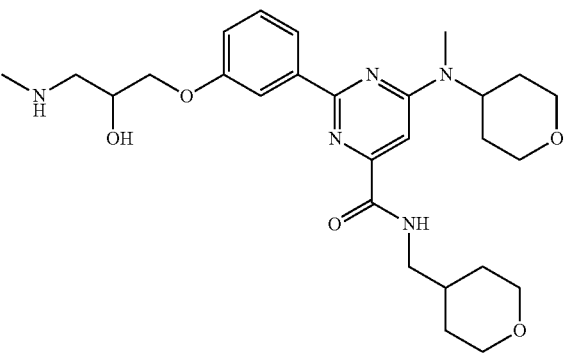 [SMILES: CNCC(O)COc1cccc(-c2nc(C(=O)NCC3CCOCC3)cc(N(C)C3CCOCC3)n2)c1] | 514.3 |

TABLE 1B-continued

Exemplary Compounds

| # | Structure | LC-MS m/z (M + H) |
|---|---|---|
| 549-1a | 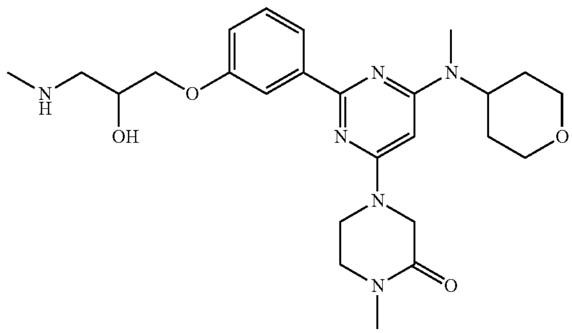 [SMILES: CNCC(O)COc1cccc(-c2nc(N3CCN(C)C(=O)C3)cc(N(C)C3CCOCC3)n2)c1] | 485.4 |
| 550-1a | 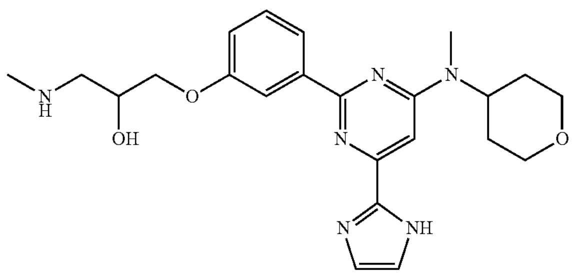 [SMILES: CNCC(O)COc1cccc(-c2nc(-c3ncc[nH]3)cc(N(C)C3CCOCC3)n2)c1] | 439.3 |
| 551-1a | 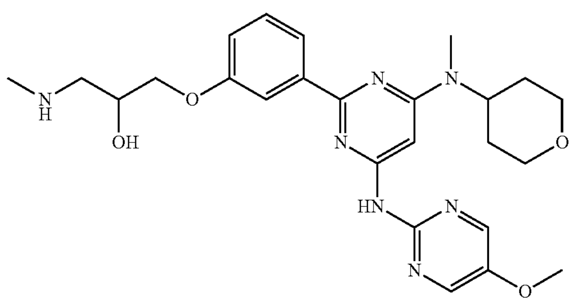 | 496.3 |
| 552-1a | 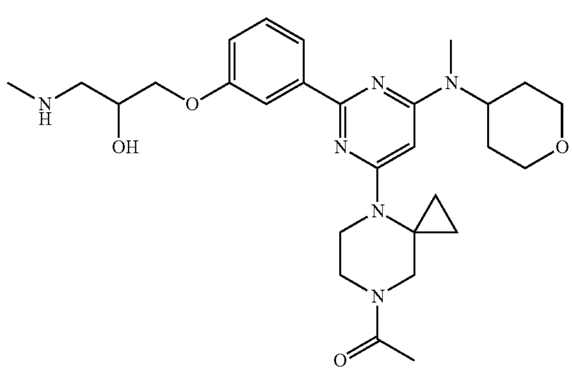 [SMILES: CNCC(O)COc1cccc(-c2nc(N(C)C3CCOCC3)cc(N3CCN(C(C)=O)CC34CC4)n2)c1] | 525.2 |

TABLE 1B-continued
Exemplary Compounds
| # | Structure | LC-MS m/z (M + H) |
|---|---|---|
| 553-1a | 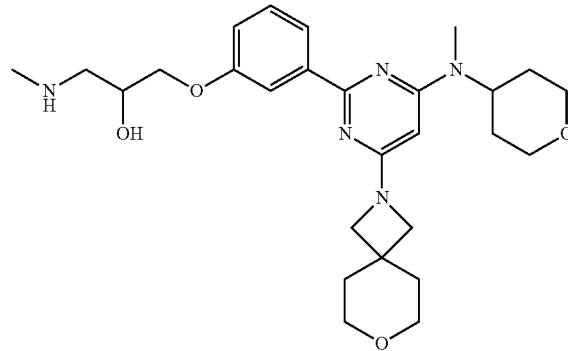 [SMILES: CNCC(O)COc1cccc(-c2nc(N3CC4(CCOCC4)C3)cc(N(C)C3CCOCC3)n2)c1] | 498.0 |
| 554-1a | 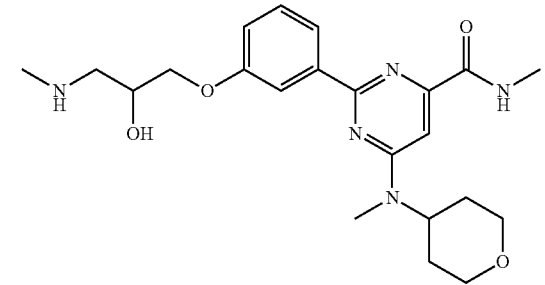 | 430.3 |
| 555-1a | 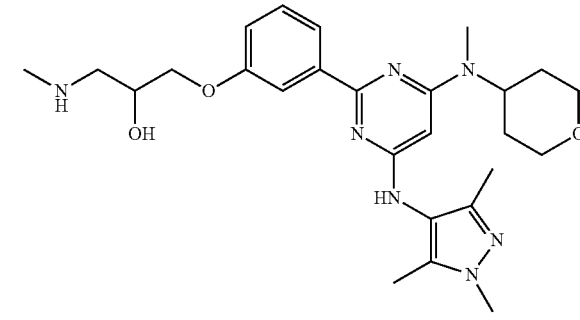 | 496.3 |
| 556-1a | 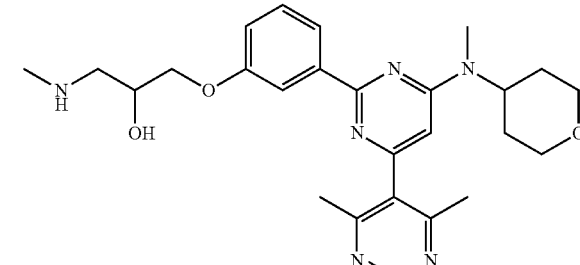 | 479.1 |

TABLE 1B-continued

Exemplary Compounds

| # | Structure | LC-MS m/z (M + H) |
|---|---|---|
| 557-1a | 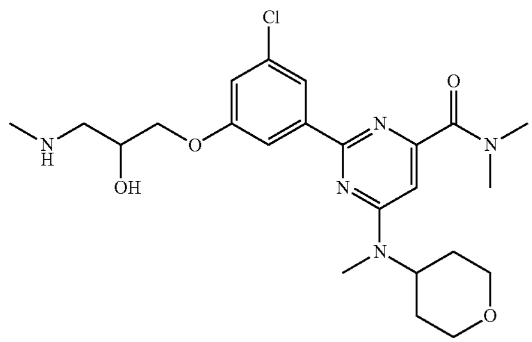 | 478.3 |
| 559-1a | 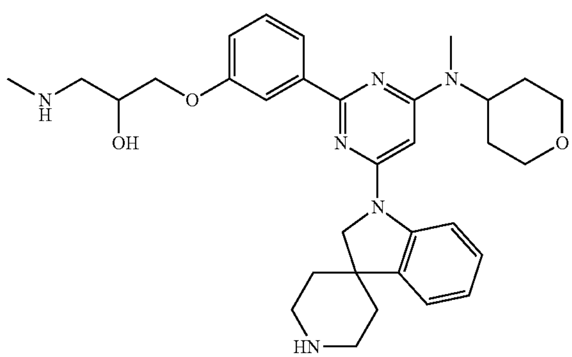 [SMILES: CNCC(O)COc1cccc(-c2nc(N3CC4(CCNCC4)c4ccccc43)cc(N(C)C3CCOCC3)n2)c1] | 559.0 |
| 560-1a | 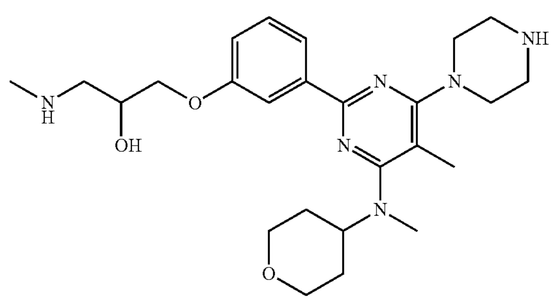 [SMILES: CNCC(O)COc1cccc(-c2nc(N3CCNCC3)c(C)c(N(C)C3CCOCC3)n2)c1] | 471.3 |
| 561-1a | 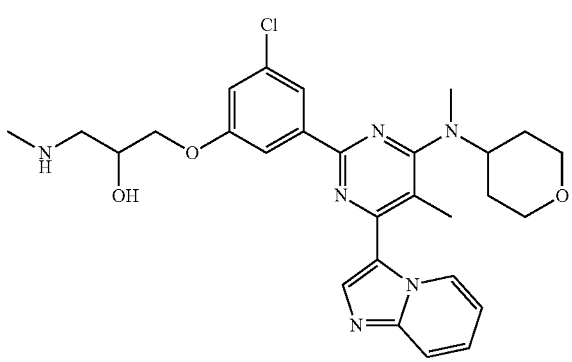 [SMILES: CNCC(O)COc1cc(Cl)cc(-c2nc(-c3cnc4ccccn34)c(C)c(N(C)C3CCOCC3)n2)c1] | 537.3 |

TABLE 1B-continued
Exemplary Compounds
| # | Structure | LC-MS m/z (M + H) |
|---|---|---|
| 562-1a | 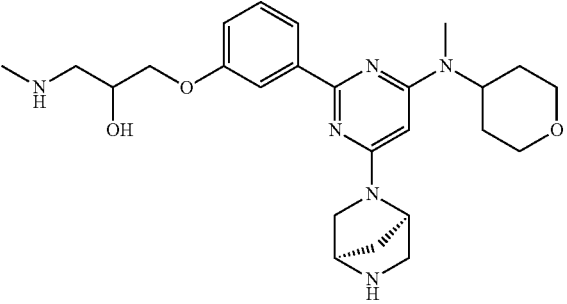 [SMILES: CNCC(O)COc1cccc(-c2nc(N(C)C3CCOCC3)cc(N3C[C@H]4C[C@@H]3CN4)n2)c1] | 469.4 |
| 563-1a | 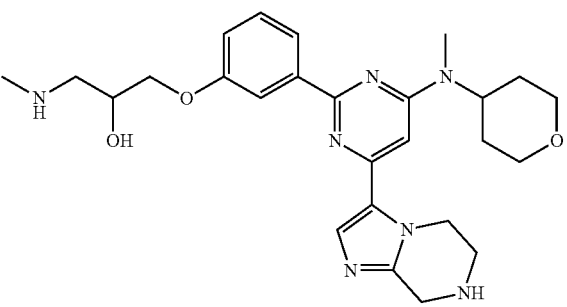 [SMILES: CNCC(O)COc1cccc(-c2nc(-c3cnc4n3CCNC4)cc(N(C)C3CCOCC3)n2)c1] | 494.3 |
| 564-1a | 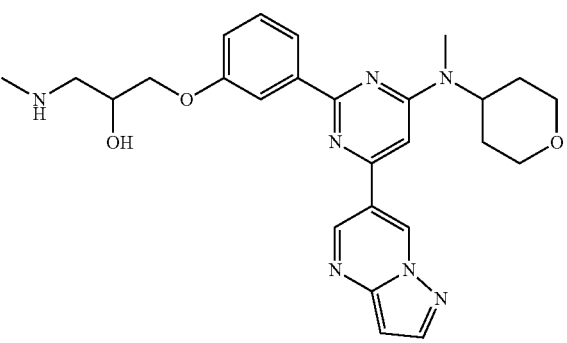 [SMILES: CNCC(O)COc1cccc(-c2nc(-c3cnc4ccnn4c3)cc(N(C)C3CCOCC3)n2)c1] | 490.3 |
| 565-1a | 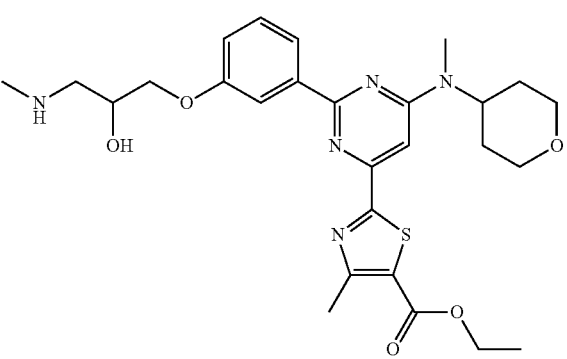 [SMILES: CCOC(=O)c1sc(-c2cc(N(C)C3CCOCC3)nc(-c3cccc(OCC(O)CNC)c3)n2)nc1C] | 541.9 |

TABLE 1B-continued

Exemplary Compounds

| # | Structure | LC-MS m/z (M + H) |
|---|---|---|
| 566-1a | 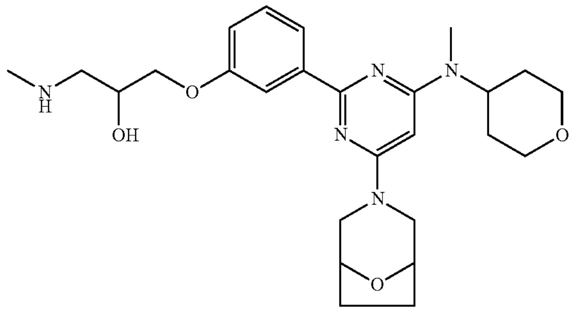 [SMILES: CNCC(O)COc1cccc(-c2nc(N3CC4CCC(C3)O4)cc(N(C)C3CCOCC3)n2)c1] | 484.4 |
| 567-1a | 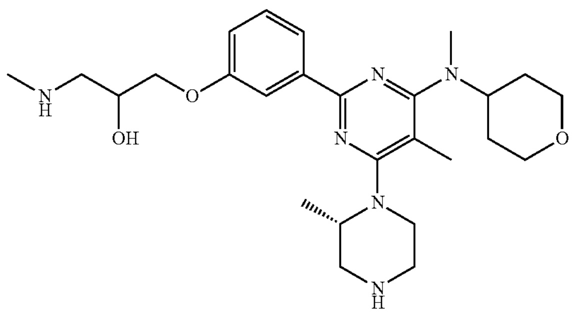 [SMILES: CNCC(O)COc1cccc(-c2nc(N(C)C3CCOCC3)c(C)c(N3CCNC[C@@H]3C)n2)c1] | 485.3 |
| 568-1a | 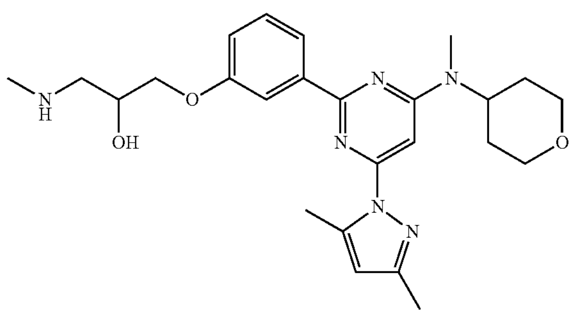 [SMILES: CNCC(O)COc1cccc(-c2nc(N(C)C3CCOCC3)cc(-n3nc(C)cc3C)n2)c1] | 467.0 |
| 569-1a | 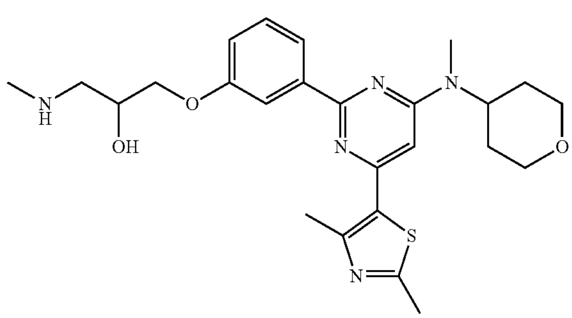 [SMILES: CNCC(O)COc1cccc(-c2nc(-c3sc(C)nc3C)cc(N(C)C3CCOCC3)n2)c1] | 483.9 |

TABLE 1B-continued
Exemplary Compounds
| # | Structure | LC-MS m/z (M + H) |
|---|---|---|
| 570-1a | 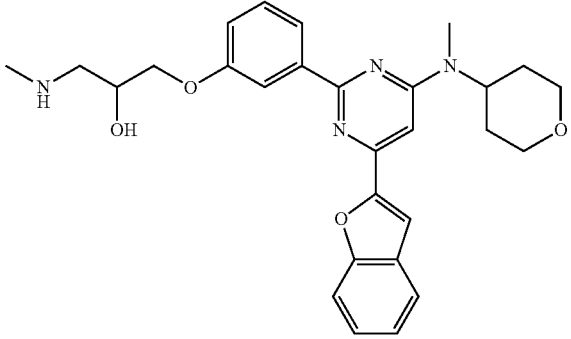 [SMILES: CNCC(O)COc1cccc(-c2nc(-c3cc4ccccc4o3)cc(N(C)C3CCOCC3)n2)c1] | 488.8 |
| 571-1a | 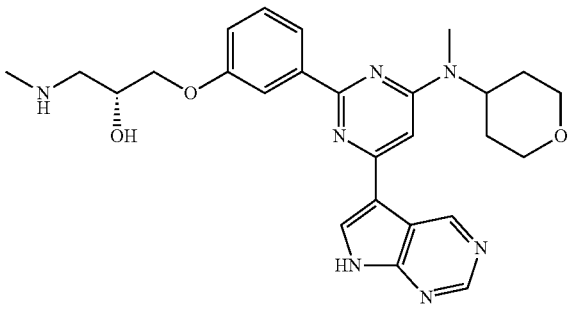 [SMILES: CNC[C@@H](O)COc1cccc(-c2nc(-c3c[nH]c4ncncc34)cc(N(C)C3CCOCC3)n2)c1] | 490.2 |
| 572-1a | 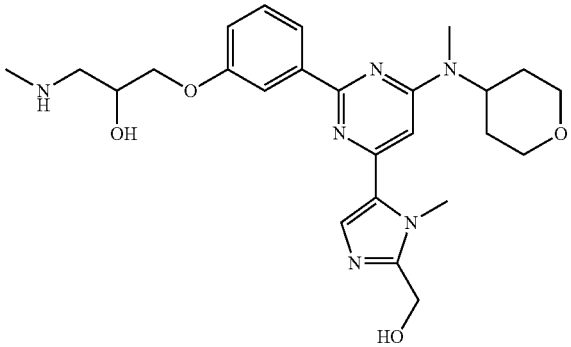 [SMILES: CNCC(O)COc1cccc(-c2nc(-c3cnc(CO)n3C)cc(N(C)C3CCOCC3)n2)c1] | 483.3 |
| 573-1a | 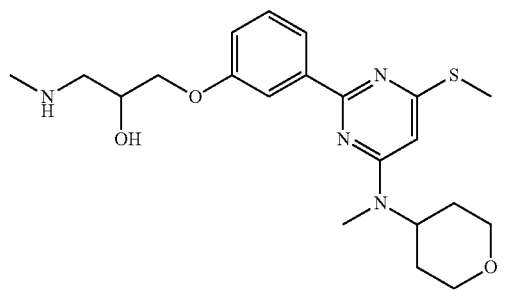 [SMILES: CNCC(O)COc1cccc(-c2nc(SC)cc(N(C)C3CCOCC3)n2)c1] | 419.2 |

TABLE 1B-continued
Exemplary Compounds
| # | Structure | LC-MS m/z (M + H) |
|---|---|---|
| 574-1a | 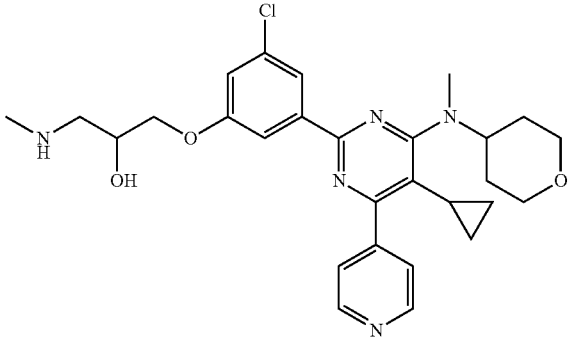 [SMILES: CNCC(O)COc1cc(Cl)cc(-c2nc(-c3ccncc3)c(C3CC3)c(N(C)C3CCOCC3)n2)c1] | 524.3 |
| 575-1a | 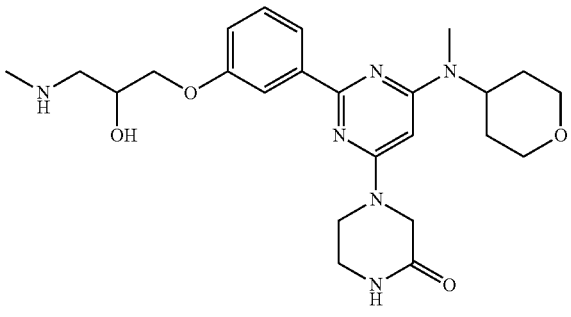 [SMILES: CNCC(O)COc1cccc(-c2nc(N3CCNC(=O)C3)cc(N(C)C3CCOCC3)n2)c1] | 471.3 |
| 576-1a | 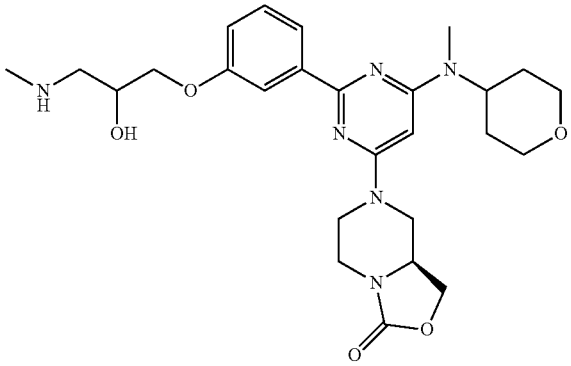 [SMILES: CNCC(O)COc1cccc(-c2nc(N3CCN4C(=O)OC[C@@H]4C3)cc(N(C)C3CCOCC3)n2)c1] | 513.3 |
| 577-1a | 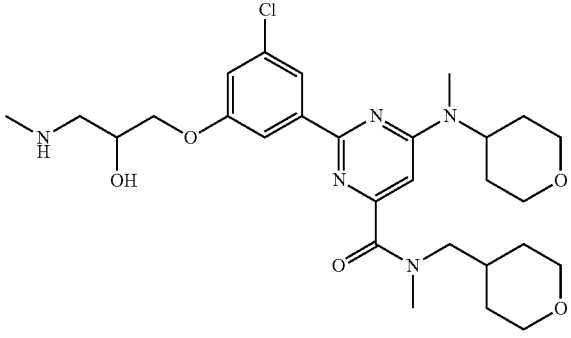 [SMILES: CNCC(O)COc1cc(Cl)cc(-c2nc(C(=O)N(C)CC3CCOCC3)cc(N(C)C3CCOCC3)n2)c1] | 562.3 |

TABLE 1B-continued

Exemplary Compounds

| # | Structure | LC-MS m/z (M + H) |
|---|---|---|
| 578-1a | 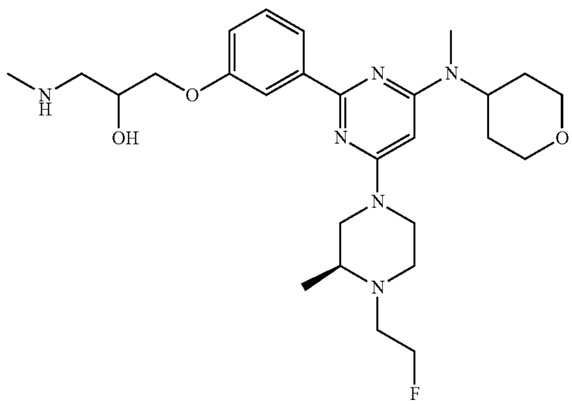 [SMILES: CNCC(O)COc1cccc(-c2nc(N3CCN(CCF)[C@@H](C)C3)cc(N(C)C3CCOCC3)n2)c1] | 517.3 |
| 579-1a | 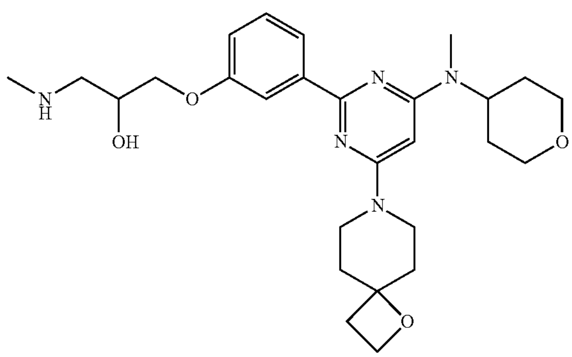 [SMILES: CNCC(O)COc1cccc(-c2nc(N3CCC4(CCO4)CC3)cc(N(C)C3CCOCC3)n2)c1] | 498.4 |
| 580-1a | 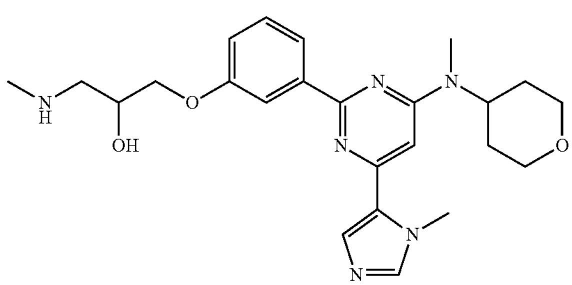 [SMILES: CNCC(O)COc1cccc(-c2nc(-c3cncn3C)cc(N(C)C3CCOCC3)n2)c1] | 453.4 |
| 581-1a | 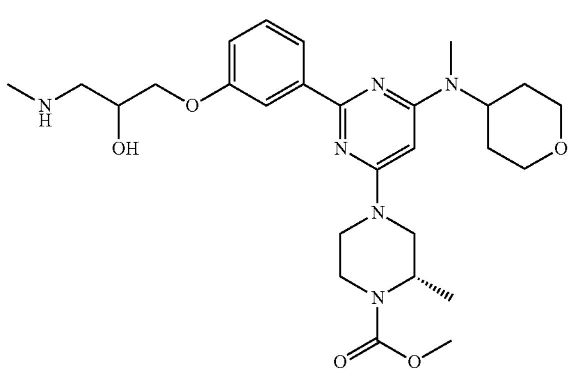 [SMILES: CNCC(O)COc1cccc(-c2nc(N3CCN(C(=O)OC)[C@@H](C)C3)cc(N(C)C3CCOCC3)n2)c1] | 529.3 |

TABLE 1B-continued
Exemplary Compounds
| # | Structure | LC-MS m/z (M + H) |
|---|---|---|
| 582-1a | 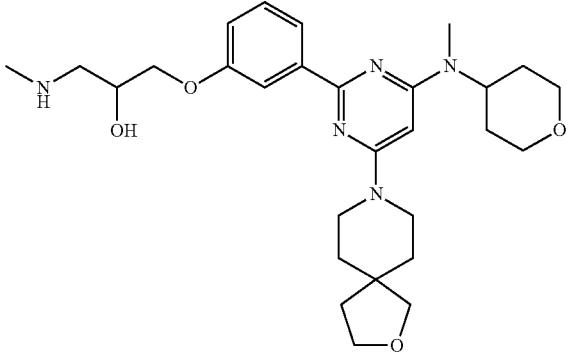 [SMILES: CNCC(O)COc1cccc(-c2nc(N3CCC4(CCOC4)CC3)cc(N(C)C3CCOCC3)n2)c1] | 512.0 |
| 583-1a | 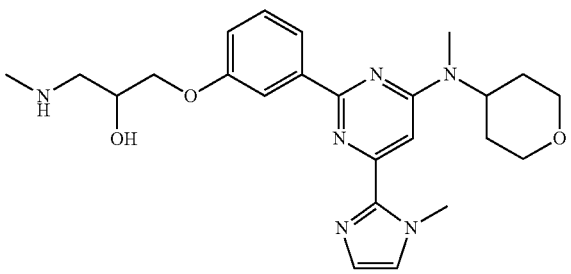 [SMILES: CNCC(O)COc1cccc(-c2nc(-c3nccn3C)cc(N(C)C3CCOCC3)n2)c1] | 453.3 |
| 584-1a | 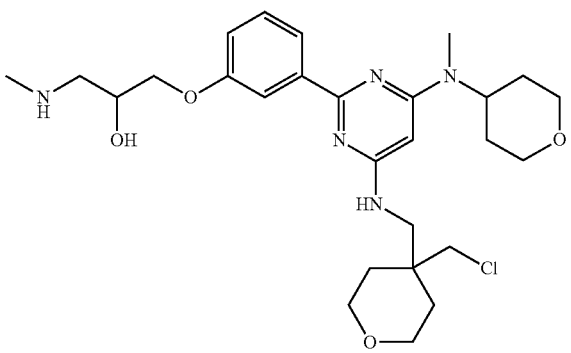 [SMILES: CNCC(O)COc1cccc(-c2nc(NCC3(CCl)CCOCC3)cc(N(C)C3CCOCC3)n2)c1] | 535.0 |
| 585-1a | 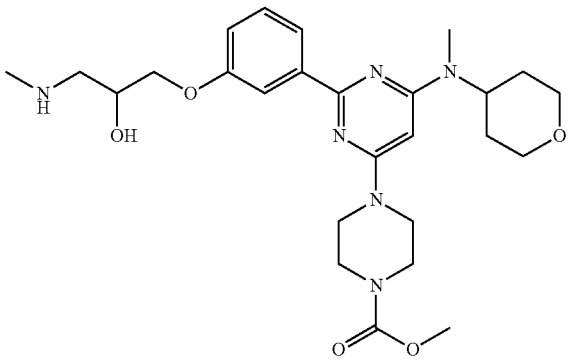 [SMILES: CNCC(O)COc1cccc(-c2nc(N3CCN(C(=O)OC)CC3)cc(N(C)C3CCOCC3)n2)c1] | 515.4 |

TABLE 1B-continued
Exemplary Compounds
| # | Structure | LC-MS m/z (M + H) |
|---|-----------|-------------------|
| 586-1a | 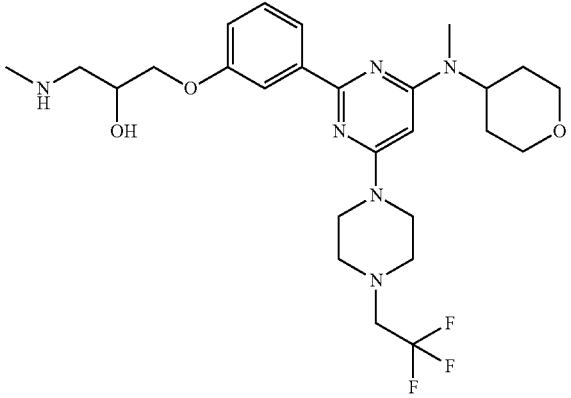 [SMILES: CNCC(O)COc1cccc(-c2nc(N3CCN(CC(F)(F)F)CC3)cc(N(C)C3CCOCC3)n2)c1] | 539.2 |
| 587-1a | 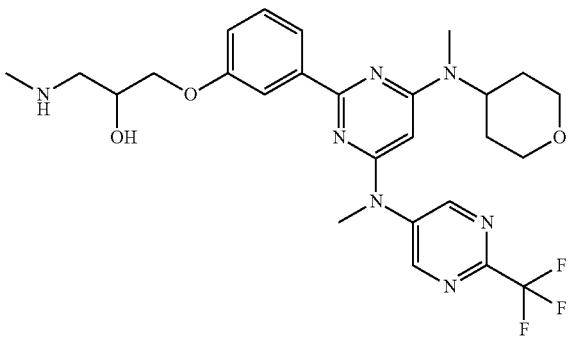 [SMILES: CNCC(O)COc1cccc(-c2nc(N(C)c3cnc(C(F)(F)F)nc3)cc(N(C)C3CCOCC3)n2)c1] | 548.2 |
| 588-1a | 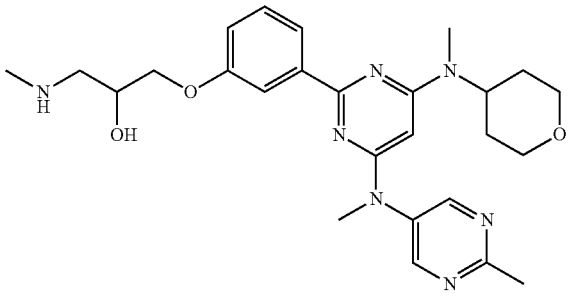 [SMILES: CNCC(O)COc1cccc(-c2nc(N(C)c3cnc(C)nc3)cc(N(C)C3CCOCC3)n2)c1] | 494.2 |
| 589-1a | 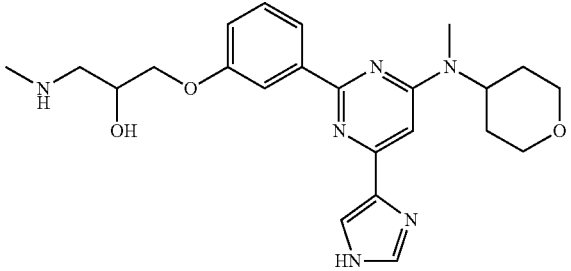 [SMILES: CNCC(O)COc1cccc(-c2nc(-c3c[nH]cn3)cc(N(C)C3CCOCC3)n2)c1] | 439.3 |

TABLE 1B-continued

Exemplary Compounds

| # | Structure | LC-MS m/z (M + H) |
|---|---|---|
| 590-1a | 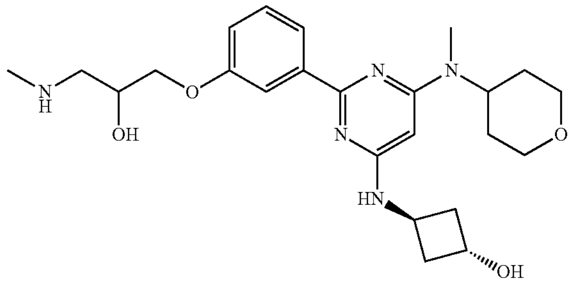 [SMILES: CNCC(O)COc1cccc(-c2nc(N[C@H]3C[C@H](O)C3)cc(N(C)C3CCOCC3)n2)c1] | 458.3 |
| 591-1a | 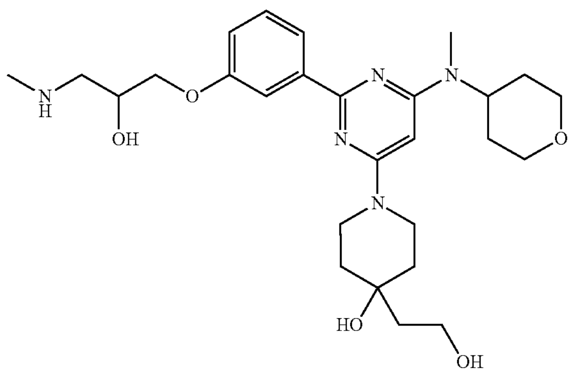 [SMILES: CNCC(O)COc1cccc(-c2nc(N3CCC(O)(CCO)CC3)cc(N(C)C3CCOCC3)n2)c1] | 516.4 |
| 592-1a | 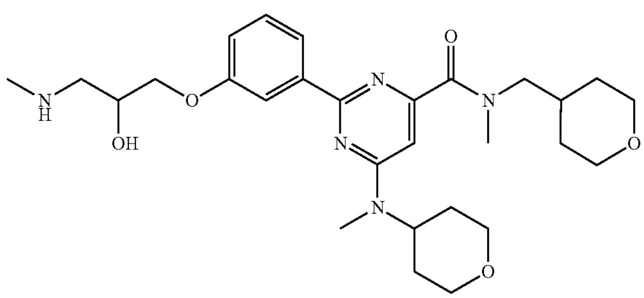 [SMILES: CNCC(O)COc1cccc(-c2nc(C(=O)N(C)CC3CCOCC3)cc(N(C)C3CCOCC3)n2)c1] | 528.4 |
| 593-1a | 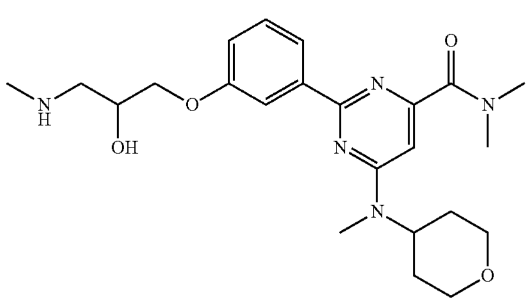 | 444.3 |

TABLE 1B-continued

Exemplary Compounds

| # | Structure | LC-MS m/z (M + H) |
|---|---|---|
| 594-1a | 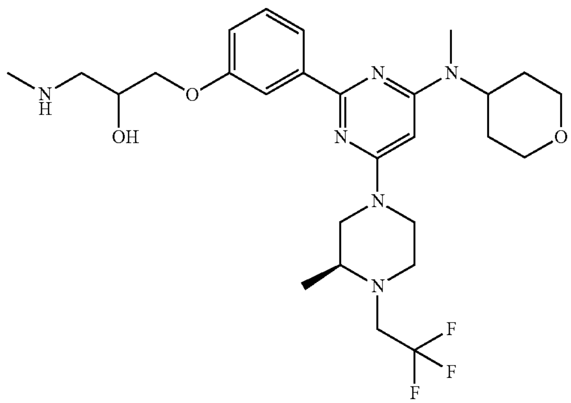 [SMILES: CNCC(O)COc1cccc(-c2nc(N3CCN(CC(F)(F)F)[C@@H](C)C3)cc(N(C)C3CCOCC3)n2)c1] | 553.3 |
| 595-1a | 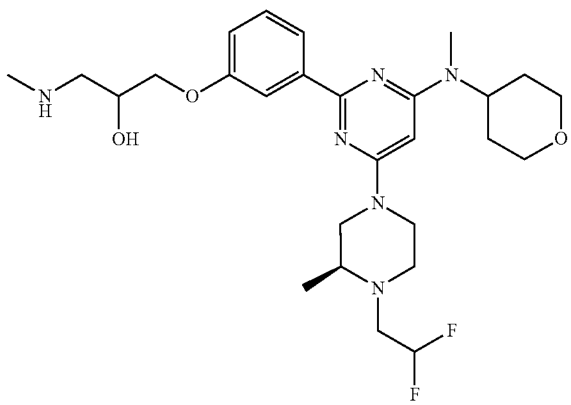 [SMILES: CNCC(O)COc1cccc(-c2nc(N3CCN(CC(F)F)[C@@H](C)C3)cc(N(C)C3CCOCC3)n2)c1] | 535.3 |
| 596-1a | 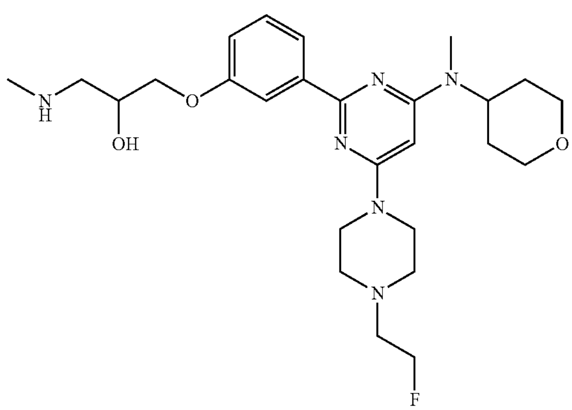 [SMILES: CNCC(O)COc1cccc(-c2nc(N3CCN(CCF)CC3)cc(N(C)C3CCOCC3)n2)c1] | 504.3 |
| 597-1a | 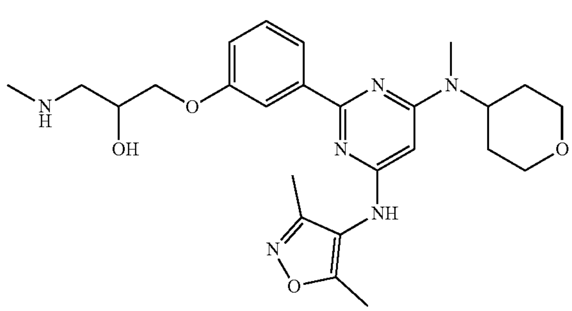 [SMILES: CNCC(O)COc1cccc(-c2nc(Nc3c(C)noc3C)cc(N(C)C3CCOCC3)n2)c1] | 483.4 |

TABLE 1B-continued
Exemplary Compounds
| # | Structure | LC-MS m/z (M + H) |
|---|---|---|
| 598-1a | 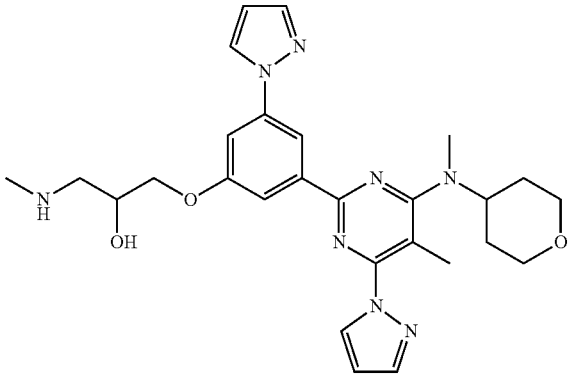 [SMILES: CNCC(O)COc1cc(-c2nc(N(C)C3CCOCC3)c(C)c(-n3cccn3)n2)cc(-n2cccn2)c1] | 518.9 |
| 599-1a | 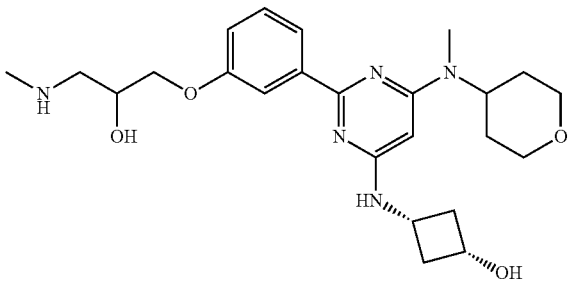 [SMILES: CNCC(O)COc1cccc(-c2nc(N[C@H]3C[C@@H](O)C3)cc(N(C)C3CCOCC3)n2)c1] | 458.3 |
| 600-1a | 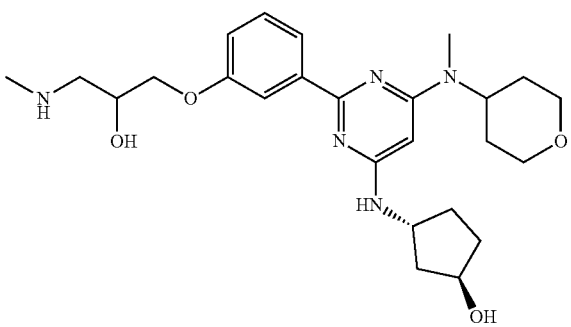 [SMILES: CNCC(O)COc1cccc(-c2nc(N[C@@H]3CC[C@@H](O)C3)cc(N(C)C3CCOCC3)n2)c1] | 472.4 |
| 601-1a | 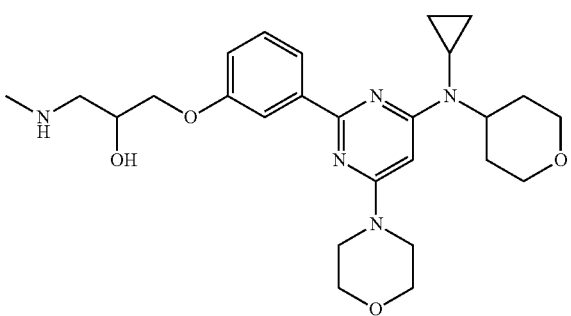 [SMILES: CNCC(O)COc1cccc(-c2nc(N3CCOCC3)cc(N(C3CCOCC3)C3CC3)n2)c1] | 484.4 |

TABLE 1B-continued

Exemplary Compounds

| # | Structure | LC-MS m/z (M + H) |
|---|-----------|-------------------|
| 602-1a | 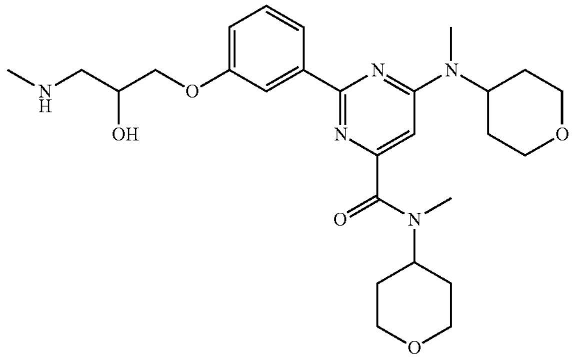 [SMILES: CNCC(O)COc1cccc(-c2nc(C(=O)N(C)C3CCOCC3)cc(N(C)C3CCOCC3)n2)c1] | 514.3 |
| 603-1a | 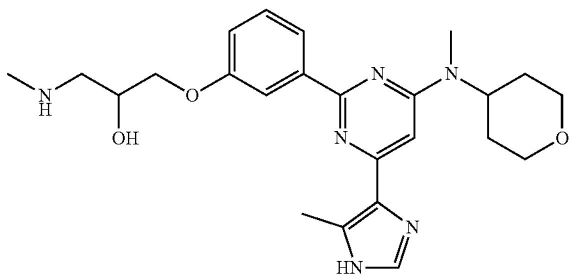 [SMILES: CNCC(O)COc1cccc(-c2nc(-c3nc[nH]c3C)cc(N(C)C3CCOCC3)n2)c1] | 453.3 |
| 604-1a | 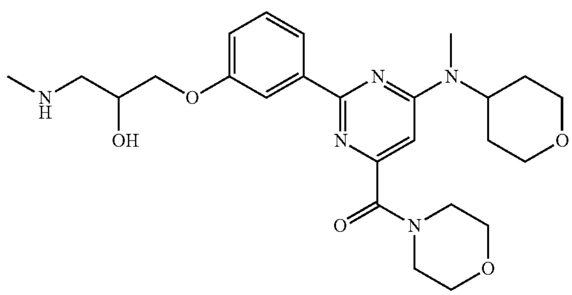 [SMILES: CNCC(O)COc1cccc(-c2nc(C(=O)N3CCOCC3)cc(N(C)C3CCOCC3)n2)c1] | 486.3 |
| 605-1a | 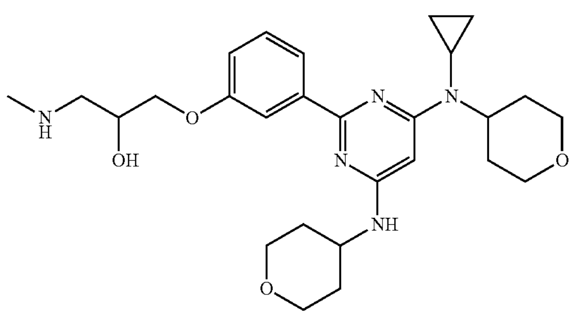 [SMILES: CNCC(O)COc1cccc(-c2nc(NC3CCOCC3)cc(N(C3CCOCC3)C3CC3)n2)c1] | 498.5 |
| 606-1a | 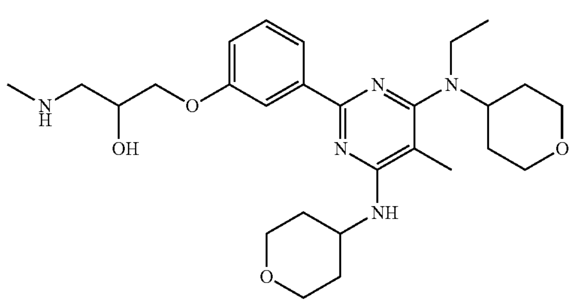 [SMILES: CCN(c1nc(-c2cccc(OCC(O)CNC)c2)nc(NC2CCOCC2)c1C)C1CCOCC1] | 500.4 |

TABLE 1B-continued
Exemplary Compounds
| # | Structure | LC-MS m/z (M + H) |
|---|---|---|
| 607-1a | 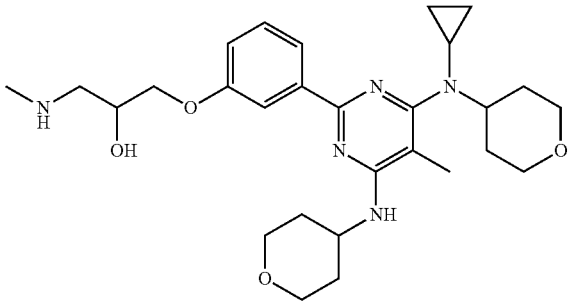 [SMILES: CNCC(O)COc1cccc(-c2nc(NC3CCOCC3)c(C)c(N(C3CCOCC3)C3CC3)n2)c1] | 512.4 |
| 608-1a | 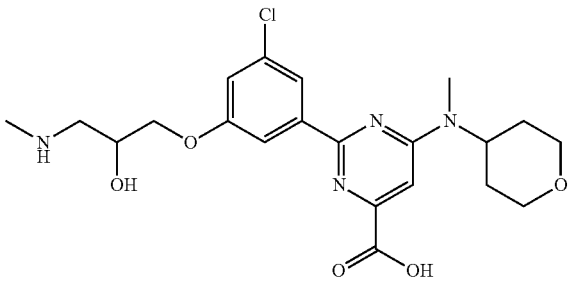 [SMILES: CNCC(O)COc1cc(Cl)cc(-c2nc(C(=O)O)cc(N(C)C3CCOCC3)n2)c1] | 451.3 |
| 609-1a | 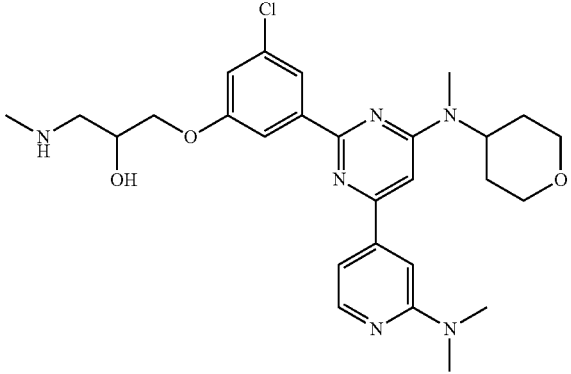 [SMILES: CNCC(O)COc1cc(Cl)cc(-c2nc(-c3ccnc(N(C)C)c3)cc(N(C)C3CCOCC3)n2)c1] | 527.3 |
| 610-1a | 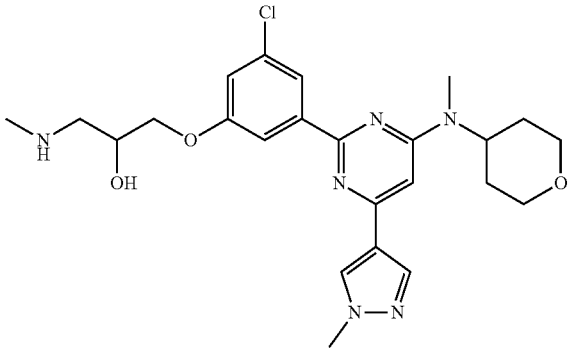 [SMILES: CNCC(O)COc1cc(Cl)cc(-c2nc(-c3cnn(C)c3)cc(N(C)C3CCOCC3)n2)c1] | 487.3 |

TABLE 1B-continued
Exemplary Compounds
| # | Structure | LC-MS m/z (M + H) |
|---|-----------|-------------------|
| 611-1a | 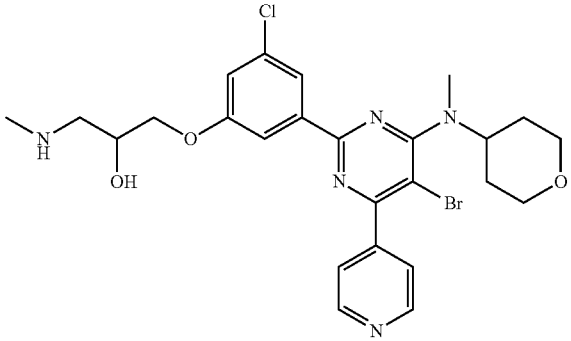 [SMILES: CNCC(O)COc1cc(Cl)cc(-c2nc(-c3ccncc3)c(Br)c(N(C)C3CCOCC3)n2)c1] | 564.2 |
| 612-1a | 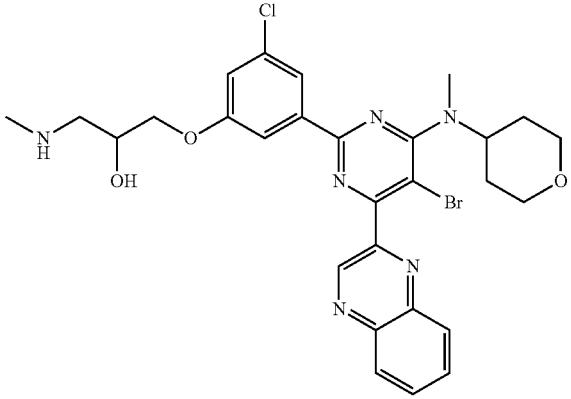 [SMILES: CNCC(O)COc1cc(Cl)cc(-c2nc(-c3cnc4ccccc4n3)c(Br)c(N(C)C3CCOCC3)n2)c1] | 548.8 |
| 613-1a | 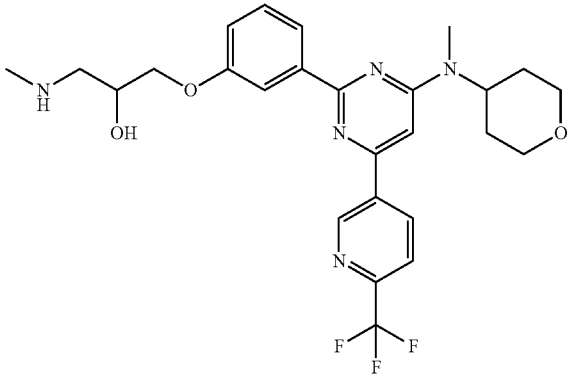 [SMILES: CNCC(O)COc1cccc(-c2nc(-c3ccc(C(F)(F)F)nc3)cc(N(C)C3CCOCC3)n2)c1] | 518.2 |
| 614-1a | 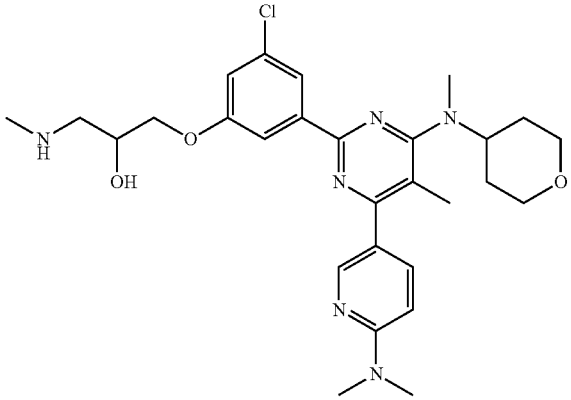 [SMILES: CNCC(O)COc1cc(Cl)cc(-c2nc(-c3ccc(N(C)C)nc3)c(C)c(N(C)C3CCOCC3)n2)c1] | 541.3 |

TABLE 1B-continued

Exemplary Compounds

| # | Structure | LC-MS m/z (M + H) |
|---|-----------|-------------------|
| 615-1a | 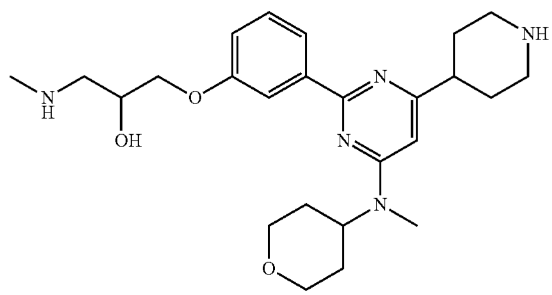 [SMILES: CNCC(O)COc1cccc(-c2nc(C3CCNCC3)cc(N(C)C3CCOCC3)n2)c1] | 456.4 |
| 616-1a | 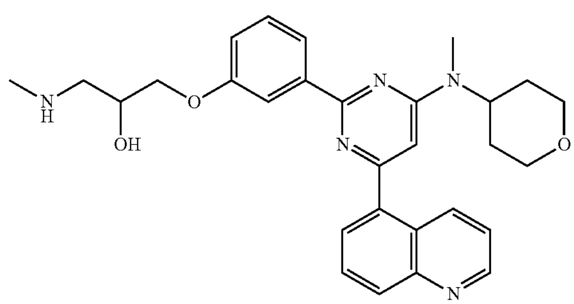 [SMILES: CNCC(O)COc1cccc(-c2nc(-c3cccc4ncccc34)cc(N(C)C3CCOCC3)n2)c1] | 499.9 |
| 617-1a | 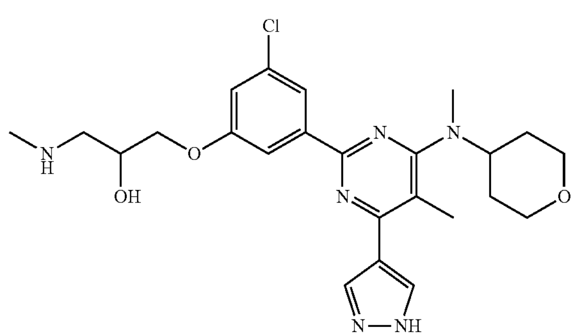 [SMILES: CNCC(O)COc1cc(Cl)cc(-c2nc(-c3cn[nH]c3)c(C)c(N(C)C3CCOCC3)n2)c1] | 487.3 |
| 618-1a | 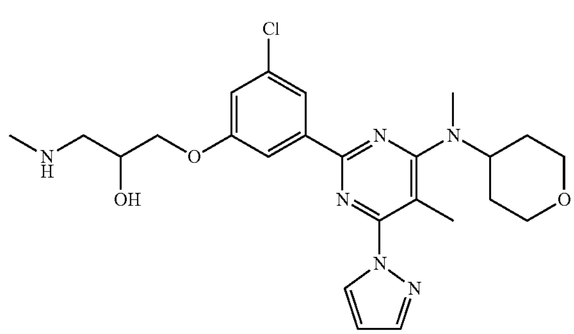 [SMILES: CNCC(O)COc1cc(Cl)cc(-c2nc(N(C)C3CCOCC3)c(C)c(-n3cccn3)n2)c1] | 486.9 |

TABLE 1B-continued
Exemplary Compounds
| # | Structure | LC-MS m/z (M + H) |
|---|---|---|
| 619-1a | 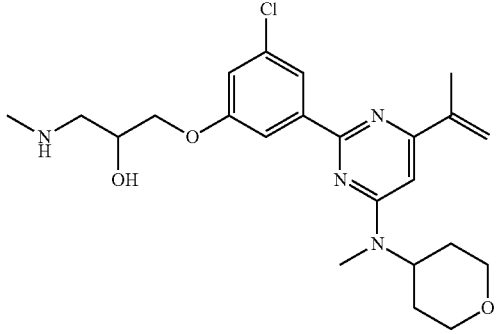 [SMILES: C=C(C)c1cc(N(C)C2CCOCC2)nc(-c2cc(Cl)cc(OCC(O)CNC)c2)n1] | 447.2 |
| 620-1a | 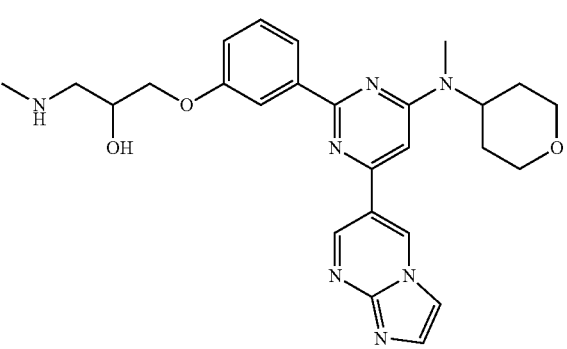 | 490.2 |
| 621-1a | 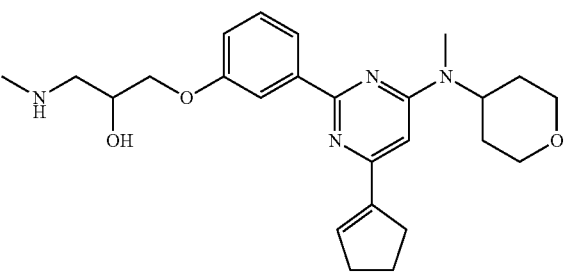 [SMILES: CNCC(O)COc1cccc(-c2nc(C3=CCCC3)cc(N(C)C3CCOCC3)n2)c1] | 439.2 |
| 622-1a | 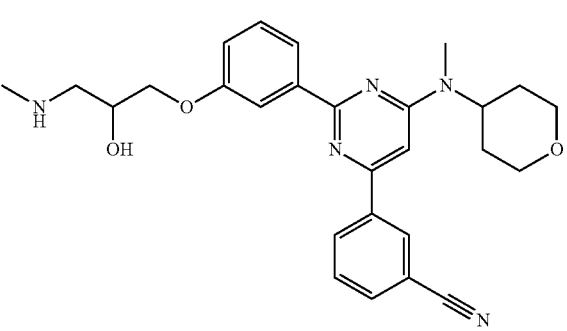 [SMILES: CNCC(O)COc1cccc(-c2nc(-c3cccc(C#N)c3)cc(N(C)C3CCOCC3)n2)c1] | 473.9 |

TABLE 1B-continued
Exemplary Compounds
| # | Structure | LC-MS m/z (M + H) |
|---|-----------|-------------------|
| 623-1a | 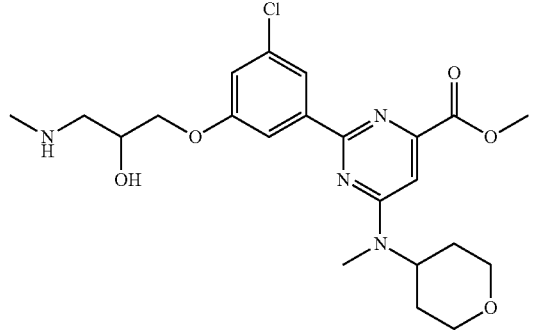 | 465.1 |
| 624-1a | 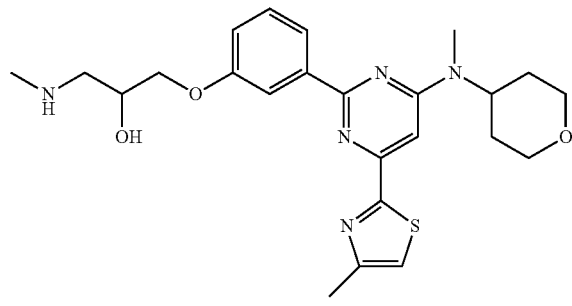 [SMILES: CNCC(O)COc1cccc(-c2nc(-c3nc(C)cs3)cc(N(C)C3CCOCC3)n2)c1] | 470.0 |
| 625-1a | 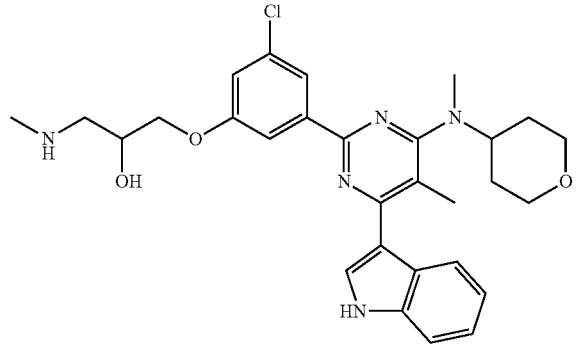 [SMILES: CNCC(O)COc1cc(Cl)cc(-c2nc(-c3c[nH]c4ccccc34)c(C)c(N(C)C3CCOCC3)n2)c1] | 536.3 |
| 626-1a | 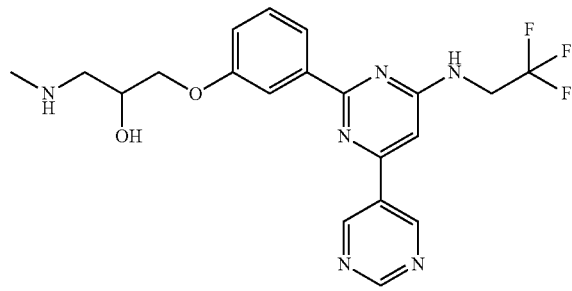 [SMILES: CNCC(O)COc1cccc(-c2nc(NCC(F)(F)F)cc(-c3cncnc3)n2)c1] | 435.1 |

TABLE 1B-continued

Exemplary Compounds

| # | Structure | LC-MS m/z (M + H) |
|---|-----------|-------------------|
| 627-1a | 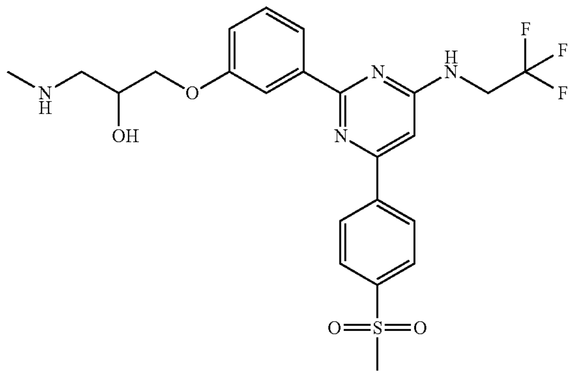 [SMILES: CNCC(O)COc1cccc(-c2nc(NCC(F)(F)F)cc(-c3ccc(S(C)(=O)=O)cc3)n2)c1] | 511.0 |
| 628-1a | 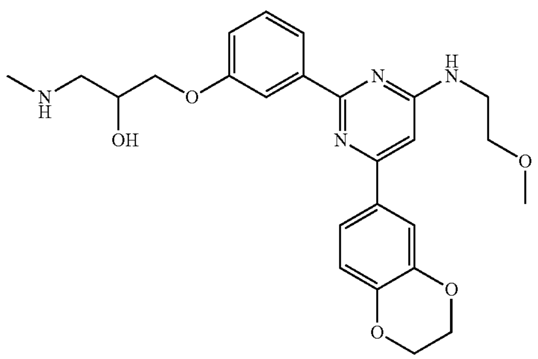 | 467.3 |
| 629-1a | 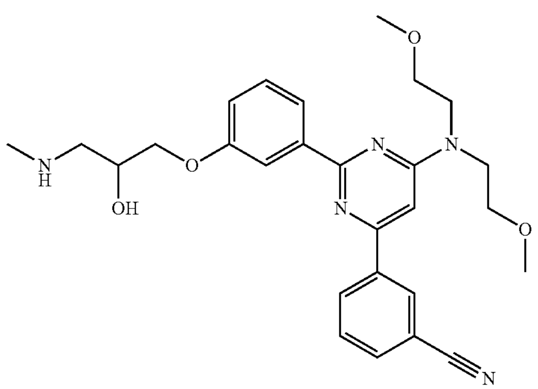 | 491.9 |
| 630-1a | 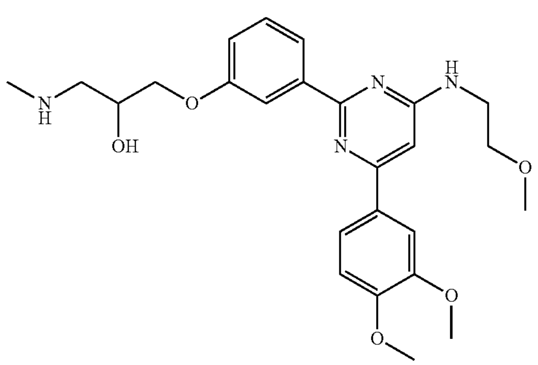 | 469.3 |

TABLE 1B-continued
Exemplary Compounds
| # | Structure | LC-MS m/z (M + H) |
|---|---|---|
| 631-1a | 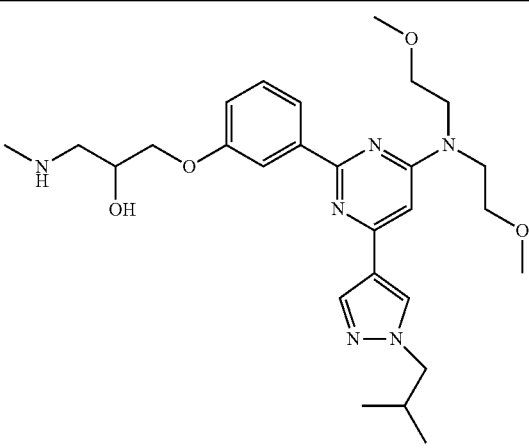 | 512.9 |
| 632-1a | 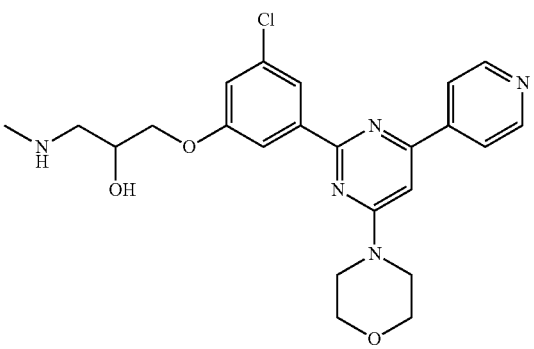 [SMILES: CNCC(O)COc1cc(Cl)cc(-c2nc(-c3ccncc3)cc(N3CCOCC3)n2)c1] | 456.3 |
| 635-1a | 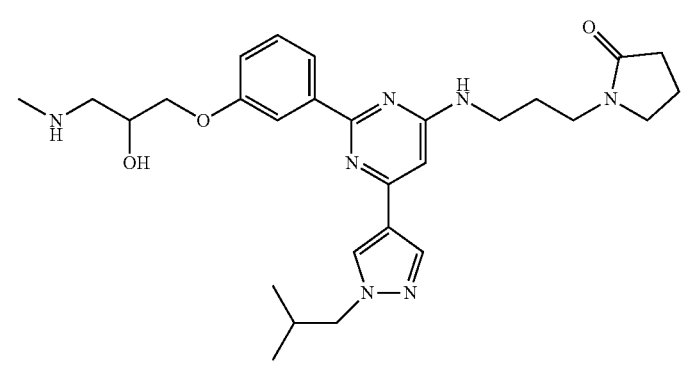 [SMILES: CNCC(O)COc1cccc(-c2nc(NCCCN3CCCC3=O)cc(-c3cnn(CC(C)C)c3)n2)c1] | 522.2 |
| 636-1a | 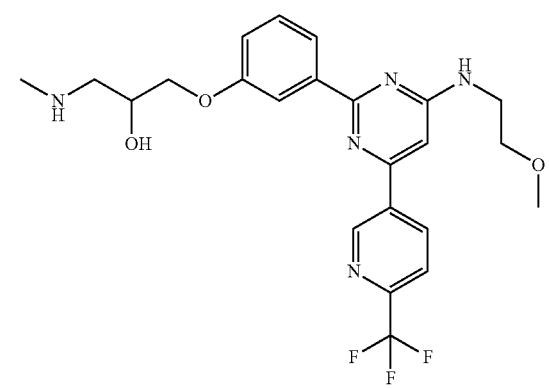 | 477.9 |

TABLE 1B-continued

Exemplary Compounds

| # | Structure | LC-MS m/z (M + H) |
|---|---|---|
| 637-1a | 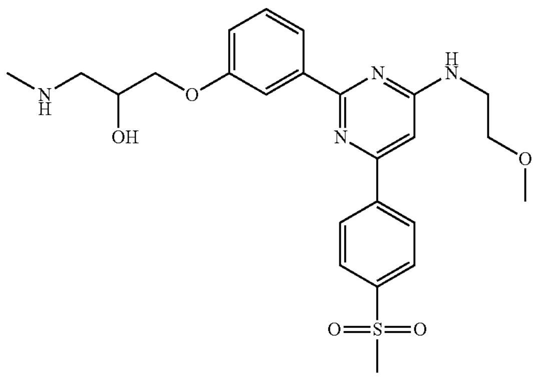 | 486.9 |
| 638-1a | 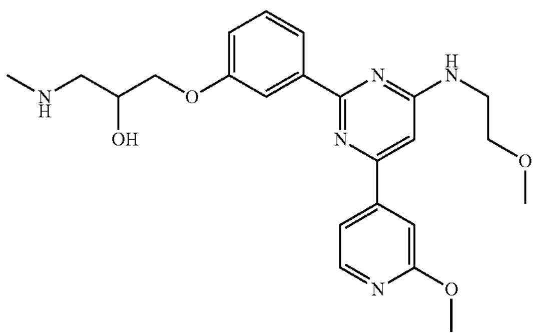 | 440.0 |
| 639-1a | 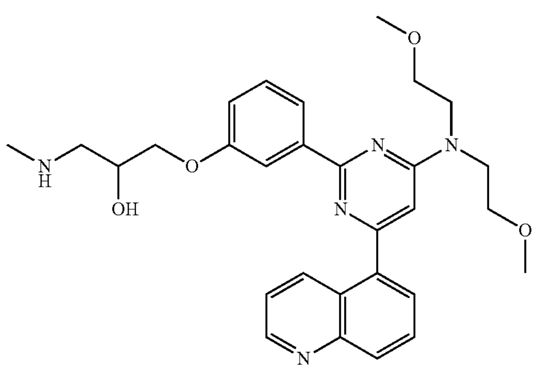 | 518.9 |
| 640-1a | 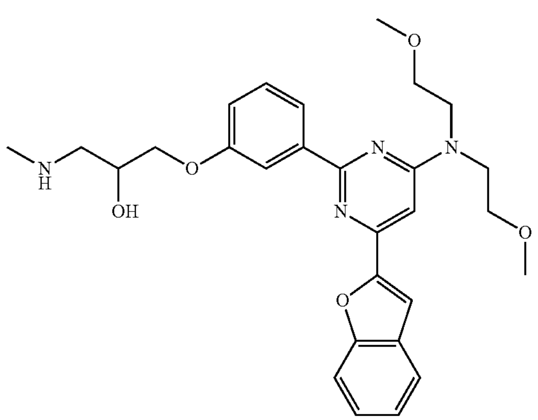 | 506.8 |

TABLE 1B-continued

Exemplary Compounds

| # | Structure | LC-MS m/z (M + H) |
|---|---|---|
| 641-1a | 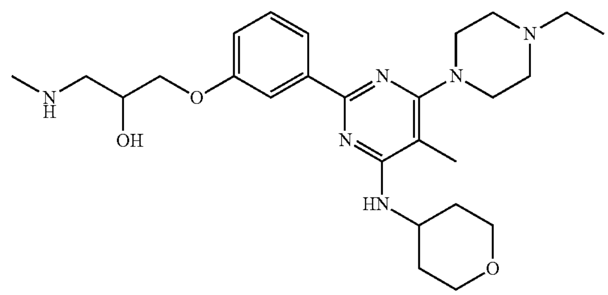 [SMILES: CCN1CCN(c2nc(-c3cccc(OCC(O)CNC)c3)nc(NC3CCOCC3)c2C)CC1] | 485.4 |
| 642-1a | 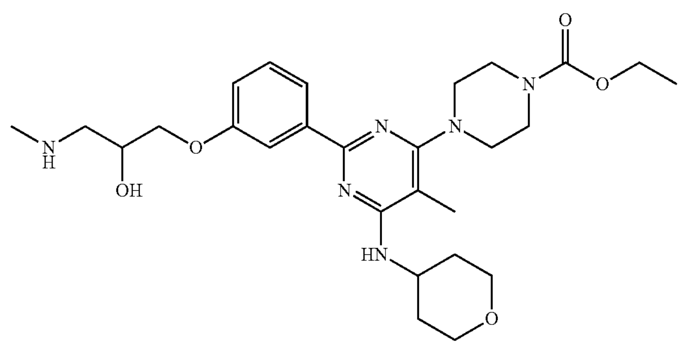 [SMILES: CCOC(=O)N1CCN(c2nc(-c3cccc(OCC(O)CNC)c3)nc(NC3CCOCC3)c2C)CC1] | 529.4 |
| 643-1a | 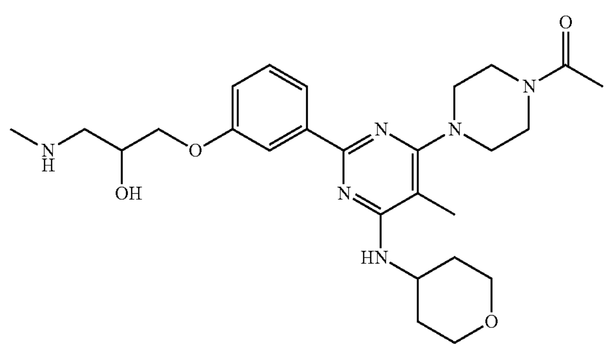 [SMILES: CNCC(O)COc1cccc(-c2nc(NC3CCOCC3)c(C)c(N3CCN(C(C)=O)CC3)n2)c1] | 499.4 |
| 644-1a | 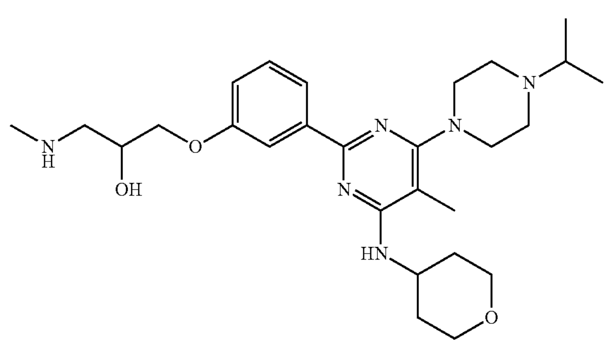 [SMILES: CNCC(O)COc1cccc(-c2nc(NC3CCOCC3)c(C)c(N3CCN(C(C)C)CC3)n2)c1] | 499.4 |

TABLE 1B-continued

Exemplary Compounds

| # | Structure | LC-MS m/z (M + H) |
|---|---|---|
| 645-1a | 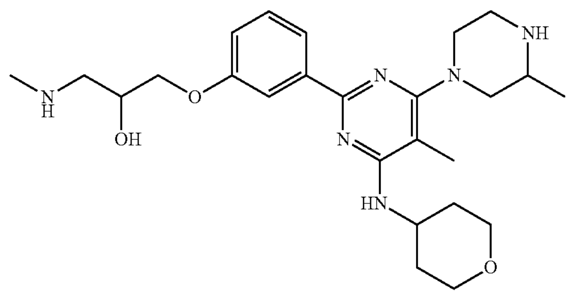 | 471.4 |
| 646-1a | 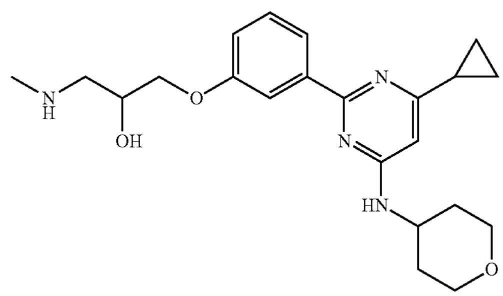 [SMILES: CNCC(O)COc1cccc(-c2nc(NC3CCOCC3)cc(C3CC3)n2)c1] | 399.3 |
| 647-1a | 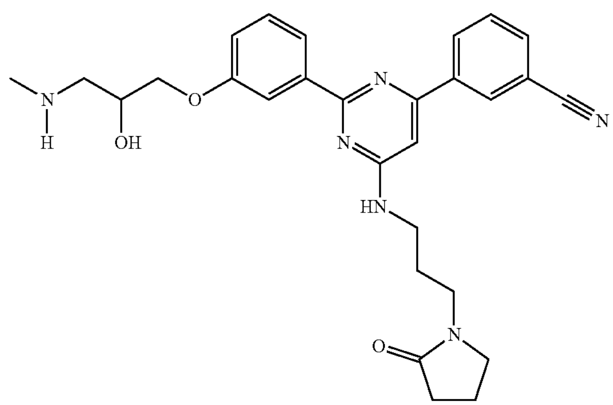 [SMILES: CNCC(O)COc1cccc(-c2nc(NCCCN3CCCC3=O)cc(-c3cccc(C#N)c3)n2)c1] | 501.2 |
| 648-1a | 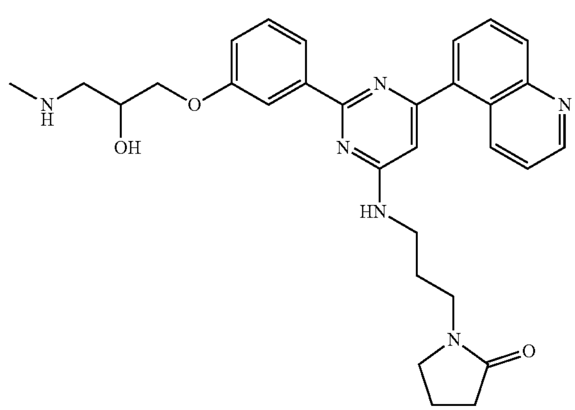 [SMILES: CNCC(O)COc1cccc(-c2nc(NCCCN3CCCC3=O)cc(-c3cccc4ncccc34)n2)c1] | 527.2 |

TABLE 1B-continued
Exemplary Compounds
| # | Structure | LC-MS m/z (M + H) |
|---|---|---|
| 649-1a | 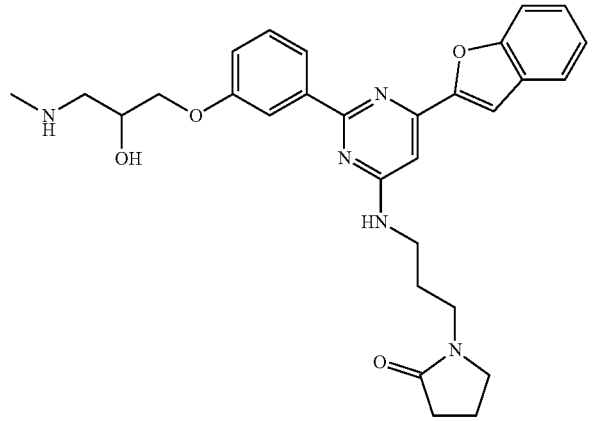 [SMILES: CNCC(O)COc1cccc(-c2nc(NCCCN3CCCC3=O)cc(-c3cc4ccccc4o3)n2)c1] | 515.8 |
| 650-1a | 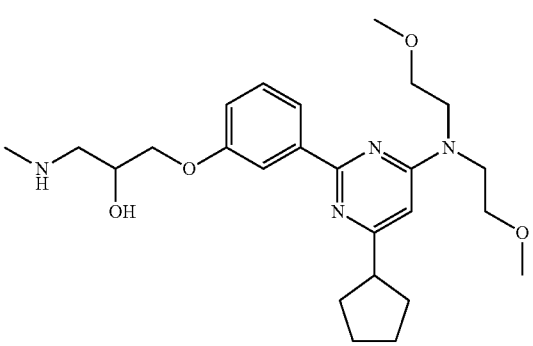 | 458.9 |
| 651-1a | 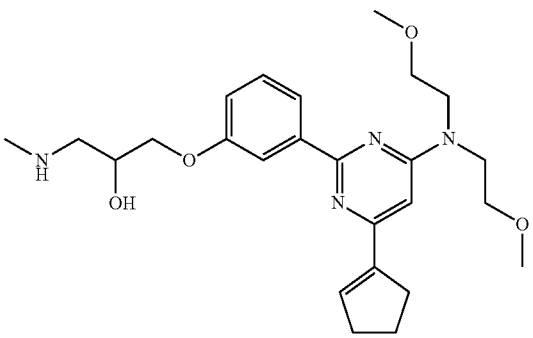 | 456.9 |
| 652-1a | 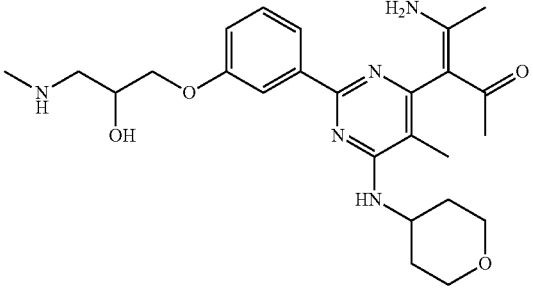 [SMILES: CNCC(O)COc1cccc(-c2nc(NC3CCOCC3)c(C)c(/C(C(C)=O)=C(/C)N)n2)c1] | 470.4 |

TABLE 1B-continued
Exemplary Compounds
| # | Structure | LC-MS m/z (M + H) |
|---|---|---|
| 653-1a | 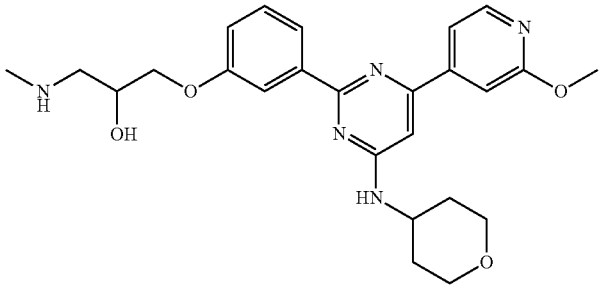 | 466.0 |
| 654-1a | 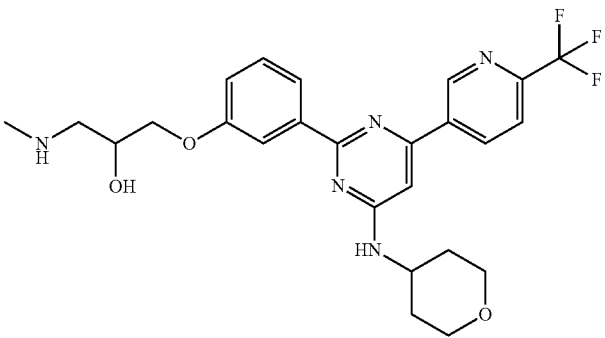 [SMILES: CNCC(O)COc1cccc(-c2nc(NC3CCOCC3)cc(-c3ccc(C(F)(F)F)nc3)n2)c1] | 503.9 |
| 655-1a | 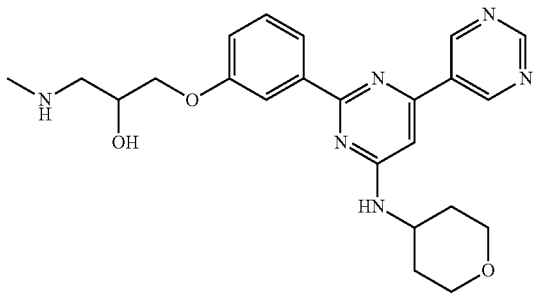 [SMILES: CNCC(O)COc1cccc(-c2nc(NC3CCOCC3)cc(-c3cncnc3)n2)c1] | 437.0 |
| 656-1a | 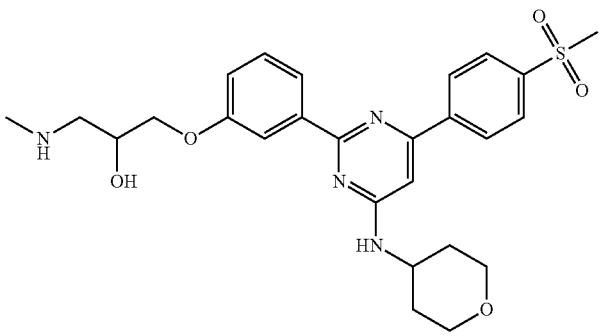 | 512.9 |
| 657-1a | 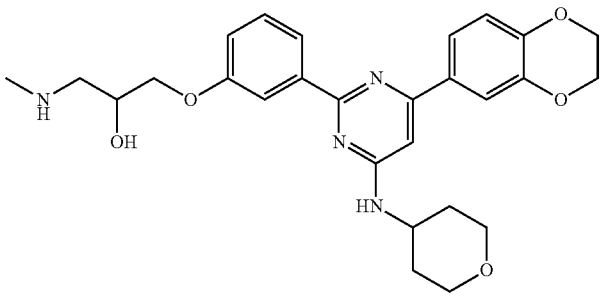 [SMILES: CNCC(O)COc1cccc(-c2nc(NC3CCOCC3)cc(-c3ccc4c(c3)OCCO4)n2)c1] | 492.9 |

TABLE 1B-continued

Exemplary Compounds

| # | Structure | LC-MS m/z (M + H) |
|---|---|---|
| 658-1a | 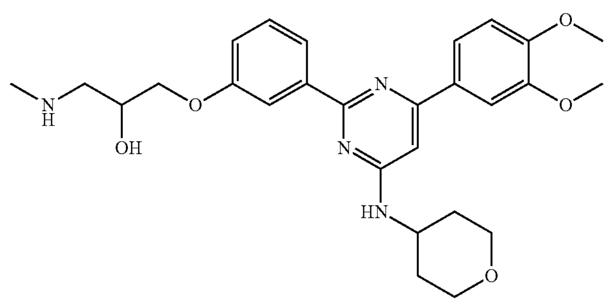 | 494.9 |
| 659-1a | 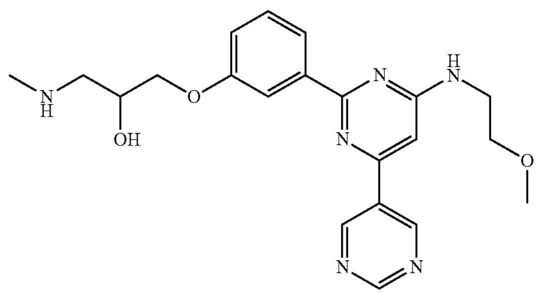 | 410.9 |
| 660-1a | 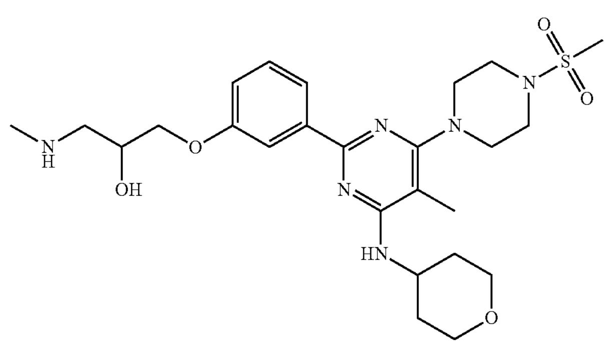 | 535.3 |
| 661-1a | 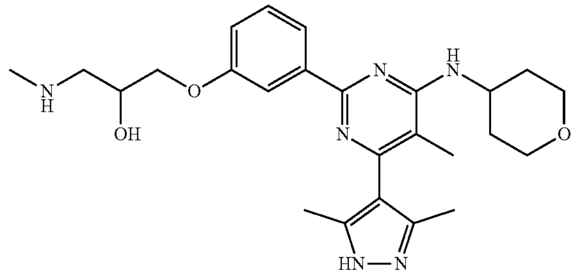 [SMILES: CNCC(O)COc1cccc(-c2nc(NC3CCOCC3)c(C)c(-c3c(C)n[nH]c3C)n2)c1] | 467.4 |

TABLE 1B-continued

Exemplary Compounds

| # | Structure | LC-MS m/z (M + H) |
|---|---|---|
| 662-1a | 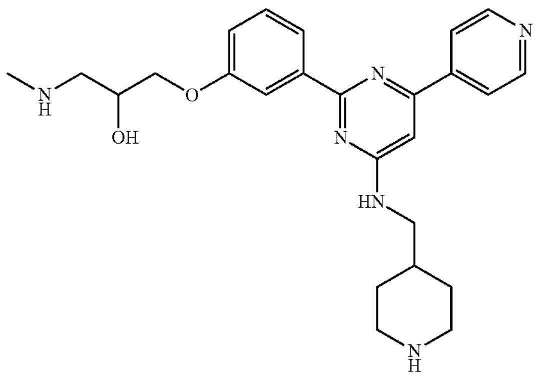 [SMILES: CNCC(O)COc1cccc(-c2nc(NCC3CCNCC3)cc(-c3ccncc3)n2)c1] | 449.0 |
| 663-1a | 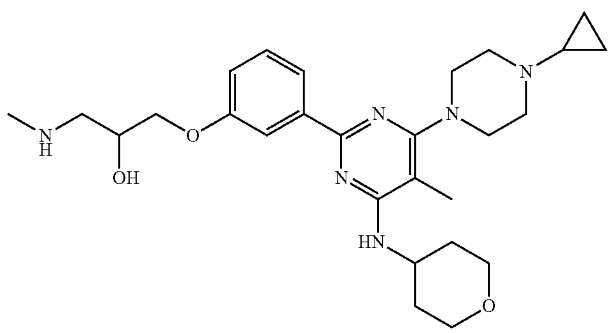 [SMILES: CNCC(O)COc1cccc(-c2nc(NC3CCOCC3)c(C)c(N3CCN(C4CC4)CC3)n2)c1] | 497.4 |
| 664-1a | 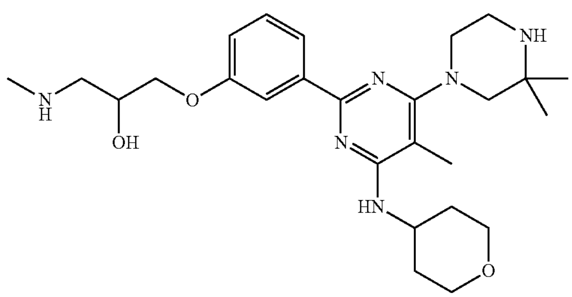 | 485.4 |
| 665-1a | 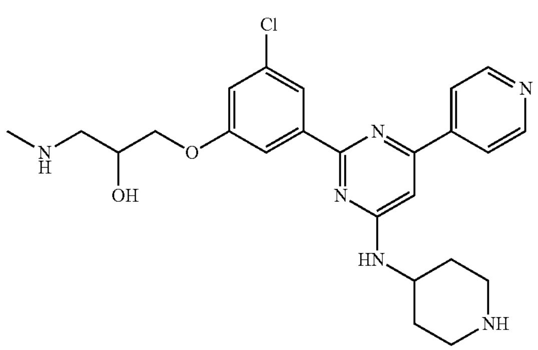 [SMILES: CNCC(O)COc1cc(Cl)cc(-c2nc(NC3CCNCC3)cc(-c3ccncc3)n2)c1] | 469.3 |

TABLE 1B-continued

Exemplary Compounds

| # | Structure | LC-MS m/z (M + H) |
|---|---|---|
| 666-1a | 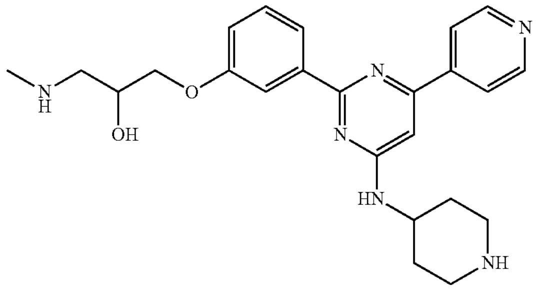 [SMILES: CNCC(O)COc1cccc(-c2nc(NC3CCNCC3)cc(-c3ccncc3)n2)c1] | 435.4 |
| 667-1a | 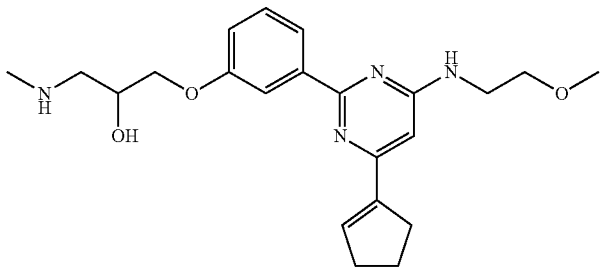 | 398.9 |
| 668-1a | 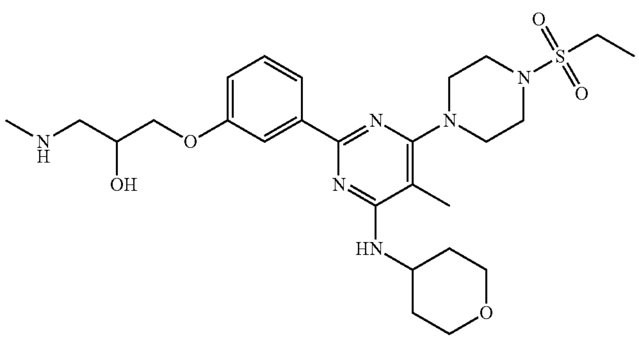 [SMILES: CCS(=O)(=O)N1CCN(c2nc(-c3cccc(OCC(O)CNC)c3)nc(NC3CCOCC3)c2C)CC1] | 549.3 |
| 669-1a | 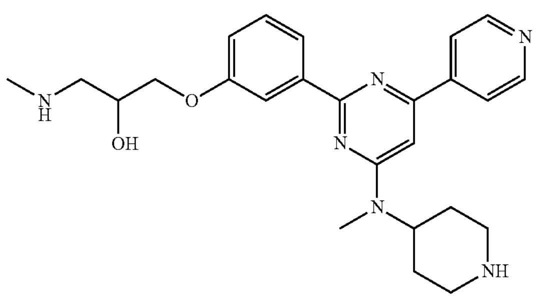 [SMILES: CNCC(O)COc1cccc(-c2nc(-c3ccncc3)cc(N(C)C3CCNCC3)n2)c1] | 449.0 |
| 670-1a | 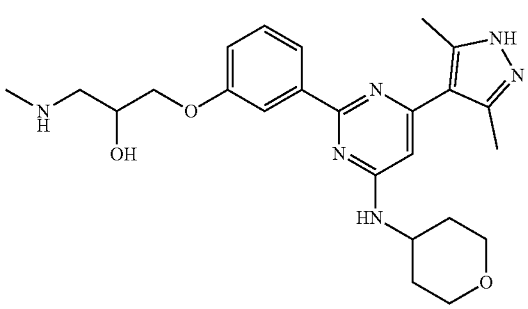 [SMILES: CNCC(O)COc1cccc(-c2nc(NC3CCOCC3)cc(-c3c(C)n[nH]c3C)n2)c1] | 453.4 |

TABLE 1B-continued

Exemplary Compounds

| # | Structure | LC-MS m/z (M + H) |
|---|---|---|
| 671-1a | 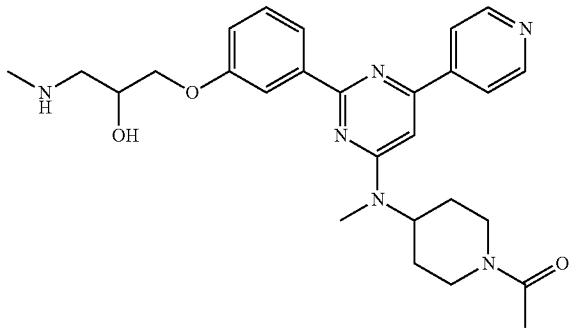 [SMILES: CNCC(O)COc1cccc(-c2nc(-c3ccncc3)cc(N(C)C3CCN(C(C)=O)CC3)n2)c1] | 491.0 |
| 672-1a | 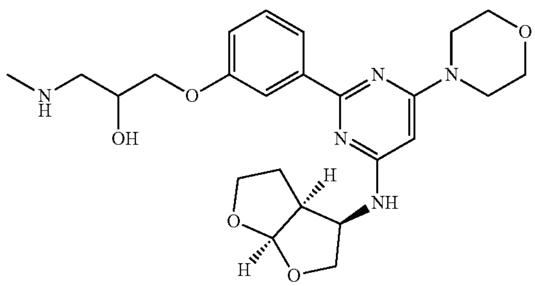 [SMILES: CNCC(O)COc1cccc(-c2nc(N[C@H]3CO[C@H]4OCC[C@H]43)cc(N3CCOCC3)n2)c1] | 472.3 |
| 673-1a | 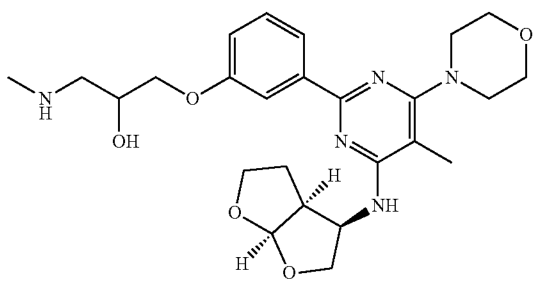 [SMILES: CNCC(O)COc1cccc(-c2nc(N[C@H]3CO[C@H]4OCC[C@H]43)c(C)c(N3CCOCC3)n2)c1] | 486.3 |
| 674-1a | 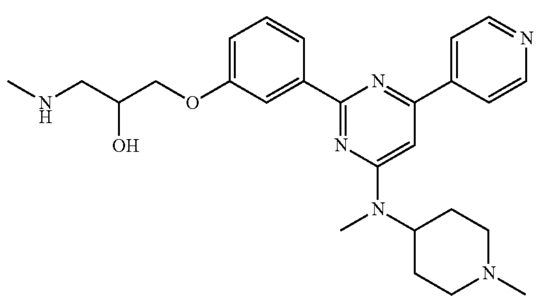 [SMILES: CNCC(O)COc1cccc(-c2nc(-c3ccncc3)cc(N(C)C3CCN(C)CC3)n2)c1] | 463.0 |
| 675-1a | 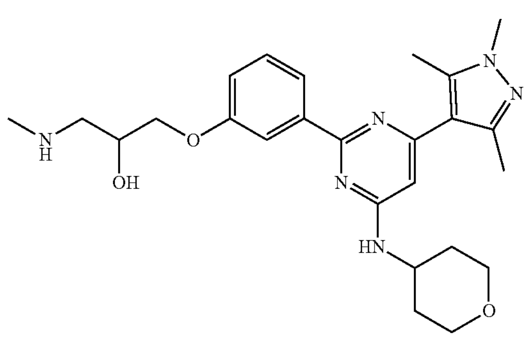 [SMILES: CNCC(O)COc1cccc(-c2nc(NC3CCOCC3)cc(-c3c(C)nn(C)c3C)n2)c1] | 467.4 |

TABLE 1B-continued
Exemplary Compounds
| # | Structure | LC-MS m/z (M + H) |
|---|-----------|-------------------|
| 676-1a | 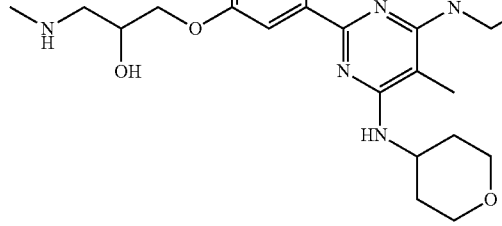 | 416.4 |
| 677-1a | 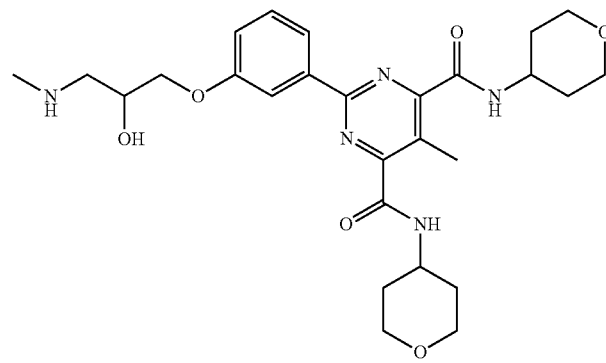 [SMILES: CNCC(O)COc1cccc(-c2nc(C(=O)NC3CCOCC3)c(C)c(C(=O)NC3CCOCC3)n2)c1] | 528.2 |
| 678-1a | 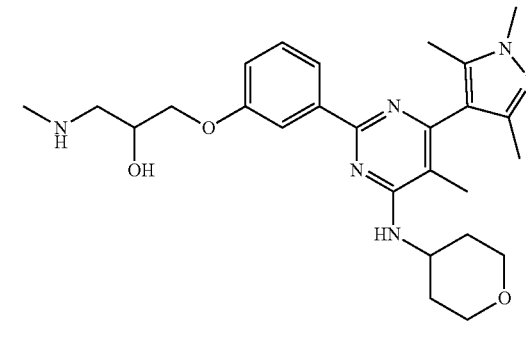 | 481.0 |
| 679-1a | 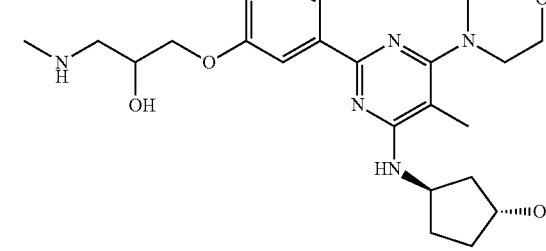 | 458.0 |
| 680-1a | 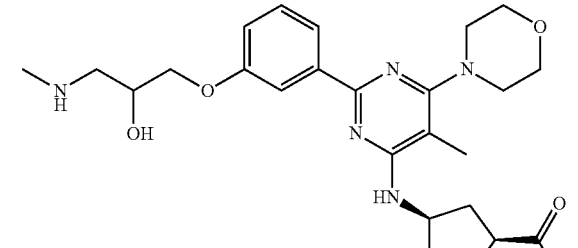 | 499.4 |

TABLE 1B-continued

Exemplary Compounds

| # | Structure | LC-MS m/z (M + H) |
|---|-----------|-------------------|
| 681-1a | 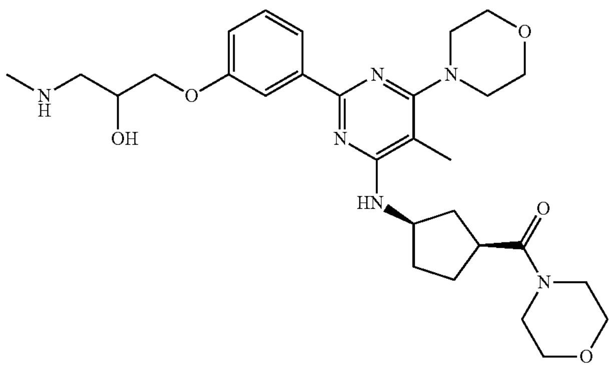 [SMILES: CNCC(O)COc1cccc(-c2nc(N[C@@H]3CC[C@H](C(=O)N4CCOCC4)C3)c(C)c(N3CCOCC3)n2)c1] | 555.4 |
| 682-1a | 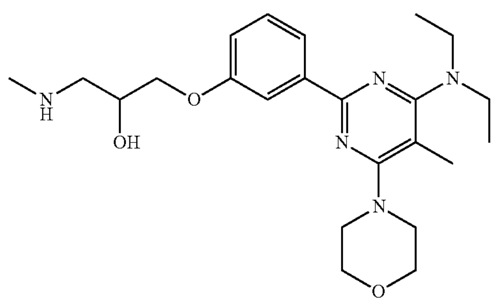 [SMILES: CCN(CC)c1nc(-c2cccc(OCC(O)CNC)c2)nc(N2CCOCC2)c1C] | 430.3 |
| 683-1a | 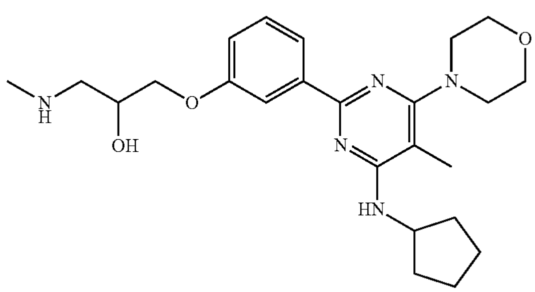 [SMILES: CNCC(O)COc1cccc(-c2nc(NC3CCCC3)c(C)c(N3CCOCC3)n2)c1] | 442.3 |
| 684-1a | 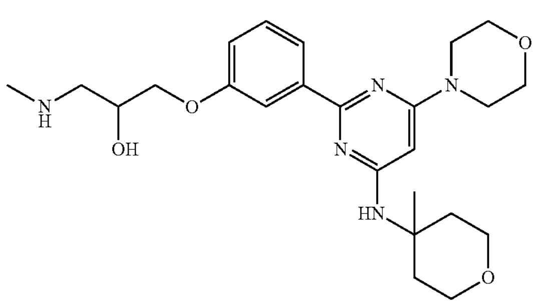 [SMILES: CNCC(O)COc1cccc(-c2nc(NC3(C)CCOCC3)cc(N3CCOCC3)n2)c1] | 458.3 |

TABLE 1B-continued

Exemplary Compounds

| # | Structure | LC-MS m/z (M + H) |
|---|---|---|
| 685-1a | 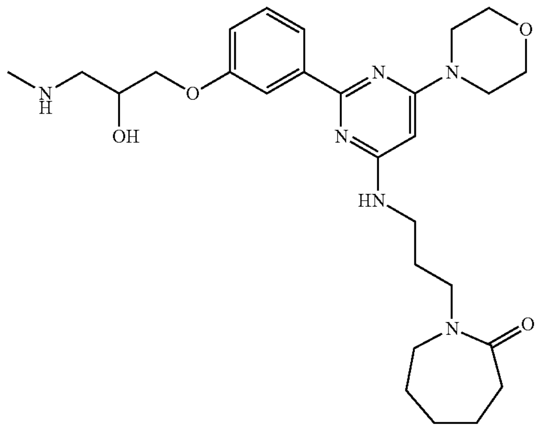 [SMILES: CNCC(O)COc1cccc(-c2nc(NCCCN3CCCCCC3=O)cc(N3CCOCC3)n2)c1] | 513.3 |
| 686-1a | 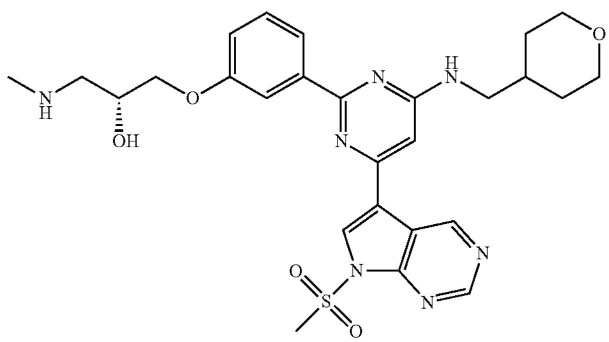 [SMILES: CNC[C@@H](O)COc1cccc(-c2nc(NCC3CCOCC3)cc(-c3cn(S(C)(=O)=O)c4ncncc34)n2)c1] | 567.8 |
| 687-1a | 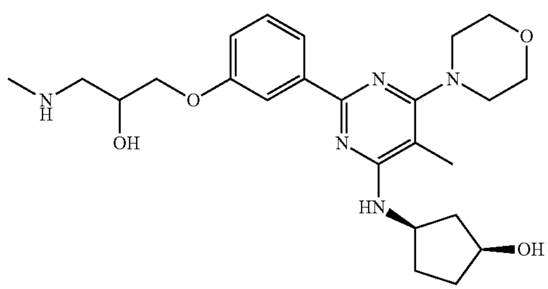 [SMILES: CNCC(O)COc1cccc(-c2nc(N[C@@H]3CC[C@H](O)C3)c(C)c(N3CCOCC3)n2)c1] | 458.3 |

TABLE 1C

Exemplary Compounds

| # | Structure | LC-MS m/z (M + H) |
|---|---|---|
| 1-3 | 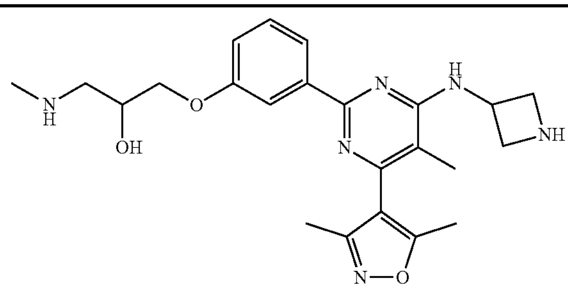 | 439.00 |

TABLE 1C-continued

Exemplary Compounds

| # | Structure | LC-MS m/z (M + H) |
|---|-----------|-------------------|
| 2-3 | 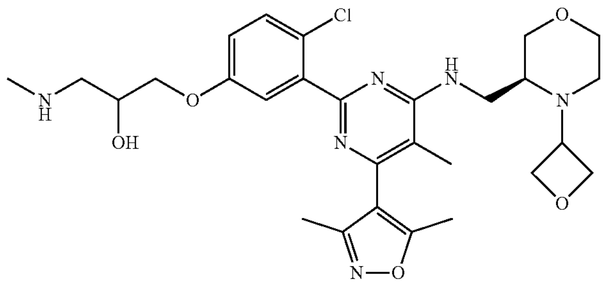 [SMILES: CNCC(O)COc1ccc(Cl)c(-c2nc(NC[C@H]3COCCN3C3COC3)c(C)c(-c3c(C)noc3C)n2)c1] | 573.20 |
| 3-3 | 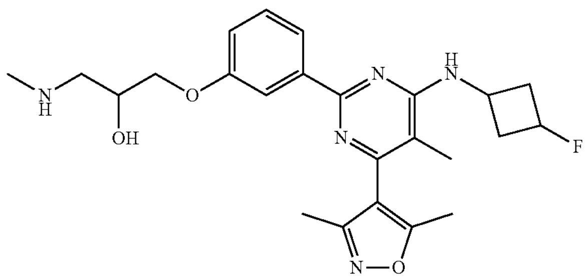 [SMILES: CNCC(O)COc1cccc(-c2nc(NC3CC(F)C3)c(C)c(-c3c(C)noc3C)n2)c1] | 456.00 |
| 4-3 | 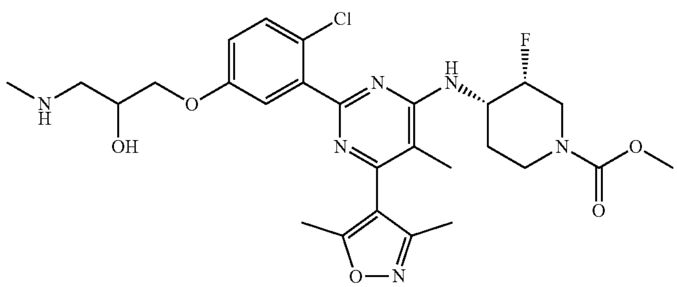 | 577.00 |
| 5-3 | 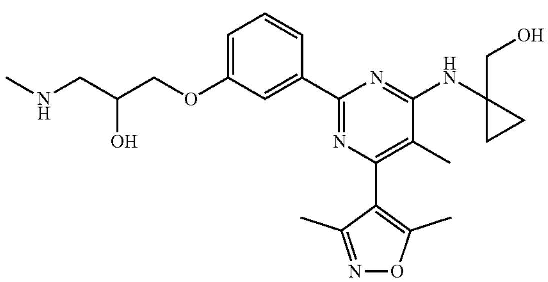 [SMILES: CNCC(O)COc1cccc(-c2nc(NC3(CO)CC3)c(C)c(-c3c(C)noc3C)n2)c1] | 454.20 |
| 6-3 | 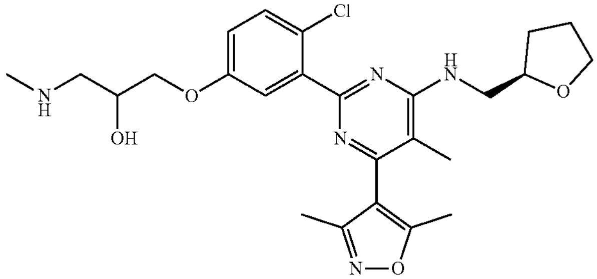 [SMILES: CNCC(O)COc1ccc(Cl)c(-c2nc(NC[C@H]3CCCO3)c(C)c(-c3c(C)noc3C)n2)c1] | 502.20 |

TABLE 1C-continued

Exemplary Compounds

| # | Structure | LC-MS m/z (M + H) |
|---|---|---|
| 7-3 | 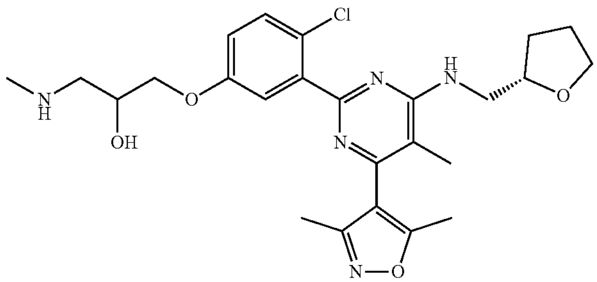 [SMILES: CNCC(O)COc1ccc(Cl)c(-c2nc(NC[C@@H]3CCCO3)c(C)c(-c3c(C)noc3C)n2)c1] | 502.20 |
| 8-3 | 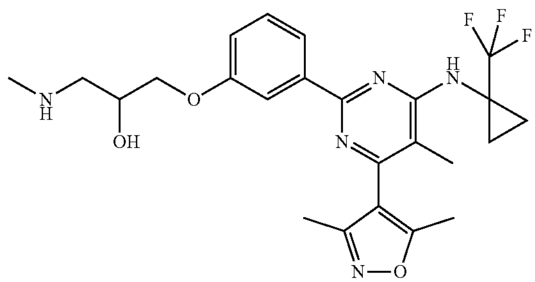 [SMILES: CNCC(O)COc1cccc(-c2nc(NC3(C(F)(F)F)CC3)c(C)c(-c3c(C)noc3C)n2)c1] | 492.30 |
| 9-3 | 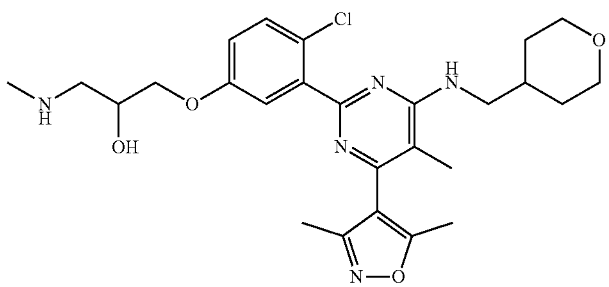 [SMILES: CNCC(O)COc1ccc(Cl)c(-c2nc(NCC3CCOCC3)c(C)c(-c3c(C)noc3C)n2)c1] | 516.30 |
| 10-3 | 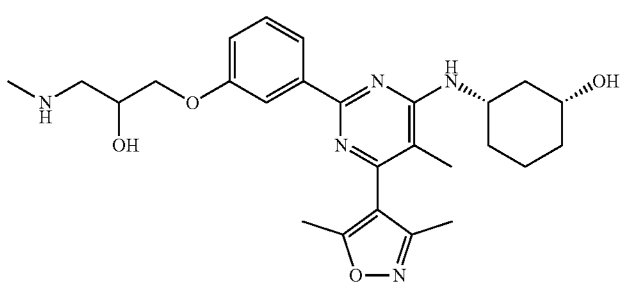 [SMILES: CNCC(O)COc1cccc(-c2nc(N[C@H]3CCC[C@@H](O)C3)c(C)c(-c3c(C)noc3C)n2)c1] | 482.00 |
| 11-3 | 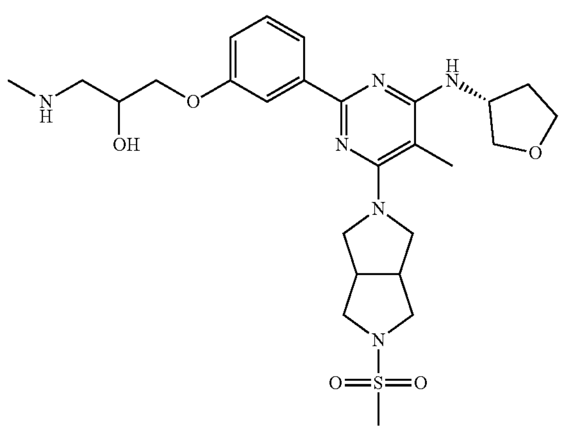 [SMILES: CNCC(O)COc1cccc(-c2nc(N[C@@H]3CCOC3)c(C)c(N3CC4CN(S(C)(=O)=O)CC4C3)n2)c1] | 547.2 |

TABLE 1C-continued

Exemplary Compounds

| # | Structure | LC-MS m/z (M + H) |
|---|-----------|-------------------|
| 12-3 | | 497.20 |
| 13-3 | | 510.20 |
| 14-3 | | 495.10 |
| 15-3 | | 539.30 |
| 16-3 | | 557.30 |

TABLE 1C-continued

Exemplary Compounds

| # | Structure | LC-MS m/z (M + H) |
|---|---|---|
| 17-3 | 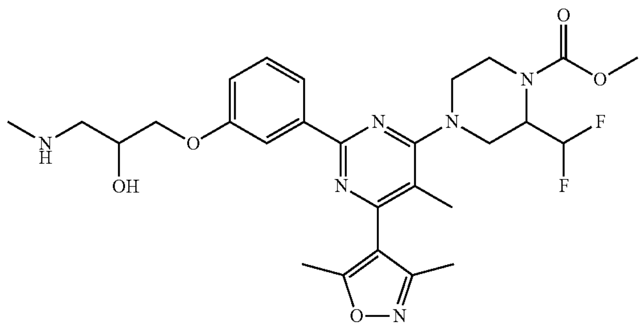 | 560.90 |
| 18-3 | 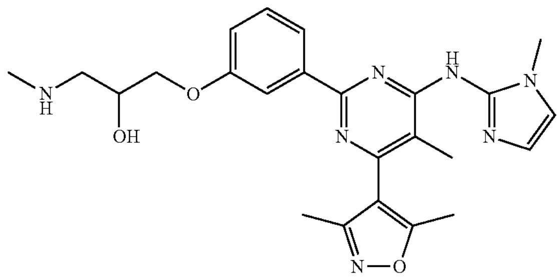 [SMILES: CNCC(O)COc1cccc(-c2nc(Nc3nccn3C)c(C)c(-c3c(C)noc3C)n2)c1] | 464.30 |
| 19-3 | 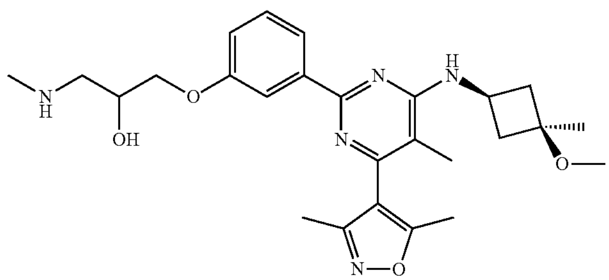 | 482.30 |
| 20-3 | 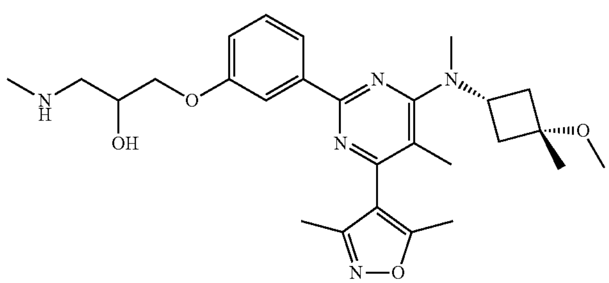 | 496.30 |
| 21-3 | 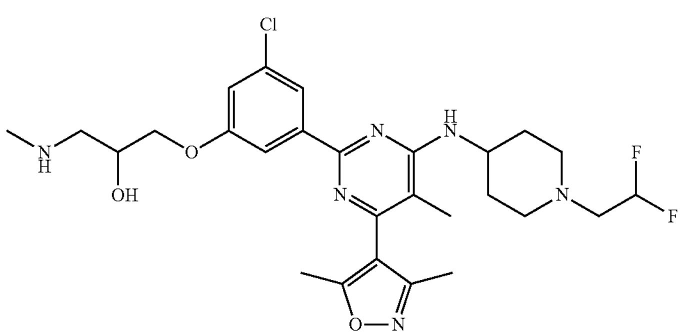 [SMILES: CNCC(O)COc1cc(Cl)cc(-c2nc(NC3CCN(CC(F)F)CC3)c(C)c(-c3c(C)noc3C)n2)c1] | 565.30 |

TABLE 1C-continued

Exemplary Compounds

| # | Structure | LC-MS m/z (M + H) |
|---|-----------|-------------------|
| 22-3 | 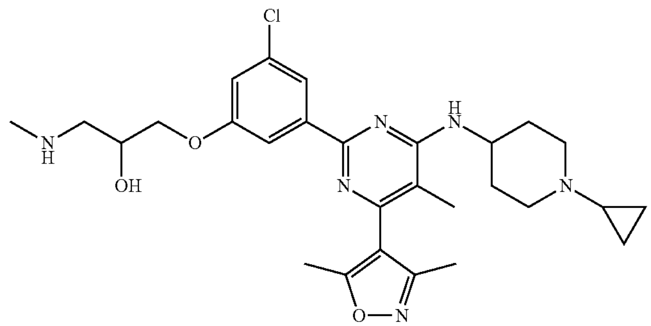 [SMILES: CNCC(O)COc1cc(Cl)cc(-c2nc(NC3CCN(C4CC4)CC3)c(C)c(-c3c(C)noc3C)n2)c1] | 541.30 |
| 23-3 | 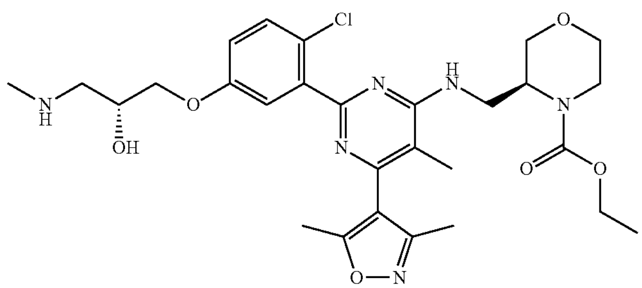 [SMILES: CCOC(=O)N1CCOC[C@@H]1CNc1nc(-c2cc(OC[C@H](O)CNC)ccc2Cl)nc(-c2c(C)noc2C)c1C] | 589.30 |
| 24-3 | 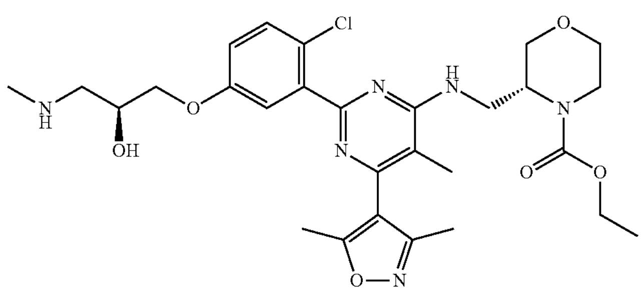 [SMILES: CCOC(=O)N1CCOC[C@H]1CNc1nc(-c2cc(OC[C@@H](O)CNC)ccc2Cl)nc(-c2c(C)noc2C)c1C] | 589.20 |
| 25-3 | 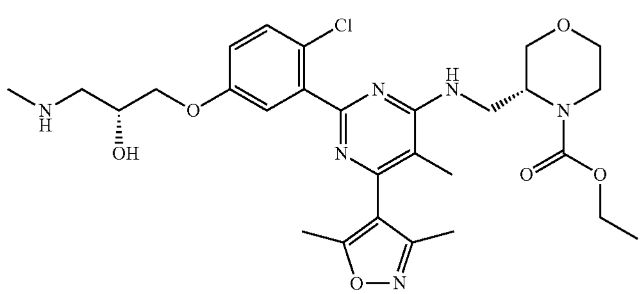 [SMILES: CCOC(=O)N1CCOC[C@H]1CNc1nc(-c2cc(OC[C@H](O)CNC)ccc2Cl)nc(-c2c(C)noc2C)c1C] | 589.30 |
| 26-3 | 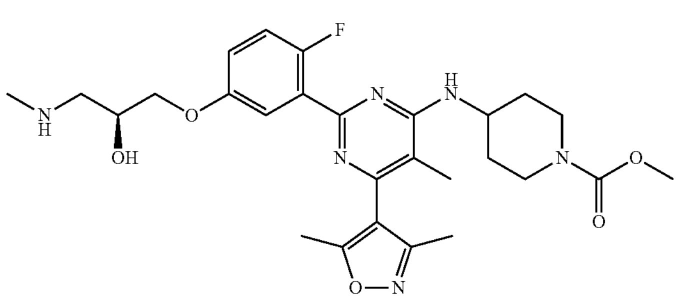 | 543.20 |

US 10,118,931 B2
435                                                                                                        436
TABLE 1C-continued
Exemplary Compounds
| # | Structure | LC-MS m/z (M + H) |
|---|-----------|-------------------|
| 27-3 | 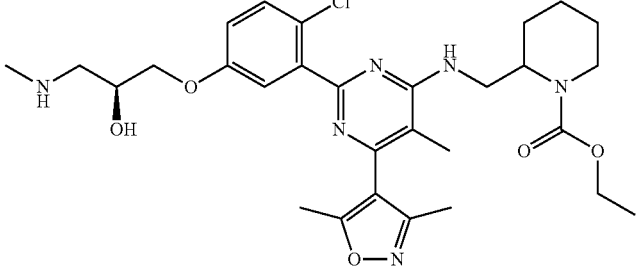 | 587.30 |
| 28-3 | 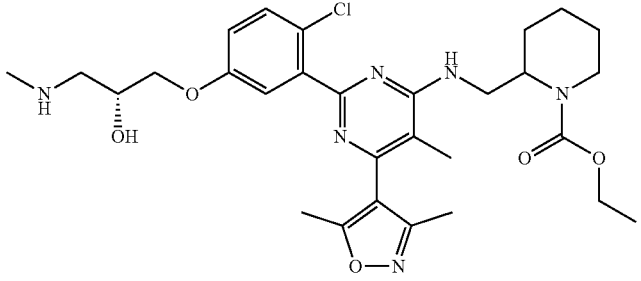 [SMILES: CCOC(=O)N1CCCCC1CNc1nc(-c2cc(OC[C@H](O)CNC)ccc2Cl)nc(-c2c(C)noc2C)c1C] | 587.30 |
| 29-3 | 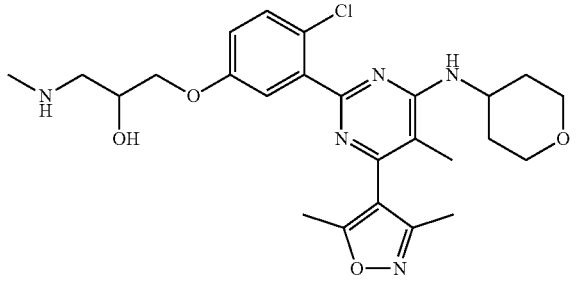 [SMILES: CNCC(O)COc1ccc(Cl)c(-c2nc(NC3CCOCC3)c(C)c(-c3c(C)noc3C)n2)c1] | 502.20 |
| 30-3 | 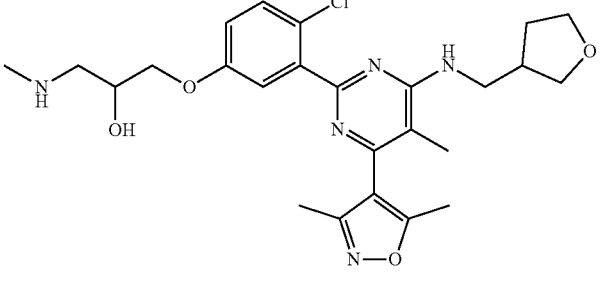 | 502.20 |
| 31-3 | 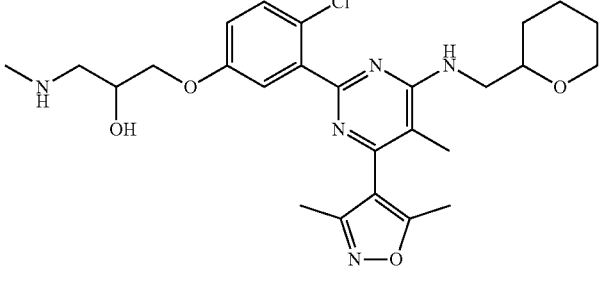 | 516.30 |

TABLE 1C-continued
Exemplary Compounds
| # | Structure | LC-MS m/z (M + H) |
|---|---|---|
| 32-3 | 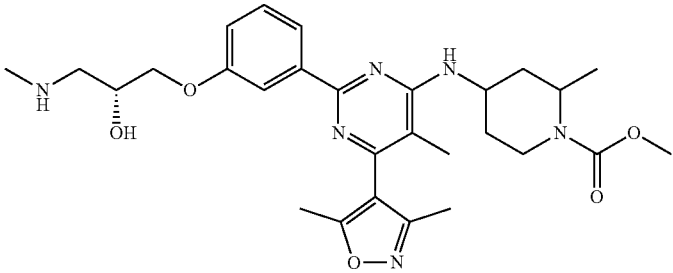 | 539.30 |
| 33-3 | 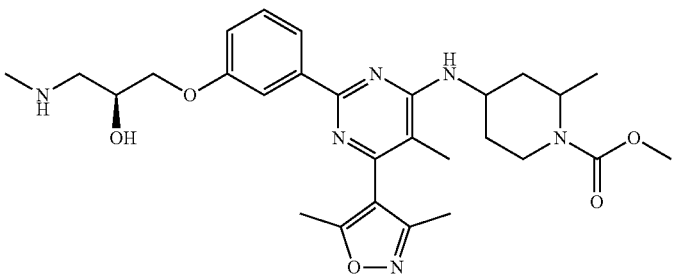 | 539.30 |
| 34-3 | 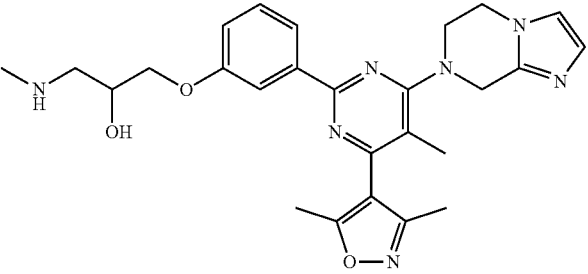 [SMILES: CNCC(O)COc1cccc(-c2nc(-c3c(C)noc3C)c(C)c(N3CCn4ccnc4C3)n2)c1] | 490.00 |
| 35-3 | 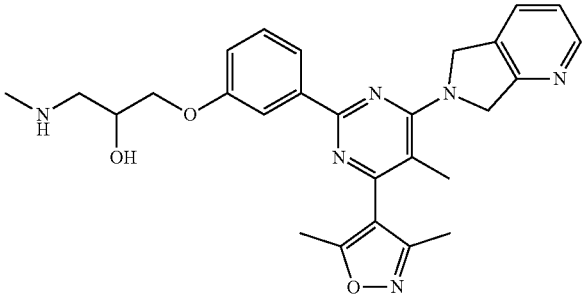 [SMILES: CNCC(O)COc1cccc(-c2nc(-c3c(C)noc3C)c(C)c(N3Cc4cccnc4C3)n2)c1] | 487.00 |
| 36-3 | 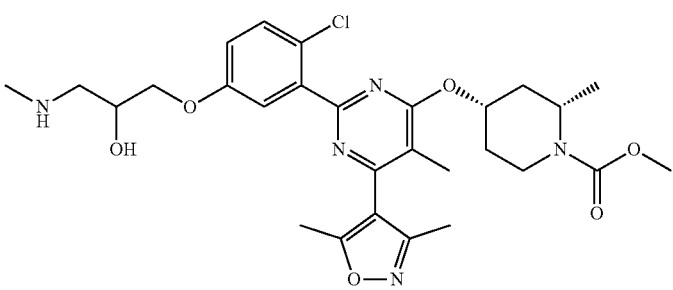 | 574.20 |

TABLE 1C-continued

Exemplary Compounds

| # | Structure | LC-MS m/z (M + H) |
|---|---|---|
| 37-3 | 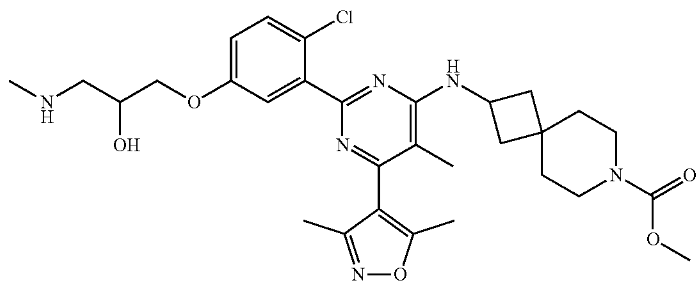 [SMILES: CNCC(O)COc1ccc(Cl)c(-c2nc(NC3CC4(CCN(C(=O)OC)CC4)C3)c(C)c(-c3c(C)noc3C)n2)c1] | 599.00 |
| 38-3 | 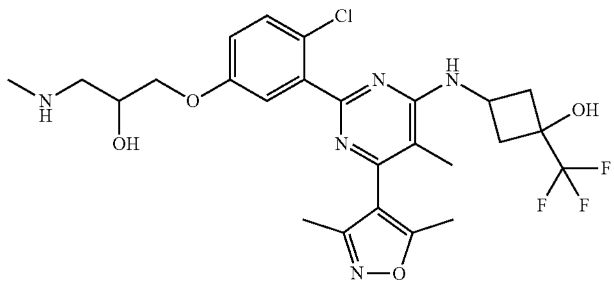 [SMILES: CNCC(O)COc1ccc(Cl)c(-c2nc(NC3CC(O)(C(F)(F)F)C3)c(C)c(-c3c(C)noc3C)n2)c1] | 556.00 |
| 39-3 | 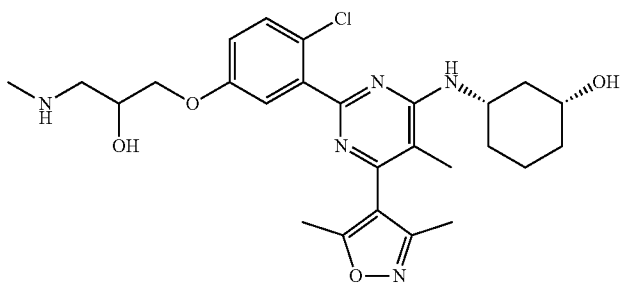 [SMILES: CNCC(O)COc1ccc(Cl)c(-c2nc(N[C@H]3CCC[C@@H](O)C3)c(C)c(-c3c(C)noc3C)n2)c1] | 516.30 |
| 40-3 | 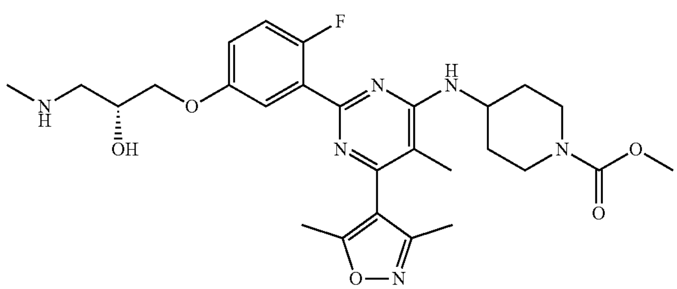 | 543.30 |
| 41-3 | 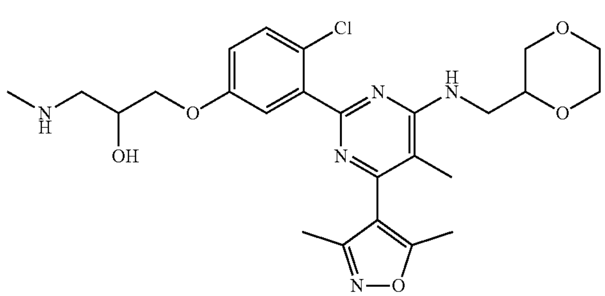 [SMILES: CNCC(O)COc1ccc(Cl)c(-c2nc(NCC3COCCO3)c(C)c(-c3c(C)noc3C)n2)c1] | 518.00 |

TABLE 1C-continued

Exemplary Compounds

| # | Structure | LC-MS m/z (M + H) |
|---|-----------|-------------------|
| 42-3 | 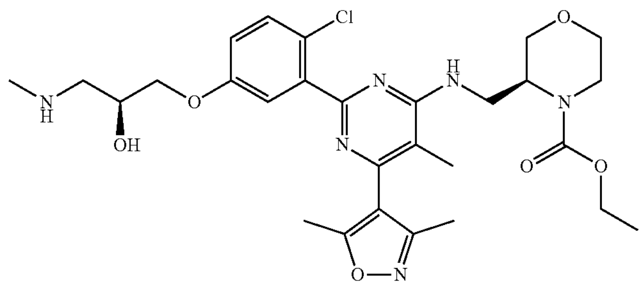 [SMILES: CCOC(=O)N1CCOC[C@@H]1CNc1nc(-c2cc(OC[C@@H](O)CNC)ccc2Cl)nc(-c2c(C)noc2C)c1C] | 589.20 |
| 43-3 | 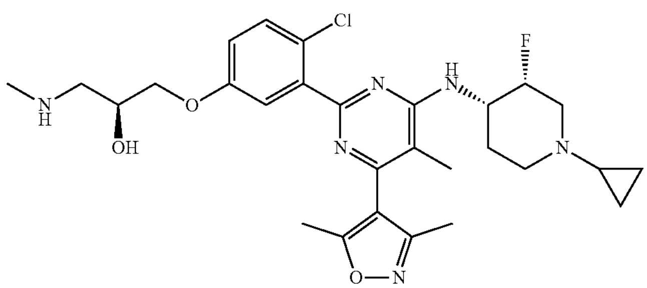 | 559.20 |
| 44-3 | 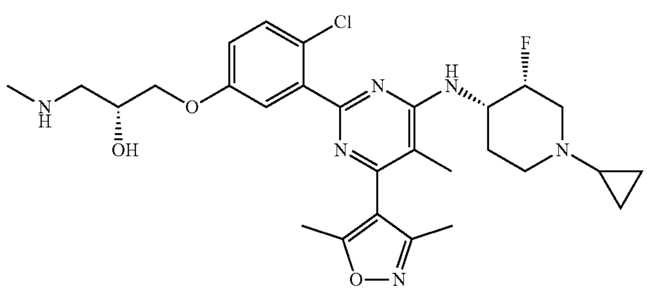 [SMILES: CNC[C@@H](O)COc1ccc(Cl)c(-c2nc(N[C@H]3CCN(C4CC4)C[C@H]3F)c(C)c(-c3c(C)noc3C)n2)c1] | 559.20 |
| 45-3 | 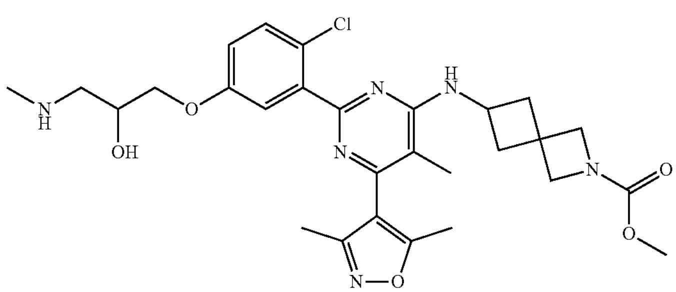 | 571.00 |
| 46-3 | 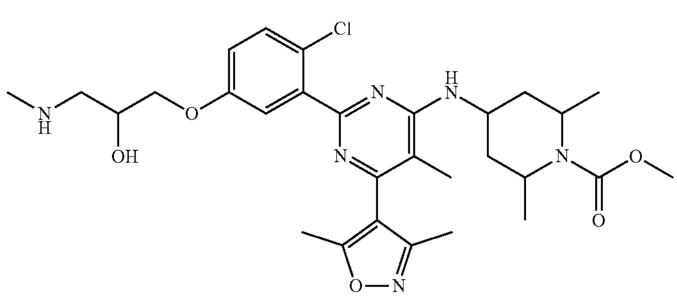 | 586.90 |

TABLE 1C-continued

Exemplary Compounds

| # | Structure | LC-MS m/z (M + H) |
|---|-----------|-------------------|
| 47-3 | 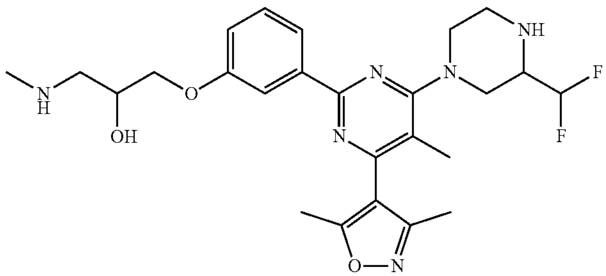 [SMILES: CNCC(O)COc1cccc(-c2nc(-c3c(C)noc3C)c(C)c(N3CCNC(C(F)F)C3)n2)c1] | 503.00 |
| 48-3 | 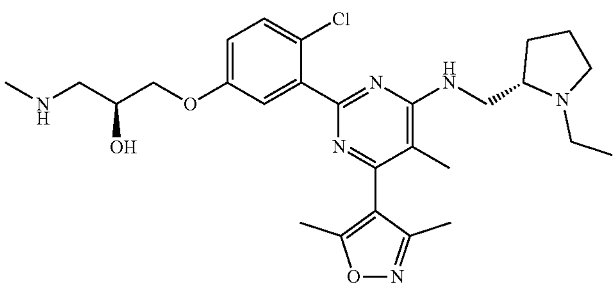 [SMILES: CCN1CCC[C@H]1CNc1nc(-c2cc(OC[C@@H](O)CNC)ccc2Cl)nc(-c2c(C)noc2C)c1C] | 529.00 |
| 49-3 | 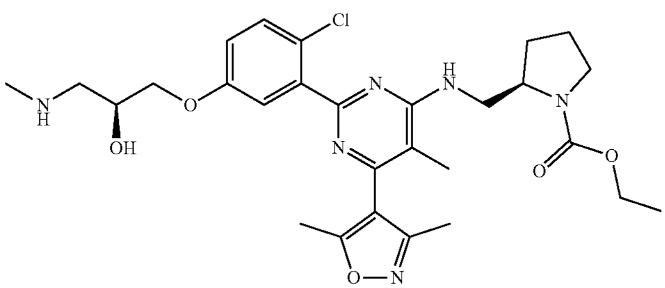 [SMILES: CCOC(=O)N1CCC[C@@H]1CNc1nc(-c2cc(OC[C@@H](O)CNC)ccc2Cl)nc(-c2c(C)noc2C)c1C] | 573.00 |
| 50-3 | 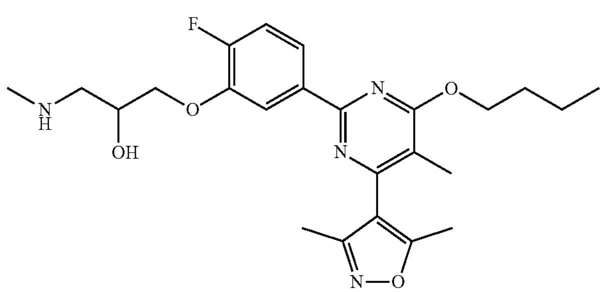 [SMILES: CCCCOc1nc(-c2ccc(F)c(OCC(O)CNC)c2)nc(-c2c(C)noc2C)c1C] | 459.20 |
| 51-3 | 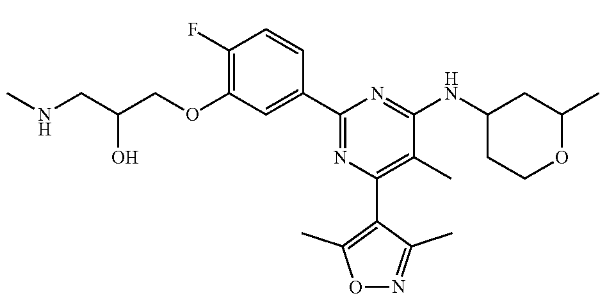 | 500.30 |

TABLE 1C-continued

Exemplary Compounds

| # | Structure | LC-MS m/z (M + H) |
|---|-----------|-------------------|
| 52-3 | 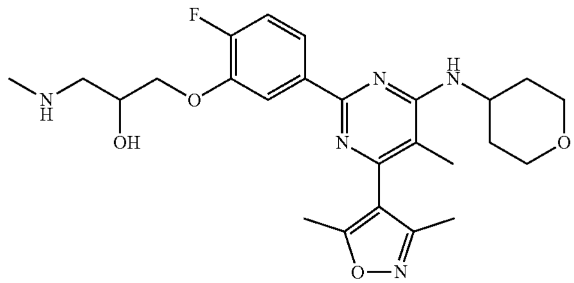 [SMILES: CNCC(O)COc1cc(-c2nc(NC3CCOCC3)c(C)c(-c3c(C)noc3C)n2)ccc1F] | 486.20 |
| 53-3 | 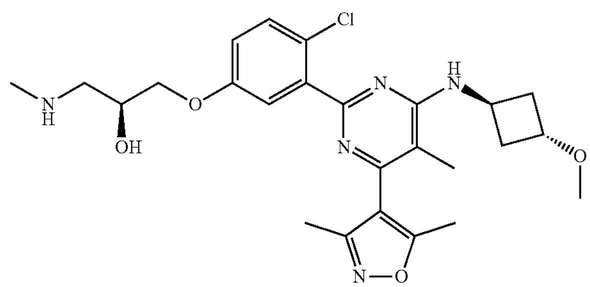 | 502.00 |
| 54-3 | 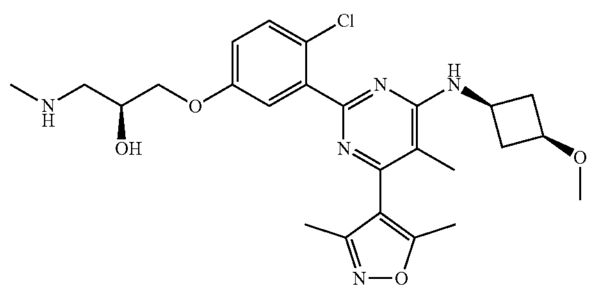 | 502.00 |
| 55-3 | 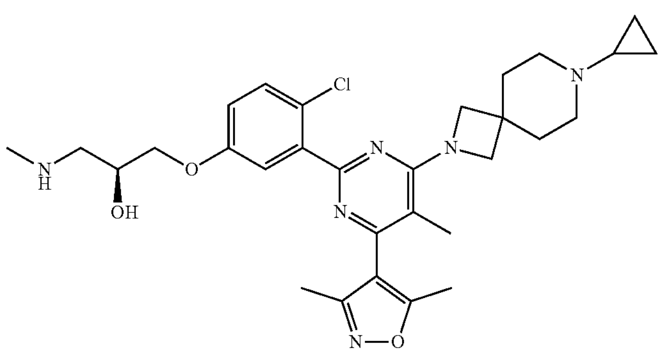 [SMILES: CNC[C@H](O)COc1ccc(Cl)c(-c2nc(-c3c(C)noc3C)c(C)c(N3CC4(CCN(C5CC5)CC4)C3)n2)c1] | 567.30 |
| 56-3 | 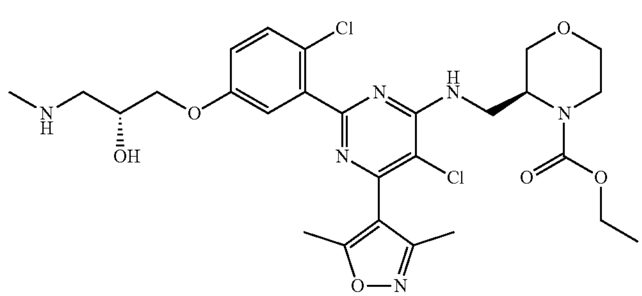 [SMILES: CCOC(=O)N1CCOC[C@@H]1CNc1nc(-c2cc(OC[C@H](O)CNC)ccc2Cl)nc(-c2c(C)noc2C)c1Cl] | 609.20 |

TABLE 1C-continued

Exemplary Compounds

| # | Structure | LC-MS m/z (M + H) |
|---|---|---|
| 57-3 | 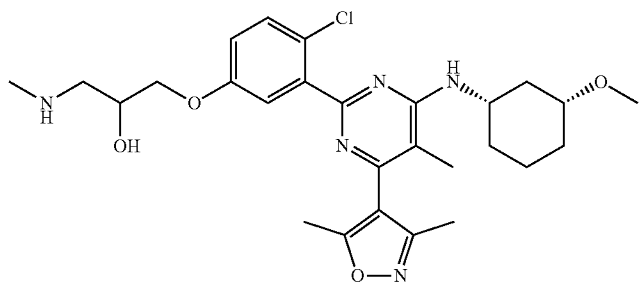 | 530.20 |
| 58-3 | 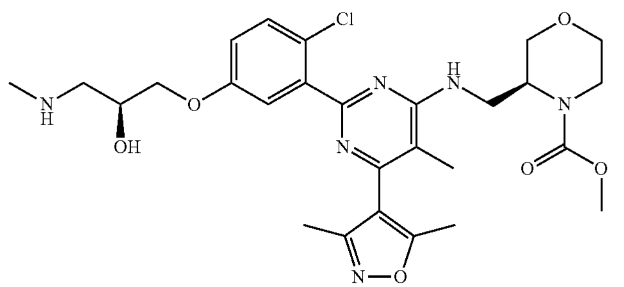 [SMILES: CNC[C@H](O)COc1ccc(Cl)c(-c2nc(NC[C@H]3COCCN3C(=O)OC)c(C)c(-c3c(C)noc3C)n2)c1] | 575.00 |
| 59-3 | 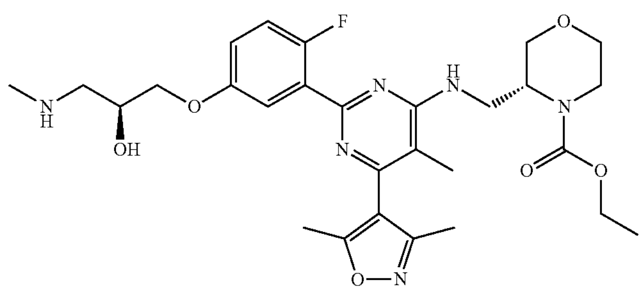 [SMILES: CCOC(=O)N1CCOC[C@H]1CNc1nc(-c2cc(OC[C@@H](O)CNC)ccc2F)nc(-c2c(C)noc2C)c1C] | 573.30 |
| 60-3 | 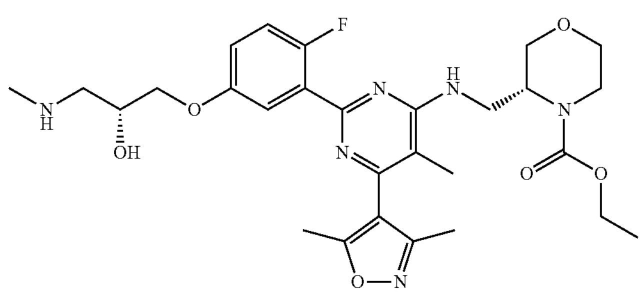 [SMILES: CCOC(=O)N1CCOC[C@H]1CNc1nc(-c2cc(OC[C@H](O)CNC)ccc2F)nc(-c2c(C)noc2C)c1C] | 573.30 |
| 61-3 | 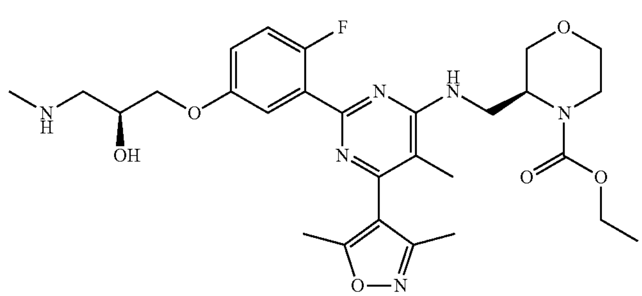 [SMILES: CCOC(=O)N1CCOC[C@@H]1CNc1nc(-c2cc(OC[C@@H](O)CNC)ccc2F)nc(-c2c(C)noc2C)c1C] | 573.30 |

TABLE 1C-continued

Exemplary Compounds

| # | Structure | LC-MS m/z (M + H) |
|---|---|---|
| 62-3 | 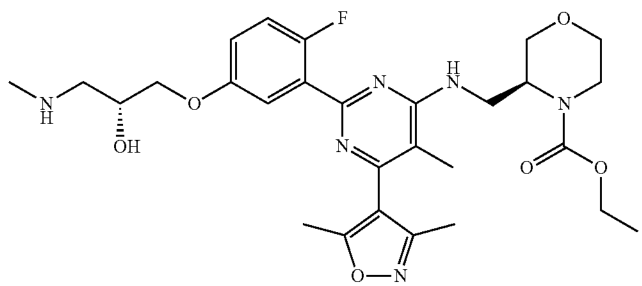 | 573.30 |
| 63-3 | 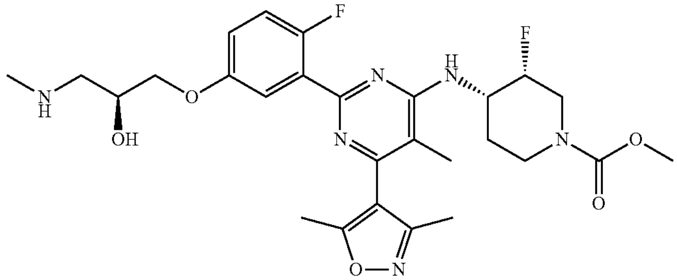 | 561.00 |
| 64-3 | 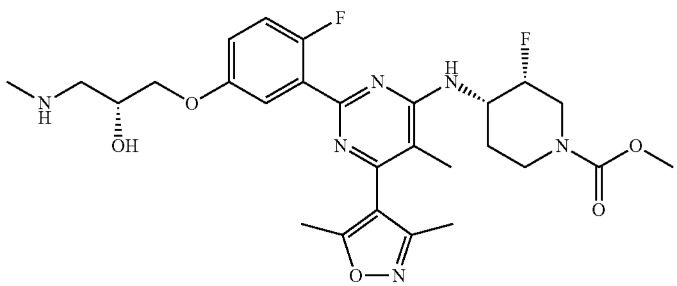 | 561.00 |
| 65-3 | 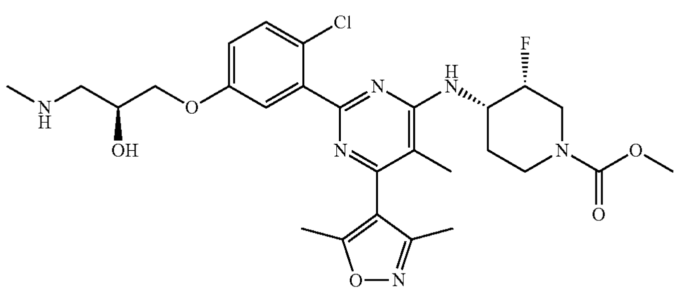 | 576.90 |
| 66-3 | 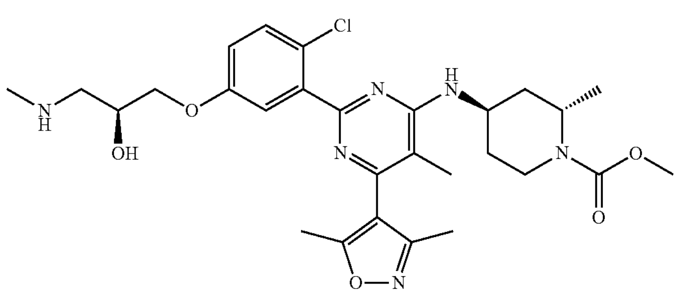 | 573.00 |

TABLE 1C-continued

Exemplary Compounds

| # | Structure | LC-MS m/z (M + H) |
|---|---|---|
| 67-3 | 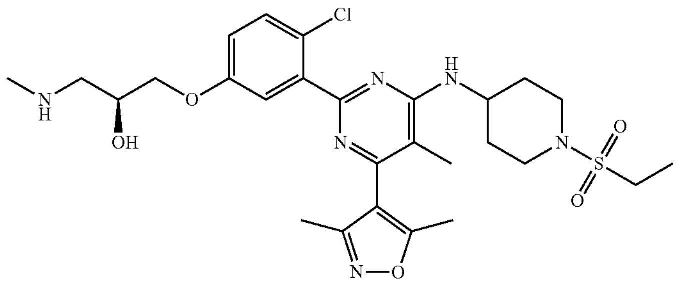 [SMILES: CCS(=O)(=O)N1CCC(Nc2nc(-c3cc(OC[C@@H](O)CNC)ccc3Cl)nc(-c3c(C)noc3C)c2C)CC1] | 593.20 |
| 68-3 | 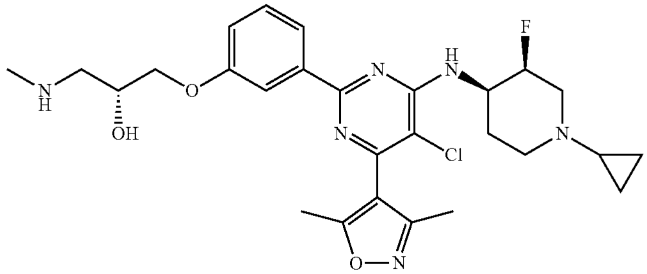 [SMILES: CNC[C@@H](O)COc1cccc(-c2nc(N[C@@H]3CCN(C4CC4)C[C@@H]3F)c(Cl)c(-c3c(C)noc3C)n2)c1] | 545.00 |
| 69-3 | 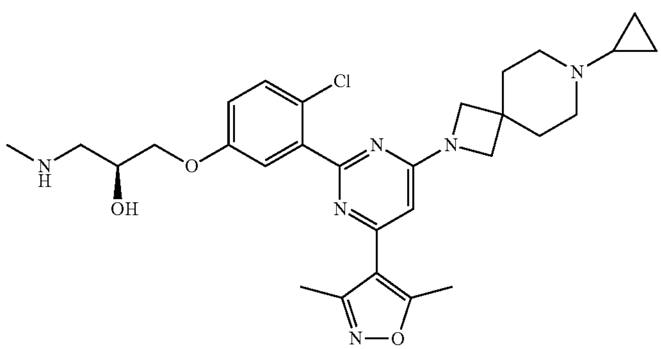 [SMILES: CNC[C@H](O)COc1ccc(Cl)c(-c2nc(-c3c(C)noc3C)cc(N3CC4(CCN(C5CC5)CC4)C3)n2)c1] | 553.30 |
| 70-3 | 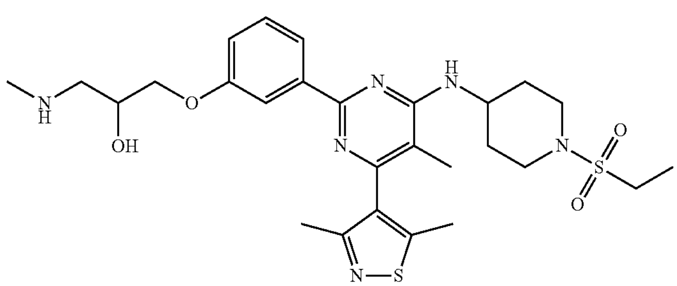 [SMILES: CCS(=O)(=O)N1CCC(Nc2nc(-c3cccc(OCC(O)CNC)c3)nc(-c3c(C)nsc3C)c2C)CC1] | 575.2 |
| 71-3 | 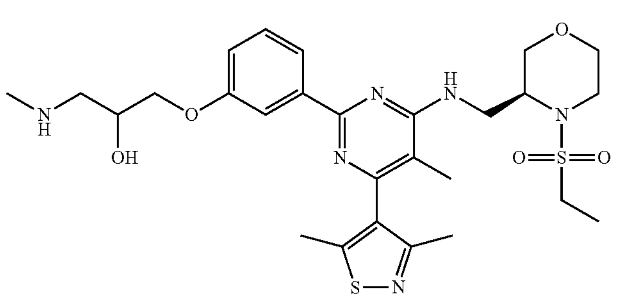 [SMILES: CCS(=O)(=O)N1CCOC[C@@H]1CNc1nc(-c2cccc(OCC(O)CNC)c2)nc(-c2c(C)nsc2C)c1C] | 591.2 |

TABLE 1C-continued
Exemplary Compounds
| # | Structure | LC-MS m/z (M + H) |
|---|---|---|
| 72-3 | 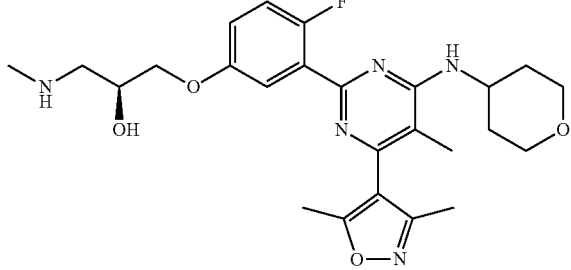 | 486.20 |
| 73-3 | 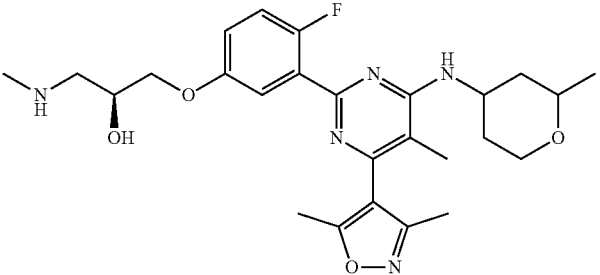 | 500.30 |
| 74-3 | 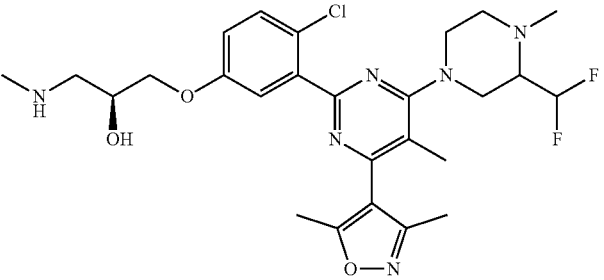 [SMILES: CNC[C@H](O)COc1ccc(Cl)c(-c2nc(-c3c(C)noc3C)c(C)c(N3CCN(C)C(C(F)F)C3)n2)c1] | 550.90 |
| 75-3 | 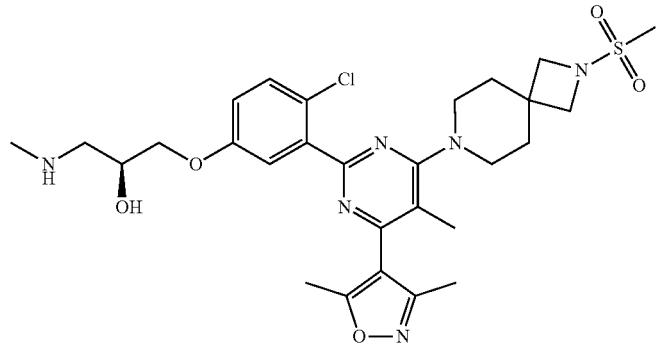 | 605.20 |
| 76-3 | 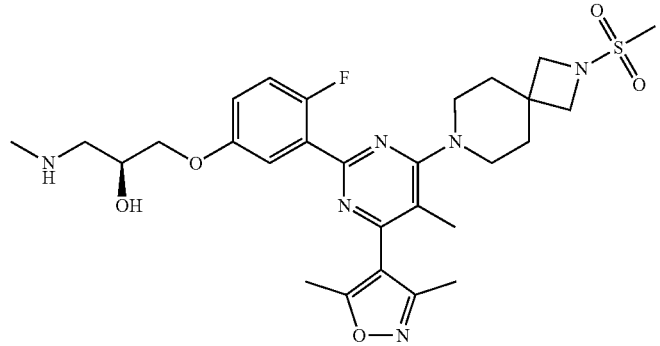 | 589.30 |

TABLE 1C-continued

Exemplary Compounds

| # | Structure | LC-MS m/z (M + H) |
|---|-----------|-------------------|
| 77-3 | 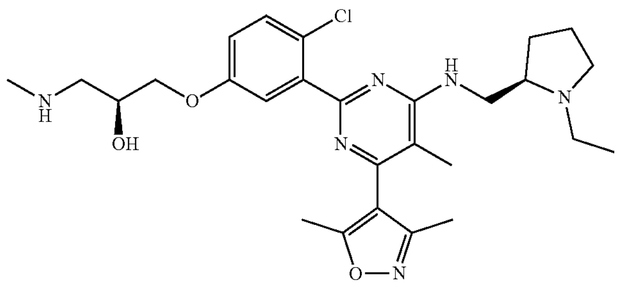 [SMILES: CCN1CCC[C@@H]1CNc1nc(-c2cc(OC[C@@H](O)CNC)ccc2Cl)nc(-c2c(C)noc2C)c1C] | 529.20 |
| 78-3 | 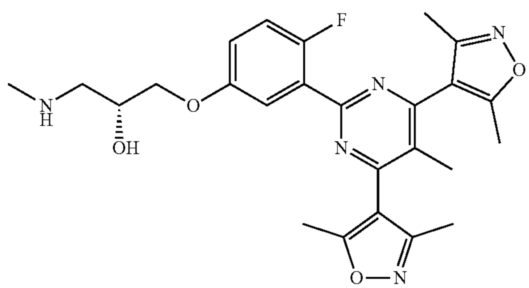 [SMILES: CNC[C@@H](O)COc1ccc(F)c(-c2nc(-c3c(C)noc3C)c(C)c(-c3c(C)noc3C)n2)c1] | 481.90 |
| 79-3 | 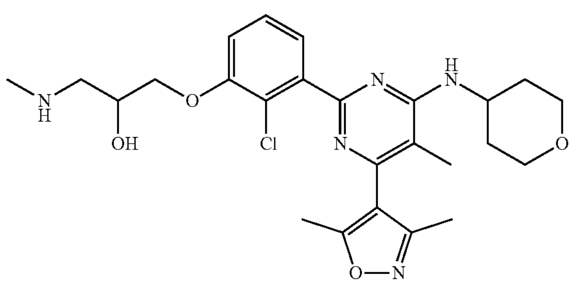 [SMILES: CNCC(O)COc1cccc(-c2nc(NC3CCOCC3)c(C)c(-c3c(C)noc3C)n2)c1Cl] | 502.20 |
| 80-3 | 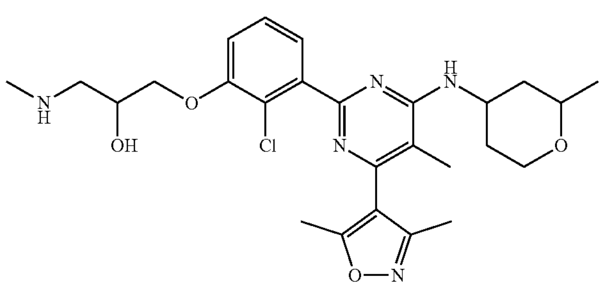 | 516.20 |
| 81-3 | 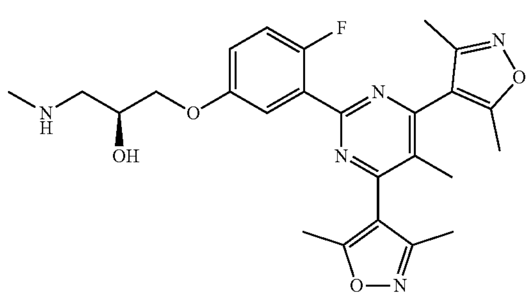 [SMILES: CNC[C@H](O)COc1ccc(F)c(-c2nc(-c3c(C)noc3C)c(C)c(-c3c(C)noc3C)n2)c1] | 482.00 |

TABLE 1C-continued
Exemplary Compounds
| # | Structure | LC-MS m/z (M + H) |
|---|---|---|
| 82-3 | 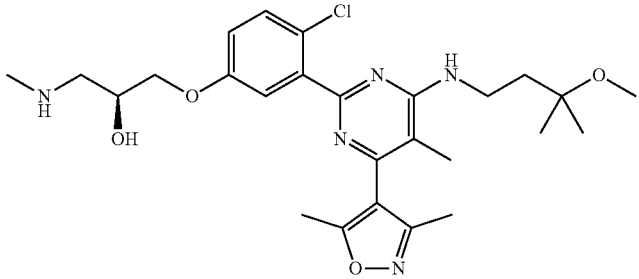 | 518.00 |
| 83-3 | 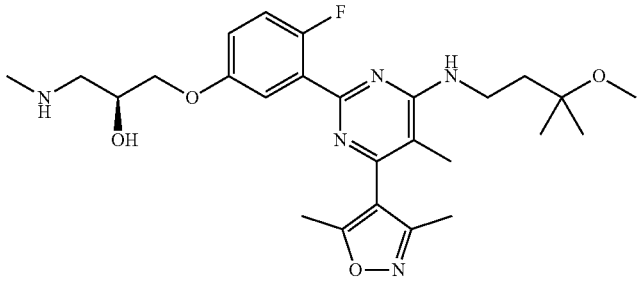 | 502.00 |
| 84-3 | 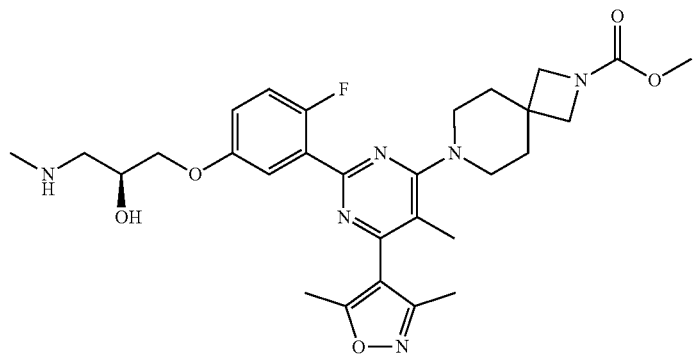 | 569.30 |
| 85-3 | 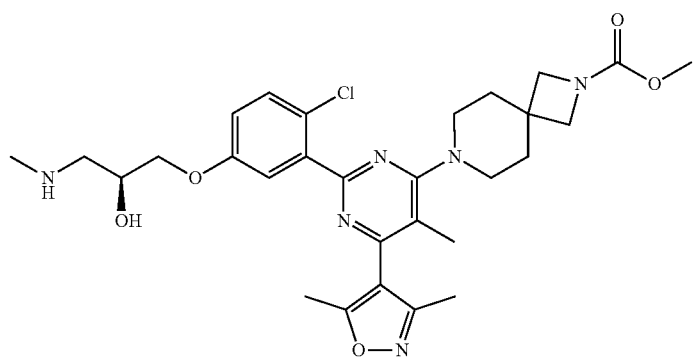 | 585.30 |

TABLE 1C-continued

Exemplary Compounds

| # | Structure | LC-MS m/z (M + H) |
|---|-----------|-------------------|
| 86-3 | 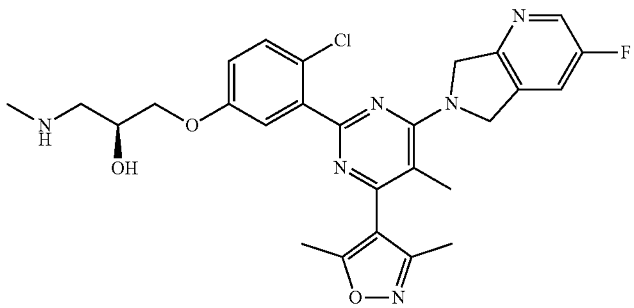 [SMILES: CNC[C@H](O)COc1ccc(Cl)c(-c2nc(-c3c(C)noc3C)c(C)c(N3Cc4cc(F)cnc4C3)n2)c1] | 539.20 |
| 87-3 | 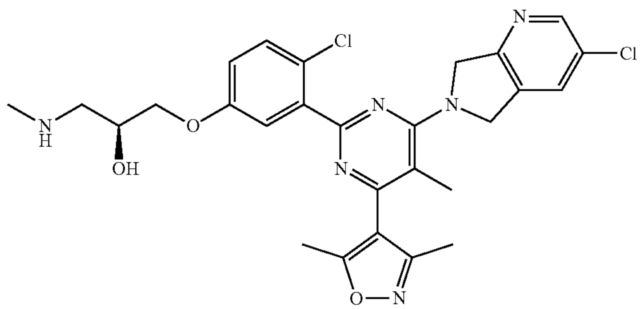 [SMILES: CNC[C@H](O)COc1ccc(Cl)c(-c2nc(-c3c(C)noc3C)c(C)c(N3Cc4cc(Cl)cnc4C3)n2)c1] | 555.20 |
| 88-3 | 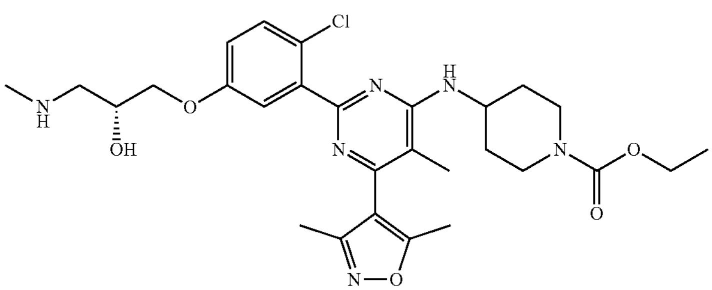 [SMILES: CCOC(=O)N1CCC(Nc2nc(-c3cc(OC[C@H](O)CNC)ccc3Cl)nc(-c3c(C)noc3C)c2C)CC1] | 573.20 |
| 89-3 | 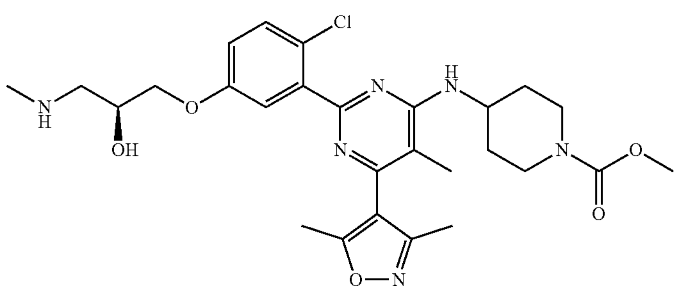 | 559.20 |
| 90-3 | 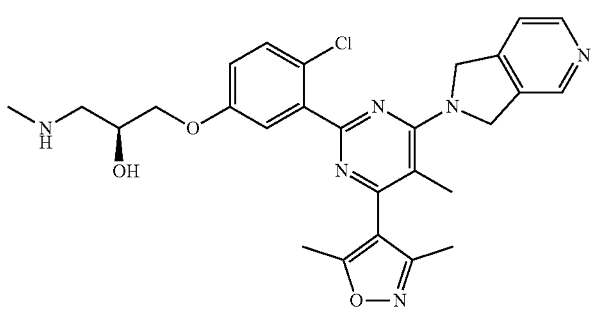 [SMILES: CNC[C@H](O)COc1ccc(Cl)c(-c2nc(-c3c(C)noc3C)c(C)c(N3Cc4ccncc4C3)n2)c1] | 521.00 |

TABLE 1C-continued

Exemplary Compounds

| # | Structure | LC-MS m/z (M + H) |
|---|---|---|
| 91-3 | 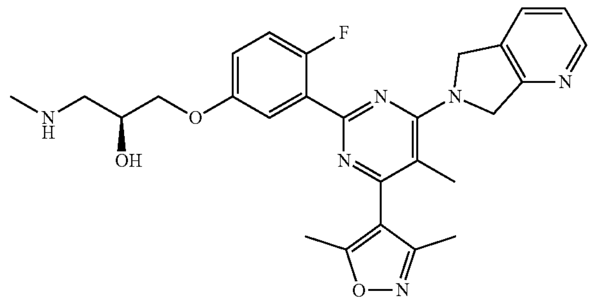 [SMILES: CNC[C@H](O)COc1ccc(F)c(-c2nc(-c3c(C)noc3C)c(C)c(N3Cc4cccnc4C3)n2)c1] | 505.30 |
| 92-3 | 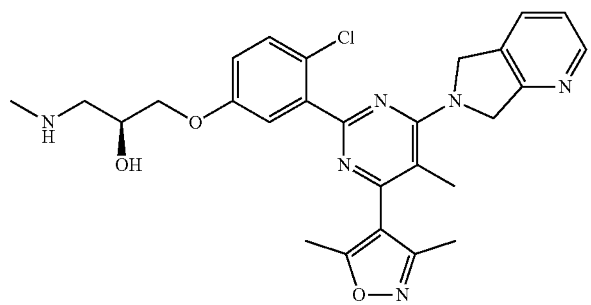 [SMILES: CNC[C@H](O)COc1ccc(Cl)c(-c2nc(-c3c(C)noc3C)c(C)c(N3Cc4cccnc4C3)n2)c1] | 521.20 |
| 93-3 | 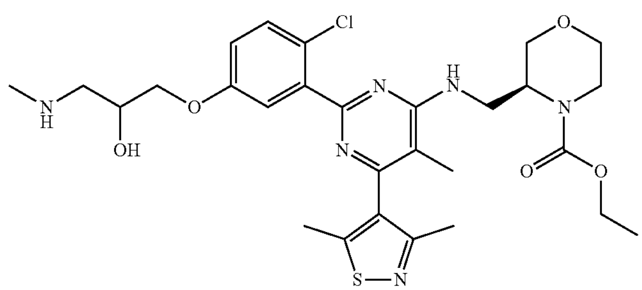 [SMILES: CCOC(=O)N1CCOC[C@@H]1CNc1nc(-c2cc(OCC(O)CNC)ccc2Cl)nc(-c2c(C)nsc2C)c1C] | 605.2 |
| 94-3 | 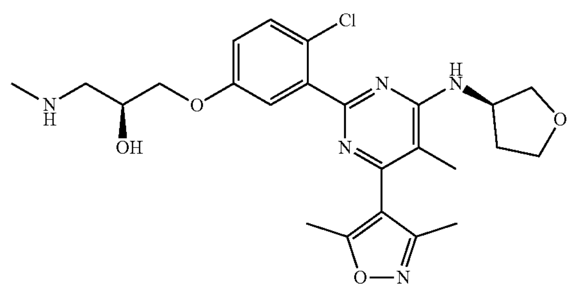 [SMILES: CNC[C@H](O)COc1ccc(Cl)c(-c2nc(N[C@@H]3CCOC3)c(C)c(-c3c(C)noc3C)n2)c1] | 488.30 |
| 95-3 | 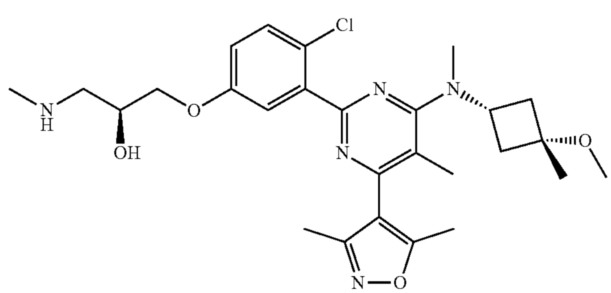 | 530.00 |

TABLE 1C-continued

Exemplary Compounds

| # | Structure | LC-MS m/z (M + H) |
|---|---|---|
| 96-3 | 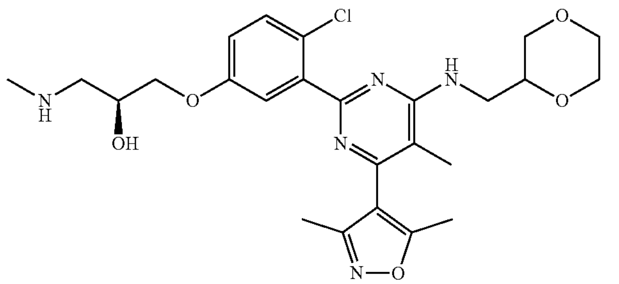 [SMILES: CNC[C@H](O)COc1ccc(Cl)c(-c2nc(NCC3COCCO3)c(C)c(-c3c(C)noc3C)n2)c1] | 518.20 |
| 97-3 | 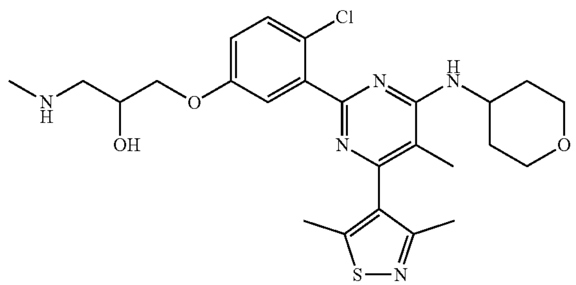 [SMILES: CNCC(O)COc1ccc(Cl)c(-c2nc(NC3CCOCC3)c(C)c(-c3c(C)nsc3C)n2)c1] | 518.2 |
| 98-3 | 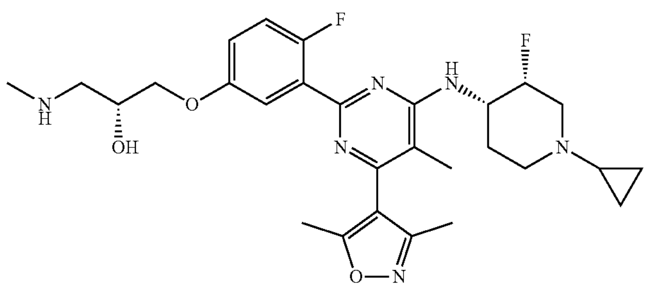 | 543.3 |
| 99-3 | 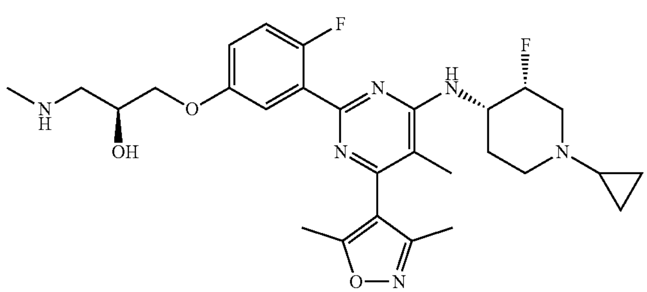 [SMILES: CNC[C@H](O)COc1ccc(F)c(-c2nc(N[C@H]3CCN(C4CC4)C[C@H]3F)c(C)c(-c3c(C)noc3C)n2)c1] | 543.3 |
| 100-3 | 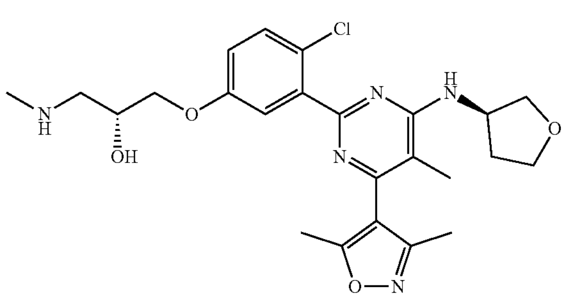 [SMILES: CNC[C@@H](O)COc1ccc(Cl)c(-c2nc(N[C@@H]3CCOC3)c(C)c(-c3c(C)noc3C)n2)c1] | 488 |

TABLE 1C-continued

Exemplary Compounds

| # | Structure | LC-MS m/z (M + H) |
|---|-----------|-------------------|
| 101-3 | 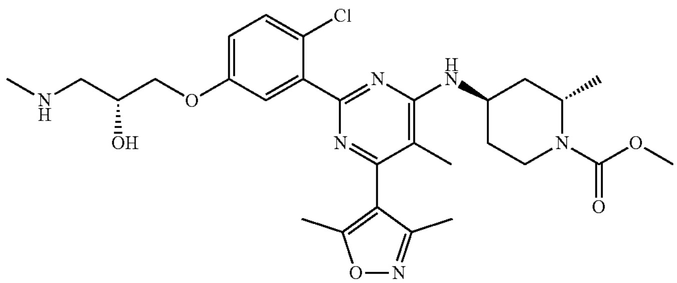 | 573.2 |
| 102-3 | 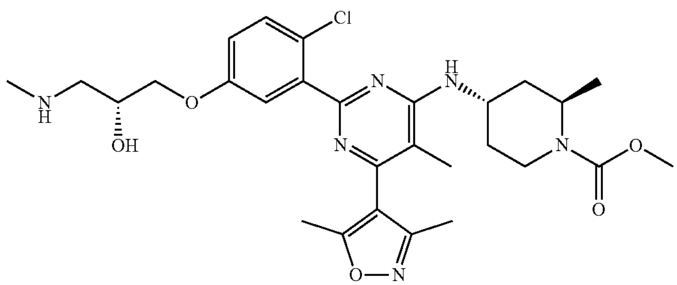 | 573.2 |
| 103-3 | 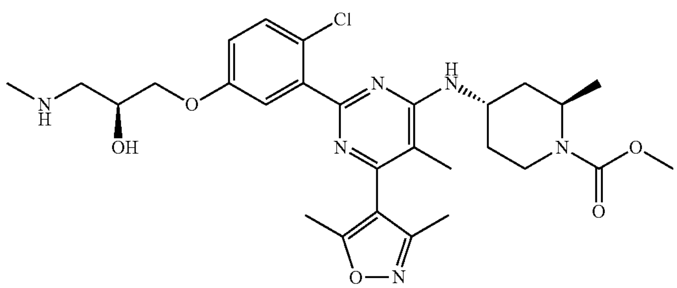 | 573.2 |
| 104-3 | 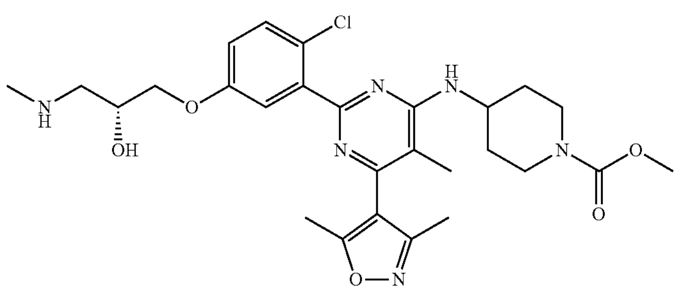 | 558.9 |
| 105-3 | 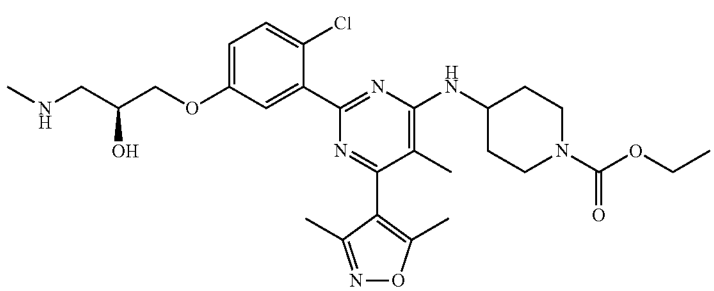 [SMILES: CCOC(=O)N1CCC(Nc2nc(-c3cc(OC[C@@H](O)CNC)ccc3Cl)nc(-c3c(C)noc3C)c2C)CC1] | 573.3 |

TABLE 1C-continued

Exemplary Compounds

| # | Structure | LC-MS m/z (M + H) |
|---|---|---|
| 106-3 | 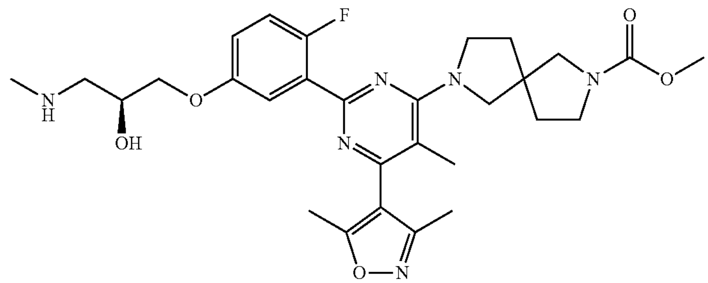 | 569.3 |
| 107-3 | 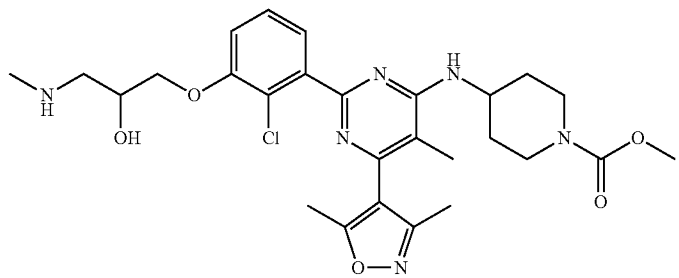 | 558.8 |
| 108-3 | 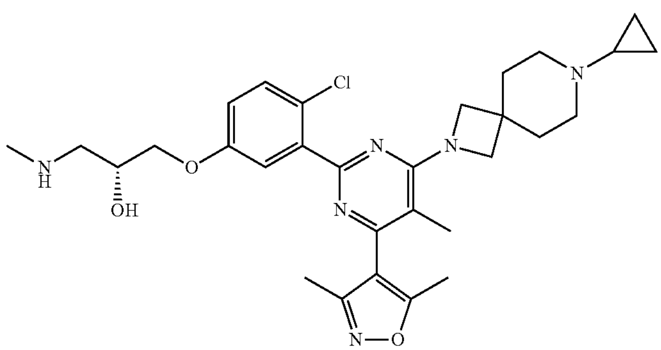 [SMILES: CNC[C@@H](O)COc1ccc(Cl)c(-c2nc(-c3c(C)noc3C)c(C)c(N3CC4(CCN(C5CC5)CC4)C3)n2)c1] | 567.3 |
| 109-3 | 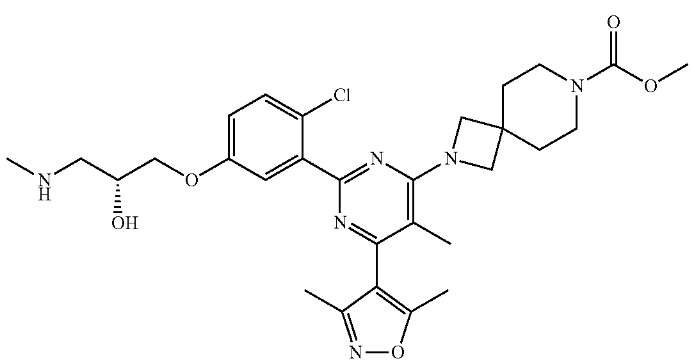 | 585.3 |
| 110-3 | 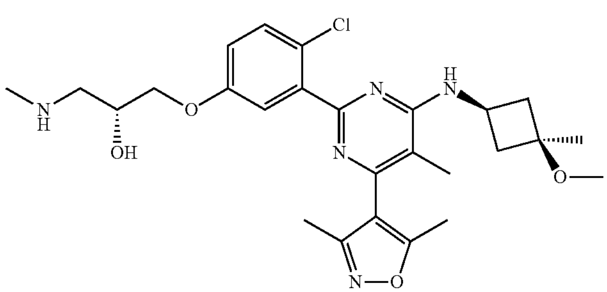 | 516.2 |

TABLE 1C-continued

Exemplary Compounds

| # | Structure | LC-MS m/z (M + H) |
|---|-----------|-------------------|
| 111-3 | 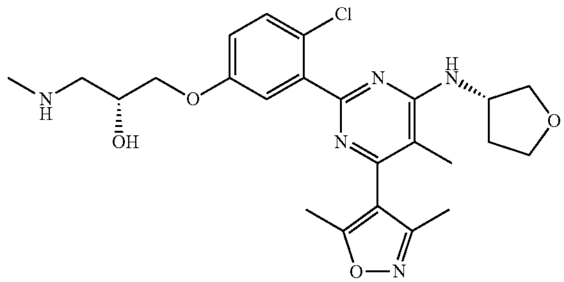 [SMILES: CNC[C@@H](O)COc1ccc(Cl)c(-c2nc(N[C@H]3CCOC3)c(C)c(-c3c(C)noc3C)n2)c1] | 487.8 |
| 112-3 | 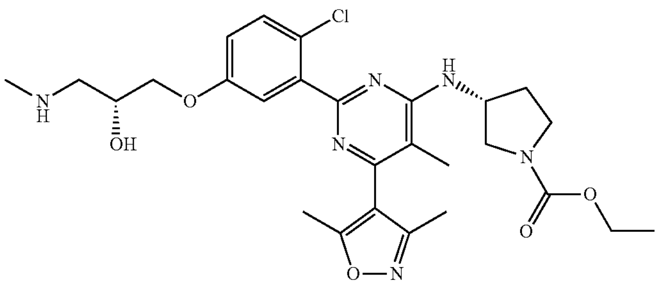 [SMILES: CCOC(=O)N1CC[C@@H](Nc2nc(-c3cc(OC[C@H](O)CNC)ccc3Cl)nc(-c3c(C)noc3C)c2C)C1] | 559.2 |
| 113-3 | 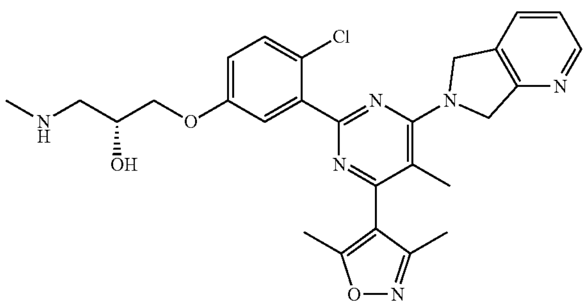 [SMILES: CNC[C@@H](O)COc1ccc(Cl)c(-c2nc(-c3c(C)noc3C)c(C)c(N3Cc4cccnc4C3)n2)c1] | 521.20 |
| 114-3 | 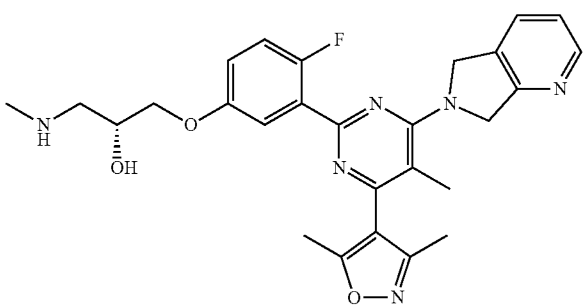 [SMILES: CNC[C@@H](O)COc1ccc(F)c(-c2nc(-c3c(C)noc3C)c(C)c(N3Cc4cccnc4C3)n2)c1] | 504.9 |
| 115-3 | 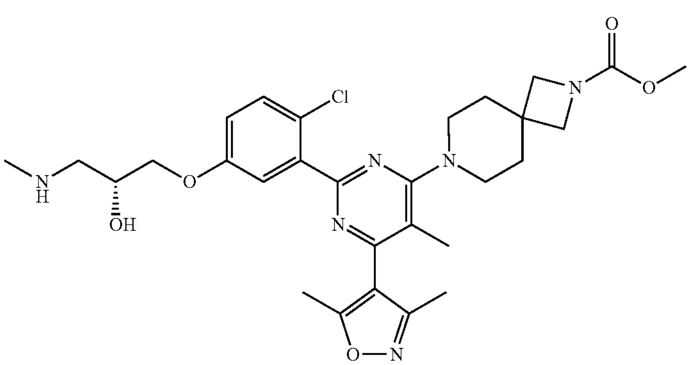 | 585.3 |

TABLE 1C-continued

Exemplary Compounds

| # | Structure | LC-MS m/z (M + H) |
|---|---|---|
| 116-3 | 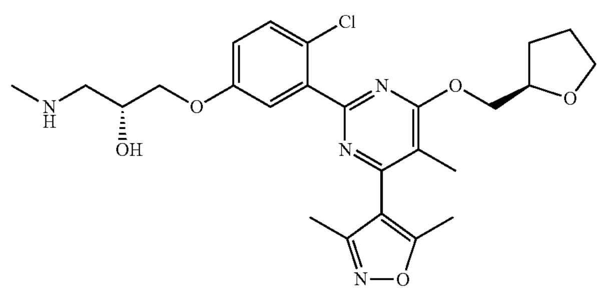 [SMILES: CNC[C@@H](O)COc1ccc(Cl)c(-c2nc(OC[C@H]3CCCO3)c(C)c(-c3c(C)noc3C)n2)c1] | 503.3 |
| 117-3 | 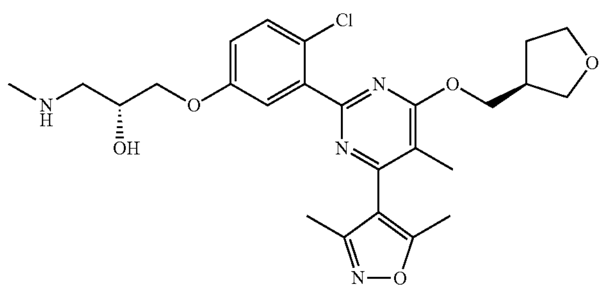 [SMILES: CNC[C@@H](O)COc1ccc(Cl)c(-c2nc(OC[C@H]3CCOC3)c(C)c(-c3c(C)noc3C)n2)c1] | 503.3 |
| 118-3 | 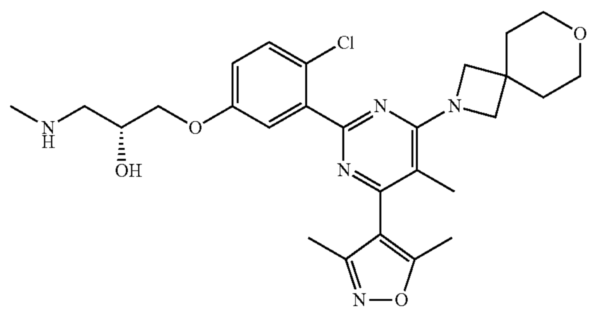 | 528.3 |
| 119-3 | 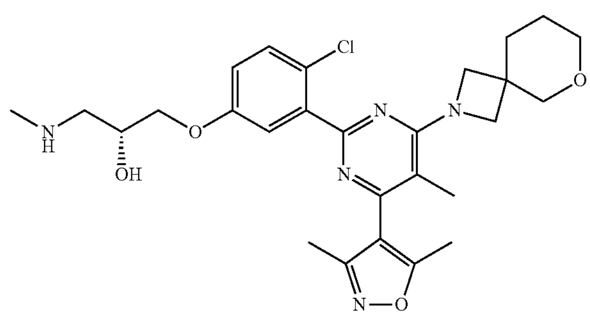 [SMILES: CNC[C@@H](O)COc1ccc(Cl)c(-c2nc(-c3c(C)noc3C)c(C)c(N3CC4(CCCOC4)C3)n2)c1] | 528.2 |
| 120-3 | 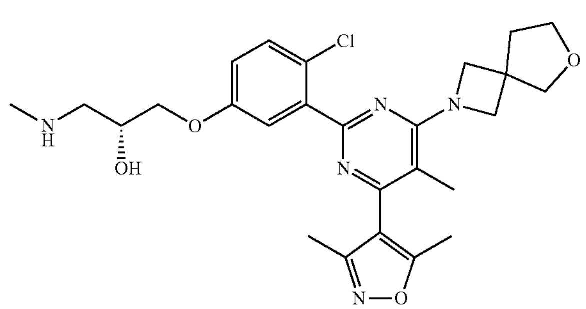 [SMILES: CNC[C@@H](O)COc1ccc(Cl)c(-c2nc(-c3c(C)noc3C)c(C)c(N3CC4(CCOC4)C3)n2)c1] | 514.3 |

TABLE 1C-continued
Exemplary Compounds
| # | Structure | LC-MS m/z (M + H) |
|---|---|---|
| 121-3 | 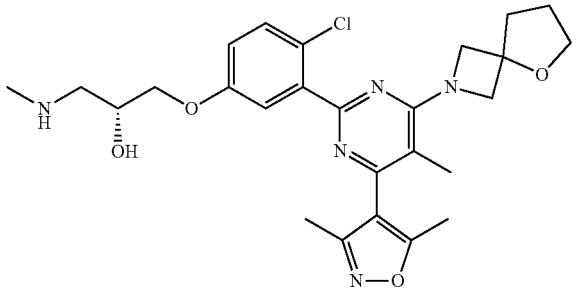 [SMILES: CNC[C@@H](O)COc1ccc(Cl)c(-c2nc(-c3c(C)noc3C)c(C)c(N3CC4(CCCO4)C3)n2)c1] | 514.2 |
| 122-3 | 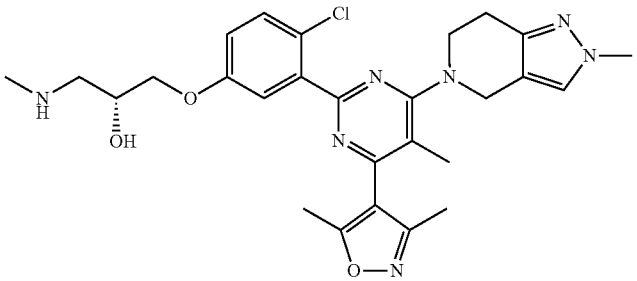 | 538 |
| 123-3 | 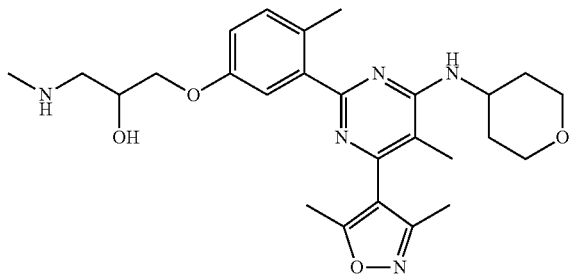 [SMILES: CNCC(O)COc1ccc(C)c(-c2nc(NC3CCOCC3)c(C)c(-c3c(C)noc3C)n2)c1] | 482.3 |
| 124-3 | 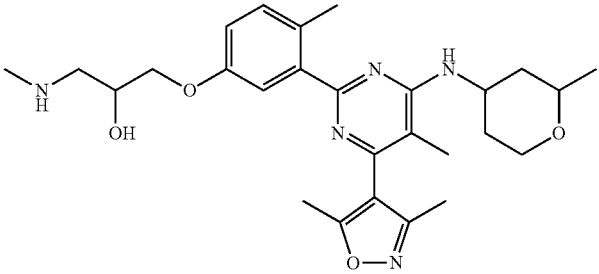 | 496.4 |
| 125-3 | 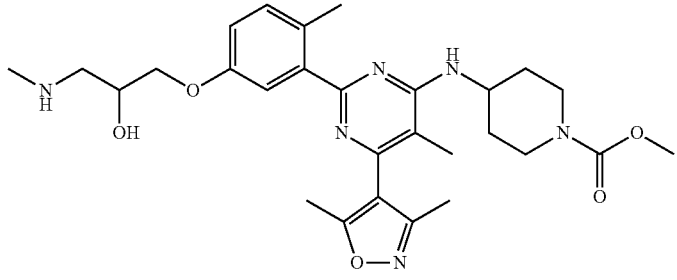 | 539.3 |

TABLE 1C-continued

Exemplary Compounds

| # | Structure | LC-MS m/z (M + H) |
|---|---|---|
| 126-3 | 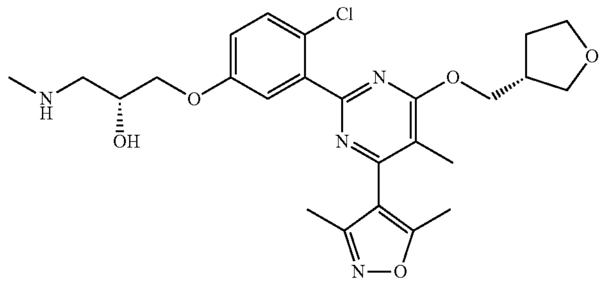 [SMILES: CNC[C@@H](O)COc1ccc(Cl)c(-c2nc(OC[C@@H]3CCOC3)c(C)c(-c3c(C)noc3C)n2)c1] | 503.3 |
| 127-3 | 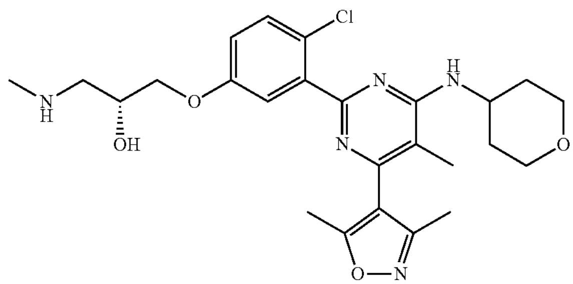 [SMILES: CNC[C@@H](O)COc1ccc(Cl)c(-c2nc(NC3CCOCC3)c(C)c(-c3c(C)noc3C)n2)c1] | 502.2 |
| 128-3 | 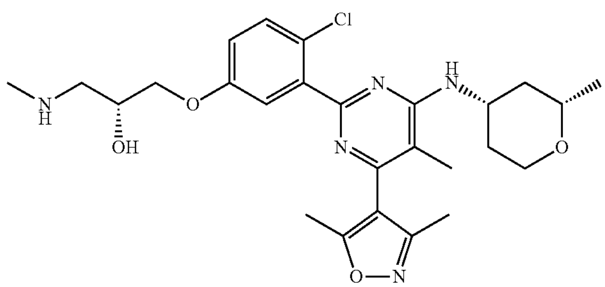 | 515.8 |
| 129-3 | 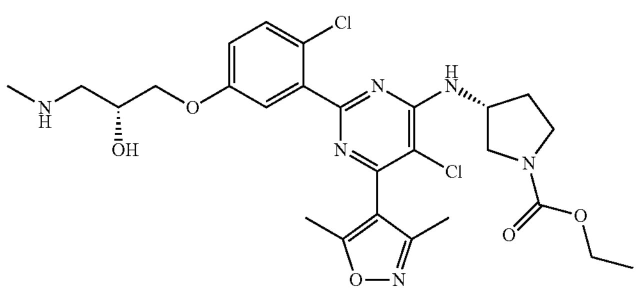 [SMILES: CCOC(=O)N1CC[C@@H](Nc2nc(-c3cc(OC[C@H](O)CNC)ccc3Cl)nc(-c3c(C)noc3C)c2Cl)C1] | 579.2 |
| 130-3 | 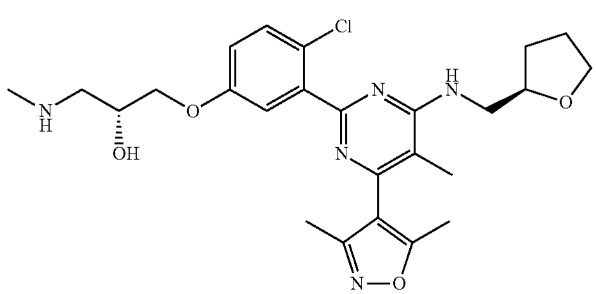 [SMILES: CNC[C@@H](O)COc1ccc(Cl)c(-c2nc(NC[C@H]3CCCO3)c(C)c(-c3c(C)noc3C)n2)c1] | 502.2 |

TABLE 1C-continued

Exemplary Compounds

| # | Structure | LC-MS m/z (M + H) |
|---|---|---|
| 131-3 | 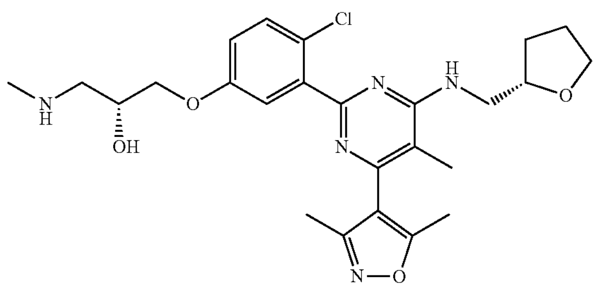 [SMILES: CNC[C@@H](O)COc1ccc(Cl)c(-c2nc(NC[C@@H]3CCCO3)c(C)c(-c3c(C)noc3C)n2)c1] | 502.2 |
| 132-3 | 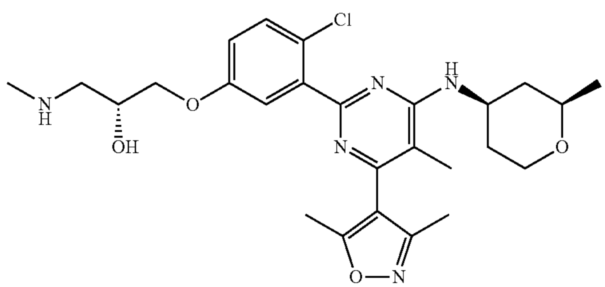 | 515.8 |
| 133-3 | 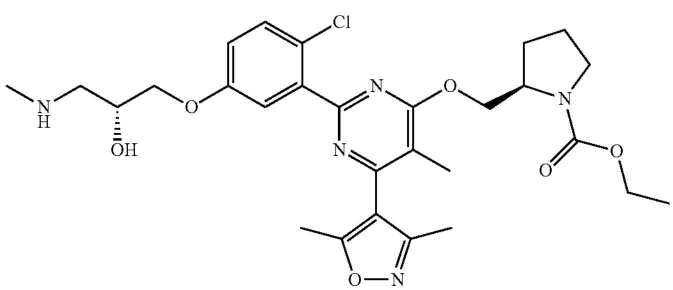 [SMILES: CCOC(=O)N1CCC[C@@H]1COc1nc(-c2cc(OC[C@H](O)CNC)ccc2Cl)nc(-c2c(C)noc2C)c1C] | 574.2 |
| 134-3 | 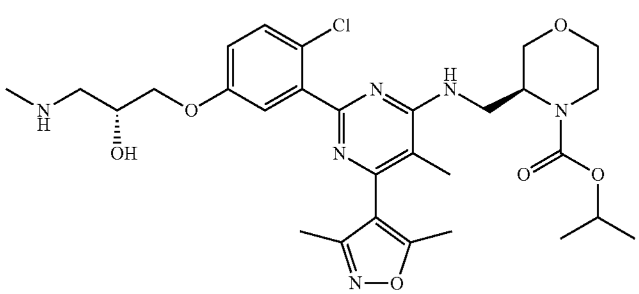 [SMILES: CNC[C@@H](O)COc1ccc(Cl)c(-c2nc(NC[C@H]3COCCN3C(=O)OC(C)C)c(C)c(-c3c(C)noc3C)n2)c1] | 603.3 |
| 135-3 | 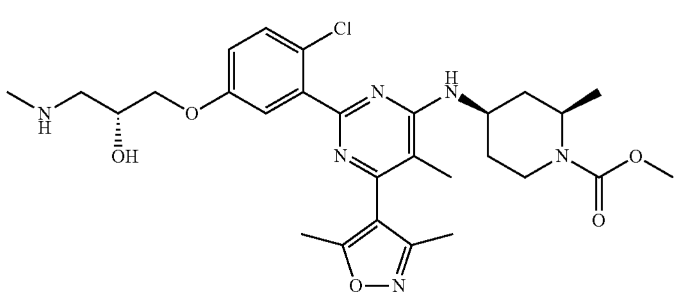 | 573.3 |

TABLE 1C-continued

Exemplary Compounds

| # | Structure | LC-MS m/z (M + H) |
|---|---|---|
| 136-3 | 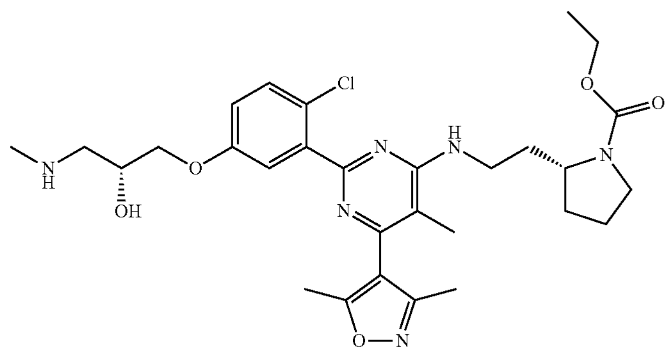 [SMILES: CCOC(=O)N1CCC[C@@H]1CCNc1nc(-c2cc(OC[C@H](O)CNC)ccc2Cl)nc(-c2c(C)noc2C)c1C] | 586.8 |
| 137-3 | 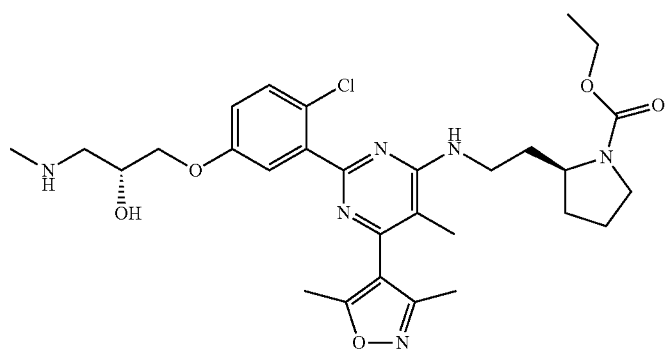 [SMILES: CCOC(=O)N1CCC[C@H]1CCNc1nc(-c2cc(OC[C@H](O)CNC)ccc2Cl)nc(-c2c(C)noc2C)c1C] | 586.9 |
| 138-3 | 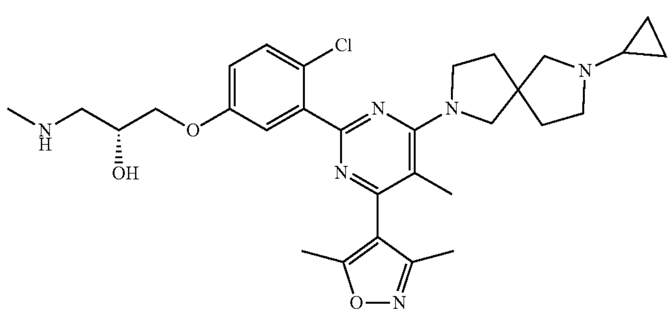 [SMILES: CNC[C@@H](O)COc1ccc(Cl)c(-c2nc(-c3c(C)noc3C)c(C)c(N3CCC4(CCN(C5CC5)C4)C3)n2)c1] | 567.3 |
| 139-3 | 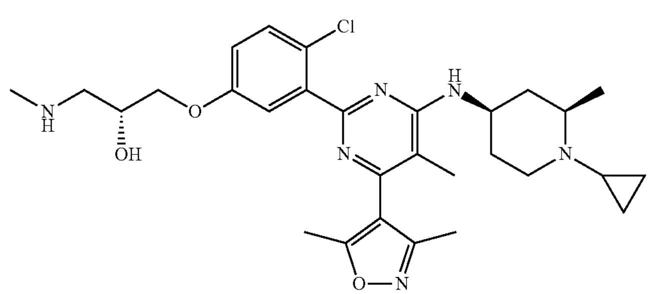 [SMILES: CNC[C@@H](O)COc1ccc(Cl)c(-c2nc(N[C@@H]3CCN(C4CC4)[C@H](C)C3)c(C)c(-c3c(C)noc3C)n2)c1] | 555 |

TABLE 1C-continued
Exemplary Compounds
| # | Structure | LC-MS m/z (M + H) |
|---|---|---|
| 140-3 | 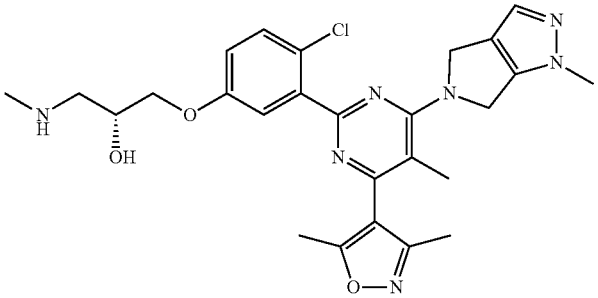 | 524.2 |
| 141-3 | 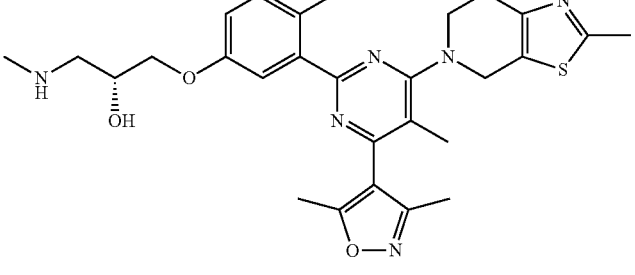 | 555.2 |
| 142-3 | 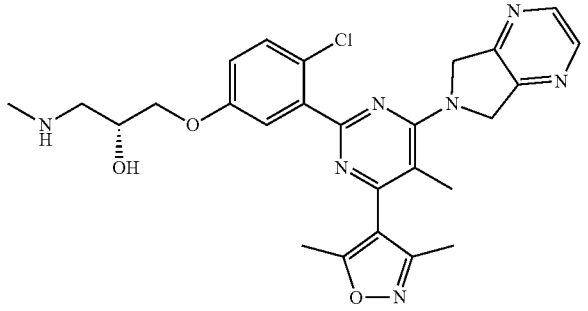 [SMILES: CNC[C@@H](O)COc1ccc(Cl)c(-c2nc(-c3c(C)noc3C)c(C)c(N3Cc4nccnc4C3)n2)c1] | 522.2 |
| 143-3 | 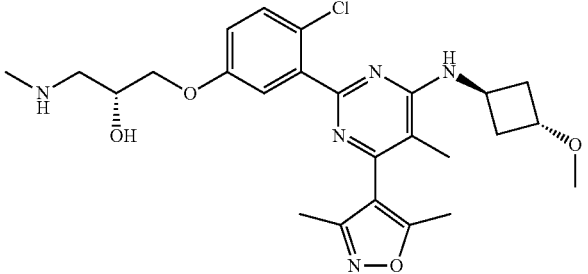 | 501.9 |
| 144-3 | 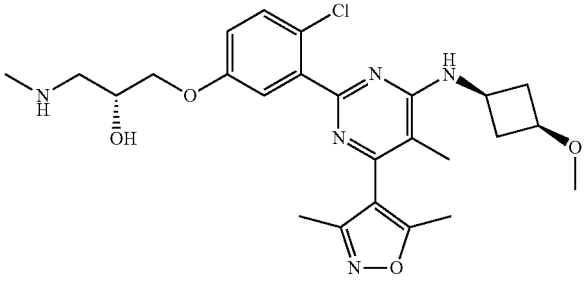 | 501.9 |

TABLE 1C-continued
Exemplary Compounds
| # | Structure | LC-MS m/z (M + H) |
|---|---|---|
| 145-3 | 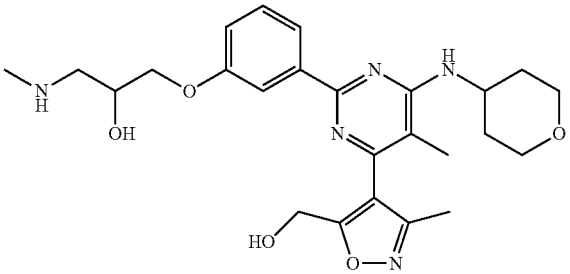 [SMILES: CNCC(O)COc1cccc(-c2nc(NC3CCOCC3)c(C)c(-c3c(C)noc3CO)n2)c1] | 484.2 |
| 146-3 | 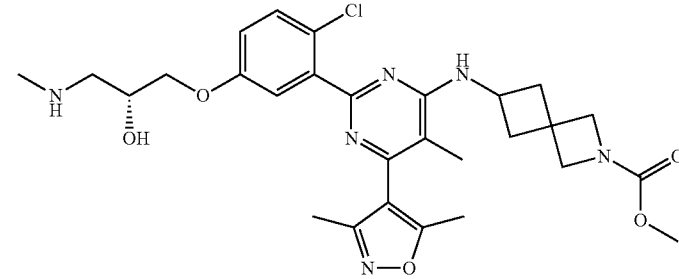 | 571.3 |
| 147-3 | 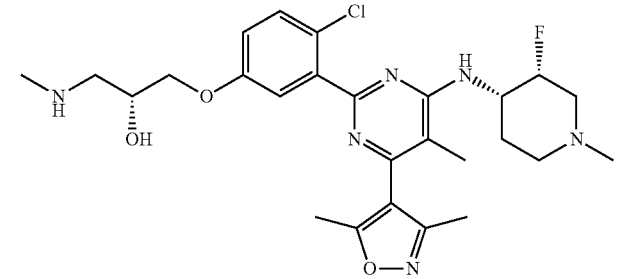 | 533.2 |
| 148-3 | 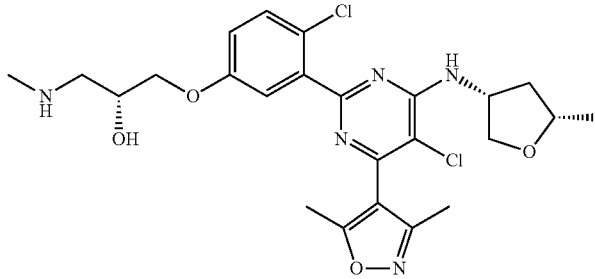 | 522.2 |
| 149-3 | 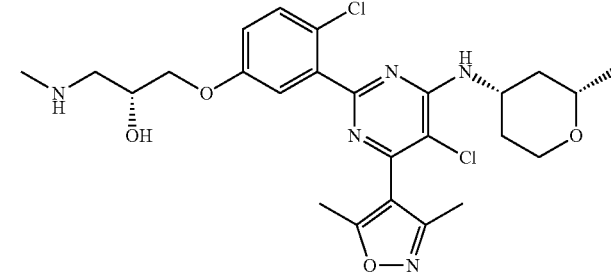 | 535.7 |

TABLE 1C-continued

Exemplary Compounds

| # | Structure | LC-MS m/z (M + H) |
|---|-----------|-------------------|
| 150-3 | 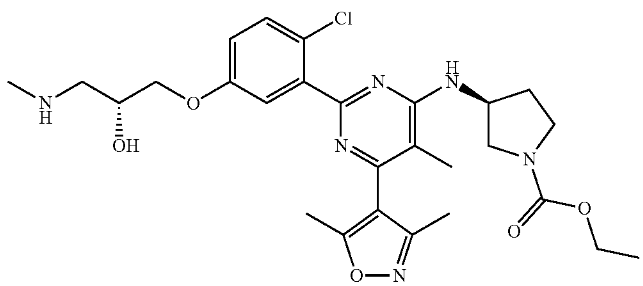 | 559.2 |
| 151-3 | 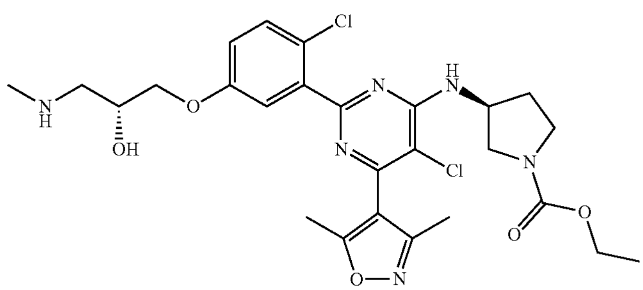 [SMILES: CCOC(=O)N1CC[C@H](Nc2nc(-c3cc(OC[C@H](O)CNC)ccc3Cl)nc(-c3c(C)noc3C)c2C)C1] | 579.2 |
| 152-3 | 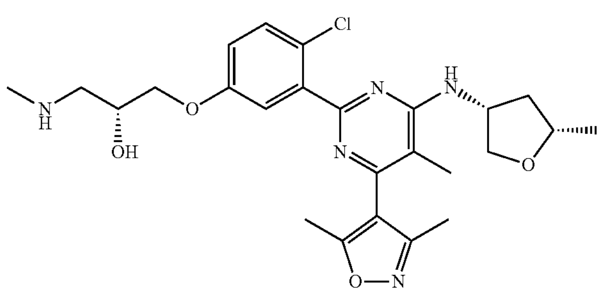 | 501.9 |
| 153-3 | 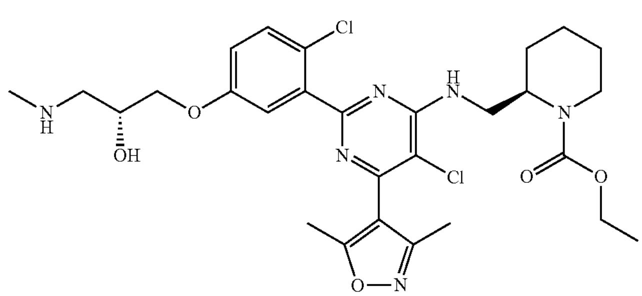 [SMILES: CCOC(=O)N1CCCC[C@@H]1CNc1nc(-c2cc(OC[C@H](O)CNC)ccc2Cl)nc(-c2c(C)noc2C)c1Cl] | 606.7 |
| 154-3 | 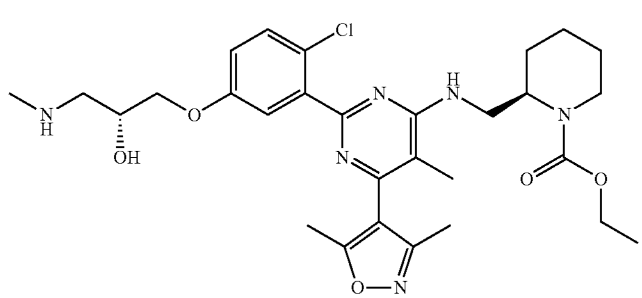 | 586.8 |

TABLE 1C-continued

Exemplary Compounds

| # | Structure | LC-MS m/z (M + H) |
|---|-----------|-------------------|
| 155-3 | 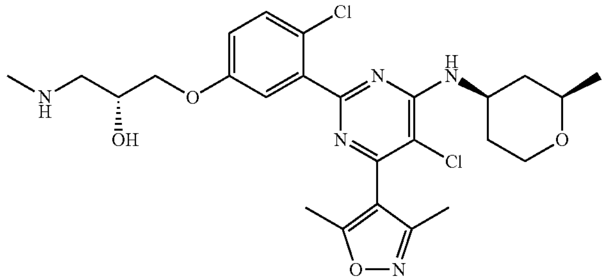 | 535.7 |
| 156-3 | 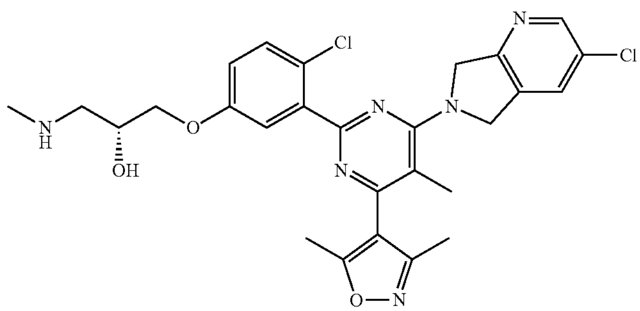 [SMILES: CNC[C@@H](O)COc1ccc(Cl)c(-c2nc(-c3c(C)noc3C)c(C)c(N3Cc4cc(Cl)cnc4C3)n2)c1] | 556.9 |
| 157-3 | 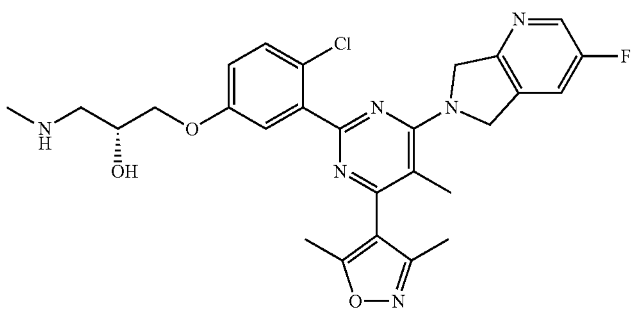 [SMILES: CNC[C@@H](O)COc1ccc(Cl)c(-c2nc(-c3c(C)noc3C)c(C)c(N3Cc4cc(F)cnc4C3)n2)c1] | 539.2 |
| 158-3 | 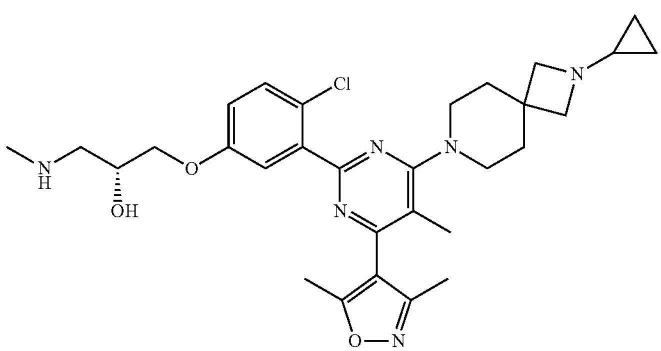 [SMILES: CNC[C@@H](O)COc1ccc(Cl)c(-c2nc(-c3c(C)noc3C)c(C)c(N3CCC4(CC3)CN(C3CC3)C4)n2)c1] | 567.3 |
| 159-3 | 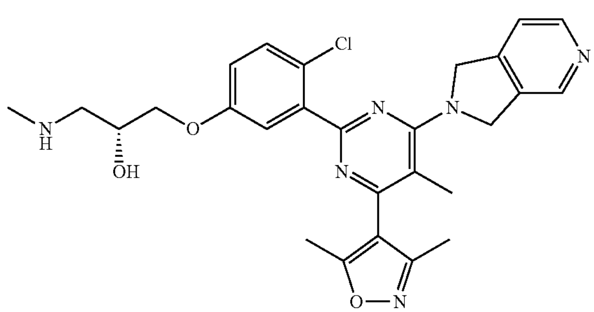 [SMILES: CNC[C@@H](O)COc1ccc(Cl)c(-c2nc(-c3c(C)noc3C)c(C)c(N3Cc4ccncc4C3)n2)c1] | 520.9 |

TABLE 1C-continued
Exemplary Compounds
| # | Structure | LC-MS m/z (M + H) |
|---|---|---|
| 160-3 | 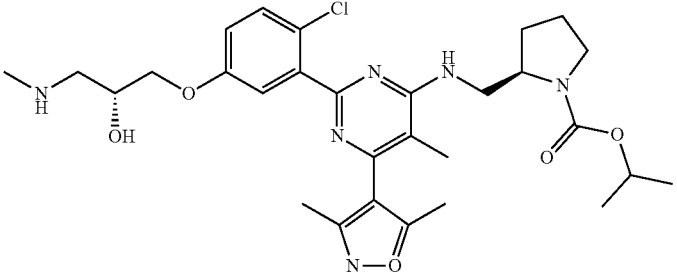 | 587.3 |
| 161-3 | 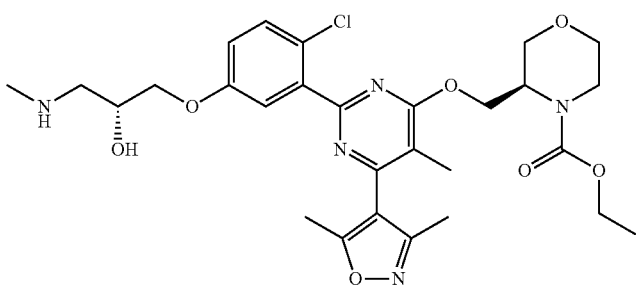 [SMILES: CCOC(=O)N1CCOC[C@@H]1COc1nc(-c2cc(OC[C@H](O)CNC)ccc2Cl)nc(-c2c(C)noc2C)c1C] | 589.7 |
| 162-3 | 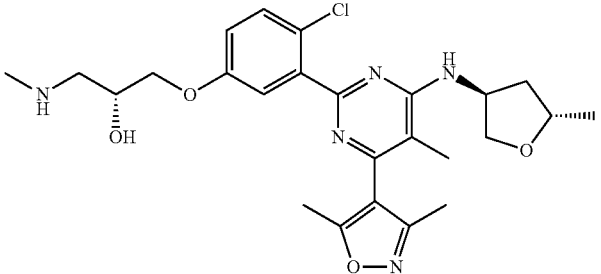 | 502.2 |
| 163-3 | 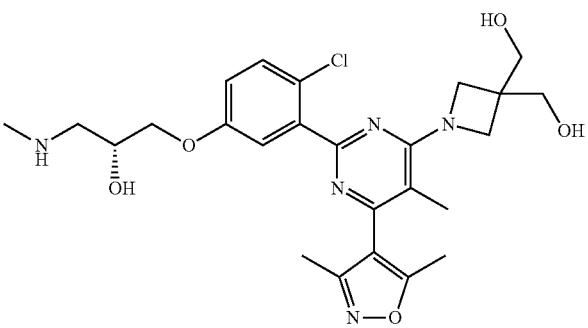 [SMILES: CNC[C@@H](O)COc1ccc(Cl)c(-c2nc(-c3c(C)noc3C)c(C)c(N3CC(CO)(CO)C3)n2)c1] | 518.2 |
| 164-3 | 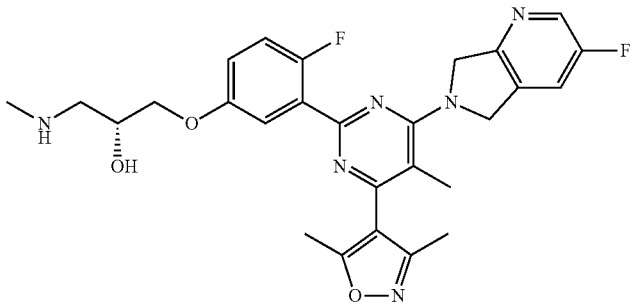 [SMILES: CNC[C@@H](O)COc1ccc(F)c(-c2nc(-c3c(C)noc3C)c(C)c(N3Cc4cc(F)cnc4C3)n2)c1] | 523.2 |

TABLE 1C-continued

Exemplary Compounds

| # | Structure | LC-MS m/z (M + H) |
|---|---|---|
| 165-3 | 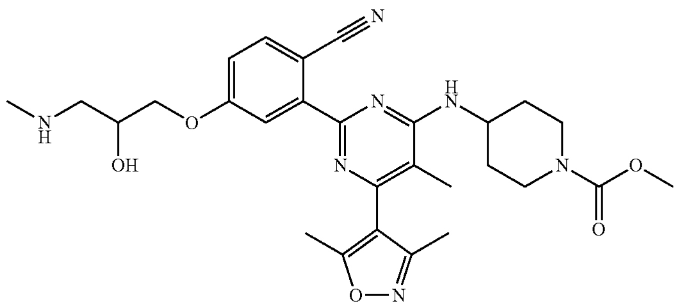 | 550.3 |
| 166-3 | 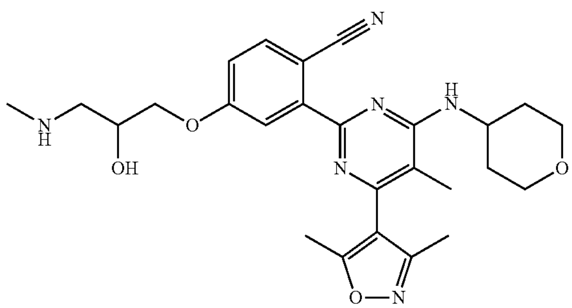 [SMILES: CNCC(O)COc1ccc(C#N)c(-c2nc(NC3CCOCC3)c(C)c(-c3c(C)noc3C)n2)c1] | 493.3 |
| 167-3 | 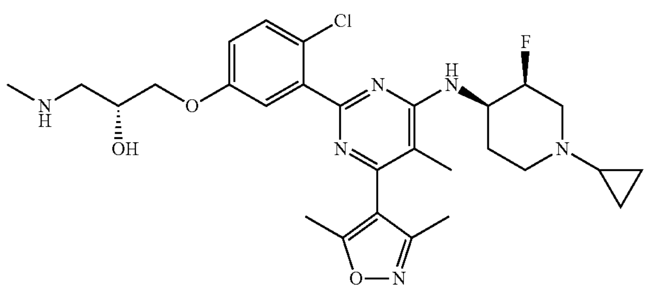 [SMILES: CNC[C@@H](O)COc1ccc(Cl)c(-c2nc(N[C@@H]3CCN(C4CC4)C[C@@H]3F)c(C)c(-c3c(C)noc3C)n2)c1] | 559.2 |
| 168-3 | 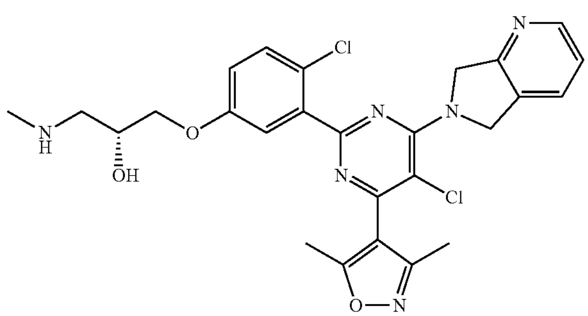 [SMILES: CNC[C@@H](O)COc1ccc(Cl)c(-c2nc(-c3c(C)noc3C)c(Cl)c(N3Cc4cccnc4C3)n2)c1] | 541.2 |
| 169-3 | 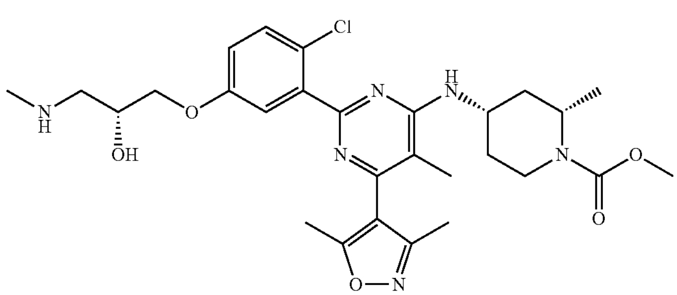 | 573.3 |

TABLE 1C-continued

Exemplary Compounds

| # | Structure | LC-MS m/z (M + H) |
|---|-----------|-------------------|
| 170-3 | 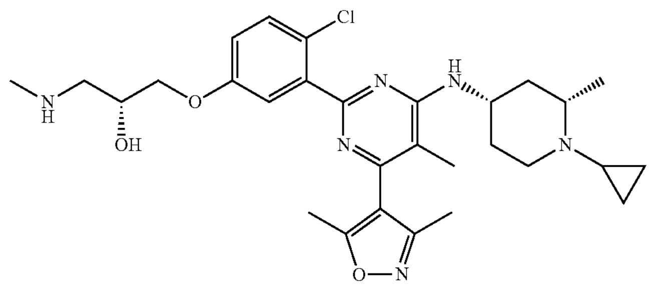 [SMILES: CNC[C@@H](O)COc1ccc(Cl)c(-c2nc(N[C@H]3CCN(C4CC4)[C@@H](C)C3)c(C)c(-c3c(C)noc3C)n2)c1] | 554.8 |
| 171-3 | 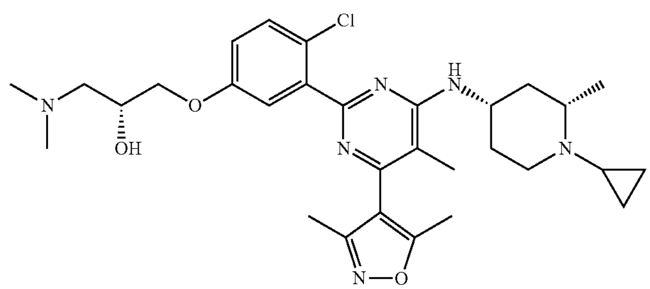 [SMILES: Cc1noc(C)c1-c1nc(-c2cc(OC[C@H](O)CN(C)C)ccc2Cl)nc(N[C@H]2CCN(C3CC3)[C@@H](C)C2)c1C] | 568.9 |
| 172-3 | 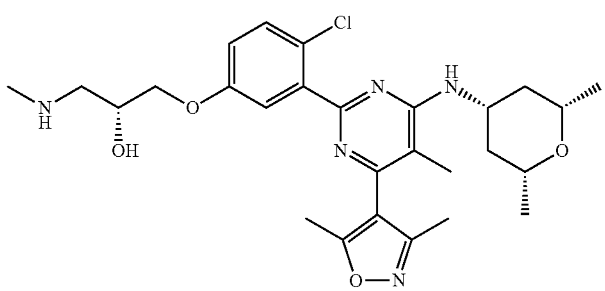 | 529.8 |
| 173-3 | 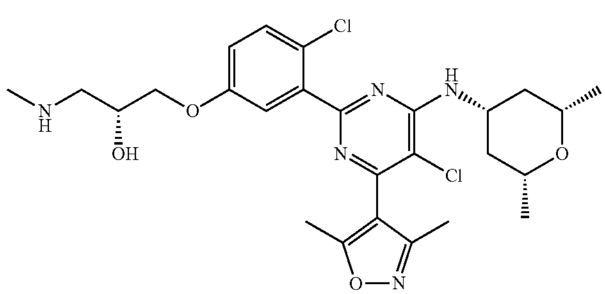 | 549.8 |
| 174-3 | 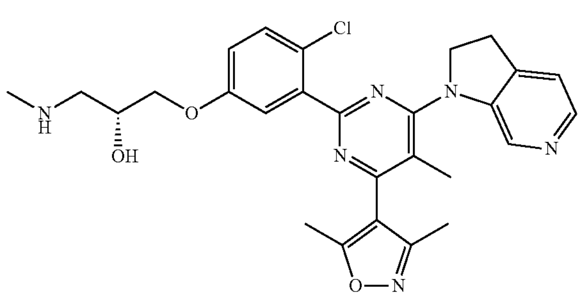 [SMILES: CNC[C@@H](O)COc1ccc(Cl)c(-c2nc(-c3c(C)noc3C)c(C)c(N3CCc4ccncc43)n2)c1] | 520.8 |

TABLE 1C-continued

Exemplary Compounds

| # | Structure | LC-MS m/z (M + H) |
|---|---|---|
| 175-3 | 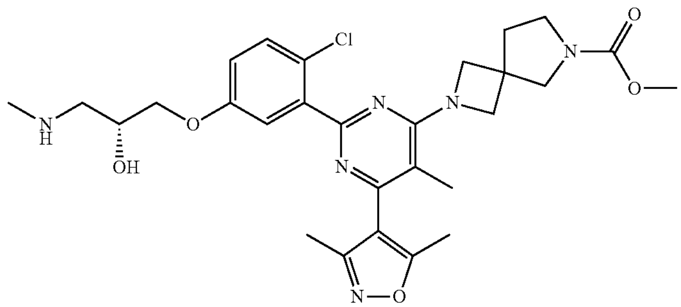 | 571.2 |
| 176-3 | 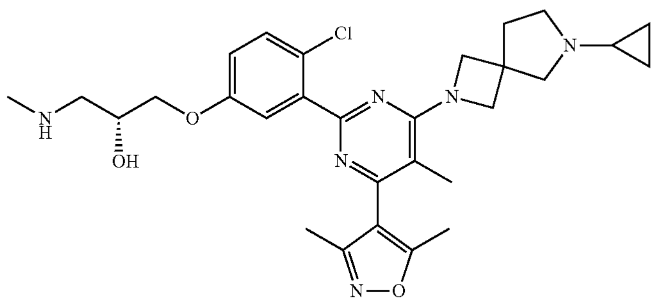 [SMILES: CNC[C@@H](O)COc1ccc(Cl)c(-c2nc(-c3c(C)noc3C)c(C)c(N3CC4(CCN(C5CC5)C4)C3)n2)c1] | 553.3 |
| 177-3 | 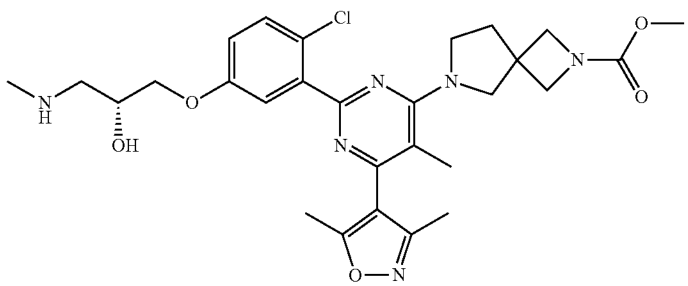 | 571.2 |
| 178-3 | 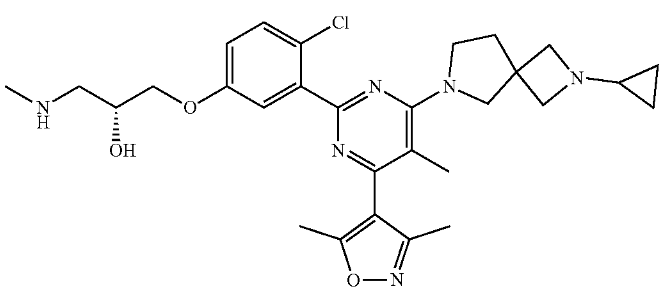 [SMILES: CNC[C@@H](O)COc1ccc(Cl)c(-c2nc(-c3c(C)noc3C)c(C)c(N3CCC4(C3)CN(C3CC3)C4)n2)c1] | 553.3 |
| 179-3 | 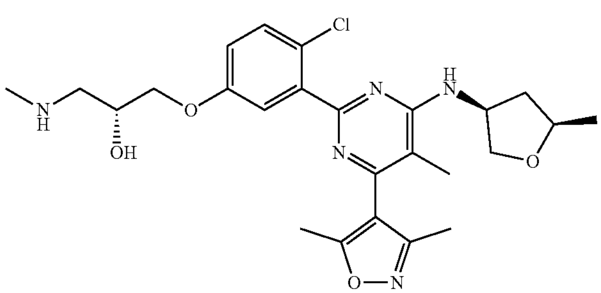 | 502.2 |

TABLE 1C-continued

Exemplary Compounds

| # | Structure | LC-MS m/z (M + H) |
|---|---|---|
| 180-3 | 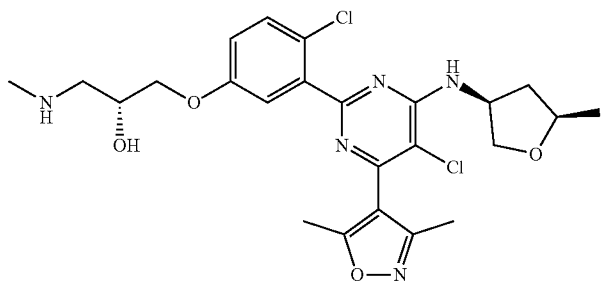 | 522.2 |
| 181-3 | 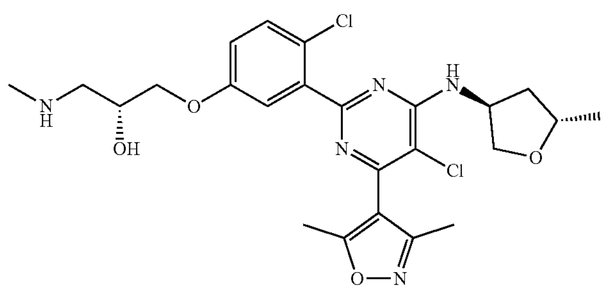 | 522.2 |
| 182-3 | 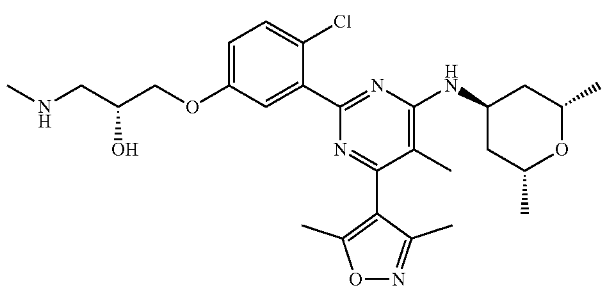 | 529.8 |
| 183-3 | 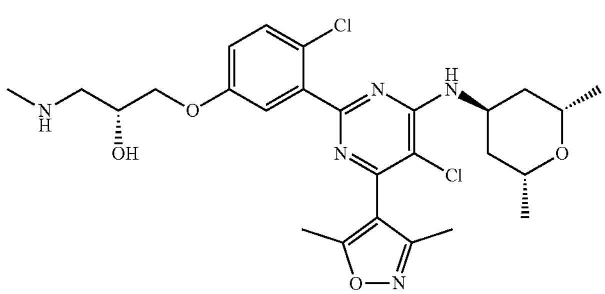 | 549.8 |
| 184-3 | 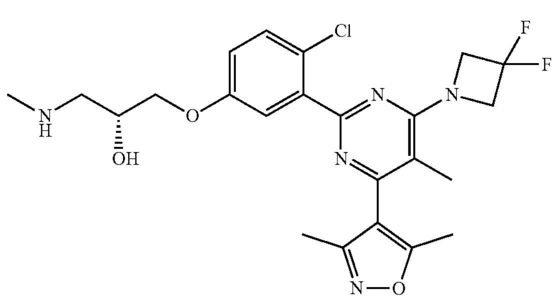 [SMILES: CNC[C@@H](O)COc1ccc(Cl)c(-c2nc(-c3c(C)noc3C)c(C)c(N3CC(F)(F)C3)n2)c1] | 494.2 |

TABLE 1C-continued

Exemplary Compounds

| # | Structure | LC-MS m/z (M + H) |
|---|---|---|
| 185-3 | 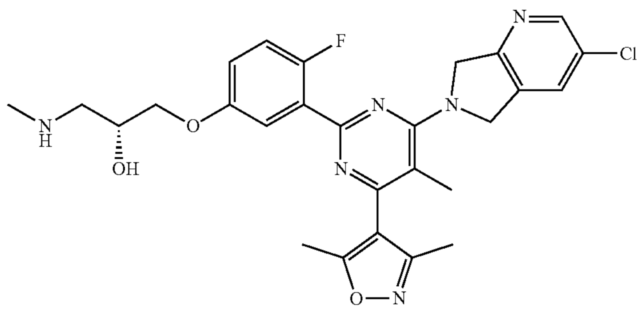 [SMILES: CNC[C@@H](O)COc1ccc(F)c(-c2nc(-c3c(C)noc3C)c(C)c(N3Cc4cc(Cl)cnc4C3)n2)c1] | 539.2 |
| 186-3 | 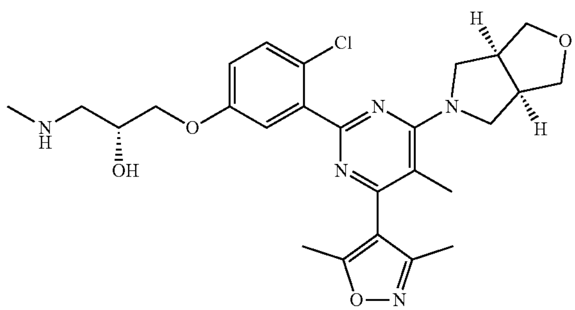 [SMILES: CNC[C@@H](O)COc1ccc(Cl)c(-c2nc(-c3c(C)noc3C)c(C)c(N3C[C@H]4COC[C@H]4C3)n2)c1] | 513.9 |
| 187-3 | 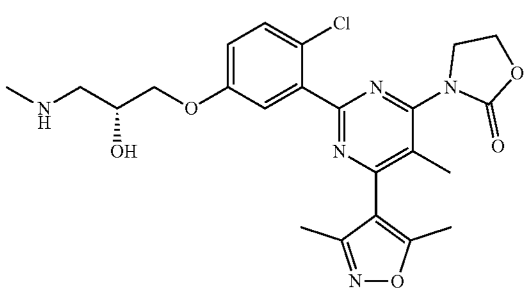 [SMILES: CNC[C@@H](O)COc1ccc(Cl)c(-c2nc(-c3c(C)noc3C)c(C)c(N3CCOC3=O)n2)c1] | 487.7 |
| 188-3 | 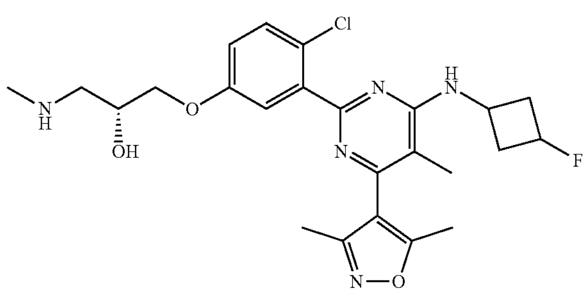 [SMILES: CNC[C@@H](O)COc1ccc(Cl)c(-c2nc(NC3CC(F)C3)c(C)c(-c3c(C)noc3C)n2)c1] | 490.2 |
| 189-3 | 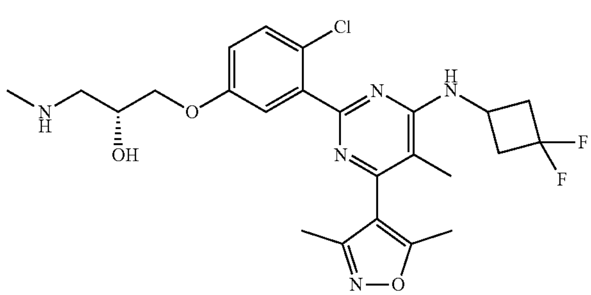 [SMILES: CNC[C@@H](O)COc1ccc(Cl)c(-c2nc(NC3CC(F)(F)C3)c(C)c(-c3c(C)noc3C)n2)c1] | 508.2 |

TABLE 1C-continued
Exemplary Compounds
| # | Structure | LC-MS m/z (M + H) |
|---|---|---|
| 190-3 | 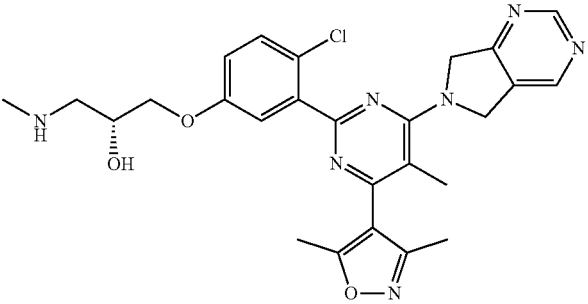 [SMILES: CNC[C@@H](O)COc1ccc(Cl)c(-c2nc(-c3c(C)noc3C)c(C)c(N3Cc4cncnc4C3)n2)c1] | 521.9 |
| 191-3 | 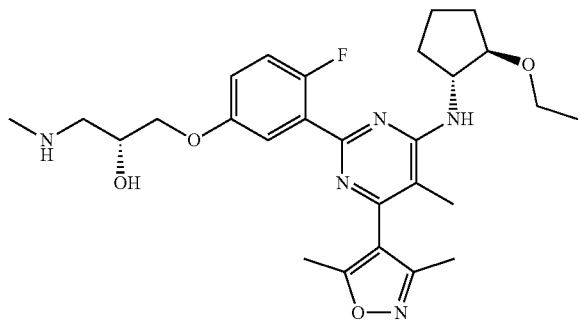 [SMILES: CCO[C@@H]1CCC[C@H]1Nc1nc(-c2cc(OC[C@H](O)CNC)ccc2F)nc(-c2c(C)noc2C)c1C] | 514.3 |
| 192-3 | 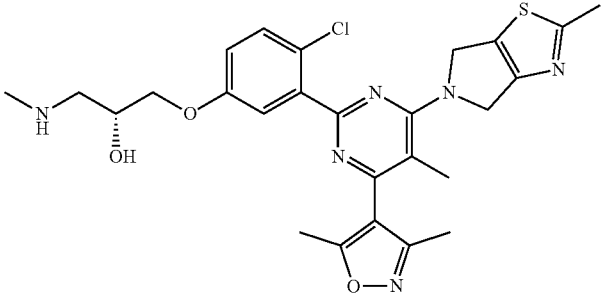 | 540.8 |
| 193-3 | 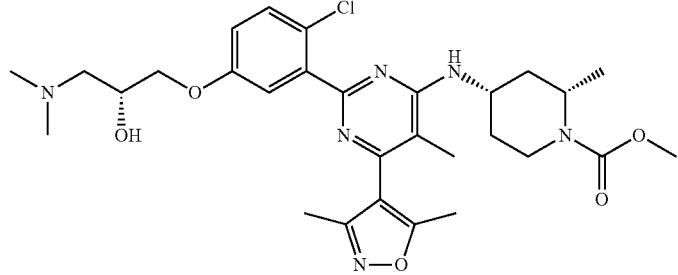 | 587.3 |
| 194-3 | 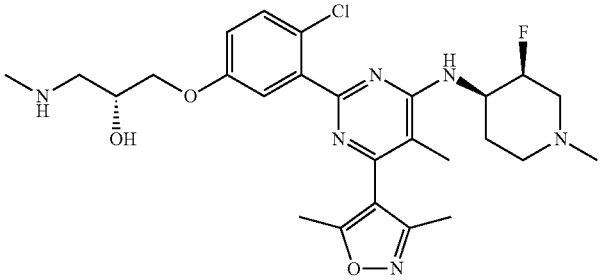 | 533.2 |

TABLE 1C-continued
Exemplary Compounds
| # | Structure | LC-MS m/z (M + H) |
|---|---|---|
| 195-3 | 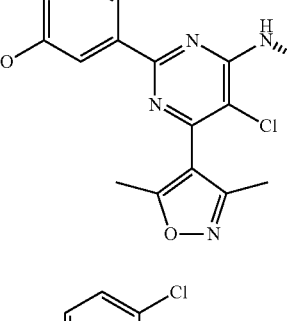 | 579.2 |
| 196-3 | 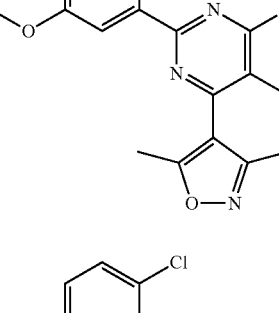 | 516.30 |
| 197-3 | 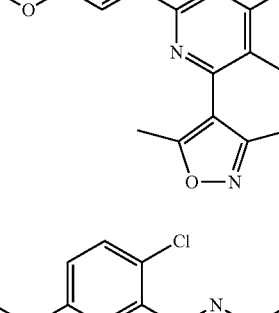 | 535.7 |
| 198-3 | 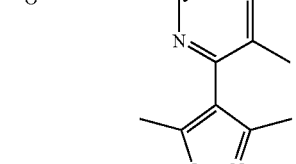 | 502 |
| 199-3 | 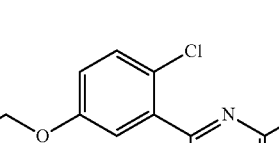 | 521 |

TABLE 1C-continued

Exemplary Compounds

| # | Structure | LC-MS m/z (M + H) |
|---|---|---|
| 200-3 | 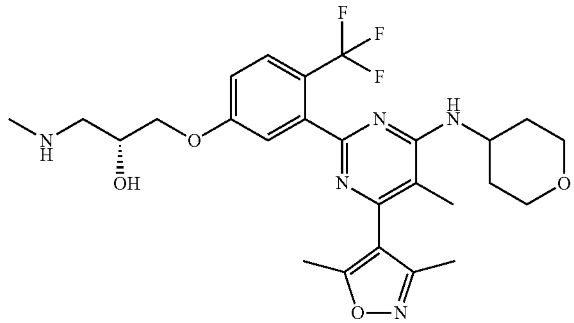 [SMILES: CNC[C@@H](O)COc1ccc(C(F)(F)F)c(-c2nc(NC3CCOCC3)c(C)c(-c3c(C)noc3C)n2)c1] | 536.2 |
| 201-3 | 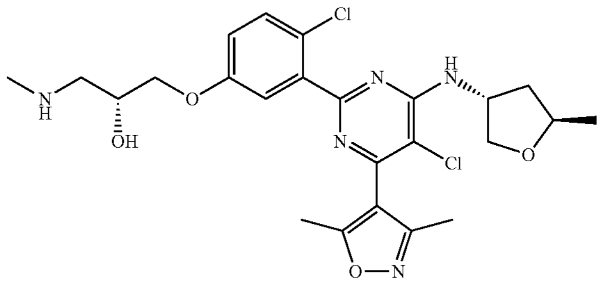 | 522.2 |
| 202-3 | 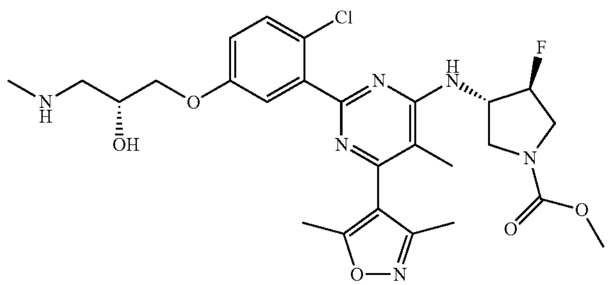 | 563.2 |
| 203-3 | 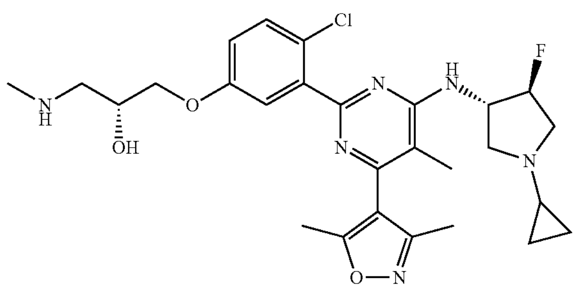 [SMILES: CNC[C@@H](O)COc1ccc(Cl)c(-c2nc(N[C@H]3CN(C4CC4)C[C@@H]3F)c(C)c(-c3c(C)noc3C)n2)c1] | 545.3 |
| 204-3 | 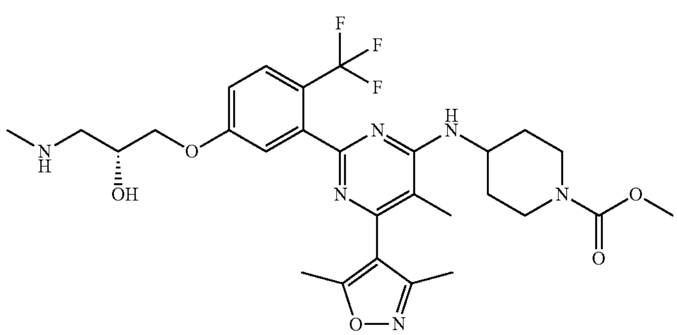 | 593.3 |

TABLE 1C-continued

Exemplary Compounds

| # | Structure | LC-MS m/z (M + H) |
|---|-----------|-------------------|
| 205-3 | 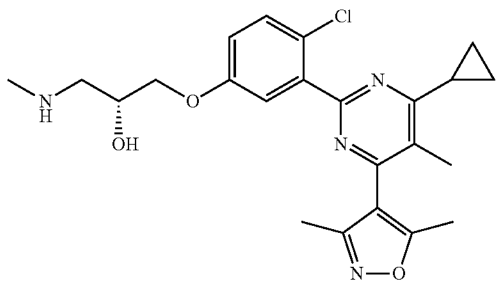 [SMILES: CNC[C@@H](O)COc1ccc(Cl)c(-c2nc(-c3c(C)noc3C)c(C)c(C3CC3)n2)c1] | 443.2 |
| 206-3 | 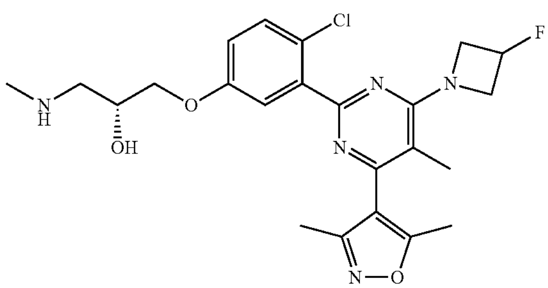 [SMILES: CNC[C@@H](O)COc1ccc(Cl)c(-c2nc(-c3c(C)noc3C)c(C)c(N3CC(F)C3)n2)c1] | 475.8 |
| 207-3 | 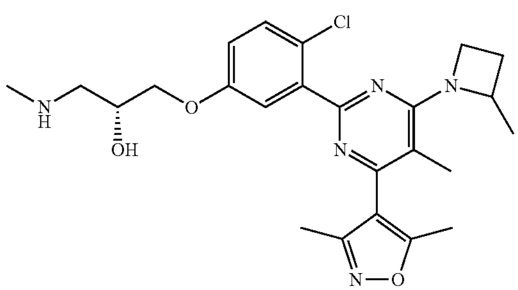 | 472.3 |
| 208-3 | 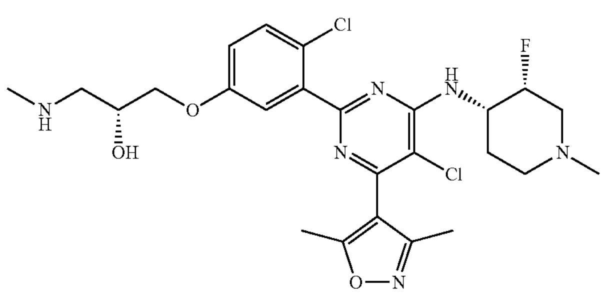 | 553.2 |
| 209-3 | 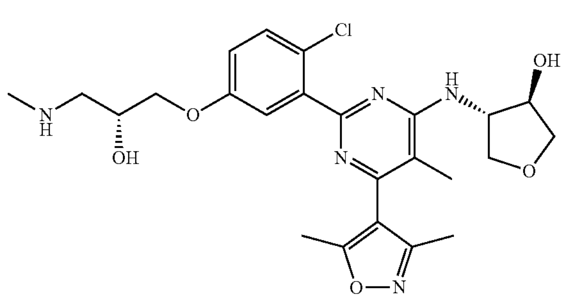 [SMILES: CNC[C@@H](O)COc1ccc(Cl)c(-c2nc(N[C@H]3COC[C@@H]3O)c(C)c(-c3c(C)noc3C)n2)c1] | 504.2 |

TABLE 1C-continued

Exemplary Compounds

| # | Structure | LC-MS m/z (M + H) |
|---|---|---|
| 210-3 | 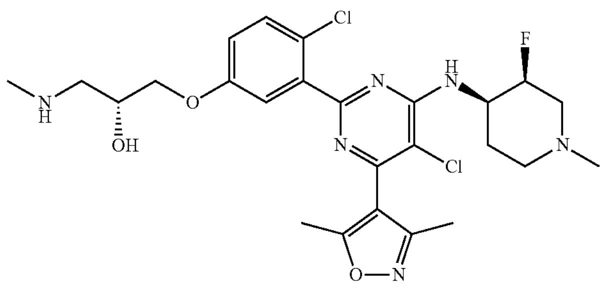 | 553.2 |
| 211-3 | 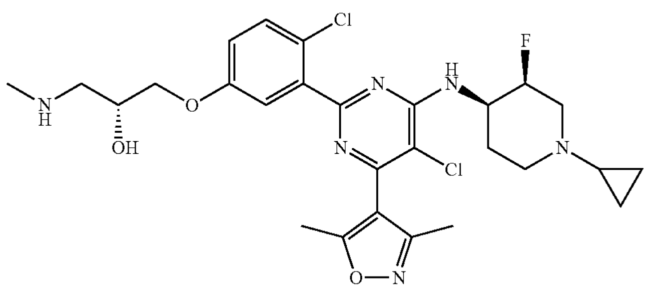 [SMILES: CNC[C@@H](O)COc1ccc(Cl)c(-c2nc(N[C@@H]3CCN(C4CC4)C[C@@H]3F)c(Cl)c(-c3c(C)noc3C)n2)c1] | 579.2 |
| 212-3 | 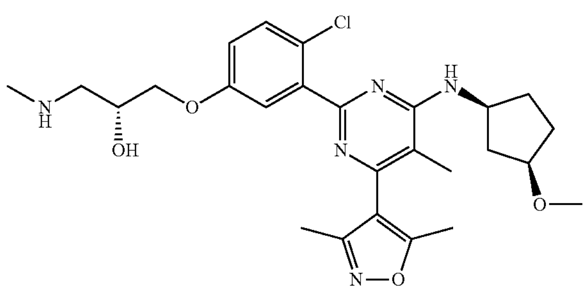 | 516.3 |
| 213-3 | 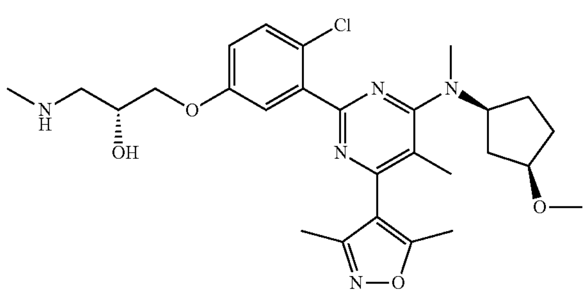 | 530.2 |
| 214-3 | 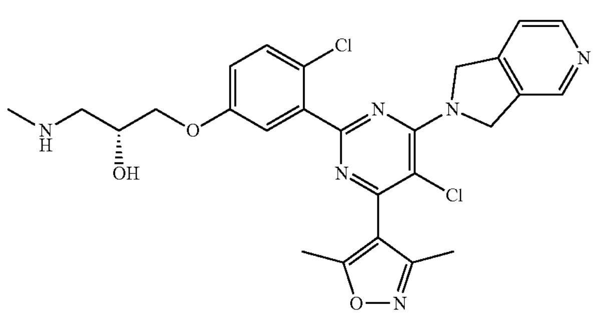 [SMILES: CNC[C@@H](O)COc1ccc(Cl)c(-c2nc(-c3c(C)noc3C)c(Cl)c(N3Cc4ccncc4C3)n2)c1] | 541.1 |

TABLE 1C-continued
Exemplary Compounds
| # | Structure | LC-MS m/z (M + H) |
|---|---|---|
| 215-3 | 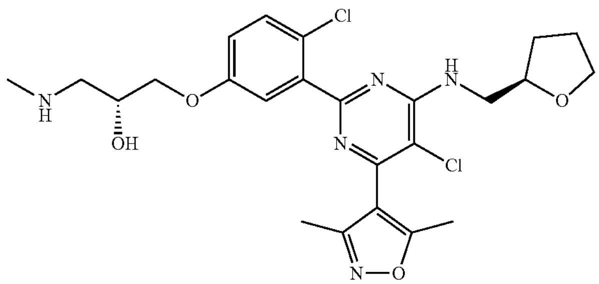 [SMILES: CNC[C@@H](O)COc1ccc(Cl)c(-c2nc(NC[C@H]3CCCO3)c(Cl)c(-c3c(C)noc3C)n2)c1] | 521.7 |
| 216-3 | 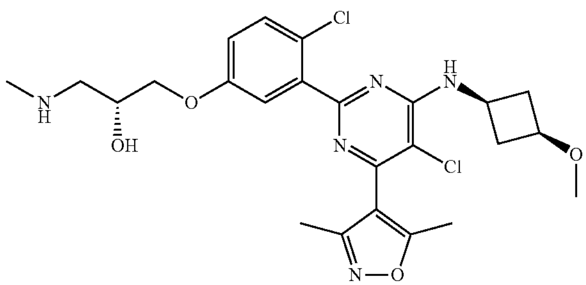 | 521.8 |
| 217-3 | 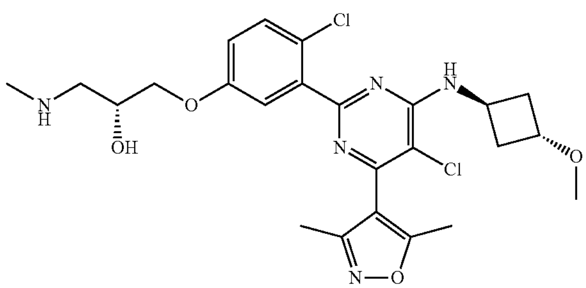 | 521.8 |
| 218-3 | 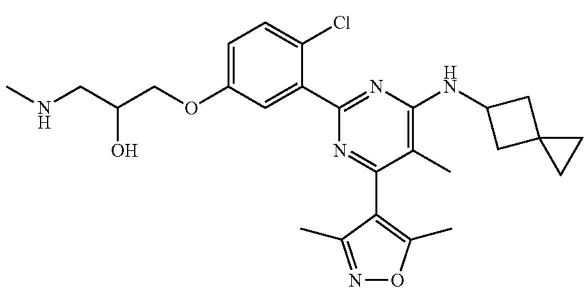 [SMILES: CNCC(O)COc1ccc(Cl)c(-c2nc(NC3CC4(CC4)C3)c(C)c(-c3c(C)noc3C)n2)c1] | 498.2 |
| 219-3 | 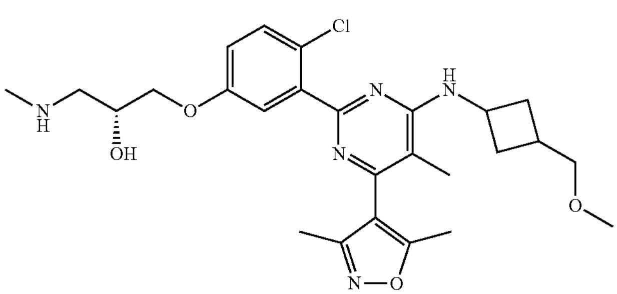 | 515.8 |

| # | Structure | LC-MS m/z (M + H) |
|---|---|---|
| 220-3 | 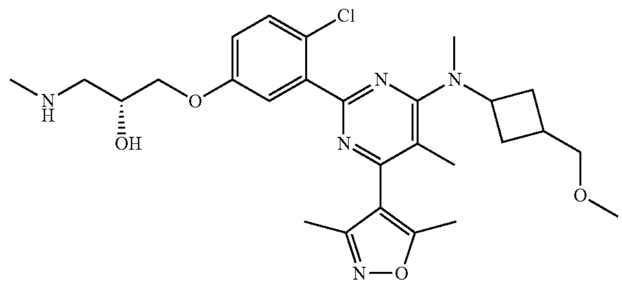 | 529.9 |
| 221-3 | 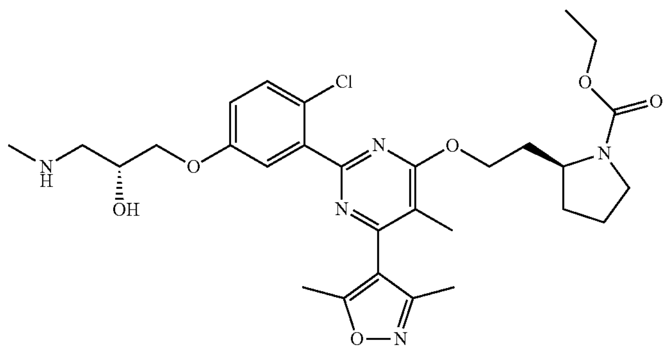 [SMILES: CCOC(=O)N1CCC[C@H]1CCOc1nc(-c2cc(OC[C@H](O)CNC)ccc2Cl)nc(-c2c(C)noc2C)c1C] | 587.8 |
| 222-3 | 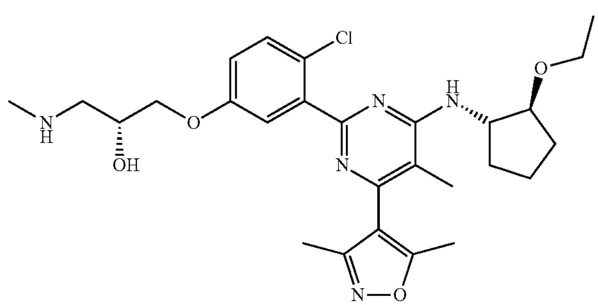 | 530.3 |
| 223-3 | 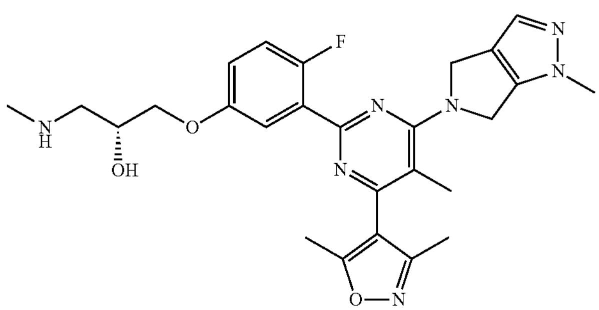 | 508.2 |
| 224-3 | 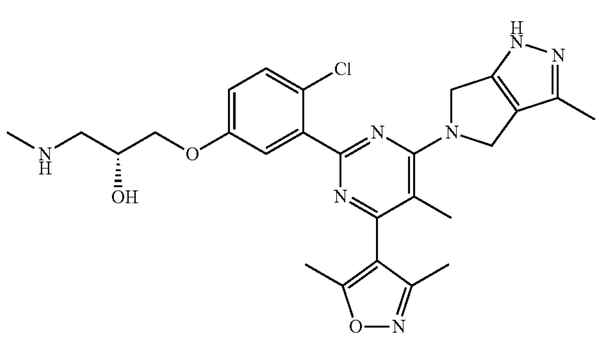 | 524.3 |

TABLE 1C-continued

Exemplary Compounds

| # | Structure | LC-MS m/z (M + H) |
|---|-----------|-------------------|
| 225-3 | 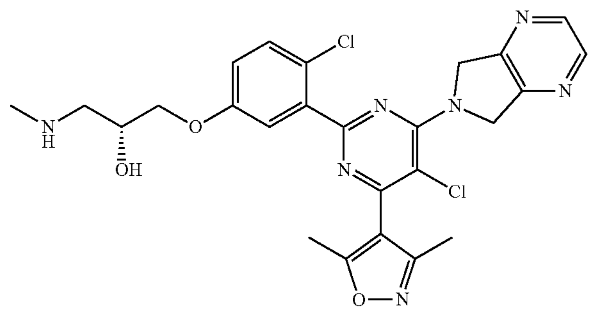 | 542.2 |
| 226-3 | 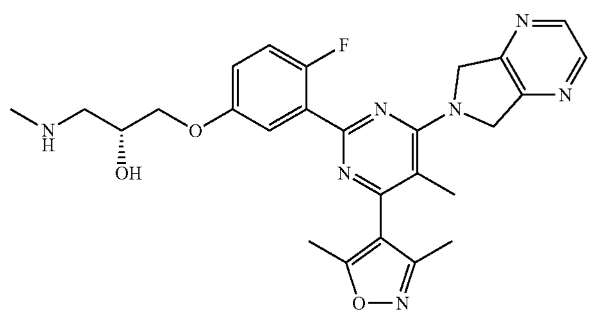 [SMILES: CNC[C@@H](O)COc1ccc(F)c(-c2nc(-c3c(C)noc3C)c(C)c(N3Cc4nccnc4C3)n2)c1] | 506.2 |
| 227-3 | 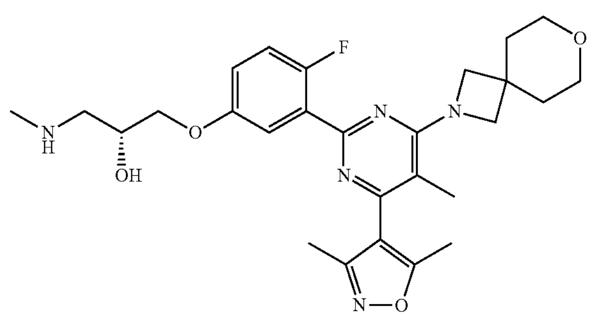 [SMILES: CNC[C@@H](O)COc1ccc(F)c(-c2nc(-c3c(C)noc3C)c(C)c(N3CC4(CCOCC4)C3)n2)c1] | 512.3 |
| 228-3 | 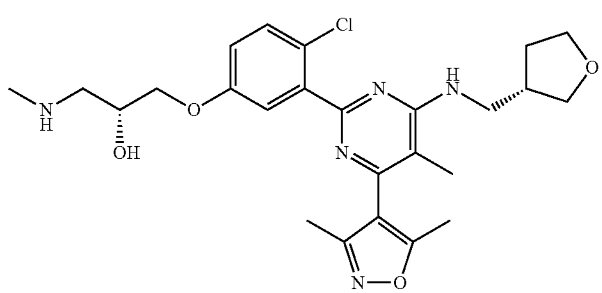 [SMILES: CNC[C@@H](O)COc1ccc(Cl)c(-c2nc(NC[C@@H]3CCOC3)c(C)c(-c3c(C)noc3C)n2)c1] | 501.8 |
| 229-3 | 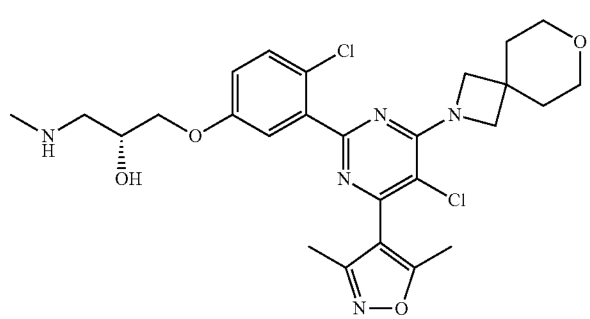 [SMILES: CNC[C@@H](O)COc1ccc(Cl)c(-c2nc(-c3c(C)noc3C)c(Cl)c(N3CC4(CCOCC4)C3)n2)c1] | 548.2 |

TABLE 1C-continued

Exemplary Compounds

| # | Structure | LC-MS m/z (M + H) |
|---|-----------|-------------------|
| 230-3 | 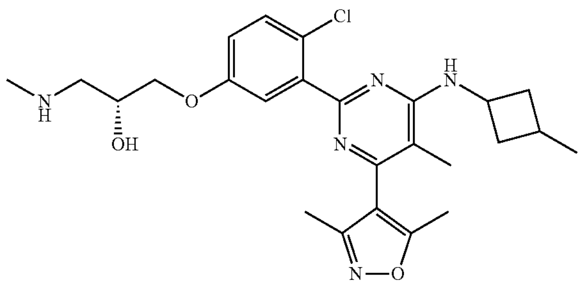 | 486.2 |
| 231-3 | 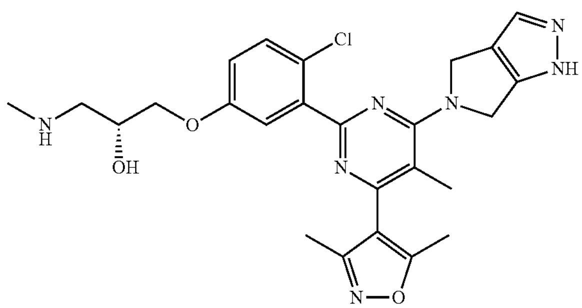 [SMILES: CNC[C@@H](O)COc1ccc(Cl)c(-c2nc(-c3c(C)noc3C)c(C)c(N3Cc4cn[nH]c4C3)n2)c1] | 510.20 |
| 232-3 | 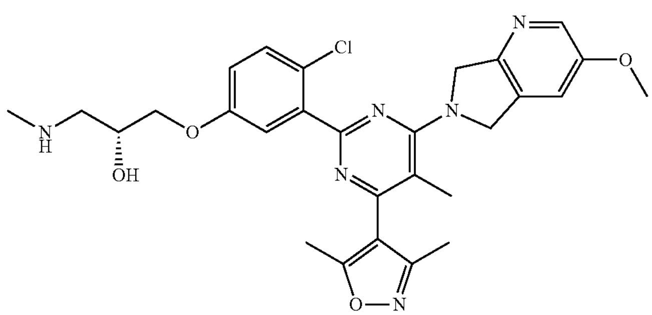 | 551.10 |
| 233-3 | 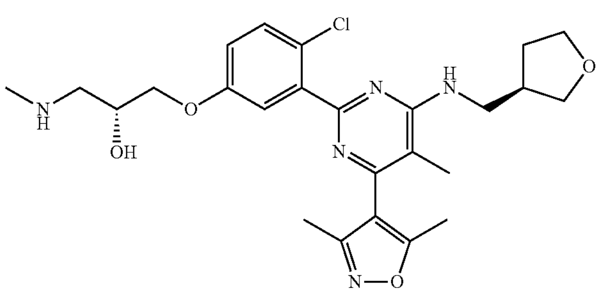 [SMILES: CNC[C@@H](O)COc1ccc(Cl)c(-c2nc(NC[C@H]3CCOC3)c(C)c(-c3c(C)noc3C)n2)c1] | 501.90 |
| 234-3 | 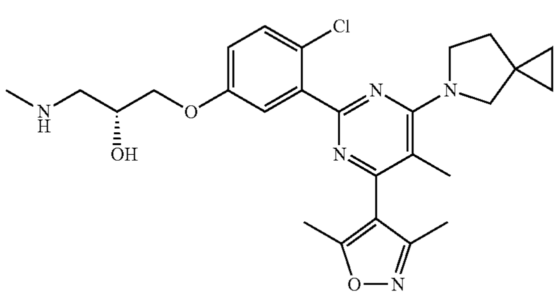 [SMILES: CNC[C@@H](O)COc1ccc(Cl)c(-c2nc(-c3c(C)noc3C)c(C)c(N3CCC4(CC4)C3)n2)c1] | 498.30 |

TABLE 1C-continued

Exemplary Compounds

| # | Structure | LC-MS m/z (M + H) |
|---|-----------|-------------------|
| 235-3 | | 484.20 |
| 236-3 | | 538.30 |
| 237-3 | | 538.20 |
| 238-3 | | 458.30 |
| 239-3 | | 483.00 |

TABLE 1C-continued

Exemplary Compounds

| # | Structure | LC-MS m/z (M + H) |
|---|-----------|-------------------|
| 240-3 | 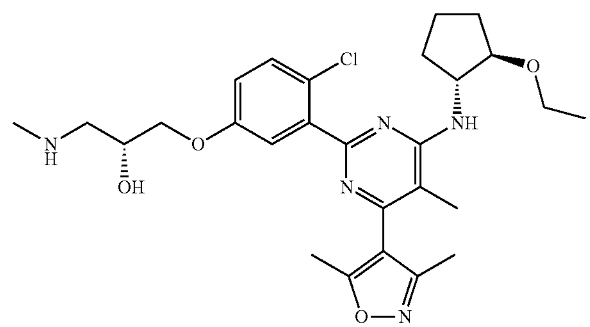 [SMILES: CCO[C@@H]1CCC[C@H]1Nc1nc(-c2cc(OC[C@H](O)CNC)ccc2Cl)nc(-c2c(C)noc2C)c1C] | 530.20 |
| 241-3 | 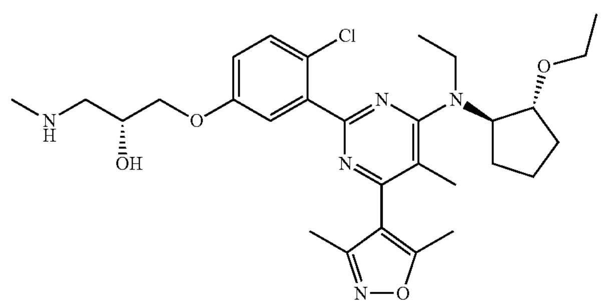 [SMILES: CCO[C@@H]1CCC[C@H]1N(CC)c1nc(-c2cc(OC[C@H](O)CNC)ccc2Cl)nc(-c2c(C)noc2C)c1C] | 558.30 |
| 242-3 | 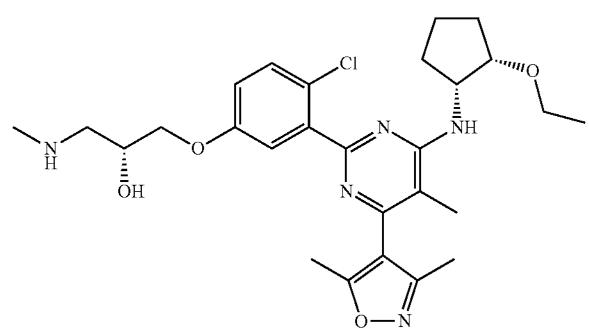 [SMILES: CCO[C@H]1CCC[C@H]1Nc1nc(-c2cc(OC[C@H](O)CNC)ccc2Cl)nc(-c2c(C)noc2C)c1C] | 530.20 |
| 243-3 | 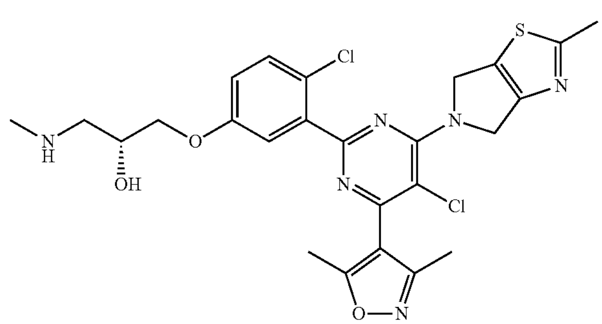 | 560.80 |

TABLE 1C-continued
Exemplary Compounds
| # | Structure | LC-MS m/z (M + H) |
|---|---|---|
| 244-3 | 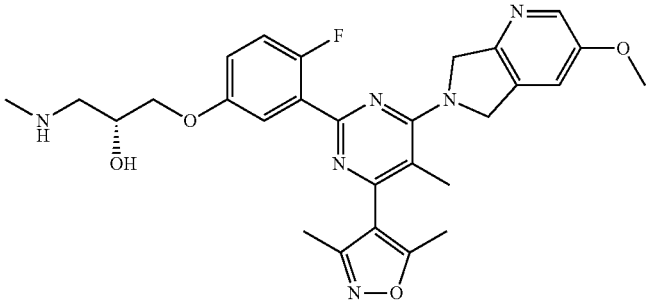 | 534.90 |
| 245-3 | 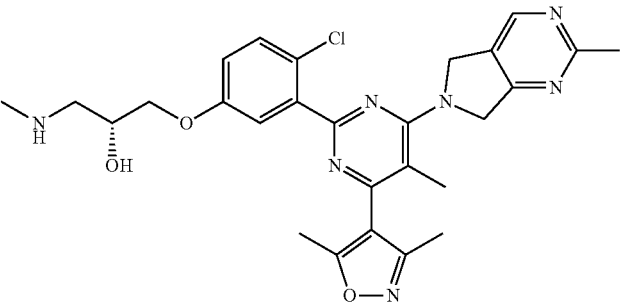 | 536.20 |
| 246-3 | 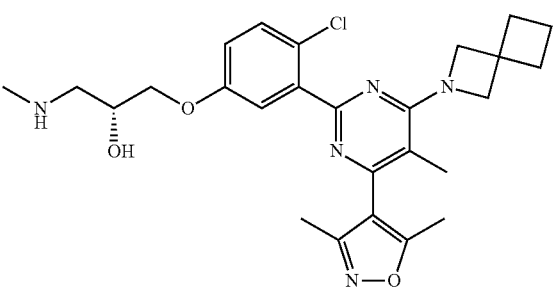 [SMILES: CNC[C@@H](O)COc1ccc(Cl)c(-c2nc(-c3c(C)noc3C)c(C)c(N3CC4(CCC4)C3)n2)c1] | 498.00 |
| 247-3 | 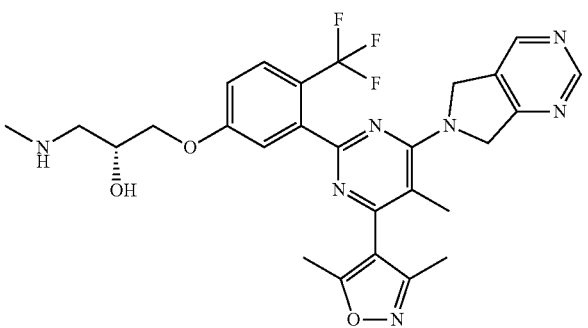 [SMILES: CNC[C@@H](O)COc1ccc(C(F)(F)F)c(-c2nc(-c3c(C)noc3C)c(C)c(N3Cc4cncnc4C3)n2)c1] | 556.30 |
| 248-3 | 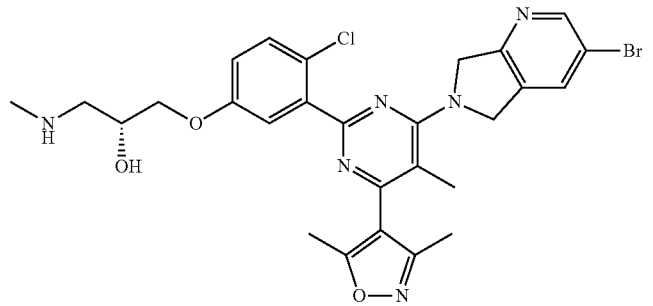 [SMILES: CNC[C@@H](O)COc1ccc(Cl)c(-c2nc(-c3c(C)noc3C)c(C)c(N3Cc4cc(Br)cnc4C3)n2)c1] | 601.10 |

TABLE 1C-continued

Exemplary Compounds

| # | Structure | LC-MS m/z (M + H) |
|---|---|---|
| 249-3 | 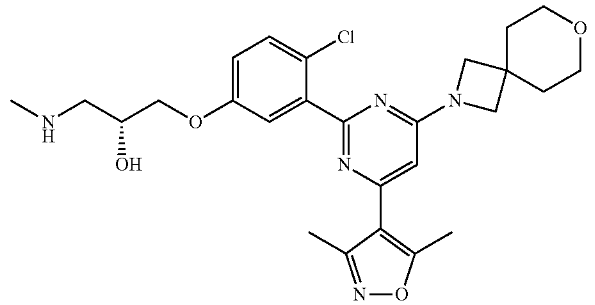 [SMILES: CNC[C@@H](O)COc1ccc(Cl)c(-c2nc(-c3c(C)noc3C)cc(N3CC4(CCOCC4)C3)n2)c1] | 514.20 |
| 250-3 | 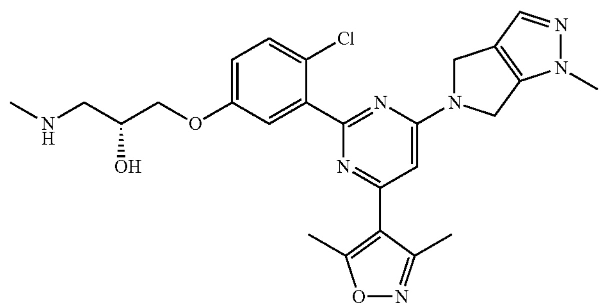 | 510.20 |
| 251-3 | 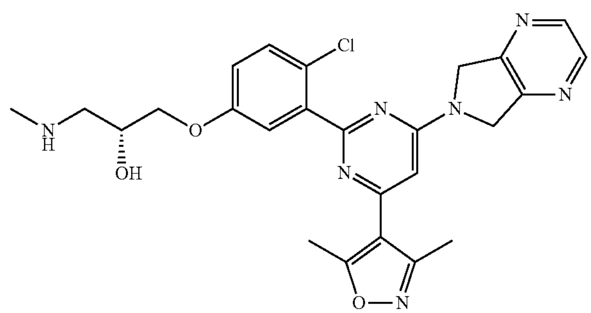 [SMILES: CNC[C@@H](O)COc1ccc(Cl)c(-c2nc(-c3c(C)noc3C)cc(N3Cc4nccnc4C3)n2)c1] | 508.20 |
| 252-3 | 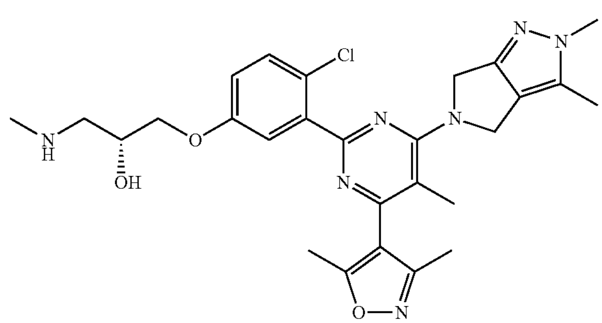 | 538.20 |
| 253-3 | 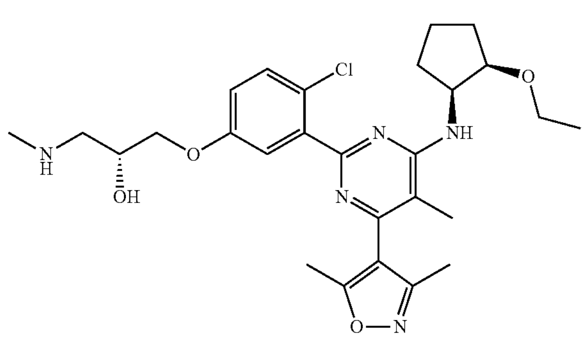 [SMILES: CCO[C@@H]1CCC[C@@H]1Nc1nc(-c2cc(OC[C@H](O)CNC)ccc2Cl)nc(-c2c(C)noc2C)c1C] | 530.20 |

TABLE 1C-continued

Exemplary Compounds

| # | Structure | LC-MS m/z (M + H) |
|---|-----------|-------------------|
| 254-3 | 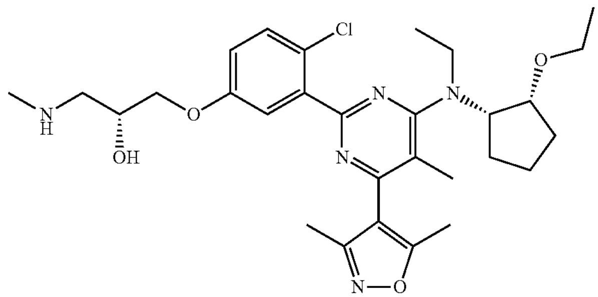 [SMILES: CCO[C@@H]1CCC[C@@H]1N(CC)c1nc(-c2cc(OC[C@H](O)CNC)ccc2Cl)nc(-c2c(C)noc2C)c1C] | 558.30 |
| 255-3 | 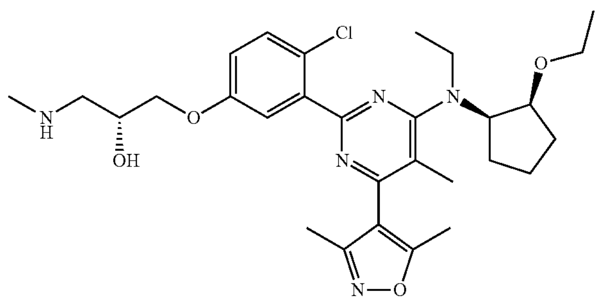 [SMILES: CCO[C@H]1CCC[C@H]1N(CC)c1nc(-c2cc(OC[C@H](O)CNC)ccc2Cl)nc(-c2c(C)noc2C)c1C] | 558.30 |
| 256-3 | 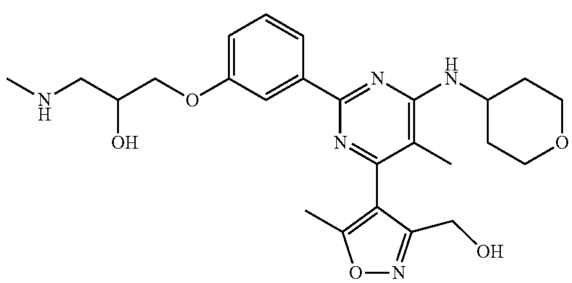 [SMILES: CNCC(O)COc1cccc(-c2nc(NC3CCOCC3)c(C)c(-c3c(CO)noc3C)n2)c1] | 484.20 |
| 257-3 | 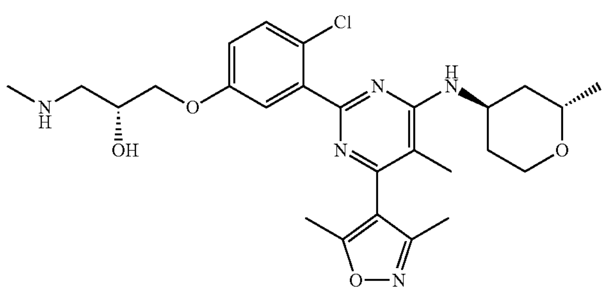 | 516.30 |
| 258-3 | 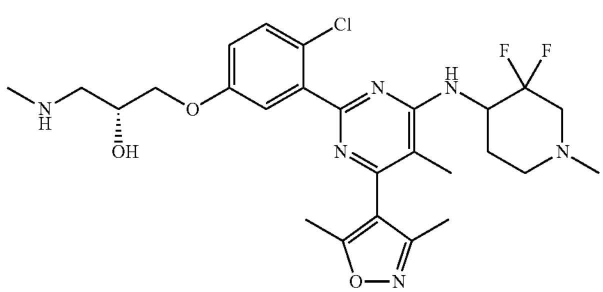 | 550.80 |

TABLE 1C-continued

Exemplary Compounds

| # | Structure | LC-MS m/z (M + H) |
|---|---|---|
| 259-3 | 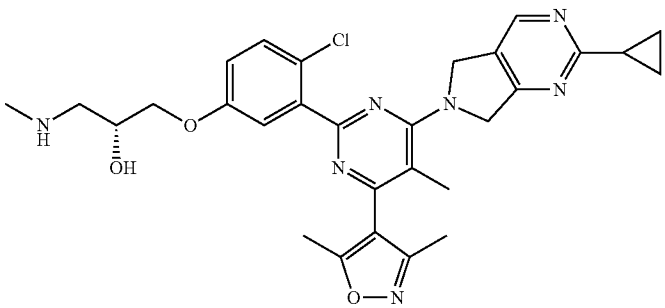 [SMILES: CNC[C@@H](O)COc1ccc(Cl)c(-c2nc(-c3c(C)noc3C)c(C)c(N3Cc4cnc(C5CC5)nc4C3)n2)c1] | 561.70 |
| 260-3 | 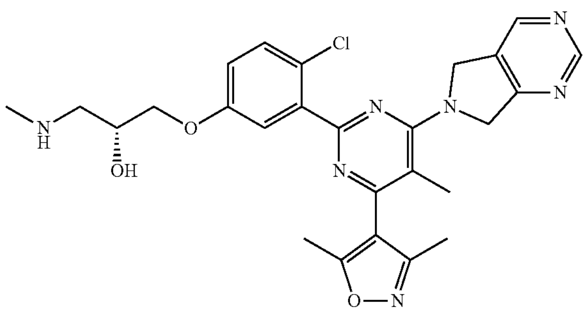 [SMILES: CNC[C@@H](O)COc1ccc(Cl)c(-c2nc(-c3c(C)noc3C)c(C)c(N3Cc4cncnc4C3)n2)c1] | 506.30 |
| 261-3 | 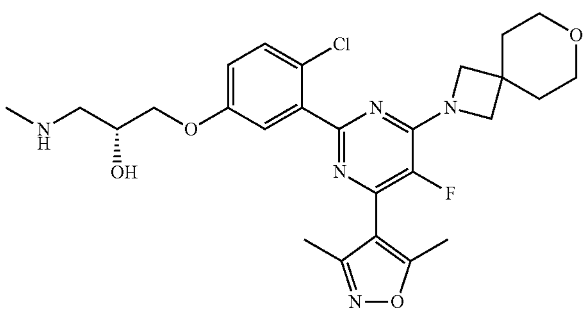 [SMILES: CNC[C@@H](O)COc1ccc(Cl)c(-c2nc(-c3c(C)noc3C)c(F)c(N3CC4(CCOCC4)C3)n2)c1] | 532.20 |
| 262-3 | 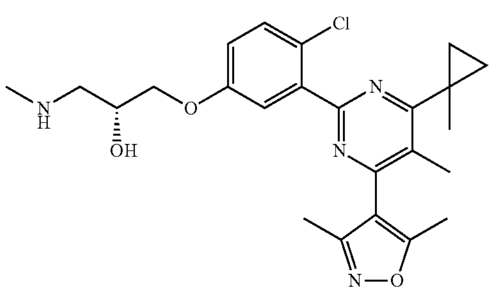 [SMILES: CNC[C@@H](O)COc1ccc(Cl)c(-c2nc(-c3c(C)noc3C)c(C)c(C3(C)CC3)n2)c1] | 457.20 |
| 263-3 | 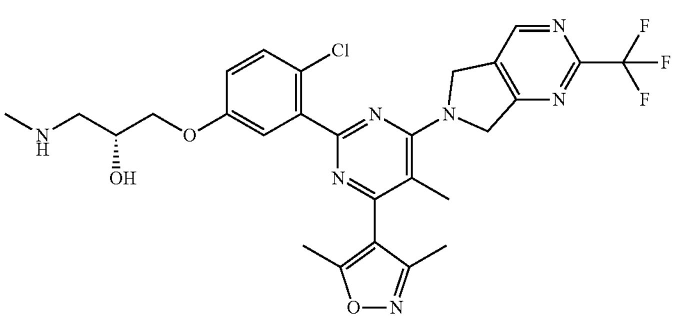 [SMILES: CNC[C@@H](O)COc1ccc(Cl)c(-c2nc(-c3c(C)noc3C)c(C)c(N3Cc4cnc(C(F)(F)F)nc4C3)n2)c1] | 590.20 |

TABLE 1C-continued
Exemplary Compounds
| # | Structure | LC-MS m/z (M + H) |
|---|---|---|
| 264-3 | 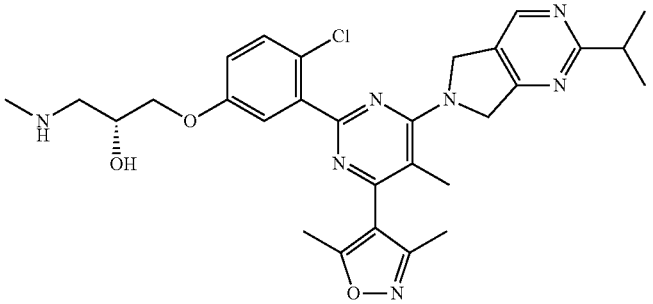 [SMILES: CNC[C@@H](O)COc1ccc(Cl)c(-c2nc(-c3c(C)noc3C)c(C)c(N3Cc4cnc(C(C)C)nc4C3)n2)c1] | 564.20 |
| 265-3 | 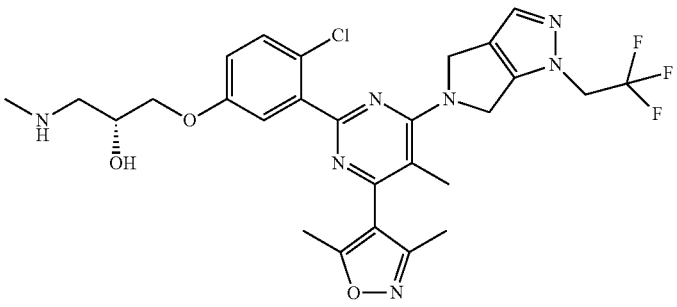 [SMILES: CNC[C@@H](O)COc1ccc(Cl)c(-c2nc(-c3c(C)noc3C)c(C)c(N3Cc4cnn(CC(F)(F)F)c4C3)n2)c1] | 592.20 |
| 266-3 | 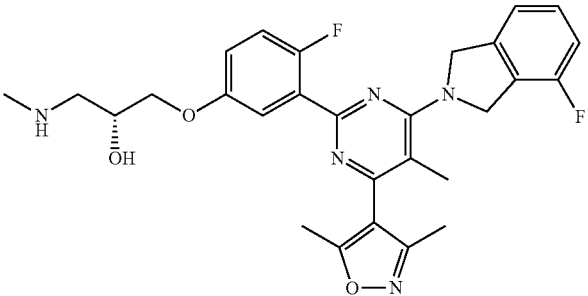 [SMILES: CNC[C@@H](O)COc1ccc(Cl)c(-c2nc(-c3c(C)noc3C)c(C)c(N3Cc4cccc(F)c4C3)n2)c1] | 521.80 |
| 267-3 | 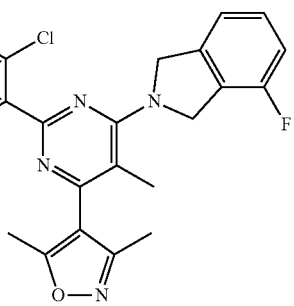 | 537.70 |
| 268-3 | 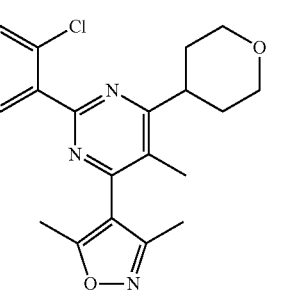 | 487.20 |

TABLE 1C-continued

Exemplary Compounds

| # | Structure | LC-MS m/z (M + H) |
|---|---|---|
| 269-3 | 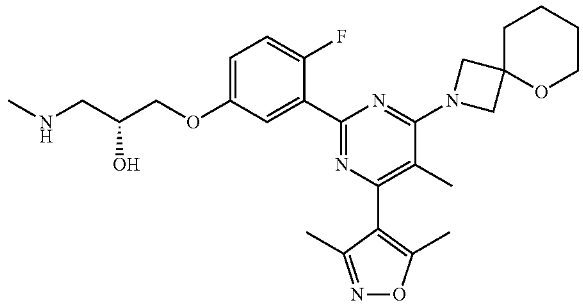 [SMILES: CNC[C@@H](O)COc1ccc(F)c(-c2nc(-c3c(C)noc3C)c(C)c(N3CC4(CCCCO4)C3)n2)c1] | 512.30 |
| 270-3 | 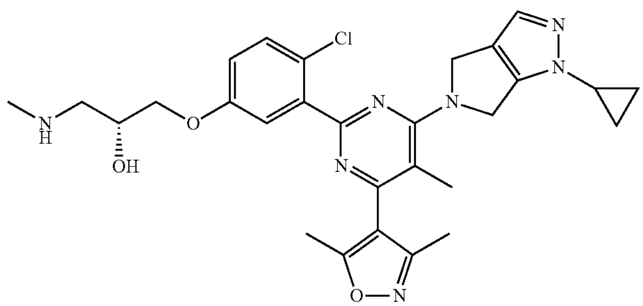 [SMILES: CNC[C@@H](O)COc1ccc(Cl)c(-c2nc(-c3c(C)noc3C)c(C)c(N3Cc4cnn(C5CC5)c4C3)n2)c1] | 550.20 |
| 271-3 | 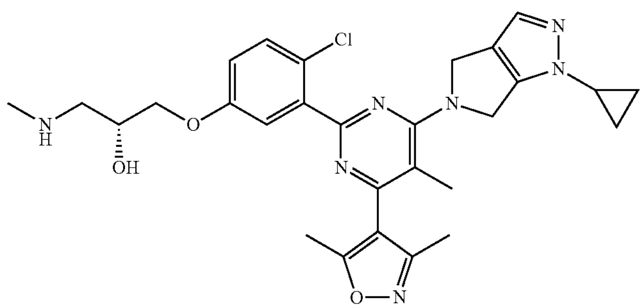 [SMILES: CNC[C@@H](O)COc1ccc(Cl)c(-c2nc(-c3c(C)noc3C)c(C)c(N3Cc4cnn(C5CC5)c4C3)n2)c1] | 550.20 |
| 272-3 | 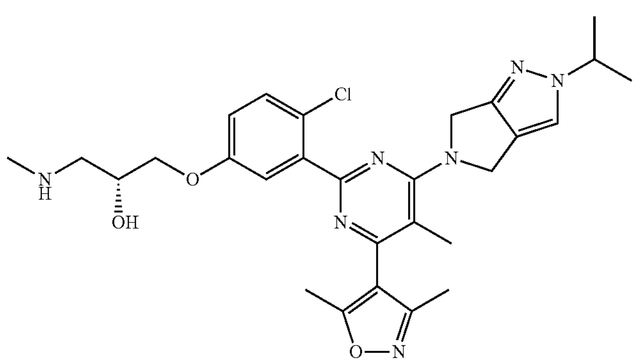 [SMILES: CNC[C@@H](O)COc1ccc(Cl)c(-c2nc(-c3c(C)noc3C)c(C)c(N3Cc4cn(C(C)C)nc4C3)n2)c1] | 552.20 |
| 273-3 | 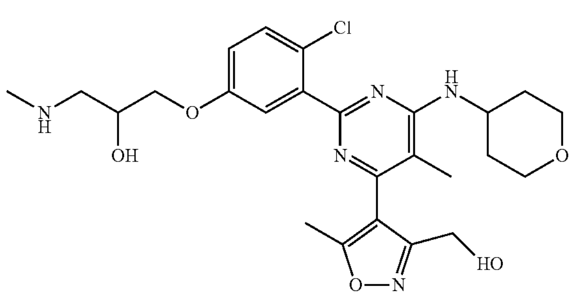 [SMILES: CNCC(O)COc1ccc(Cl)c(-c2nc(NC3CCOCC3)c(C)c(-c3c(CO)noc3C)n2)c1] | 518.20 |

TABLE 1C-continued
Exemplary Compounds
| # | Structure | LC-MS m/z (M + H) |
|---|---|---|
| 274-3 | 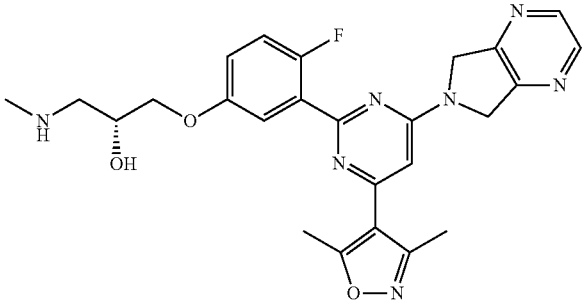 | 492.20 |
| 275-3 | 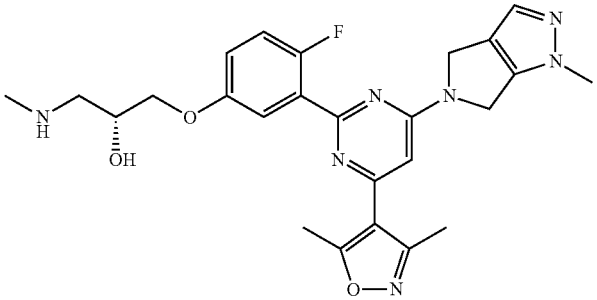 | 494.20 |
| 276-3 | 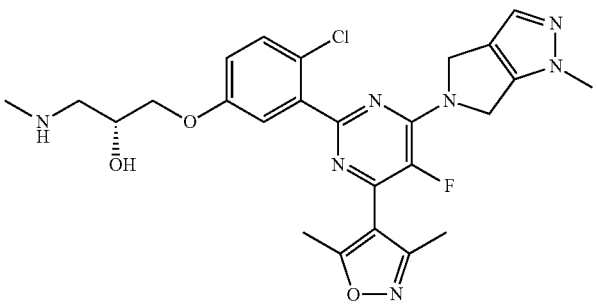 | 528.20 |
| 277-3 | 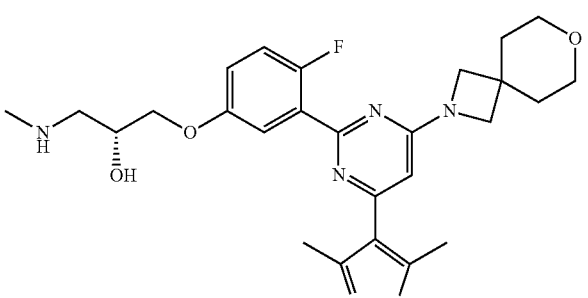 | 498.20 |
| 278-3 | 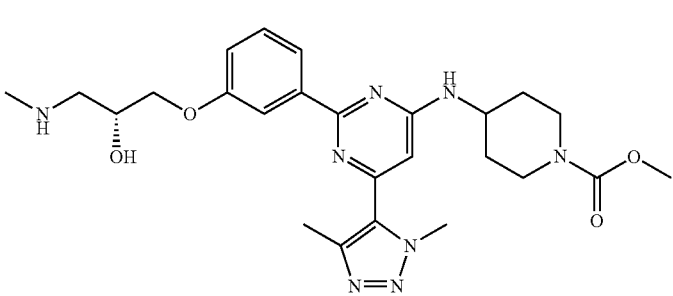 | 511.2 |

TABLE 1C-continued

| Exemplary Compounds | | |
|---|---|---|
| # | Structure | LC-MS m/z (M + H) |
| 279-3 | | 554.00 |
| 280-3 | | 575.20 |
| 281-3 | | 597.40 |
| 282-3 | | 583.30 |

TABLE 1C-continued

Exemplary Compounds

| # | Structure | LC-MS m/z (M + H) |
|---|-----------|-------------------|
| 283-3 | 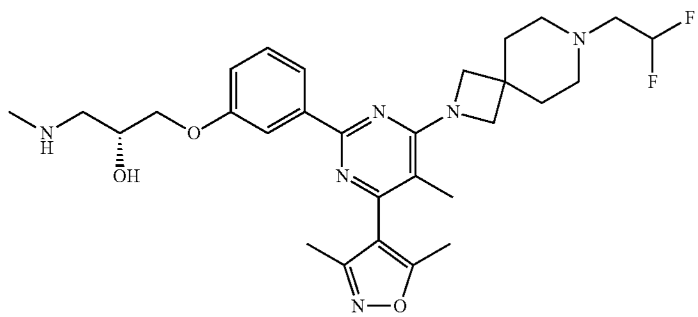 | 591.20 |
| 284-3 | 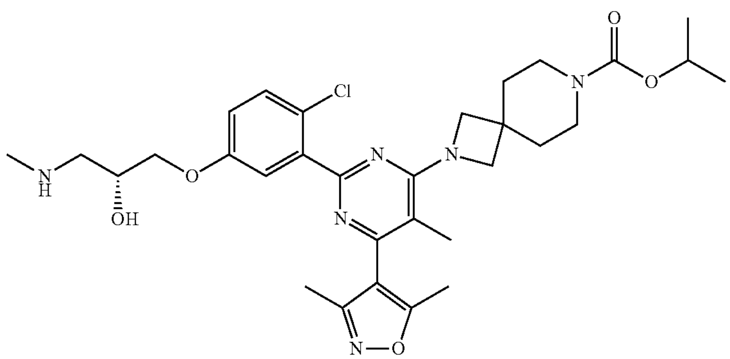 [SMILES: CNC[C@@H](O)COc1ccc(F)c(-c2nc(-c3c(C)noc3C)c(C)c(N3CC4(CCN(C(=O)OC(C)C)CC4)C3)n2)c1] | 613.30 |
| 285-3 | 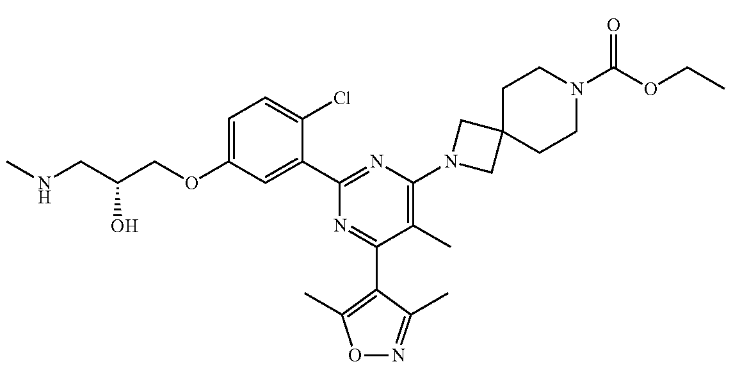 [SMILES: CCOC(=O)N1CCC2(CC1)CN(c1nc(-c3cc(OC[C@H](O)CNC)ccc3Cl)nc(-c3c(C)noc3C)c1C)C2] | 599.20 |
| 286-3 | 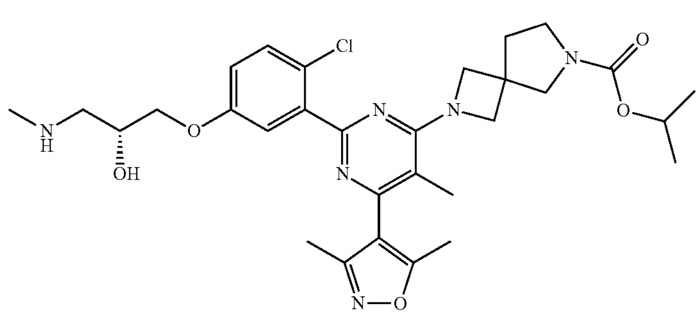 [SMILES: CNC[C@@H](O)COc1ccc(Cl)c(-c2nc(-c3c(C)noc3C)c(C)c(N3CC4(CCN(C(=O)OC(C)C)C4)C3)n2)c1] | 599.30 |

TABLE 1C-continued
Exemplary Compounds
| # | Structure | LC-MS m/z (M + H) |
|---|---|---|
| 287-3 | 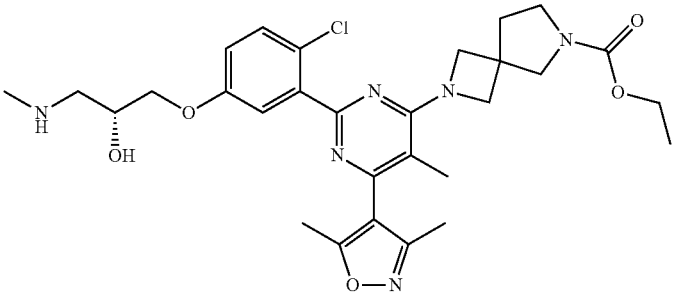 [SMILES: CCOC(=O)N1CCC2(C1)CN(c1nc(-c3cc(OC[C@H](O)CNC)ccc3Cl)nc(-c3c(C)noc3C)c1C)C2] | 585.30 |
| 288-3 | 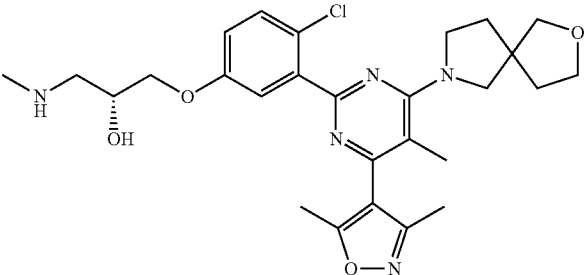 [SMILES: CNC[C@@H](O)COc1ccc(Cl)c(-c2nc(-c3c(C)noc3C)c(C)c(N3CCC4(CCOC4)C3)n2)c1] | 527.80 |
| 289-3 | 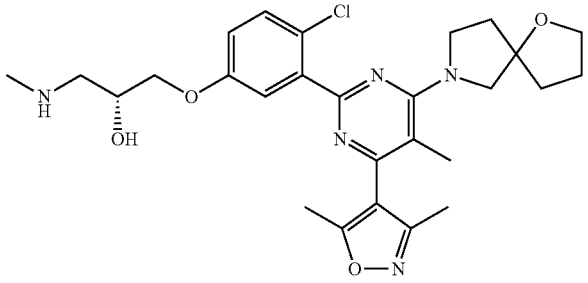 [SMILES: CNC[C@@H](O)COc1ccc(Cl)c(-c2nc(-c3c(C)noc3C)c(C)c(N3CCC4(CCCO4)C3)n2)c1] | 528.00 |
| 290-3 | 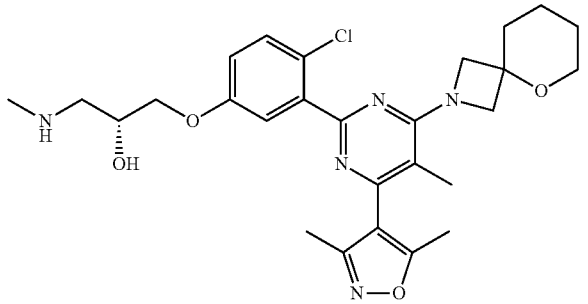 | 528.20 |
| 291-3 | 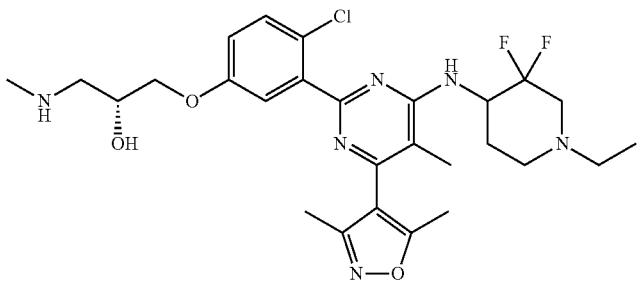 [SMILES: CCN1CCC(Nc2nc(-c3cc(OC[C@H](O)CNC)ccc3Cl)nc(-c3c(C)noc3C)c2C)C(F)(F)C1] | 564.70 |

TABLE 1C-continued
Exemplary Compounds
| # | Structure | LC-MS m/z (M + H) |
|---|-----------|-------------------|
| 292-3 | 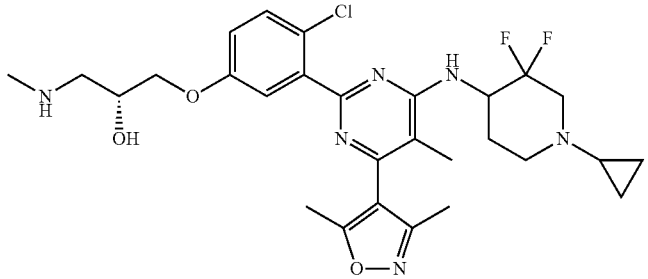 [SMILES: CNC[C@@H](O)COc1ccc(Cl)c(-c2nc(NC3CCN(C4CC4)CC3(F)F)c(C)c(-c3c(C)noc3C)n2)c1] | 576.70 |
| 293-3 | 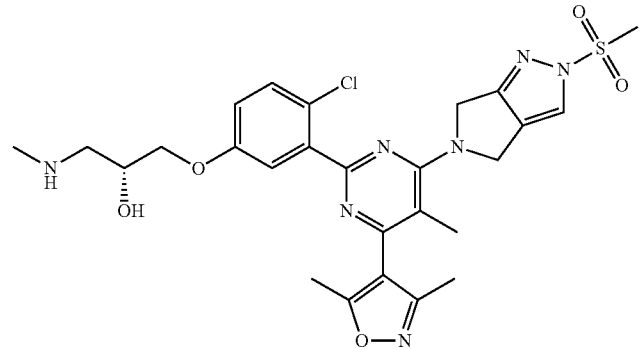 | 588.20 |
| 294-3 | 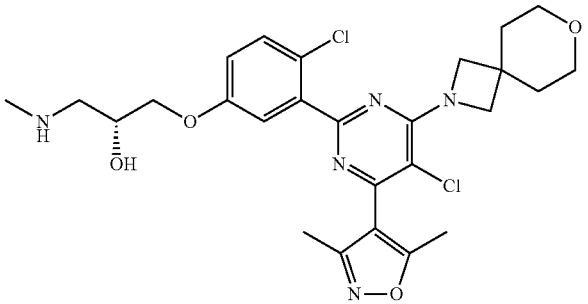 [SMILES: CNC[C@@H](O)COc1ccc(Cl)c(-c2nc(-c3c(C)noc3C)c(Cl)c(N3CC4(CCOCC4)C3)n2)c1] | 532.30 |
| 295-3 | 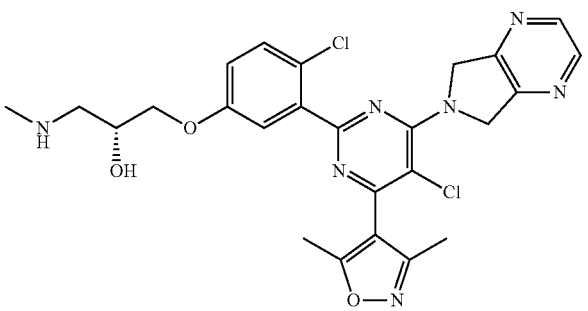 [SMILES: CNC[C@@H](O)COc1ccc(Cl)c(-c2nc(-c3c(C)noc3C)c(Cl)c(N3Cc4nccnc4C3)n2)c1] | 526.20 |
| 296-3 | 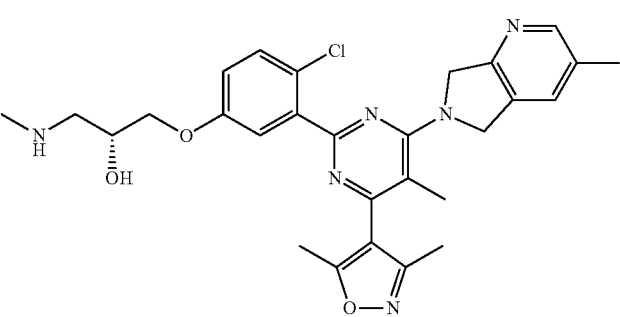 | 535.20 |

TABLE 1C-continued

Exemplary Compounds

| # | Structure | LC-MS m/z (M + H) |
|---|---|---|
| 297-3 | 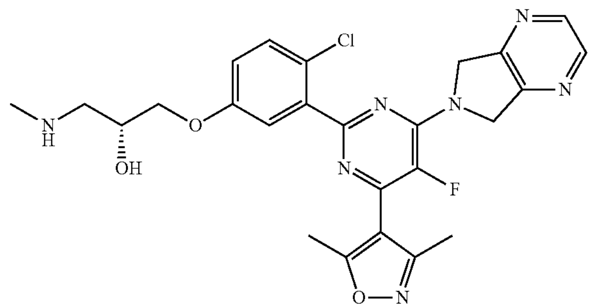 [SMILES: CNC[C@@H](O)COc1ccc(Cl)c(-c2nc(-c3c(C)noc3C)c(F)c(N3Cc4nccnc4C3)n2)c1] | 526.30 |

TABLE 2

Exemplary Compounds

| # | Structure | LC-MS m/z (M + H) |
|---|---|---|
| 1-2 | 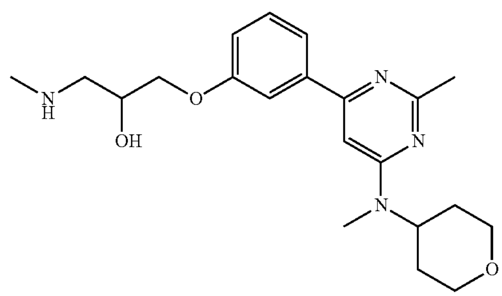 [SMILES: CNCC(O)COc1cccc(-c2cc(N(C)C3CCOCC3)nc(C)n2)c1] | 387.2 |
| 2-2 | 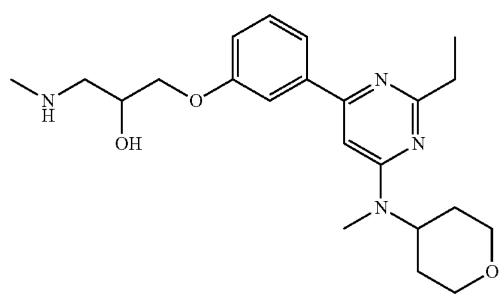 [SMILES: CCc1nc(-c2cccc(OCC(O)CNC)c2)cc(N(C)C2CCOCC2)n1] | 401.3 |
| 3-2 | 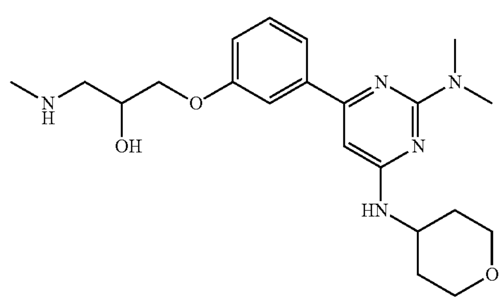 [SMILES: CNCC(O)COc1cccc(-c2cc(NC3CCOCC3)nc(N(C)C)n2)c1] | 402.2 |

TABLE 2-continued

Exemplary Compounds

| # | Structure | LC-MS m/z (M + H) |
|---|---|---|
| 4-2 | 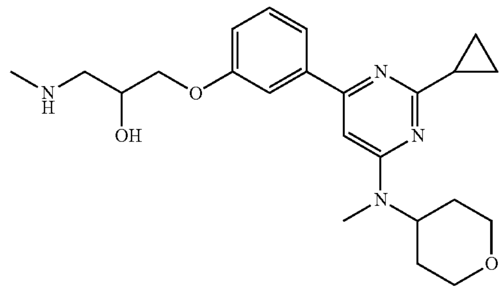 | 413.2 |
| 5-2 | 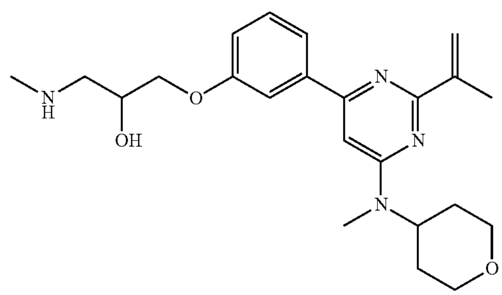 | 413.3 |
| 6-2 | 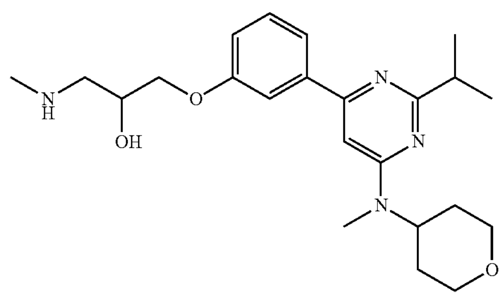 [SMILES: CNCC(O)COc1cccc(-c2cc(N(C)C3CCOCC3)nc(C(C)C)n2)c1] | 415.3 |
| 7-2 | 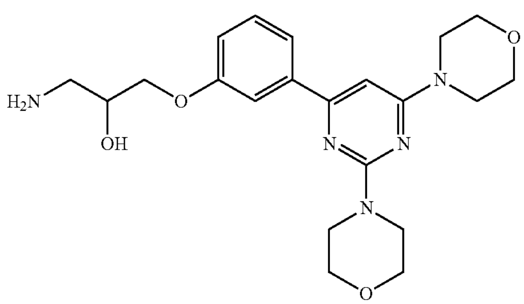 [SMILES: NCC(O)COc1cccc(-c2cc(N3CCOCC3)nc(N3CCOCC3)n2)c1] | 416.3 |
| 8-2 | 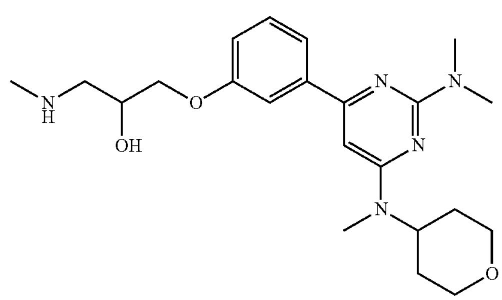 | 416.3 |

TABLE 2-continued
Exemplary Compounds
| # | Structure | LC-MS m/z (M + H) |
|---|---|---|
| 9-2 | 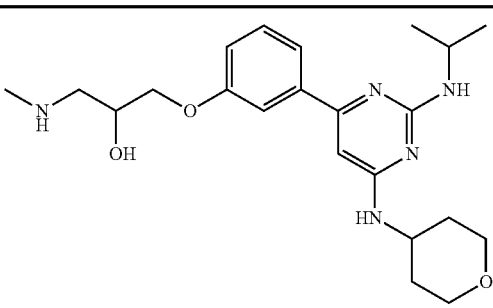 | 416.3 |
| 10-2 | 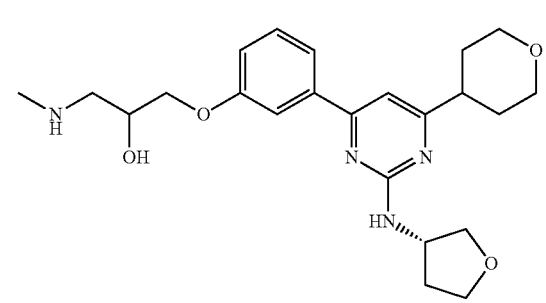 [SMILES: CNCC(O)COc1cccc(-c2cc(C3CCOCC3)nc(N[C@H]3CCOC3)n2)c1] | 429.3 |
| 11-2 | 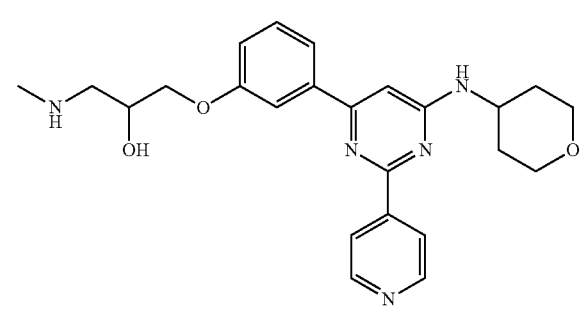 [SMILES: CNCC(O)COc1cccc(-c2cc(NC3CCOCC3)nc(-c3ccncc3)n2)c1] | 436.3 |
| 12-2 | 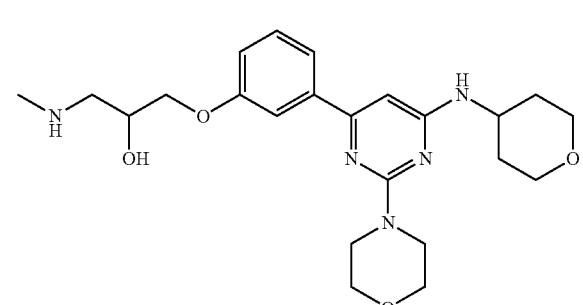 | 444.3 |
| 13-2 | 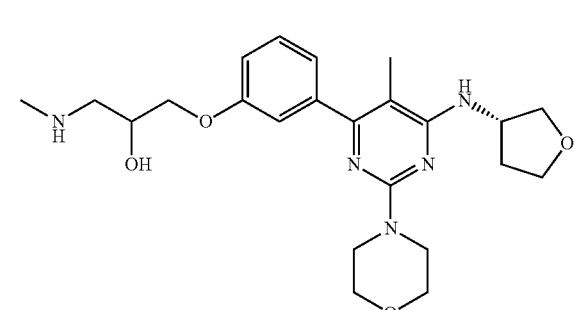 | 444.2 |

TABLE 2-continued

Exemplary Compounds

| # | Structure | LC-MS m/z (M + H) |
|---|---|---|
| 14-2 | 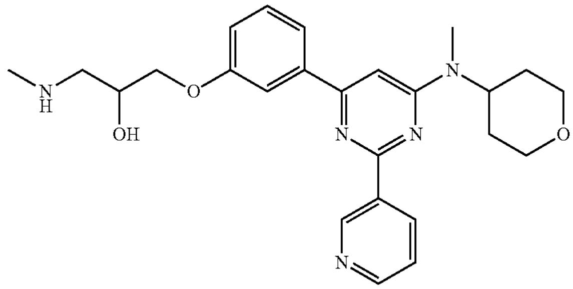 [SMILES: CNCC(O)COc1cccc(-c2cc(N(C)C3CCOCC3)nc(-c3cccnc3)n2)c1] | 450.2 |
| 15-2 | 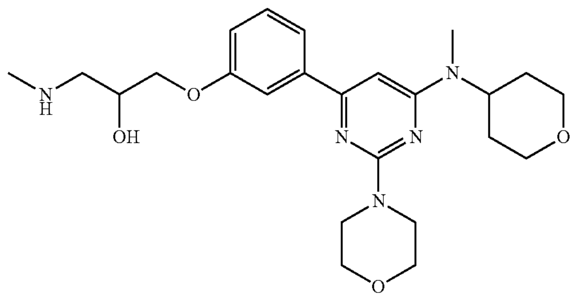 [SMILES: CNCC(O)COc1cccc(-c2cc(N(C)C3CCOCC3)nc(N3CCOCC3)n2)c1] | 458.2 |
| 16-2 | 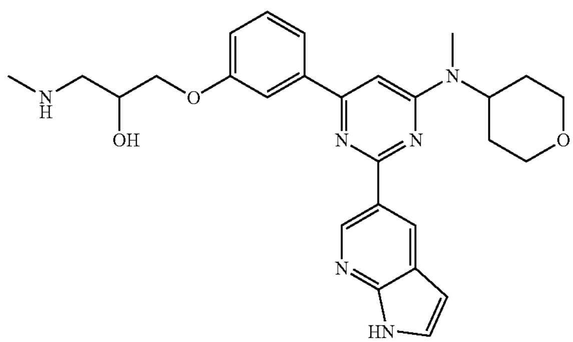 [SMILES: CNCC(O)COc1cccc(-c2cc(N(C)C3CCOCC3)nc(-c3cnc4[nH]ccc4c3)n2)c1] | 489.2 |
| 2-1 | 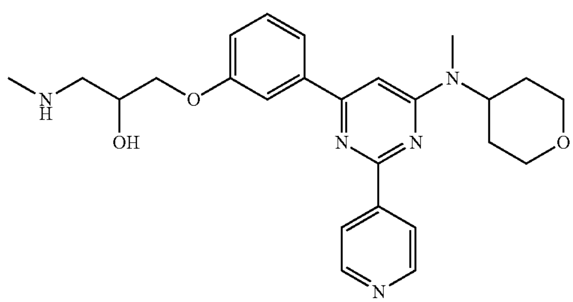 [SMILES: CNCC(O)COc1cccc(-c2cc(N(C)C3CCOCC3)nc(-c3ccncc3)n2)c1] | 450.3 |

In certain embodiments, a provided compound inhibits CARM1. In certain embodiments, a provided compound inhibits wild-type CARM1. In certain embodiments, a provided compound inhibits a mutant CARM1. In certain embodiments, a provided compound inhibits CARM1, e.g., as measured in an assay described herein. In certain embodiments, the CARM1 is from a human. In certain embodiments, a provided compound inhibits CARM1 at an $IC_{50}$ less than or equal to 10 μM. In certain embodiments, a provided compound inhibits CARM1 at an $IC_{50}$ less than or equal to 1 μM. In certain embodiments, a provided compound inhibits CARM1 at an $IC_{50}$ less than or equal to 0.1 μM. In certain embodiments, a provided compound inhibits CARM1 in a cell at an $EC_{50}$ less than or equal to 10 μM. In certain embodiments, a provided compound inhibits CARM1 in a cell at an $EC_{50}$ less than or equal to 1 μM. In certain embodiments, a provided compound inhibits CARM1 in a cell at an $EC_{50}$ less than or equal to 0.1 μM. In certain embodiments, a provided compound inhibits cell proliferation at an $EC_{50}$ less than or equal to 10 μM. In certain embodiments, a provided compound inhibits cell proliferation at an $EC_{50}$ less than or equal to 1 μM. In certain embodiments, a provided compound inhibits cell proliferation at an $EC_{50}$ less than or equal to 0.1 μM. In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT1 relative to one or more other methyltransferases.

It will be understood by one of ordinary skill in the art that the CARM1 can be wild-type CARM1, or any mutant or variant of CARM1.

The present disclosure provides pharmaceutical compositions comprising a compound described herein, e.g., a compound of Formula (I), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting CARM1. In certain embodiments, the effective amount is an amount effective for treating a CARM1-mediated disorder. In certain embodiments, the effective amount is a prophylactically effective amount. In certain embodiments, the effective amount is an amount effective to prevent a CARM1-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of CARM1. In some embodiments, the CARM1 is human CARM1. In some embodiments, methods of treating CARM1-mediated disorder in a subject are provided which comprise administering an effective amount of a compound described herein (e.g., a compound of Formula (I), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a CARM1-mediated disorder. In certain embodiments, the subject is susceptible to a CARM1-mediated disorder.

As used herein, the term "CARM1-mediated disorder" means any disease, disorder, or other pathological condition in which CARM1 is known to play a role. Accordingly, in some embodiments, the present disclosure relates to treating or lessening the severity of one or more diseases in which CARM1 is known to play a role.

In some embodiments, the present disclosure provides a method of inhibiting CARM1 comprising contacting CARM1 with an effective amount of a compound described herein, e.g., a compound of Formula (I), or a pharmaceutically acceptable salt thereof. The CARM1 may be purified or crude, and may be present in a cell, tissue, or subject. Thus, such methods encompass both inhibition of in vitro and in vivo CARM1 activity. In certain embodiments, the method is an in vitro method, e.g., such as an assay method. It will be understood by one of ordinary skill in the art that inhibition of CARM1 does not necessarily require that all of the CARM1 be occupied by an inhibitor at once. Exemplary levels of inhibition of CARM1 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting CARM1 activity in a subject in need thereof comprising administering to the subject an effective amount of a compound described herein (e.g., a compound of Formula (I), or a pharmaceutically acceptable salt thereof, or a pharmaceutical composition thereof.

In certain embodiments, provided is a method of modulating gene expression or activity in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, a method is provided of selecting a therapy for a subject having a disease associated with CARM1-mediated disorder or mutation comprising the steps of determining the presence of CARM1-mediated disorder or gene mutation in the CARM1 gene or and selecting, based on the presence of CARM1-mediated disorder a gene mutation in the CARM1 gene a therapy that includes the administration of a provided compound. In certain embodiments, the disease is cancer.

In certain embodiments, a method of treatment is provided for a subject in need thereof comprising the steps of determining the presence of CARM1-mediated disorder or a gene mutation in the CARM1 gene and treating the subject in need thereof, based on the presence of a CARM1-mediated disorder or gene mutation in the CARM1 gene with a therapy that includes the administration of a provided compound. In certain embodiments, the subject is a cancer patient.

In some embodiments, a compound provided herein is useful in treating a proliferative disorder, such as cancer. For example, while not being bound to any particular mechanism, protein arginine methylation by CARM1 is a modification that has been implicated in signal transduction, gene transcription, DNA repair and mRNA splicing, among others; and overexpression of CARM1 within these pathways is often associated with various cancers. Thus, compounds which inhibit the action of PRMTs, and specifically CARM1, as provided herein, are effective in the treatment of cancer.

In some embodiments, compounds provided herein are effective in treating cancer through the inhibition of CARM1. For example, CARM1 levels have been shown to be elevated in castration-resistant prostate cancer (CRPC) (e.g., see Di Lorenzo et al., *Drugs* (2010) 70:983-1000), as well as in aggressive breast tumors (Hong et al., *Cancer* 2004 101, 83-89; El Messaoudi et al., *Proc. Natl. Acad. Sci. U.S.A.* 2006, 103, 13351-13356; Majumder et al., *Prostate* 2006 66, 1292-1301). Thus, in some embodiments, inhibitors of CARM1, as described herein, are useful in treating cancers associated with aberrant CARM1 activity, e.g., CARM1 overexpression or aberrant protein methylation. For example, aberrant CARM1 activity has been found in prostate cancer (e.g., see Hong et al., *Cancer* (2004), 101: 83-89); plays a coactivator role in the dysragulation of beta-catenin activity in colorectal cancer (e.g., see Ou et al., *Mol. Cancer Res.* (2011) 9:660); and has been linked to estrogen signaling and estrogen related cancers such as breast cancer (see, e.g., Teyssiewr et al., *Trends in Endocrinology and Metabolism* (2010) 21:181-189). CARM1 has also been shown to affect estrogen receptor alpha (ER-alpha) dependent breast cancer cell differentiation and proliferation (Al-Dhaheri et al., *Cancer Res.* 2011 71, 2118-2128), thus in some aspects CARM1 inhibitors, as described herein, are useful in treating ERα-dependent breast cancer by inhibiting cell differentiation and proliferation. In another example, CARM1 has been shown to be recruited to the promoter of E2F1 (which encodes a cell cycle regulator) as a transcriptional co-activator (Frietze et al., *Cancer Res.* 2008 68, 301-306). Thus, CARM1-mediated upregulation of E2F1 expression may contribute to cancer progression and chemoresistance as increased abundance of E2F1 triggers invasion and metastasis by activating growth receptor signaling pathways, which in turn promote an antiapoptotic tumor environment (Engelmann and Pützer, *Cancer Res* 2012 72; 571). Accordingly, in some embodiments, the inhibition of CARM1, e.g., by compounds provided herein, is useful in treating cancers associated with E2F1 upregulation, e.g., such as lung cancer (see, e.g., Eymin et al., *Oncogene* (2001) 20:1678-1687), and breast cancer (see, e.g., Brietz et al., *Cancer Res.* (2008) 68:301-306). Thus, without being bound by any particular mechanism, the inhibition of CARM1, e.g., by compounds described herein, is beneficial in the treatment of cancer. CARM1 overexpression has also been demonstrated to be elevated in 75% of colorectal cancers (Kim et al., BMC Cancer, 10, 197). It has been additionally been determined that depletion of CARM1 in WNT/β-catenin dysregulated colorectal cancer suppressed anchorage independent growth (Ou et al., Mol. Cancer. Res., 2011 9, 660-670). This, in some embodiments, the inhibition of CARM1, e.g. by compounds provided herein, is useful in colorectal cancer associated with elevated CARM1 expression or dysregulated WNT/β-catenin signaling.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

In certain embodiments, the cancer is a solid cancer. In certain embodiments, the cancer is a liquid cancer.

In certain embodiments, the cancer is breast cancer, prostate cancer, colorectal cancer, or a hematopoietic cancer (e.g., multiple myeloma).

CARM1 is also the most abundant PRMT expressed in skeletal muscle cells, and has been found to selectively control the pathways modulating glycogen metabolism, and associated AMPK (AMP-activated protein kinase) and p38 MAPK (mitogen-activated protein kinase) expression. See, e.g., Wang et al., Biochem (2012) 444:323-331. Thus, in some embodiments, inhibitors of CARM1, as described herein, are useful in treating metabolic disorders, e.g., for example skeletal muscle metabolic disorders, e.g., glycogen and glucose metabolic disorders. Exemplary skeletal muscle metabolic disorders include, but are not limited to, Acid Maltase Deficiency (Glycogenosis type 2; Pompe disease), Debrancher deficiency (Glycogenosis type 3), Phosphorylase deficiency (McArdle's; GSD 5), X-linked syndrome (GSD9D), Autosomal recessive syndrome (GSD9B), Tarui's disease (Glycogen storage disease VII; GSD 7), Phosphoglycerate Mutase deficiency (Glycogen storage disease X; GSDX; GSD 10), Lactate dehydrogenase A deficiency (GSD 11), Branching enzyme deficiency (GSD 4), Aldolase A (muscle) deficiency, β-Enolase deficiency, Triosephosphate isomerase (TIM) deficiency, Lafora's disease (Progressive myoclonic epilepsy 2), Glycogen storage disease (Muscle, Type 0, Phosphoglucomutase 1 Deficiency (GSD 14)), and Glycogenin Deficiency (GSD 15).

Other Aspects of the Invention

Aspect 1 provides a compound of Formula (I):

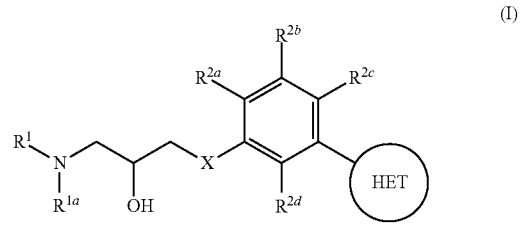

or a pharmaceutically acceptable salt thereof;
wherein:
X is —O—, —S—, or —CH$_2$—;
R$^1$ is hydrogen or optionally substituted C$_{1-4}$ aliphatic;
R$^{1a}$ is hydrogen or optionally substituted C$_{1-4}$ aliphatic;
each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;

Ring HET is a 6-membered monocylic heteroaryl ring system of the Formula:

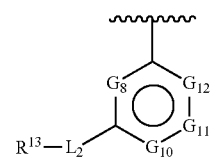

wherein:
G$_8$ is C—R$^8$ or N;
G$_{10}$ is C—R$^{10}$ or N;
G$_{11}$ is C—R$^{11}$ or N;
G$_{12}$ is C—R$^{12}$ or N;
provided at least one instance of G$_8$, G$_{10}$, G$_{11}$, or G$_{12}$ is N;
each instance of R$^8$, R$^{10}$, R$^{11}$, and R$^{12}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;
each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;
each instance of L$^1$ and L$^2$ is independently a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—,

567

—NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, an optionally substituted C$_{1-10}$ saturated or unsaturated hydrocarbon chain, wherein one or more moieties selected from the group consisting of —O—, —N(R$^L$)—, —S—, —C(O—), —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and optionally and independently present at one or both ends of the hydrocarbon chain;

each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;

R$^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when R$^3$ is hydrogen, then L$^1$ is not a bond; and R$^{13}$ is optionally substituted carbocyclyl, optionally substituted heterocyclyl, optionally substituted aryl, or optionally substituted heteroaryl, Aspect 2 provides a compound of Formula (I-1-Aa2) or (I-1-Aa2'):

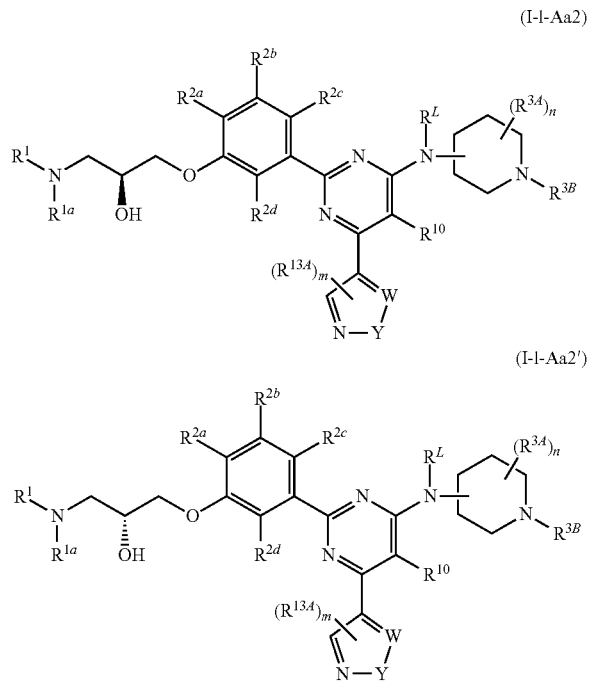

or a pharmaceutically acceptable salt thereof;

568 wherein:

R$^1$ is hydrogen or optionally substituted C$_{1-4}$ aliphatic;

R$^{1a}$ is hydrogen or optionally substituted C$_{1-4}$ aliphatic;

each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^2$ groups attached to the same nitrogen atom are joined to form an optionally substituted heterocyclyl or optionally substituted heteroaryl ring;

R$^{10}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;

each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;

R$^{13}$ is optionally substituted carbocyclyl, optionally substituted heterocyclyl, optionally substituted aryl, or optionally substituted heteroaryl;

R$^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{3A}$ groups are joined to form an optionally substituted carbocyclic, optionally substituted heterocyclic, optionally substituted aryl, or optionally substituted heteroaryl ring, or R$^{3A}$ and R$^{3B}$ groups are joined to form an optionally substituted carbocyclic, optionally substituted heterocyclic, optionally substituted aryl, or optionally substituted heteroaryl ring;

R$^{3B}$ is hydrogen, optionally substituted alkyl, or a nitrogen protecting group;

R$^{13A}$ each instance of R$^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{13A}$ groups are joined to form an optionally substituted carbocyclic, optionally substituted heterocyclic, optionally substituted aryl, or optionally substituted heteroaryl ring, or R$^{13A}$ and R$^{13B}$ group are joined to form an optionally substituted carbocyclic, optionally substituted heterocyclic, optionally substituted aryl, or optionally substituted heteroaryl ring;

R$^{13B}$ is hydrogen, optionally substituted alkyl, or a nitrogen protecting group;

Y is O, S, N, or NR$^{13B}$;

W is CH, CR$^{13A}$, N, or NR$^{13B}$, as valency permits;

m is 0, 1, 2, or 3; and n is 0, 1, 2, or 3.

Aspect 3 provides a compound of Formula (I-1-Aa3) or (I-1-Aa3'):

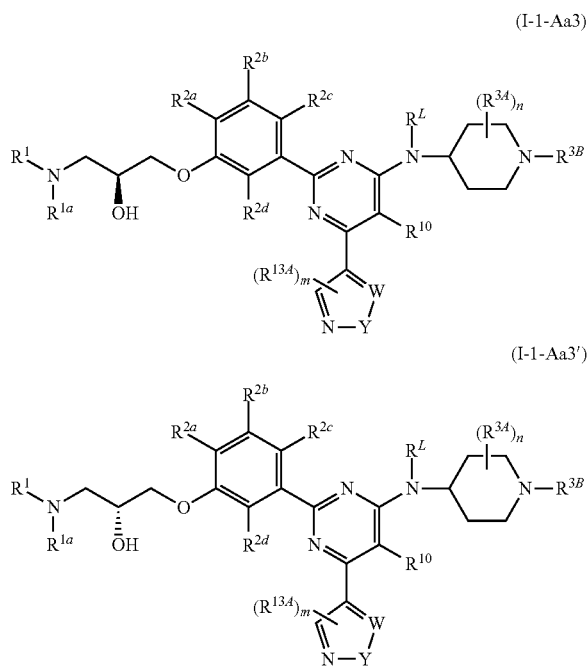

(I-1-Aa3)

(I-1-Aa3')

or a pharmaceutically acceptable salt thereof;
wherein:
$R^1$ is hydrogen or optionally substituted $C_{1-4}$ aliphatic;
$R^{1a}$ is hydrogen or optionally substituted $C_{1-4}$ aliphatic;
each of $R^{2a}$, $R^{2b}$, $R^{2c}$, and $R^{2d}$ is independently hydrogen, halogen, —CN, —NO$_2$, —C(=O)$R^{A2}$, —C(=O)O$R^{A2}$, —C(=O)N($R^2$)$_2$, —O$R^{A2}$, —S$R^{A2}$, —N($R^{A2}$)$_2$, —S(=O)$R^{A2}$, —S(=O)$_2R^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;
$R^{10}$ is independently selected from the group consisting of hydrogen, halo, —CN, —NO$_2$, —C(=O)R', —C(=O)OR', —C(=O)N(R')$_2$, optionally substituted alkyl, and -L-$R^3$;
each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;
each $R^L$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring;
$R^{13}$ is optionally substituted carbocyclyl, optionally substituted heterocyclyl, optionally substituted aryl, or optionally substituted heteroaryl;

$R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring;
$R^{3B}$ is hydrogen, optionally substituted alkyl, or a nitrogen protecting group;
$R^{13A}$ each instance of $R^{13A}$ is independently hydroxyl, substituted hydroxyl, thiol, substituted thiol, amino, substituted amino, carbonyl, sulfonyl, sulfinyl, —CN, —NO$_z$, halogen, optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring;
$R^{13B}$ is hydrogen, optionally substituted alkyl, or a nitrogen protecting group;
Y is O, S, N, or N$R^{13B}$;
W is CH, C$R^{13A}$, N, or N$R^{13B}$, as valency permits;
m is 0, 1, 2, or 3; and
n is 0, 1, 2, or 3.
Aspect 4 provides a compound of Formula (I-1-Aa4) or (I-1-Aa4'):

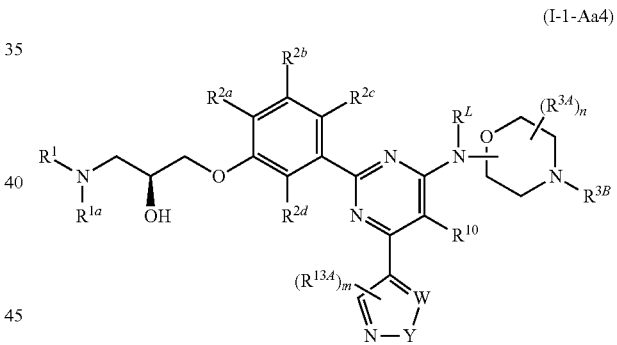

(I-1-Aa4)

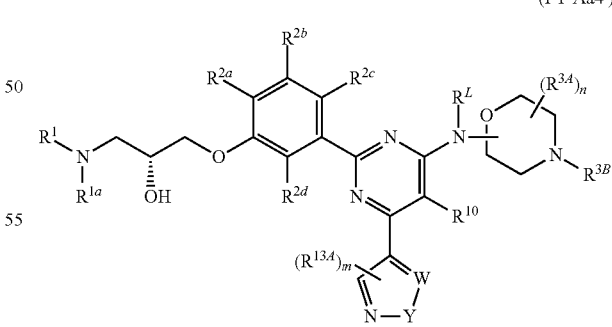

(I-1-Aa4')

or a pharmaceutically acceptable salt thereof;
wherein:
$R^1$ is hydrogen or optionally substituted $C_{1-4}$ aliphatic;
$R^{1a}$ is hydrogen or optionally substituted $C_{1-4}$ aliphatic;
each of $R^{2a}$, $R^{2b}$, $R^{2c}$, and $R^{2d}$ is independently hydrogen, halogen, —CN, —NO$_2$, —C(=O)$R^{A2}$, —C(=O)O$R^{A2}$, —C(=O)N(R$^1$)$_2$, —OR, —SR, —N(R)$_2$, —S(=O)$R^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{2A}$ groups attached to the same nitrogen atom are joined to form an optionally substituted heterocyclyl or optionally substituted heteroaryl ring;

R$^{10}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$; each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;

R$^{13}$ is optionally substituted carbocyclyl, optionally substituted heterocyclyl, optionally substituted aryl, or optionally substituted heteroaryl;

R$^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{3A}$ groups are joined to form an optionally substituted carbocyclic, optionally substituted heterocyclic, optionally substituted aryl, or optionally substituted heteroaryl ring, or R$^{3A}$ and R$^{3B}$ groups are joined to form an optionally substituted carbocyclic, optionally substituted heterocyclic, optionally substituted aryl, or optionally substituted heteroaryl ring;

R$^{3B}$ is hydrogen, optionally substituted alkyl, or a nitrogen protecting group;

R$^{13A}$ each instance of R$^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{13A}$ groups are joined to form an optionally substituted carbocyclic, optionally substituted heterocyclic, optionally substituted aryl, or optionally substituted heteroaryl ring, or R$^{13A}$ and R$^{13B}$ group are joined to form an optionally substituted carbocyclic, optionally substituted heterocyclic, optionally substituted aryl, or optionally substituted heteroaryl ring;

R$^{13B}$ is hydrogen, optionally substituted alkyl, or a nitrogen protecting group;

Y is O, S, N, or NR$^{13B}$;

W is CH, CR$^{13A}$, N, or NR$^{13B}$, as valency permits;

m is 0, 1, 2, or 3; and n is 0, 1, 2, or 3.

Aspect 5 provides a compound of Formula (I-1-Aa5) or (I-1-Aa5'):

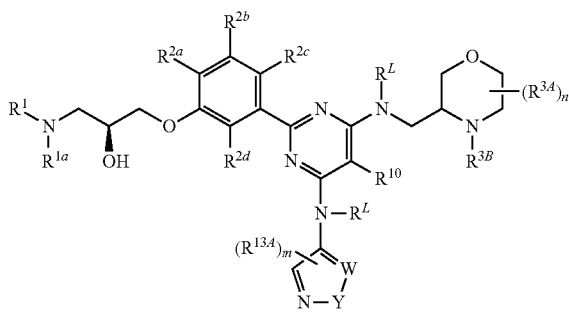

(I-1-Aa5)

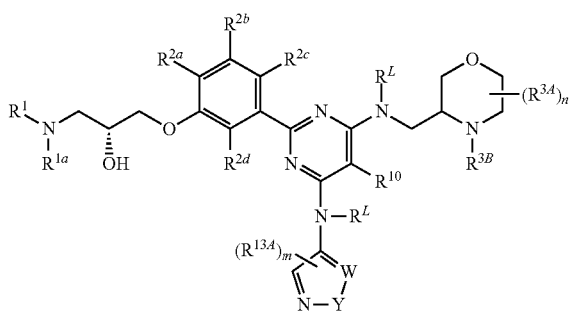

(I-1-Aa5')

or a pharmaceutically acceptable salt thereof;
wherein:

R$^1$ is hydrogen or optionally substituted C$_{1-4}$ aliphatic;

R$^{1a}$ is hydrogen or optionally substituted C$_{1-4}$ aliphatic;

each of R$^{2a}$, R$^{2b}$, R$^{2c}$, and R$^{2d}$ is independently hydrogen, halogen, —CN, —NO$_2$, —C(=O)R$^{A2}$, —C(=O)OR, —C(=O)N(R$^{A2}$)$_2$, —OR$^{A2}$, —SR$^2$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;

R$^{10}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;

each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;

R$^{13}$ is optionally substituted carbocyclyl, optionally substituted heterocyclyl, optionally substituted aryl, or optionally substituted heteroaryl;

$R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring;

$R^{3B}$ is hydrogen, optionally substituted alkyl, or a nitrogen protecting group;

$R^{13A}$ each instance of $R^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring;

$R^{13B}$ is hydrogen, optionally substituted alkyl, or a nitrogen protecting group;

Y is O, S, N, or $NR^{13B}$;

W is CH, $CR^{13A}$, N, or $NR^{13B}$, as valency permits;

m is 0, 1, 2, or 3; and n is 0, 1, 2, or 3.

Aspect 6 provides a compound of Formula (I-1-Aa6) or (I-1-Aa6'):

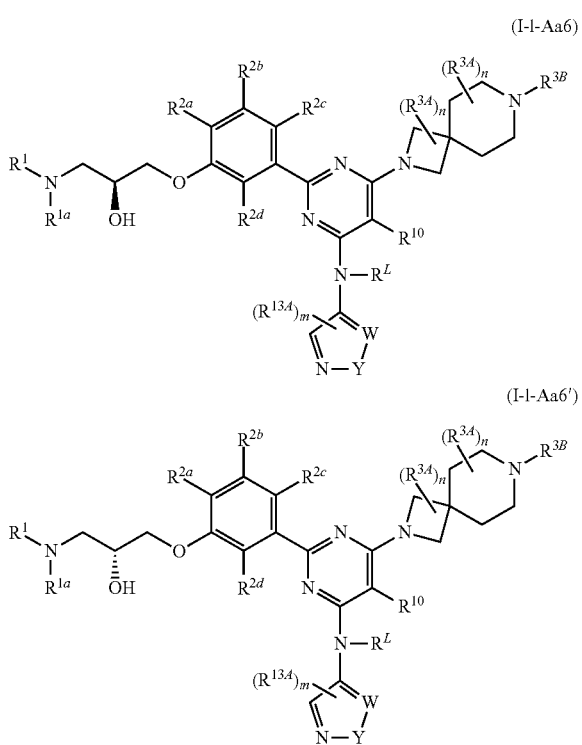

or a pharmaceutically acceptable salt thereof;
wherein:
$R^1$ is hydrogen or optionally substituted $C_{1-4}$ aliphatic;
$R^{1a}$ is hydrogen or optionally substituted $C_{1-4}$ aliphatic;
each of $R^{2a}$, $R^{2b}$, $R^{2c}$, and $R^{2d}$ is independently hydrogen, halogen, —CN, —NO$_2$, —C(=O)$R^{A2}$, —C(=O)O$R^2$, —C(=O)N(R$^2$)$_2$, —O$R^{A2}$, —S$R^2$, —N(R$^2$)$_2$, —S(=O)$R^{A2}$, —S(=O)$_2R^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;

$R^{10}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$;

each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;

each $R^L$ is independently hydrogen, optionally substituted alkyl, or a nitrogen protecting group, or $R^L$ and $R^3$ taken together form an optionally substituted heterocyclyl or optionally substituted heteroaryl ring, or $R^L$ and $R^{13}$ taken together form an optionally substituted heterocyclyl or optionally substituted heteroaryl ring;

$R^{13}$ is optionally substituted carbocyclyl, optionally substituted heterocyclyl, optionally substituted aryl, or optionally substituted heteroaryl;

$R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3I}$ groups are joined to form an optionally substituted carbocyclic, optionally substituted heterocyclic, optionally substituted aryl, or optionally substituted heteroaryl ring;

$R^{3B}$ is hydrogen, optionally substituted alkyl, or a nitrogen protecting group;

$R^{13A}$ each instance of $R^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{13A}$ groups are joined to form an optionally substituted carbocyclic, optionally substituted heterocyclic, optionally substituted aryl, or optionally substituted heteroaryl ring, or $R^{13A}$ and $R^{13B}$ group are joined to form an optionally substituted carbocyclic, optionally substituted heterocyclic, optionally substituted aryl, or optionally substituted heteroaryl ring;

$R^{13B}$ is hydrogen, optionally substituted alkyl, or a nitrogen protecting group;

Y is O, S, N, or $NR^{13B}$;

W is CH, $CR^{13A}$, N, or $NR^{13B}$, as valency permits;

m is 0, 1, 2, or 3; and n is 0, 1, 2, or 3.

Aspect 7 provides a compound of Formula (I-1-Aa7) or (I-1-Aa7'):

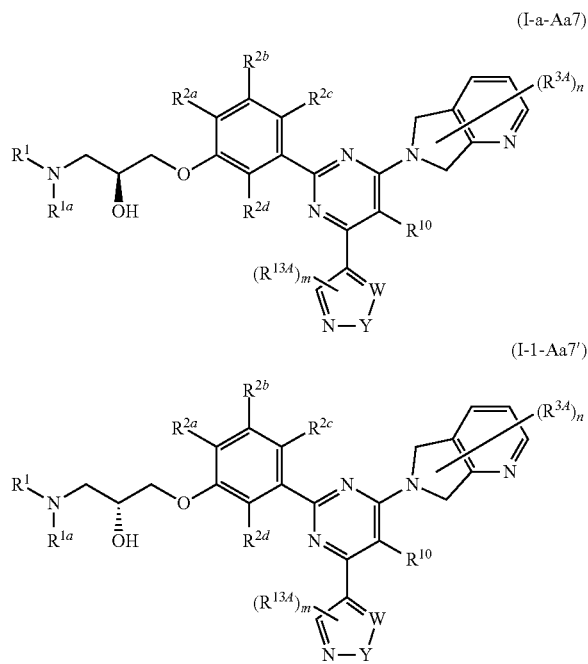

(I-a-Aa7)

(I-1-Aa7')

or a pharmaceutically acceptable salt thereof;
wherein:
R$^1$ is hydrogen or optionally substituted C$_{1-4}$ aliphatic;
R$^{1a}$ is hydrogen or optionally substituted C$_{1-4}$ aliphatic;
each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^2$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;
R$^{10}$ is independently selected from the group consisting of hydrogen, halo, —CN, —NO$_2$, —C(=O)R', —C(=O)OR', —C(=O)N(R')$_2$, optionally substituted alkyl, and -L$^1$-R$^3$; each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring;
each R$^L$ is independently hydrogen, optionally substituted alkyl, or a nitrogen protecting group, or R$^L$ and R$^3$ taken together form an optionally substituted heterocyclyl or optionally substituted heteroaryl ring, or R$^L$ and R$^{13}$ taken together form an optionally substituted heterocyclyl or optionally substituted heteroaryl ring;
R$^{13}$ is optionally substituted carbocyclyl, optionally substituted heterocyclyl, optionally substituted aryl, or optionally substituted heteroaryl;

R$^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{3A}$ groups are joined to form an optionally substituted carbocyclic, optionally substituted heterocyclic, optionally substituted aryl, or optionally substituted heteroaryl ring, or R$^{3A}$ and R$^{3B}$ groups are joined to form an optionally substituted carbocyclic, optionally substituted heterocyclic, optionally substituted aryl, or optionally substituted heteroaryl ring;
R$^{3B}$ is hydrogen, optionally substituted alkyl, or a nitrogen protecting group;
R$^{13A}$ each instance of R$^{13A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two R$^{13A}$ groups are joined to form an optionally substituted carbocyclic, optionally substituted heterocyclic, optionally substituted aryl, or optionally substituted heteroaryl ring, or R$^{13A}$ and R$^{13B}$ group are joined to form an optionally substituted carbocyclic, optionally substituted heterocyclic, optionally substituted aryl, or optionally substituted heteroaryl ring;
R$^{13B}$ is hydrogen, optionally substituted alkyl, or a nitrogen protecting group;
Y is O, S, N, or NR$^{13B}$;
W is CH, CR$^{13A}$, N, or NR$^{13B}$, as valency permits;
m is 0, 1, 2, or 3; and
n is 0, 1, 2, or 3.
Aspect 8 provides a compound of Aspect 1, wherein the compound of Formula (I) is of Formula (I-a):

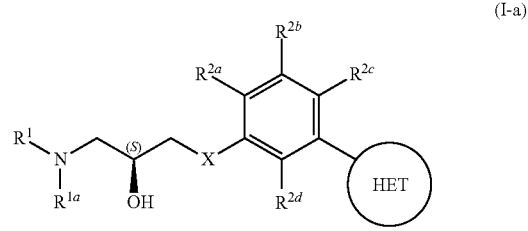

(I-a)

or a pharmaceutically acceptable salt thereof.
Aspect 9 provides a compound of Aspect 1, wherein the compound of Formula (I) is of Formula (I-b):

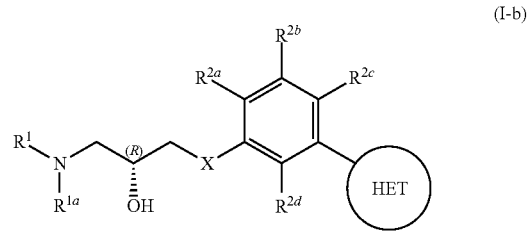

(I-b)

or a pharmaceutically acceptable salt thereof.
Aspect 10 provides a compound of any of Aspects 1, 8, and 9, wherein X is —O—.
Aspect 11 provides a compound of any of Aspects 1, 8, and 9, wherein X is —S—.
Aspect 12 provides a compound of any of Aspects 1, 8, and 9, wherein X is —CH$_2$—.
Aspect 13 provides a compound of any of Aspects 1, and 8-12, wherein Ring HET is:

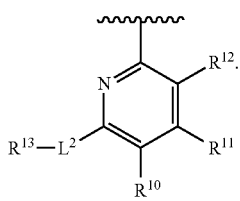
(i-a)

Aspect 14 provides a compound of any of Aspects 1, and 8-12, wherein Ring HET is:

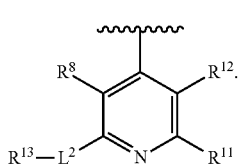
(i-b)

Aspect 15 provides a compound of any of Aspects 1, and 8-12, wherein Ring HET is:

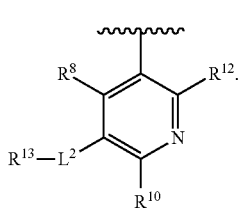
(i-c)

Aspect 16 provides a compound of any of Aspects 1, and 8-12, wherein Ring HET is:

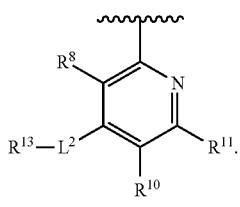
(i-d)

Aspect 17 provides a compound of any of Aspects 1, and 8-12, wherein Ring HET is:

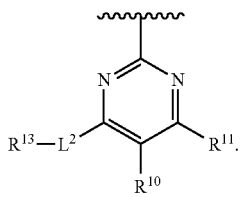
(i-e)

Aspect 18 provides a compound of any of Aspects 1, and 8-12, wherein Ring HET is:

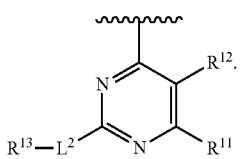
(i-f)

Aspect 19 provides a compound of any of Aspects 1, and 8-12, wherein Ring HET is:

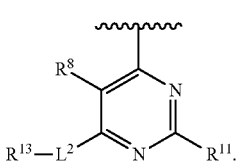
(i-g)

Aspect 20 provides a compound of any of Aspects 1, and 8-12, wherein Ring HET is:

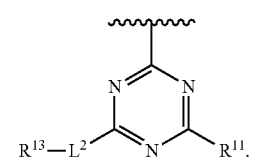
(i-h)

Aspect 21 provides a compound of Aspects 1, and 8-12, wherein Ring HET is selected from the group consisting of:

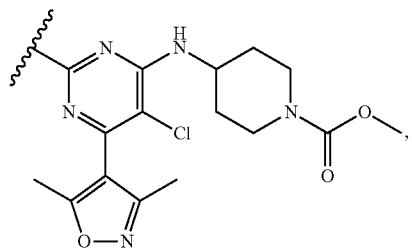

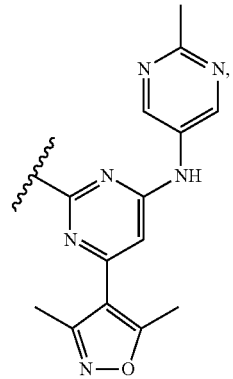

579
-continued
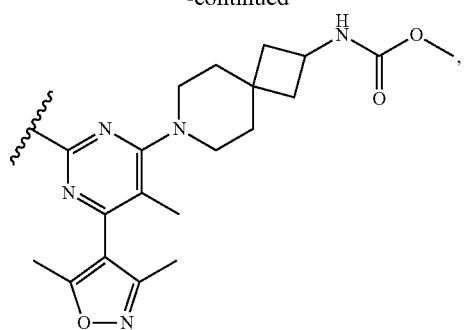
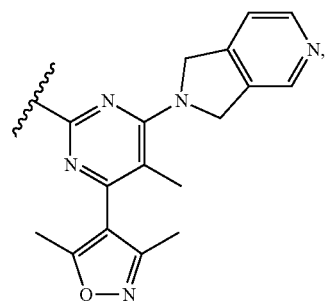
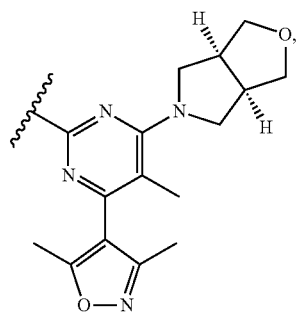
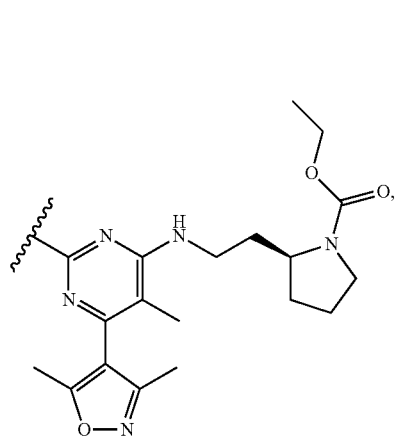
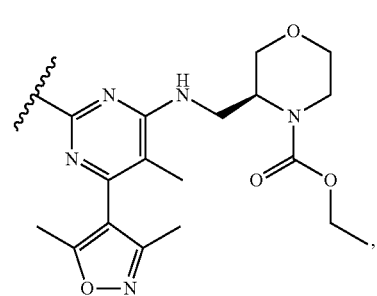
580
-continued
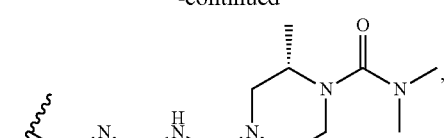
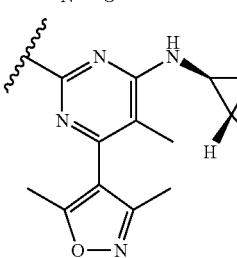
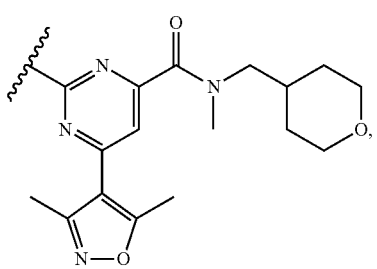
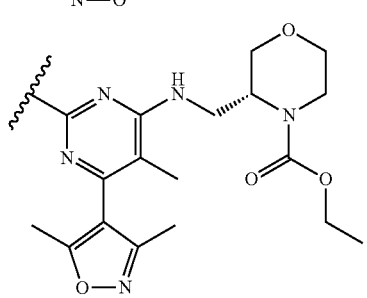
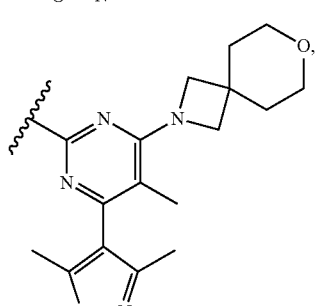
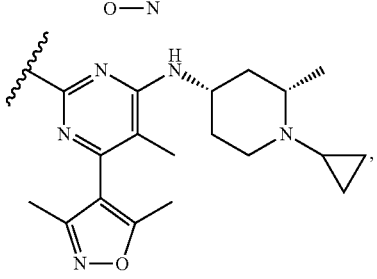

581
-continued
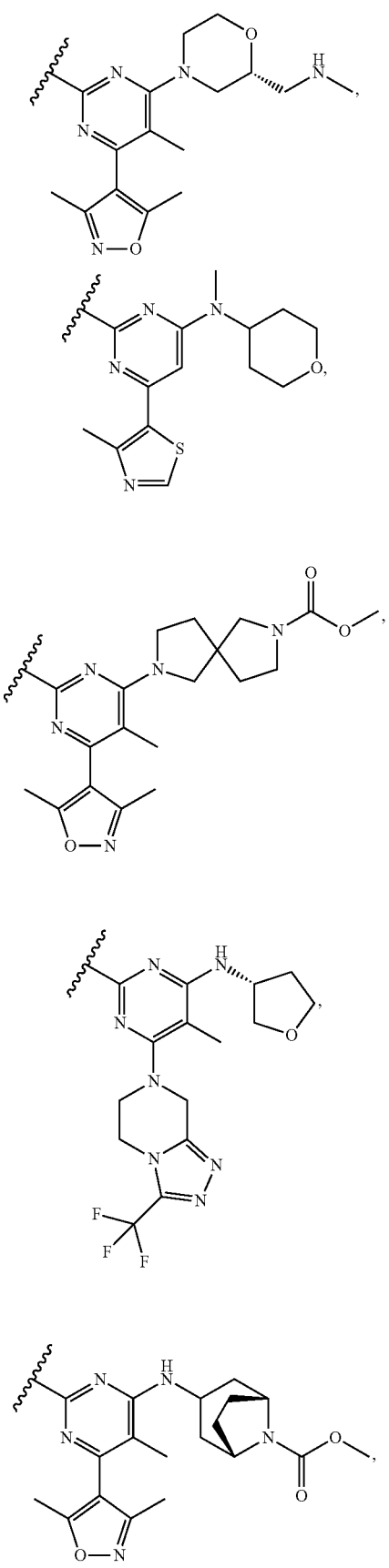
582
-continued
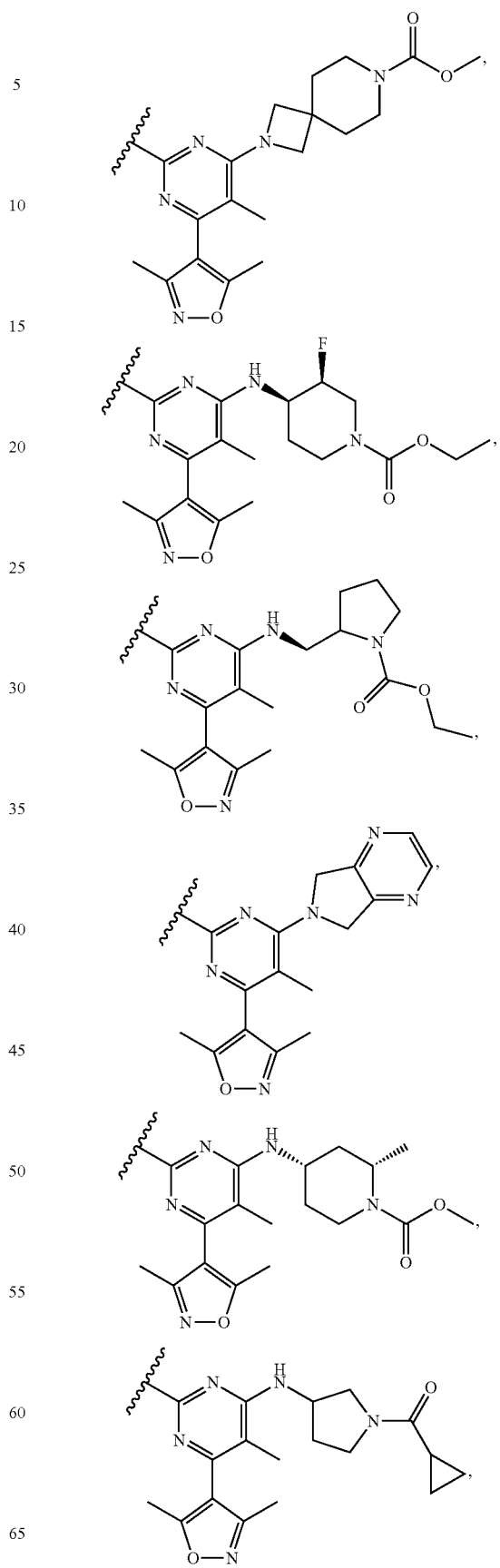

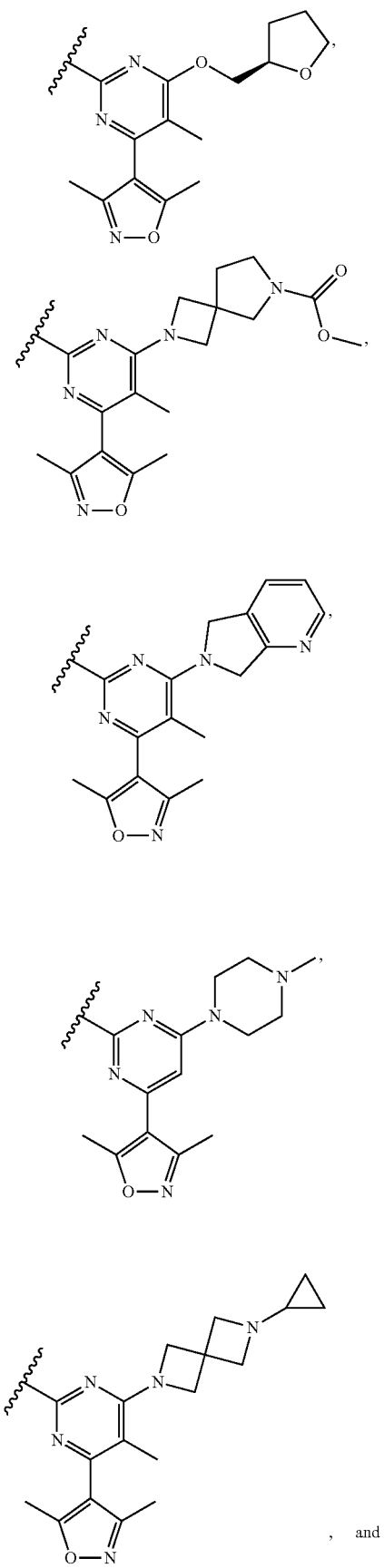

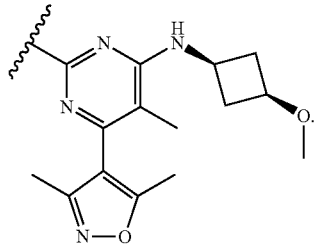

Aspect 22 provides a compound of any of Aspects 1-21 wherein, $R^1$ is hydrogen, methyl, ethyl, n-propyl, isopropyl, or cyclopropyl.

Aspect 23 provides a compound of any of Aspects 1-22, wherein $R^2$, $R^{2c}$, and $R^{2d}$ are hydrogen.

Aspect 24 provides a provides a compound of any of Aspects 1-23, wherein $R^{2b}$ is halogen or —$OR^{A2}$.

Aspect 25 provides a provides a compound of any of Aspects 1, 8-20, and 22-24, wherein $L^2$ is a bond, —N($R^L$)—, —$NR^L$C(O)O—, —$NR^L$C(O)N($R^L$)—, —N($R^L$)—, —N($R^L$)SO$_2$N($R^L$), —$NR^L$—(CH$_2$)$_x$—C(O)O—, —$NR^L$—(CH$_2$)$_x$—O—, —$NR^L$C(O)N($R^L$), —$NR^L$—(CH$_2$)$_x$—, —(CH$_2$)$_x$—$NR^L$—, —$NR^L$C(O)O(CH$_2$)$_x$, —$NR^L$C(O)$NR^L$(CH$_2$)$_x$—, or —$NR^L$(CH$_2$)$_x$$NR^L$C(O)—.

Aspect 26 provides a compound of any of Aspects 1, 8-20, and 22-24, wherein Ring HET comprises a group -$L^1$-$R^3$ is attached thereto.

Aspect 27 provides a compound of any of Aspects 1, 8-20, and 22-24, wherein $L^1$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$-(CH$_2$)$_x$—C(O)O—, —$NR^L$—(CH$_2$)$_x$—O—, —$NR^L$C(O)N($R^L$)—, —$NR^L$—(CH$_2$)$_x$—, —(CH$_2$)$_x$—$NR^L$—, —$NR^L$C(O)O(CH$_2$)$_x$—, —$NR^L$C(O)$NR^L$(CH$_2$)$_x$—, or —$NR^L$(CH$_2$)$_x$$NR^L$C(O)—.

Aspect 28 provides a compound of any of Aspects 1-27, wherein $R^{1a}$ is hydrogen, methyl, ethyl, n-propyl, isopropyl, or cyclopropyl.

Aspect 29 provides a compound of any of Aspects 1, 8-20, and 22-28, wherein an $R^{13}$ group is present and is selected from the group consisting of:

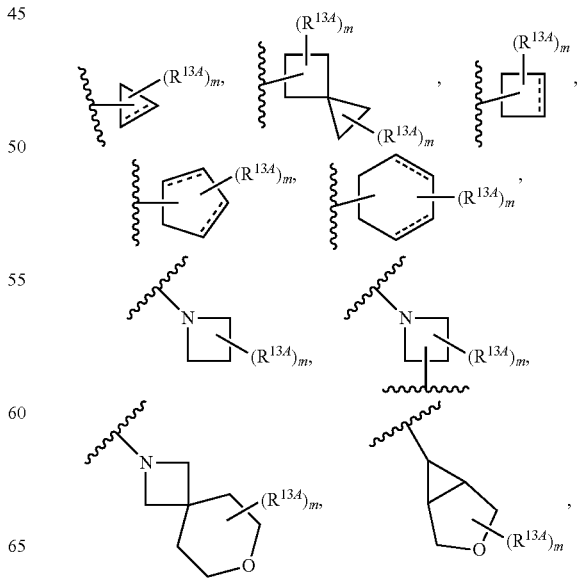

-continued
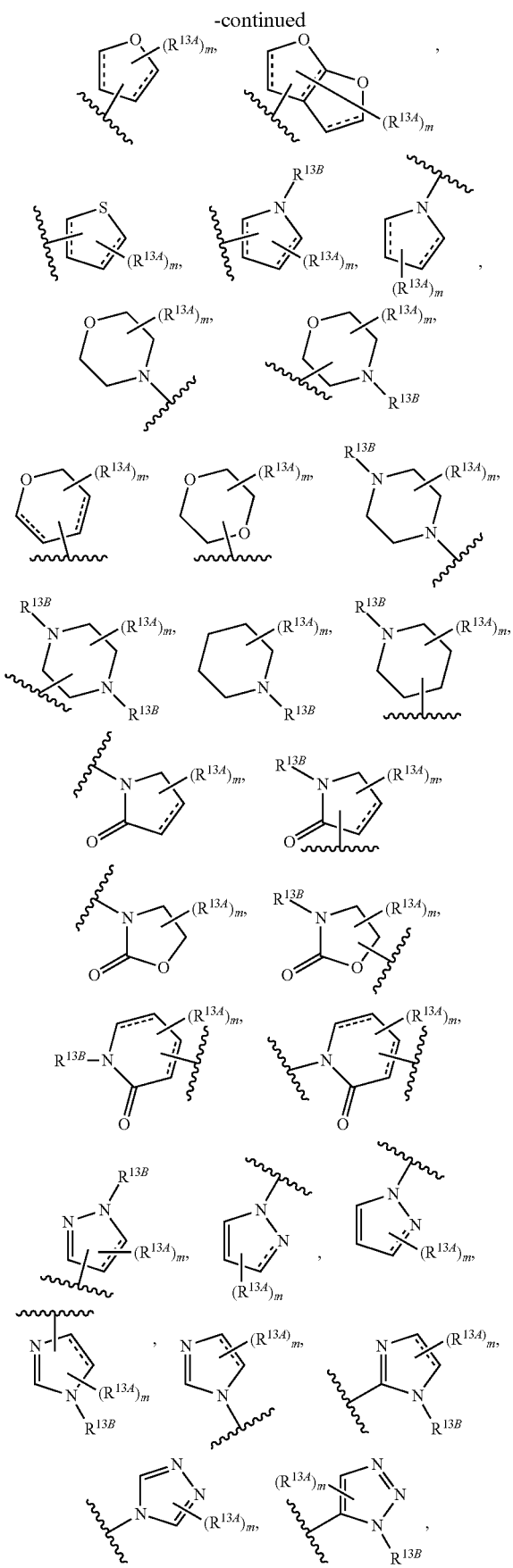
-continued
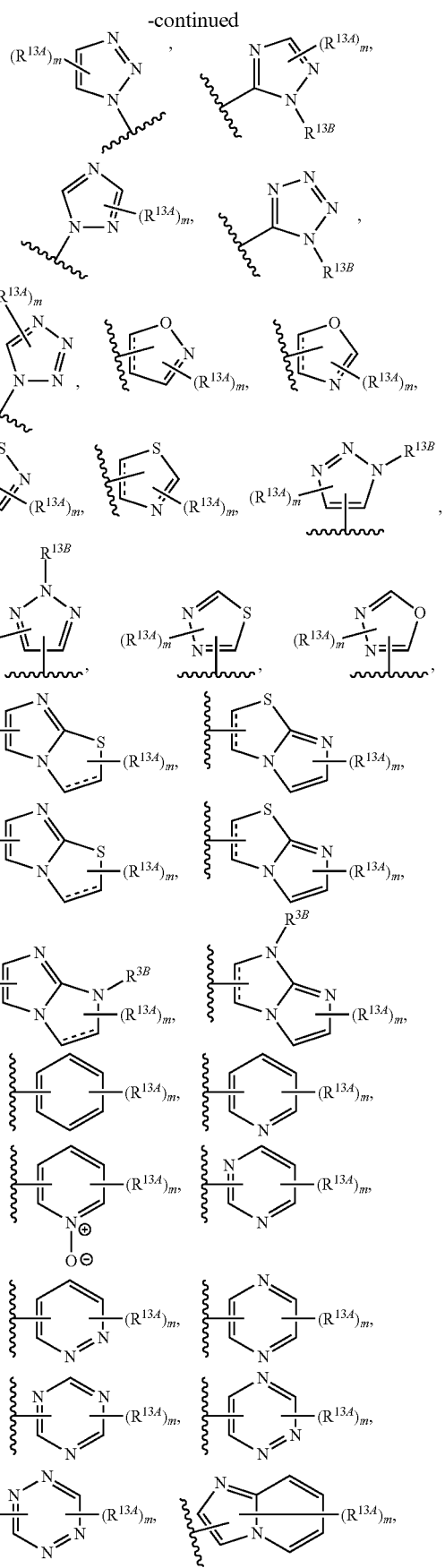

-continued
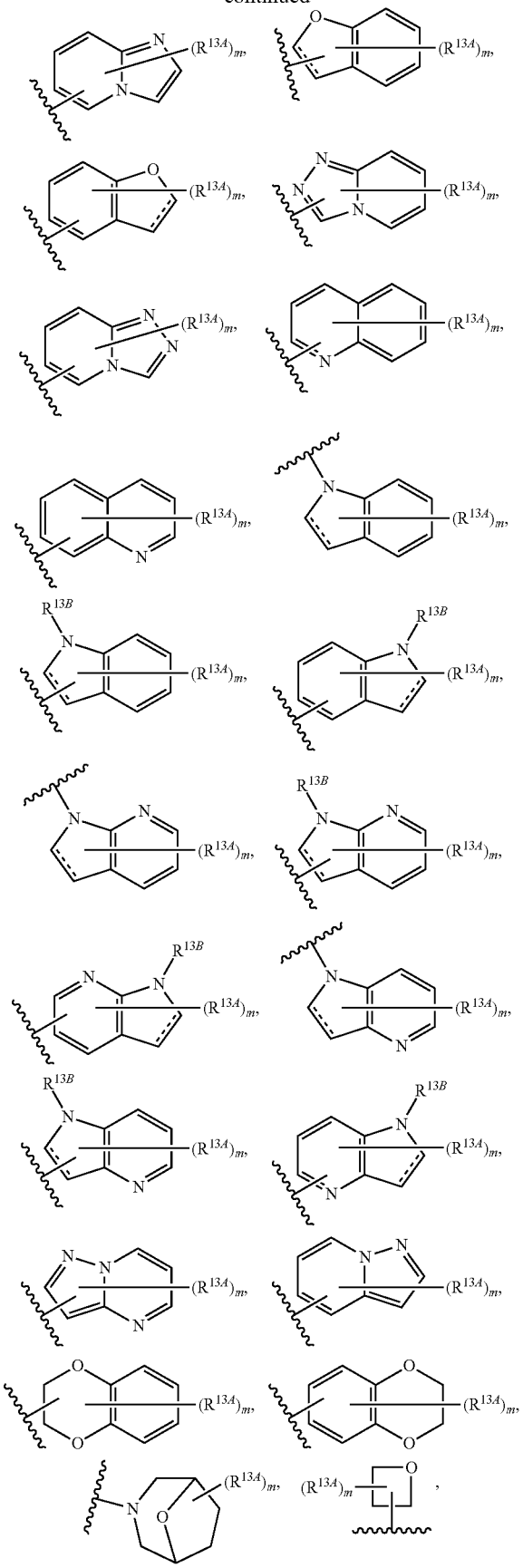
-continued
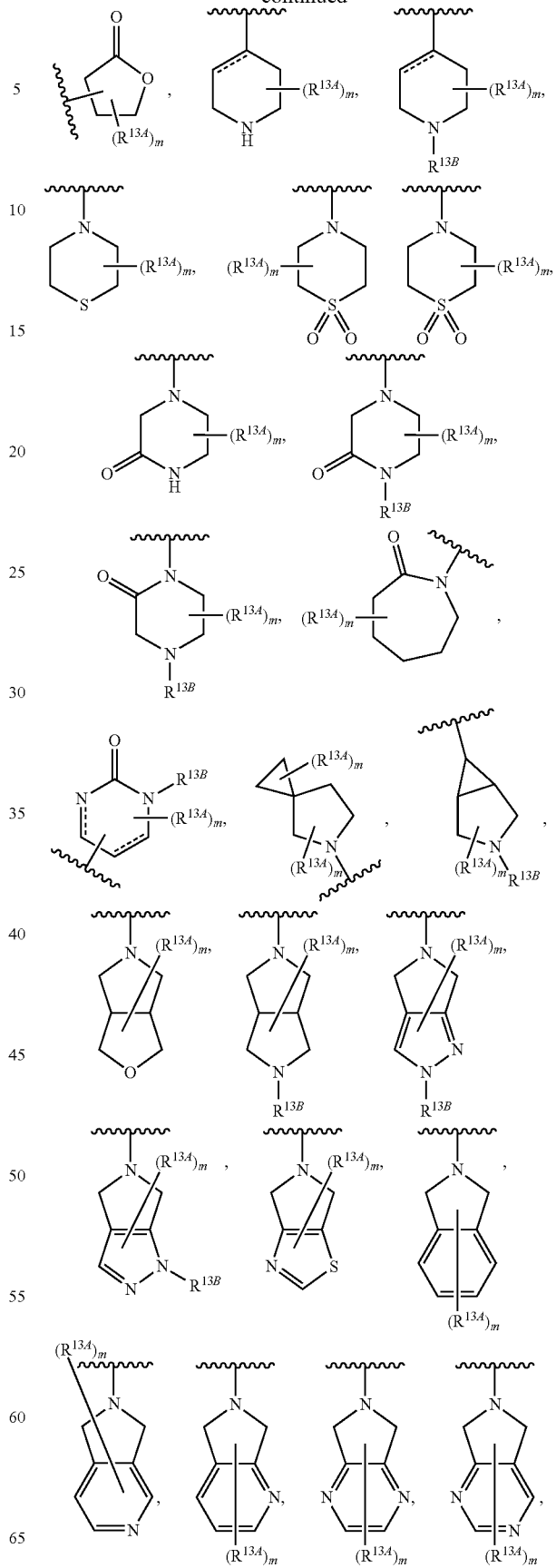

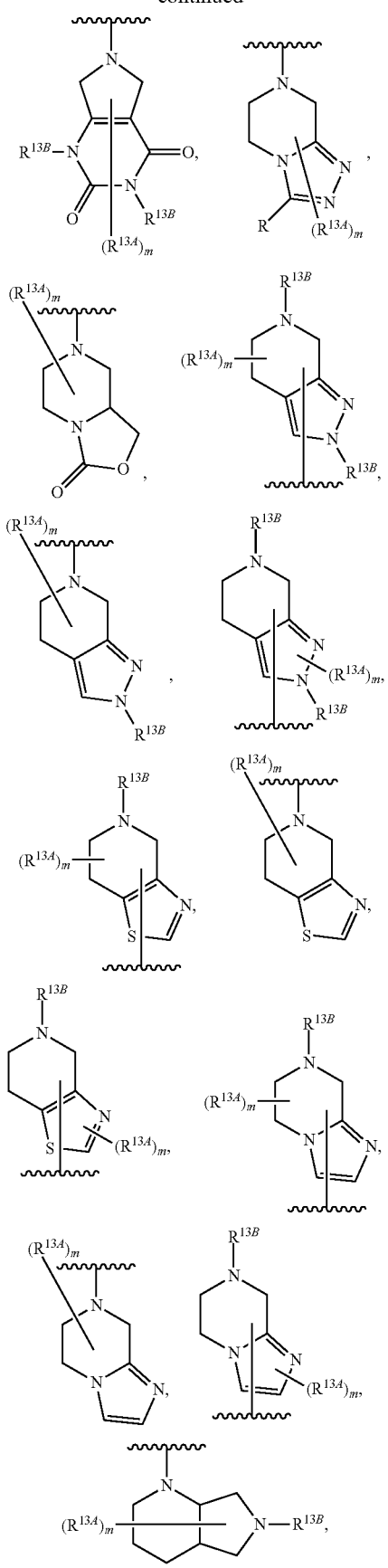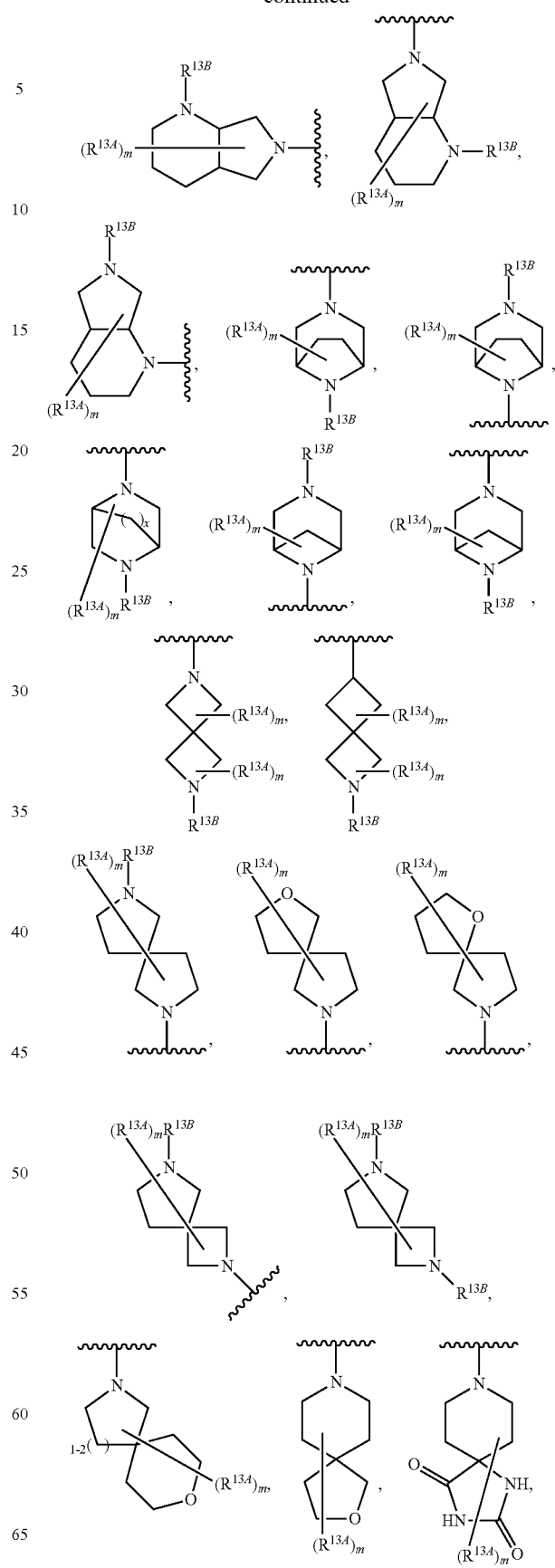

591
-continued
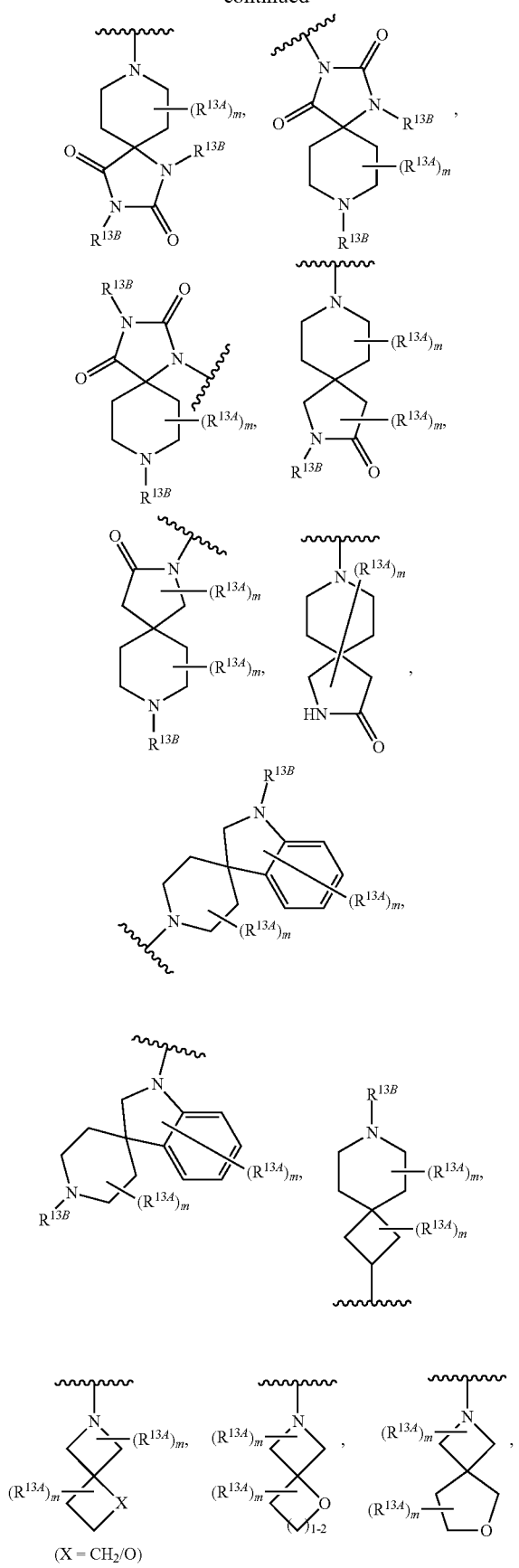
592
-continued
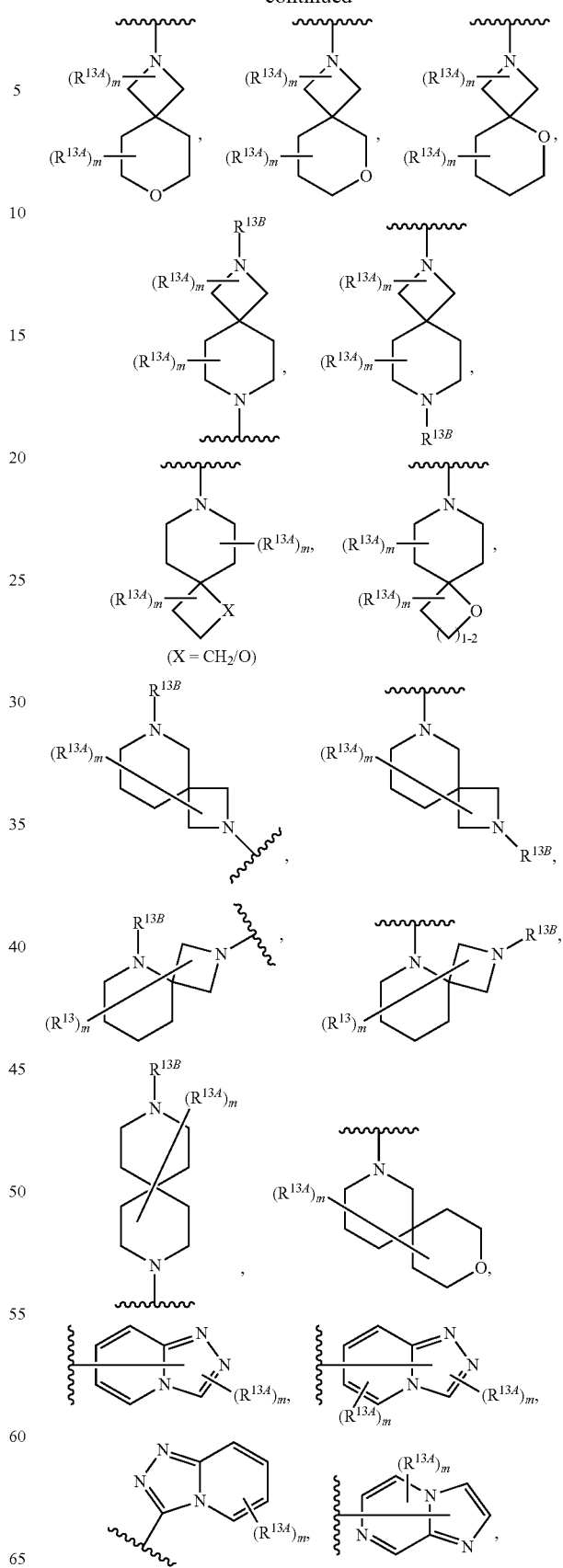

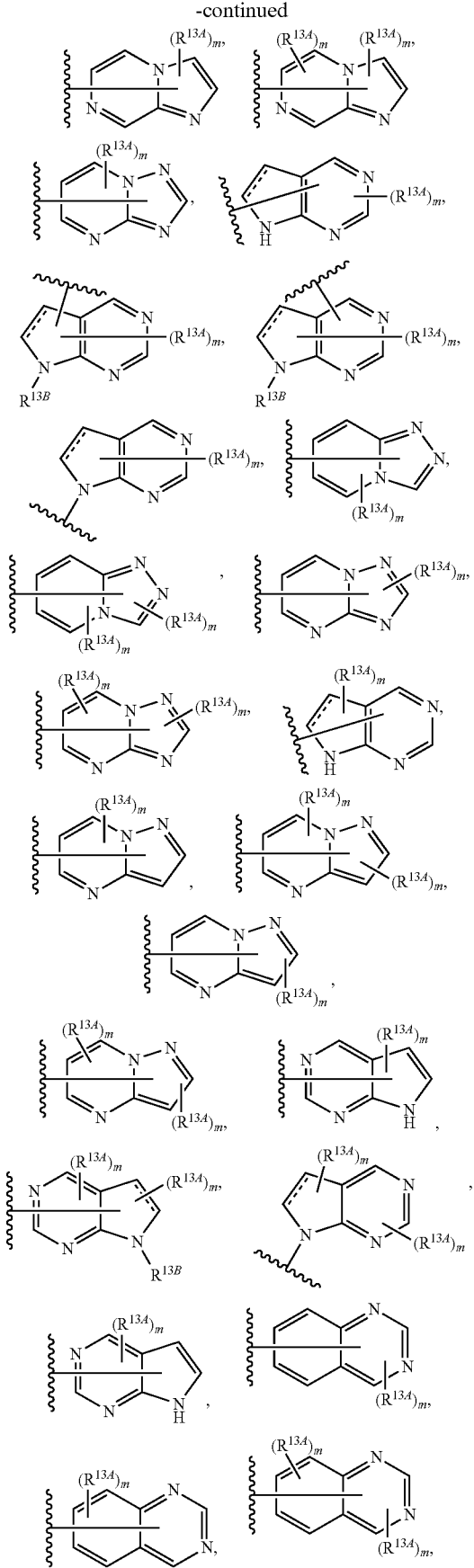

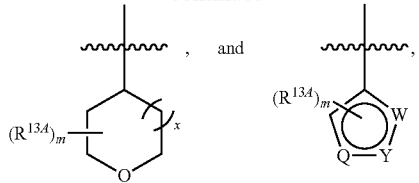

wherein:
each instance of ═ independently represents a single or double bond;
x is 0 or 1;
m is 0, 1, 2, or 3;
Y is O, S, N, or $NR^{13B}$ and each instance of Q and W is independently CH, $CR^{13A}$, N, or $NR^{13B}$, as valency permits;
each instance of $R^{13A}$ is independently hydroxyl, substituted hydroxyl, thiol, substituted thiol, amino, substituted amino, carbonyl, sulfonyl, sulfinyl, —CN, —$NO_2$, halogen, optionally substituted alkyl, optionally substituted alkenyl, optionally substituted alkynyl, optionally substituted carbocyclic, optionally substituted heterocyclic, optionally substituted aryl, or optionally substituted heteroaryl, or two $R^{13A}$ groups are joined to form an optionally substituted carbocyclic, optionally substituted heterocyclic, optionally substituted aryl, optionally substituted heteroaryl, or oxo (═O) group, or $R^{13A}$ and $R^{13B}$ groups are joined to form an optionally substituted carbocyclic, optionally substituted heterocyclic, optionally substituted aryl, or optionally substituted heteroaryl ring; and
$R^{13B}$ is hydrogen, optionally substituted alkyl, hydroxyl, substituted hydroxyl, amino, substituted amino, carbonyl, sulfonyl, optionally substituted carbocyclic, optionally substituted heterocyclic, optionally substituted aryl, optionally substituted heteroaryl, or a nitrogen protecting group.

Aspect 30 provides a compound of any of Aspects 1, 8-20, and 22-28, wherein an $R^3$ group is present and is selected from the group consisting of:

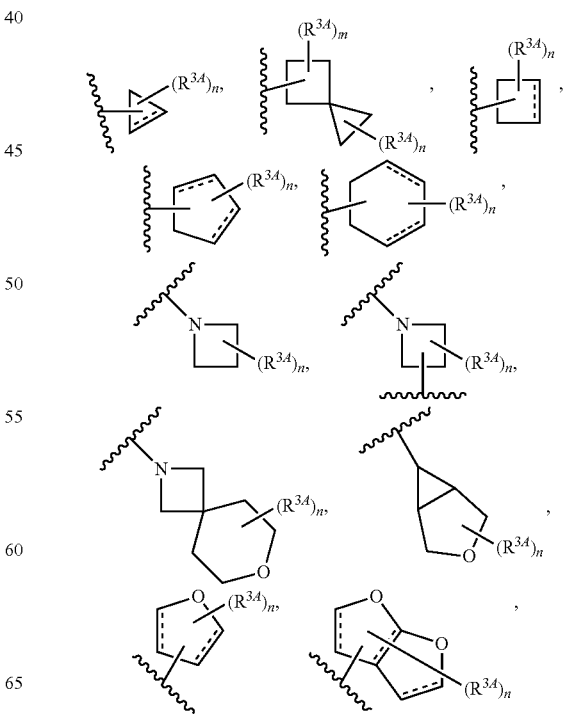

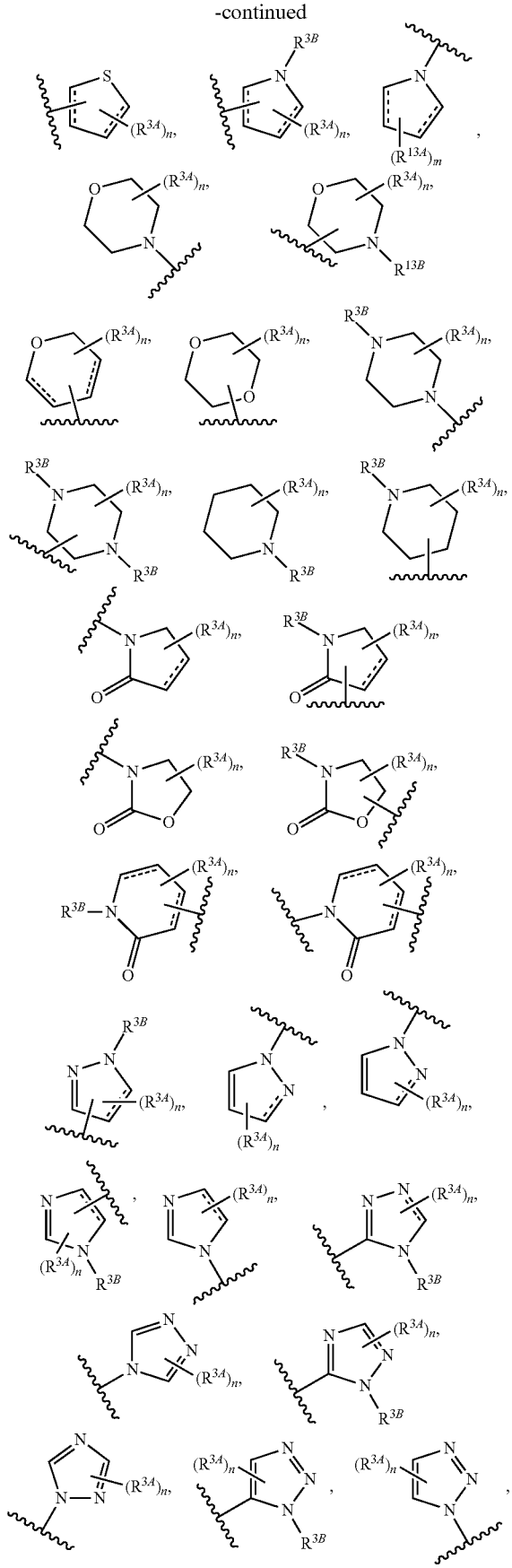
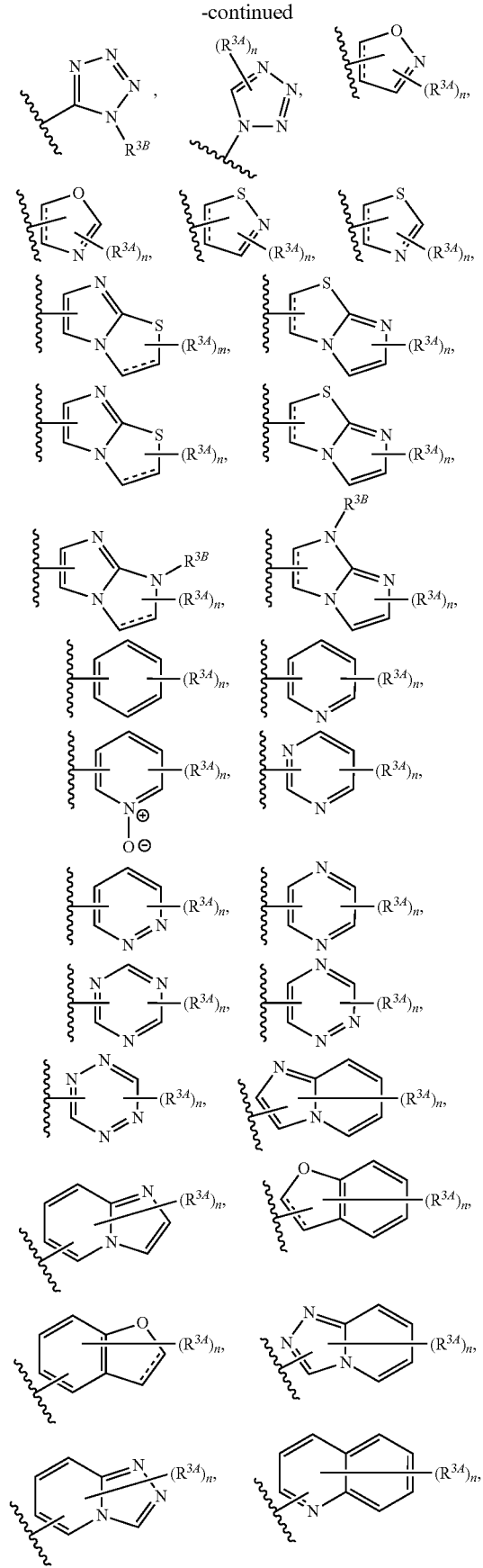

597
-continued
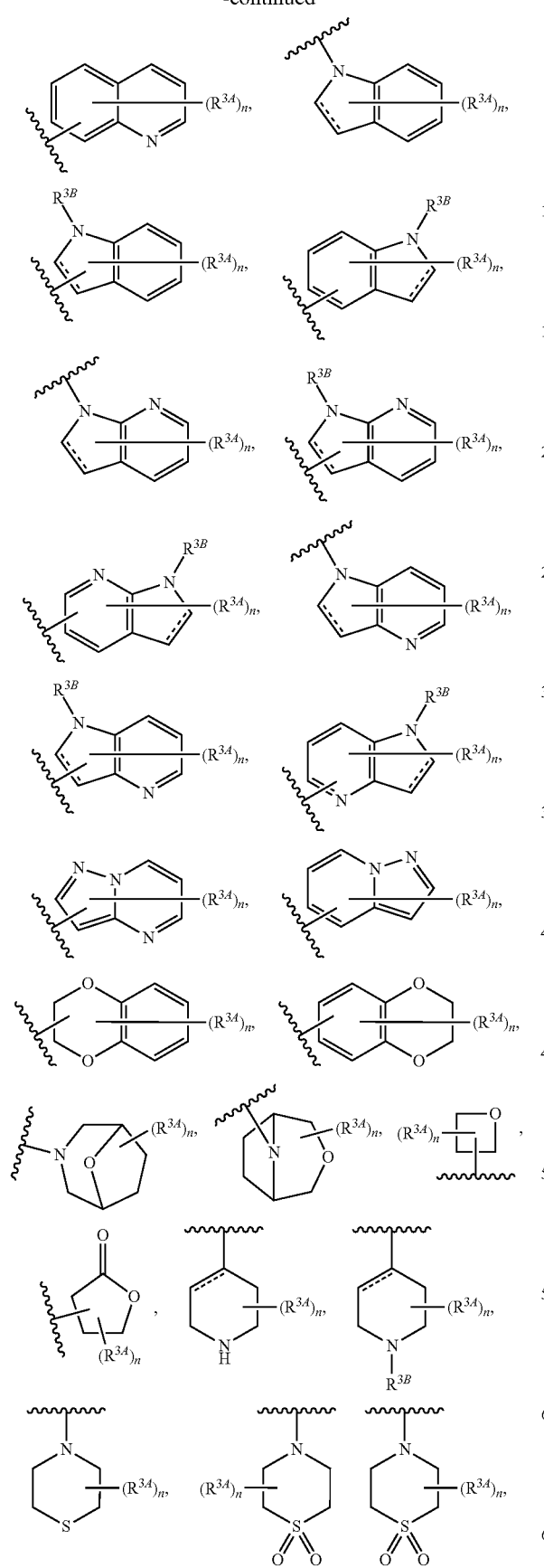
598
-continued
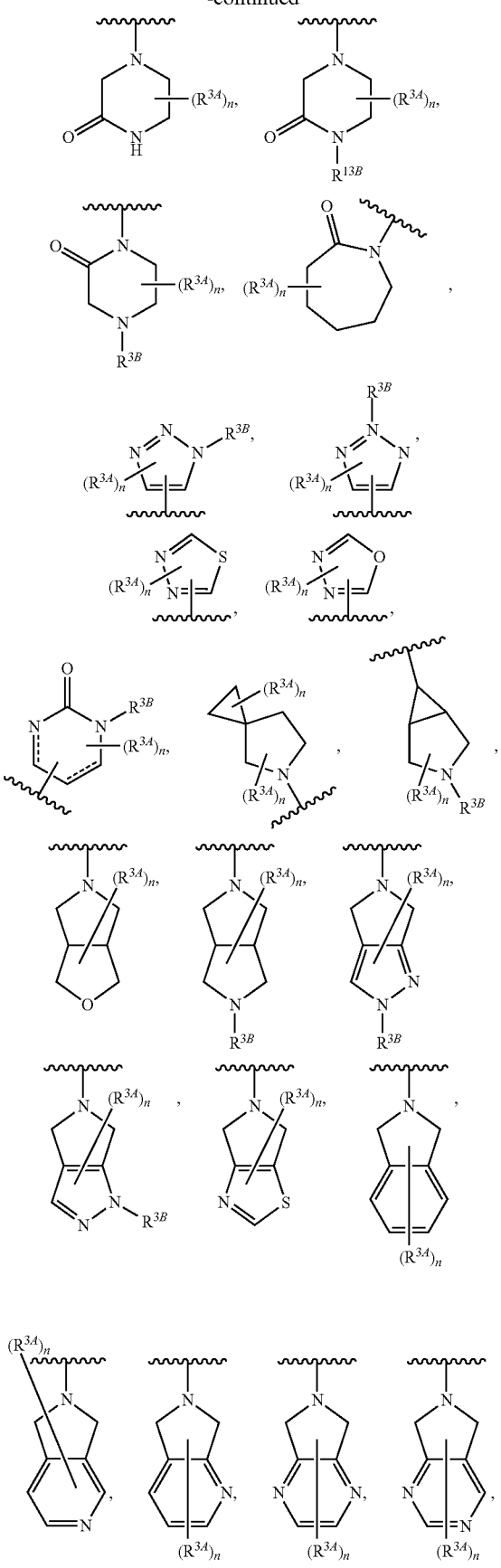

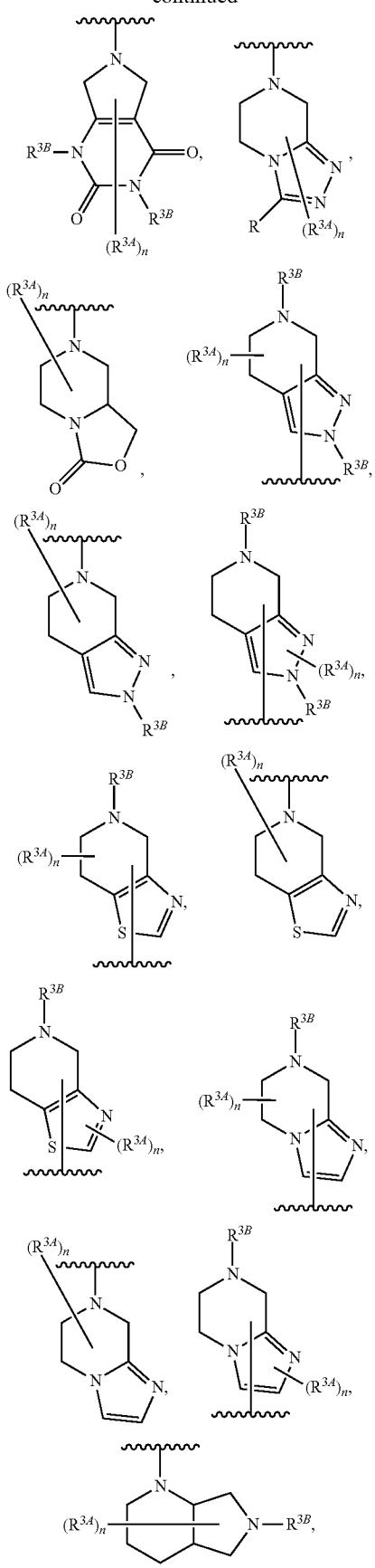
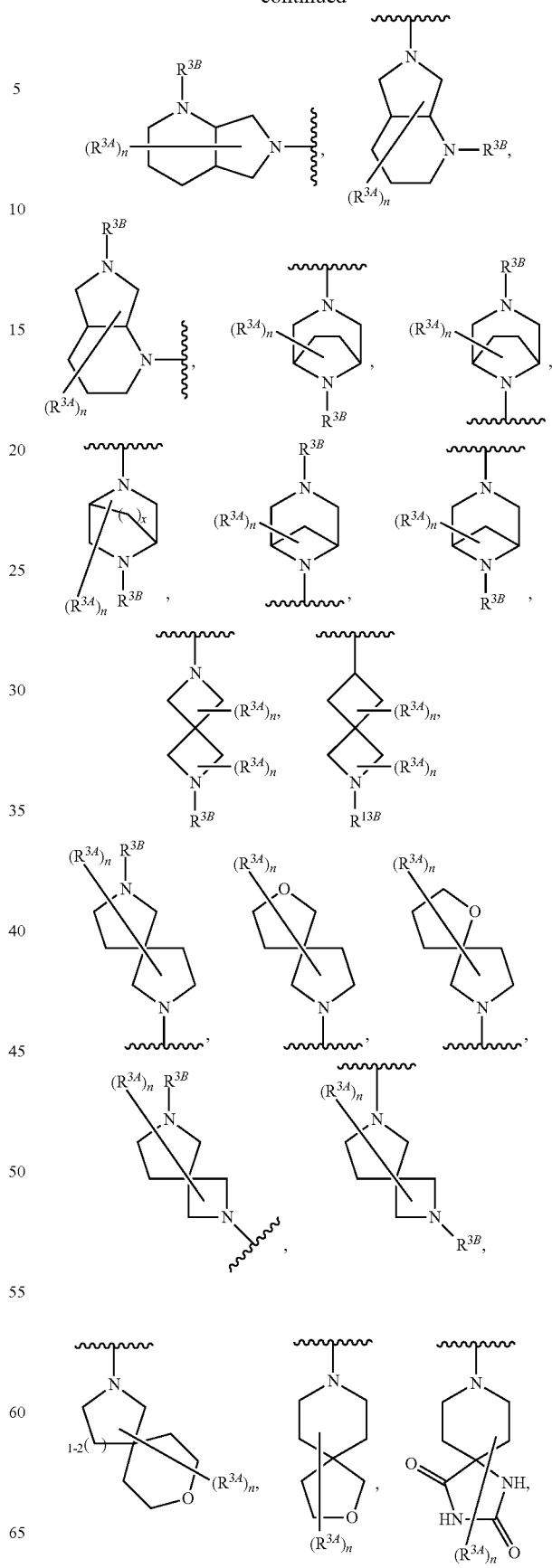

601
-continued
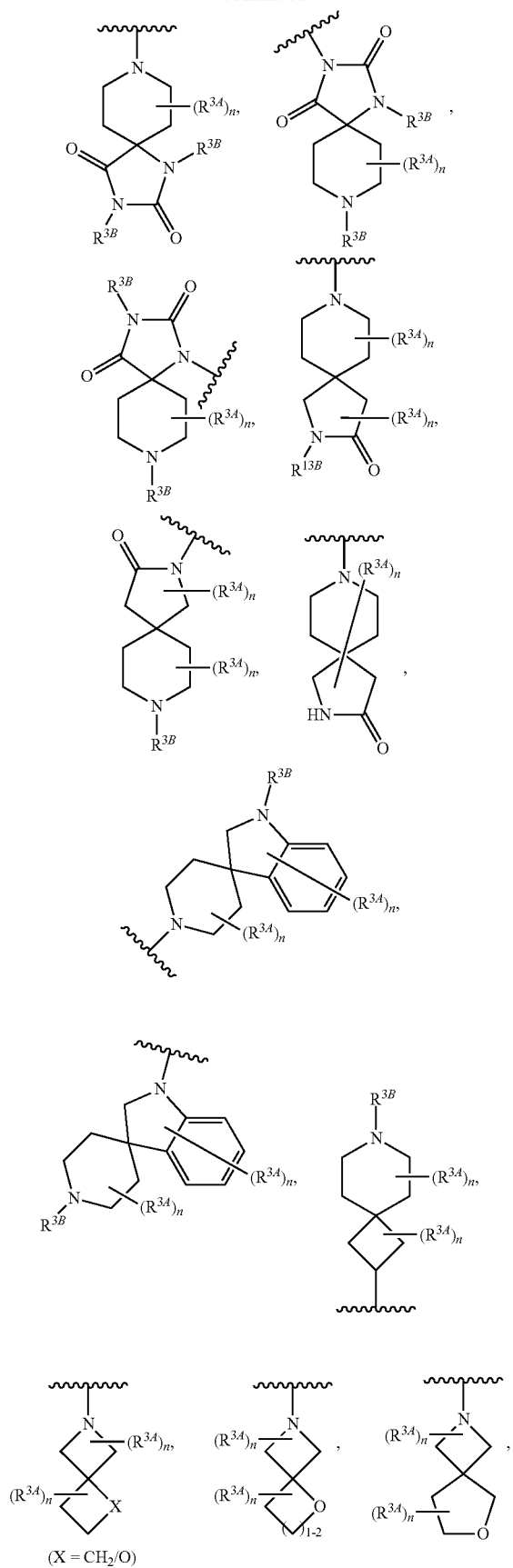
602
-continued
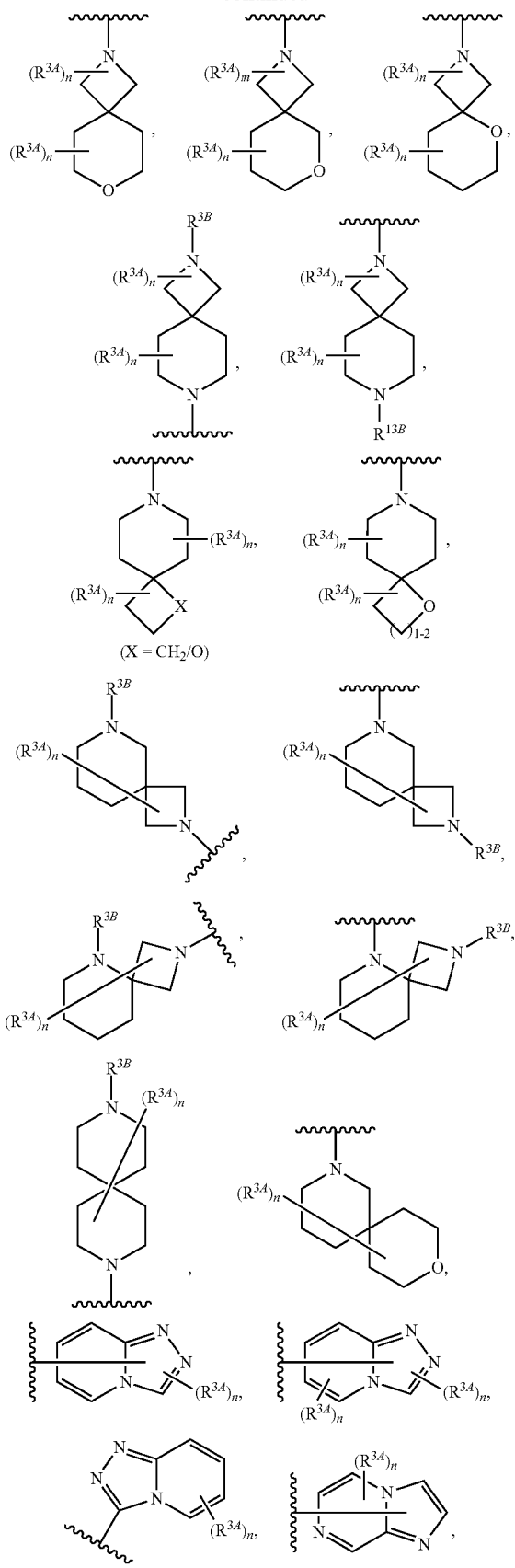

-continued

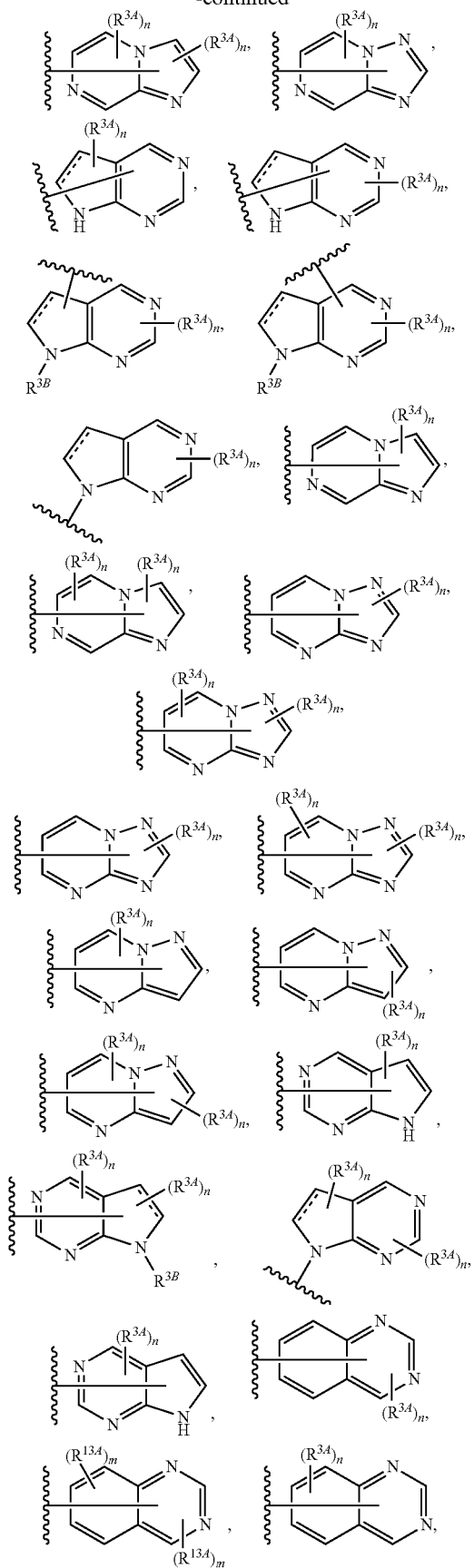

-continued

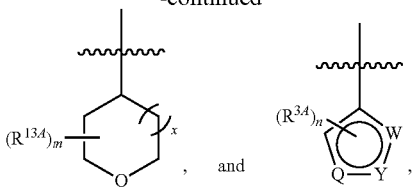

wherein:
each instance of ══ independently represents a single or double bond;
n is 0, 1, 2, or 3;
x is 0 or 1;
Y is O, S, N, or $NR^{3B}$ and each instance of Q and W is independently CH, $CR^{3A}$, N, or $NR^{13B}$, as valency permits;
each instance of $R^{3A}$ is independently hydroxyl, substituted hydroxyl, thiol, substituted thiol, amino, substituted amino, carbonyl, sulfonyl, sulfinyl, —CN, —$NO_2$, halogen, optionally substituted alkyl, optionally substituted alkenyl, optionally substituted alkynyl, optionally substituted carbocyclic, optionally substituted heterocyclic, optionally substituted aryl, or optionally substituted heteroaryl, or two $R^{3A}$ groups are joined to form an optionally substituted carbocyclic, optionally substituted heterocyclic, optionally substituted aryl, optionally substituted heteroaryl, or oxo (═O) group, or $R^{3A}$ and $R^{3B}$ groups are joined to form an optionally substituted carbocyclic, optionally substituted heterocyclic, optionally substituted aryl, or optionally substituted heteroaryl ring; and
$R^{3B}$ is hydrogen, optionally substituted alkyl, hydroxyl, substituted hydroxyl, amino, substituted amino, carbonyl, sulfonyl, optionally substituted carbocyclic, optionally substituted heterocyclic, optionally substituted aryl, optionally substituted heteroaryl, or a nitrogen protecting group.

Aspect 31 provides a compound selected from the group consisting of compounds depicted in Tables 1A, 1B, 1C, and 2, or a pharmaceutically acceptable salt thereof.

Aspect 32 provides a compound selected from the following list: 77-1a, 304-1a, 102-1a, 187-1a, 226-1a, 257-1a, 277-1a, 278-1a, 304-1a, 305-1a, 2-3, 4-3, 23-3, 17-3, 22-3, 24-3, 25-3, 26-3, 27-3, 28-3, 32-3, 33-3, 35-3, 36-3, 37-3, 40-3, 42-3, 55-3, 56-3, 58-3, 59-3, 60-3, 61-3, 62-3, 63-3, 64-3, 65-3, 66-3, 69-3, 84-3, 85-3, 86-3, 87-3, 88-3, 89-3, 90-3, 91-3, 92-3, 93-3, 101-3, 102-3, 103-3, 104-3, 105-3, 107-3, 108-3, 109-3, 113-3, 114-3, 115-3, 125-3, 134-3, 135-3, 153-3, 154-3, 158-3, 159-3, 161-3, 165-3, 204-3, 278-3, 282-3, and 285-3.

Aspect 33 provides a pharmaceutical composition comprising a compound of any one of Aspects 1-32 or a pharmaceutically acceptable salt thereof, and a pharmaceutically acceptable excipient.

Aspect 34 provides a kit or packaged pharmaceutical comprising a compound of any one of Aspects 1-32 or a pharmaceutically acceptable salt thereof, and instructions for use thereof.

Aspect 35 provides a method of treating a CARM1-mediated disorder, comprising administering to a subject in need thereof an effective amount of a compound of any one of claims Aspects 1-32, or a pharmaceutically acceptable salt thereof, or a pharmaceutical composition of claim 33.

Aspect 36 provides the method of Aspect 35, wherein the disorder is a proliferative disorder.

Aspect 37 provides the method of Aspect 36, wherein the disorder is cancer.

Aspect 38 provides the method of Aspect 37, wherein the cancer is associated with E2F1 upregulation.

Aspect 39 provides the method of Aspect 36 or 37, wherein the cancer is associated with aberrant CARM1 activity.

Aspect 40 provides the method of any one of Aspects 37-39, wherein the cancer is breast cancer, prostate cancer, or colorectal cancer.

Aspect 41 provides the method of any one of Aspects 37-39, wherein the cancer is ERα-dependent breast cancer.

Aspect 42 provides the method of any one of Aspects 37-39, wherein the cancer is castration-resistant prostate cancer.

Aspect 43 provides the method of any one of Aspects 37-39, wherein the cancer is colorectal cancer associated with dysregulated WNT/3-catenin signaling.

Aspect 44 provides the method of any one of Aspects 37-39, wherein the cancer is multiple myeloma.

Aspect 45 provides the method of Aspect 35, wherein the disorder is a metabolic disorder.

Compound Synthesis

Scheme 1 shows a general synthesis route to compounds of Formula I-(ii) wherein $R^{3'}$ is the same as $R^3$ as defined above or is a suitable precursor that may be converted to $R^3$. This method is based on Suzuki coupling reactions of heteroaryl chloride intermediates of general Formula XI-(ii) with pinacol borane intermediates of general Formula X. In a first step, Suzuki coupling reaction of these intermediates is typically conducted in the presence of a palladium catalyst (e.g. $PdCl_2(dppf)$) and a base (e.g. potassium carbonate) in an organic solvent (e.g. toluene) at elevated temperature. In a second optional set of steps the $R^{3'}$ group as well as other groups in the molecule may be converted to the defined final substituents in Formula I-(ii). In a final deprotection step the N-Boc protecting is removed by for example using an acid (e.g. HCl) in a suitable organic solvent (e.g. ethanol) to give certain corresponding embodiments of compounds of Formula I-(ii).

Scheme 1

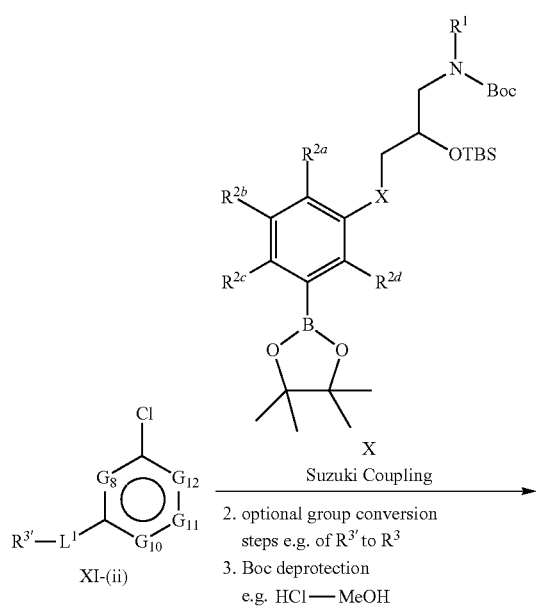

-continued

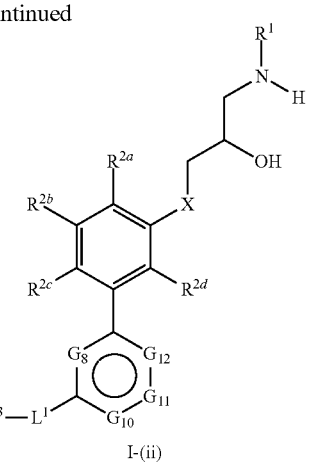

I-(ii)

Compounds of general Formula XI-(ii) can be prepared from heteroaryl dichlorides of general Formula XX-(ii) as depicted in Scheme 2. In certain embodiments when L is —N($R^L$)—, —C(O)N($R^L$)—, or —OC(O)N($R^L$)—, —$NR^LC(O)N(R^L)$—, Buchwald coupling of XX-(ii) respectively with active amines $R^{3'}N(R^L)H$, amides $R^{3'}C(O)N(R^L)$H, carbamates —OC(O)N($R^L$)H, or ureas —$NR^LC(O)N(R^L)$H, may be implemented in the first step.

In certain embodiments when $L^1$ is a bond, and the monocyclic heterocycle core structure is directly attached to $R^{3'}$ by a carbon-carbon bond, Suzuki coupling of XXI-(i) with boronic acids or ester intermediates $R^3B(OH)_2$ may be implemented to yield the corresponding certain embodiments of XI-(ii). In certain embodiments the formation of compounds of Formula XI-(ii) using the methods described above can be accompanied by formation of the regioisomeric intermediate compounds of Formula XI-(ii)-a. In certain embodiments when a mixture of XI-(ii) and XI-(ii)-regioisomers is formed they may be separated by chromatography. Intermediates of Formula XI-(ii)-a may in turn be implemented to prepare compounds of the invention using the same general method described in Scheme 1.

Scheme 2

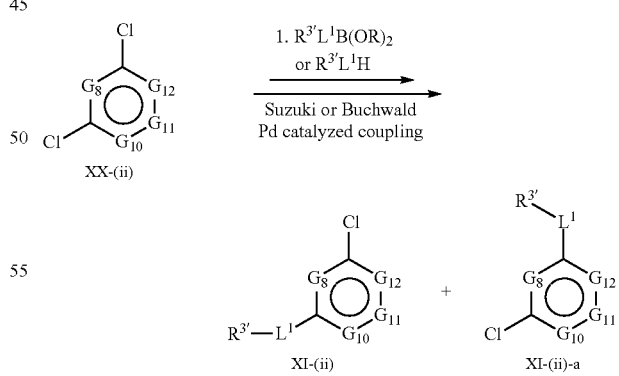

In certain embodiments wherein X in general Formulas I-(ii) is O, pinacol borane intermediates of general Formula X can be prepared using standard methods as depicted in Scheme 3. Thus, in a first step 3-bromophenols of general structure XXX are treated with epibromohydrin to give epoxides XXXI. Opening of the epoxide group of intermediates XXXI in with amines of Formula $R^1NH_2$ in an organic solvent with heating as necessary followed by protection of the resulting amine with Boc-anhydride gives intermediates XXXII. TBS protection of the alcohol group in the next step using t-butyldimethylsilyltriflate gives intermediate bromides XXXIII. In a final step the Br group is converted to the pinacol borane function to give intermediates XX under standard Suzuki-Miyura conditions.

EXAMPLES

In order that the invention described herein may be more fully understood, the following examples are set forth. It should be understood that these examples are for illustrative purposes only and are not to be construed as limiting this invention in any manner.

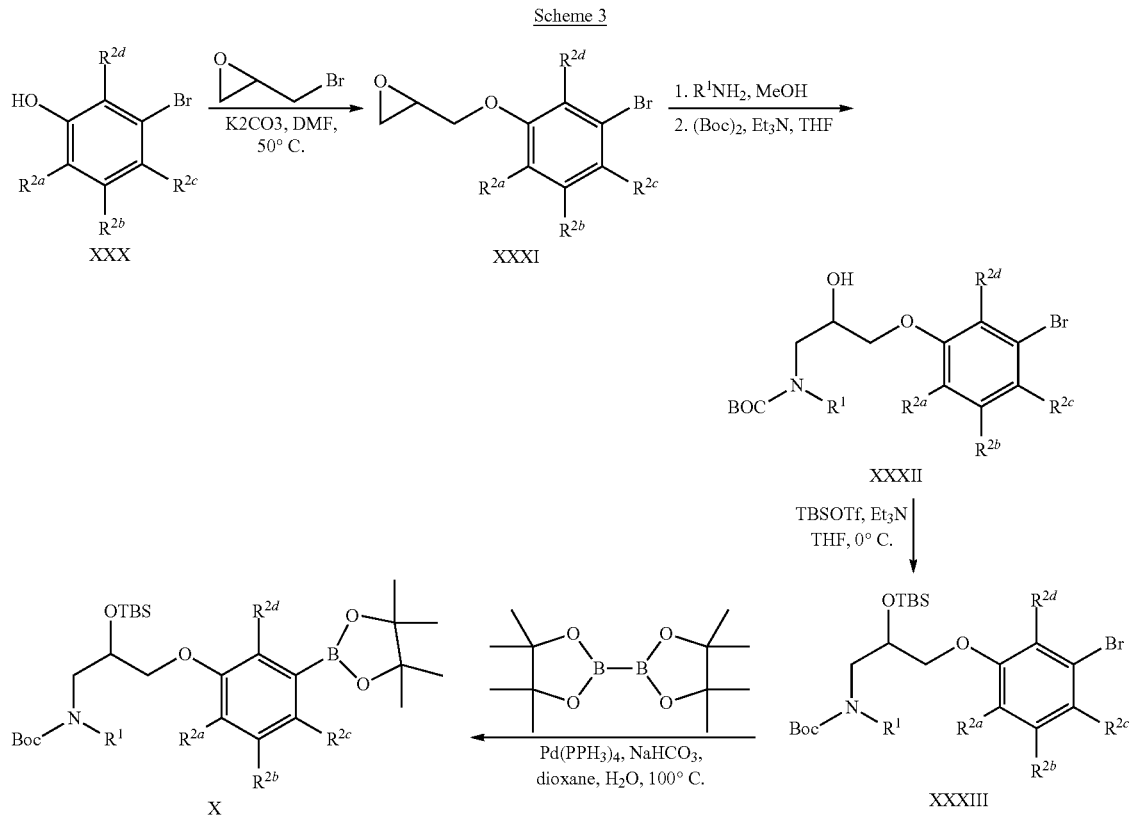

Certain heteroaryl dichlorides of general Formula XX-(ii) are commercially available. Certain embodiments of general structure XX-(ii) may be prepared by known methods. For example embodiments of intermediates of general structure XX-(ii)-x may be prepared from trichloropyrimidine intermediates L-(ii)-x as depicted in Scheme 4. In certain embodiments Suzuki coupling of L-(ii)-x with aryl or heteroaryl boronates gives intermediate compounds of Formula L-(ii)-x a wherein $R^{11}$ is aryl or heteroaryl. In certain embodiments Buchwald coupling of L-(ii)-x with primary or secondary cyclic (e.g. morpholine) or acyclic amines gives intermediate compounds of Formula L-(ii)-x a wherein $R^{11}$ is an acyclic or cyclic amino group.

Synthetic Methods

The synthesis of an exemplary set of compounds of Formula (I) is provided below. These compounds are also listed in Tables 1A, 1B, 1C, and 2, infra. Compounds provided in Tables 1A, 1B, 1C, and 2 have been prepared following Examples 1-3.

Example 1. Preparation of 1-(3-(4-(methyl(tetrahydro-2H-pyran-4-yl)amino)-6-(pyridine-4-yl)pyrimidin-2-yl)phenoxy)-3-(methylamino)propan-2-ol

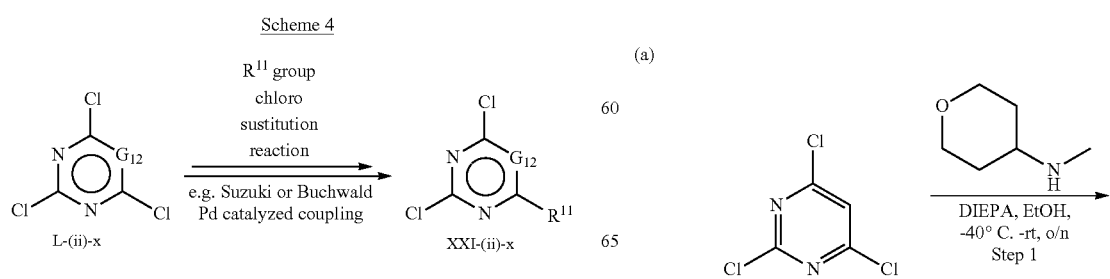

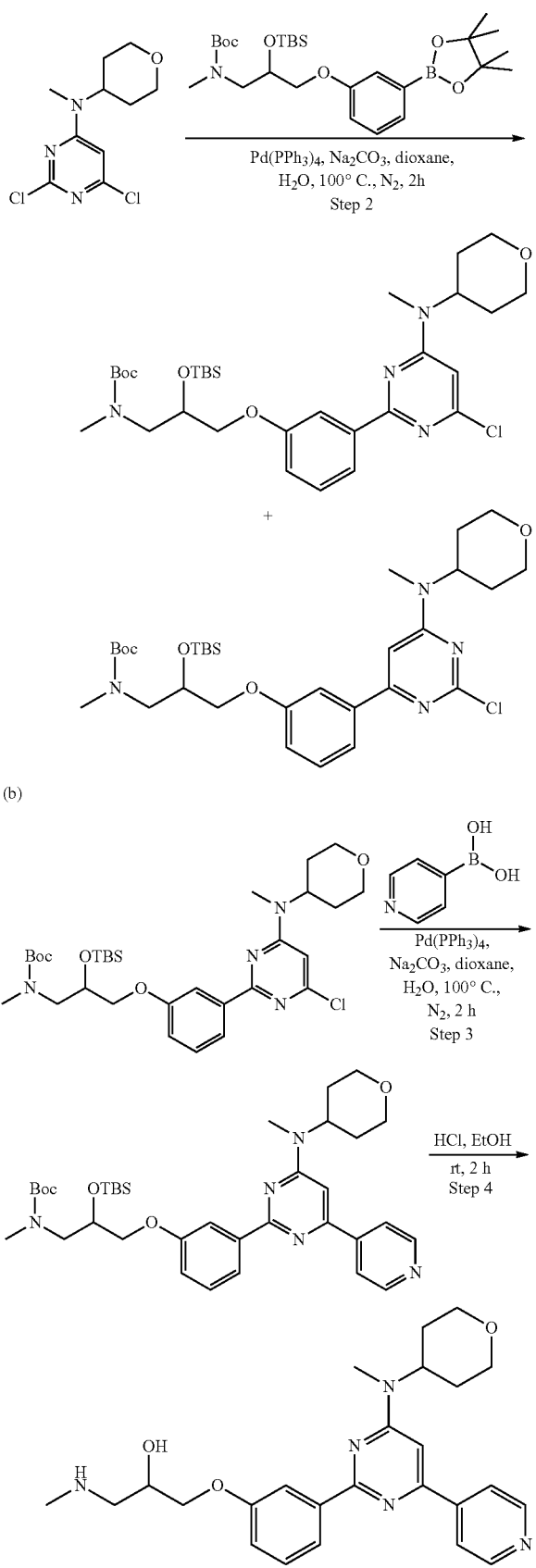

Step 1: Synthesis of (2,6-dichloro-pyrimidin-4-yl)-methyl-(tetrahydro-pyran-4-yl)-amine To a solution of 2,4,6-trichloro-pyrimidine (9.2 g, 50 mmol) and triethylamine (10.1 g, 100 mmol) in EtOH (100 mL) was added N-methyltetrahydro-2H-pyran-4-amine (5.17 g, 45 mmol) dropwise at −40° C. The mixture was warmed up to room temperature then stirred for 14 h., quenched with H₂O (25 mL), concentrated and the residue was extracted with EtOAc (100 mL×3). The combined organic layers were dried over Na₂SO₄, filtered and concentrated. The residue was purified by chromatographic column on silica gel (petroleum ether/EtOAc=30/1 to 2/1) to give (2,6-dichloro-pyrimidin-4-yl)-methyl-(tetrahydro-pyran-4-yl)amine as white solid (7.8 g, 60% yield). ESI-LCMS (m/z): 263.14 [M+1]⁺;

Step 2: Synthesis of [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester and [2-(tert-Butyl-dimethyl-silanyloxy)-3-(3-{2-chloro-6-[methyl-(tetrahydro-pyran-4-yl)-amino]-pyrimidin-4-yl}-phenoxy)-propyl]-methyl-carbamic acid tert-butyl ester To a solution of (2,6-dichloro-pyrimidin-4-yl)-methyl-(tetrahydro-pyran-4-yl)amine (0.4 g, 1.5 mmol) in degassed dioxane and H₂O (4/1, 25 mL) was added Na₂CO₃ (315 mg, 3.0 mmol); Pd(PPh₃)₄ (86 mg, 0.075 mmol) and {2-(tert-Butyl-dimethyl-silanyloxy)-3-[3-(4,4,5,5-tetramethyl-[1,3,2]dioxaborolan-2-yl)-phenoxy]-propyl}-methyl-carbamic acid tert-butyl ester (703 mg, 1.35 mmol). The system was purged with N₂ stream and the mixture was stirred at 100° C. for 2 h., cooled to room temperature, diluted with water (50 mL) and extracted with EtOAc (50 mL×2). The organic layers were combined, dried over Na₂SO₄, filtered and concentrated. The residue was purified by preparative HPLC to give [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester (373 mg, 40% yield) as major product. ESI-LCMS (m/z): 411.2 [M+1]⁺ along with the minor product [2-(tert-Butyl-dimethyl-silanyloxy)-3-(3-{2-chloro-6-[methyl-(tetrahydro-pyran-4-yl)-amino]-pyrimidin-4-yl}-phenoxy)-propyl]-methyl-carbamic acid tert-butyl ester (140 mg, 15% yield). ESI-LCMS (m/z): 411.2 [M+1]⁺.

Step 3: Synthesis of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester To a solution of [2-(tert-Butyl-dimethyl-silanyloxy)-3-(3-{4-chloro-6-[methyl-(tetrahydro-pyran-4-yl)-amino]-pyrimidin-2-yl}-phenoxy)-propyl]-methyl-carbamic acid tert-butyl ester (160 mg, 0.26 mmol) in degassed dioxane and H₂O (4/1, 25 mL) was added Na₂CO₃ (83 mg, 0.78 mmol); Pd(PPh₃)₄ (30 mg, 0.026 mmol) and pyridin-4-ylboronic acid (64 mg, 0.52 mmol). The system was purged with N₂ stream and the mixture was stirred 100° C. for 2 h., cooled down to room temperature, diluted with water (25 mL) and extracted with EtOAc (25 mL×2). The organic layers were combined, dried over Na₂SO₄, filtered and concentrated. The residue was purified by chromatographic column on silica gel (petroleum ether/EtOAc=10/1 to 1/1) to give [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (128 mg, 75% yield). ESI-LCMS (m/z): 664.4 [M+1]$^+$.

Step 4: Synthesis of 1-methylamino-3-(3-{4-[methyl-(tetrahydro-pyran-4-yl)-amino]-6-pyridin-4-yl-pyrimidin-2-yl}-phenoxy)-propan-2-ol A solution of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (135 mg, 0.20 mmol) was treated with a 2.5 N HCl solution in methanol (10 mL) and the mixture was stirred at room temperature for 4 h., concentrated under vacuum and the residue was purified by preparative HPLC to give 1-methylamino-3-(3-{4-[methyl-(tetrahydro-pyran-4-yl)-amino]-6-pyridin-4-yl-pyrimidin-2-yl}-phenoxy)-propan-2-ol as white solid (49 mg, 56% yield). $^1$HNMR (500 MHz, CD$_3$OD) δ ppm: 8.72-8.70 (m, 2H), 8.23 (brs, 2H), 8.14-8.10 (m, 2H), 7.43 (t, J=8.5 Hz, 1H), 7.16-7.10 (m, 2H), 4.24-4.18 (m, 1H), 4.15-4.08 (m, 4H), 3.72-3.65 (m, 2H), 3.14 (s, 3H), 3.00-2.85 (m, 2H), 2.56 (s, 3H), 2.09-1.98 (m, 2H), 1.79-1.72 (m, 2H). ESI-LCMS: 450.5 (M+1)$^+$.

Example 2. Preparation of I-Methylamino-3-(3-{6-[methyl-(tetrahydro-pyran-4-yl)-amino]-2-pyridin-4-yl-pyrimidin-4-yl}-phenoxy)-propan-2-ol

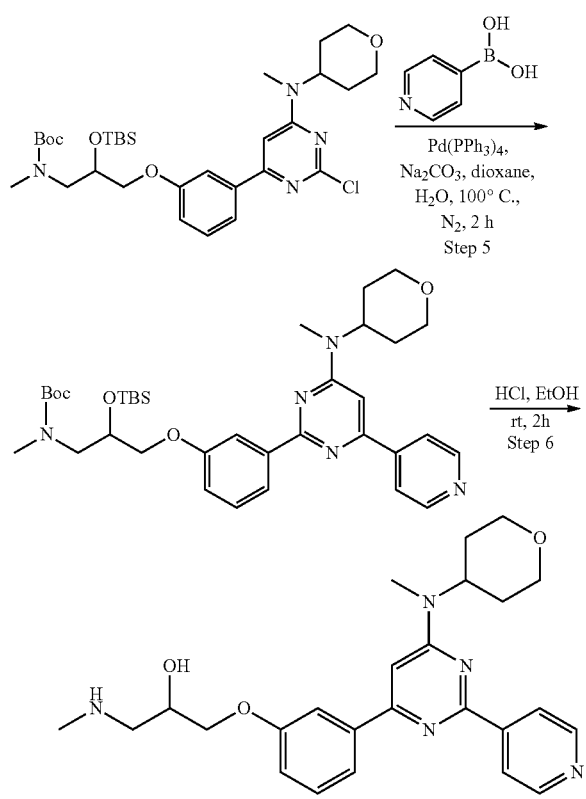

Step 5: Synthesis of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester To a solution of [2-(tert-Butyl-dimethyl-silanyloxy)-3-(3-{2-chloro-6-[methyl-(tetrahydro-pyran-4-yl)-amino]-py-rimidin-4-yl}-phenoxy)-propyl]-methyl-carbamic acid tert-butyl ester (160 mg, 0.26 mmol) in degassed dioxane and H$_2$O (4/1, 25 mL) was added Na$_2$CO$_3$ (83 mg, 0.78 mmol); Pd(PPh$_3$)$_4$ (30 mg, 0.026 mmol) and pyridin-4-ylboronic acid (64 mg, 0.52 mmol). The system purged with N$_2$ stream and the mixture was stirred to 100° C. for 2 h., cooled down to room temperature, diluted with water (25 mL) and extracted with EtOAc (25 mL×2). The organic layers were combined, dried over Na$_2$SO$_4$, filtered and concentrated. The residue was purified by chromatographic column on silica gel (petroleum ether/EtOAc=10/1 to 2/3) to give [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (135 mg, 79% yield). ESI-LCMS (m/z): 664.4 [M+1]$^+$.

Step 6: Synthesis of 1-Methylamino-3-(3-{6-[methyl-(tetrahydro-pyran-4-yl)-amino]-2-pyridin-4-yl-pyrimidin-4-yl}-phenoxy)-propan-2-ol A solution of [2-(tert-Butyl-dimethyl-silanyloxy)-3-(3-{4-[methyl-(tetrahydro-pyran-4-yl)-amino]-6-pyridin-4-yl-pyrimidin-2-yl}-phenoxy)-propyl]-methyl-carbamic acid tert-butyl ester (128 mg, 0.19 mmol) was treated with a 2.5 N HCl solution in methanol, (10 mL), and the mixture was stirred at room temperature for 4 h., concentrated under vacuum and the residue was purified by preparative HPLC to give 1-methylamino-3-(3-{6-[methyl-(tetrahydro-pyran-4-yl)-amino]-2-pyridin-4-yl-pyrimidin-4-yl}-phenoxy)-propan-2-ol as white solid (52 mg, 57% yield). $^1$HNMR (500 MHz, CD$_3$OD) δ ppm: 8.71 (d, J=5.5 Hz, 2H), 8.47 (d, J=5.0 Hz, 2H), 7.84 (s, 1H), 7.79 (d, J=8.0 Hz, 1H), 7.47-7.43 (m, 1H), 7.13 (d, J=8.0 Hz, 1H), 7.09 (s, 1H), 4.22-4.17 (m, 1H), 4.15-4.09 (m, 4H), 3.74-3.66 (m, 2H), 3.15 (s, 3H), 2.96-2.82 (m, 2H), 2.53 (s, 3H), 2.07-1.97 (m, 2H), 1.78-1.73 (m, 2H); LCMS: 450.3 (M+H)$^+$;

Example 3. Preparation of 1-(3-(5-methyl-4-morpholino-6-((R)-tetrahydrofuran-3-ylamino) pyrimidin-2-yl)phenoxy)-3-(methylamino)propan-2-ol

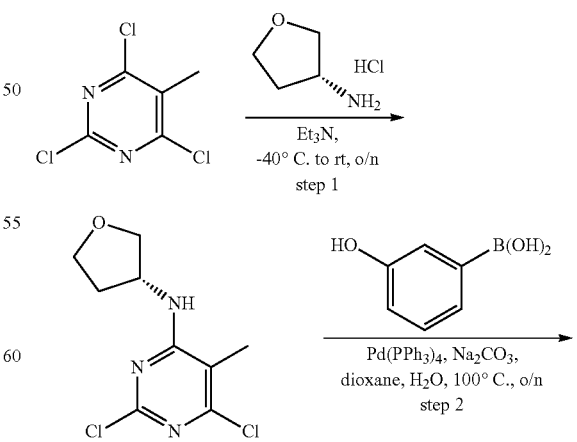

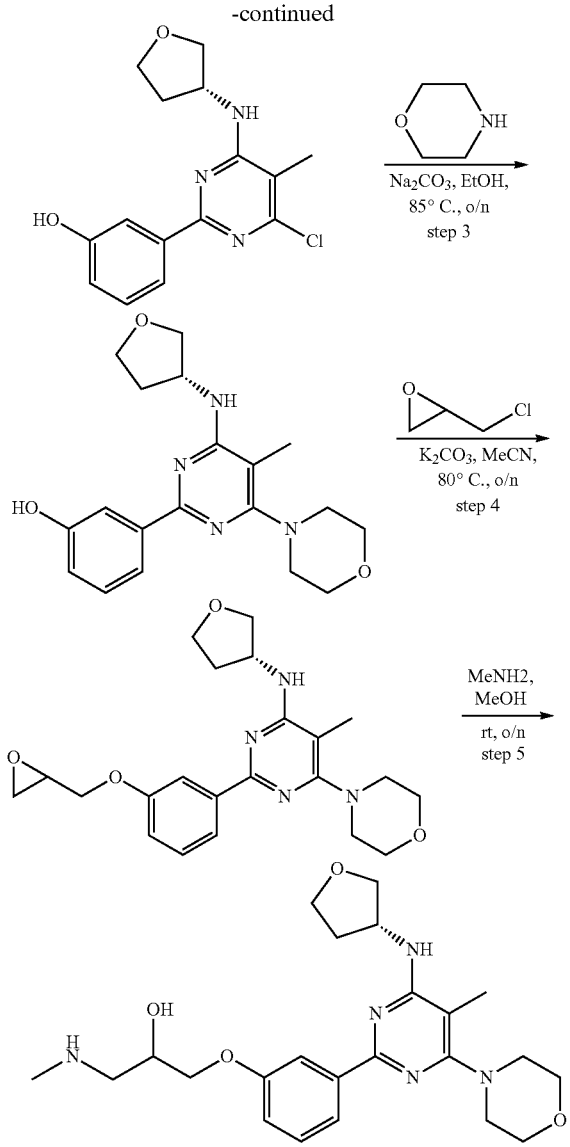

Step 1: Synthesis of (R)-2,6-dichloro-5-methyl-N-(tetrahydrofuran-3-yl) pyrimidin-4-amine A mixture of 2,4,6-trichloro-5-methylpyrimidine (2 g, 10.2 mmol), (R)-tetrahydrofuran-3-amine hydrochloride (1.12 g, 9.2 mmol) and Et₃N (2.1 g, 20.3 mmol) in EtOH (20 mL) was stirred at room temperature for 14 h., concentrated under vacuum and the residue was purified by chromatographic column on silica gel (EtOAc/petroleum ether, gradient elution, from 1/10 to 2/1) to give the (R)-2,6-dichloro-5-methyl-N-(tetrahydrofuran-3-yl)pyrimidin-4-amine (1.25 g, 53% yield) as a white solid. ESI-LCMS (m/z): 248.1 [M+1]⁺.

Step 2: Synthesis of (R)-3-(4-chloro-5-methyl-6-(tetrahydrofuran-3-ylamino) pyrimidin-2-yl)phenol To a solution of of (R)-2,6-dichloro-5-methyl-N-(tetrahydrofuran-3-yl)pyrimidin-4-amine (1.8 g, 7.3 mmol) in degassed dioxane and H₂O (4/1, 21 mL) was added Na₂CO₃ (1.5 g, 14.5 mmol); Pd(PPh₃)₄ (296 mg, 0.36 mmol) and 3-hydroxy-phenylboronic acid (1.21 g, 8.8 mmol). The system was purged with nitrogen stream and then stirred at 100° C. for 14 h., cooled down to room temperature, diluted with water (30 mL) and the resulting mixture extracted with EtOAc (30 mL×2). The combined organic layer were dried over Na₂SO₄, filtered and concentrated. The residue was purified by chromatographic column on silica gel (EtOAc/petroleum ether, gradient elution, from 1/10 to 2:1) to give (R)-3-(4-chloro-5-methyl-6-(tetrahydrofuran-3-ylamino)pyrimidin-2-yl) phenol (2.4 g, 33%) as a white solid. ESI-LCMS (m/z): 306.1 [M+1]⁺.

Step 3: Synthesis of (R)-3-(5-methyl-4-morpholino-6-(tetrahydrofuran-3-ylamino) pyrimidin-2-yl)phenol A mixture of (R)-3-(4-chloro-5-methyl-6-(tetrahydrofuran-3-ylamino)pyrimidin-2-yl) phenol (800 mg, 2.6 mmol); neat morpholine (274 mg, 3.1 mmol) and Na₂CO₃ (556 mg, 5.2 mmol) in EtOH (12 mL) was stirred at 80° C. in a sealed vial for 14 h. The mixture was filtered and the filtrate was concentrated. The residue was purified by chromatographic column on silica gel (EtOAc/petroleum ether, gradient elution, from 1/2 to 2/1) to give the (R)-3-(5-methyl-4-morpholino-6-(tetrahydrofuran-3-ylamino)pyrimidin-2-yl)phenol (120 mg, 13% yield) as a light yellow solid. ESI-LCMS (m/z): 357.1 [M+1]⁺.

Step 4: Synthesis of 5-methyl-6-morpholino-2-(3-(oxiran-2-ylmethoxy)phenyl)-N—((R)-tetrahydrofuran-3-yl)pyrimidin-4-amine A mixture of (R)-3-(5-methyl-4-morpholino-6-(tetrahydrofuran-3-ylamino)pyrimidin-2-yl)phenol (50 mg, 0.14 mmol); 2-(chloromethyl)oxirane (16 mg, 0.17 mmol) and K₂CO₃ (39 mg, 0.28 mmol) in MeCN (10 mL) was heated at 80° C. in a sealed vial for 14 h. The mixture was filtered and the filtrate was concentrated. The residue was purified by chromatographic column on silica gel (EtOAc/petroleum ether, gradient elution, from 1/5 to 4:1) to give the 5-methyl-6-morpholino-2-(3-(oxiran-2-ylmethoxy) phenyl)-N—((R)-tetrahydrofuran-3-yl)pyrimidin-4-amine (20 mg, 34% yield) as a light yellow solid. ESI-LCMS (m/z): 413.2 [M+1]⁺.

Step 5: Synthesis of 1-(3-(5-methyl-4-morpholino-6-((R)-tetrahydrofuran-3-ylamino)pyrimidin-2-yl) phenoxy)-3-(methylamino)propan-2-ol 5-Methyl-6-morpholino-2-(3-(oxiran-2-ylmethoxy)phenyl)-N—((R)-tetra-hydrofuran-3-yl)pyrimidin-4-amine (20 mg, 0.05 mmol) was dissolved in a 2N MeNH₂ solution in methanol, (10 mL) and the mixture was stirred at room temperature for 14 h., concentrated under vacuum and the residue was purified by preparative HPLC to obtain the 1-(3-(5-methyl-4-morpholino-6-((R)-tetrahydrofuran-3-ylamino)pyrimidin-2-yl)phenoxy)-3-(methyl-amino)propan-2-ol (8 mg, 37% yield) as a white solid. ¹H NMR (500 MHz, CD₃OD) δ ppm:8.02-7.96 (m, 2H), 7.34 (t, J=8.0 Hz, 1H), 7.05-7.00 (m, 1H), 4.85-4.80 (m, 1H), 4.20-4.14 (m, 2H), 4.07-4.01 (m, 3H), 3.93-3.84 (m, 5H), 3.78-3.74 (m, 1H), 2.96-2.92 (m, 1H), 2.88-2.82 (m, 1H), 2.53 (s, 3H), 2.42-2.35 (m, 1H), 2.11-2.04 (m, 4H); ESI-LCMS (m/z): 444.3 [M+1]⁺.

Example 4. Preparation of methyl4-(6-(3,5-dimethylisoxazol-4-yl)-2-(3-((S)-2-hydroxy-3-(methylamino)propoxy)phenyl)-5-methylpyrimidin-4-ylamino)piperidine-1-carboxylate formate
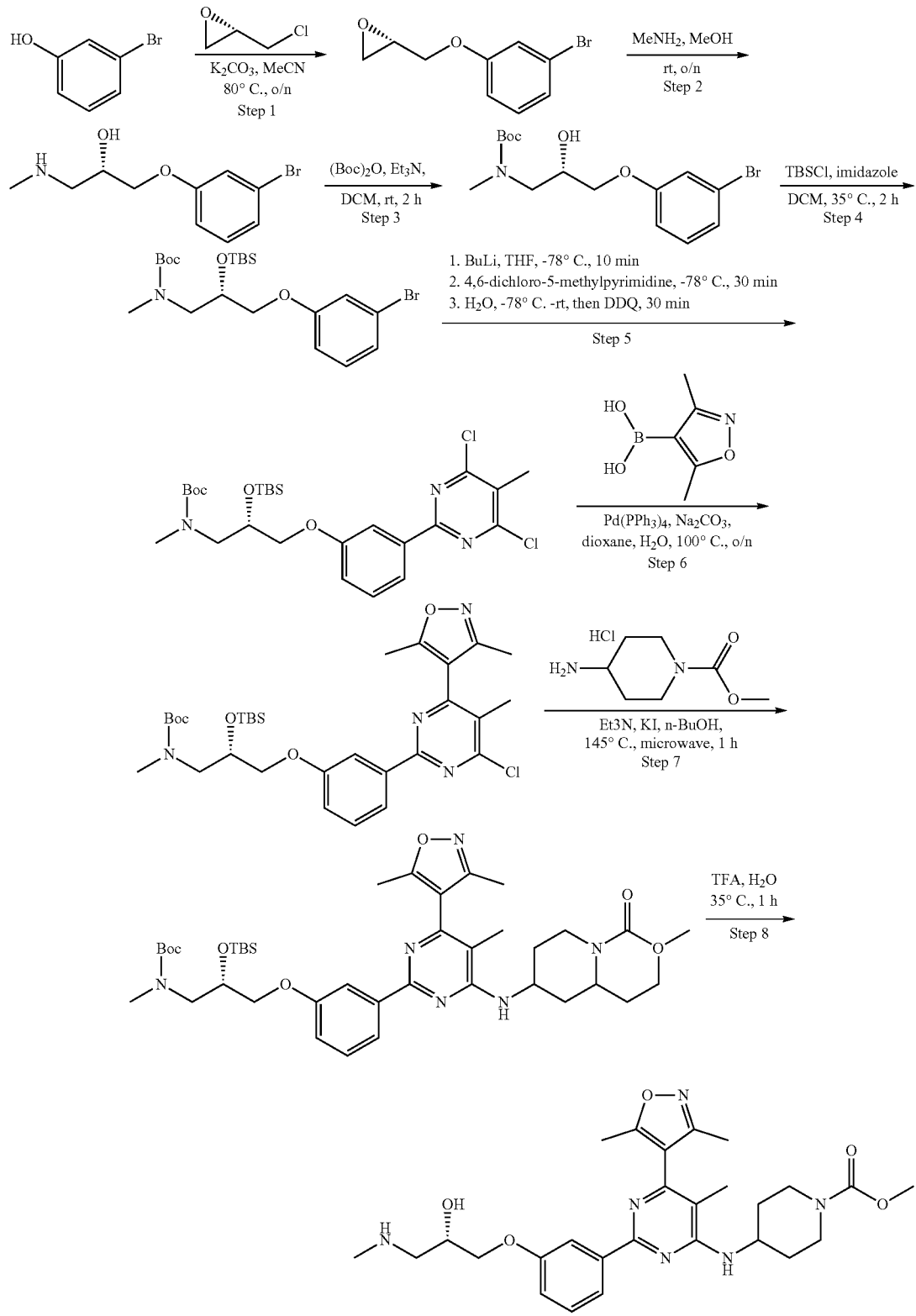

Step 1: Synthesis of (S)-2-((3-bromophenoxy)methyl)oxirane

To a suspension of 3-bromophenol (or any other substituted or unsubstituted phenol, 0.29 mol) and $K_2CO_3$ (120.35 g, 0.87 mol) in MeCN (600 mL) was treated with (S)-2-(chloromethyl)oxirane (applies also to the corresponding R-enantiomer or any other. substituted oxirane, 0.58 mol) with slow addition at room temperature, then the reaction mixture was heated at 80° C. and stirred at the same temperature for 12 h. After being cooled to room temperature, the mixture was filtered and the filtrate was concentrated. The residue was purified by chromatographic column on silica gel (petroleum ether/EtOAc=80/1 to 60/1) to give (S)-2-((3-bromophenoxy)methyl) oxirane (36 g, 54% yield) as colorless oil. ESI-LCMS (m/z): 228.7 $[M+1]^+$.

Step 2: Synthesis of (S)-1-(3-bromophenoxy)-3-(methylamino)propan-2-ol

A 33% solution of $MeNH_2$ (or any other substituted amine or ammonia) in MeOH (50 mL) was slowly added to a solution of (S)-2-((3-bromophenoxy)methyl)oxirane (36 g, 0.157 mol) in MeOH (100 mL) kept at 0° C., after the addition was completed the cooling bath was removed and the reaction mixture further stirred at room temperature for 12 h; and finally concentrated and stored under vacuum to give (S)-1-(3-bromophenoxy)-3-(methylamino)propan-2-ol in quantitative yield. The title product was used directly in the next step without further purification. ESI-LCMS (m/z): 260.1 $[M+1]^+$.

Step 3: Synthesis of (S)-tert-butyl 3-(3-bromophenoxy)-2-hydroxypropyl(methyl) carbamate Neat $Boc_2O$ (42.44 g, 0.18 mol) was added portionwise into a solution of (S)-1-(3-bromophenoxy)-3-(methylamino) propan-2-ol (or any other primary or secondary amine; 0.157 mol) and triethylamine (31.89 g, 0.31 mol) in DCM (600 mL) while stirring at 0° C.; after completing addition, the mixture was stirred at room temperature for 3 h. The reaction mixture was consecutively washed with water (300 mL×2), saturated $NH_4Cl$ aqueous solution (200 mL×2) and brine (300 mL). The organic phase was dried over $Na_2SO_4$, filtered and concentrated to render (S)-tert-butyl 3-(3-bromophenoxy)-2-hydroxypropyl (methyl)carbamate as a pale a yellow oil in quantitative yield. This material was submitted to the next step without further purification. ESI-LCMS (m/z): 382.0 $[M+23]^+$.

Step 4: Synthesis of (S)-tert-butyl 3-(3-bromophenoxy)-2-(tert-butyldimethyl-silyloxy) propyl(methyl)carbamate A solution of (S)-tert-butyl 3-(3-bromophenoxy)-2-hydroxypropyl(methyl) carbamate (or any other alcohol; 0.157 mol) and imidazole (23.47 g, 0.34 mol) in DCM (500 mL) was treated with neat TBSCl (47.37 g, 0.31 mol) added slowly at 0° C. The reaction mixture was then stirred at 35° C. for 2 h followed by washing with water (300 mL×2) and brine (300 mL). The organic layer was dried over $Na_2SO_4$, filtered and concentrated and the resulting residue was purified by chromatographic column on silica gel (petroleum ether/EtOAc=80/1 to 60/1) to give (S)-tert-butyl 3-(3-bromo-phenoxy)-2-(tert-butyldimethylsilyloxy)propyl (methyl) carbamate as a pale yellow oil (66 g, 88% yield for 3 steps). ESI-LCMS: 496.1 $[M+23]^+$.

Step 5: Synthesis of (S)-tert-butyl 2-(tert-butyldimethylsilyloxy)-3-(3-(4,6-di-chloro-5-methylpyrimidin-2-yl)phenoxy)propyl(methyl)carbamate To a solution of (S)-tert-butyl 3-(3-bromophenoxy)-2-(tert-butyldimethylsilyloxy) propyl (methyl)carbamate (105 mmol) (or any other conveniently substituted tert-butyl 3-(3-bromophenoxy)-2-(tert-butyldimethyl silyloxy) propyl (methyl)carbamate) in dry THF (210 mL) stirred at −78° C. under $N_2$ atmosphere, was treated with 2.5 M n-butyl lithium in hexane (44.3 mL, 1.05 eq.) added over 20 min., the mixture was then stirred for another 10 min. at −78° C. before a solution of 4,6-dichloro-5-methylpyrimidine (or any other substituted or unsubstituted pyrimidine, 126 mmol) in THF (20 mL) was added slowly over 10 min. The resulting mixture was stirred at same temperature for 30 min., then quenched with water (10 mL) and slowly warmed to 0° C. DDQ (33 g, 147 mmol) was then added portionwise and the mixture further stirred at for 0° C. 30 min.; diluted with $CH_2Cl_2$ (300 mL), successively washed with 10% NaOH (100 mL) and brine (100 mL) and finally dried over $Na_2SO_4$, filtered and concentrated. The residue was purified by cromatographic column on silicagel eluted with petroleum ether/EtOAc=80/1 to afford (S)-tert-butyl 2-(tert-butyldimethylsilyloxy)-3-(3-(4,6-di-chloro-5-methyl-pyrimidin-2-yl)phenoxy)propyl(methyl) carbamate (30 g, 52% yield) as a white solid. ESI-LCMS (m/z): 577.8 $[M+23]^+$.

For other examples disclosed elsewhere in this document, (S)-tert-butyl 3-(3-bromophenoxy)-2-(tert-butyldimethylsilyloxy) propyl(methyl)carbamate can be replaced for its corresponding (R)-enantiomer, its racemic mixture or any other conveniently substituted derivative of any of these coupling partners.

Step 6: Synthesis of tert-butyl (S)-2-(tert-butyldimethylsilyloxy)-3-(3-(4-chloro-6-(3,5-dimethylisoxazol-4-yl)-5-methylpyrimidin-2-yl)phenoxy)propyl (methyl) carbamate To a solution of (S)-tert-butyl 2-(tert-butyldimethylsilyloxy)-3-(3-(4,6-dichloro-5-methyl pyrimidin-2-yl)phenoxy) propyl(methyl)carbamate (or any other heteroaryl or aryl substituted with a leaving group, e.g., halo (e.g., chloro, bromo, iodo) and sulfonyl substituted hydroxyl groups (e.g., tosyl, mesyl, besyl); 2.5 g, 4.5 mmol) in degassed 10:1 dioxane:$H_2O$ mixture (50 mL), was added 3,5-dimethylisoxazol-4-ylboronic acid (or any other boronic acid or ester; 635 mg, 4.5 mmol), $Pd(PPh_3)_4$ (260 mg, 0.22 mmol) and $Na_2CO_3$ (1.43 g, 13.52 mmol). The system was purged with $N_2$ stream and heated at 100° C. for 12 h. After cooling down to room temperature, the mixture was diluted with water (25 mL) and extracted with EtOAc (25 mL×2). The organic layers were combined, dried over $Na_2SO_4$, filtered and concentrated; the resulting residue was purified by chromatographic column on silicagel (eluted with petroleum ether/EtOAc=60/1 to 30/1) to give tert-butyl (S)-2-(tert-butyldimethylsilyloxy)-3-(3-(4-chloro-6-(3,5-dimethylisoxazol-4-yl)-5-methyl-pyrimidin-2-yl)phenoxy)propyl (methyl)carbamate as a white solid (1.6 g, 58% yield). ESI-LCMS: 616.8 $[M+1]^+$.

Step 7: Synthesis of methyl 4-(2-(3-((S)-3-(tert-butoxycarbonyl(methyl)amino)-2-(tert-butyldimethylsilyloxy)propoxy)phenyl)-6-(3,5-dimethylisoxazol-4-yl)-5-methylpyrimidin-4-ylamino) piperidine-1-carboxylate A pressure vessel containing a solution of tert-butyl (S)-2-(tert-butyldimethylsilyloxy)-3-(3-(4-chloro-6-(3,5-dimethylisoxazol-4-yl)-5-methylpyrimidin-2-yl)phenoxy)propyl(methyl) carbamate (or any other heteroaryl or aryl substituted with a leaving group, e.g., halo (e.g., chloro, bromo, iodo) and sulfonyl substituted hydroxyl groups (e.g., tosyl, mesyl, besyl), 0.56 mmol), methyl 4-aminopiperidine-1-carboxylate hydrochloride (or any other primary or secondary amine, 2.84 mmol), triethylamine (287 mg, 2.84 mmol) and KI (47 mg, 0.28 mmol) in DMSO (7 mL) was placed in a microwave reactor and the mixture irradiated for 60 min. at external temperature of 145° C. After cooling down to room temperature, the mixture was diluted with EtOAc (30 mL), washed with water (10 mL×2) followed by brine (10 mL); the organic layer was dried over $Na_2SO_4$, filtered and concentrated. The residue was purified by preparative TLC (petroleum ether/EtOAc=1.5/1) to obtain methyl 4-(2-(3-((S)-3-(tert-butoxycarbonyl (methyl) amino)-2-(tert-butyldimethylsilyloxy) propoxy)phenyl)-6-(3,5-dimethyl isoxazol-4-yl)-5-methyl-pyrimidin-4-ylamino)piperidine-1-carboxylate (290 mg, 71% yield) as a white solid. ESI-LCMS: 739.0 [M+1]$^+$.

Step 8: Synthesis of methyl 4-(6-(3, 5-dimethyl-isoxazol-4-yl)-2-(3-((S)-2-hydroxy-3-(methylamino)propoxy)phenyl)-5-methylpyrimidin-4-ylamino)piperidine-1-carboxylate Methyl 4-(2-(3-((S)-3-(tert-butoxycarbonyl (methyl) amino)-2-(tert-butyl-dimethylsilyloxy) propoxy)phenyl)-6-(3,5-dimethylisoxazol-4-yl)-5-methylpyrimidin-4-ylamino) piperidine-1-carboxylate (or any other aminoalcohol bearing a silyl protecting group; 0.393 mmol) was dissolved in 90% TFA aqueous solution (5 mL), and the mixture was stirred at 35° C. for 2 h. After removing the solvent under vacuum, the residue was dissolved in MeOH (5 mL) and the solution pH adjusted to 9 with saturated aqueous $K_2CO_3$. The mixture was filtered, the filtrate was concentrated and the resulting residue was purified by preparative HPLC to give methyl 4-(6-(3,5-dimethylisoxazol-4-yl)-2-(3-((S)-2-hydroxy-3-(methylamino)propoxy)phenyl)-5-methylpyrimidin-4-ylamino)piperidine-1-carboxylate as a formic acid salt (white solid, 116 mg, 51% yield). $^1$HNMR (500 MHz, CD$_3$OD) δ ppm: 8.56 (brs, 1H), 7.93 (d, J=7.5 Hz, 1H), 7.89 (s, 1H), 7.37 (t, J=8.0 Hz, 1H), 7.06 (d, J=7.5 Hz, 1H), 4.50-4.42 (m, 1H), 4.30-4.20 (m, 3H), 4.15-4.06 (m, 2H), 3.71 (s, 3H), 3.26-3.20 (m, 1H), 3.18-3.05 (m, 3H), 2.72 (s, 3H), 2.35 (s, 3H), 2.24 (s, 3H), 2.16-2.10 (m, 2H), 2.00 (s, 3H), 1.66-1.56 (m, 2H); ESI-LCMS:525.3 [M+1]$^+$.

Example 5. Preparation of 1-(3-chloro-5-(4-(3,5-dimethylisoxazol-4-yl)-5-methyl-6-(tetrahydro-2H-pyran-4-ylamino)pyrimidin-2-yl)phenoxy)-3-(methylamino)propan-2-ol

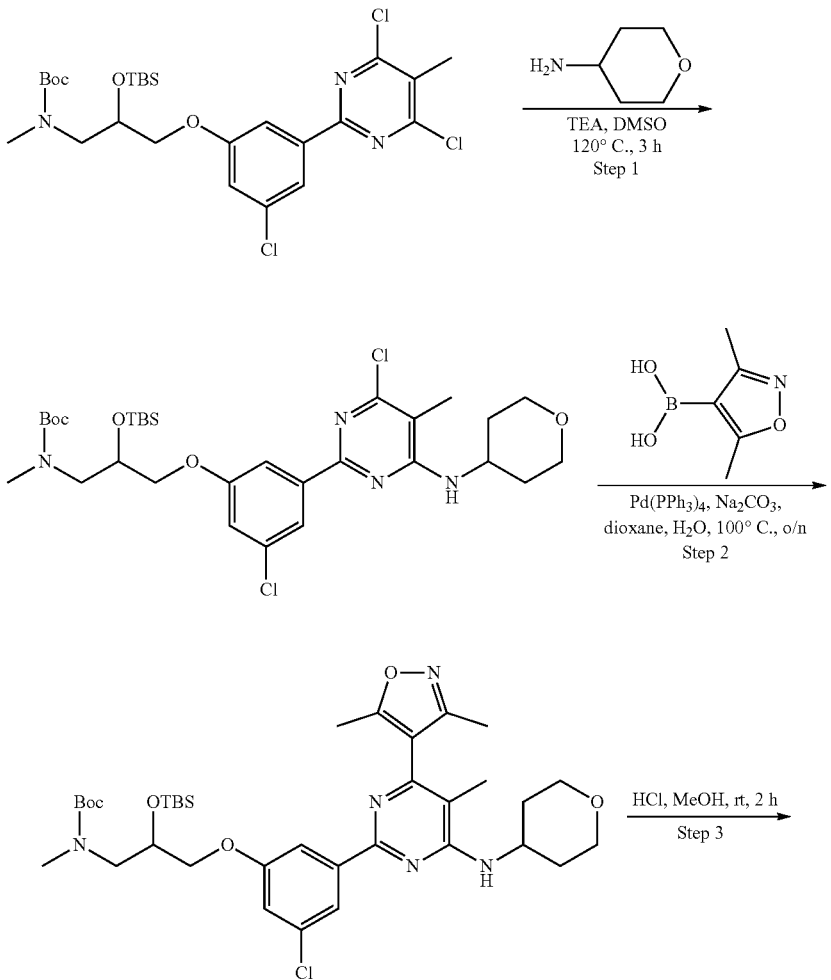

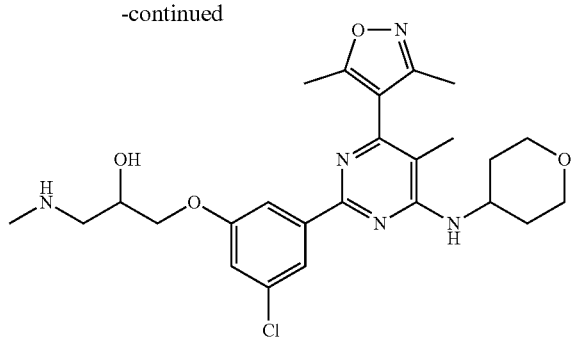

Step 1: Synthesis of tert-butyl 2-(tert-butyldimethylsilyloxy)-3-(3-chloro-5-(4-chloro-5-methyl-6-(tetrahydro-2H-pyran-4-ylamino)pyrimidin-2-yl)phenoxy)propyl(methyl) carbamate To a solution of tert-butyl 2-(tert-butyldimethylsilyloxy)-3-(3-chloro-5-(4,6-dichloro-5-methylpyrimidin-2-yl)phenoxy)propyl(methyl)carbamate (1 g, 1.7 mmol) in DMSO (30 ml), tetrahydro-2H-pyran-4-amine (or any other suitable amine, 2.5 mmol) and triethylamine (344 mg, 3.4 mmol) was added at room temperature. The mixture was then placed in a heating bath preheated at 120° C. and stirred at the same temperature for 3 h; the mixture was then cooled down to room temperature, diluted with EtOAc (150 mL) and washed with water (80 mL×3). The aqueous layer was extracted with EtOAc (50 ml) and the combined organic layers dried over Na₂SO₄, filtered and the filtrate concentrated in vacuo. The crude residue was purified by preparative TLC (petroleum ether/EtOAc=2:1) to obtain tert-butyl 2-(tert-butyldimethyl silyloxy)-3-(3-chloro-5-(4-chloro-5-methyl-6-(tetrahydro-2H-pyran-4-ylamino)pyrimidin-2-yl)phenoxy)propyl (methyl)carbamate (740 mg, 67% yield) as a white solid. ESI-LCMS (m/z): 654.7 [M+1]⁺.

Step 2: Synthesis of tert-butyl 2-(tert-butyldimethylsilyloxy)-3-(3-chloro-5-(4-(3,5-dimethylisoxazol-4-yl)-5-methyl-6-(tetrahydro-2H-pyran-4-ylamino) pyrimidin-2-yl) phenoxy)propyl(methyl)carbamate To a solution of tert-butyl 2-(tert-butyldimethylsilyloxy)-3-(3-chloro-5-(4-chloro-5-methyl-6-(tetrahydro-2H-pyran-4-ylamino)pyrimidin-2-yl)phenoxy)propyl(methyl) carbamate (120 mg, 0.18 mmol) in degassed dioxane:H₂O 3:1 mixture (4 mL) was added Na₂CO₃ (57 mg, 0.54 mmol), Pd(PPh₃)₄ (30 mg, 0.026 mmol) and 3,5-dimethylisoxazol-4-ylboronic acid (or any other suitable boronic acid; 0.36 mmol). The system was purged with N₂ stream and the mixture was stirred 100° C. for 12 h. After being cooled down to room temperature, the reaction mixture was diluted with EtOAc (25 mL) and washed with water (10 mL) and brine (10 mL). The organic layer was dried over Na₂SO₄, filtered and concentrated. The residue was purified by chromatographic column on silicagel (petroleum ether/EtOAc=10/1 to 1/1) to give tert-butyl 2-(tert-butyldimethylsilyloxy)-3-(3-chloro-5-(4-(3,5-dimethylisoxazol-4-yl)-5-methyl-6-(tetrahydro-2H-pyran-4-yl amino)pyrimidin-2-yl) phenoxy)propyl(methyl)carbamate (30 mg, 23% yield). ESI-LCMS (m/z): 716.7 [M+1]⁺.

Step 3: Synthesis of 1-(3-chloro-5-(4-(3,5-dimethylisoxazol-4-yl)-5-methyl-6-(tetrahydro-2H-pyran-4-yl-amino)pyrimidin-2-yl)phenoxy)-3-(methylamino) propan-2-ol The tert-butyl 2-(tert-butyldimethylsilyloxy)-3-(3-chloro-5-(4-(3,5-dimethylisoxazol-4-yl)-5-methyl-6-(tetrahydro-2H-pyran-4-ylamino)pyrimidin-2-yl)phenoxy)propyl (methyl)carbamate (30 mg, 0.04 mmol) was treated with 2.5N HCl solution in methanol (10 mL) and the mixture was stirred at room temperature for 2 h. After concentrated under vacuum, the residue was purified by preparative HPLC to give 1-(3-chloro-5-(4-(3,5-dimethylisoxazol-4-yl)-5-methyl-6-(tetrahydro-2H-pyran-4-yl-amino)pyrimidin-2-yl) phenoxy)-3-(methylamino)propan-2-ol as a white solid (10 mg, 48% yield). ¹HNMR (500 MHz, CD₃OD) δ ppm: 7.91 (d, J=2.0 Hz, 1H), 7.86 (d, J=2.5 Hz, 1H), 7.10 (t, J=2.0 Hz, 1H), 4.53-4.48 (m, 1H), 4.16-4.12 (m, 1H), 4.09-4.02 (m, 4H), 3.68-3.63 (m, 2H), 2.91-2.79 (m, 2H), 2.51 (s, 3H), 2.39 (s, 3H), 2.26 (s, 3H), 2.11-2.08 (m, 2H), 2.03 (s, 3H), 1.83-1.75 (m, 2H); ESI-LCMS: 502.7 [M+1]⁺.

Example 6. Preparation of (3S)-ethyl 3-((6-(3, 5-dimethylisoxazol-4-yl)-2-(3-(2-hydroxy-3-(methylamino)propoxy)phenyl)-5-methylpyrimidin-4-ylamino)methyl)morpholine-4-carboxylate (a)

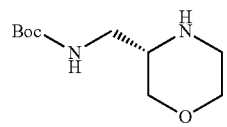 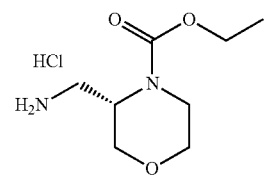

ClCO₂Et, Et₃N, DCM, 0° C. to rt, 2h
step 1
HCl, dioxane, MeOH, rt, 1 h
step 2

(b)

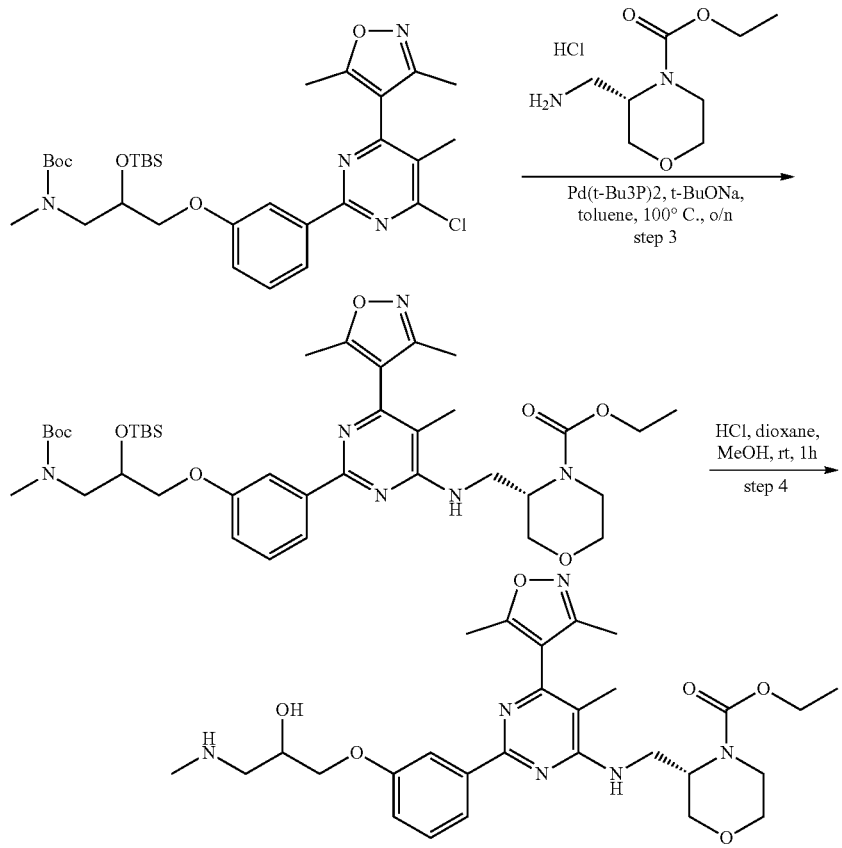

Step 1: Synthesis of (S)-ethyl 3-((tert-butoxycarbonylamino)methyl) morpholine-4-carboxylate To a solution of (S)-tert-butyl morpholin-3-ylmethylcarbamate (or any other suitable amine, 2.3 mmol) and triethylamine (350 mg, 3.4 mmol) in DCM (20 mL) stirred at 0° C. under $N_2$ atmosphere, was added ethyl chloroformate* (325 mg, 3.0 mmol). The mixture was warmed to room temperature and stirred for 2 h. Water (30 mL) was added and the mixture was extracted with DCM (30 mL×2). The combined organic layers were dried over $Na_2SO_4$, filtered and concentrated to give the crude (S)-ethyl 3-((tert-butoxycarbonylamino) methyl) morpholine-4-carboxylate, which was used directly without further purification. Quantitative yield.

*Alternatively, other alkylating, acylating, carbamoylating, or sulfonylating agents can be employed is similar manner.

Step 2: Synthesis of (S)-ethyl 3-(aminomethyl)morpholine-4-carboxylate hydrochloride To a solution of ((S)-ethyl 3-((tert-butoxycarbonylamino) methyl)morpholine-4-carboxylate (3.4 mmol) in MeOH (5 mL) was added 4 mL of 4N HCl in dioxane and the mixture was stirred at room temperature for 1 h. Then the solution was concentrated and titurated with EtOAc (15 mL) to give the (S)-ethyl 3-(aminomethyl) morpholine-4-carboxylate hydrochloride as a white solid, (750 mg, 3.3 mmol, 98% yield).

Step 3: Synthesis of (3S)-ethyl 3-((2-(3-(3-(tert-butoxycarbonyl(methyl) amino)-2-(tert-butyldimethylsilyloxy)propoxy)phenyl)-6-(3,5-dimethyl-isoxazol-4-yl)-5-methylpyrimidin-4-ylamino)methyl) morpholine-4-carboxylate To a solution of tert-butyl 2-(tert-butyldimethylsilyloxy)-3-(3-(4-chloro-6-(3,5-di-methylisoxazol-4-yl)-5-methylpyrimidin-2-yl)phenoxy)propyl(methyl)carbamate (400 mg, 0.64 mmol) in toluene (5 mL) was added (S)-ethyl 3-(aminomethyl) morpholine-4-carboxylate hydrochloride (or any other suitable substituted primary amine, 0.89 mmol), Pd(t-Bu$_3$P)$_2$ (40 mg, 0.008 mmol) and t-BuONa (180 mg, 1.87 mmol). The system was purged with $N_2$ stream, sealed and heated at 100° C. for 12 h. After being cooled down to room temperature, water (30 mL) was added and the mixture was extracted with EtOAc (30 mL×2). The combined organic layers were dried over $Na_2SO_4$, filtered and concentrated. The residue was purified by preparative TLC (petroleum ether/EtOAc=1/2) to obtain (3S)-ethyl 3-((2-(3-(3-(tert-butoxycarbonyl(methyl)amino)-2-(tert-butyldimethylsilyloxy) propoxy)phenyl)-6-(3,5-dimethylisoxazol-4-yl)-5-methyl-pyrimidin-4-ylamino)methyl)morpholine-4-carboxylate (200 mg, 40% yield). ESI-LCMS (m/z): 769 [M+1]$^+$.

Step 4: Synthesis of (3S)-ethyl 3-((6-(3, 5-dimethylisoxazol-4-yl)-2-(3-(2-hydroxy-3-(methylamino) propoxy)phenyl)-5-methylpyrimidin-4-ylamino) methyl)morpholine-4-carboxylate A solution of (3S)-ethyl 3-((2-(3-(3-(tert-butoxycarbonyl (methyl)amino)-2-(tert-butyldimethyl silyloxy)propoxy)

phenyl)-6-(3,5-dimethylisoxazol-4-yl)-5-methylpyrimidin-4-ylamino)methyl)morpholine-4-carboxylate (200 mg) in MeOH (5 mL) stirred at room temperature, was treated with 4N HCl solution in dioxane (4 mL). The reaction mixture was then stirred at same temperature for 1 h; concentrated under vacuum, the residue was dissolved in MeOH (5 mL) and treated with aqueous ammonium hydroxide till pH=8. The mixture was concentrated and the residue was purified by preparative HPLC to give (3S)-ethyl 3-((6-(3, 5-dimethylisoxazol-4-yl)-2-(3-(2-hydroxy-3-(methylamino)propoxy)phenyl)-5-methylpyrimidin-4-ylamino)methyl) morpholine-4-carboxylate (100 mg, 69% yield) as white solid. $^1$HNMR (500 MHz, CD$_3$OD) δ ppm: 7.94 (brs, 2H), 7.37 (t, J=8.5 Hz, 1H), 7.07 (dd, J=2.0 and 8.0 Hz, 1H), 4.70-4.30 (m, 2H), 4.18-4.11 (m, 1H), 4.06 (d, J=5.0 Hz, 1H), 4.02-3.90 (m, 4H), 3.89-3.68 (m, 4H), 3.58-3.45 (m, 2H), 2.90-2.85 (m, 1H), 2.82-2.76 (m, 1H), 2.49 (s, 3H), 2.37 (s, 3H), 2.26 (s, 3H), 1.99 (s, 3H), 1.20-0.80 (m, 3H); ESI-LCMS (m/z): 555.4 [M+1]$^+$.

Example 7. Preparation of 1-(3-(4-(5-cyclopropyl-1,3,4-thiadiazol-2-ylamino)-6-(3,5-di-methylisoxazol-4-yl)-5-methylpyrimidin-2-yl)phenoxy)-3-(methylamino)propan-2-ol rimidin-2-yl)phenoxy)propyl(methyl)carbamate (100 mg, 0.16 mmol) in toluene (4 mL) was added Cs$_2$CO$_3$ (105 mg, 0.32 mmol); (t-Bu$_3$P)$_2$Pd (20 mg, 0.016 mmol) and 5-cyclopropyl-1,3,4-thiadiazol-2-amine (or any other aromatic amine, 0.32 mmol). The system was purged with N$_2$ stream, sealed and heated at 110° C. for 12 h. After being cooled down to room temperature, the reaction mixture was diluted with water (25 mL) and extracted with EtOAc (25 mL×2). The organic layers were combined, dried over Na$_2$SO$_4$, filtered and concentrated. The residue was purified by chromatographic column on silicagel (petroleum ether/EtOAc=10/1 to 2/3) to give tert-butyl 2-(tert-butyl dimethylsilyloxy)-3-(3-(4-(5-cyclopropyl-1,3,4-thiadiazol-2-ylamino)-6-(3,5-dimethylisoxazol-4-yl)-5-methylpyrimidin-2-yl)phenoxy)propyl(methyl) carbamate (100 mg, 85% yield). ESI-LCMS (m/z): 721.9 [M+1]$^+$.

Step 2: Synthesis of 1-(3-(4-(5-cyclopropyl-1,3,4-thiadiazol-2-ylamino)-6-(3,5-dimethylisoxazol-4-yl)-5-methylpyrimidin-2-yl)phenoxy)-3-(methylamino)propan-2-ol tert-Butyl 2-(tert-butyldimethylsilyloxy)-3-(3-(4-(5-cyclopropyl-1,3,4-thiadiazol-2-ylamino)-6-(3,5-dimethylisoxazol-4-yl)-5-methylpyrimidin-2-yl)phenoxy)propyl

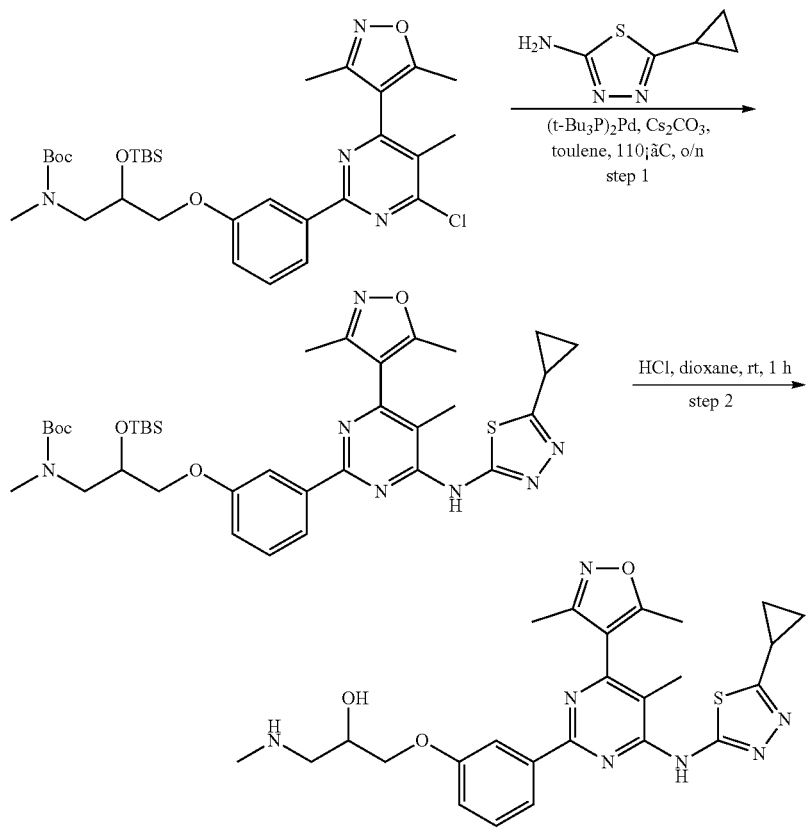

Step 1: Synthesis of [tert-butyl 2-(tert-butyldimethylsilyloxy)-3-(3-(4-(5-cyclopropyl-1,3,4-thiadiazol-2-ylamino)-6-(3,5-dimethylisoxazol-4-yl)-5-methylpyrimidin-2-yl)phenoxy) propyl(methyl)carbamate To a solution of [tert-butyl 2-(tert-butyldimethylsilyloxy)-3-(3-(4-chloro-6-(3,5-dimethylisoxazol-4-yl)-5-methylpy- (methyl)carbamate (100 mg, 0.14 mmol) was dissolved in 4N HCl solution in dioxane (5 mL) at room temperature and the mixture was stirred at the same temperature for 1 h; concentrated in vacuo and the residue was purified by preparative HPLC to give 1-(3-(4-(5-cyclopropyl-1,3,4-thiadiazol-2-ylamino)-6-(3,5-dimethylisoxazol-4-yl)-5-methylpyrimidin-2-yl)phenoxy)-3-(methylamino)propan-2-ol as formic acid salt (white solid, 14 mg, 19% yield). ¹HNMR (500 MHz, CD₃OD) δ ppm: 8.56 (s, 1H), 8.12 (d, J=8.0 Hz, 1H), 8.07 (d, J=1.5 Hz, 1H), 7.49 (t, J=8.0 Hz, 1H), 7.18 (dd, J=8.0 and 1.5 Hz, 1H), 4.33-4.29 (m, 1H), 4.20-4.15 (m, 2H), 3.32-3.26 (m, 1H), 3.23-3.16 (m, 1H), 2.76 (s, 3H), 2.50-2.40 (m, 4H), 2.30 (s, 3H), 2.29 (s, 3H), 1.31-1.26 (m, 2H), 1.16-1.13 (m, 2H); LCMS: 508.1 [M+H]⁺.
Example 8. Preparation of 1-(3-(4-(4-(2,2-difluoroethyl)piperazin-1-yl)-5-methyl-6-((R)-tetrahydrofuran-3-ylamino)pyrimidin-2-yl)phenoxy)-3-(methylamino)propan-2-ol
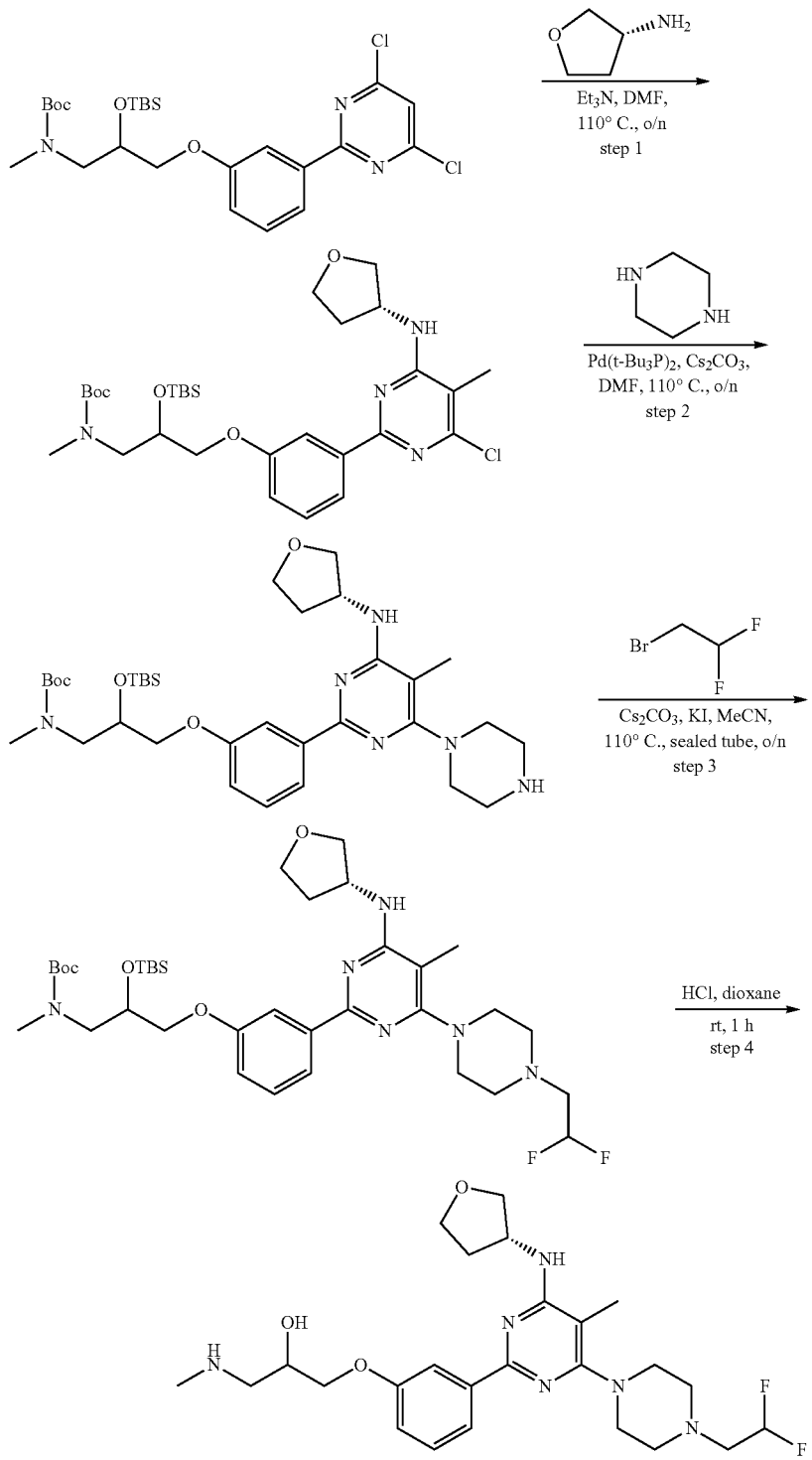

Step 1: Synthesis of tert-butyl 2-(tert-butyldimethylsilyloxy)-3-(3-(4-chloro-5-methyl-6-((R)-tetrahydrofuran-3-ylamino)pyrimidin-2-yl)phenoxy)propyl(methyl)carbamate To a solution of tert-butyl 2-(tert-butyldimethylsilyloxy)-3-(3-(4,6-dichloro-5-methyl-pyrimidin-2-yl)phenoxy)propyl(methyl)carbamate (2.0 g, 3.6 mmol) in DMF (35 mL) was added triethylamine (1.46 g, 14.4 mmol), (R)-tetrahydrofuran-3-amine (or any other suitable amine, 5.4 mmol) at room temperature, and the mixture was placed in a preheated bath at 110° C. and stirred for 12 h. After being cooled down to room temperature, the reaction mixture was diluted with water (50 mL) and extracted with EtOAc (40 mL×2). The combined organic phase was washed with saturated aqueous ammonium chloride solution (40 mL×2) and brine (40 mL×1), dried over $Na_2SO_4$, filtered and concentrated. The residue was purified by chromatographic column on silica gel (petroleum ether/EtOAc=50/1 to 1/1) to give tert-butyl 2-(tert-butyldimethylsilyloxy)-3-(3-(4-chloro-5-methyl-6-((R)-tetrahydrofuran-3-yl-amino)pyrimidin-2-yl)phenoxy) propyl (methyl)carbamate (1.3 g, 59% yield). ESI-LCMS (m/z): 606.8 [M+1]$^+$.

Step 2: Synthesis of [tert-butyl 2-(tert-butyldimethylsilyloxy)-3-(3-(5-methyl-4-(piperazin-1-yl)-6-((R)-tetrahydrofuran-3-ylamino)pyrimidin-2-yl)phenoxy)propyl(methyl)carbamate To a solution of tert-butyl 2-(tert-butyldimethylsilyloxy)-3-(3-(4-chloro-5-methyl-6-((R)-tetrahydrofuran-3-yl-amino)pyrimidin-2-yl)phenoxy)propyl(methyl)carbamate (700 mg, 1.2 mmol) in degassed toulene (15 mL) was added $Cs_2CO_3$ (750 mg, 2.3 mmol), piperazine (or any other appropriate diamine, 2.3 mmol) and (t-Bu$_3$P)$_2$Pd (70 mg, 0.2 mmol). The system was purged with $N_2$ stream, the reaction vessel was sealed and heated at 110° C. for 12 h. After being cooled down to room temperature, the reaction mixture was diluted with EtOAc (50 mL), washed with water (30 mL×2), the organic layer was dried over $Na_2SO_4$, filtered and concentrated. The residue was purified by preparative TLC (petroleum ether/EtOAc=1/2) to give tert-butyl 2-(tert-butyldimethylsilyloxy)-3-(3-(5-methyl-4-(piperazin-1-yl)-6-((R)-tetrahydrofuran-3-ylamino) pyrimidin-2-yl)phenoxy)propyl(methyl)carbamate (373 mg, 49% yield). ESI-LCMS (m/z): 657.0 [M+1]$^+$.

Step 3: Synthesis of tert-butyl 2-(tert-butyldimethylsilyloxy)-3-(3-(4-(4-(2,2-di-fluoroethyl)piperazin-1-yl)-5-methyl-6-((R)-tetrahydrofuran-3-ylamino)pyrimidin-2-yl)phenoxy)propyl(methyl)carbamate To a solution of tert-butyl 2-(tert-butyldimethylsilyloxy)-3-(3-(5-methyl-4-(piperazin-1-yl)-6-((R)-tetrahydrofuran-3-ylamino)pyrimidin-2-yl)phenoxy)propyl(methyl) carbamate (120 mg, 0.18 mmol) in $CH_3CN$ (5 mL) was added potassium iodide (50 mg, 0.36 mmol), 2-bromo-1,1-difluoroethane (or any other suitable alkylating reagent, 1.7 mmol) and $Cs_2CO_3$ (120 mg, 0.36 mmol) at room temperature; the reaction vessel was sealed and heated at 110° C. for 12 h. After being cooled down to room temperature, the mixture was diluted with EtOAc (50 mL) and washed with water (35 mL×2). The organic layer was dried over $Na_2SO_4$, filtered and concentrated. The residue was purified by preparative TLC (petroleum ether/EtOAc=1/1) to give [tert-butyl 2-(tert-butyldimethylsilyloxy)-3-(3-(4-(4-(2,2-difluoroethyl)piperazin-1-yl)-5-methyl-6-((R)-tetrahydrofuran-3-ylamino)pyrimidin-2-yl)phenoxy)propyl(methyl)carbamate (90 mg, 68% yield). ESI-LCMS (m/z): 721.4 [M+1]$^+$.

Step 4: Synthesis of 1-(3-(4-(4-(2,2-difluoroethyl)piperazin-1-yl)-5-methyl-6-((R)-tetrahydrofuran-3-ylamino)pyrimidin-2-yl)phenoxy)-3-(methylamino) propan-2-ol The tert-butyl 2-(tert-butyldimethylsilyloxy)-3-(3-(4-(4-(2,2-difluoroethyl)piperazin-1-yl)-5-methyl-6-((R)-tetrahydrofuran-3-ylamino)pyrimidin-2-yl)phenoxy)propyl (methyl)carbamate (90 mg, 0.12 mmol) was treated with 2.5N HCl solution in dioxane (5 mL) and the mixture was stirred at room temperature for 1 h; concentrated under vacuum and the residue submitted to purification by preparative HPLC to give 1-(3-(4-(4-(2, 2-difluoroethyl)piperazin-1-yl)-5-methyl-6-((R)-tetrahydrofuran-3-ylamino)pyrimidin-2-yl) phenoxy)-3-(methyl amino) propan-2-ol as a yellow solid (33 mg, 52% yield). $^1$HNMR (500 MHz, CDCl$_3$) δ ppm: 8.01 (d, J=8.9 Hz, 1H), 7.97 (d, J=2.5 Hz, 1H), 7.32 (t, J=8.0 Hz, 1H), 6.96 (dd, J=2.5 and 8.5 Hz, 1H), 5.93 (tt, J=4.5 and 56.0 Hz, 1H), 4.90-4.84 (m, 1H), 4.48 (d, J=6.5 Hz, 1H), 4.17-4.11 (m, 1H), 4.10-3.98 (m, 4H), 3.90-3.84 (m, 1H), 3.81-3.76 (m, 1H), 3.36-3.30 (s, 4H), 2.90-2.75 (m, 4H), 2.74-2.70 (m, 4H), 2.50 (s, 3H), 2.45-2.37 (m, 1H), 2.26 (brs, 2H), 1.98 (s, 3H), 1.95-1.89 (m, 1H); ESI-LCMS (m/z): 507.3 [M+H]$^+$.

Example 9. Preparation of 1-(3-(4-(methyl(tetrahydro-2H-pyran-4-yl)amino)-6-(7-(methylsulfonyl)-7H-pyrrolo[2,3-d]pyrimidin-5-yl)pyrimidin-2-yl)phenoxy)-3-(methyl-amino)propan-2-ol (a)

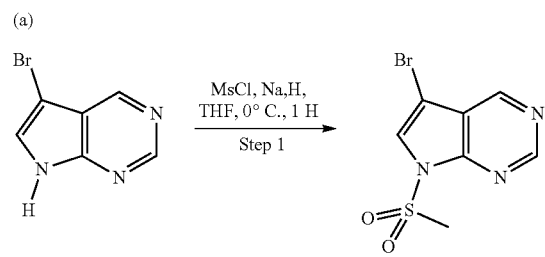

(b)

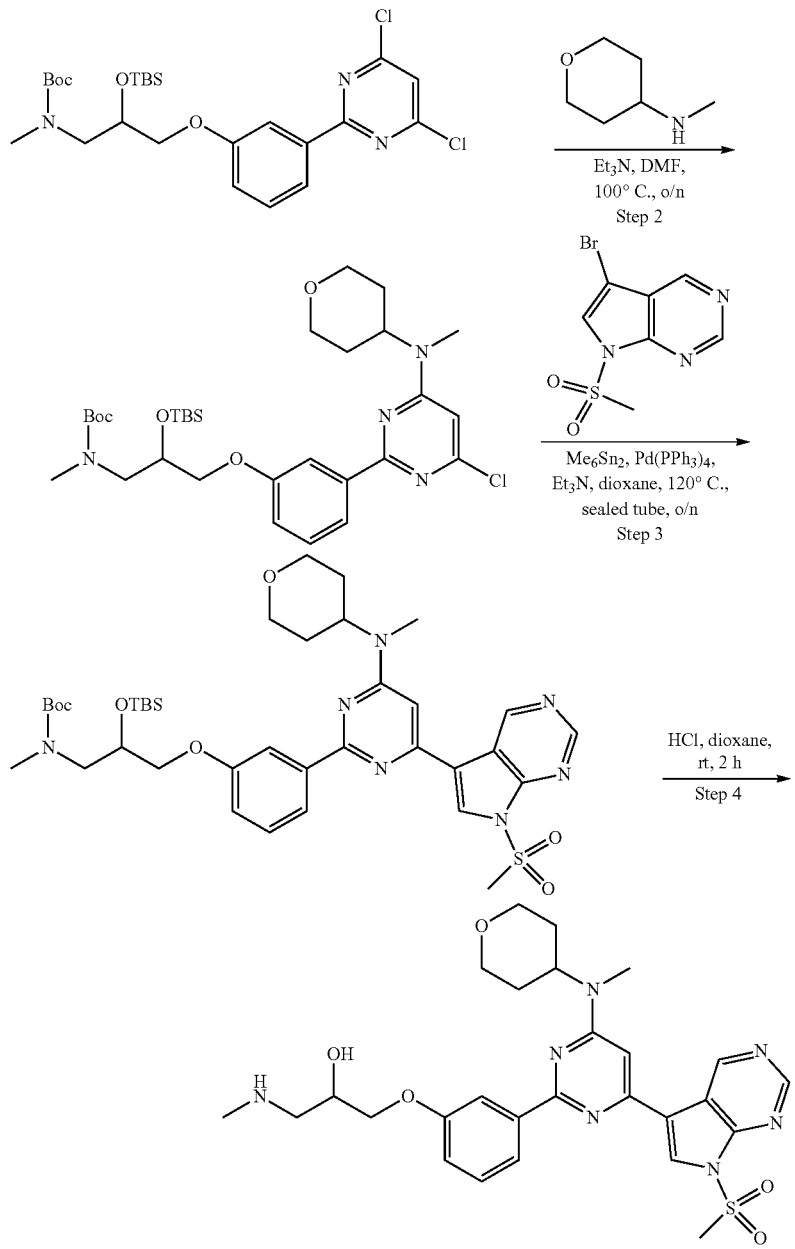

Step 1: Synthesis of 5-bromo-7-(methylsulfonyl)-7H-pyrrolo[2,3-d]pyrimidine

To a solution of 5-bromo-7H-pyrrolo[2,3-d]pyrimidine (or any other suitable aromatic halide, 1 mmol) in DMF (5 mL) was added NaH (43 mg, 60%, 1.1 mmol) at 0° C., After 5 min., MsCl* (114 mg, 1.0 mmol) was added and the mixture was stirred at 0° C. for 1 h. The mixture was diluted with EtOAc (20 mL), successively washed with water (20 mL) and brine (20 mL). The organic layer was dried over Na$_2$SO$_4$, filtered and concentrated. The residue was purified by chromatographic column on silicagel to give 5-bromo-7-(methylsulfonyl)-7H-pyrrolo[2,3-d]pyrimidine (265 mg, 95% yield). ESI-LCMS (m/z): 275.9 [M+1]$^+$.

*Alternatively, other alkylating, acylating, carbamoylating, or sulfonylating agents can be employed is similar manner.

Step 2: Synthesis of (2,6-dichloro-pyrimidin-4-yl)-methyl-(tetrahydro-pyran-4-yl)-amine To a solution of tert-butyl 2-(tert-butyldimethylsilyloxy)-3-(3-(4,6-dichloro-pyrimidin-2-yl)phenoxy)propyl(methyl) carbamate (5.4 g, 10 mmol) and triethylamine (2.0 g, 20 mmol) in DMF (25 mL) was added N-methyltetrahydro-2H-pyran-4-amine (or any other substituted or unsubstituted amine, 15 mmol) and the mixture was stirred at 100° C. for 14 h. After cooling down to room temperature, the mixture was diluted with EtOAc (50 mL) and washed with H$_2$O (20 mL×2), saturated NH₄Cl aqueous solution (20 mL×2) and brine (20 mL). The organic layer was dried over Na₂SO₄, filtered and concentrated. The residue was purified by chromatographic column on silicagel (petroleum ether/EtOAc=10/1 to 3/1) to give [2-(tert-butyl-dimethyl-silanyloxy)-3-(3-{4-chloro-6-[methyl-(tetrahydro-pyran-4-yl)-amino]pyrimidin-2-yl}phenoxy)propyl]methyl-carbamic acid tert-butyl ester as a white solid (5.3 g, 85% yield). ESI-LCMS (m/z): 621.3 [M+1]⁺.

Step 3: Synthesis of tert-butyl 2-(tert-butyldimethylsilyloxy)-3-(3-(4-(methyl (tetra-hydro-2H-pyran-4-yl)amino)-6-(7-(methylsulfonyl)-7H-pyrrolo[2,3-d]pyrimidin-5-yl)pyrimidin-2-yl)phenoxy)propyl (methyl)carbamate To a solution of tert-butyl 2-(tert-butyldimethylsilyloxy)-3-(3-(4-chloro-6-(methyl (tetrahydro-2H-pyran-4-yl)amino) pyrimidin-2-yl)phenoxy)propyl(methyl)carbamate (150 mg, 0.24 mmol) in dioxane (3 mL) was added 5-bromo-7-(methylsulfonyl)-7H-pyrrolo[2,3-d]pyrimidine (134 mg, 0.48 mmol), Pd(PPh₃)₄ (28 mg, 0.024 mmol) and triethylamine (48 mg, 0.48 mmol). The system was purged with N₂ stream, sealed and stirred at 120° C. for 12 h. After being cooled down to room temperature, the mixture was filtered through celite, the filtrate was concentrated and the residue was purified by preparative TLC to give tert-butyl 2-(tert-butyldimethylsilyloxy)-3-(3-(4-(methyl(tetra-hydro-2H-pyran-4-yl)amino)-6-(7-(methylsulfonyl)-7H-pyrrolo[2,3-d]pyrimidin-5-yl)pyrimidin-2-yl)phenoxy)propyl(methyl) carbamate (65 mg, 34% yield). ESI-LCMS (m/z): 781.8 [M+1]⁺.

Step 3: Synthesis of 1-(3-(4-(methyl(tetrahydro-2H-pyran-4-yl)amino)-6-(7-(methylsulfonyl)-7H-pyrrolo [2,3-d]pyrimidin-5-yl)pyrimidin-2-yl)phenoxy)-3-(methylamino)propan-2-ol A solution of tert-butyl 2-(tert-butyldimethylsilyloxy)-3-(3-(4-(methyl(tetrahydro-2H-pyran-4-yl)amino)-6-(7-(methylsulfonyl)-7H-pyrrolo [2,3-d]pyrimidin-5-yl)pyrimidin-2-yl) phenoxy)propyl(methyl)carbamate (65 mg, 0.08 mmol) in 4N HCl in dioxane (1 mL) was stirred at room temperature for 1 h, concentrated under vacuum and the residue was purified by preparative HPLC to give 1-(3-(4-(methyl(tetrahydro-2H-pyran-4-yl)amino)-6-(7-(methylsulfonyl)-7H-pyrrolo[2,3-d]pyrimidin-5-yl)pyrimidin-2-yl) phenoxy)-3-(methylamino) propan-2-ol as a formic acid salt (35 mg, 68% yield). ¹HNMR (500 MHz, CD₃OD) δ ppm: 10.06 (s, 1H), 9.07 (s, 1H), 8.66 (s, 1H), 8.55 (s, 1H), 8.12-8.08 (m, 2H), 7.45 (t, J=8.5 Hz, 1H), 7.15-7.11 (m, 2H), 4.37-4.32 (m, 1H), 4.24-4.19 (m, 1H), 4.18-4.10 (m, 3H), 3.78 (s, 3H), 3.72-3.65 (m, 2H), 3.39-3.36 (m, 1H), 3.28-3.24 (m, 2H), 3.14 (s, 3H), 2.82 (s, 3H), 2.10-2.00 (m, 2H), 1.79-1.75 (m, 2H). ESI-LCMS (m/z): 568.3 [M+1]⁺.

Example 10. Preparation of 1-(3-(6-(3,5-dimethyl-isoxazol-4-yl)-4,5'-bipyrimidin-2-yl)phenoxy)-3-(methylamino)propan-2-ol

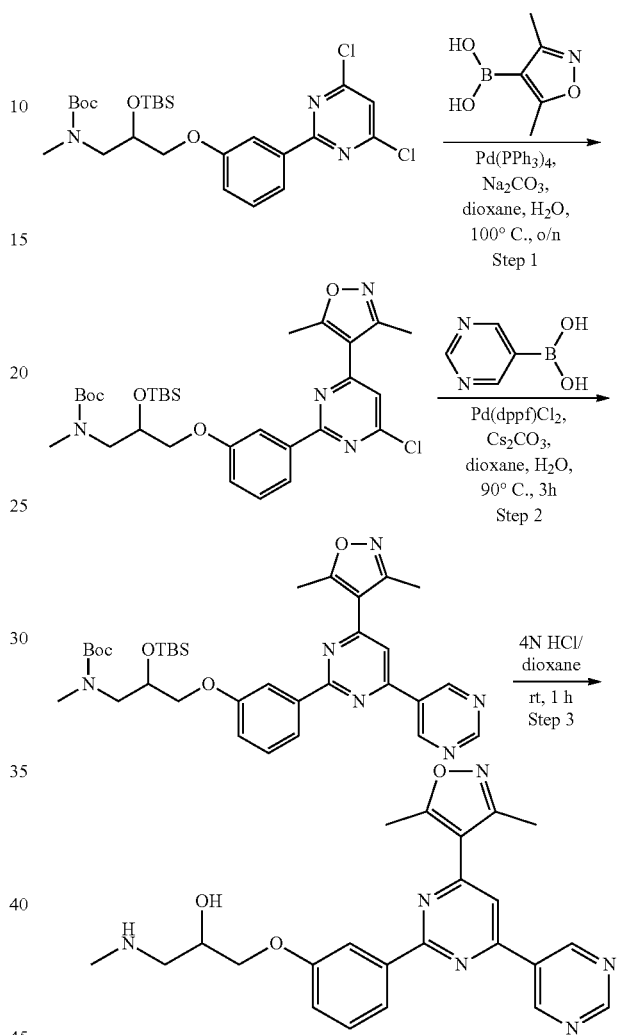

Step 1: Synthesis of tert-butyl 2-(tert-butyldimethylsilyloxy)-3-(3-(4-chloro-6-(3,5-dimethylisoxazol-4-yl)pyrimidin-2-yl)phenoxy)propyl(methyl)carbamate To a solution of tert-butyl 2-(tert-butyldi-methylsilyloxy)-3-(3-(4,6-di-chloro-pyrimidin-2-yl)phenoxy)propyl(methyl) carbamate (or any other bis-halide, 14.7 mmol) in degassed dioxane and H₂O (3/1, 150 mL) was added 3,5-dimethyl-isoxazol-4-ylboronic acid (or any other suitable boron specie, 14.7 mmol), Pd(PPh₃)₄ (853 mg, 0.74 mmol) and Na₂CO₃ (4.7 g, 44.3 mmol). The system was purged with N₂ stream and heated at 100° C. for 12 h. After being cooled down to room temperature, the mixture was diluted with water (100 mL) and extracted with EtOAc (50 mL×2). The organic layers were combined, dried over Na₂SO₄, filtered and concentrated. The residue was purified by chromatographic column on silicagel (petroleum ether/EtOAc=60/1 to 30/1) to give the tert-butyl 2-(tert-butyldimethylsilyloxy)-3-(3-(4-chloro-6-(3,5-dimethylisoxazol-4-yl)-5-methyl-pyrimidin-2-yl)phenoxy)propyl(methyl)carbamate as a white solid (4.2 g, 46% yield). ESI-LCMS (m/z): 624.9 [M+23]+.

Step 2: Synthesis of tert-butyl 2-(tert-butyldimethylsilyloxy)-3-(3-(6-(3,5-di-methylisoxazol-4-yl)-4,5'-bipyrimidin-2-yl)phenoxy)propyl(methyl)carbamate To a solution of tert-butyl 2-(tert-butyldimethylsilyloxy)-3-(3-(4-chloro-6-(3,5-dimethylisoxazol-4-yl)pyrimidin-2-yl)phenoxy)propyl(methyl)carbamate (300 mg, 0.5 mmol) in degassed dioxane and H$_2$O (10/1, 10 mL) was added pyrimidin-5-yl boronic acid (or any other boronic acid, 0.75 mmol), Pd(dppf)Cl$_2$ (40 mg, 0.05 mmol) and Cs$_2$CO$_3$ (490 mg, 1.5 mmol). The system was purged with N$_2$ stream and heated at 90° C. for 3 h. After being cooled down to room temperature, the mixture was filtered and the filtrate was concentrated. The residue was purified by chromatographic column on silicagel (petroleum ether/EtOAc=6/1 to 3/1) to give the tert-butyl 2-(tert-butyldimethylsilyloxy)-3-(3-(6-(3,5-dimethylisoxazol-4-yl)-4,5'-bipyrimidin-2-yl)phenoxy)propyl(methyl) carbamate as a white solid (100 mg, 31% yield). ESI-LCMS (m/z): 646.8 [M+H]+.

Step 3: 1-(3-(6-(3,5-dimethylisoxazol-4-yl)-4,5'-bipyrimidin-2-yl)phenoxy)-3-(methylamino) propan-2-ol The tert-butyl 2-(tert-butyldimethylsilyloxy)-3-(3-(6-(3,5-dimethylisoxazol-4-yl)-4,5'-bipyrimidin-2-yl)phenoxy)propyl(methyl)carbamate (80 mg, 0.12 mmol) was treated with a 4N HCl in dioxane (5 mL), and the mixture was stirred at room temperature for 1 h. After concentrated under vacuum, the residue was purified by preparative HPLC to give 1-(3-(6-(3,5-dimethylisoxazol-4-yl)-4,5'-bipyrimidin-2-yl)phenoxy)-3-(methylamino)propan-2-ol as a formic acid salt (white solid, 30 mg, 51% yield). $^1$HNMR (500 MHz, CD$_3$OD) δ ppm: 9.62 (s, 2H), 9.34 (s, 1H), 8.54 (brs, 1H), 8.19 (d, J=8.0 Hz, 1H), 8.14 (s, 1H), 7.98 (s, 1H), 7.48 (t, J=8.0 Hz, 1H), 7.16 (dd, J=2.5 and 8.5 Hz, 1H), 4.36-4.32 (m, 1H), 4.20-4.10 (m, 2H), 3.62 (s, 3H), 3.37-3.33 (m, 1H), 3.28-3.23 (m, 1H), 2.82 (s, 3H), 2.63 (s, 3H); ESI-LCMS (m/z): 433.1 [M+H]+.

Example 11. Preparation of 1-(3-(4-(3,5-dimethyl-isoxazol-4-yl)-5-fluoro-6-((tetrahydro-2H-pyran-4-yl)methylamino)pyrimidin-2-yl)phenoxy)-3-(methyl-amino)propan-2-ol

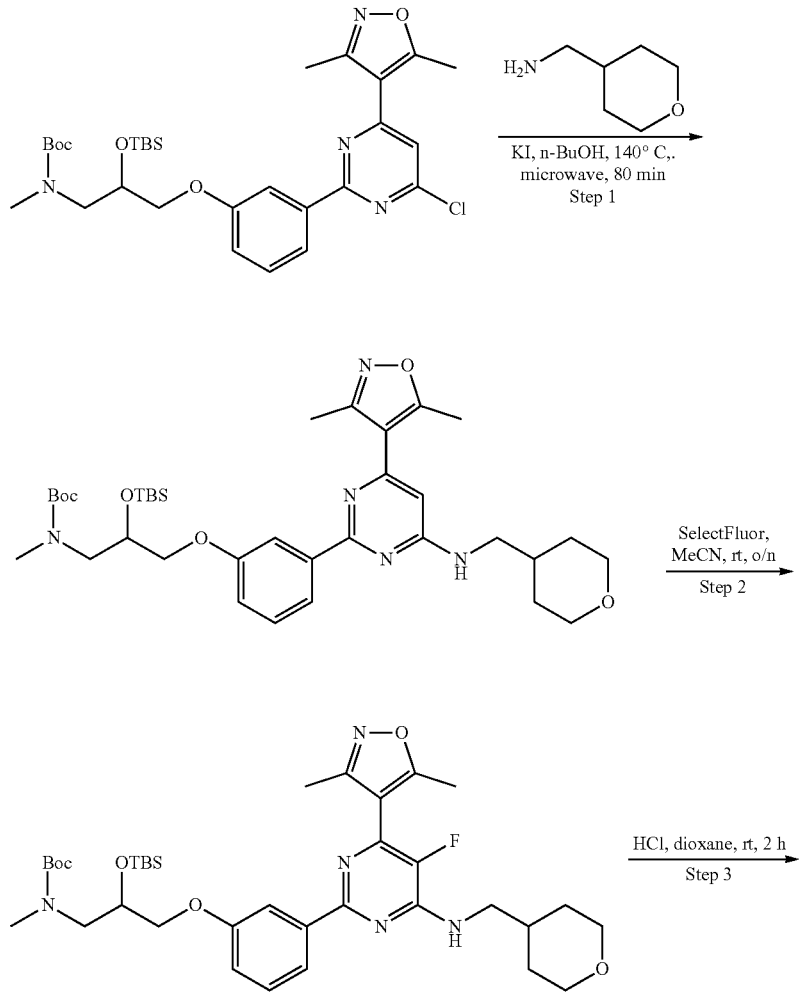

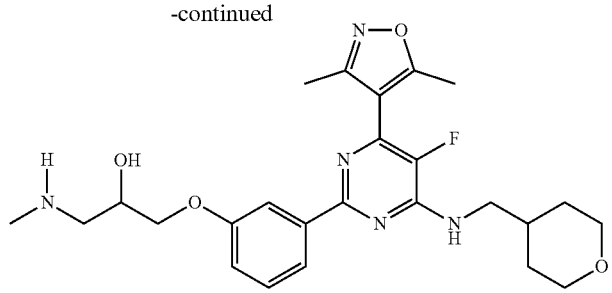

Step 1: Synthesis of tert-butyl 2-(tert-butyldimethylsilyloxy)-3-(3-(4-(3,5-di-methylisoxazol-4-yl)-6-((tetrahydro-2H-pyran-4-yl)methylamino)pyrimidin-2-yl)phenoxy)propyl(methyl) carbamate A mixture of tert-butyl 2-(tert-butyldimethylsilyloxy)-3-(3-(4-chloro-6-(3,5-di-methylisoxazol-4-yl)pyrimidin-2-yl)phenoxy)propyl(methyl)carbamate (602 mg, 1.0 mmol), (tetrahydro-2H-pyran-4-yl)methanamine (345 mg, 3.0 mmol) and KI (166 mg, 1.0 mmol) in n-BuOH (5 mL) was places in a microwave reactor and irradiated for 70 min at external temperature of 140° C. After being cooled down to room temperature, the mixture was diluted with EtOAc (30 mL), and washed with water (30 mL×2). The organic phase was dried over Na$_2$SO$_4$, filtered and concentrated. The residue was purified by chromatographic column on silicagel (petroleum ether/EtOAc=30/1 to 2/1) to give tert-butyl 2-(tert-butyldimethylsilyloxy)-3-(3-(4-(3,5-dimethylisoxazol-4-yl)-6-((tetrahydro-2H-pyran-4-yl)methylamino)pyrimidin-2-yl)phenoxy)propyl(methyl)carbamate as a white solid (560 mg, 82% yield). ESI-LCMS (m/z): 682.4 [M+1]$^+$.

Step 2: Synthesis of tert-butyl 2-(tert-butyldimethylsilyloxy)-3-(3-(4-(3,5-di-methylisoxazol-4-yl)-5-fluoro-6-((tetrahydro-2H-pyran-4-yl)methylamino)pyrimidin-2-yl)phenoxy)propyl(methyl)carbamate A solution of tert-butyl 2-(tert-butyldimethylsilyloxy)-3-(3-(4-(3,5-di-methyl-isoxazol-4-yl)-6-((tetrahydro-2H-pyran-4-yl)methylamino)pyrimidin-2-yl)phenoxy) propyl (methyl)carbamate (136 mg, 0.2 mmol) in MeCN (5 mL), stirred under N$_2$ atmosphere at room temperature was treated with neat SelectFluor (105 mg, 0.3 mmol) added slowly. The reaction mixture was further stirred at the same temperature for 12 h, diluted with EtOAc (50 mL) and washed with water (50 mL×2). The organic layer was dried over Na$_2$SO$_4$, filtered and concentrated. The residue was purified by chromatographic column on silica gel (petroleum ether/EtOAc=30/1 to 2/1) to give tert-butyl 2-(tert-butyldimethylsilyloxy)-3-(3-(4-(3,5-dimethylisoxazol-4-yl)-5-fluoro-6-((tetrahydro-2H-pyran-4-yl)methylamino) pyrimidin-2-yl) phenoxy)propyl(methyl)carbamate as a white solid (100 mg, 71% yield). ESI-LCMS (m/z): 700.4 [M+1]$^+$.

Step 3: Synthesis of (4-(3,5-dimethylisoxazol-4-yl)-5-fluoro-6-((tetrahydro-2H-pyran-4-yl)methylamino) pyrimidin-2-yl)phenoxy)-3-(methylamino)propan-2-ol tert-Butyl 2-(tert-butyldimethylsilyloxy)-3-(3-(4-(3,5-di-methylisoxazol-4-yl)-5-fluoro-6-((tetrahydro-2H-pyran-4-yl)methylamino)pyrimidin-2-yl)phenoxy)propyl (methyl) carbamate (100 mg, 0.14 mmol) was dissolved in 4N HCl solution in dioxane (4 mL) and the mixture stirred at room temperature for 2 h, concentrated under vacuum and the residue was purified by preparative HPLC to give 1-(3-(4-(3,5-dimethylisoxazol-4-yl)-5-fluoro-6-((tetrahydro-2H-pyran-4-yl) methylamino)pyrimidin-2-yl)phenoxy)-3-(methylamino)propan-2-ol as a formic acid salt (white solid, 36 mg, 48% yield). $^1$HNMR (500 MHz, CD$_3$OD) δ ppm: 8.55 (brs, 1H), 7.97 (d, J=8.0 Hz, 1H), 7.94 (s, 1H), 7.40 (t, J=8.5 Hz 1H), 7.09 (dd, J=2.0 and 8.0 Hz, 1H), 4.34-4.27 (m, 1H), 4.15-4.06 (m, 2H), 4.03-3.97 (m, 2H), 3.57 (d, J=6.5 Hz, 2H), 3.50-3.42 (m, 2H), 3.32-3.28 (m, 1H), 3.22-3.17 (m, 1H), 2.78 (s, 3H), 2.52 (s, 3H), 2.41 (s, 3H), 2.12-2.02 (m, 1H), 1.82-1.75 (d, 2H), 1.48-1.40 (m, 2H). ESI-LCMS: 486.3 [M+1]$^+$.

Example 12. Preparation of 1-(3-(5-chloro-4-(3,5-dimethylisoxazol-4-yl)-6-((tetrahydro-2H-pyran-4-yl)methylamino)pyrimidin-2-yl)phenoxy)-3-(methylamino)propan-2-ol

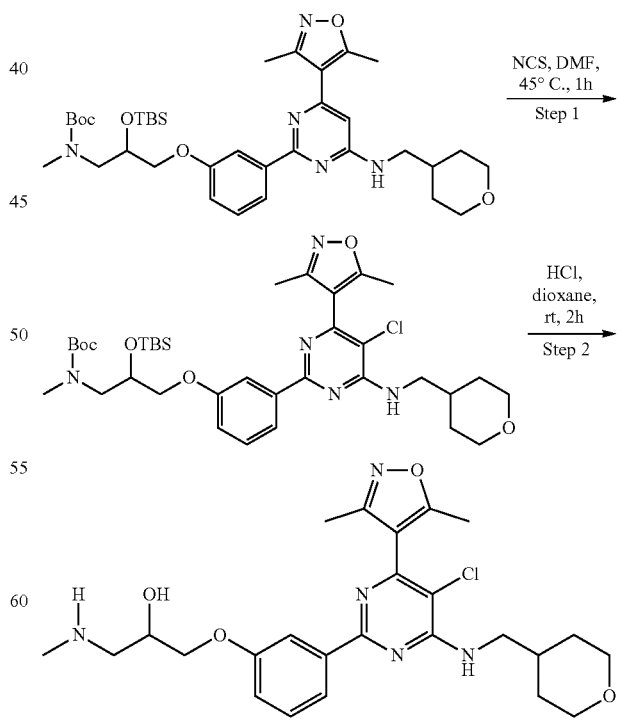

Step 1: tert-butyl 2-(tert-butyldimethylsilyloxy)-3-(3-(5-chloro-4-(3,5-dimethyl-isoxazol-4-yl)-6-((tetrahydro-2H-pyran-4-yl)methylamino)pyrimidin-2-yl) phenoxy)propyl(methyl) carbamate A solution of tert-butyl 2-(tert-butyldimethylsilyloxy)-3-(3-(4-(3,5-dimethyl-isoxazol-4-yl)-6-((tetrahydro-2H-pyran-4-yl)methylamino)pyrimidin-2-yl)phenoxy) propyl (methyl)carbamate (136 mg, 0.2 mmol) in DMF (5 mL) stirred at room temperature was treated with NCS (53 mg, 0.4 mmol) and the reaction mixture further stirred at 45° C. for 1 h; the excess of reagent was the quenched by addition of saturated $Na_2S_2O_3$ aqueous solution (2 mL) and the resulting mixture was diluted with EtOAc (20 mL), washed with water (20 mL) and brine (20 mL). The organic layer was dried over $Na_2SO_4$, filtered and concentrated. The residue was purified by chromatographic column on silicagel (petroleum ether/EtOAc=30/1 to 2/1) to give tert-butyl 2-(tert-butyldimethylsilyloxy)-3-(3-(5-chloro-4-(3,5-dimethyl-isoxazol-4-yl)-6-((tetrahydro-2H-pyran-4-yl)methylamino)pyrimidin-2-yl)phenoxy) propyl(methyl)carbamate (100 mg, 70% yield) as white solid. ESI-LCMS (m/z): 716.3 [M+1]⁺.

Step 2: Synthesis of 1-(3-(5-chloro-4-(3,5-dimethyl-isoxazol-4-yl)-6-((tetrahydro-2H-pyran-4-yl)methylamino)pyrimidin-2-yl)phenoxy)-3-(methylamino)propan-2-ol tert-Butyl 2-(tert-butyldimethylsilyloxy)-3-(3-(5-chloro-4-(3,5-dimethylisoxazol-4-yl)-6-((tetrahydro-2H-pyran-4-yl)methylamino)pyrimidin-2-yl)phenoxy)propyl (methyl) carbamate (100 mg, 0.14 mmol) was treated with 4N HCl solution in dioxane (4 mL) and the mixture was stirred at room temperature for 2 h., concentrated under vacuum and the residue was purified by preparative HPLC to give 1-(3-(5-chloro-4-(3,5-dimethylisoxazol-4-yl)-6-((tetrahydro-2H-pyran-4-yl)methylamino)pyrimidin-2-yl)phenoxy)-3-(methylamino)propan-2-ol as a formic acid salt (white solid, 36 mg, 51% yield). ¹HNMR (500 MHz, CD₃OD) δ ppm: 8.56 (s, 1H), 7.99 (d, J=8.0 Hz, 1H), 7.95 (s, 1H), 7.41 (t, J=8.0 Hz, 1H), 7.11 (dd, J=2.0 and 8.0 Hz, 1H), 4.30-4.26 (m, 1H), 4.14-4.06 (m, 2H), 4.03-3.98 (m, 2H), 3.61 (d, J=7.0 Hz, 2H), 3.47-3.42 (m, 2H), 3.30-3.27 (m, 1H), 3.22-3.16 (m, 1H), 2.77 (s, 3H), 2.44 (s, 3H), 2.31 (s, 3H), 2.12-2.08 (m, 1H), 1.80-1.75 (m, 2H), 1.50-1.40 (m, 2H); ESI-LCMS: 502.2 [M+1]⁺.

Example 13. Preparation of methyl 4-(5-chloro-2-(2-chloro-5-(2-hydroxy-3-(methylamino) propoxy) phenyl)-6-(3,5-dimethylisoxazol-4-yl)pyrimidin-4-ylamino)piperidine-1-carboxylate

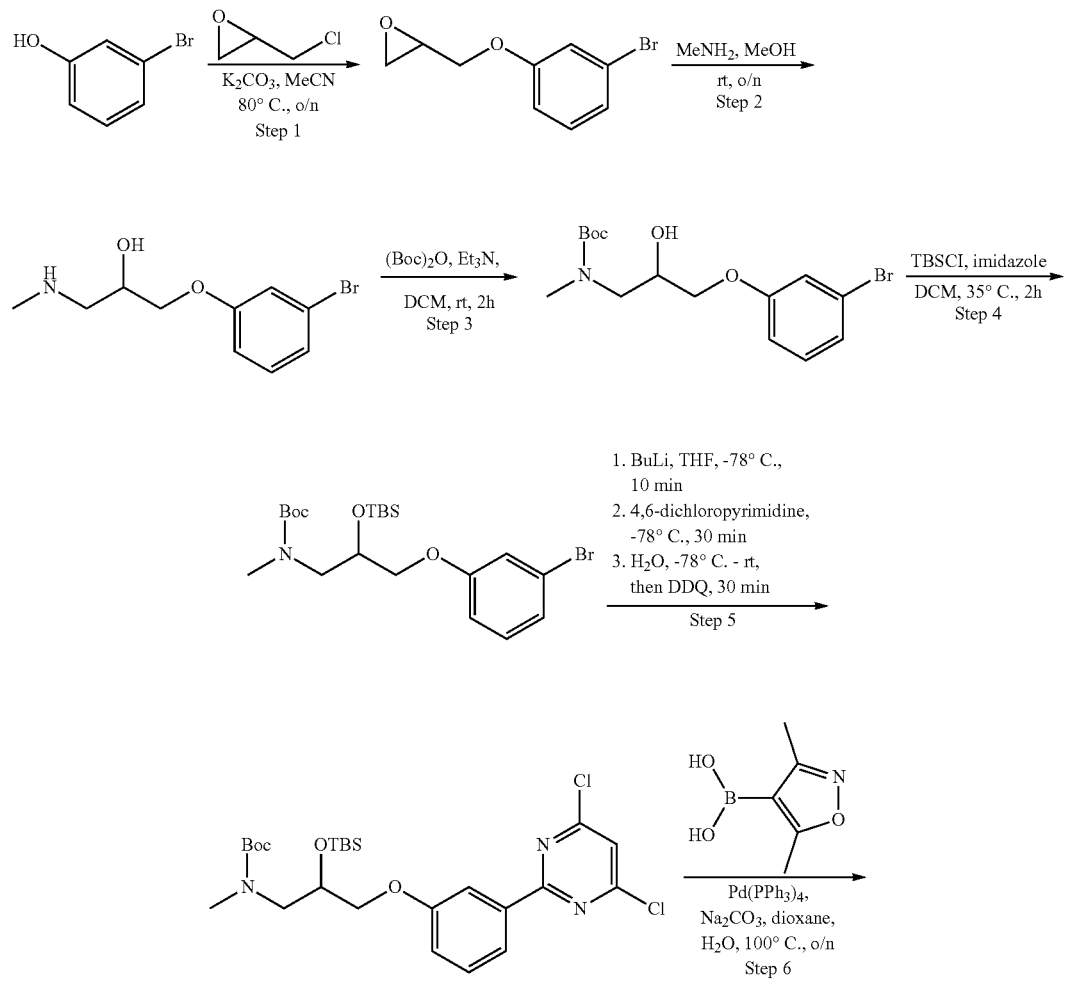

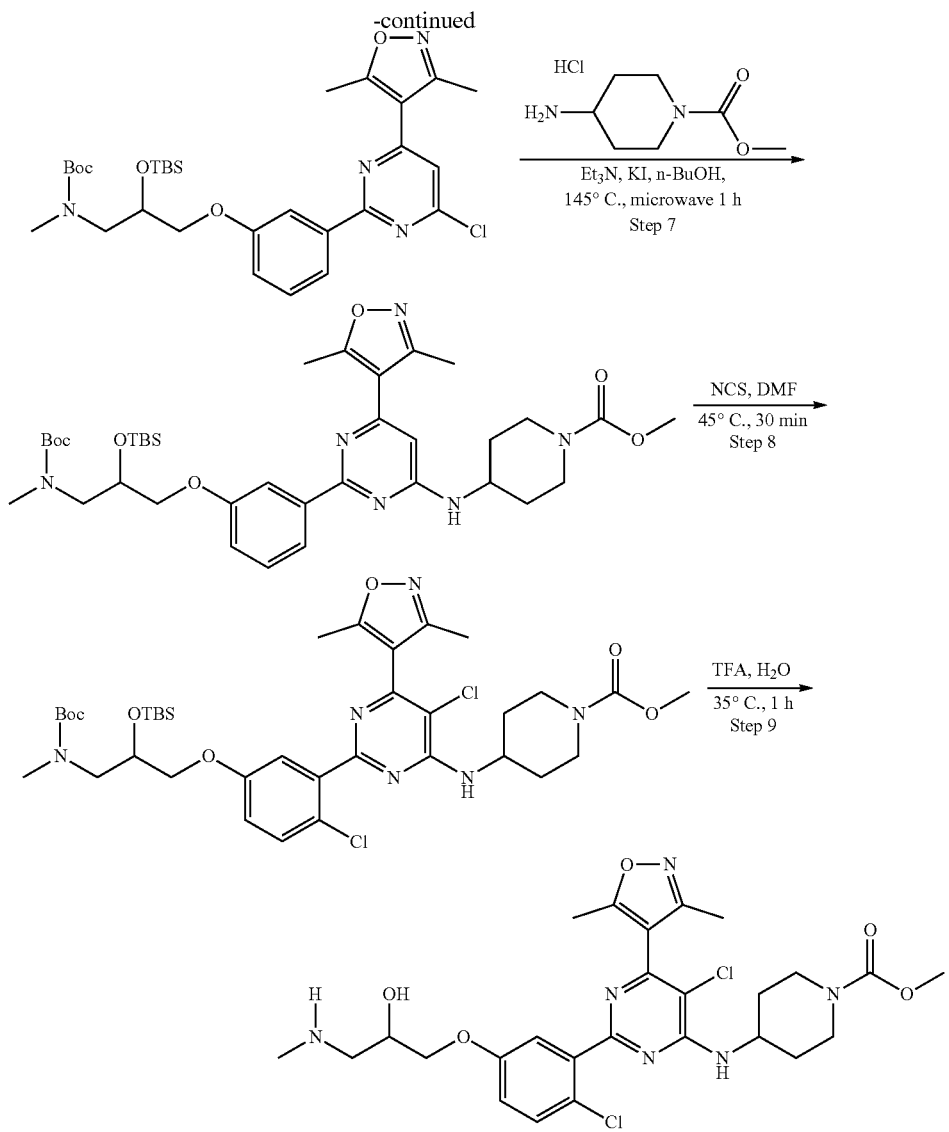

Step 1: Synthesis of 2-((3-bromophenoxy)methyl)oxirane

To a suspension of 3-bromophenol (100 g, 0.58 mol) and K₂CO₃ (240.7 g, 1.74 mol) in MeCN (1 L) was added 2-(chloromethyl)oxirane (106.98 g, 1.16 mol) slowly at room temperature and then the reaction mixture was stirred at external temperature of 80° C. for 14 h. After being cooled down to room temperature, the mixture was filtered and the filtrate was concentrated. The residue was purified by chromatographic column on silica gel (petroleum ether/EtOAc=80/1 to 60/1) to give 2-((3-bromophenoxy) methyl) oxirane (74 g, 62% yield) as colorless oil. ESI-LCMS (m/z): 228.7 [M+1]⁺.

Step 2: Synthesis of 1-(3-bromophenoxy)-3-(methylamino)propan-2-ol

To a solution of 2-((3-bromophenoxy)methyl)oxirane (56 g, 0.24 mol) in MeOH (150 mL) was added the 33% MeNH₂ solution in MeOH (150 mL) slowly at 0° C.; the mixture was then stirred at room temperature for 12 h. and finally concentrated under vacuum to give the 2-((3-bromophenoxy)methyl) oxirane (72 g, crude), which was used directly in the next step without further purification, assumed quantitative yield. ESI-LCMS (m/z): 260.1 [M+1]⁺.

Step 3: Synthesis of tert-butyl 3-(3-bromophenoxy)-2-hydroxypropyl(methyl) carbamate To a solution of 1-(3-bromophenoxy)-3-(methylamino) propan-2-ol (0.24 mol) and triethylamine (46.5 g, 0.46 mol) in DCM (1 L) was added a solution of Boc₂O (74.42 g, 0.34 mol) in DCM (100 mL) slowly at 0° C.; then the mixture was further stirred at room temperature for 3 h., washed consecutively with water (300 mL×2), saturated NH₄Cl aqueous solution (200 mL×2) and brine (300 mL×2). The organic phase was dried over Na₂SO₄, filtered and concentrated to give tert-butyl 3-(3-bromophenoxy)-2-hydroxypropyl (methyl)carbamate tert-butyl 3-(3-bromophenoxy)-2-hydroxypropyl(methyl)carbamate as a pale yellow oil, which

Step 4: Synthesis of tert-butyl 3-(3-bromophenoxy)-2-(tert-butyldimethylsilyloxy) propyl(methyl)carbamate A solution of tert-butyl 3-(3-bromophenoxy)-2-hydroxypropyl(methyl)carbamate (0.24 mol) and imidazole (33.47 g, 0.49 mol) in DCM (600 mL) stirred at 0° C. was treated with slow addition of TBSCl (73.5 g, 0.49 mol). The mixture was then stirred at 35 C° for 2 h., washed with water (300 mL×2) and brine (300 mL). The organic layer was dried over $Na_2SO_4$, filtered and concentrated. And the resulting the residue was purified by chromatographic column on silica gel (petroleum ether/EtOAc=80/1 to 60/1) to give tert-butyl 3-(3-bromo-phenoxy)-2-(tert-butyl-dimethylsilyloxy)propyl (methyl)carbamate (100 g, 86% yield) as a pale yellow oil. ESI-LCMS: 496.1 [M+23]+.

Step 5: Synthesis of tert-butyl 2-(tert-butyldimethylsilyloxy)-3-(3-(4,6-di-chloro-pyrimidin-2-yl)phenoxy)propyl(methyl)carbamate To a solution of tert-butyl 3-(3-bromophenoxy)-2-(tert-butyldimethylsilyloxy)propyl (methyl)carbamate (20 g, 42 mmol) in dry THF (30 mL) stirred at −78° C. was added n-butyl lithium (18.4 mL, 2.5 M in hexane) over 10 min., the mixture was further stirred for another 10 min. at −78° C. before 4,6-dichloro-pyrimidine (7.5 g, 50.4 mmol) in THF (10 mL) was added slowly over 10 min. The resulting mixture was stirred at same temperature for 10 min., then quenched with HOAc (4 mL) and warmed to 0° C. slowly. DDQ (13 g, 58.8 mmol) was then added portionwise and the resulting mixture was stirred at room temperature for 10 min, diluted with $CH_2Cl_2$ (100 mL) and filtered through a pad of silica gel. The filtrate was concentrated and the residue was purified chromatographic column on silicagel (petroleum ether/EtOAc=80/1) to afford tert-butyl 2-(tert-butyldi-methylsilyloxy)-3-(3-(4,6-di-chloro-pyrimidin-2-yl) phenoxy) propyl(methyl)carbamate (10.0 g, 45% yield) as a white solid. ESI-LCMS (m/z): 563.7 [M+23]+.

Step 6: Synthesis of tert-butyl 2-(tert-butyldimethylsilyloxy)-3-(3-(4-chloro-6-(3,5-dimethylisoxazol-4-yl)pyrimidin-2-yl)phenoxy)propyl(methyl)carbamate To a solution of tert-butyl 2-(tert-butyldi-methylsilyloxy)-3-(3-(4,6-di-chloro-pyrimidin-2-yl)phenoxy)propyl(methyl) carbamate (8.0 g, 14.7 mmol) in degassed mixture of dioxane and $H_2O$ (3/1, 150 mL) was added 3,5-dimethylisoxazol-4-ylboronic acid (2.09 g, 14.7 mmol), $Pd(PPh_3)_4$ (853 mg, 0.74 mmol) and $Na_2CO_3$ (4.7 g, 44.3 mmol). The system was purged with $N_2$ stream and heated at 100° C. for 12 h. After being cooled down to room temperature, the mixture was diluted with water (100 mL) and extracted with EtOAc (50 mL×2). The organic layers were combined, dried over $Na_2SO_4$, filtered and concentrated. The residue was purified by chromatographic column on silicagel (petroleum ether/EtOAc=60/1 to 30/1) to give tert-butyl 2-(tert-butyldimethylsilyloxy)-3-(3-(4-chloro-6-(3,5-dimethylisoxazol-4-yl)-5-methyl-pyrimidin-2-yl)phenoxy)propyl(methyl)carbamate as a white solid (4.2 g, 46% yield). ESI-LCMS: 624.9 [M+23]+.

Step 7: Synthesis of methyl 4-(2-(3-(3-(tert-butoxycarbonyl(methyl)amino)-2-(tert-butyldimethylsilyloxy)propoxy)phenyl)-6-(3,5-dimethylisoxazol-4-yl)pyrimidin-4-ylamino)piperidine-1-carboxylate A solution of tert-butyl 2-(tert-butyldimethylsilyloxy)-3-(3-(4-chloro-6-(3,5-di-methylisoxazol-4-yl)-5-methylpyrimidin-2-yl)phenoxy)propyl(methyl)carbamate (100 mg, 0.16 mmol), methyl 4-aminopiperidine-1-carboxylate hydrochloride (130 mg, 0.66 mmol), triethylamine (67 mg, 0.66 mmol) and KI (15 mg, 0.083 mmol) in DMSO (2 mL) was placed in a microwave reactor, the temperature was set at 145° C. and irradiated for 1 h. After being cooled down to room temperature, the mixture was diluted with EtOAc (30 mL), washed with water (6 mL×2) and brine (6 mL). The organic layer was dried over $Na_2SO_4$, filtered and concentrated. The residue was purified by preparative TLC (petroleum ether/EtOAc=1.5/1) to obtain methyl 4-(2-(3-(3-(tert-butoxycarbonyl(methyl) amino)-2-(tert-butyl-dimethylsilyloxy) propoxy) phenyl)-6-(3, 5-dimethylisoxazol-4-yl)-5-methyl-pyrimidin-4-ylamino) piperidine-1-carboxylate (96 mg, 80% yield) as a pale yellow solid. ESI-LCMS: 725.0 [M+1].

Step 8: Synthesis of methyl 4-(2-(5-(3-(tert-butoxycarbonyl(methyl)amino)-2-(tert-butyldimethylsilyloxy)propoxy)-2-chlorophenyl)-5-chloro-6-(3,5-dimethyl-isoxazol-4-yl)pyrimidin-4-ylamino)piperidine-1-carboxylate A solution of methyl 4-(2-(3-(3-(tert-butoxycarbonyl (methyl) amino)-2-(tert-butyl-dimethylsilyloxy)propoxy) phenyl)-6-(3,5-dimethylisoxazol-4-yl)-5-methylpyrimidin-4-ylamino) piperidine-1-carboxylate (96 mg, 0.13 mmol) in DMF (3 mL) stirred at room temperature was treated with NCS (35 mg, 0.26 mmol) solution in 0.5 mL of DMF. The mixture was stirred at 45° C. for 30 min., and then cooled to room temperature, diluted with EtOAc (30 mL), washed consecutively with water (10 mL×2), saturated $Na_2S_2O_3$ aqueous solution (10 mL) and brine (10 mL). The organic layer was dried over $Na_2SO_4$, filtered and concentrated. The residue was purified by preparative TLC (petroleum ether/EtOAc=1.5/1) to obtain then methyl 4-(2-(5-(3-(tert-butoxycarbonyl (methyl)amino)-2-hydroxypropoxy)-2-chlorophenyl)-5-chloro-6-(3,5-dimethylisoxazol-4-yl)pyrimidin-4-ylamino) piperidine-1-carboxylate (84 mg, 80% yield) as a pale yellow solid. ESI-LCMS: 792.7 [M+1]+

Step 9: Synthesis of methyl 4-(5-chloro-2-(2-chloro-5-(2-hydroxy-3-(methylamino) propoxy)phenyl)-6-(3,5-dimethylisoxazol-4-yl)pyrimidin-4-ylamino)piperidine-1-carboxylate A solution of methyl 4-(2-(5-(3-(tert-butoxycarbonyl (methyl)amino)-2-(tert-butyl-dimethyl-silyloxy)propoxy)-2-chlorophenyl)-5-chloro-6-(3,5-dimethylisoxazol-4-yl)pyrimidin-4-ylamino) piperidine-1-carboxylate (84 mg, 0.11 mmol) in 90% TFA aqueous solution (2 mL) was stirred at 35° C. for 1 h., concentrated under vacuum, the residue was dissolved in MeOH (5 mL) and the pH adjusted to 9 with saturated aqueous $K_2CO_3$ solution. The mixture was filtered and the filtrate was concentrated. The residue was purified by preparative HPLC to give methyl 4-(5-chloro-2-(2-chloro-5-(2-hydroxy-3-(methylamino)propoxy)phenyl)-6-(3,5-di-methylisoxazol-4-yl) pyrimidin-4-ylamino)piperidine-1-carboxylate as a formic acid salt (white solid, 25 mg, 37% yield). $^1$HNMR (500 MHz, MeOD) δ ppm: 8.60 (brs, 1H), 7.42 (d, J=9.0 Hz, 1H), 7.28 (d, J=3.0 Hz, 1H), 7.06 (dd, J=3.0 and 8.0 Hz, 1H), 4.42-4.36 (m, 1H), 4.25-4.12 (m, 3H), 4.10-4.02 (m, 2H), 3.70 (s, 3H), 3.23-3.18 (m, 1H), 3.14-3.07 (m, 1H), 3.04-2.90 (m, 2H), 2.71 (s, 3H), 2.42 (s, 3H), 2.27 (s, 3H), 2.08-2.02 (m, 2H), 1.70-1.58 (m, 2H); ESI-LCMS: 578.8 [M+1]+.

was used directly in next step without further purification, assumed quantitative yield. ESI-LCMS (m/z): 382.1 [M+23]+.

Example 14. Preparation of 1-(3-(4-(3,5-dimethyl-isoxazol-4-yl)-5-(hydroxymethyl)-6-(tetrahydro-2H-pyran-4-ylamino)pyrimidin-2-yl)phenoxy)-3-(methylamino)propan-2-ol

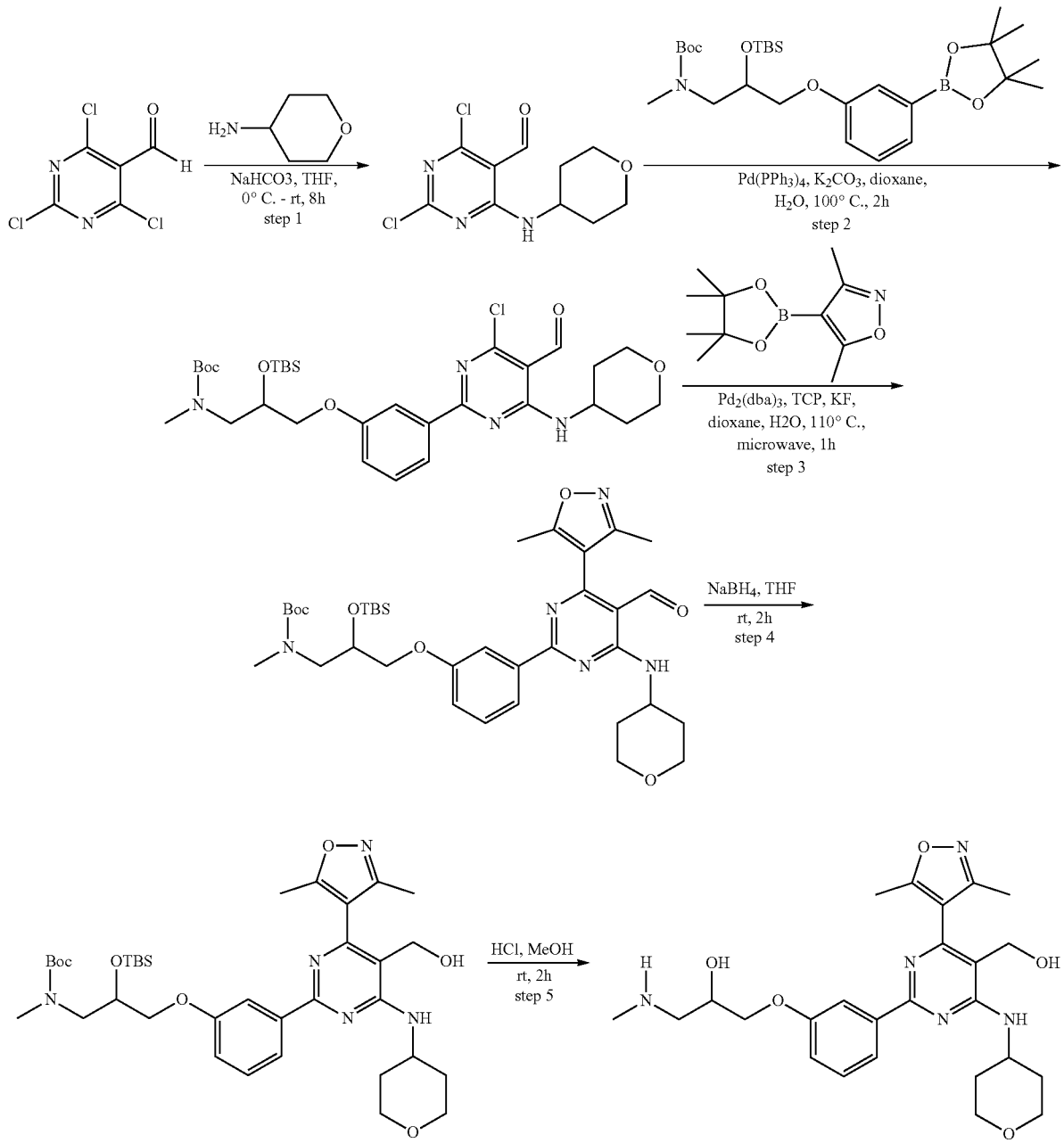

Step 1: Synthesis of 2,4-dichloro-6-(tetrahydro-2H-pyran-4-ylamino)pyrimidine-5-carbaldehyde and 4,6-dichloro-2-(tetrahydro-2H-pyran-4-ylamino)pyrimidine-5-carbaldehyde To a mixture of 2,4,6-trichloropyrimidine-5-carbaldehyde (1.5 g, 7.2 mmol) and NaHCO$_3$ (0.91 g, 10 mmol) in THF (100 mL) was added tetrahydro-2H-pyran-4-amine (0.73 g, 7.2 mmol) slowly at 0° C. The mixture was warmed up to room temperature and stirred for 8 h. The reaction mixture was filtered and the filtrate was concentrated. The residue was purified by chromatographic column on silicagel (petroleum ether/EtOAc=10/1 to 1/1) to give 2,4-dichloro-6-(tetrahydro-2H-pyran-4-ylamino) pyrimidine-5-carbaldehyde (1.0 g, 51% yield) as major product. The minor isomer 4,6-dichloro-2-(tetrahydro-2H-pyran-4-ylamino)pyrimidine-5-carbaldehyde (400 mg, 21% yield) was also obtained. ESI-LCMS (m/z): 276.0 [M+1]$^+$.

Step 2: Synthesis of tert-butyl 2-(tert-butyldimethylsilyloxy)-3-(3-(4-chloro-5-formyl-6-(tetrahydro-2H-pyran-4-ylamino)pyrimidin-2-yl)phenoxy)propyl (methyl)carbamate To a solution of 2,4-dichloro-6-(tetrahydro-2H-pyran-4-ylamino)pyrimidine-5-carbaldehyde (0.4 g, 1.4 mmol) in degassed dioxane and H$_2$O (10/1, 25 mL) was added tert-butyl 2-(tert-butyldimethylsilyloxy)-3-(3-(4,4,5,5-tetramethyl-1,3,2-dioxa-borolan-2-yl)phenoxy)propyl (methyl) carbamate (830 mg, 1.6 mmol), K$_2$CO$_3$ (600 mg, 4.35 mmol) and Pd(PPh$_3$)$_4$ (83 mg, 0.07 mmol). The system was purged with N$_2$ stream and the mixture was stirred at 100° C. for 2 h. After being cooled down to room temperature, the reaction mixture was diluted with water (50 mL) and extracted with EtOAc (50 mL×2). The organic layers were combined, dried over Na$_2$SO$_4$, filtered and concentrated. The residue was purified by chromatographic column on silicagel (petroleum ether/EtOAc=5/1 to 1/1) to afford the tert-butyl 2-(tert-butyldimethyl silyloxy)-3-(3-(4-chloro-5-formyl-6-(tetrahydro-2H-pyran-4-ylamino)pyrimidin-2-yl) phenoxy) propyl(methyl)carbamate (710 mg, 77% yield) as major product. ESI-LCMS (m/z): 635.0 [M+1]$^+$.

Step 3: Synthesis of tert-butyl 2-(tert-butyldimethylsilyloxy)-3-(3-(4-(3,5-dimethyl-isoxazol-4-yl)-5-formyl-6-(tetrahydro-2H-pyran-4-ylamino)pyrimidin-2-yl)phenoxy)propyl (methyl)carbamate To a solution of tert-butyl 2-(tert-butyldimethylsilyloxy)-3-(3-(4-chloro-5-formyl-6-(tetrahydro-2H-pyran-4-ylamino)pyrimidin-2-yl)phenoxy)propyl(methyl)carbamate (600 mg, 0.95 mmol) in degassed dioxane and H$_2$O (10/1, 50 mL) was added Pd$_2$(dba)$_3$ (92 mg, 0.10 mmol), tricyclohexylphosphine (80 mg, 0.30 mmol), KF (18 mg, 0.30 mmol) and 3,5-dimethyl-4-(4,4,5,5-tetramethyl-1,3,2-dioxaborolan-2-yl) isoxazole (255 mg, 1.1 mmol). The system was purged with N$_2$ stream, placed in a microwave reactor and irradiated for 1 h at 110° C. After being cooled down to room temperature, the mixture was diluted with water (25 mL) and extracted with EtOAc (25 mL×2). The organic layers were combined, dried over Na$_2$SO$_4$, filtered and concentrated. The residue was purified by chromatographic column on silicagel (petroleum ether/EtOAc=5/1 to 1/1) to give tert-butyl 2-(tert-butyldimethylsilyloxy)-3-(3-(4-(3,5-dimethyl-isoxazol-4-yl)-5-formyl-6-(tetrahydro-2H-pyran-4-ylamino)pyrimidin-2-yl)phenoxy) propyl(methyl)carbamate (530 mg, 80% yield). ESI-LCMS (m/z): 696.0 [M+1]$^+$.

Step 4: tert-butyl 2-(tert-butyldimethylsilyloxy)-3-(3-(4-(3,5-dimethylisoxazol-4-yl)-5-(hydroxymethyl)-6-(tetrahydro-2H-pyran-4-ylamino)pyrimidin-2-yl)phenoxy)propyl (methyl)carbamate A solution of tert-butyl 2-(tert-butyldimethylsilyloxy)-3-(3-(4-(3,5-dimethylisoxazol-4-yl)-5-formyl-6-(tetrahydro-2H-pyran-4-ylamino)pyrimidin-2-yl)phenoxy)propyl (methyl)carbamate (200 mg, 0.29 mmol) in THF (10 mL) was treated with NaBH$_4$ (25 mg, 0.6 mmol) and the mixture stirred at room temperature for 2 h, concentrated under vacuum and the resulting residue was purified by preparative TLC to give tert-butyl 2-(tert-butyldimethylsilyloxy)-3-(3-(4-(3,5-dimethyl-isoxazol-4-yl)-5-(hydroxymethyl)-6-(tetrahydro-2H-pyran-4-ylamino)pyrimidin-2-yl)phenoxy)propyl(methyl)carbamate (180 mg, 91% yield). ESI-LCMS: 698.0 [M+1]$^+$.

Step 5: Synthesis of 1-(3-(4-(3,5-dimethylisoxazol-4-yl)-5-(hydroxymethyl)-6-(tetra-hydro-2H-pyran-4-ylamino)pyrimidin-2-yl)phenoxy)-3-(methylamino)propan-2-ol tert-Butyl 2-(tert-butyldimethylsilyloxy)-3-(3-(4-(3,5-dimethylisoxazol-4-yl)-5-(hydroxymethyl)-6-(tetrahydro-2H-pyran-4-ylamino)pyrimidin-2-yl)phenoxy)propyl(methyl)carbamate (80 mg, 0.11 mmol) was dissolved in a 2.5 N HCl solution in methanol (10 mL), and the mixture was stirred at room temperature for 2 h., concentrated under vacuum and purified by preparative HPLC to give 1-(3-(4-(3,5-dimethylisoxazol-4-yl)-5-(hydroxymethyl)-6-(tetrahydro-2H-pyran-4-yl-amino)pyrimidin-2-yl)phenoxy)-3-(methylamino)propan-2-ol as a TFA salt (34 mg, 51% yield). $^1$HNMR (500 MHz, CD$_3$OD) δ ppm: 7.43-7.40 (t, J=8.0 Hz, 1H), 7.18-7.10 (m, 3H), 4.46 (s, 2H), 4.43-4.38 (m, 1H), 4.22-4.18 (m, 2H), 4.03-3.96 (m, 2H), 3.93-3.89 (m, 2H), 3.50-3.45 (m, 2H), 3.20-3.06 (m, 1H), 2.66 (s, 3H), 2.60 (s, 3H), 2.41 (s, 3H), 1.95-1.91 (m, 2H), 1.72-1.64 (m, 2H); LCMS: 484.0 [M+H]$^+$.

Example 15. Preparation of 1-(3-(5-(difluoromethyl)-4-(3,5-dimethylisoxazol-4-yl)-6-(tetra-hydro-2H-pyran-4-ylamino)pyrimidin-2-yl)phenoxy)-3-(methylamino)propan-2-ol

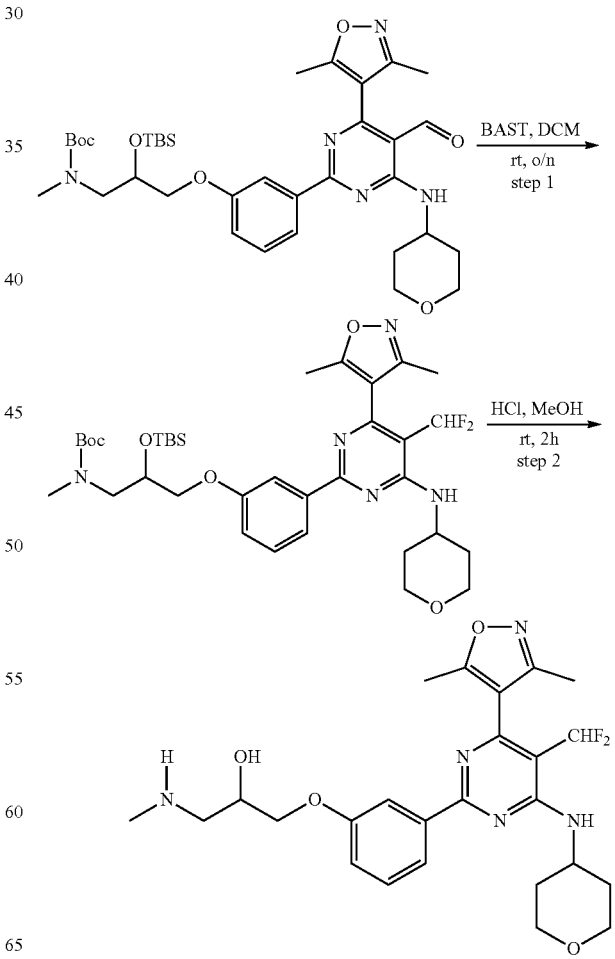

Step 1: tert-butyl 2-(tert-butyldimethylsilyloxy)-3-(3-(5-(difluoromethyl)-4-(3,5-dimethylisoxazol-4-yl)-6-(tetrahydro-2H-pyran-4-ylamino)pyrimidin-2-yl) phenoxy)propyl(methyl)carbamate tert-butyl 2-(tert-butyldimethylsilyloxy)-3-(3-(4-(3,5-dimethylisoxazol-4-yl)-5-formyl-6-(tetrahydro-2H-pyran-4-ylamino)pyrimidin-2-yl)phenoxy)propyl(methyl) carbamate (200 mg, 0.29 mmol) was treated with bis-(2-methoxyethyl) aminosulfur trifluoride (BAST, 5 mL, excess) and the mixture was stirred at room temperature for 12 h, excess of reagent quenched by pouring the mixture into ice water (50 mL) and extracted with DCM (25 mL×2). The combined organic layers were dried over $Na_2SO_4$, filtered and concentrated. The residue was purified by chromatographic column on silicagel (petroleum ether/EtOAc=20/1 to 8/1) to give tert-butyl 2-(tert-butyldimethylsilyloxy)-3-(3-(5-(difluoromethyl)-4-(3,5-dimethylisoxazol-4-yl)-6-(tetrahydro-2H-pyran-4-ylamino) pyrimidin-2-yl)phenoxy)propyl (methyl)carbamate (35 mg, 18% yield). ESI-LCMS (m/z): 718 $[M+1]^+$.

Step 2: Synthesis of 1-(3-(5-(difluoromethyl)-4-(3,5-dimethylisoxazol-4-yl)-6-(tetrahydro-2H-pyran-4-ylamino)pyrimidin-2-yl)phenoxy)-3-(methylamino) propan-2-ol tert-Butyl 2-(tert-butyldimethylsilyloxy)-3-(3-(5-(difluoromethyl)-4-(3,5-di-methylisoxazol-4-yl)-6-(tetrahydro-2H-pyran-4-ylamino)pyrimidin-2-yl)phenoxy)propyl (methyl)carbamate (35 mg, 0.05 mmol) was treated with 2.5 N HCl solution in methanol (10 mL), and the mixture was stirred at room temperature for 2 h., concentrated under vacuum and the resulting residue purified by preparative HPLC to give 1-(3-(5-(difluoromethyl)-4-(3,5-dimethylisoxazol-4-yl)-6-(tetrahydro-2H-pyran-4-ylamino)pyrimidin-2-yl)phenoxy)-3-(methylamino)propan-2-ol as a TFA salt (18 mg, 62% yield). $^1$HNMR (500 MHz, $CD_3OD$) δ ppm: 7.37-7.34 (m, 1H), 7.08-7.02 (m, 3H), 6.74-6.53 (t, J=53.0 Hz, 1H), 4.41-4.36 (m, 1H), 4.21-4.16 (m, 2H), 4.02-3.90 (m, 4H), 3.47-3.43 (m, 2H), 3.20-3.06 (m, 1H), 2.68 (s, 3H), 2.66 (s, 3H), 2.46 (s, 3H), 1.94-1.91 (m, 2H), 1.65-1.59 (m, 2H); LCMS: 504 $[M+H]^+$.

Example 16. Preparation of 6-(3,5-Dimethyl-isoxazol-4-yl)-2-[3-(2-hydroxy-3-methylamino-propoxy) phenyl]pyrimidine-4-carboxylic acid (tetrahydro-pyran-4-ylmethyl)-amide

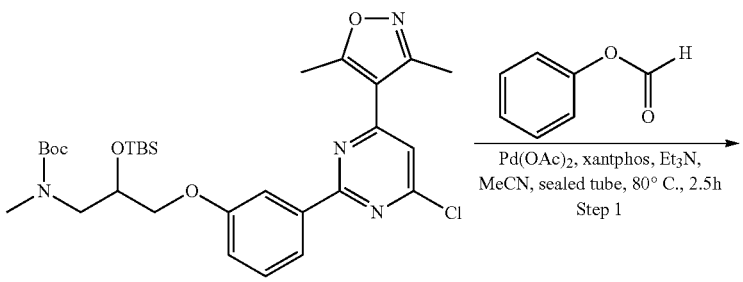

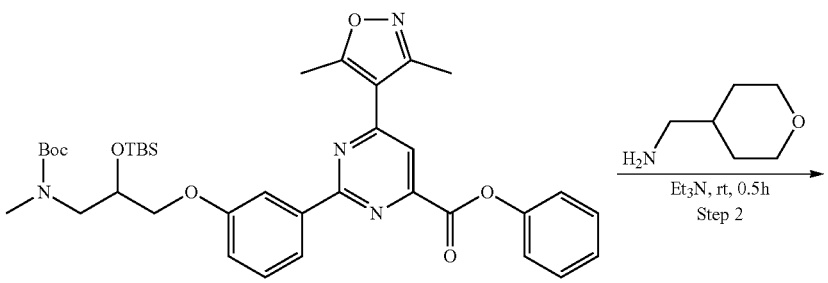

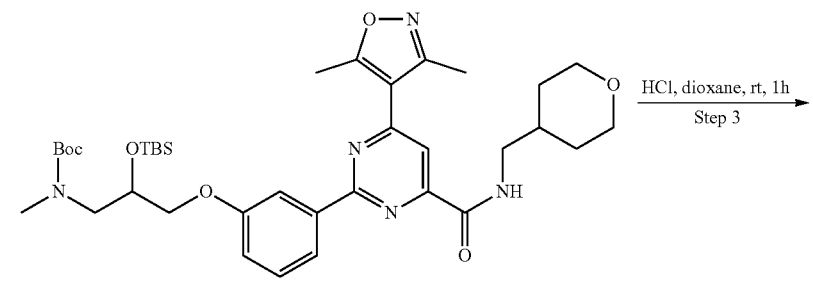

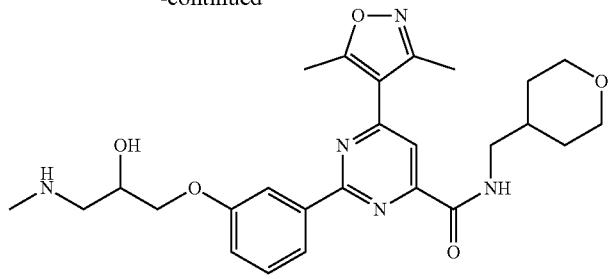

-continued

Step 1: Synthesis of phenyl 2-(3-(3-(tert-butoxycarbonyl(methyl)amino)-2-(tert-butyldimethylsilyloxy)propoxy)phenyl)-6-(3,5-dimethylisoxazol-4-yl)pyrimidine-4-carboxylate To a solution of tert-butyl 2-(tert-butyldimethylsilyloxy)-3-(3-(4-chloro-6-(3,5-dimethylisoxazol-4-yl)pyrimidin-2-yl)phenoxy)propyl(methyl)carb amate (122 mg, 0.20 mmol) in degassed MeCN (5 mL) was added phenyl formate (37 mg, 0.30 mmol), xantphos (2 mg, 0.002 mmol), Pd(OAc)$_2$ (2 mg, 0.006 mmol) and Et$_3$N (1 mL). The system was purged with N$_2$ stream, the reaction vessel was sealed and the mixture was stirred at 80° C. for 2.5 h. After being cooled down to room temperature, the mixture was filtered through a pad of Celite and concentrated to give phenyl 2-(3-(3-(tert-butoxycarbonyl(methyl) amino)-2-(tert-butyldimethylsilyloxy)propoxy) phenyl)-6-(3,5-dimethylisoxazol-4-yl) pyrimidine-4-carboxylate, which was used for next reaction without further purification. Quantitative yield. ESI-LCMS (m/z): 689.0 [M+1]$^+$.

Step 2: Synthesis of tert-butyl 2-(tert-butyldimethylsilyloxy)-3-(3-(4-(3,5-di-methylisoxazol-4-yl)-6-((tetrahydro-2H-pyran-4-yl)methylcarbamoyl)pyrimidin-2-yl)phenoxy)propyl (methyl) carbamate A solution of phenyl 2-(3-(3-(tert-butoxycarbonyl (methyl)amino)-2-(tert-butyl-dimethyl silyloxy)propoxy) phenyl)-6-(3,5-dimethylisoxazol-4-yl)pyrimidine-4-carboxylate (0.2 mmol) in MeCN (3 mL) stirred at room temperature was treated with (tetrahydro-2H-pyran-4-yl) methanamine (30 mg, 0.34 mmol) and Et$_3$N (1 mL). The mixture was further stirred at room temperature for 0.5 h., concentrated and the residue was purified by preparative TLC to give tert-butyl 2-(tert-butyldimethyl-silyloxy)-3-(3-(4-(3,5-dimethylisoxazol-4-yl)-6-((tetrahydro-2H-pyran-4-yl)methyl-carbamoyl)pyrimidin-2-yl)phenoxy)propyl (methyl)carbamate (80 mg, 55% yield for 2 steps). ESI-LCMS (m/z): 710.3 [M+1]$^+$.

Step 3: Synthesis of 6-(3,5-dimethylisoxazol-4-yl)-2-(3-(2-hydroxy-3-(methyl-amino)propoxy)phenyl)-N-((tetrahydro-2H-pyran-4-yl)methyl)pyrimidine-4-carboxamide A solution of tert-butyl 2-(tert-butyldimethylsilyloxy)-3-(3-(4-(3,5-dimethyl-isoxazol-4-yl)-6-((tetrahydro-2H-pyran-4-yl)methylcarbamoyl)pyrimidin-2-yl)phenoxy)propyl(methyl)carbamate (80 mg, 0.11 mmol) in MeOH (3 mL) was treated with 4N HCl in dioxane (1 mL), and the mixture was stirred at room temperature for 1 h., concentrated and the residue was dissolved in MeOH (5 mL) and treated with saturated K$_2$CO$_3$ aqueous solution till pH=9. The mixture was filtered, the filtrate was concentrated and the residue was purified by preparative HPLC to give 6-(3,5-dimethyl-isoxazol-4-yl)-2-(3-(2-hydroxy-3-(methyl-amino)propoxy) phenyl)-N-((tetrahydro-2H-pyran-4-yl)methyl)pyrimidine-4-carboxamide as a formic acid salt (white solid, 11 mg, 20% yield). $^1$HNMR (500 MHz, CD$_3$OD) δ ppm: 9.21 (brs, 1H), 8.26 (d, J=7.5 Hz, 1H), 8.17 (s, 1H), 8.04 (d, J=3.5 Hz, 1H), 7.49 (t, J=7.5 Hz, 1H), 7.19 (d, J=8.0 Hz, 1H), 4.36-4.30 (m, 1H), 4.22-4.14 (m, 2H), 4.02-3.98 (m, 2H), 3.50-3.42 (m, 4H), 3.40-3.34 (m, 1H), 3.27-3.22 (m, 1H), 2.81 (s, 6H), 2.62 (s, 3H), 2.06-1.97 (m, 1H), 1.78-1.70 (m, 2H), 1.48-1.38 (m, 2H); ESI-LCMS (m/z): 396.3 [M+1]$^+$.

Example 17. Preparation of 1-(3-(4-(3,5-dimethyl-isoxazol-4-yl)-5-methyl-6-((tetrahydro-2H-pyran-4-yl)methoxy)pyrimidin-2-yl)phenoxy)-3-(methyl-amino)propan-2-ol

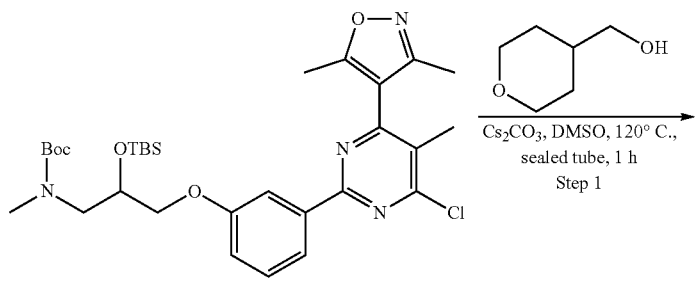

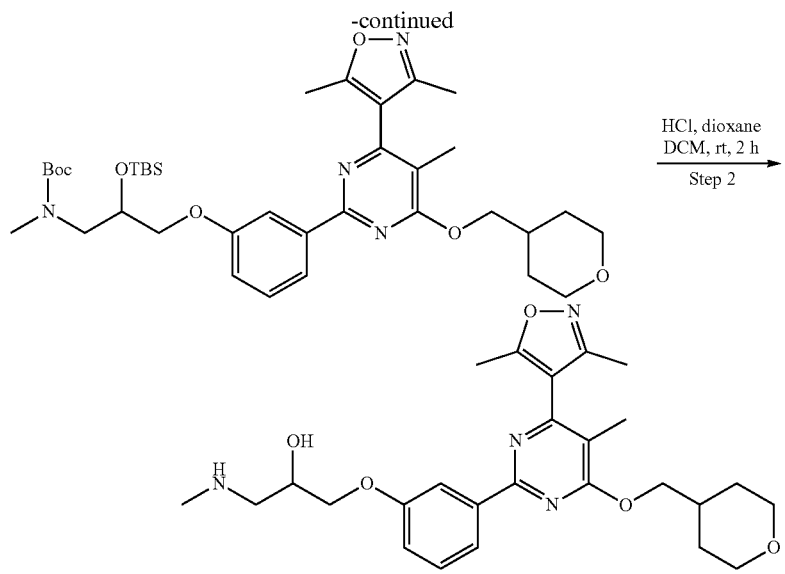

Step 1: Synthesis of tert-butyl 2-(tert-butyldimethylsilyloxy)-3-(3-(4-(3,5-di-methylisoxazol-4-yl)-5-methyl-6-((tetrahydro-2H-pyran-4-yl)methoxy)pyrimidin-2-yl)phenoxy)propyl (methyl) carbamate A mixture of tert-butyl 2-(tert-butyldimethylsilyloxy)-3-(3-(4-chloro-6-(3,5-dimethylisoxazol-4-yl)-5-methylpyrimidin-2-yl)phenoxy)propyl(methyl)carbamate (0.41 mmol), (tetrahydro-2H-pyran-4-yl)methanol (or any other alcohol or thiol, 0.81 mmol) and $Cs_2CO_3$ (330 mg, 1.01 mmol) in DMSO (5 mL) was stirred at 120° C. for 1 h in a sealed tube. After being cooled down to room temperature, the mixture was diluted with EtOAc (50 mL) and washed with water (30 mL×3) followed by brine (50 mL). The organic phase was dried over $Na_2SO_4$, filtered and concentrated. The residue was purified by automated chromatographic column eluted with 0% to 50% EtOAc/petroleum ether, 40 mL/min, to give tert-butyl 2-(tert-butyldimethylsilyloxy)-3-(3-(4-(3,5-dimethylisoxazol-4-yl)-5-methyl-6-((tetra-hydro-2H-pyran-4-yl)methoxy)pyrimidin-2-yl)phenoxy)propyl(methyl)carbamate as a yellow solid (170 mg, 60% yield). ESI-LCMS (m/z): 697.0 [M+1]$^+$.

Step 2: Synthesis of 1-(3-(4-(3,5-dimethylisoxazol-4-yl)-5-methyl-6-((tetrahydro-2H-pyran-4-yl)methoxy)pyrimidin-2-yl)phenoxy)-3-(methylamino)propan-2-ol A solution of tert-butyl 2-(tert-butyldimethylsilyloxy)-3-(3-(4-(3,5-dimethyl-isoxazol-4-yl)-5-methyl-6-((tetrahydro-2H-pyran-4-yl)methoxy)pyrimidin-2-yl) phenoxy)propyl (methyl) carbamate (160 mg, 0.24 mmol) in DCM (6 mL) was treated with 4N HCl solution in dioxane (2 mL) and the mixture was stirred at room temperature for 2 h., concentrated and the residue was dissolved in MeOH (5 mL) and treated with saturated $NaHCO_3$ aqueous solution till pH=8. The mixture was concentrated under vacuum and the residue was purified by preparative HPLC to give 1-(3-(4-(3, 5-dimethylisoxazol-4-yl)-5-methyl-6-((tetrahydro-2H-pyran-4-yl)methoxy) pyrimidin-2-yl)phenoxy)-3-(methylamino)propan-2-ol as a formic acid salt (white solid, 97 mg, 75% yield). $^1$HNMR (500 MHz, CD3OD) δ ppm: 8.56 (brs, 1H), 8.04 (d, J=8.0 Hz, 1H), 7.99 (s, 1H), 7.43 (t, J=8.0 Hz, 1H), 7.12 (dd, J=8.0 and 2.0 Hz, 1H), 4.49 (d, J=6.5 Hz, 2H), 4.29-4.25 (m, 1H), 4.15-4.06 (m, 2H), 4.05-4.00 (m, 2H), 3.56-3.49 (m, 2H), 3.29-3.25 (m, 1H), 3.18-3.14 (m, 1H), 2.75 (s, 3H), 2.39 (s, 3H), 2.28 (s, 3H), 2.26-2.23 (m, 1H), 2.14 (s, 3H), 1.86-1.82 (m, 2H), 1.62-1.52 (m, 2H). ESI-LCMS: 483.0 (M+1)$^+$.

Example 18. Preparation of 1-(3-(4-(5-cyclopropyl-3-methylisoxazol-4-yl)-5-methyl-6-(tetrahydro-2H-pyran-4-ylamino)pyrimidin-2-yl)phenoxy)-3-(methylamino)propan-2-ol (a)

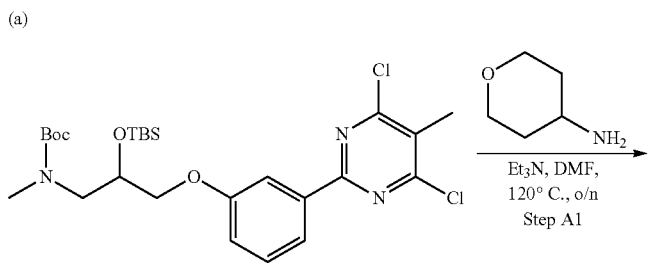

-continued
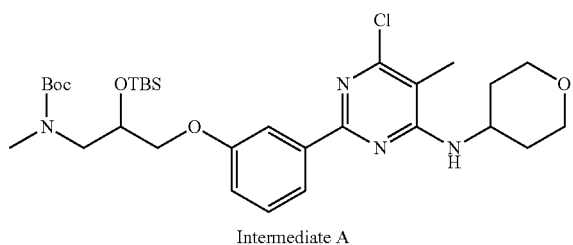
Intermediate A
(b)
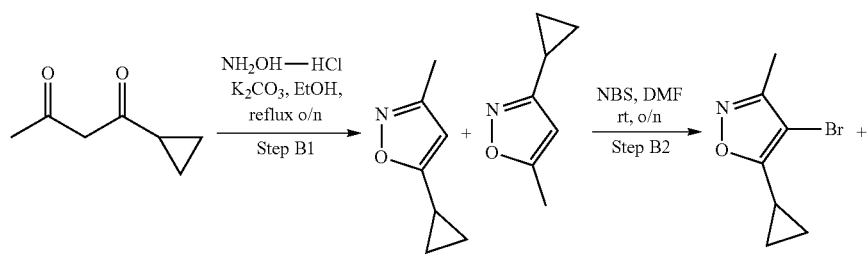
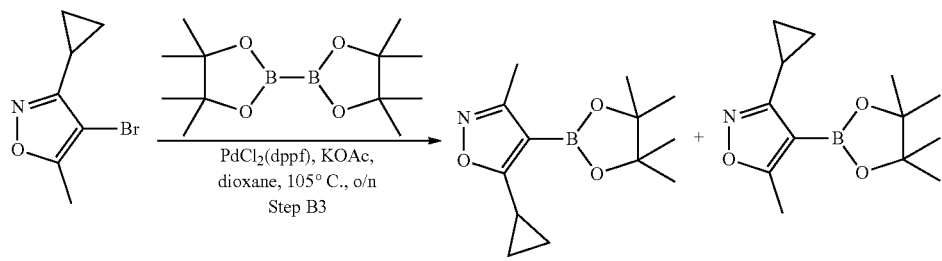
Intermediate B
(c)
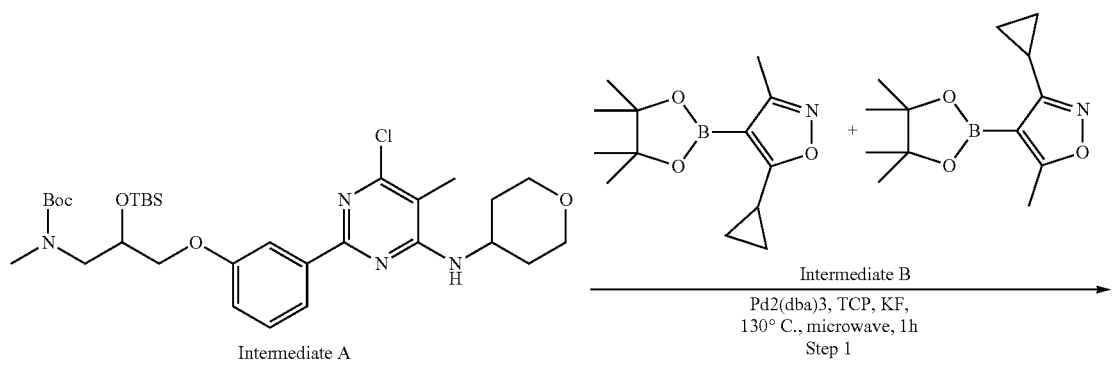

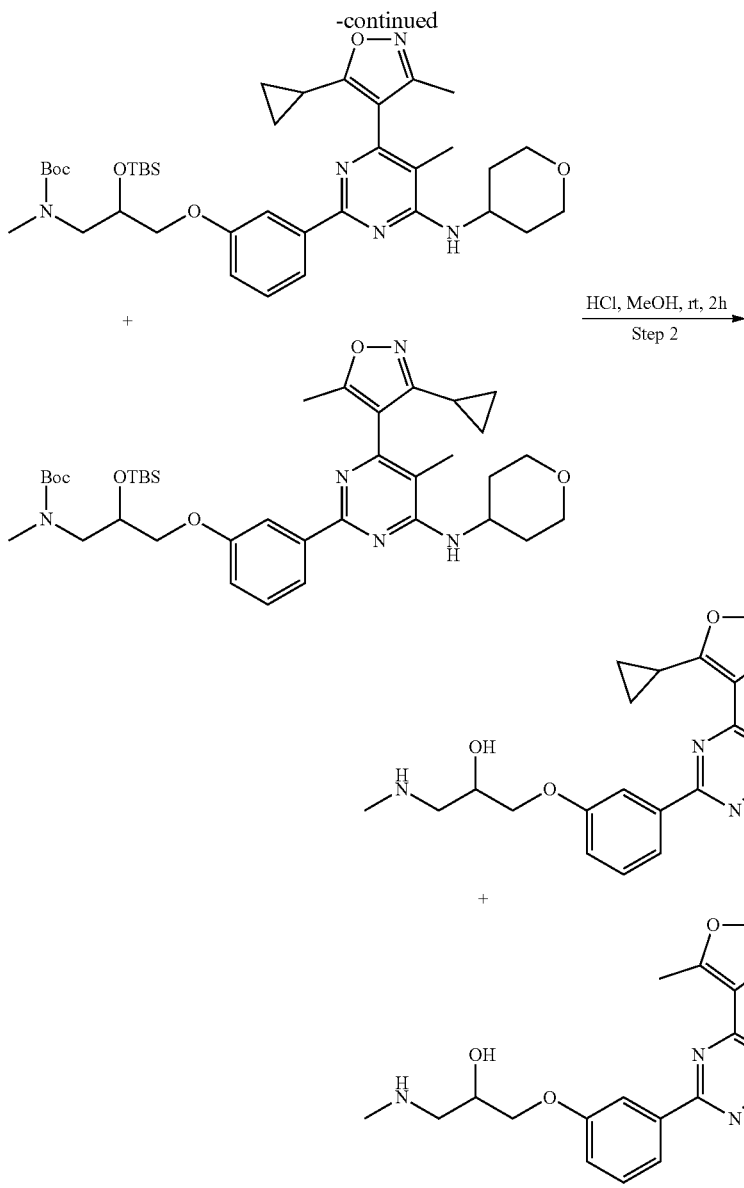

Step A1: Synthesis of tert-butyl 2-(tert-butyldimethylsilyloxy)-3-(3-(4-chloro-5-methyl-6-(tetrahydro-2H-pyran-4-ylamino)pyrimidin-2-yl)phenoxy)propyl (methyl)carbamate To a solution of tert-butyl 2-(tert-butyldimethylsilyloxy)-3-(3-(4,6-dichloro-5-methylpyrimidin-2-yl)phenoxy)propyl (methyl)carbamate (2.2 g, 4.0 mmol) and triethylamine (610 mg, 6.0 mmol) in DMF (20 mL) was added tetrahydro-2H-pyran-4-amine (610 mg, 6.0 mmol) at room temperature. The mixture was then heated at 120° C. and stirred for 12 h., cooled down to room temperature, diluted with EtOAc (30 mL) and successively washed with $H_2O$ (25 mL×2), saturated aqueous $NH_4Cl$ solution (30 mL×2) and brine (30 mL). The organic layer was dried over $Na_2SO_4$, filtered and concentrated and the resulting residue was purified by chromatographic column on silicagel (petroleum ether/EtOAc=10/1 to 4/1) to give tert-butyl 2-(tert-butyldimethylsilyloxy)-3-(3-(4-chloro-5-methyl-6-(tetrahydro-2H-pyran-4-ylamino) pyrimidin-2-yl)phenoxy)propyl(methyl) carbamate as a white solid (1.9 g, Yeild:76% yield). ESI-LCMS (m/z)=621.3 $[M+1]^+$.

Step B1: Synthesis of the mixture of 5-cyclopropyl-3-methylisoxazole and 3-cyclopropyl-5-methylisoxazole A mixture of 1-cyclopropylbutane-1,3-dione (or any other suitable 1,3-dione, 15.9 mmol), $NH_2OH$—HCl (2.2 g, 31.75 mmol) and $K_2CO_3$ (6.6 g, 47.62 mmol). in EtOH (12 mL) was stirred under reflux for 12 h., cooled to room temperature filtered and concentrated to render a mixture of 5-cyclopropyl-3-methylisoxazole and 3-cyclopropyl-5-methylisoxazole (ratio=4/1, determined by HNMR) as a yellow oil. Assumed quantitative yield. ESI-LCMS (m/z): 124 $[M+1]^+$.

Step B2: Synthesis of the mixture of 4-bromo-5-cyclopropyl-3-methylisoxazole and 4-bromo-3-cyclopropyl-5-methylisoxazole A solution of 5-cyclopropyl-3-methylisoxazole and 3-cyclo-propyl-5-methylisoxazole (15.9 mmol) in DMF (10 mL) was treated with NBS (3.1 g, 17.4 mmol) and the resulting mixture was stirred at room temperature for 12 h., diluted with EtOAc (150 mL) and washed with H₂O (100 mL×3) followed by brine (50 mL). The organic layer was dried over Na₂SO₄, filtered and concentrated and the residue was purified by automated chromatographic column on silicagel eluted with 0% to 8% EtOAc/petroleum ether to give a mixture of 4-bromo-5-cyclopropyl-3-methyl-isoxazole and 4-bromo-3-cyclopropyl-5-methylisoxazole as a yellow oil (2.5 g, 12.3 mmol, 78% yield in two steps). ESI-LCMS (m/z): 201.9 [M+11].

Step B3: Synthesis of a mixture of 5-cyclopropyl-3-methyl-4-(4,4,5,5-tetramethyl-1,3,2-dioxaborolan-2-yl)isoxazole and 3-cyclopropyl-5-methyl-4-(4,4,5,5-tetra-methyl-1,3,2-dioxaborolan-2-yl)isoxazole To a mixture of 4-bromo-5-cyclopropyl-3-methylisoxazole and 4-bromo-3-cyclopropyl-5-methylisoxazole (500 mg, 2.48 mmol) in dioxane (15 mL) was added 4,4,4',4',5,5,5',5'-octamethyl-2,2'-bi(1,3,2-dioxaborolane) (943 mg, 3.71 mmol), KOAc (1.17 g, 7.43 mmol) and PdCl₂(dppf) (181 mg, 0.25 mmol); the system was purged with N₂ stream, sealed and heated at 105° C. for 12 h. After being cooled down to room temperature, the mixture was filtered through a pad of celite and concentrated to give a mixture of 5-cyclopropyl-3-methyl-4-(4,4,5,5-tetramethyl-1,3,2-dioxaborolan-2-yl)isoxazole and 3-cyclopropyl-5-methyl-4-(4,4,5,5-tetramethyl-1,3,2-dioxaborolan-2-yl)isoxazole as a yellow solid, which was used directly in next step without further purification. ESI-LCMS (m/z): 250.1 [M+1]⁺.

Step 1: Synthesis of tert-butyl 2-(tert-butyldimethylsilyloxy)-3-(3-(4-(5-cyclo-propyl-3-methylisoxazol-4-yl)-5-methyl-6-(tetrahydro-2H-pyran-4-ylamino) pyrimidin-2-yl) phenoxy)propyl(methyl)carbamate To a solution of tert-butyl 2-(tert-butyldimethylsilyloxy)-3-(3-(4-chloro-5-methyl-6-(tetrahydro-2H-pyran-4-ylamino)pyrimidin-2-yl)phenoxy)propyl(methyl)carbamate (400 mg, 0.64 mmol) in degassed dioxane and H₂O (3/1, 4 mL) was added KF (37 mg, 0.64 mmol), Pd₂(dba)₃ (46 mg, 0.06 mmol), TCP (36 mg, 0.13 mmol) and 5-cyclo-propyl-3-methyl-4-(4,4,5,5-tetramethyl-1,3,2-dioxaborolan-2-yl) isoxazole (containing 30% of regioisomer: 3-cyclopropyl-5-methyl-4-(4,4,5,5-tetramethyl-1,3,2-dioxa-borolan-2-yl) isoxazole) (319 mg, 1.28 mmol). The system was purged with N₂ stream, the reaction vessel was sealed, placed in a microwave reactor and irradiated for 1 h at external temperature of 130° C. After being cooled down to room temperature, the mixture was diluted with EtOAc (25 mL) and washed with water (20 mL) followed by brine (20 mL). The organic layer was dried over Na₂SO₄, filtered and concentrated and the residue was purified by chromatographic column on silicagel (petroleum ether/EtOAc=10/1 to 1/1) to give a mixture of tert-butyl 2-(tert-butyldimethylsilyloxy)-3-(3-(4-(5-cyclopropyl-3-methylisoxazol-4-yl)-5-methyl-6-(tetrahydro-2H-pyran-4-yl-amino)pyrimidin-2-yl)phenoxy)propyl(methyl)carbamate, along with its regiosiomer tert-butyl 2-(tert butyldimethylsilyloxy)-3-(3-(4-(3-cyclopropyl-5-methyl-isoxazol-4-yl)-5-methyl-6-(tetrahydro-2H-pyran-4-ylamino)pyrimidin-2-yl)phenoxy) propyl(methyl)carbamate (total: 200 mg, 44% yield). ESI-LCMS (m/z): 708.7 [M+1]⁺.

Step 2: Synthesis of 1-(3-(4-(5-cyclopropyl-3-methylisoxazol-4-yl)-5-methyl-6-(tetrahydro-2H-pyran-4-ylamino)pyrimidin-2-yl)phenoxy)-3-(methylamino) propan-2-ol A mixture of tert-butyl 2-(tert-butyldimethylsilyloxy)-3-(3-(4-(5-cyclo-propyl-3-methyl-isoxazol-4-yl)-5-methyl-6-(tetrahydro-2H-pyran-4-ylamino)pyrimidin-2-yl) phenoxy) propyl (methyl)carbamate and tert-butyl 2-(tert-butyldimethyl-silyloxy)-3-(3-(4-(3-cyclopropyl-5-methylisoxazol-4-yl)-5-methyl-6-(tetrahydro-2H-pyran-4-yl-amino)pyrimidin-2-yl)phenoxy) propyl(methyl) carbamate (200 mg, 0.28 mmol) was dissolved in 2.5 N HCl solution in methanol (10 mL) and the mixture stirred at room temperature for 2 h., concentrated under vacuum, and the residue was purified by preparative HPLC to give 1-(3-(4-(5-cyclopropyl-3-methylisoxazol-4-yl)-5-methyl-6-(tetrahydro-2H-pyran-4-ylamino)pyrimidin-2-yl)phenoxy)-3-(methylamino) propan-2-ol along with the its regiosiomer 1-(3-(4-(3-cyclopropyl-5-methylisoxazol-4-yl)-5-methyl-6-(tetrahydro-2H-pyran-4-ylamino)pyrimidin-2-yl)phenoxy)-3-(methylamino) propan-2-ol (isomeric ration: 2/1, total: 49 mg, 36% yield) as a white solid. ¹HNMR (500 MHz, CD₃OD) δ ppm: 7.94-7.91 (m, 2H), 7.37 (t, J=8.5 Hz, 1H), 7.06 (dd, J=2.5 and 8.0 Hz, 1H), 4.54-4.49 (m, 1H), 4.19-4.14 (m, 1H), 4.10-4.04 (m, 3H), 3.70-2.92 (m, 5H), 2.78 (s, 3H), 2.25 (s, 3H), 2.13 (s, 3H), 2.12-2.05 (m, 1H), 1.97-1.77 (m, 4H), 1.12-1.07 (m, 2H), 0.98-0.96 (m, 2H); ESI-LCMS: 494.3 [M+1]⁺.

Example 19. Preparation of 1-(3-(4-(3,5-dimethyl-isothiazol-4-yl)-5-methyl-6-(tetrahydro-2H-pyran-4-ylamino)pyrimidin-2-yl)phenoxy)-3-(methylamino) propan-2-ol

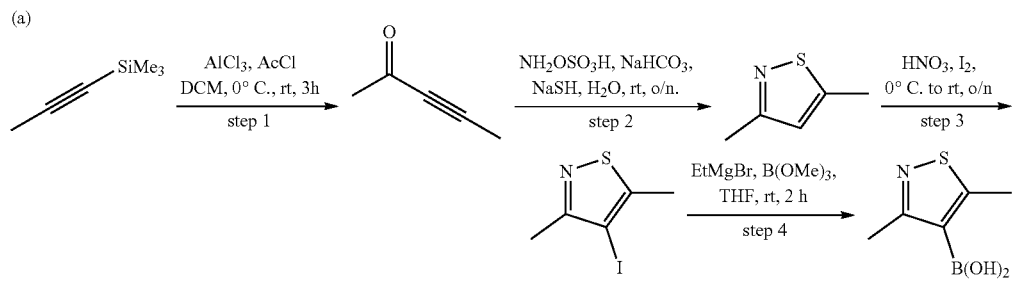

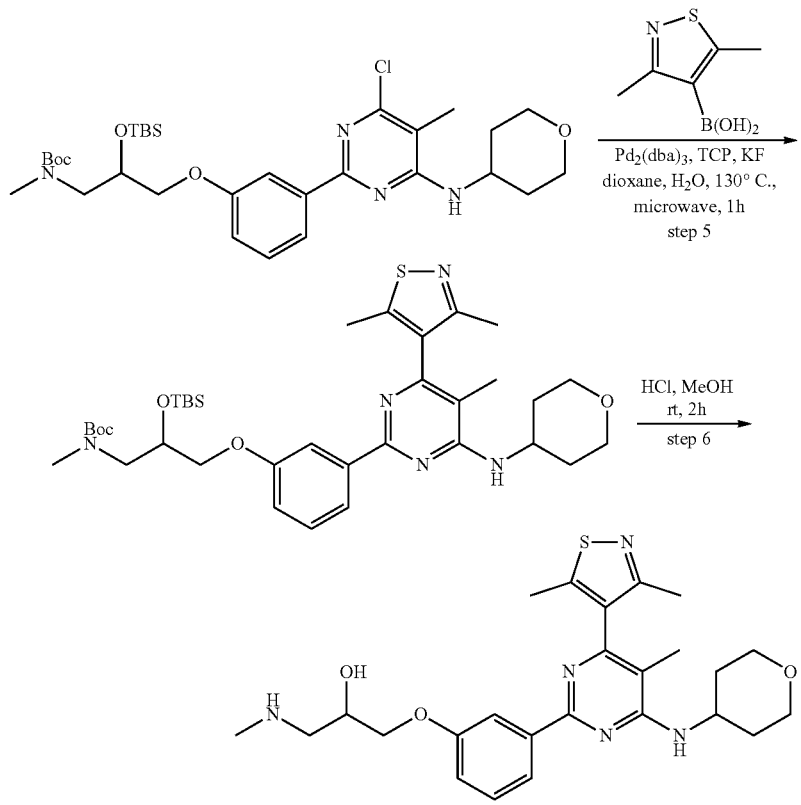

Step 1: Synthesis of pent-3-yn-2-one

A 100 mL round-bottom flask equipped with a reflux condenser, a thermometer, an addition funnel and an argon inlet was loaded with AlCl₃ (5.94 g, 0.045 mmol) and DCM (40 mL), and cooled to 0° C. A freshly prepared solution of trimethyl(prop-1-ynyl)silane (5.0 g, 0.045 mol) and AcCl (3.2 mL, 0.045 mol) in 10 mL of DCM was added slowly with stirring at 0° C., once the addition was completed the cooling bath was removed and the reaction mixture was further stirred at room temperature for 3 h., was poured into ice water and extracted with DCM (50 mL×3). The combined organic layers were dried over Na₂SO₄, filtered and concentrated. The residue was distilled to give pent-3-yn-2-one (1.6 g, 44% yield). ¹HNMR (500 MHz, CDCl₃) δ ppm: 2.30 (s, 3H), 2.01 (s, 3H).

Step 2: Synthesis of 3,5-dimethylisothiazole

A mixture of pent-3-yn-2-one (5.42 g, 0.066 mol) and H₂NOSO₃H (7.46 g, 0.066 mol) in 40 mL of water was stirred at 0° C. for 30 min. Then NaHCO₃ (5.54 g, 0.066 mol) followed by NaHS (4.1 g, 0.073 mol) were slowly added. The cooling bath was removed and the reaction mixture was stirred at room temperature for 12 h., then extracted with diethyl ether (50 mL×3). The combined organic layers were dried over Na₂SO₄, filtered and concentrated to give 3,5-dimethylisothiazole (4.27 g, 60% yield) as an oil. ESI-LCMS (m/z): 114.1 [M+1]⁺.

Step 3: Synthesis of 4-iodo-3,5-dimethylisothiazole

A mixture of 3,5-dimethylisothiazole (4.27 g, 0.038 mol) and I₂ (9.59 g, 0.038 mol) was slowly added to HNO₃ (50 mL) with stirring at 0° C., the cooling bath was then removed and the mixture was further stirred at room temperature for 12 h., poured into ice water and extracted with EtOAc (50 mL×3). The combined organic layers were dried over Na₂SO₄, filtered and concentrated. The residue was purified by chromatographic column on silicagel to give 4-iodo-3,5-dimethylisothiazole (3.5 g, 33% yield). ESI-LCMS (m/z): 239.9 [M+1]⁺.

Step 4: Synthesis of 3,5-dimethylisothiazol-4-ylboronic acid

A solution of 4-iodo-3,5-dimethylisothiazole (100 mg, 0.41 mmol) in 5 mL of THF stirred at −15° C. under N₂ atmosphere, was treated with a 3 M solution of EtMgBr in diethyl ether (0.42 mL, 1.25 mmol), stirred at the same temperature for 5 min and then B(OMe)₃ (131 mg, 1.25 mmol) was added. The final mixture was stirred at room temperature for 2 h., quenched with slow addition of aqueous HCl, poured into ice water and extracted with ethyl acetate (20 mL×3). The combined organic layers were dried over Na₂SO₄, filtered and concentrated to give 3,5-dimethylisothiazol-4-ylboronic acid (65 mg, crude), which was used directly without further purification. ESI-LCMS (m/z): 158.0 [M+1]⁺.

Step 5: Synthesis of tert-butyl 2-(tert-butyldimethylsilyloxy)-3-(3-(4-(3,5-di-methylisothiazol-4-yl)-5-methyl-6-(tetrahydro-2H-pyran-4-ylamino)pyrimidin-2-yl) phenoxy)propyl(methyl)carbamate A mixture of tert-butyl 2-(tert-butyldimethylsilyloxy)-3-(3-(4-chloro-5-methyl-6-(tetrahydro-2H-pyran-4-ylamino)

pyrimidin-2-yl)phenoxy)propyl(methyl)carbamate (100 mg, 0.16 mmol), 3,5-dimethylisothiazol-4-ylboronic acid (50 mg, 0.32 mmol), KF (10 mg, 0.17 mmol), Pd$_2$(dba)$_3$ (22 mg, 0.02 mmol) and TCP (13 mg, 0.05 mmol) in degassed dioxane and H$_2$O (3/1, 5.5 mL) was purged with N$_2$ stream, the reaction vessel was sealed, placed in a microwave reactor and irradiated for 1 h at external temperature of 130° C., cooled down to room temperature, diluted with water (5 mL) and the mixture was extracted with EtOAc (10 mL×3). The combined organic layers was dried over Na$_2$SO$_4$, filtered and concentrated. The residue was purified by preparative TLC to give tert-butyl 2-(tert-butyldimethylsilyloxy)-3-(3-(4-(3,5-dimethylisothiazol-4-yl)-5-methyl-6-(tetrahydro-2H-pyran-4-ylamino)pyrimidin-2-yl)phenoxy) propyl(methyl) carbamate (42 mg, 38% yield). ESI-LCMS (m/z): 698.0 [M+1]$^+$.

Step 6: Synthesis of 1-(3-(4-(3,5-dimethylisothiazol-4-yl)-5-methyl-6-(tetrahydro-2H-pyran-4-ylamino)pyrimidin-2-yl)phenoxy)-3-(methylamino)propan-2-ol A solution of tert-butyl 2-(tert-butyldimethylsilyloxy)-3-(3-(4-(3,5-dimethyl-isothiazol-4-yl)-5-methyl-6-(tetrahydro-2H-pyran-4-ylamino)pyrimidin-2-yl)phenoxy)propyl (methyl)carbamate (42 mg, 0.06 mmol) in 2.5N HCl solution in methanol (1.5 mL) was stirred at room temperature for 2 h., concentrated under vacuum and the residue was dissolved in MeOH (5 mL) and treated with aqueous NH$_4$OH till pH=9. The resulting mixture was concentrated in vacuo and the residue was purified by preparative HPLC to give 1-(3-(4-(3,5-dimethylisothiazol-4-yl)-5-methyl-6-(tetrahydro-2H-pyran-4-ylamino)pyrimidin-2-yl)phenoxy)-3-(methylamino)propan-2-ol as a formic acid salt (15 mg, 48% yield). $^1$HNMR (500 MHz, CD$_3$OD) δ ppm: 8.58 (brs, 1H), 7.96 (d, J=7.5 Hz, 1H), 7.89 (s, 1H), 7.39 (t, J=8.0 Hz, 1H), 7.08 (dd, J=2.5 and 8.0 Hz, 1H), 4.58-4.51 (m, 1H), 4.32-4.25 (m, 1H), 4.16-4.06 (m, 4H), 3.70-3.63 (m, 2H), 3.30-3.28 (m, 1H), 3.21-3.17 (m, 1H), 2.77 (s, 3H), 2.42 (s, 3H), 2.31 (s, 3H), 2.13-2.08 (m, 2H), 1.93 (s, 3H), 1.85-1.76 (m, 2H); ESI-LCMS(m/z): 484.2 [M+11]$^+$.

Example 20. Preparation of 1-(3-(4-(3,5-dimethyl-3H-1,2,3-triazol-4-yl)-5-methyl-6-(tetrahydro-2H-pyran-4-ylamino)pyrimidin-2-yl)phenoxy)-3-(methylamino) propan-2-ol

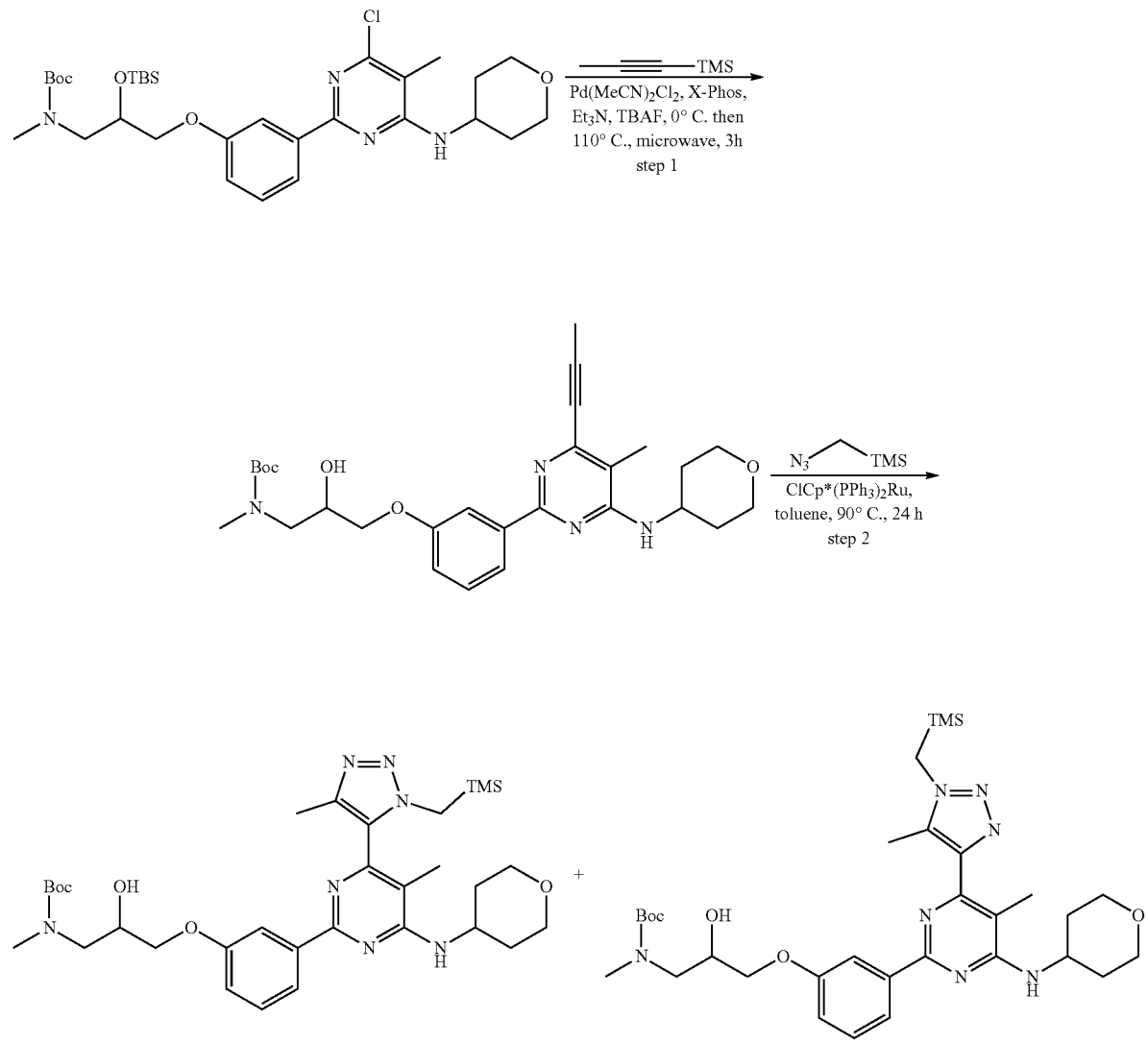

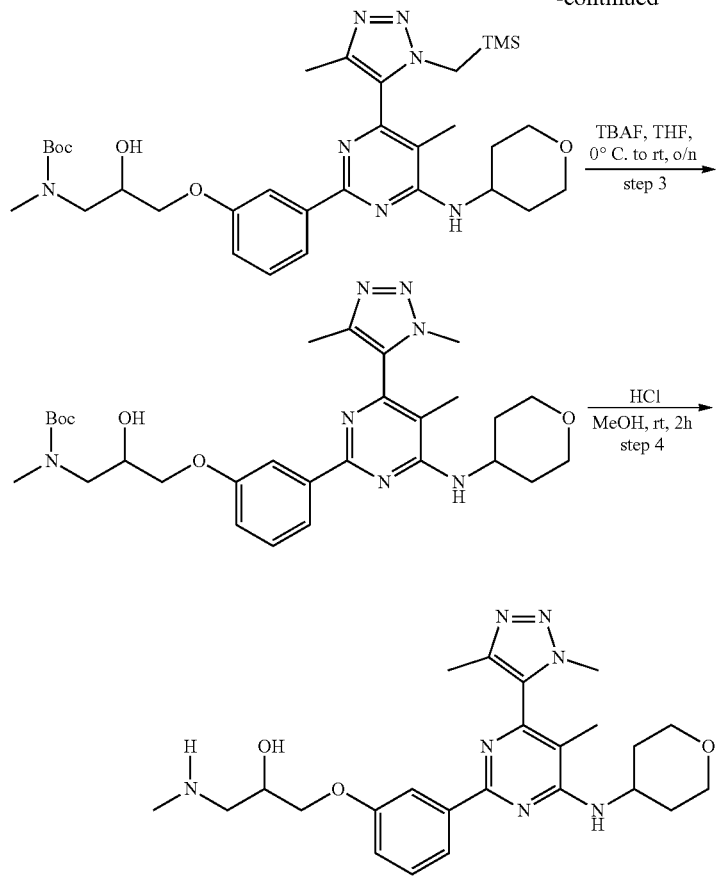

Step 1: Synthesis of tert-butyl 2-hydroxy-3-(3-(5-methyl-4-(prop-1-ynyl)-6-(tetrahydro-2H-pyran-4-ylamino)pyrimidin-2-yl)phenoxy)propyl(methyl)carbamate A solution of tert-butyl 2-(tert-butyldimethylsilyloxy)-3-(3-(4-chloro-5-methyl-6-(tetrahydro-2H-pyran-4-ylamino)pyrimidin-2-yl)phenoxy)propyl(methyl)carbamate (1.0 g, 1.61 mmol), Pd(MeCN)$_2$Cl$_2$ (42 mg, 0.16 mmol) and X-phos (230 mg, 0.48 mmol) in Et$_3$N (10 ml) was treated with trimethyl(prop-1-ynyl)silane (360 mg, 3.22 mmol). The system was purged with N$_2$ stream and then TBAF (3.22 ml, 3.22 mmol) was added slowly at 0° C. The mixture was then warmed up to room temperature the reaction vessel was sealed, placed in a microwave reactor and irradiated for 3 h at external temperature of 110° C. After being cooled down to room temperature, the mixture was diluted with water (50 ml) and extracted with EtOAc (50 ml×2). The organic layers were combined, dried over Na$_2$SO$_4$, filtered and concentrated. The residue was purified by chromatographic column on silicagel (petroleum ether/EtOAc=10/1 to 1/1) to give tert-butyl 2-hydroxy-3-(3-(5-methyl-4-(prop-1-ynyl)-6-(tetrahydro-2H-pyran-4-ylamino) pyrimidin-2-yl)phenoxy)propyl(methyl)carbamate (600 mg, 73% yield) as major product. ESI-LCMS (m/z): 511.0 [M+1]$^+$.

Step 2: Synthesis of tert-butyl 2-hydroxy-3-(3-(5-methyl-4-(5-methyl-3-((trimethylsilyl) methyl)-3H-1,2,3-triazol-4-yl)-6-(tetrahydro-2H-pyran-4-ylamino) pyrimidin-2-yl)phenoxy) propyl(methyl)carbamate and tert-butyl 2-hydroxy-3-(3-(5-methyl-4-(5-methyl-1-((trimethylsilyl)methyl)-1H-1,2,3-triazol-4-yl)-6-(tetra-hydro-2H-pyran-4-ylamino) pyrimidin-2-yl)phenoxy)propyl(methyl)carbamate To a solution of tert-butyl 2-hydroxy-3-(3-(5-methyl-4-(prop-1-ynyl)-6-(tetrahydro-2H-pyran-4-ylamino)pyrimidin-2-yl)phenoxy)propyl(methyl)carbamate (400 mg, 0.78 mmol) in degassed toluene (10 ml) was added (azidomethyl) trimethylsilane (1 g, 7.80 mmol) followed by ClCp*(PPh$_3$)$_2$Ru (176 mg, 0.24 mmol). The system was purged with N$_2$ stream, sealed and stirred at 90° C. for 24 h. The reaction mixture was cooled to room temperature, diluted with water (50 ml) and extracted with EtOAc (50 ml×2). The organic layers were combined, dried over Na$_2$SO$_4$, filtered and concentrated. The residue was purified by preparative HPLC to render tert-butyl 2-hydroxy-3-(3-(5-methyl-4-(5-methyl-3-((trimethylsilyl)methyl)-3H-1,2,3-triazol-4-yl)-6-(tetra-hydro-2H-pyran-4-ylamino)pyrimidin-2-yl)phenoxy)propyl (methyl)carbamate (62 mg, 12% yield) as major product. ESI-LCMS (m/z): 640.3 [M+1]$^+$.

The regiosiomer tert-butyl 2-hydroxy-3-(3-(5-methyl-4-(5-methyl-1-((trimethylsilyl) methyl)-1H-1,2,3-triazol-4-yl)-6-(tetrahydro-2H-pyran-4-ylamino)pyrimidin-2-yl) phenoxy)propyl (methyl)carbamate (41 mg, 8% yield yield) was also isolated as minor product. ESI-LCMS (m/z): 640.3 [M+1]$^+$.

Step 3: Synthesis of tert-butyl 3-(3-(4-(3,5-dimethyl-3H-1,2,3-triazol-4-yl)-5-methyl-6-(tetrahydro-2H-pyran-4-ylamino)pyrimidin-2-yl)phenoxy)-2-hydroxy-propyl(methyl)carbamate A solution of tert-butyl 2-hydroxy-3-(3-(5-methyl-4-(5-methyl-3-((trimethylsilyl) methyl)-3H-1,2,3-triazol-4-yl)-6-(tetrahydro-2H-pyran-4-ylamino)pyrimidin-2-yl) phenoxy) propyl(methyl) carbamate (62 mg, 0.097 mmol) in THF (10 ml) was treated with 1M TBAF in THF (0.2 mmol), slowly added at 0° C. The mixture was then warmed up to room temperature and stirred for 12 h., diluted with water (25 ml) and extracted with EtOAc (25 ml×2). The organic layers were combined, dried over $Na_2SO_4$, filtered and concentrated to give tert-butyl 3-(3-(4-(3,5-dimethyl-3H-1,2,3-triazol-4-yl)-5-methyl-6-(tetrahydro-2H-pyran-4-ylamino)pyrimidin-2-yl)phenoxy)-2-hydroxypropyl(methyl)carbamate (40 mg, crude), which was used directly without further purification. ESI-LCMS (m/z): 568.3 [M+1]$^+$.

Step 4: Synthesis of 1-(3-(4-(3,5-dimethyl-3H-1,2,3-triazol-4-yl)-5-methyl-6-(tetra-hydro-2H-pyran-4-ylamino)pyrimidin-2-yl)phenoxy)-3-(methylamino)propan-2-ol tert-Butyl 3-(3-(4-(3,5-dimethyl-3H-1,2,3-triazol-4-yl)-5-methyl-6-(tetrahydro-2H-pyran-4-ylamino)pyrimidin-2-yl) phenoxy)-2-hydroxypropyl(methyl)carbamate (40 mg, 0.07 mmol) was dissolved in a 2N HCl solution in methanol (10 ml), and the mixture was stirred at room temperature for 2 h., concentrated under vacuum and the resulting residue was purified by preparative HPLC to give 1-(3-(4-(3,5-dimethyl-3H-1,2,3-triazol-4-yl)-5-methyl-6-(tetrahydro-2H-pyran-4-ylamino)pyrimidin-2-yl)phenoxy)-3-(methylamino)propan-2-ol as a formic acid salt (11 mg, 22% yield for 2 steps). $^1$HNMR (500 MHz, $CD_3OD$) δ ppm: 8.57 (brs, 1H), 7.98 (d, J=8.0 Hz, 1H), 7.93 (s, 1H), 7.40 (t, J=8.5 Hz, 1H), 7.09 (dd, J=2.0 and 8.5 Hz, 1H), 4.58-4.51 (m, 1H), 4.27 (brs, 1H), 4.15-4.06 (m, 4H), 4.03 (s, 3H), 3.68-3.63 (m, 2H), 3.30-3.23 (m, 1H), 3.19-3.12 (m, 1H), 2.74 (s, 3H), 2.27 (s, 3H), 2.13-2.08 (m, 2H), 2.00 (s, 3H), 1.85-1.76 (m, 2H); ESI-LCMS (m/z): 468.0 [M+H]$^+$.

Example 21. Preparation of 1-(3-(4-(3-(hydroxymethyl)-5-methylisoxazol-4-yl)-5-methyl-6-(tetrahydro-2H-pyran-4-ylamino)pyrimidin-2-yl)phenoxy)-3-(methylamino) propan-2-ol

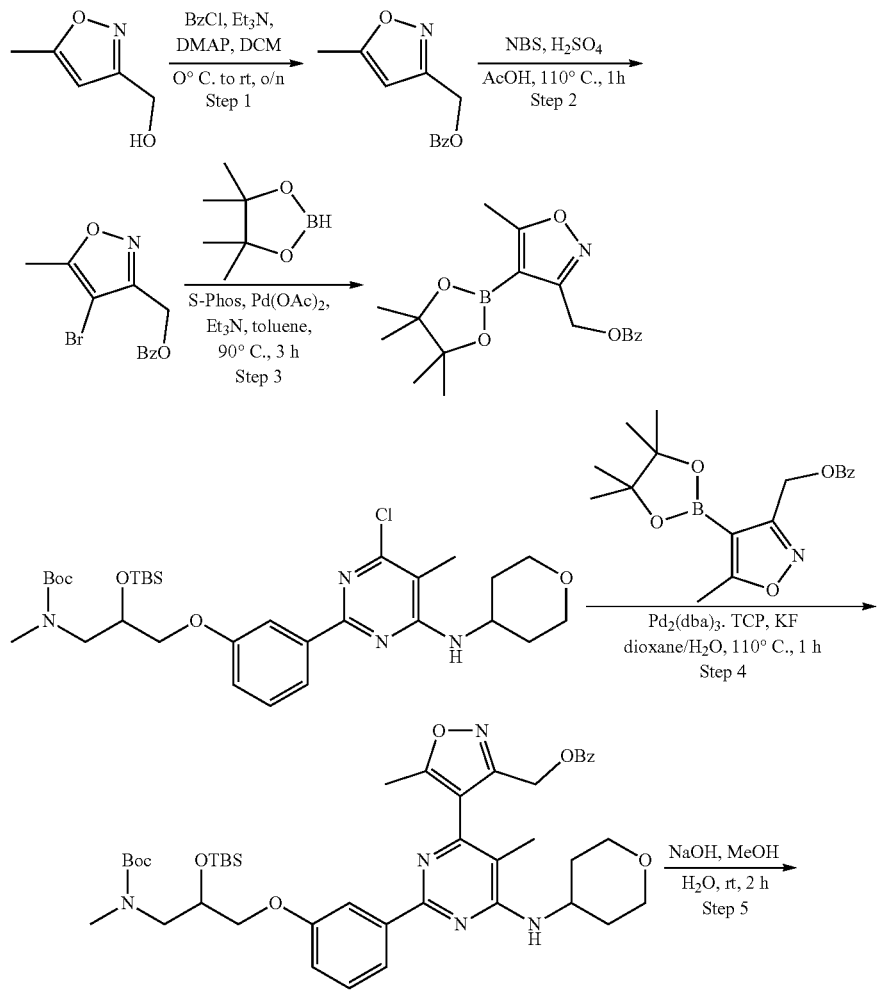

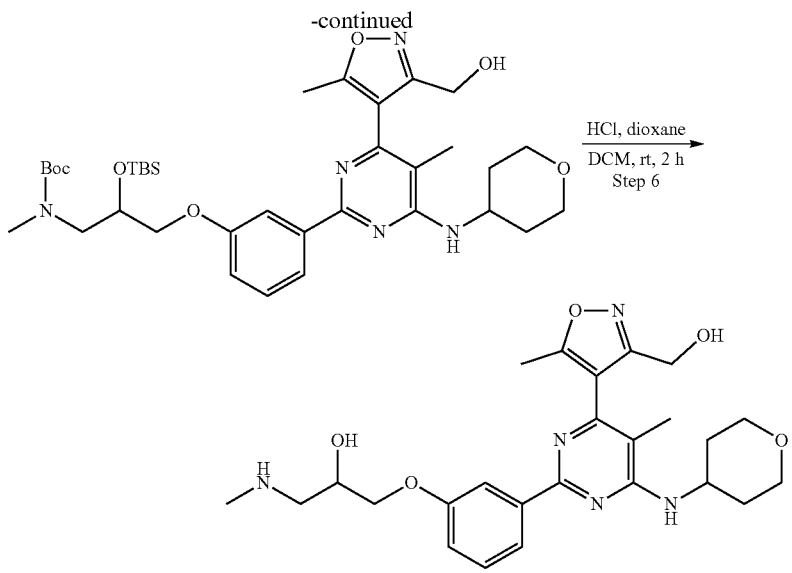

Step 1: Synthesis of (5-methylisoxazol-3-yl)methyl benzoate

Benzoyl chloride (3 g, 21.24 mmol) was slowly added to a stirred solution of (5-methylisoxazol-3-yl)methanol (2.0 g, 17.7 mmol), Et$_3$N (4.9 mL, 35.3 mmol) and DMAP (216 mg, 1.76 mmol) in DCM (50 mL) at 0° C., after the addition was complete, the reaction mixture was warmed up to room temperature and further stirred for 16 h., washed with water (30 mL), aqueous NH$_4$Cl solution (30 mL×2) and brine (30 mL). The organic layer was dried over Na$_2$SO$_4$, filtered, concentrated under vacuum and the resulting residue was purified by chromatographic column on silicagel eluted with 0% to 15% EtOAc/petroleum ether to give (5-methylisoxazol-3-yl)methyl benzoate as a white solid (3.4 g, 89% yield). ESI-LCMS: 218.1 [M+1]$^+$.

Step 2: Synthesis of (4-bromo-5-methylisoxazol-3-yl)methyl benzoate

A solution of (5-methylisoxazol-3-yl)methyl benzoate (3.16 g, 14.5 mmol) and NBS (2.98 g, 16.7 mmol) in AcOH (30 mL) was treated with concentrated H$_2$SO$_4$ (1.43 g, 14.5 mmol) slowly added at room temperature and then the reaction mixture was heated at 110° C. for 1 h., cooled down to room temperature, slowly added into iced saturated NaHCO$_3$ solution (400 mL) with stirring and extracted with DCM (200 mL×3). The combined organic layers were washed with brine (200 mL), dried over Na$_2$SO$_4$, filtered, concentrated under vacuum and the resulting residue was purified by chromatographic column on silicagel eluted with 0% to 10% EtOAc/petroleum ether, to give (4-bromo-5-methyl-isoxazol-3-yl)methyl benzoate as a white solid (3.53 g, 83% yield). ESI-LCMS: 296.0 [M+1]$^+$.

Step 3: Synthesis of (5-methyl-4-(4,4,5,5-tetramethyl-1,3,2-dioxaborolan-2-yl) isoxazol-3-yl)methyl benzoate A suspension of (4-bromo-5-methylisoxazol-3-yl)methyl benzoate (600 mg, 2.0 mmol), S-Phos (166 mg, 0.4 mmol), 4,4,5,5-tetramethyl-1,3,2-dioxaborolane (2.59 g, 20.27 mmol), Pd(OAc)$_2$ (46 mg, 0.20 mmol) and Et$_3$N (1.4 mL, 10.1 mmol) in toluene (30 mL) was stirred under N$_2$ atmosphere at external temperature of 90° C. for 3 h. After being cooled down to room temperature, the reaction mixture was filtered, and the filtrate concentrated under vacuum to give (5-methyl-4-(4,4,5,5-tetramethyl-1,3,2-dioxaborolan-2-yl)isoxazol-3-yl)methyl benzoate as an oil (900 mg, crude), which was used in next-step without further purification. Assumed quantitative yield. ESI-LCMS: 344.3 [M+1]$^+$.

Step 4: Synthesis of (4-(2-(3-(3-(tert-butoxycarbonyl(methyl)amino)-2-(tert-butyldimethylsilyloxy) propoxy)phenyl)-5-methyl-6-(tetrahydro-2H-pyran-4-yl-amino)pyrimidin-4-yl)-5-methylisoxazol-3-yl) methyl benzoate A solution of tert-butyl 2-(tert-butyldimethylsilyloxy)-3-(3-(4-chloro-5-methyl-6-(tetrahydro-2H-pyran-4-ylamino) pyrimidin-2-yl)phenoxy)propyl(methyl)carbamate (300 mg, 0.48 mmol) in dioxane and H$_2$O (3/1, 12 mL) was treated with (5-methyl-4-(4,4,5,5-tetramethyl-1,3,2-dioxaborolan-2-yl)isoxazol-3-yl)methyl benzoate (2 mmol, crude from previous step), TCP (135 mg, 0.48 mmol); KF (56 mg, 0.97 mmol) and Pd$_2$(dba)$_3$ (221 mg, 0.24 mmol). The system was purged with N$_2$ stream, the vial sealed, placed in a microwave reactor and irradiated for 60 min. at external temperature of 110° C. After being cooled down to room temperature the mixture was diluted with water (30 mL) and extracted with EtOAc (30 mL×2). The combined organic layers were washed with brine, dried over Na$_2$SO$_4$, filtered and concentrated, the resulting residue was purified by preparative TLC (petroleum ether/EtOAc=2/1) to give (4-(2-(3-(3-(tert-butoxycarbonyl(methyl)amino)-2-(tert-butyldimethyl-silyl oxy)propoxy)phenyl)-5-methyl-6-(tetrahydro-2H-pyran-4-ylamino)pyrimidin-4-yl)-5-methylisoxazol-3-yl)methyl benzoate as a yellow solid (280 mg, 74% yield). ESI-LCMS: 802.3 [M+1]$^+$.

Step 5: Synthesis of tert-butyl 2-(tert-butyldimethylsilyloxy)-3-(3-(4-(3-(hydroxyl-methyl)-5-methylisoxazol-4-yl)-5-methyl-6-(tetrahydro-2H-pyran-4-ylamino) pyrimidin-2-yl)phenoxy)propyl(methyl) carbamate A solution of (4-(2-(3-(3-(tert-butoxycarbonyl(methyl)amino)-2-(tert-butyl-di-methylsilyloxy)propoxy)phenyl)-5- methyl-6-(tetrahydro-2H-pyran-4-ylamino) pyrimidin-4-yl)-5-methylisoxazol-3-yl)methyl benzoate (140 mg, 0.17 mmol) in MeOH (5 mL) was treated with a solution of NaOH (14 mg, 0.35 mmol) in water (1 mL) and the reaction mixture was stirred at room temperature for 2 h. and then concentrated under vacuum. The residue was dissolved in DCM (50 mL), washed with water (20 mL×3) and brine (20 mL). The organic phase was dried over $Na_2SO_4$, filtered and concentrated to give tert-butyl 2-(tert-butyldimethylsilyloxy)-3-(3-(4-(3-(hydroxymethyl)-5-methylisoxazol-4-yl)-5-methyl-6-(tetrahydro-2H-pyran-4-ylamino)pyrimidin-2-yl)phenoxy)propyl(methyl)carbamate as a yellow solid (90 mg, 76% yield). ESI-LCMS: 698.3 $[M+1]^+$.

Step 6: Synthesis of 1-(3-(4-(3-(hydroxymethyl)-5-methylisoxazol-4-yl)-5-methyl-6-(tetrahydro-2H-pyran-4-ylamino)pyrimidin-2-yl)phenoxy)-3-(methylamino) propan-2-ol To a solution of tert-butyl 2-(tert-butyldimethylsilyloxy)-3-(3-(4-(3-(hydroxyl-methyl)-5-methylisoxazol-4-yl)-5-methyl-6-(tetrahydro-2H-pyran-4-ylamino)pyrimidin-2-yl)phenoxy)propyl(methyl)carbamate (90 mg, 0.13 mmol) in DCM (2 mL) was added 4N HCl in dioxane (1 mL) and the mixture was stirred at room temperature for 2 h, concentrated under vacuum and the residue was dissolved in MeOH (2 ml), treated with ammonia till pH 7-8 and then concentrated again. The residue was purified by preparative HPLC to give 1-(3-(4-(3-(hydroxymethyl)-5-methylisoxazol-4-yl)-5-methyl-6-(tetrahydro-2H-pyran-4-ylamino) pyrimidin-2-yl) phenoxy)-3-(methylamino) propan-2-ol as a formic acid salt (white solid, 14 mg, 20% yield). ESI-LCMS: 484.2 [M+11]. $^1$HNMR (400 MHz, $CD_3OD$) δ ppm: 8.54 (br s, 1H), 7.92 (d, J=7.6 Hz, 1H), 7.83 (s, 1H), 7.40 (t, J=8.0 Hz, 1H), 7.09 (dd, J=2.4 and 8.0 Hz, 1H), 4.65 (s, 2H), 4.55-4.45 (m, 1H), 4.30-4.22 (m, 1H), 4.13-4.02 (m, 4H), 3.67-3.59 (m, 2H), 3.30-3.24 (m, 1H), 3.20-3.10 (m, 1H), 2.77 (s, 3H), 2.40 (s, 3H), 2.10-2.00 (m, 5H), 1.83-1.70 (m, 2H).

Example 22. Preparation of 1-{4-Chloro-3-[4-(5,7-dihydro-pyrrolo[3,4-b]pyridin-6-yl)-6-(3,5-dimethyl-isoxazol-4-yl)-5-methyl-pyrimidin-2-yl]-phenoxy}-3-methylamino-propan-2-ol

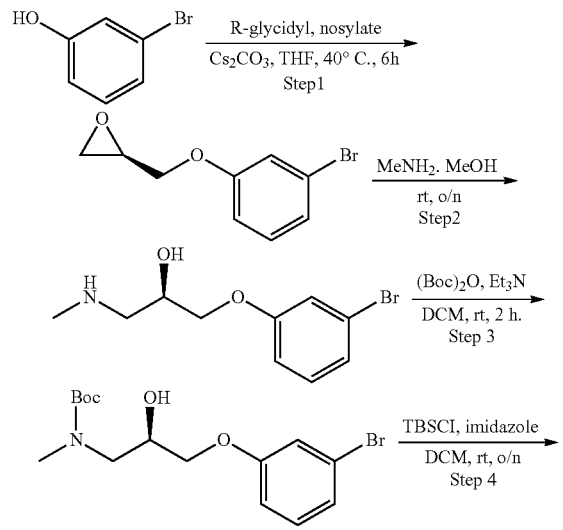

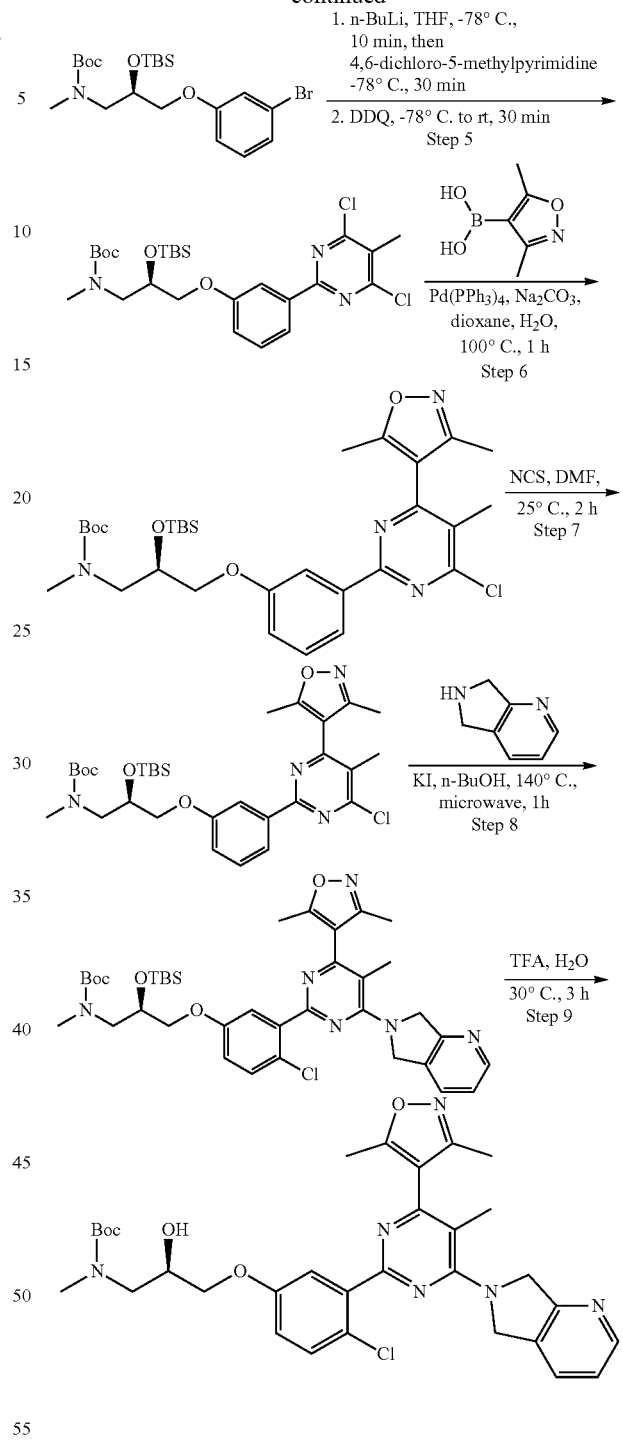

Step 1: Synthesis of (R)-2-((3-bromophenoxy)methyl)oxirane

To a suspension of 3-bromophenol (100 g, 0.58 mol) and $Cs_2CO_3$ (379 g, 1.16 mol) in THF (1500 mL) was added (R)-glycidyl nosylate (192 g, 0.74 mol) at room temperature. The reaction mixture was heated at 40° C. and stirred at the same temperature for 16 h, cooled down to room temperature, filtered and concentrated. The residue was dissolved in water (200 mL) and extracted with ethyl acetate (150 mL×3), the organic layers were combined, dried over $Na_2SO_4$, filtered and concentrated to give (R)-2-((3-bromophenoxy)methyl)oxirane (160 g, crude), which was used directly for the next step without further purification. ESI-LCMS (m/z): 228.7 [M+1]$^+$.

Step 2: Synthesis of (R)-1-(3-bromophenoxy)-3-(methylamino)propan-2-ol

A solution of (R)-2-((3-bromophenoxy)methyl)oxirane (159 g, crude from step 1) in MeOH (500 mL) was treated with 33% MeNH$_2$ in MeOH (500 mL), added slowly with stirring at 0° C. After the addition was complete, the solution was further stirred at room temperature for 16 h, the volatiles were then removed in vacuo to give the (R)-1-(3-bromophenoxy)-3-(methylamino)propan-2-ol (181 g, crude), which was used for the next step directly without further purification. ESI-LCMS (m/z): 260.0 [M+1]$^+$.

Step 3: Synthesis of (R)-tert-butyl 3-(3-bromophenoxy)-2-hydroxypropyl(methyl) carbamate A solution of (R)-1-(3-bromophenoxy)-3-(methylamino)propan-2-ol (181 g, crude from step 2) and triethylamine (178 g, 1.76 mol) in DCM (1 L) stirred at 0° C. was treated with portion wise addition of a solution of Boc$_2$O (289 g, 1.32 mol) in DCM (100 mL). Then the cooling bath was removed and the reaction mixture was further stirred at room temperature for 2 h., washed consecutively with water (300 mL×2), saturated NH$_4$Cl aqueous solution (200 mL×2) and brine (300 mL). The organic phase was dried over Na$_2$SO$_4$, filtered and concentrated to give (R)-tert-butyl 3-(3-bromophenoxy)-2-hydroxypropyl(methyl)carbamate (276 g, crude) as pale yellow oil, which was used into next step directly without further purification. ESI-LCMS (m/z): 382.0 [M+23]$^+$.

Step 4: Synthesis of (R)-tert-butyl 3-(3-bromophenoxy)-2-(tert-butyldimethyl-silyloxy)propyl(methyl) carbamate A solution of (R)-tert-butyl 3-(3-bromophenoxy)-2-hydroxypropyl(methyl) carbamate (276 g, crude from step 3) and imidazole (132 g, 1.94 mol) in DCM (1 L) stirred at 0° C. under N$_2$ atmosphere, was treated with slow addition of TBSCl (189 g, 1.26 mol) and the reaction mixture was further stirred at room temperature for 16 h., washed with water (300 mL×2) and brine (300 mL). The organic layer was dried over Na$_2$SO$_4$, filtered, concentrated and the resulting residue residue was purified by chromatographic column on silica gel (petroleum ether/EtOAc=80/1 to 60/1) to give the (R)-tert-butyl 3-(3-bromo-phenoxy)-2-(tert-butyldimethylsilyloxy)propyl(methyl) carbamate (105 g, 39% yield for 4 steps) as a pale yellow oil. ESI-LCMS: 495.9 [M+23]$^+$.

Step 5: Synthesis of (R)-tert-butyl 2-(tert-butyldimethylsilyloxy)-3-(3-(4,6-dichloro-5-methylpyrimidin-2-yl)phenoxy)propyl(methyl)carbamate A solution of (R)-tert-butyl 3-(3-bromophenoxy)-2-(tert-butyldimethylsilyloxy) propyl (methyl)carbamate (24 g, 50.58 mmol) in dry THF (100 mL), stirred at −78° C. under N$_2$ atmosphere was treated with slow addition of n-butyl lithium (21.1 mL, 2.4 M in hexane) over 20 minutes. The mixture was stirred for another 10 minutes at the same temperature followed by slow addition of a solution of 4,6-dichloro-5-methyl-pyrimidine (9.1 g, 55.64 mmol) in THF (20 mL) and further stirred at −78° C. for 30 minutes. DDQ (16.1 g, 70.9 mmol) was then added portion wise, the mixture warmed up to 0° C. and stirred for 30 minutes, concentrated and the residue was diluted with CH$_2$Cl$_2$ (300 mL), washed with 10% NaOH (50 mL), water (100 mL×2) and brine (100 mL). The organic layer was dried over Na$_2$SO$_4$, filtered, concentrated and the residue was purified by chromatographic column on silicagel eluted with petroleum ether/EtOAc=80/1 to 40/1 to render (R)-tert-butyl 2-(tert-butyldimethylsilyloxy)-3-(3-(4,6-dichloro-5-methylpyrimidin-2-yl)phenoxy)propyl(methyl) carbamate (10.8 g, 38% yield) as a white solid. ESI-LCMS (m/z): 578.2 [M+23]$^+$.

Step 6: Synthesis of tert-butyl (R)-2-(tert-butyldimethylsilyloxy)-3-(3-(4-chloro-6-(3,5-dimethylisoxazol-4-yl)-5-methylpyrimidin-2-yl)phenoxy) propyl (methyl) carbamate To a solution of (R)-tert-butyl 2-(tert-butyldimethylsilyloxy)-3-(3-(4,6-dichloro-5-methylpyrimidin-2-yl)phenoxy) propyl(methyl)carbamate (10.8 g, 19.4 mmol) in degassed dioxane and H$_2$O (3/1, 240 mL) was added 3,5-dimethylisoxazol-4-ylboronic acid (2.73 g, 19.4 mmol), Pd(PPh$_3$)$_4$ (2.24 g, 1.94 mmol) and Na$_2$CO$_3$ (4.1 g, 38.81 mmol). The system was purged with N$_2$ stream and the mixture was stirred at 100° C. for 1 h., cooled down to room temperature, diluted with water (100 mL) and extracted with EtOAc (250 mL×2). The organic layers were combined and washed with brine (200 mL), dried over Na$_2$SO$_4$, filtered, concentrated and the residue was purified by chromatographic column on silicagel, eluted with 0% to 15% EtOAc/petroleum ether, 50 min, to give tert-butyl (R)-2-(tert-butyldimethylsilyloxy)-3-(3-(4-chloro-6-(3,5-dimethyl isoxazol-4-yl)-5-methylpyrimidin-2-yl)phenoxy)propyl (methyl)carbamate as a white solid (7.1 g, 59% yield). ESI-LCMS: 639.3 [M+23]$^+$.

Step 7: Synthesis of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy) propyl(methyl)carbamate To a solution of tert-butyl (R)-2-(tert-butyldimethylsilyloxy)-3-(3-(4-chloro-6-(3,5-dimethylisoxazol-4-yl)-5-methylpyrimidin-2-yl)phenoxy)propyl(methyl)carbamate (7.1 g, 11.5 mmol) in DMF (100 mL) was added NCS (2.3 g, 17.25 mmol) and the reaction mixture was stirred at 25° C. for 2 h., diluted with EtOAc (300 mL) and washed with water (200 mL×3) and brine (200 mL). The organic layer was dried over Na$_2$SO$_4$, filtered, concentrated and the residue was purified by chromatographic column on silicagel, eluted with 0% to 15% EtOAc/petroleum ether, to give tert-butyl (R)-2-(tert-butyldimethylsilyloxy)-3(4-chloro-3-(4-chloro-6-(3,5-dimethylisoxazol-4-yl)-5-methylpyrimidin-2-yl)phenoxy)propyl(methyl)carbamate as white solid (6.2 g, 83% yield). ESI-LCMS: 673.2 [M+23]$^+$.

Step 8: tert-butyl (R)-2-(tert-butyldimethylsilyloxy)-3-(4-chloro-3-(4-(3,5-di-methylisoxazol-4-yl)-5-methyl-6-(5H-pyrrolo[3,4-b]pyridin-6(7H)-yl)pyrimidin-2-yl)phenoxy)propyl(methyl) carbamate A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (150 mg, 0.23 mmol); 6,7-dihydro-5H-pyrrolo[3,4-b]pyridine (or any other suitably substituted primary or secondary amine, 0.34 mmol), KI (81 mg, 0.46 mmol) and n-BuOH (1.5 mL), capped, placed in a microwave reactor and irradiated for 60 min. at external temperature of 140° C. After being cooled down to room temperature the mixture was diluted with water (50 mL) and extracted with EtOAc (40 mL×3). The organic layers were combined, dried over Na$_2$SO$_4$, filtered and concentrated to give tert-butyl (R)-2-(tert-butyldimethylsilyloxy)-3-(4-chloro-3-(4-(3,5-dimethyl-isoxazol-4-yl)-5-methyl-6-(5H-pyrrolo[3,4-b]pyridine-6(7H)-yl) pyrimidin-2-yl) phenoxy)propyl(methyl)carbamate as a brown solid (169 mg, crude), which was used directly for the next step without further purification. ESI-LCMS (m/z): 735.0 [M+1]$^+$.

Step 9: Synthesis of (2R)-1-(4-chloro-3-(4-(3,5-dimethylisoxazol-4-yl)-5-methyl-6-(5H-pyrrolo[3,4-b]pyridin-6(7H)-yl)pyrimidin-2-yl)phenoxy)-3-(methylamino)propan-2-ol A solution of tert-butyl (R)-2-(tert-butyldimethylsilyloxy)-3-(4-chloro-3-(4-(3,5-dimethyl-isoxazol-4-yl)-5-methyl-6-(5H-pyrrolo[3,4-b]pyridin-6(7H)-yl) pyrimidin-2-yl) phenoxy)propyl (methyl)carbamate (169 mg, crude, from step 1) in 90% TFA (6.6 mL) was stirred at room temperature for 3 h, the solvent was then removed in vacuo and the resulting residue was dissolved in MeOH (3 ml), treated with ammonia till pH 7-8 and concentrated. The residue was purified by preparative HPLC to give (2R)-1-(4-chloro-3-(4-(3,5-di-methylisoxazol-4-yl)-5-methyl-6-(5H-pyrrolo[3,4-b]pyridin-6(7H)-yl)pyrimidin-2-yl)phenoxy)-3-(methyl amino) propan-2-ol as a white solid (67 mg, 56% yield for 2 steps). ESI-LCMS (m/z): 520.8 [M+H]$^+$. $^1$HNMR (400 MHz, CD$_3$OD) δ ppm: 8.49 (d, J=4.4 Hz, 1H), 7.87 (d, J=7.6 Hz, 1H), 7.43-7.37 (m, 2H), 7.31 (d, J=2.8 Hz, 1H), 7.05 (dd, J=3.2 and 8.8 Hz, 1H), 5.31 (s, 2H), 5.28 (s, 2H), 4.15-4.08 (m, 1H), 4.05-3.97 (m, 2H), 2.84-2.75 (m, 2H), 2.47 (s, 3H), 2.46 (s, 3H), 2.43 (s, 3H), 2.29 (s, 3H).

Example 23. Preparation of (R)-1-{4-Chloro-3-[5-chloro-4-(5,7-dihydro-pyrrolo[3,4-b]pyridine-6-yl)-6-(3,5-dimethyl-isoxazol-4-yl)-pyrimidin-2-yl]-phenoxy}-3-methyl-amino-propan-2-ol

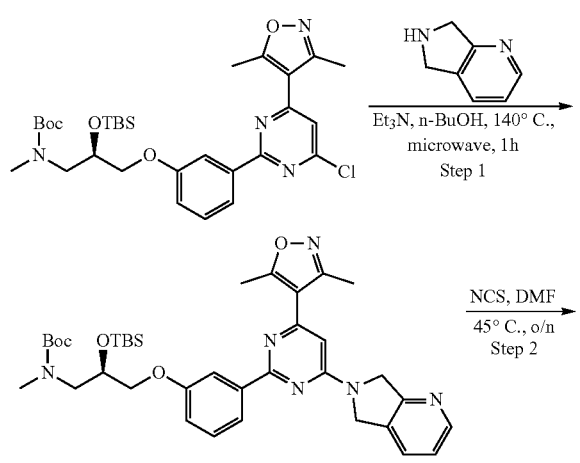

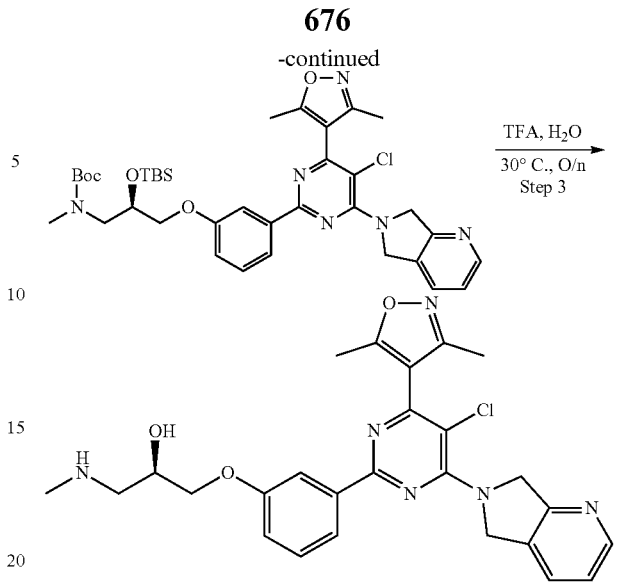

Step 1: Synthesis of (R)-tert-butyl 2-(tert-butyldimethylsilyloxy)-3-(3-(4-(3,5-di-methylisoxazol-4-yl)-6-(5H-pyrrolo[3,4-b]pyridin-6(7H)-yl)pyrimidin-2-yl) phenoxy)propyl (methyl)carbamate A reaction pressure vessel was charged with a mixture of (R)-tert-butyl 2-(tert-butyldimethylsilyloxy)-3-(3-(4-chloro-6-(3,5-dimethylisoxazol-4-yl)pyrimidin-2-yl)phenoxy)propyl(methyl)carbamate (100 mg, 0.16 mmol); 6,7-dihydro-5H-pyrrolo[3,4-b]pyridine (20 mg, 0.24 mmol), triethylamine (34 mg, 0.33 mmol) and n-BuOH (3 mL), capped, placed in a microwave reactor and irradiated for 60 min. at external temperature of 140° C. After being cooled down to room temperature, the mixture was diluted with water (20 mL) and extracted with EtOAc (20 mL×3). The organic layers were combined, dried over Na$_2$SO$_4$, filtered and concentrated. The crude was purified by preparative TLC with (petroleum ether/EtOAc=3/1) to give (R)-tert-butyl 2-(tert-butyldimethylsilyloxy)-3-(3-(4-(3,5-dimethyl-isoxazol-4-yl)-6-(5H-pyrrolo[3,4-b]pyridin-6(7H)-yl)pyrimidin-2-yl)phenoxy) propyl(methyl)carbamate as a white solid (95 mg, 84% yield). ESI-LCMS (m/z): 687.3 [M+H]$^+$.

Step 2: Synthesis of tert-butyl (R)-2-(tert-butyldimethylsilyloxy)-3-(4-chloro-3-(5-chloro-4-(3,5-dimethylisoxazol-4-yl)-6-(5H-pyrrolo[3,4-b]pyridin-6(7H)-yl) pyrimidin-2-yl)phenoxy)propyl(methyl) carbamate A solution of (R)-tert-butyl 2-(tert-butyldimethyl silyloxy)-3-(3-(4-(3,5-dimethyl-isoxazol-4-yl)-6-(5H-pyrrolo[3,4-b]pyridin-6(7H)-yl)pyrimidin-2-yl)phenoxy)propyl (methyl)carbamate (95 mg, 0.14 mmol) in DMF (4 mL) was treated with NCS (110 mg, 0.83 mmol) and the reaction mixture was stirred at 45° C. for 16 h. After being cooled down to room temperature, the mixture was diluted with EtOAc (30 mL) and washed with water (40 mL×2). The organic layer was dried over Na$_2$SO$_4$, filtered and concentrated in vacuo and the resulting residue was purified by preparative TLC (petroleum ether/EtOAc=1/1) to give tert-butyl (R)-2-(tert-butyldimethylsilyloxy)-3-(4-chloro-3-(5-chloro-4-(3,5-di-methyl isoxazol-4-yl)-6-(5H-pyrrolo[3,4-b]pyridine-6(7H)-yl)pyrimidin-2-yl)phenoxy)propyl (methyl) carbamate as a light yellow solid (50 mg, 48% yield). ESI-LCMS (m/z): 755.3 [M+H]+.

Step 3: Synthesis of (R)-1-{4-Chloro-3-[5-chloro-4-(5,7-dihydro-pyrrolo[3,4-b]pyridine-6-yl)-6-(3,5-dimethyl-isoxazol-4-yl)-pyrimidin-2-yl]-phenoxy}-3-methyl-amino-propan-2-ol A solution of tert-butyl (R)-2-(tert-butyldimethylsilyloxy)-3-(4-chloro-3-(5-chloro-4-(3,5-di-methylisoxazol-4-yl)-6-(5H-pyrrolo[3,4-b]pyridin-6(7H)-yl)pyrimidin-2-yl) phenoxy)propyl (methyl)carbamate (50 mg, 0.066 mmol) in 90% TFA (3 mL) was stirred at room temperature for 16 h, the solvent was then removed in vacuo and the resulting residue was dissolved in MeOH (5 ml), treated with ammonia till pH 7-8 and concentrated. The residue was purified by preparative HPLC to give (2R)-1-(4-chloro-3-(5-chloro-4-(3,5-di-methylisoxazol-4-yl)-6-(5H-pyrrolo [3,4-b]pyridin-6(7H)-yl)pyrimidin-2-yl)phenoxy)-3-(methylamino)propan-2-ol as a white solid (10 mg, 29% yield). ESI-LCMS (m/z): 541.2 [M+H]+; 1HNMR (400 MHz, CD3OD) δ ppm: 8.51 (d, J=4.0 Hz, 1H), 7.89 (d, J=8.4 Hz, 1H), 7.45-7.40 (m, 1H), 7.37 (d, J=2.8 Hz, 1H), 7.32-7.31 (d, 1H), 7.08 (dd, J=2.8 and 8.8 Hz, 1H), 5.44 (s, 2H), 5.41 (s, 2H), 4.16-4.10 (m, 1H), 4.08-4.00 (m, 2H), 2.90-2.70 (m, 2H), 2.49 (s, 3H), 2.47 (s, 3H), 2.32 (s, 3H).

Example 24. Preparation of methyl 4-(5-chloro-2-(2-chloro-5-((R)-2-hydroxy-3-(methylamino)propoxy)phenyl)-6-(3,5-dimethylisoxazol-4-yl)pyrimidin-4-ylamino) piperidine-1-carboxylate

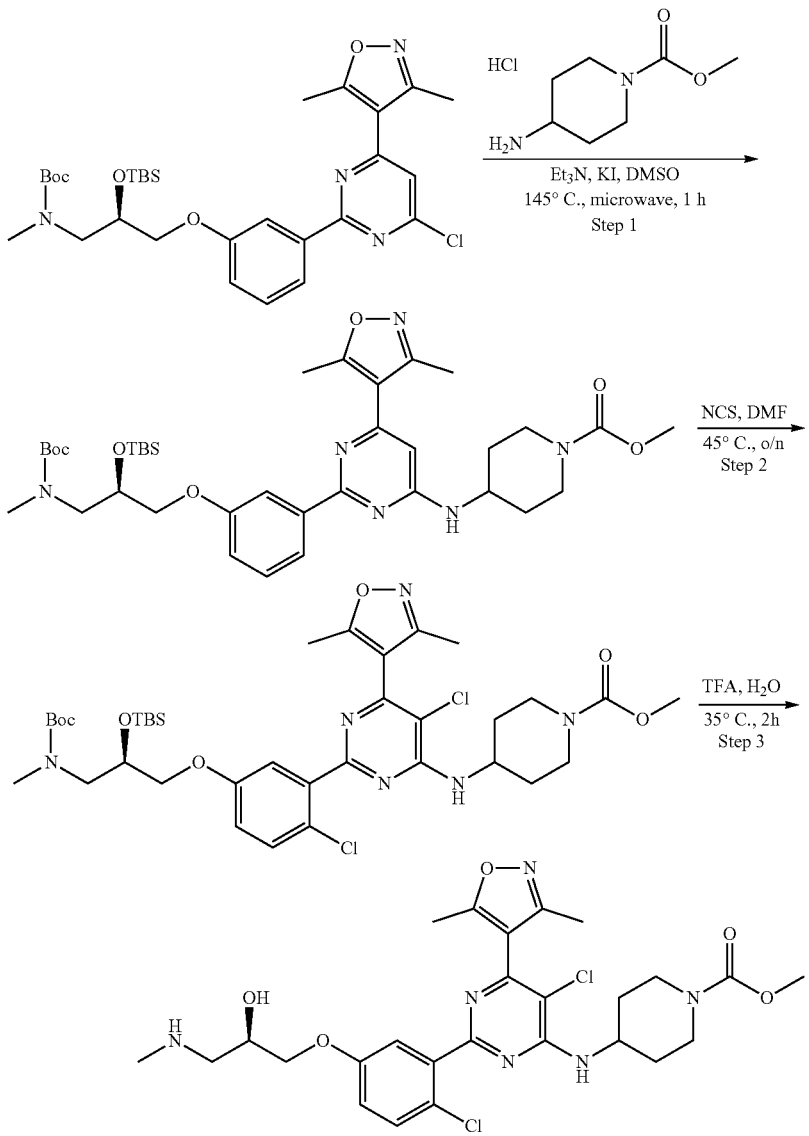

Step 1: Synthesis of (R)-methyl 4-(2-(3-(3-(tert-butoxycarbonyl(methylamino))-2-(tert-butyldimethylsilyloxy)propoxy)phenyl)-6-(3,5-dimethylisoxazol-4-yl)pyrimidin-4-ylamino)piperidine-1-carboxylate A reaction pressure vessel was charged with a mixture of (R)-tert-butyl 2-(tert-butyldimethylsilyloxy)-3-(3-(4-chloro- 6-(3,5-di-methylisoxazol-4-yl)pyrimidin-2-yl)phenoxy)propyl(methyl)carbamate (850 mg, 1.41 mmol), methyl 4-amino piperidine-1-carboxylate HCl (or any other suitable substituted primary or secondary amine, 5.65 mmol), Et₃N (714 mg, 7.06 mmol), KI (116 mg, 0.70 mmol) and DMSO (15 mL), capped, placed in a microwave reactor and irradiated for 60 min. at external temperature of 145° C., cooled down to room temperature, diluted with water (50 mL) and extracted with EtOAc (50 mL×3). The organic layers were combined, concentrated and the resulting residue was purified by preparative TLC (petroleum ether/EtOAc=1.5/1) to give the (R)-methyl 4-(2-(3-(3-(tert-butoxy-carbonyl (methyl)amino)-2-(tert-butyldimethylsilyloxy)propoxy) phenyl)-6-(3,5-di-methyl isoxazol-4-yl)pyrimidin-4-ylamino)piperidine-1-carboxylate (880 mg, 86% yield) as a pale yellow solid. ESI-LCMS (m/z): 725.5 [M+1]⁺.

Step 2: Synthesis of methyl 4-(2-(5-((R)-3-(tert-butoxycarbonyl(methyl)amino)-2-(tert-butyldimethylsilyloxy)propoxy)-2-chlorophenyl)-5-chloro-6-(3,5-dimethyl-isoxazol-4-yl)pyrimidin-4-ylamino) piperidine-1-carboxylate A solution of (R)-methyl 4-(2-(3-(3-(tert-butoxycarbonyl (methyl)amino)-2-(tert-butyldimethylsilyloxy)propoxy) phenyl)-6-(3,5-dimethyl isoxazol-4-yl)pyrimidin-4-ylamino)piperidine-1-carboxylate (800 mg, 1.10 mmol) in DMF (8 mL) was treated with a solution of NCS (440 mg, 3.31 mmol) in DMF (0.5 mL), the reaction flask was place in a heating bath set at 45° C. and the mixture stirred for 16 h., cooled down to room temperature, diluted with water (50 mL) and extracted with EtOAc (50 mL×3), The organic layers were combined, washed with aqueous saturated Na₂S₂O₃ solution (30 mL) and brine (30 mL), then dried over Na₂SO₄, filtered and concentrated. The residue was purified by preparative TLC (petroleum ether/EtOAc=1.5/1) to give 4-(2-(5-((R)-3-(tert-butoxycarbonyl(methyl)amino)-2-(tert-butyldimethylsilyloxy) propoxy)-2-chlorophenyl)-5-chloro-6-(3,5-dimethylisoxazol-4-yl)pyrimidin-4-ylamino) piperidine-1-carboxylate (600 mg, 69% yield) as a pale yellow solid. ESI-LCMS (m/z): 793.4 [M+1]⁺. The side product from silyl ester cleavage, methyl 4-(2-(5-((R)-3-(tert-butoxy carbonyl(methyl)amino)-2-hydroxylpropoxy)-2-chloro phenyl)-5-chloro-6-(3,5-di methyl isoxazol-4-yl) pyrimidin-4-ylamino)piperidine-1-carboxylate] was also isolated (120 mg, 16% yield) as a pale yellow solid. ESI-LCMS (m/z): 678.7 [M+1]⁺

Step 3: Synthesis of methyl 4-(5-chloro-2-(2-chloro-5-((R)-2-hydroxy-3-(methyl-amino)propoxy) phenyl)-6-(3,5-dimethylisoxazol-4-yl)pyrimidin-4-ylamino) piperidine-1-carboxylate A solution of 4-(2-(5-((R)-3-(tert-butoxycarbonyl (methyl)amino)-2-(tert-butyl dimethylsilyloxy) propoxy)-2-chlorophenyl)-5-chloro-6-(3,5-dimethylisoxazol-4-yl) pyrimidin-4-yl-amino)piperidine-1-carboxylate (600 mg, 0.76 mmol) in 90% TFA (6 mL) was stirred at 35° C. for 3 h, the solvent was removed in vacuo, and the residue was dissolved in MeOH (3 ml), treated with ammonia till pH 7-8 and then concentrated again. The residue was purified by preparative HPLC to give methyl 4-(5-chloro-2-(2-chloro-5-((R)-2-hydroxy-3-(methyl amino)propoxy)phenyl)-6-(3,5-dimethylisoxazol-4-yl)pyrimidin-4-ylamino)piperidine-1-carboxylate as a formic acid salt (white solid, 385 mg, 81% yield). ESI-LCMS (m/z): 579.2 [M+1]⁺; ¹HNMR (400 MHz, MeOD) δ ppm: 8.50 (br s, 1H), 7.43-7.46 (d, J=9.2 Hz, 1H), 7.28-7.30 (d, J=3.2 Hz, 1H), 7.06-7.10 (dd, J=9.2 and 3.2 Hz, 1H), 4.43-4.37 (m, 1H), 4.29-4.14 (m, 3H), 4.11-4.03 (m, 2H), 3.71 (s, 3H), 3.29-3.13 (m, 2H), 2.96 (br s, 2H), 2.76 (s, 3H), 2.43 (s, 3H), 2.29 (s, 3H), 2.06-2.03 (m, 2H), 1.70-1.59 (m, 2H).

Example 25. Preparation of (R)-1-{4-Chloro-3-[4-(5,7-dihydro-pyrrolo[3,4-d]pyrimidin-6-yl)-6-(3,5-dimethyl-isoxazol-4-yl)-5-methyl-pyrimidin-2-yl]-phenoxy}-3-methylamino-propan-2-ol

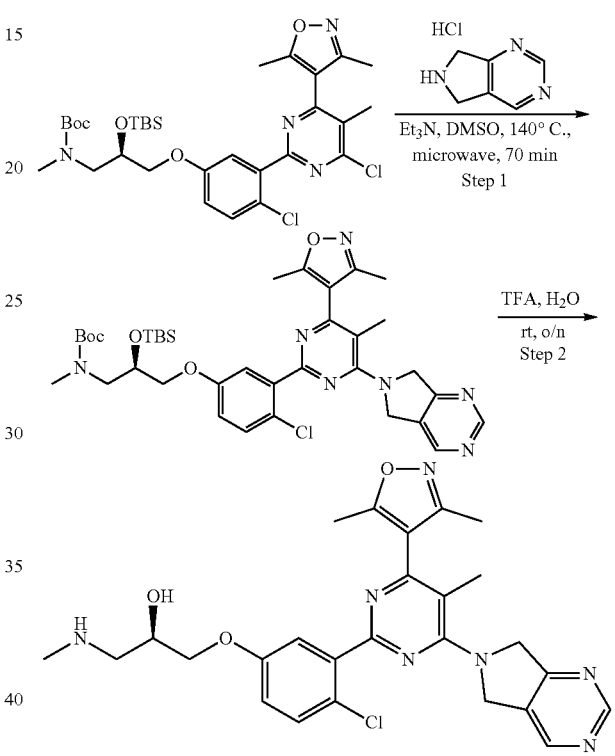

Step 1: Synthesis of tert-butyl (R)-2-(tert-butyldimethylsilyloxy)-3-(4-chloro-3-(4-(3,5-dimethylisoxazol-4-yl)-5-methyl-6-(5H-pyrrolo[3,4-d]pyrimidin-6(7H)-yl)pyrimidin-2-yl)phenoxy)propyl(methyl) carbamate A reaction pressure vessel was charged with a mixture of (R)-(2-(tert-Butyl-dimethyl-silanyloxy)-3-{4-chloro-3-[4-chloro-6-(3, 5-dimethyl-isoxazol-4-yl)-5-methyl-pyrimidin-2-yl]-phenoxy}-propyl)-methyl-carbamic acid tert-butyl ester (120 mg, 0.18 mmol); 6,7-dihydro-5H-pyrrolo[3,4-d] pyrimidine HCl (or any other suitably substituted secondary amine 0.28 mmol) and triethylamine (0.5 mL, 3.5 mmol) in DMSO (2 mL), capped, placed in a microwave reactor and irradiated for 70 min. at external temperature of 140° C. After being cooled down to room temperature, the mixture was diluted with water (20 mL) and extracted with EtOAc (20 mL×3). The organic layers were combined, dried over Na₂SO₄, filtered and concentrated. The residue was purified by chromatographic column on silicagel to give (R)-(2-(tert-butyl-dimethyl-silanyloxy)-3-{4-chloro-3-[4-(5,7-dihydro-pyrrolo [3,4-d]pyrimidin-6-yl)-6-(3,5-dimethyl-isoxazol-4- yl)-5-methyl-pyrimidin-2-yl]-phenoxy}-propyl)-methyl-carbamic acid tert-butyl ester (106 mg, 81% yield). ESI-LCMS (m/z): 735.8[M+H]+.

Step 2: Synthesis of (2R)-1-(4-chloro-3-(4-(3,5-dimethylisoxazol-4-yl)-5-methyl-6-(5H-pyrrolo[3,4-d]pyrimidin-6(7H)-yl)pyrimidin-2-yl)phenoxy)-3-(methylamino) propan-2-ol tert-Butyl (R)-2-(tert-butyldimethylsilyloxy)-3-(4-chloro-3-(4-(3,5-dimethyl-isoxazol-4-yl)-5-methyl-6-(5H-pyrrolo[3,4-d]pyrimidin-6(7H)-yl)pyrimidin-2-yl) phenoxy) propyl (methyl) carbamate (100 mg, 0.13 mmol) was treated with 90% TFA (3 mL) and the mixture was stirred at room temperature for 16 h, concentrated in vacuo, the residue was dissolved in MeOH (2 ml) and the resulting solution was adjusted to pH 7-8 by the addition of ammonia, then concentrated again. The residue was purified by preparative HPLC to give (2R)-1-(4-chloro-3-(4-(3,5-dimethylisoxazol-4-yl)-5-methyl-6-(5H-pyrrolo[3,4-d] pyrimidin-6(7H)-yl) pyrimidin-2-yl)phenoxy)-3-(methylamino)propan-2-ol (45 mg, 64% yield). ESI-LCMS (m/z): 521.9 [M+H]+; $^1$HNMR (400 MHz, CD$_3$OD) δ ppm: 9.12 (s, 1H), 8.82 (s, 1H), 7.42 (d, J=8.8 Hz, 1H), 7.32 (d, J=2.4 Hz, 1H), 7.066 (dd, J=2.8 and 8.4 Hz, 1H), 5.36 (s, 2H), 5.31 (s, 2H), 4.15-4.09 (m, 1H), 4.07-4.00 (m, 2H), 2.87-2.72 (m, 2H), 2.48 (s, 3H), 2.46 (s, 3H), 2.44 (s, 3H), 2.30 (s, 3H).

Example 26. Preparation of (2R)-1-(4-chloro-3-(4-(2-cyclopropyl-5H-pyrrolo[3,4-d]pyrimidin-6(7H)-yl)-6-(3,5-dimethylisoxazol-4-yl)-5-methylpyrimidin-2-yl) phenoxy)-3-(methylamino)propan-2-ol

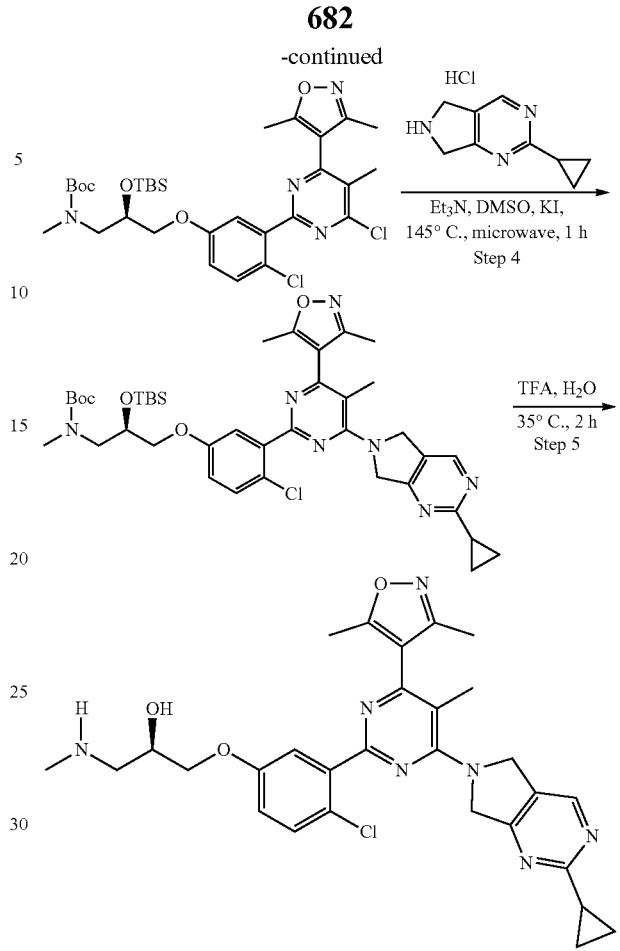

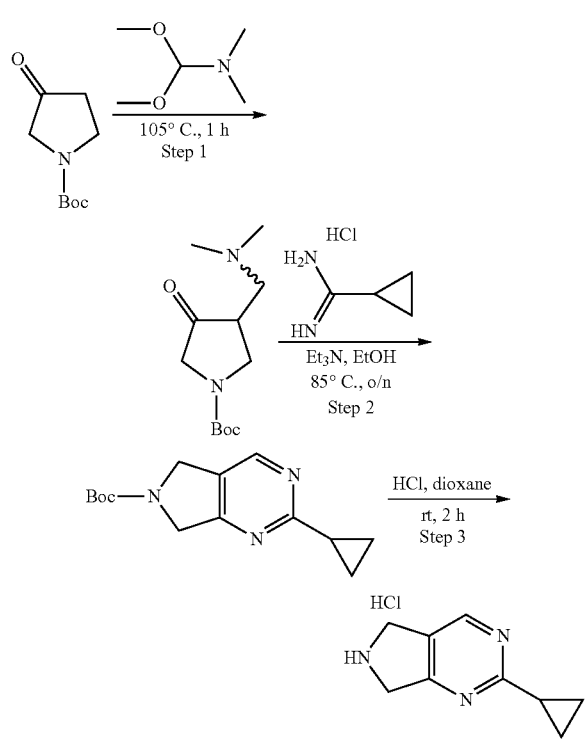

Step 1: Synthesis of tert-butyl 3-((dimethylamino)methylene)-4-oxopyrrolidine-1-carboxylate A suspension of tert-butyl 3-oxopyrrolidine-1-carboxylate (10 g, 54.05 mmol) in 1,1-dimethoxy-N,N-dimethyl-methanamine (120 mL) was stirred at 105° C. for 1 h., cooled down to room temperature, the solvent was removed in vacuo and the residue was purified by chromatographic column on silicagel (DCM/MeOH=60/1 to 20/1) to give tert-butyl 3-((di-methyl-amino)methylene)-4-oxopyrrolidine-1-carboxylate (10.78 g, 83% yield). ESI-LCMS (m/z): 241.2[M+1]+; $^1$HNMR (400 MHz, CDCl$_3$) δ ppm: 7.26 (s, 1H), 4.57 (s, 2H), 3.86 (s, 2H), 3.09 (s, 6H), 1.48 (s, 9H).

Step 2: Synthesis of tert-butyl 2-cyclopropyl-5H-pyrrolo[3, 4-d]pyrimidine-6(7H)-carboxylate To a solution of tert-butyl 3-((dimethylamino)methylene)-4-oxopyrrolidine-1-carboxylate (400 mg, 1.67 mmol) in EtOH (15 mL) was added cyclopropane-carboximidamide HCl (or any other suitably substituted carboximidamide, 8.29 mmol) and Et$_3$N (1.01 g, 10 mmol). The mixture was stirred at 85° C. for 16 h., cooled down to room temperature, the solvent was removed in vacuo and the residue was purified by preparative TLC (petroleum ether/EtOAc=3/1) to give tert-butyl 2-cyclopropyl-5H-pyrrolo[3,4-d]pyrimidine-6(7H)-carboxylate (280 mg, 64% yield) as a pale yellow solid. ESI-LCMS (m/z): 262.2[M+1]+.

Step 3: Synthesis of 2-cyclopropyl-6,7-dihydro-5H-pyrrolo[3,4-d]pyrimidine HCl A solution of tert-butyl 2-cyclopropyl-5H-pyrrolo[3,4-d]pyrimidine-6(7H)-carboxylate (280 mg, 1.07 mmol) in MeOH (3 ml) was treated with 4N HCl in dioxane (5 ml) and the mixture was stirred at room temperature for 2 h. and then concentrated in vacuo to give 2-cyclo-propyl-6, 7-dihydro-5H-pyrrolo [3,4-d]pyrimidine hydrochloride (240 mg, crude) as a yellow solid, which was used directly for the next step without further purification. ESI-LCMS (m/z): 162.1 [M+1]$^+$. $^1$HNMR (400 MHz, DMSO-d6) δ ppm: 10.44 (br s, 2H), 8.67 (s, 1H), 4.54 (t, J=4.8 Hz, 2H), 4.43 (t, J=5.2 Hz, 2H), 2.28-2.21 (m, 1H), 1.11-1.06 (m, 2H), 1.02-0.98 (m, 2H).

Step 4: Synthesis of tert-butyl (R)-2-(tert-butyldimethylsilyloxy)-3-(4-chloro-3-(4-(2-cyclopropyl-5H-pyrrolo[3,4-d]pyrimidin-6(7H)-yl)-6-(3,5-dimethyl-isoxazol-4-yl)-5-methyl pyrimidin-2-yl)phenoxy)propyl(methyl)carbamate A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (160 mg, 0.24 mmol), 2-cyclopropyl-6,7-dihydro-5H-pyrrolo[3,4-d]pyrimidine HCl (240 mg, crude from step 3), Et$_3$N (148 mg, 1.47 mmol), KI (20 mg, 0.12 mmol) and DMSO (3 mL), capped, placed in a microwave reactor and irradiated for 60 min. at external temperature of 145° C. After being cooled down to room temperature, the mixture was diluted with water (20 mL) and extracted with EtOAc (20 mL×3). The organic layers were combined, dried over Na$_2$SO$_4$, filtered, concentrated and the resulting residue was purified by preparative TLC (petroleum ether/EtOAc=2/1) to give tert-butyl (R)-2-(tert-butyl-dimethyl silyloxy)-3-(4-chloro-3-(4-(2-cyclopropyl-5H-pyrrolo[3,4-d]pyrimidin-6(7H)-yl)-6-(3, 5-dimethylisoxazol-4-yl)-5-methylpyrimidin-2-yl) phenoxy)propyl(methyl) carbamate (160 mg, 84% yield) as a pale yellow solid. ESI-LCMS (m/z): 776.3 [M+1]$^+$.

Step 5: Synthesis of (2R)-1-(4-chloro-3-(4-(2-cyclopropyl-5H-pyrrolo[3,4-d]pyrimidin-6(7H)-yl)-6-(3, 5-dimethylisoxazol-4-yl)-5-methylpyrimidin-2-yl) phenoxy)-3-(methyl amino) propan-2-ol A solution of tert-butyl (R)-2-(tert-butyldimethylsilyloxy)-3-(4-chloro-3-(4-(2-cyclopropyl-5H-pyrrolo[3,4-d] pyrimidin-6(7H)-yl)-6-(3,5-dimethylisoxazol-4-yl)-5-methyl pyrimidin-2-yl)phenoxy)propyl(methyl)carbamate (160 mg, 0.21 mmol) in 90% aqueous solution TFA (4 mL) was stirred at 35° C. for 2 h, the solvent was then removed in vacuo, and the residue was dissolved in MeOH (3 ml), treated with ammonia till pH 7-8 and then concentrated again. The residue was purified by preparative HPLC to give (2R)-1-(4-chloro-3-(4-(2-cyclopropyl-5H-pyrrolo[3,4-d] pyrimidin-6(7H)-yl)-6-(3,5-dimethyl-isoxazol-4-yl)-5-methyl pyrimidin-2-yl)phenoxy)-3-(methylamino)propan-2-ol (45 mg, 38% yield) as a white solid. ESI-LCMS (m/z): 561.7 [M+1]$^+$; $^1$HNMR (400 MHz, CD$_3$OD) δ ppm: 8.56 (s, 1H), 7.38 (d, J=8.8 Hz, 1H), 7.29 (d, J=2.8 Hz, 1H), 7.02 (dd, J=8.8 and 2.8 Hz, 1H), 5.23 (s, 2H), 5.17 (s, 2H), 4.13-4.04 (m, 1H), 4.02-3.94 (m, 2H), 2.82-2.68 (m, 2H), 2.43 (s, 3H), 2.40 (s, 3H), 2.39 (s, 3H), 2.30-2.20 (m, 4H), 1.15-1.06 (m, 4H).

Example 27. Preparation of (2R)-1-(4-chloro-3-(4-(3,5-dimethylisoxazol-4-yl)-6-(3-fluoro-5H-pyrrolo[3,4-b]pyridin-6(7H)-yl)-5-methylpyrimidin-2-yl)phenoxy)-3-(methyl-amino)propan-2-ol

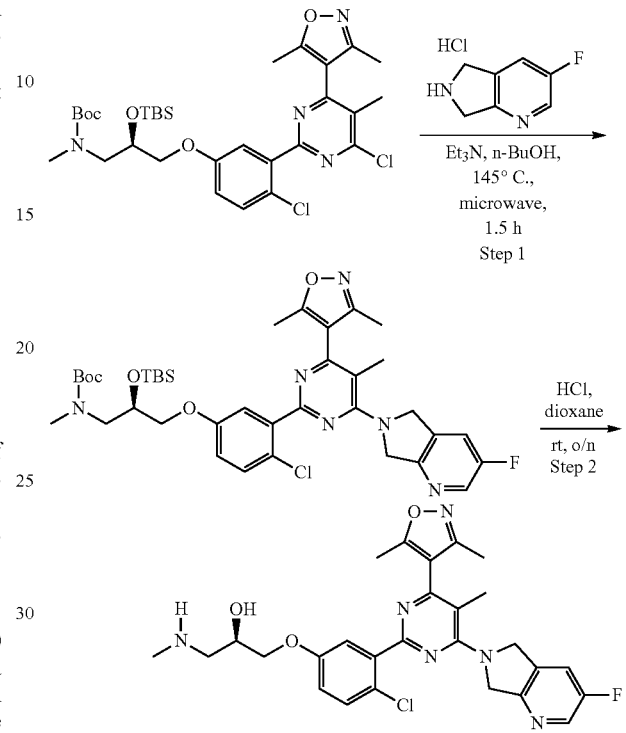

Step 1: Synthesis of tert-butyl (R)-2-(tert-butyldimethylsilyloxy)-3-(4-chloro-3-(4-(3,5-dimethylisoxazol-4-yl)-6-(3-fluoro-5H-pyrrolo[3,4-b]pyridin-6(7H)-yl)-5-methylpyrimidin-2-yl)phenoxy)propyl (methyl)carbamate A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (120 mg, 0.18 mmol), 3-fluoro-6,7-dihydro-5H-pyrrolo[3,4-b]pyridine HCl salt (or any other suitably substituted primary or secondary amine, 0.36 mmol), triethylamine (56 mg, 0.55 mmol) and n-BuOH (1.5 mL), capped, placed in a microwave reactor and irradiated for 90 min. at external temperature of 145° C., cooled down to room temperature, the mixture was diluted with water (50 mL) and extracted with EtOAc (40 mL×3). The organic layers were combined, dried over Na$_2$SO$_4$, concentrated and the residue was purified by preparative TLC (petroleum ether/EtOAc=2/1) to give tert-butyl (R)-2-(tert-butyldimethylsilyloxy)-3-(4-chloro-3-(4-(3,5-di-methyl isoxazol-4-yl)-6-(3-fluoro-5H-pyrrolo[3,4-b]pyridin-6(7H)-yl)-5-methyl-pyrimidin-2-yl) phenoxy) propyl(methyl)carbamate as a white solid (110 mg, 79% yield). ESI-LCMS (m/z): 752.8[M+H]$^+$.

Step 2: Synthesis of (2R)-1-(4-chloro-3-(4-(3,5-dimethylisoxazol-4-yl)-6-(3-fluoro-5H-pyrrolo[3,4-b]pyridin-6(7H)-yl)-5-methylpyrimidin-2-yl)phenoxy)-3-(methyl-amino)propan-2-ol A solution of tert-butyl (R)-2-(tert-butyldimethylsilyloxy)-3-(4-chloro-3-(4-(3,5-dimethyl-isoxazol-4-yl)-6-(3- fluoro-5H-pyrrolo[3,4-b]pyridin-6(7H)-yl)-5-methyl pyrimidin-2-yl)phenoxy)propyl(methyl)carbamate (110 mg, 0.14 mmol) in 4N HCl in dioxane (2 mL) was stirred at room temperature for 16 h., the solvent was then removed in vacuo, and the residue was dissolved in MeOH (3 ml), treated with ammonia till pH 7-8 and then concentrated again. The residue was purified by preparative HPLC to give (2R)-1-(4-chloro-3-(4-(3,5-dimethylisoxazol-4-yl)-6-(3-fluoro-5H-pyrrolo[3,4-b]pyridin-6(7H)-yl)-5-methylpyrimidin-2-yl)phenoxy)-3-(methylamino)propan-2-ol (35 mg, 45% yield). ESI-LCMS (m/z): 539.2 [M+H]+; 1HNMR (400 MHz, CD3OD) δ ppm: 8.42 (s, 1H), 7.71-7.69 (m, 1H), 7.44-7.41 (d, J=8.8 Hz, 1H), 7.32-7.30 (d, J=2.8 Hz, 1H), 7.08-7.05 (dd, J=2.8 Hz and 8.8 Hz, 1H), 5.32 (s, 2H), 5.25 (s, 2H), 4.16-4.09 (m, 1H), 4.06-3.99 (m, 2H), 2.90-2.77 (m, 2H), 2.51 (s, 3H) 2.46 (s, 3H), 2.44 (s, 3H), 2.30 (s, 3H).

Example 28. Preparation of (R)-1-{4-Chloro-3-[4-(3,5-dimethyl-isoxazol-4-yl)-5-methyl-6-(1-cyclopropyl-4,6-dihydro-1H-pyrrolo[3,4-c]pyrazol-5-yl)pyrimidin-2-yl]-phenoxy}-3-methylamino-propan-2-ol

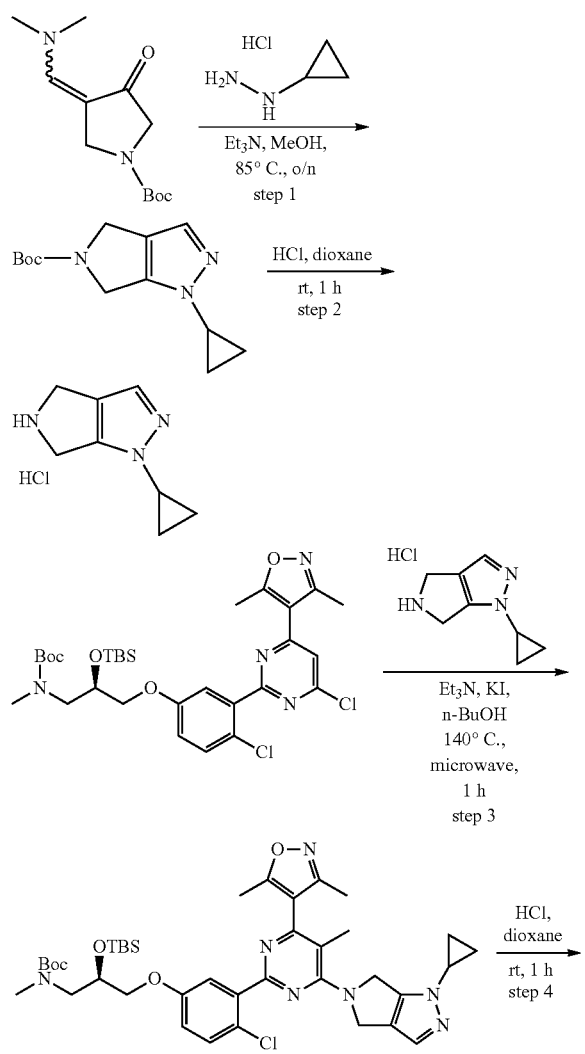

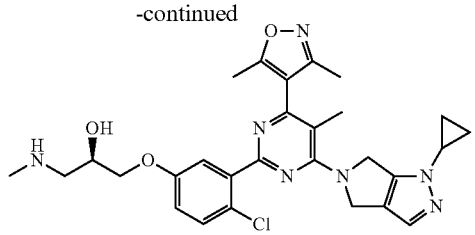

Step 1: Synthesis of tert-butyl 1-cyclopropyl-4,6-dihydropyrrolo[3,4-c]pyrazole-5(1H)-carboxylate To a solution of tert-butyl 3-((dimethylamino)methylene)-4-oxopyrrolidine-1-carboxylate (100 mg, 0.42 mmol) in MeOH (3 mL) was added cyclopropylhydrazine hydrochloride (or any other suitably substituted hydrazine, 0.63 mmol) followed by Et3N (84 mg, 0.83 mmol), and the mixture was heated at 85° C. for 16 h., cooled down to room temperature, diluted with water (20 mL) and extracted with EtOAc (20 mL×3). The organic layers were combined, dried over Na2SO4, filtered and concentrated to give tert-butyl 1-cyclopropyl-4,6-dihydropyrrolo[3,4-c]pyrazole-5(1H)-carboxylate as a yellow solid, which was used directly without further purification. Assumed quantitative yield. ESI-LCMS (m/z): 250.2 [M+1]+.

Step 2: Synthesis of 1-cyclopropyl-1,4,5,6-tetrahydropyrrolo[3,4-c]pyrazole HCl

A solution of tert-butyl 1-cyclopropyl-4,6-dihydropyrrolo[3,4-c]pyrazole-5(1H)-carboxylate (0.42 mmol) in 4N HCl in dioxane (2 mL) was stirred at room temperature for 16 h. and then concentrated in vacuo to give 1-cyclopropyl-1,4,5,6-tetrahydropyrrolo[3,4-c]pyrazole as HCl salt, which was used directly for the next step without further purification. Assumed quantitative yield ESI-LCMS (m/z): 150.3 [M+1]+.

Step 3: Synthesis of (R)-(2-(tert-Butyl-dimethyl-silanyloxy)-3-{4-chloro-3-[4-(3,5-dimethyl-isoxazol-4-yl)-5-methyl-6-(1-cyclopropyl-4,6-dihydro-1H-pyrrolo[3,4-c]pyrazol-5-yl)-pyrimidin-2-yl]-phenoxy}-propyl)-methyl-carbamic acid tert-butyl ester A reaction pressure vessel was charged with a mixture of tert-butyl (2R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (200 mg, 0.31 mmol), 1-cyclopropyl-1,4, 5,6-tetrahydropyrrolo[3,4-c]pyrazole HCl salt (0.42 mmol), KI (102 mg, 0.62 mmol), Et3N (62 mg, 0.62 mmol) and n-BuOH (3 mL), capped, placed in a microwave reactor and irradiated for 60 min. at external temperature of 140° C. After being cooled down to room temperature, the mixture was diluted with water (20 mL) and extracted with EtOAc (20 mL×3). The organic layers were combined, dried over Na2SO4, filtered, concentrated and the residue was purified by preparative TLC (petroleum ether/EtOAc=2/1) to obtain (R)-(2-(tert-butyl-dimethyl-silanyloxy)-3-{4-chloro-3-[4-(3,5-dimethyl-isoxazol-4-yl)-5-methyl-6-(1-cyclopropyl-4,6-dihydro-1H-pyrrolo[3,4-c]pyrazol-5-yl)-pyrimidin-2-yl]-phenoxy}-propyl)-methyl-carbamic acid tert-butyl ester (140 mg, 59% yield). ESI-LCMS (m/z): 764.4 [M+1]+.

Step 4: Synthesis of (R)-1-{4-Chloro-3-[4-(3,5-dimethyl-isoxazol-4-yl)-5-methyl-6-(1-cyclopropyl-4,6-dihydro-1H-pyrrolo[3,4-c]pyrazol-5-yl)pyrimidin-2-yl]-phenoxy}-3-methylamino-propan-2-ol A solution of (R)-(2-(tert-Butyl-dimethyl-silanyloxy)-3-{4-chloro-3-[4-(3,5-dimethyl-isoxazol-4-yl)-5-methyl-6-(1-cyclopropyl-4,6-dihydro-1H-pyrrolo[3,4-c]pyrazol-5-yl)-pyrimidin-2-yl]-phenoxy-propyl)-methyl-carbamic acid tert-butyl ester (140 mg, 0.18 mmol) in 4N HCl in dioxane (2 mL), was stirred at room temperature for 1 h, the solvent was then removed in vacuo, and the residue was dissolved in MeOH (3 ml), treated with ammonia till pH 7-8 and then concentrated again. The residue was purified by preparative HPLC to give (R)-1-{4-Chloro-3-[4-(3,5-dimethyl-isoxazol-4-yl)-5-methyl-6-(1-cyclopropyl-4,6-dihydro-1H-pyrrolo[3,4-c]pyrazol-5-yl)pyrimidin-2-yl]-phenoxy}-3-methylamino-propan-2-ol as a formic acid salt (white solid, 60 mg, 56% yield). ESI-LCMS (m/z): 550.2 [M+1]$^+$; $^1$HNMR (400 MHz, CD$_3$OD) δ ppm: 8.56 (s, 1H), 7.45-7.43 (d, J=8.8 Hz, 1H), 7.33 (s, 1H), 7.29 (d, J=3.2 Hz, 1H), 7.08 (dd, J=3.2 and 8.0 Hz, 1H), 5.15 (s, 2H), 5.01 (s, 2H), 4.28-4.22 (m, 1H), 4.11-4.03 (m, 2H), 3.63-3.57 (m, 1H), 3.28-3.12 (m, 2H), 2.75 (s, 3H), 2.43 (s, 6H), 2.29 (s, 3H), 1.14-1.05 (m, 4H).

Examples 29 and 30. Preparation of (2R)-1-{4-chloro-3-[4-(2,3-dimethyl-2,6-dihydro-4H-pyrrolo[3,4-c]pyrazol-5-yl)-6-(3,5-dimethyl-isoxazol-4-yl)-5-methyl-pyrimidin-2-yl]-phenoxy}-3-methylamino-propan-2-ol and (2R)-1-{4-Chloro-3-[4-(1,3-dimethyl-4,6-dihydro-1H-pyrrolo[3,4-c]pyrazol-5-yl)-6-(3,5-dimethyl-isoxazol-4-yl)-5-methyl-pyrimidin-2-yl]-phenoxy}-3-methylamino-propan-2-ol

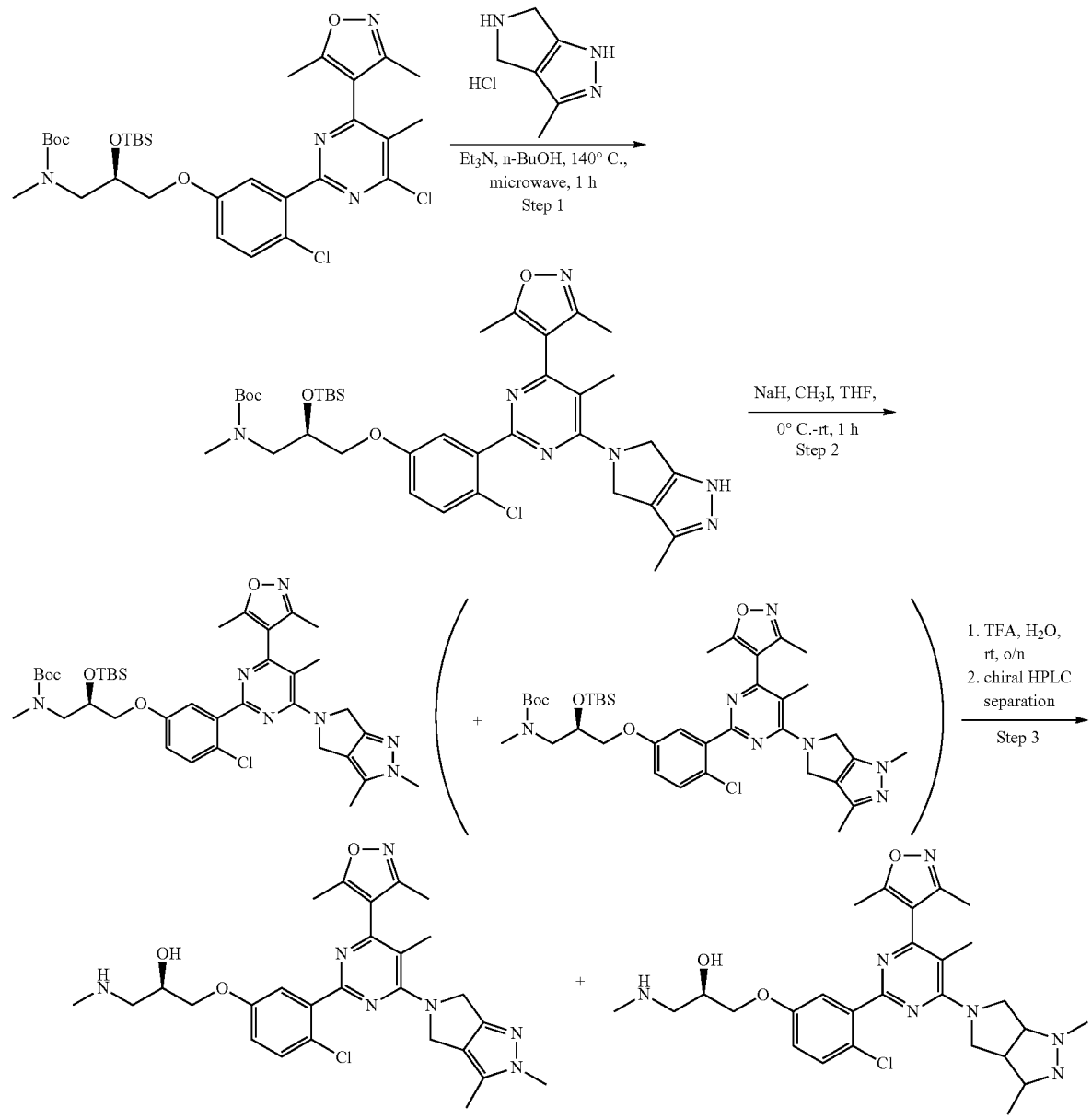

Step 1: Synthesis of (R)-(2-(tert-Butyl-dimethyl-silanyloxy)-3-{4-chloro-3-[4-(3,5-dimethyl-isoxazol-4-yl)-5-methyl-6-(3-methyl-4,6-dihydro-1H-pyrrolo[3,4-c]pyrazol-5-yl)pyrimidin-2-yl]phenoxy}propyl) methyl-carbamic acid tert-butyl ester A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (200 mg, 0.31 mmol); 3-methyl-1,4,5,6-tetrahydropyrrolo[3,4-c]pyrazole hydrochloride (74 mg, 0.46 mmol), Et₃N (63 mg, 0.62 mmol) and n-BuOH (2 mL), capped, placed in a microwave reactor and irradiated for 60 min. at external temperature of 140° C. After being cooled down to room temperature, the mixture was diluted with water (10 mL) and extracted with EtOAc (20 mL×2). The combined organic layers were washed with brine, dried over Na₂SO₄, filtered and concentrated. The residue was purified by preparative TLC (petroleum ether/EtOAc=1/1.5) to give (R)-(2-(tert-Butyl-dimethyl-silanyloxy)-3-{4-chloro-3-[4-(3,5-dimethyl-isoxazol-4-yl)-5-methyl-6-(3-methyl-4,6-dihydro-1H-pyrrolo[3,4-c]pyrazol-5-yl)pyrimidin-2-yl]phenoxy} propyl) methyl-carbamic acid tert-butyl ester as a light yellow solid (195 mg, 86% yield). ESI-LCMS (m/z): 738.3 [M+H]⁺.

Step 2: (R)-(2-(tert-Butyl-dimethyl-silanyloxy)-3-{4-chloro-3-[4-(2,3-dimethyl-2,6-dihydro-4H-pyrrolo[3,4-c]pyrazol-5-yl)-6-(3,5-dimethyl-isoxazol-4-yl)-5-methyl-pyrimidin-2-yl]-phenoxy}-propyl)-methyl-carbamic acid tert-butyl ester To a solution of (R)-(2-(tert-Butyl-dimethyl-silanyloxy)-3-{4-chloro-3-[4-(3,5-di-methyl-isoxazol-4-yl)-5-methyl-6-(3-methyl-4,6-dihydro-1H-pyrrolo[3,4-c]pyrazol-5-yl)pyrimidin-2-yl]phenoxy}propyl)methyl-carbamic acid tert-butyl ester (195 mg, 0.26 mmol) in dry THF (10 mL) stirred at 0° C. under nitrogen atmosphere, was added NaH (19 mg, 60%, 0.46 mmol), stirred for 5 minutes and then treated with neat MeI (56 mg, 0.39 mmol). The mixture was further stirred at room temperature for 1 h., diluted with water (20 mL) and extracted with EtOAc (20 mL×3). The combined organic layers were dried over Na₂SO₄, filtered and concentrated. The residue was purified by preparative TLC (petroleum ether/EtOAc=1/1.5) to give (R)-(2-(tert-butyl-dimethyl-silanyloxy)-3-{4-chloro-3-[4-(2,3-dimethyl-2,6-dihydro-4H-pyrrolo[3, 4-c]pyrazol-5-yl)-6-(3,5-dimethyl-isoxazol-4-yl)-5-methyl-pyrimidin-2-yl]-phenoxy}-propyl)-methyl-carbamic acid tert-butyl ester along with its inseparable regioisomer (R)-(2-(tert-butyl-dimethyl-silanyloxy)-3-{4-chloro-3-[4-(1,3-dimethyl-4,6-dihydro-1H-pyrrolo[3,4-c]pyrazol-5-yl)-6-(3,5-dimethyl-isoxazol-4-yl)-5-methyl-pyrimidin-2-yl]-phenoxy}-propyl)-methyl-carbamic acid tert-butyl ester as a yellow solid (199 mg, 100% yield). ESI-LCMS (m/z): 752.3 [M+H]⁺.

Step 3: Synthesis of (2R)-1-{4-Chloro-3-[4-(2,3-dimethyl-2,6-dihydro-4H-pyrrolo[3,4-c]pyrazol-5-yl)-6-(3,5-dimethyl-isoxazol-4-yl)-5-methyl-pyrimidin-2-yl]-phenoxy}-3-methylamino-propan-2-ol A solution of the mixture of regioisomers from previous step (199 mg, 0.26 mmol) in 90% TFA (6 mL) was stirred at room temperature for 16 h; the solvent was then removed in vacuo and the resulting residue was dissolved in MeOH (3 ml), treated with ammonia till pH 7-8 and concentrated. The residue was purified by preparative HPLC to give (2R)-1-{4-chloro-3-[4-(2,3-dimethyl-2,6-dihydro-4H-pyrrolo[3,4-c]pyrazol-5-yl)-6-(3,5-di-methyl-isoxazol-4-yl)-5-methyl-pyrimidin-2-yl]-phenoxy}-3-methylamino-propan-2-ol and its inseparable regioisomer 1-{4-Chloro-3-[4-(1,3-dimethyl-4,6-dihydro-1H-pyrrolo[3,4-c]pyrazol-5-yl)-6-(3, 5-dimethyl-isoxazol-4-yl)-5-methyl-pyrimidin-2-yl]-phenoxy}-3-methylamino-propan-2-ol (86 mg, 60% yield). The mixture (75 mg) was separated by HPLC to obtain pure (2R)-1-{4-chloro-3-[4-(2,3-dimethyl-2,6-dihydro-4H-pyrrolo[3,4-c]pyrazol-5-yl)-6-(3,5-di methyl-isoxazol-4-yl)-5-methyl-pyrimidin-2-yl]-phenoxy}-3-methylamino-propan-2-ol (16 mg recovered). ESI-LCMS (m/z): 538.2 [M+H]⁺. ¹HNMR (400 MHz, CD₃OD) δ ppm: 7.28 (d, J=8.8 Hz, 1H), 7.16 (d, J=1.6 Hz, 1H), 6.92 (dd, J=1.2 and 8.8 Hz, 1H), 4.86 (s, 2H), 4.84 (s, 2H), 4.05-3.95 (m, 1H), 3.94-3.85 (m, 2H), 3.68 (s, 3H), 2.80-2.62 (m, 2H), 2.37 (s, 3H), 2.30 (s, 3H), 2.28 (s, 3H), 2.21 (s, 3H), 2.16 (s, 3H); along with its regioisomer (2R)-1-{4-Chloro-3-[4-(1,3-dimethyl-4,6-dihydro-1H-pyrrolo[3,4-c]pyrazol-5-yl)-6-(3,5-dimethyl-isoxazol-4-yl)-5-methyl-pyrimidin-2-yl]-phenoxy}-3-methylamino-propan-2-ol (24 mg). ESI-LCMS (m/z): 538.2 [M+H]⁺. ¹HNMR (400 MHz, CD₃OD) δ ppm: 7.28 (d, J=8.4 Hz, 1H), 7.15 (d, J=2.0 Hz, 1H), 6.92 (dd, J=2.8 and 8.8 Hz, 1H), 4.93 (s, 2H), 4.85 (s, 2H), 4.04-3.96 (m, 1H), 3.94-3.85 (m, 2H), 3.66 (s, 3H), 2.78-2.60 (m, 2H), 2.35 (s, 3H), 2.29 (s, 3H), 2.28 (s, 3H), 2.16 (s, 3H), 2.10 (s, 3H).

Example 31. -6-(3,5-dimethyl-isoxazol-4-yl)-5-methyl-pyrimidin-2-yl]-phenoxy}-3-methyl-amino-propan-2-ol

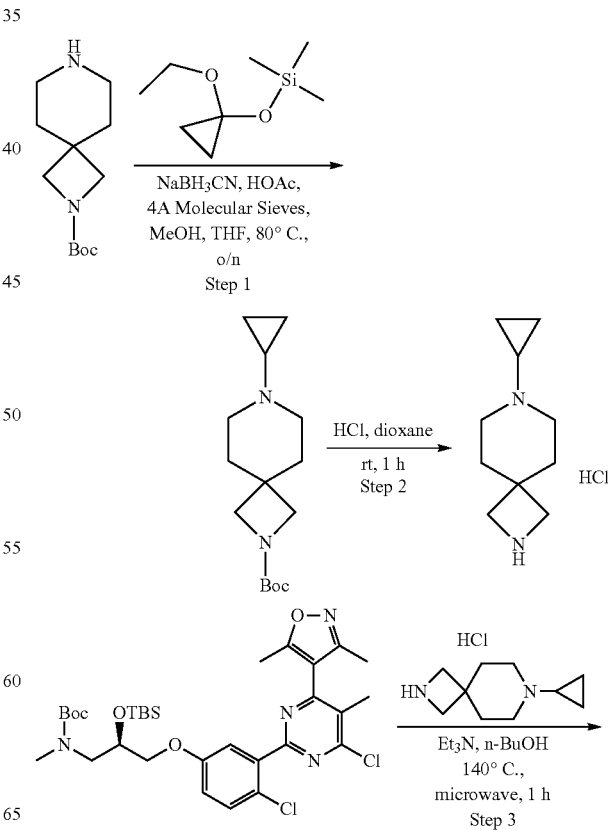

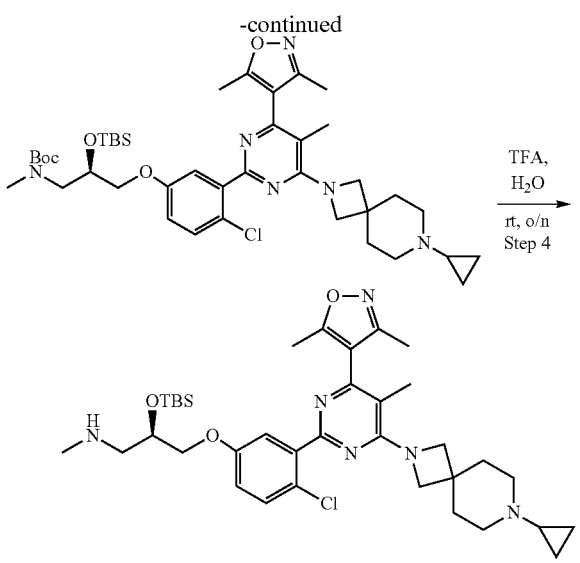

Step 1: Synthesis of 7-Cyclopropyl-2,7-diaza-spiro [3.5]nonane-2-carboxylic acid tert-butyl ester To a solution of 2,7-Diaza-spiro[3.5]nonane-2-carboxylic acid tert-butyl ester (452 mg, 2.0 mmol) in MeOH and THF (1/1, 12 mL) was added (1-ethoxy-cyclo-propoxy)trimethylsilane (696 mg, 4.0 mmol), 4A molecular sieves (450 mg), HOAc (240 mg, 4.0 mmol) and NaBH$_3$CN (504 mg, 8.0 mmol). The mixture was stirred at 80° C. for 16 h.; cooled down to room temperature, filtered; the filtrate was diluted with water (40 mL) and extracted with EtOAc (50 mL×3). The organic layers were combined, dried over Na$_2$SO$_4$, filtered and concentrated to give 7-cyclo propyl-2,7-diaza-spiro[3.5]nonane-2-carboxylic acid tert-butyl ester as a white solid (550 mg, 100% yield), which was used for the next step without further purification. ESI-LCMS (m/z): 267.0 [M+H]$^+$.

Step 2: Synthesis of 7-Cyclopropyl-2,7-diaza-spiro[3.5]nonane HCl salt

7-Cyclopropyl-2,7-diaza-spiro[3.5]nonane-2-carboxylic acid tert-butyl ester (550 mg) was dissolved 4 N HCl in dioxane (6 ml) and the solution was stirred at room temperature for 1 h., and then concentrated in vacuo to give 7-cyclo propyl-2,7-diaza-spiro[3.5]nonane as HCl salt (550 mg, crude), which was used for the next step without further purification. ESI-LCMS (m/z): 167.1 [M+H]$^+$.

Step 3: Synthesis of (R)-(2-(tert-Butyl-dimethyl-silanyloxy)-3-{4-chloro-3-[4-(7-cyclopropyl-2,7-diaza-spiro[3.5]non-2-yl)-6-(3,5-dimethyl-isoxazol-4-yl)-5-methyl-pyrimidin-2-yl]-phenoxy}-propyl)-methyl-carbamic acid tert-butyl ester A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (100 mg, 0.154 mmol); 7-cyclopropyl-2,7-diaza-spiro[3.5]nonane HCl salt (93 mg, crude from step 2), triethylamine (78 mg, 0.77 mmol) and n-BuOH (3 mL), capped, placed in a microwave reactor and irradiated for 60 min. at external temperature of 140° C. After being cooled down to room temperature, the mixture was diluted with water (20 mL) and extracted with EtOAc (20 mL×3). The organic layers were combined, dried over Na$_2$SO$_4$, filtered and concentrated. The residue was purified by preparative TLC (petroleum ether/EtOAc=1/1 to give (R)-(2-(tert-butyl-dimethyl-silanyloxy)-3-{4-chloro-3-[4-(7-cyclopropyl-2,7-diaza-spiro [3.5]non-2-yl)-6-(3,5-dimethyl-isoxazol-4-yl)-5-methyl-pyrimidin-2-yl]-phenoxy}-propyl)-methyl-carbamic acid tert-butyl ester as a light yellow solid (80 mg, 67% yield). ESI-LCMS (m/z): 781.0 [M+H]$^+$.

Step 4: Synthesis of (R)-1-{4-Chloro-3-[4-(7-cyclopropyl-2,7-diaza-spiro[3.5]non-2-yl)-6-(3,5-dimethyl-isoxazol-4-yl)-5-methyl-pyrimidin-2-yl]-phenoxy}-3-methyl-amino-propan-2-ol A solution of (R)-(2-(tert-Butyl-dimethyl-silanyloxy)-3-{4-chloro-3-[4-(7-cyclo propyl-2,7-diaza-spiro[3.5]non-2-yl)-6-(3,5-dimethyl-isoxazol-4-yl)-5-methyl-pyrimidin-2-yl]-phenoxy}-propyl)-methyl-carbamic acid tert-butyl ester (80 mg) in 90% TFA (6.6 mL) was stirred at room temperature for 16 h, the solvent was then removed in vacuo and the residue was dissolved in MeOH (5 ml), treated with ammonia till pH 7-8 and concentrated. The residue was purified by preparative HPLC to give (R)-1-{4-chloro-3-[4-(7-cyclopropyl-2,7-diaza-spiro[3.5] non-2-yl)-6-(3,5-dimethyl-isoxazol-4-yl)-5-methyl-pyrimidin-2-yl]-phenoxy}-3-methyl-amino-propan-2-ol as a formic acid salt (white solid, 40 mg, 64% yield). ESI-LCMS (m/z): 567.3 [M+H]$^+$; $^1$HNMR (400 MHz, CD$_3$OD) δ ppm: 8.53 (br s, 1H), 7.42 (d, J=8.8 Hz, 1H), 7.21 (d, J=2.4 Hz, 1H), 7.06 (dd, J=2.4 and 8.8 Hz, 1H), 4.32-4.15 (m, 5H), 4.12-4.02 (m, 2H), 3.30-3.26 (m, 1H), 3.22-3.13 (m, 1H), 3.08 (br s, 4H), 2.77 (s, 3H), 2.38 (s, 3H), 2.29-2.26 (m, 1H), 2.25 (s, 3H), 2.17 (s, 3H), 2.03 (br s, 4H), 0.82-0.68 (m, 4H).

Example 32. Preparation of (R)-1-{4-Chloro-3-[4-(7-cyclopropyl-2,7-diaza-spiro[4.4]non-2-yl)-6-(3,5-dimethyl-isoxazol-4-yl)-5-methyl-pyrimidin-2-yl]-phenoxy}-3-methyl-amino-propan-2-ol

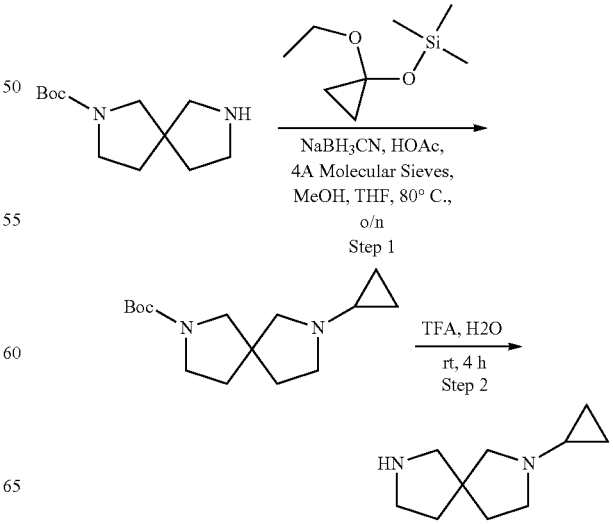

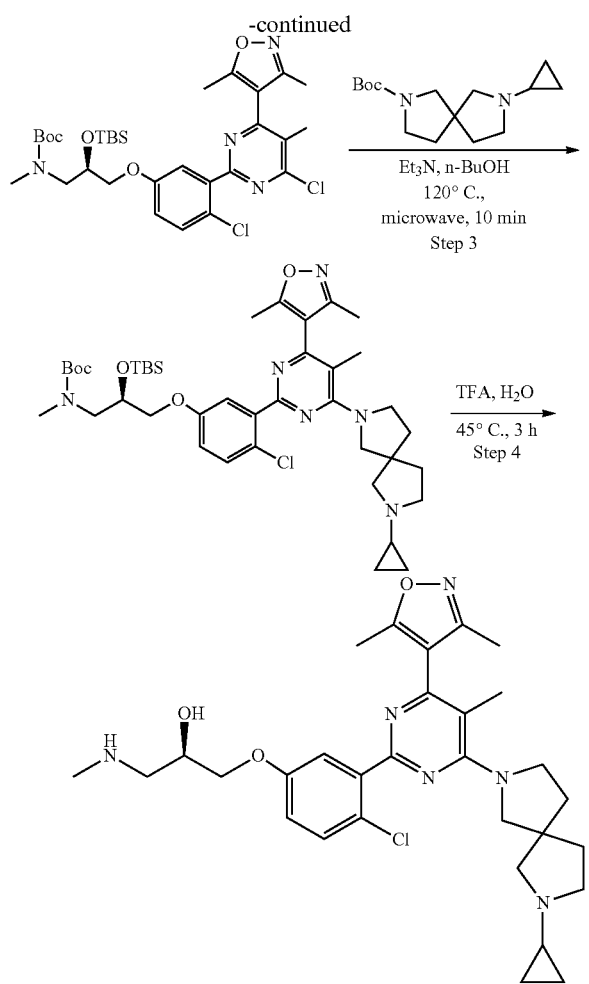

Step 1: Synthesis of 7-Cyclopropyl-2,7-diaza-spiro[4.4]nonane-2-carboxylic acid tert-butyl ester To a solution of 2,7-diaza-spiro[4.4]nonane-2-carboxylic acid tert-butyl ester (260 mg, 1.15 mmol) in MeOH and THF (1/1, 10 mL) was added (1-ethoxy-cyclo-propoxy)trimethylsilane (300 mg, 1.73 mmol), 4A molecular sieves (260 mg), HOAc (69 mg, 1.15 mmol) and NaBH$_3$CN (145 mg, 2.30 mmol). The mixture was stirred at 80° C. for 16 h., cooled down to room temperature, filtered and the filtrate was diluted with water (30 mL) and extracted with EtOAc (20 mL×3). The organic layers were combined, dried over Na$_2$SO$_4$, filtered and concentrated to give 7-cyclopropyl-2,7-diaza-spiro[4.4]nonane-2-carboxylic acid tert-butyl ester as a white solid (330 mg), which was used for the next step without further purification. ESI-LCMS (m/z): 267.3 [M+H]$^+$; 1HNMR (400 MHz, CD$_3$OD) δ ppm: 3.30-3.10 (m, 4H), 2.78-2.65 (m, 2H), 2.63-2.50 (m, 2H), 1.85-1.58 (m, 5H), 1.35 (s, 9H), 0.40-0.29 (m, 4H).

Step 2: Synthesis of 2-Cyclopropyl-2,7-diaza-spiro[4.4]nonane TFA salt

7-Cyclopropyl-2,7-diaza-spiro[4.4]nonane-2-carboxylic acid tert-butyl ester (1.15 mmol) was dissolved in 4 N HCl in dioxane (6 ml), the solution was stirred at room temperature for 4 h., and then concentrated in vacuo to give 2-cyclopropyl-2,7-diaza-spiro[4.4]nonane as HCl salt as a white solid, which was used directly in next step. Assumed quantitative yield. ESI-LCMS (m/z): 167.1 [M+H]$^+$; $^1$HNMR (400 MHz, CD$_3$OD) δ ppm: 3.58 (br s, 4H), 3.40-3.31 (m, 4H), 2.90-2.80 (m, 1H), 2.22-2.02 (m, 4H), 0.96-0.92 (m, 2H), 0.90-0.85 (m, 2H).

Step 3: Synthesis of (R)-(2-(tert-Butyl-dimethyl-silanyloxy)-3-{4-chloro-3-[4-(7-cyclopropyl-2,7-diaza-spiro[4.4]non-2-yl)-6-(3,5-dimethyl-isoxazol-4-yl)-5-methyl-pyrimidin-2-yl]-phenoxy}-propyl)-methyl-carbamic acid tert-butyl ester A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (110 mg, 0.16 mmol); 2-cyclopropyl-2,7-diaza-spiro[4.4]nonane HCl salt (113 mg), triethylamine (85 mg, 0.84 mmol) and n-BuOH (3 mL), capped, placed in a microwave reactor and irradiated for 10 min. at external temperature of 140° C. . After being cooled down to room temperature, the mixture was diluted with water (20 mL) and extracted with EtOAc (20 mL×3). The organic layers were combined, dried over Na$_2$SO$_4$, filtered and concentrated in vacuo to give (R)-(2-(tert-Butyl-dimethyl-silanyloxy)-3-{4-chloro-3-[4-(7-cyclopropyl-2,7-diaza-spiro[4.4] non-2-yl)-6-(3,5-di-methyl-isoxazol-4-yl)-5-methyl-pyrimidin-2-yl]-phenoxy}-propyl)-methyl-carbamic acid tert-butyl ester as a brown solid (132 mg), which was used for the next step without further purification. ESI-LCMS (m/z): 781.4 [M+H]$^+$.

Step 4: Synthesis of (R)-1-{4-Chloro-3-[4-(7-cyclopropyl-2,7-diaza-spiro[4.4]non-2-yl)-6-(3,5-dimethyl-isoxazol-4-yl)-5-methyl-pyrimidin-2-yl]-phenoxy}-3-methyl-amino-propan-2-ol A solution of (R)-(2-(tert-butyl-dimethyl-silanyloxy)-3-{4-chloro-3-[4-(7-cyclopropyl-2,7-diaza-spiro [4.4]non-2-yl)-6-(3,5-dimethyl-isoxazol-4-yl)-5-methyl-pyrimidin-2-yl]-phenoxy}-propyl)-methyl-carbamic acid tert-butyl ester (132 mg) in 90% TFA (6.6 mL) was stirred at 35° C. for 3 h, the solvent was removed in vacuo and the residue was dissolved in MeOH (3 ml), treated with ammonia till pH 7-8 and concentrated. The residue was purified by preparative HPLC to give (R)-1-{4-Chloro-3-[4-(7-cyclopropyl-2,7-diaza-spiro [4.4] non-2-yl)-6-(3,5-dimethyl-isoxazol-4-yl)-5-methyl-pyrimidin-2-yl]-phenoxy}-3-methyl-amino-propan-2-ol as a white solid (28 mg, 32% yield). ESI-LCMS (m/z): 567.3 [M+H]$^+$; $^1$HNMR (400 MHz, CD$_3$OD) δ ppm: 7.39 (d, J=8.8 Hz, 1H), 7.23 (d, J=2.8 Hz, 1H), 7.03 (dd, J=3.2 and 8.8 Hz, 1H), 4.15-4.08 (m, 1H), 4.05-3.94 (m, 2H), 3.91-3.83 (m, 2H), 3.82-3.70 (m, 2H), 2.95-2.72 (m, 6H), 2.48 (d, 3H), 2.40 (d, 3H), 2.70 (s, 3H), 2.26 (s, 3H), 2.09-1.96 (m, 2H), 1.94-1.85 (m, 2H), 1.80-1.74 (m, 1H), 0.53-0.42 (m, 4H).

Example 33. Preparation of (R)-2-[2-[2-Chloro-5-(2-hydroxy-3-methylamino-propoxy)-phenyl]-6-(3,5-dimethyl-isoxazol-4-yl)-5-methyl-pyrimidin-4-yl]-2,7-diaza-spiro[3.5]nonane-7-carboxylic acid methyl ester

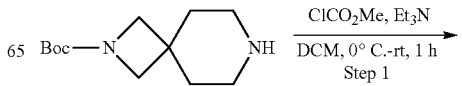

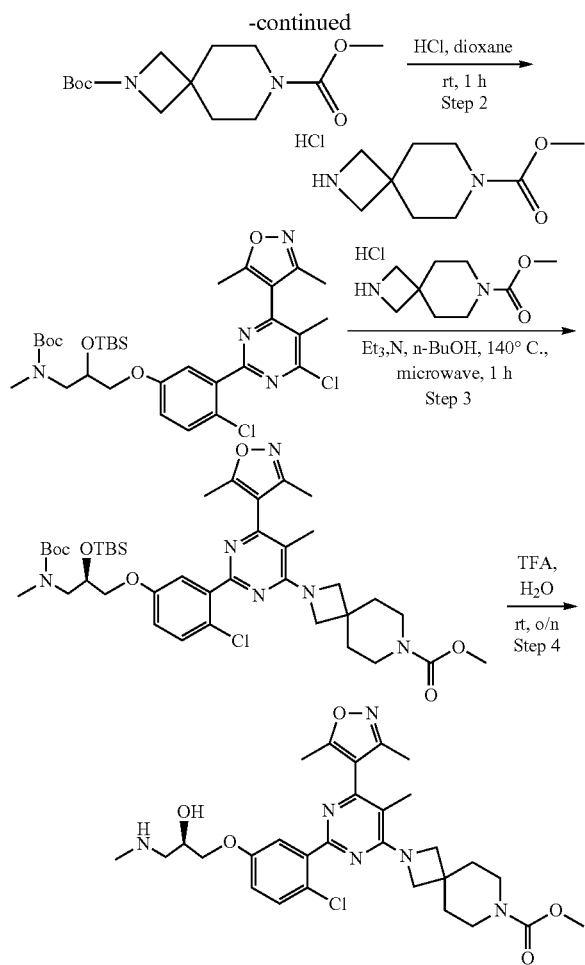

Step 1: Synthesis of 2,7-Diaza-spiro[3.5]nonane-2,7-dicarboxylic acid 2-tert-butyl ester 7-methyl ester To a solution of 2,7-Diaza-spiro[3.5]nonane-2-carboxylic acid tert-butyl ester (226 mg, 1.0 mmol) and triethylamine (303 mg, 3 mmol) in CH$_2$Cl$_2$ (6 mL) stirred at 0° C. under nitrogen atmosphere was added methyl chloroformate (188 mg, 2 mmol) dropwise, and the mixture was further stirred at room temperature for 1 h., excess of reagent was quenched with saturated NaHCO$_3$ solution (10 mL) and the mixture was then extracted with EtOAc (20 mL×2). The combined organic phases were washed with saturated NH$_4$Cl solution (20 mL) and brine (20 mL), dried over Na$_2$SO$_4$, filtered and concentrated to give 2,7-diaza-spiro[3.5]nonane-2,7-dicarboxylic acid 2-tert-butyl ester 7-methyl ester as a white solid, which was used for the next step without further purification (assumed quantitative yield). ESI-LCMS (m/z): 307.2 [M+23]$^+$.

Step 2: Synthesis of 2,7-Diaza-spiro[3.5]nonane-7-carboxylic Acid Methyl Ester HCl Salt A solution of 2,7-Diaza-spiro[3.5]nonane-2,7-dicarboxylic acid 2-tert-butyl ester 7-methyl ester (290 mg, 1.0 mmol, from step 1) in MeOH (2 mL) was treated with 4N HCl in dioxane (6 mL), and the mixture was stirred at room temperature for 1 h., and then concentrated in vacuo to give 2,7-diaza-spiro[3.5]nonane-7-carboxylic acid methyl ester as HCl salt (530 mg, crude), which was used for the next step without further purification. ESI-LCMS (m/z): 185.2 [M+H]$^+$.

Step 3: Synthesis of (R)-2-[2-{5-[3-(tert-Butoxycarbonyl-methyl-amino)-2-(tert-butyl-dimethyl-silanyloxy)-propoxy]-2-chloro-phenyl}-6-(3,5-dimethyl-isoxazol-4-yl)-5-methyl-pyrimidin-4-yl]-2,7-diaza-spiro[3.5]nonane-7-carboxylic acid methyl ester A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl (methyl)carbamate (120 mg, 0.18 mmol); 2,7-diaza-spiro[3.5]nonane-7-carboxylic acid methyl ester HCl salt (100 mg, crude from step 2), triethylamine (93 mg, 0.92 mmol). and n-BuOH (3 mL), capped, placed in a microwave reactor and irradiated for 60 min. at external temperature of 140° C. After being cooled down to room temperature, the mixture was diluted with water (20 mL) and extracted with EtOAc (20 mL×3). The organic layers were combined, dried over Na$_2$SO$_4$, filtered and concentrated to give (R)-2-[2-{5-[3-(tert-butoxycarbonyl-methyl-amino)-2-(tert-butyl-dimethyl-silanyloxy)-propoxy]-2-chloro-phenyl}-6-(3,5-dimethyl-isoxazol-4-yl)-5-methyl-pyrimidin-4-yl]-2,7-diaza-spiro[3.5]nonane-7-carboxylic acid methyl ester as a light yellow solid (147 mg, crude) which was used for the next step without further purification. ESI-LCMS (m/z): 798.8 [M+H]$^+$.

Step 4: Synthesis of (R)-2-[2-[2-Chloro-5-(2-hydroxy-3-methylamino-propoxy)-phenyl]-6-(3,5-dimethyl-isoxazol-4-yl)-5-methyl-pyrimidin-4-yl]-2,7-diaza-spiro[3.5]nonane-7-carboxylic acid methyl ester A solution of (R)-2-[2-{5-[3-(tert-butoxycarbonyl-methyl-amino)-2-(tert-butyl-dimethyl-silanyloxy)-propoxy]-2-chloro-phenyl}-6-(3,5-dimethyl-isoxazol-4-yl)-5-methyl-pyrimidin-4-yl]-2,7-diaza-spiro[3.5]nonane-7-carboxylic acid methyl ester (147 mg, from step 2) in 90% TFA (6.6 mL) was stirred at room temperature for 16 h., the solvent was removed in vacuo and the residue was dissolved in MeOH (5 ml), treated with ammonia till pH 7-8 and concentrated. The residue was purified by preparative HPLC to give (R)-2-[2-[2-Chloro-5-(2-hydroxy-3-methylamino-propoxy)-phenyl]-6-(3,5-dimethyl-isoxazol-4-yl)-5-methyl-pyrimidin-4-yl]-2,7-diaza-spiro[3.5]nonane-7-carboxylic acid methyl ester as a white solid (65 mg, 60% yield for 2 steps). ESI-LCMS (m/z): 585.3 [M+H]$^+$. 1HNMR (500 MHz, CD$_3$OD) δ ppm: 8.53 (br s, 1H), 7.42 (d, J=8.5 Hz, 1H), 7.20 (d, J=3.0 Hz, 1H), 7.06 (dd, J=3.0 and 9.0 Hz, 1H), 4.36-4.25 (m, 1H), 4.19 (br s, 4H), 4.11-4.05 (m, 2H), 3.71 (s, 3H), 3.53-3.48 (m, 4H), 3.30-3.25 (m, 1H), 3.20-3.14 (m, 1H), 2.77 (s, 3H), 2.39 (s, 3H), 2.25 (s, 3H), 2.17 (s, 3H), 1.88-1.82 (m, 4H).

Example 34. phenyl)-6-(3,5-dimethylisoxazol-4-yl)-5-methylpyrimidin-4-yl)-2,6-diazaspiro [3.4]octane-6-carboxylate

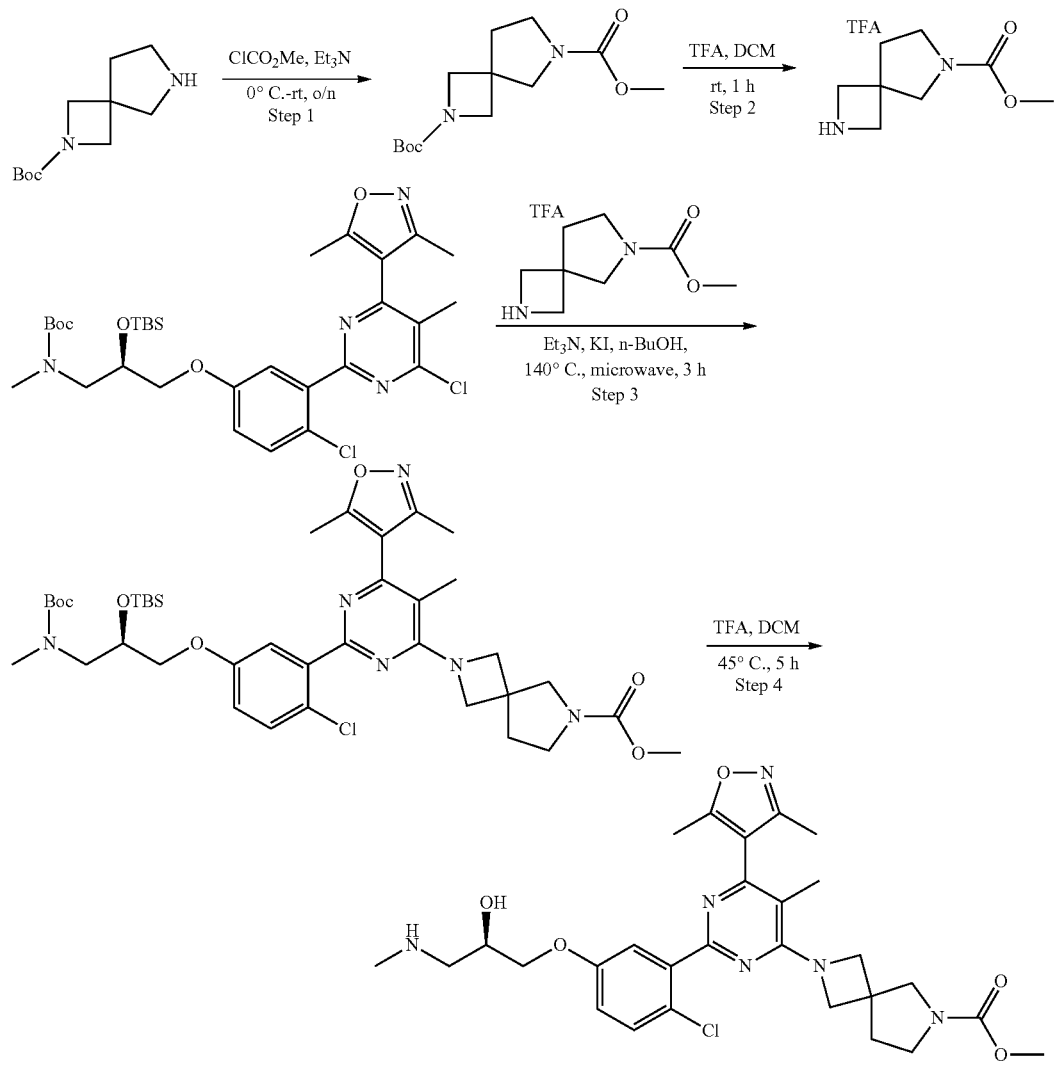

Step 1: Synthesis of 2-tert-butyl 6-methyl 2,6-diazaspiro[3.4]octane-2,6-di-Carboxylate To a solution of tert-butyl 2,6-diazaspiro[3.4]octane-2-carboxylate (100 mg, 0.47 mmol) in DCM (2 mL) stirred at 0° C. was treated with Et$_3$N (95 mg, 0.94 mmol) followed by slow addition of methyl chloroformate (89 mg, 0.94 mmol), and the reaction mixture further stirred at room temperature for 16 h., diluted with EtOAc (20 mL) and consecutively washed with H$_2$O (20 mL), aqueous NH$_4$Cl solution (20 mL) and brine (20 mL). The organic layer was dried over Na$_2$SO$_4$, filtered and concentrated to give 2-tert-butyl 6-methyl 2,6-diazaspiro[3.4]octane-2,6-dicarboxylate (100 mg, 78% yield) as a yellow solid. ESI-LCMS (m/z): 293.1 [M+Na]$^+$.

Step 2: Synthesis of methyl 2,6-diazaspiro[3.4]octane-6-carboxylate TFA salt

A solution of 2-tert-butyl 6-methyl 2,6-diazaspiro[3.4] octane-2,6-dicarboxylate (100 mg, 0.37 mmol) in DCM (1 mL) was treated with neat TFA (1 mL), the resulting mixture was stirred at room temperature for 1 h. and finally concentrated to give methyl 2,6-diazaspiro[3.4]octane-6-carboxylate as TFA salt (62 mg, crude), which was used for the next step without further purification. ESI-LCMS (m/z): 171.2 [M+1]$^+$.

Step 3: Synthesis of methyl 2-(2-(5-((R)-3-(tert-butoxycarbonyl(methyl)amino)-2-(tert-butyldimethylsilyloxy)propoxy)-2-chlorophenyl)-6-(3,5-dimethylisoxazol-4-yl)-5-methylpyrimidin-4-yl)-2,6-diazaspiro[3.4]octane-6-carboxylate A reaction pressure vessel was charged with a mixture of tert-butyl (2R)-2-(tert-butyldimethylsilyloxy)-3-(4-chloro- 3-(4-chloro-6-(3,5-dimethylisoxazol-4-yl)-5-methylpyrimidin-2-yl)phenoxy)propyl(methyl) carbamate (150 mg, 0.23 mmol); methyl 2,6-diazaspiro[3.4]octane-6-carboxylate TFA salt (59 mg, crude from step 2), Et₃N (47 mg, 0.46 mmol), KI (77 mg, 0.46 mmol) and n-BuOH (3 mL), capped, placed in a microwave reactor and irradiated for 120 min. at external temperature of 140° C. After being cooled down to room temperature, EtOAc (20 mL) was added, the mixture was washed with water (20 mL), aqueous NH₄Cl solution (20 mL) and brine (20 mL). The organic layer was dried over Na₂SO₄, filtered, concentrated and the resulting residue was purified by preparative TLC (petroleum ether/ EtOAc=2/1) to give methyl 2-(2-(5-((R)-3-(tert-butoxycarbonyl(methyl)amino)-2-(tertbutyl-dimethylsilyloxy) propoxy)-2-chlorophenyl)-6-(3,5-dimethylisoxazol-4-yl)-5-methyl-pyrimidin-4-yl)-2,6-diazaspiro[3.4]octane-6-carboxylate (100 mg, 55% yield) as a white solid. ESI-LCMS (m/z): 785.4 [M+1]⁺.

Step 4: Synthesis of methyl 2-(2-(2-chloro-5-((R)-2-hydroxy-3-(methylamino) propoxy)phenyl)-6-(3, 5-dimethylisoxazol-4-yl)-5-methylpyrimidin-4-yl)-2, 6-diaza-spiro[3.4]octane-6-carboxylate A solution of methyl 2-(2-(5-((R)-3-(tert-butoxycarbonyl (methyl)amino)-2-(tert-butyldimethylsilyloxy)propoxy)-2-chlorophenyl)-6-(3,5-dimethyl isoxazol-4-yl)-5-methylpyrimidin-4-yl)-2,6-diazaspiro[3.4] octane-6-carboxylate (100 mg, 0.12 mmol) in DCM (1 mL) was treated with neat TFA (1 mL) and the mixture was stirred at 45° C. for 5 h., the solvent was removed in vacuo, the residue was dissolved in MeOH (2 ml), treated with ammonia till pH 7-8 and concentrated. The crude residue was purified by preparative HPLC to give methyl 2-(2-(2-chloro-5-((R)-2-hydroxy-3-(methylamino)propoxy)phenyl)-6-(3,5-dimethylisoxazol-4-yl)-5-methyl-pyrimidin-4-yl)-2,6-diazaspiro[3.4]octane-6-carboxylate (42 mg, 58% yield) as a white solid. ESI-LCMS (m/z): 571.2 [M+1]; ¹HNMR (400 MHz, CD₃OD) δ ppm: 7.40 (d, J=8.4 Hz, 1H), 7.21 (d, J=3.2 Hz, 1H), 7.05 (dd, J=2.8 and 8.2 Hz, 1H), 4.42-4.32 (m, 4H), 4.23-4.16 (m, 1H), 4.04 (d, J=5.2 Hz, 2H), 3.72 (s, 3H), 3.66-3.62 (m, 2H), 3.53-3.46 (m, 2H), 3.13-3.07 (m, 1H), 3.04-2.97 (m, 1H), 2.64 (s, 3H), 2.38 (s, 3H), 2.28-2.20 (m, 6H), 2.16 (s, 2H).

Example 35. Preparation of (R)-1-(4-chloro-3-(4-(cis-1-cyclopropyl-3-fluoropiperidin-4-yl-amino)-6-(3,5-dimethylisoxazol-4-yl)-5-methylpyrimidin-2-yl) phenoxy)-3-(methyl-amino) propan-2-ol

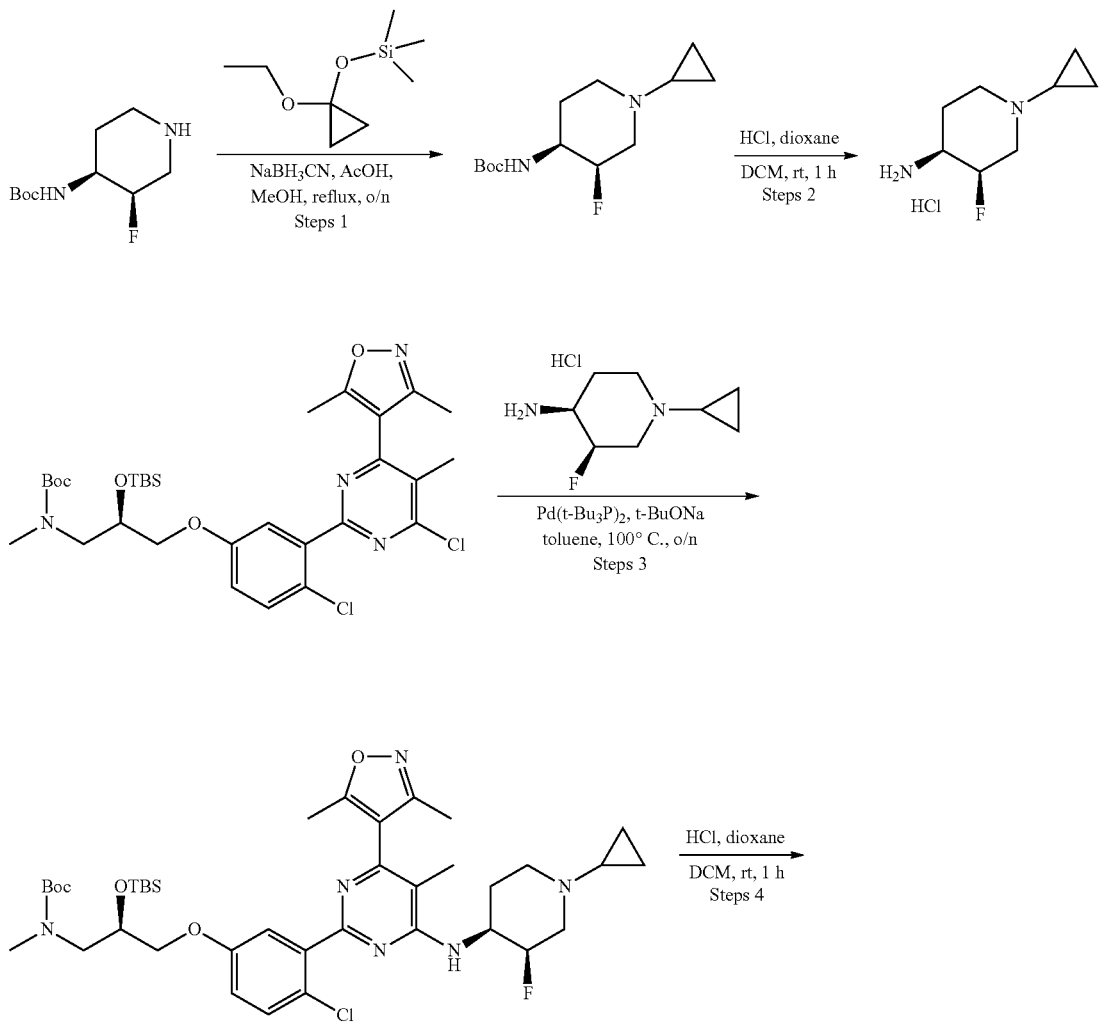

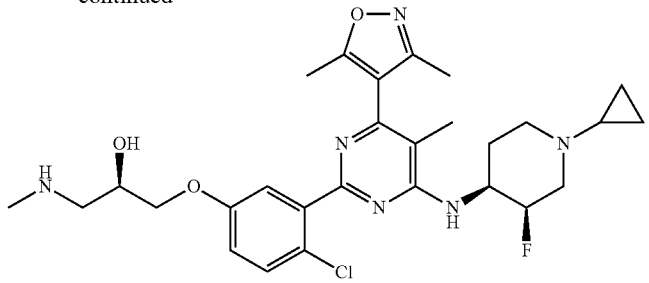

Step 1: Synthesis of tert-butyl cis-1-cyclopropyl-3-fluoropiperidin-4-yl-carbamate To a solution of tert-butyl cis-3-fluoropiperidin-4-ylcarbamate (380 mg, 1.74 mmol), (1-methoxycyclopropoxy)trimethylsilane (1.4 g, 8.72 mmol) and AcOH (209 mg, 3.5 mmol) in MeOH (10 mL), NaBH$_3$CN (439 mg, 6.97 mmol) was slowly added with stirring at room temperature; the reaction mixture was then heated under reflux for 16 h., cooled down to room temperature and the solvent was removed under vacuum. The residue was suspended in DCM (100 mL), washed with water (50 mL×2) and brine (60 mL), the organic phase was dried over Na$_2$SO$_4$, filtered and concentrated under vacuum to give tert-butyl cis-1-cyclopropyl-3-fluoropiperidin-4-yl-carbamate, which was used for the next step without further purification. Assumed quantitative yield. $^1$HNMR (500 MHz, CDCl$_3$) δ ppm: 4.84 (d, J=8.0 Hz, 1H), 4.69 (d, J=49.5 Hz, 1H), 3.75-3.60 (m, 1H), 3.37-3.30 (m, 1H), 3.11-3.04 (m, 1H), 2.50-2.36 (m, 1H), 2.35-2.27 (m, 1H), 1.83-1.70 (m, 2H), 1.47 (s, 9H), 1.27-1.39 (m, 1H), 0.53-0.40 (m, 4H).

Step 2: Synthesis of cis-1-cyclopropyl-3-fluoropiperidin-4-amine HCl

A solution of tert-butyl cis-1-cyclopropyl-3-fluoropiperidin-4-ylcarbamate (510 mg, crude from step 1) in DCM (15 mL) was treated with 4N HCl in dioxane (5 mL); the final mixture was further stirred at room temperature for 1 h and concentrated under vacuum to give cis-1-cyclopropyl-3-fluoropiperidin-4-amine HCl salt as a white solid (410 mg), which was used for the next step without further purification. ESI-LCMS: 159.3 [M+1]$^+$.

Step 3: Synthesis of tert-butyl (R)-2-(tert-butyldimethylsilyloxy)-3-(4-chloro-3-(4-(cis-1-cyclopropyl-3-fluoropiperidin-4-ylamino)-6-(3,5-dimethylisoxazol-4-yl)-5-methylpyrimidin-2-yl)phenoxy)propyl (methyl)carbamate To a solution of tert-butyl (R)-2-(tert-butyldimethylsilyloxy)-3-(4-chloro-3-(4-chloro-6-(3,5-dimethylisoxazol-4-yl)-5-methyl pyrimidin-2-yl)phenoxy)propyl(methyl) carbamate (300 mg, 0.46 mmol) in toluene (6 mL) was added t-BuONa (177 mg, 1.84 mmol), Pd(t-Bu$_3$P)$_2$ (71 mg, 0.14 mmol) and cis-1-cyclopropyl-3-fluoropiperidin-4-amine hydrochloric acid (or any other suitably substituted primary amine, 0.92 mmol). The system was purged with N$_2$ stream, sealed and heated at 100° C. for 16 h. After being cooled down to room temperature, the mixture was diluted with water (20 mL) and extracted with EtOAc (20 mL×2). The combined organic layers were washed with brine, dried over Na$_2$SO$_4$, filtered and concentrated to render a residue which was purified by preparative TLC (petroleum ether/EtOAc=2/1) to give tert-butyl (R)-2-(tert-butyldimethylsilyloxy)-3-(4-chloro-3-(4-(cis-1-cyclopropyl-3-fluoropiperidin-4-ylamino)-6-(3,5-dimethylisoxazol-4-yl)-5-methyl pyrimidin-2-yl)phenoxy)propyl(methyl)carbamate as a yellow solid (140 mg, 39% yield). ESI-LCMS: 772.9 [M+1]$^+$.

Step 4: Synthesis of (R)-1-(4-chloro-3-(4-(cis-1-cyclopropyl-3-fluoropiperidin-4-ylamino)-6-(3,5-dimethylisoxazol-4-yl)-5-methylpyrimidin-2-yl)phenoxy)-3-(methylamino)propan-2-ol A solution of tert-butyl (R)-2-(tert-butyldimethylsilyloxy)-3-(4-chloro-3-(4-(cis-1-cyclopropyl-3-fluoropiperidin-4-ylamino)-6-(3,5-dimethylisoxazol-4-yl)-5-methyl-pyrimidin-2-yl)phenoxy) propyl(methyl)carbamate (140 mg, 0.18 mmol) in DCM (5 mL) was treated with 4N HCl in dioxane (2 mL) and the reaction mixture was stirred at room temperature for 1 h., the solvent was then removed in vacuo, the resulting residue was dissolved in MeOH (2 ml), treated with ammonia till pH 7-8, concentrated and submitted to purification by preparative HPLC to give (R)-1-(4-chloro-3-(4-(cis-1-cyclopropyl-3-fluoropiperidin-4-ylamino)-6-(3,5-dimethyl-isoxazol-4-yl)-5-methylpyrimidin-2-yl)phenoxy)-3-(methylamino)propan-2-ol as a white solid (33 mg, 33% yield). ESI-LCMS: 559.2 [M+1]$^+$; $^1$HNMR (500 MHz, DMSO-d6) δ ppm: 7.44 (d, J=9.0 Hz, 1H), 7.29 (d, J=3.5 Hz, 1H), 7.05 (dd, J=3.5 and 9.0 Hz, 1H), 6.71 (d, J=7.0 Hz, 1H), 5.89 (d, J=4.5 Hz, 1H), 4.93 (d, J=49.0 Hz, 1H), 4.33-4.12 (m, 2H), 4.00 (d, J=5.0 Hz, 2H), 3.26-3.18 (m, 1H), 3.17-3.09 (m, 1H), 3.05-2.95 (m, 2H), 2.59 (s, 3H), 2.45-2.35 (m, 2H), 2.33 (s, 3H), 2.19 (s, 3H), 2.07-1.96 (m, 5H), 1.73-1.65 (m, 2H), 0.48-0.39 (m, 2H), 0.37-0.23 (m, 2H).

Example 36. Preparation of (2R)-1-(4-chloro-3-(4-(3,3-difluoro-1-methylpiperidin-4-yl-amino)-6-(3,5-dimethylisoxazol-4-yl)-5-methylpyrimidin-2-yl)phenoxy)-3-(methyl-amino) propan-2-ol

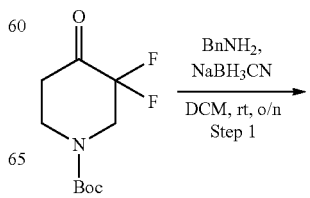

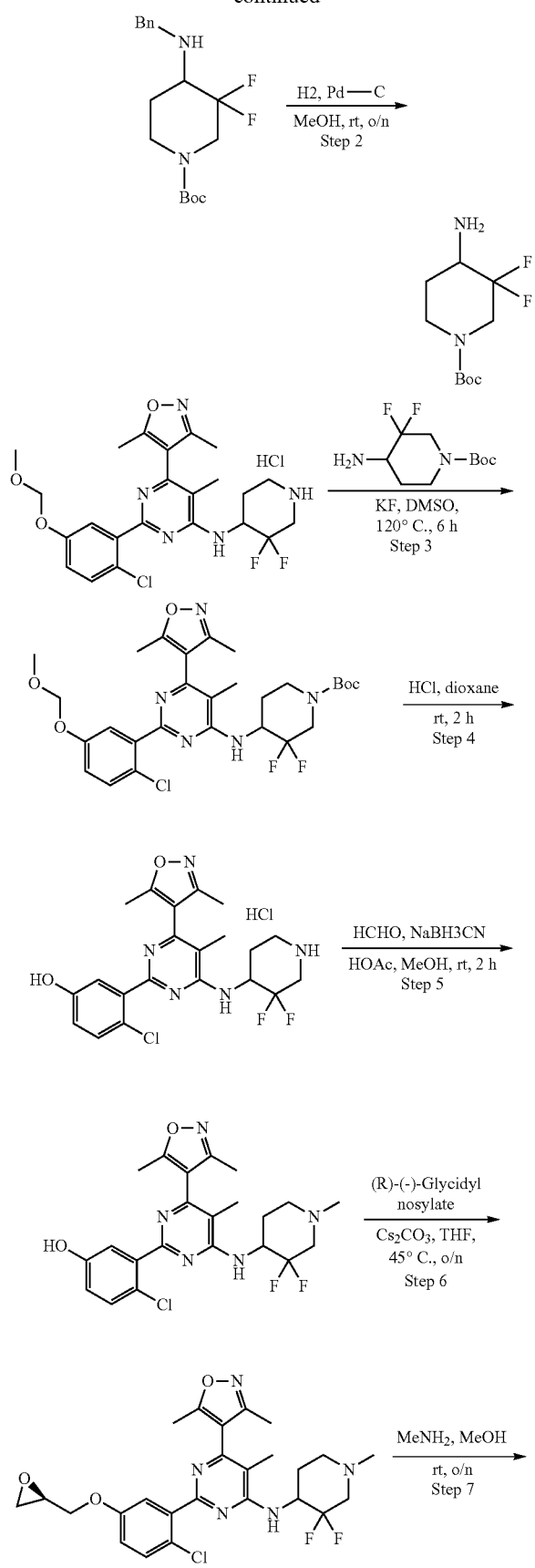

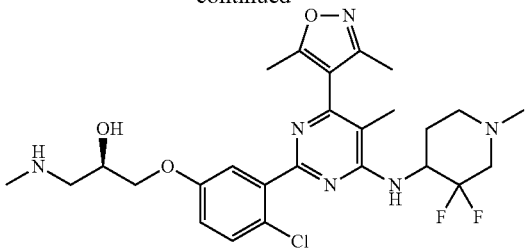

Step 1: Synthesis of tert-butyl 4-(benzylamino)-3,3-difluoropiperidine-1-carboxylate To a solution of tert-butyl 3,3-difluoro-4-oxopiperidine-1-carboxylate (1.0 g, 4.25 mmol) in DCM (15 mL) was treated with BnNH$_2$ (689 mg, 6.38 mmol) followed by addition of NaBH(OAc)$_3$ (2.71 g, 12.76 mmol) and the suspension was stirred at room temperature for 16 h., quenched with aqueous NaHCO$_3$ solution (10 mL) and extracted with DCM (30 mL×2). The combined organic layers were washed with water (20 mL×3) and brine (20 mL), dried over Na$_2$SO$_4$, filtered and concentrated. The resulting residue was purified by preparative TLC (petroleum ether/EA=3/1) to give tert-butyl 4-(benzylamino)-3,3-difluoropiperidine-1-carboxylate (570 mg, 41% yield) as a colorless oil. ESI-LCMS (m/z): 327.2 [M+1]$^+$.

Step 2: Synthesis of tert-butyl 4-amino-3,3-difluoropiperidine-1-carboxylate A solution of 4-(benzylamino)-3,3-difluoropiperidine-1-carboxylate (570 mg, 1.74 mmol) in methanol (15 mL) was stirred at room temperature under H$_2$ atmosphere in the presence of 10% Pd—C (300 mg) for 16 h, the reaction mixture was then filtered through a pad of Celite and the filtrate was concentrated to give tert-butyl 4-amino-3,3-difluoropiperidine-1-carboxylate (380 mg, 91% yield) as a colorless oil. $^1$HNMR (400 MHz, CD$_3$OD) δ ppm: 4.15-4.00 (m, 1H), 3.91-3.83 (m, 1H), 3.20-2.84 (m, 3H), 1.83-1.74 (m, 1H), 1.49-1.38 (m, 1H), 1.36 (s, 9H).

Step 3: Synthesis of tert-butyl 4-(2-(2-chloro-5-(methoxymethoxy)phenyl)-6-(3, 5-dimethylisoxazol-4-yl)-5-methylpyrimidin-4-ylamino)-3,3-difluoropiperidine-1-carboxylate A reaction pressure vessel was charged with a mixture of 4-(6-chloro-2-(2-chloro-5-(methoxymethoxy)phenyl)-5-methyl-pyrimidin-4-yl)-3,5-dimethylisoxazole (250 mg, 0.63 mmol); tert-butyl 4-amino-3, 3-difluoro piperidine-1-carboxylate (300 mg, 1.27 mmol) and KF (111 mg, 1.90 mmol) in DMSO (7 mL), capped, placed in a microwave reactor and irradiated for 6 h. at external temperature of 120° C. After being cooled down to room temperature, the mixture was diluted with EtOAc (60 mL), washed with water (10 mL×3) and brine (10 mL). The organic layer was dried over Na$_2$SO$_4$, filtered and concentrated. The residue was purified by preparative TLC (petroleum ether/EtOAc=2/1) to give tert-butyl 4-(2-(2-chloro-5-(methoxymethoxy)phenyl)-6-(3,5-dimethylisoxazol-4-yl)-5-methylpyrimidin-4-yl-amino)-3,3-difluoropiperidine-1-carboxylate (210 mg, 56% yield) as a white solid. ESI-LCMS (m/z): 594.2 [M+1]$^+$.

Step 4: Synthesis of 4-chloro-3-(4-(3,3-difluoropiperidin-4-ylamino)-6-(3,5-di-methylisoxazol-4-yl)-5-methylpyrimidin-2-yl)phenol hydrochloride A solution of tert-butyl 4-(2-(2-chloro-5-(methoxymethoxy)phenyl)-6-(3,5-di-methylisoxazol-4-yl)-5-methylpyrimidin-4-ylamino)-3,3-difluoropiperidine-1-carboxylate (210 mg, 1.45 mmol) in MeOH (10 mL) was treated with 4N HCl in dioxane (5 mL) and the mixture was stirred at room temperature for 2 h. and concentrated in vacuo to give 4-chloro-3-(4-(3,3-di-fluoropiperidin-4-ylamino)-6-(3,5-dimethylisoxazol-4-yl)-5-methylpyrimidin-2-yl) phenol HCl (320 mg, crude), which was used for the next step without further purification. Assumed quantitative yield. ESI-LCMS (m/z): 450.1 [M+1]$^+$.

Step 5: Synthesis of 4-chloro-3-(4-(3,3-difluoro-1-methylpiperidin-4-ylamino)-6-(3,5-dimethylisoxazol-4-yl)-5-methylpyrimidin-2-yl)phenol To a solution of 4-chloro-3-(4-(3,3-difluoropiperidin-4-ylamino)-6-(3,5-dimethyl-isoxazol-4-yl)-5-methylpyrimidin-2-yl)phenol HCl salt (320 mg, crude from previous step) in methanol (12 mL) was added aqueous HCHO solution (35%, 5 mL), AcOH (93 mg, 1.54 mmol) and NaBH$_3$CN (87 mg, 1.36 mmol), and the reaction mixture was stirred at room temperature for 2 h., quenched with saturated aqueous NaHCO$_3$ solution (8 mL) and extracted with EtOAc (30 mL×2). The combined organic layers were washed with brine, dried over Na$_2$SO$_4$, filtered and concentrated to give 4-chloro-3-(4-(3,3-difluoro-1-methyl-piperidin-4-ylamino)-6-(3,5-dimethyl isoxazol-4-yl)-5-methylpyrimidin-2-yl) phenol (390 mg, crude), which was used for the next step without further purification. Assumed quantitative yield. ESI-LCMS (m/z): 464.2 [M+1]$^+$.

Step 6: Synthesis of 2-(2-chloro-5-((R)-oxiran-2-ylmethoxy)phenyl)-N-(3,3-di-fluoro-1-methyl-piperidin-4-yl)-6-(3,5-dimethylisoxazol-4-yl)-5-methyl-pyrimidin-4-amine To a solution of 4-chloro-3-(4-(3,3-difluoro-1-methylpiperidin-4-ylamino)-6-(3,5-di-methylisoxazol-4-yl)-5-methylpyrimidin-2-yl)phenol (390 mg, crude from previous step) in THF (12 mL) was added (R)-oxiran-2-ylmethyl 3-nitrobenzenesulfonate (177 mg, 0.68 mmol) and Cs$_2$CO$_3$ (443 mg, 1.36 mmol), and the mixture was stirred at 45° C. for 16 h., cooled down to room temperature, diluted with water (30 mL) and extracted with EtOAc (30 mL×2). The combined organic layers were washed with brine, dried over Na$_2$SO$_4$, filtered and concentrated. The residue was purified by preparative TLC to give 2-(2-chloro-5-((R)-oxiran-2-ylmethoxy)phenyl)-N-(3,3-di-fluoro-1-methylpiperidin-4-yl)-6-(3,5-dimethylisoxazol-4-yl)-5-methylpyrimidin-4-amine (140 mg, 76% yield for 3 steps). ESI-LCMS (m/z): 520.2 [M+1]$^+$.

Step 7: Synthesis of (2R)-1-(4-chloro-3-(4-(3,3-difluoro-1-methylpiperidin-4-yl-amino)-6-(3,5-dimethylisoxazol-4-yl)-5-methylpyrimidin-2-yl)phenoxy)-3-(methyl-amino)propan-2-ol A solution of 2-(2-chloro-5-((R)-oxiran-2-ylmethoxy)phenyl)-N-(3,3-difluoro-1-methyl piperidin-4-yl)-6-(3,5-dimethylisoxazol-4-yl)-5-methylpyrimidin-4-amine (140 mg, 0.27 mmol) in MeOH (3 mL) was treated with 33% MeNH$_2$ in MeOH (5 mL), and the mixture was stirred at room temperature for 16 h., concentrated in vacuo and the resulting residue was purified by preparative HPLC to give (2R)-1-(4-chloro-3-(4-(3,3-difluoro-1-methylpiperidin-4-ylamino)-6-(3,5-dimethyl-isoxazol-4-yl)-5-methylpyrimidin-2-yl)phenoxy)-3-(methyl-amino)propan-2-ol (46 mg, 31% yield) as a white solid. ESI-LCMS: 550.8 [M+1]$^+$; $^1$HNMR (400 MHz, CD$_3$OD) δ ppm: 7.34 (d, J=9.2 Hz, 1H), 7.16 (d, J=3.2 Hz, 1H), 6.98 (dd, J=3.2 and 8.8 Hz, 1H), 5.00-4.90 (m, 1H), 4.10-4.02 (m, 1H), 3.99-3.90 (m, 2H), 3.18-3.09 (m, 1H), 2.94-2.87 (m, 1H), 2.79-2.73 (m, 1H), 2.72-2.65 (m, 1H), 2.47-2.07 (m, 14H), 2.04-1.94 (m, 5H).

Example 37. Preparation of (R)-1-(4-chloro-3-(4-(3,5-dimethylisoxazol-4-yl)-5-methyl-6-((2R, 4R)-2-methyl-tetrahydro-2H-pyran-4-ylamino)pyrimidin-2-yl)phenoxy)-3-(methyl amino)propan-2-ol

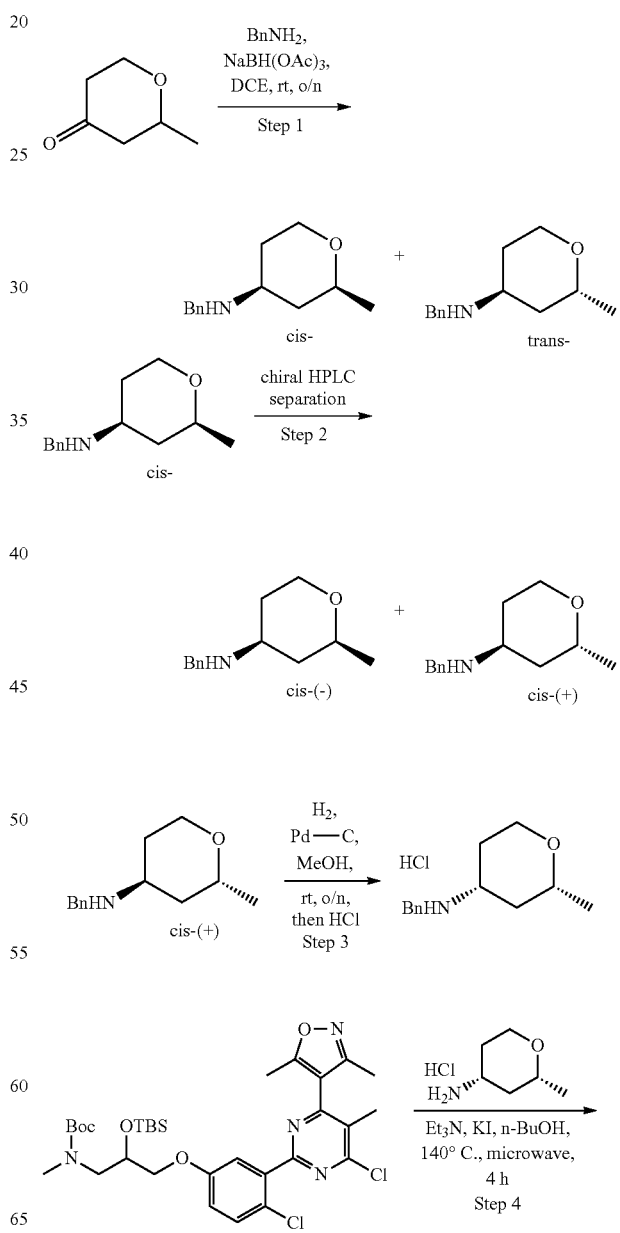

-continued

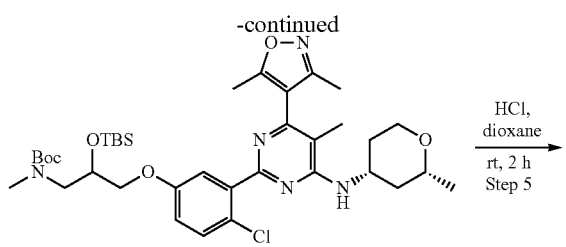

HCl, dioxane
rt, 2 h
Step 5

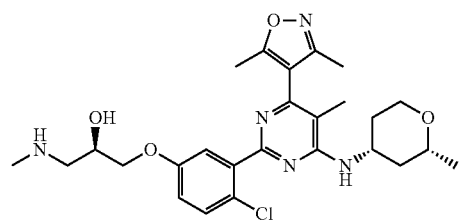

Step 1: Synthesis of cis-(+)-N-benzyl-2-methyl-tetrahydro-2H-pyran-4-amine

A solution of 2-methyl-tetrahydropyran-4-one (1.9 g, 16.6 mmol) and BnNH$_2$ (5.34 g, 49.9 mmol) in DCE (90 mL) was treated with NaBH(OAc)$_3$ (10.6 g, 50.0 mmol) and the mixture was stirred at room temperature for 16 h., diluted with water (60 mL), and extracted with DCM (50 mL×3). The combined organic layers were washed with brine, dried over Na$_2$SO$_4$, filtered and concentrated. The residue was purified by preparative TLC (petroleum ether/EA=3/1) to give cis-N-benzyl-2-methyl-tetra hydro-2H-pyran-4-amine (1.36 g, 39%) and trans-N-benzyl-2-methyl-tetra hydro-2H-pyran-4-amine (0.79 g, 23%). ESI-LCMS (m/z): 206.2 [M+H]$^+$.

Step 2: Resolution of cis-N-benzyl-2-methyl-tetrahydro-2H-pyran-4-amine

A racemic mixture of cis-N-benzyl-2-methyl-tetrahydro-2H-pyran-4-amines (1.36 g) was resolved by chiral HPLC to obtain the isolated enantiomers cis-(+)-N-benzyl-2-methyl-tetrahydro-2H-pyran-4-amine (500 mg) cis-(−)-N-benzyl-2-methyl-tetrahydro-2H-pyran-4-amine (650 mg). The configuration of cis-(+)-isomer was assumed to be (2R, 4R).

Step 3: Synthesis of (2R,4R)-2-methyl-tetrahydro-2H-pyran-4-amine

A mixture of cis-(+)-N-benzyl-2-methyl-tetrahydro-2H-pyran-4-amine (500 mg, 2.4 mmol) and 10% Pd—C (200 mg) in 20 mL of MeOH was stirred at room temperature under H$_2$ atmosphere for 16 h., filtered through a pad of Celite, the filtrate was treated with 4N HCl in dioxane (5 mL) and concentrated to give (2R, 4R)-2-methyl-tetrahydro-2H-pyran-4-amine HCl, which was used for the next step without further purification. Assumed quantitative yield. ESI-LCMS (m/z): 116.1 [M+H]$^+$.

Step 4: Synthesis of tert-butyl (R)-2-(tert-butyldimethylsilyloxy)-3-(4-chloro-3-(4-(3,5-dimethylisoxazol-4-yl)-5-methyl-6-((2R,4R)-2-methyl-tetrahydro-2H-pyran-4-ylamino) pyrimidin-2-yl) phenoxy)propyl(methyl)carbamate A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl)carbamate (200 mg, 0.31 mmol), (2R,4R)-2-methyl-tetrahydro-2H-pyran-4-amine HCl (1.1 mmol), KI (30 mg, 0.18 mmol), Et$_3$N (1 mL, 7.1 mmol) and n-BuOH (5 mL), capped, placed in a microwave reactor and irradiated for 4 h. at external temperature of 140° C. After being cooled down to room temperature, water (20 mL) was added and the mixture was extracted with EtOAc (20 mL×3). The combined organic layers were washed with brine, dried over Na$_2$SO$_4$, filtered and concentrated to give tert-butyl (R)-2-(tert-butyldimethylsilyloxy)-3-(4-chloro-3-(4-(3,5-dimethylisoxazol-4-yl)-5-methyl-6-((2R,4R)-2-methyl-tetrahydro-2H-pyran-4-ylamino)pyrimidin-2-yl) phenoxy)propyl (methyl)carbamate (262 mg, crude), which was used for the next step without further purification. ESI-LCMS (m/z): 730.3 [M+H]$^+$.

Step 5: Synthesis of (R)-1-(4-chloro-3-(4-(3,5-dimethylisoxazol-4-yl)-5-methyl-6-((2R,4R)-2-methyl-tetrahydro-2H-pyran-4-ylamino)pyrimidin-2-yl)phenoxy)-3-(methylamino)propan-2-ol A solution of tert-butyl (R)-2-(tert-butyldimethylsilyloxy)-3-(4-chloro-3-(4-(3,5-dimethyl-isoxazol-4-yl)-5-methyl-6-((2R,4R)-2-methyl-tetrahydro-2H-pyran-4-ylamino) pyrimidin-2-yl) phenoxy)propyl(methyl) carbamate (262 mg, crude from previous step) in MeOH (4 mL) was treated with 4N HCl in dioxane (2 mL) and the mixture was stirred at room temperature for 2 h., the solvent was then removed in vacuo, and the residue was dissolved in MeOH (2 ml), treated with ammonia till pH 7-8 and then concentrated again. The residue was purified by preparative HPLC to give (R)-1-(4-chloro-3-(4-(3,5-dimethylisoxazol-4-yl)-5-methyl-6-((2R,4R)-2-methyl-tetra-hydro-2H-pyran-4-ylamino)pyrimidin-2-yl)phenoxy)-3-(methylamino) propan-2-ol as a formic acid salt (white solid, 102 mg, 59% yield for 2 steps). ESI-LCMS (m/z): 515.8 [M+H]$^+$; $^1$HNMR (400 MHz, CD$_3$OD) δ ppm: 8.55 (br s, 1H), 7.42 (d, J=8.8 Hz, 1H), 7.21 (d, J=2.8 Hz, 1H), 7.06 (dd, J=2.8 and 8.8 Hz, 1H), 4.51-4.41 (m, 1H), 4.30-4.20 (m, 1H), 4.12-4.00 (m, 3H), 3.63-3.55 (m, 2H), 3.30-3.15 (m, 2H), 2.75 (s, 3H), 2.37 (s, 3H), 2.24 (s, 3H), 2.12-1.99 (m, 5H), 1.72-1.60 (m, 1H), 1.45-1.34 (m, 1H), 1.22 (d, J=6.0 Hz, 3H).

Example 38. Preparation of (S)-ethyl 3-((2-(2-chloro-5-((R)-2-hydroxy-3-(methylamino) propoxy) phenyl)-6-(3,5-dimethylisoxazol-4-yl)-5-methylpyrimidin-4-ylamino) methyl) morpholine-4-carboxylate

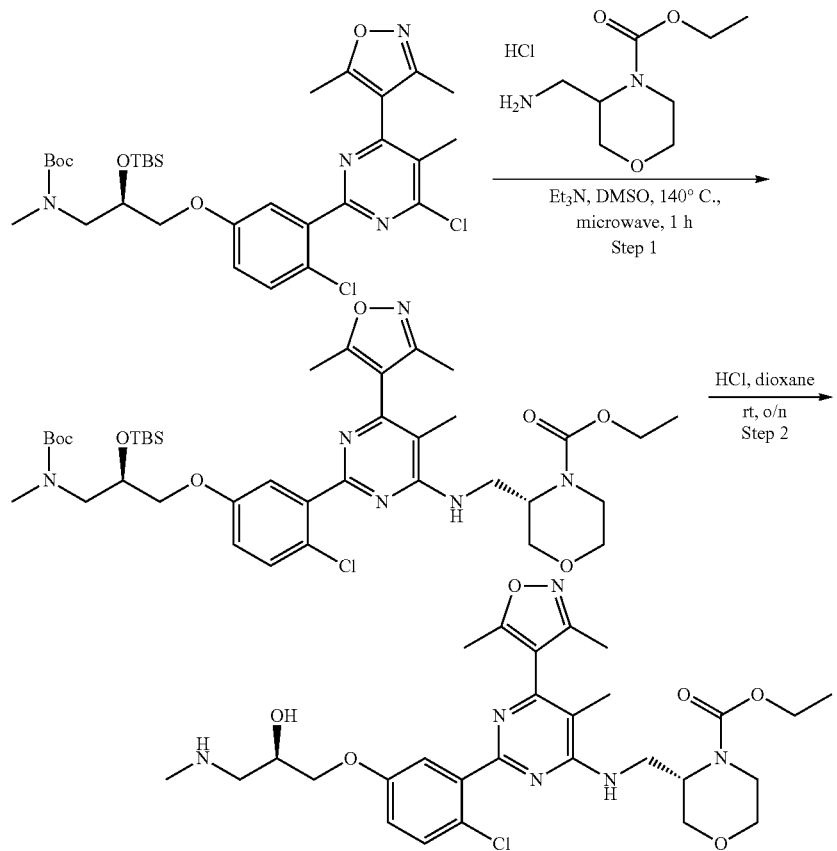

Step 1: Synthesis of (S)-ethyl 3-((2-(5-((R)-3-(tert-butoxycarbonyl(methyl) amino)-2-(tert-butyldimethylsilyloxy)propoxy)-2-chlorophenyl)-6-(3,5-dimethyl-isoxazol-4-yl)-5-methyl pyrimidin-4-ylamino) methyl)morpholine-4-carboxylate A reaction pressure vessel was charged with a mixture of tert-butyl (R)-2-(tert-butyldimethylsilyloxy)-3-(4-chloro-3-(4-chloro-6-(3,5-dimethylisoxazol-4-yl)-5-methylpyrimidin-2-yl)phenoxy)propyl(methyl) carbamate (120 mg, 0.18 mmol), (S)-ethyl 3-(amino-methyl)morpholine-4-carboxylate HCl salt (82 mg, 0.36 mmol), Et$_3$N (0.5 mL, 3.5 mmol) and DMSO (2 mL), capped, placed in a microwave reactor and irradiated for 60 min. at external temperature of 140° C., the mixture was then cooled down to room temperature, diluted with water (40 mL) and extracted with EtOAc (30 mL×3). The organic layers were combined, dried over Na$_2$SO$_4$, filtered, concentrated and the crude residue was purified by chromatographic column on silicagel to give (R)-ethyl 3-((2-(5-((R)-3-(tert-butoxycarbonyl(methyl) amino)-2-(tert-butyldimethyl-silyloxy)propoxy)-2-chlorophenyl)-6-(3,5-dimethyl isoxazol-4-yl)-5-methylpyrimidin-4-ylamino)methyl)morpholine-4-carboxylate as a white solid (81 mg, 54% yield). ESI-LCMS (m/z): 802.8 [M+H]$^+$.

Step 2: Synthesis of (S)-ethyl 3-((2-(2-chloro-5-((R)-2-hydroxy-3-(methylamino) propoxy)phenyl)-6-(3,5-dimethylisoxazol-4-yl)-5-methylpyrimidin-4-ylamino) methyl)morpholine-4-carboxylate A solution of (S)-ethyl 3-((2-(5-((R)-3-(2-tert-butoxy-2-oxoethylamino)-2-(tert-butyldimethyl-silyloxy)propoxy)-2-chlorophenyl)-6-(3,5-dimethyl isoxazol-4-yl)-5-methylpyrimidin-4-ylamino)methyl)morpholine-4-carboxylate (100 mg, 0.12 mmol) in 4N HCl in dioxane (4 mL), was stirred at room temperature for 16 h, the solvent was then removed in vacuo, and the residue was dissolved in MeOH (10 ml), treated with ammonia till pH 7-8 and then concentrated again. The residue was purified by preparative HPLC to give (R)-ethyl 3-((2-(2-chloro-5-((R)-2-hydroxy-3-(methylamino)propoxy)phenyl)-6-(3,5-dimethyl-isoxazol-4-yl)-5-methylpyrimidin-4-ylamino)methyl)morpholine-4-carboxylate as a formic acid salt (46 mg, 58% yield). ESI-LCMS (m/z): 589.3 [M+H]$^+$; $^1$HNMR (500 MHz, MeOD) δ ppm: 8.56 (s, 1H), 7.42 (d, J=9.0 Hz, 1H), 7.25 (br s, 1H), 7.06 (dd, J=3.5 and 9.0 Hz, 1H), 4.60-4.20 (m, 2H), 4.13-3.60 (m, 10H), 3.53-3.40 (m, 2H), 3.27-3.24 (m, 1H), 3.18-3.12 (m, 1H), 2.75 (s, 3H), 2.36 (s, 3H), 2.24 (s, 3H), 2.00 (s, 3H), 1.25-0.95 (m, 3H).

Example 39. Preparation of 1-{3-[4-(5,7-Dihydro-pyrrolo[3,4-b]pyridin-6-yl)-6-(3,5-dimethyl-isoxazol-4-yl)-5-methyl-pyrimidin-2-yl]-4-fluoro-phenoxy}-3-methylamino-propan-2-ol
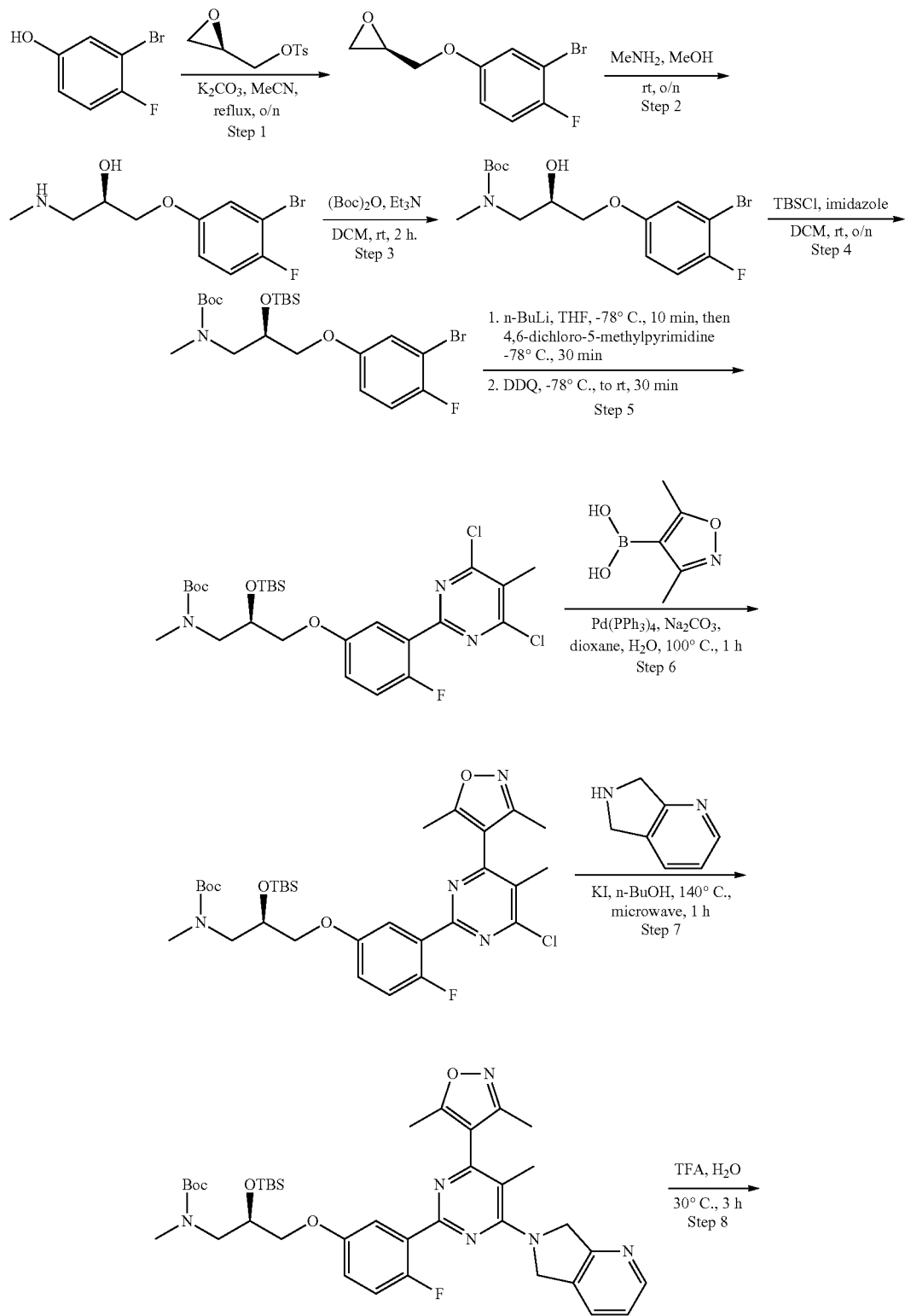

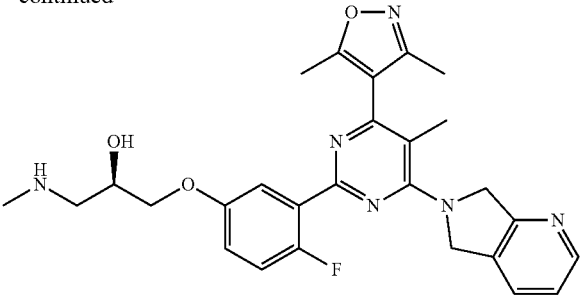

Step 1: Synthesis of (R)-2-((3-bromo-4-fluorophenoxy)methyl)oxirane

To a solution of 3-bromo-4-fluorophenol (or any other suitably substituted 3-bromophenol, 130 mmol) in 200 ml of MeCN was added K$_2$CO$_3$ (55 g, 398 mmol) and (R)-oxiran-2-ylmethyl 4-methylbenzenesulfonate (29.6 g, 130 mmol) and the mixture was stirred at 80° C. for 16 h., cooled down to room temperature, filtered and concentrated to give (R)-2-((3-bromo-4-fluorophenoxy) methyl)oxirane (30 g, crude) as a pale yellow oil, which was used into next step without further purification. Assumed quantitative yield.

Step 2: Synthesis of (R)-1-(3-bromo-4-fluorophenoxy)-3-(methylamino)propan-2-ol A solution of (R)-2-((3-bromo-4-fluorophenoxy)methyl) oxirane (30 g, crude from step 1) in MeOH (100 ml) stirred at 0° C. was treated with slow addition of 33% MeNH$_2$ in MeOH (100 ml), then further stirred at room temperature for 2 h. After removal of volatiles in vacuo, (R)-1-(3-bromo-4-fluorophenoxy)-3-(methyl-amino)propan-2-ol (33 g, crude) was obtained as a pale yellow oil, which was used into next step directly. ESI-LCMS (m/z): 279.1 [M+H]$^+$. Assumed quantitative yield.

Step 3: Synthesis of (R)-tert-butyl 3-(3-bromo-4-fluorophenoxy)-2-hydroxypropyl(methyl)carbamate A solution of (R)-1-(3-bromo-4-fluorophenoxy)-3-(methylamino) propan-2-ol (33 g, crude from step 2) in 200 ml of DCM stirred 0° C. was treated with portion wise addition of Boc$_2$O (29 g, 132 mmol) and the reaction mixture was further stirred at room temperature for 2 h., and concentrated in vacuo to give (R)-tert-butyl 3-(3-bromo-4-fluoro phenoxy)-2-hydroxypropyl(methyl)carbamate (44 g, crude) as pale yellow oil, which was used into next step directly. ESI-LCMS (m/z): 400.0 [M+23]$^+$. Assumed quantitative yield.

Step 4: Synthesis of (R)-tert-butyl 3-(3-bromo-4-fluorophenoxy)-2-(tert-butyl dimethylsilyloxy)propyl(methyl)carbamate A solution of (R)-tert-butyl 3-(3-bromo-4-fluorophenoxy)-2-hydroxylpropyl (methyl) carbamate (44 g, crude from step 3) and imidazole (27 g, 236 mmol) in 200 ml of DCM was treated with a solution of TBSCl (22 g, 141 mmol) in DCM (50 ml), added slowly from addition funnel and the reaction mixture was stirred at 35° C. under N$_2$ atmosphere for 16 h., then diluted with water (200 ml), the organic layer was dried over Na$_2$SO$_4$, filtered, concentrated and the resulting residue was purified by chromatographic column on silica gel (petroleum ether/EtOAc=20/1) to obtain (R)-tert-butyl 3-(3-bromo-4-fluorophenoxy)-2-(tert-butyldimethylsilyloxy)propyl (methyl)carbamate (47 g, 33% yield for 4 steps) as a pale yellow solid. ESI-LCMS (m/z): 515.1 [M+23]$^+$.

Step 5: Synthesis of (R)-tert-butyl 2-(tert-butyldimethylsilyloxy)-3-(3-(4,6-dichloro-5-methylpyrimidin-2-yl)-4-fluorophenoxy)propyl(methyl)carbamate A solution of (R)-tert-butyl 3-(3-bromo-4-fluorophenoxy)-2-(tert-butyldimethyl silyloxy)propyl(methyl)carbamate (10 g, 20 mmol) in dry THF (50 mL), stirred at −78° C. under N$_2$ atmosphere was treated with slow addition of n-butyl lithium (10 mL, 2.5N in hexane) over a period of 30 min. The mixture was stirred for another 10 minutes at the same temperature followed by slow addition of a solution of 4,6-dichloro-5-methyl-pyrimidine (3.3 g, 20 mmol) in THF (20 mL) and further stirred at −78° C. for 30 minutes. DDQ (6.8 g, 30 mmol) was then added portion wise, the mixture warmed up to 0° C. and stirred for 30 minutes, concentrated and the residue was diluted with CH$_2$Cl$_2$ (300 mL), washed with 10% NaOH (50 mL), water (100 mL×2) and brine (100 mL). The organic layer was dried over Na$_2$SO$_4$, filtered, concentrated and the residue was purified by chromatographic column on silicagel eluted with petroleum ether/EtOAc=15/1 to give (R)-tert-butyl 2-(tert-butyldimethyl silyloxy)-3-(3-(4,6-dichloro-5-methylpyrimidin-2-yl)-4-fluorophenoxy)propyl (methyl) carbamate (5.8 g, 51% yield) as a white solid. ESI-LCMS (m/z): 595.9 [M+23]$^+$.

Step 6: Synthesis of tert-butyl(R)-2-(tert-butyldimethylsilyloxy)-3-(3-(4-chloro-6-(3,5-dimethylisoxazol-4-yl)-5-methylpyrimidin-2-yl)-4-fluorophenoxy)propyl (methyl) carbamate To a solution of (R)-tert-butyl 2-(tert-butyldimethylsilyloxy)-3-(3-(4,6-dichloro-5-methylpyrimidin-2-yl)-4-fluorophenoxy)propyl(methyl)carbamate (5.8 g, 10 mmol) in degassed dioxane and H$_2$O (5/1, 120 mL) was added 3,5-dimethylisoxazol-4-yl boronic acid (1.2 g, 8.0 mmol), Pd(PPh$_3$)$_4$ (1.1 g, 1.0 mmol) and Na$_2$CO$_3$ (2.2 g, 20 mmol). The system was purged with N$_2$ stream and the mixture was stirred at 80° C. for 4 h., cooled down to room temperature, diluted with water (100 mL) and extracted with EtOAc (250 mL×2). The organic layers were combined and washed with brine (200 mL), dried over Na$_2$SO$_4$, filtered, concentrated and the residue was purified by chromatographic column on silicagel, eluted with 1:5 EtOAc:petroleum ether to give tert-butyl(R)-2-(tert-butyldimethylsilyloxy)-3-(3-(4-chloro-6-(3,5-dimethyl-isoxazol-4-yl)-5-methylpyrimidin-2-yl)-4- fluorophenoxy)propyl(methyl)carbamate (3.7 g, 58% yield) as a light yellow solid. ESI-LCMS (m/z): 635.0 [M+1]$^+$.

Step 7: Synthesis of tert-butyl (R)-2-(tert-butyldimethylsilyloxy)-3-(3-(4-(3,5-dimethylisoxazol-4-yl)-5-methyl-6-(5H-pyrrolo[3,4-b]pyridin-6(7H)-yl)pyrimidin-2-yl)-4-fluorophenoxy)propyl(methyl)carbamate A reaction pressure vessel was charged with a mixture of tert-butyl (R)-2-(tert-butyldimethylsilyloxy)-3-(3-(4-chloro-6-(3,5-dimethylisoxazol-4-yl)-5-methylpyrimidin-2-yl)-4-fluorophenoxy)propyl(methyl) carbamate (110 mg, 0.17 mmol); 6,7-dihydro-5H-pyrrolo[3,4-b]pyridine (or any other suitably substituted primary or secondary amine, 0.26 mmol), KI (61 mg, 0.35 mmol) and n-BuOH (1 mL), capped, placed in a microwave reactor and irradiated for 60 min. at external temperature of 140° C. After being cooled down to room temperature, the mixture was diluted with water (20 mL) and extracted with EtOAc (20 mL×3). The organic layers were combined, dried over Na$_2$SO$_4$, filtered and concentrated to give tert-butyl(R)-2-(tert-butyldimethylsilyloxy)-3-(3-(4-(3,5-dimethylisoxazol-4-yl)-5-methyl-6-(5H-pyrrolo[3,4-b]pyridine-6(7H)-yl) pyrimidin-2-yl)-4-fluoro-phenoxy) propyl (methyl) carbamate as a brown solid (124 mg, crude), which was used for the next step without further purification. ESI-LCMS (m/z): 719.0 [M+11].

Step 8: Synthesis of (2R)-1-(3-(4-(3,5-dimethyl-isoxazol-4-yl)-5-methyl-6-(5H-pyrrolo[3,4-b]pyridin-6(7H)-yl)pyrimidin-2-yl)-4-fluorophenoxy)-3-(methyl-amino)propan-2-ol tert-Butyl (R)-2-(tert-butyldimethylsilyloxy)-3-(3-(4-(3, 5-dimethylisoxazol-4-yl)-5-methyl-6-(5H-pyrrolo[3,4-b]pyridin-6(7H)-yl)pyrimidin-2-yl)-4-fluorophenoxy) propyl (methyl)carbamate (124 mg, crude, from step 1) was treated with 90% TFA (5 mL) and the solution was stirred at room temperature for 3 h; concentrated under vacuo, the residue was dissolved in MeOH (5 ml) and the resulting solution was treated with ammonia till pH 7-8 and concentrated. The residue was purified by preparative HPLC to give (2R)-1-(4-chloro-3-(4-(3,5-dimethylisoxazol-4-yl)-5-methyl-6-(5H-pyrrolo[3,4-b]pyridin-6(7H)-yl)pyrimidin-2-yl)phenoxy)-3-(methylamino)propan-2-ol as a white solid (62 mg, 71% yield for 2 steps). ESI-LCMS (m/z): 504.9 [M+H]$^+$; $^1$HNMR (400 MHz, CD3OD) δ ppm: 8.49 (d, J=4.0 Hz, 1H), 7.88 (d, J=7.6 Hz, 1H), 7.60 (dd, J=3.2 and 6.0 Hz, 1H), 7.40 (dd, J=4.8 and 7.6 Hz, 1H), 7.20-7.05 (m, 2H), 5.30 (s, 2H), 5.26 (s, 2H), 4.18-4.11 (m, 1H), 4.06-4.00 (m, 2H), 2.94-2.77 (m, 2H), 2.52 (s, 3H), 2.44 (s, 3H), 2.43 (s, 3H), 2.31 (s, 3H).

Example 40. Preparation of (R)-4-{6-(3,5-Dimethyl-isoxazol-4-yl)-2-[5-(2-hydroxy-3-methyl-amino-propoxy)-2-trifluoromethyl-phenyl]-5-methyl-pyrimidin-4-ylamino}-piperidine-1-carboxylic acid methyl ester

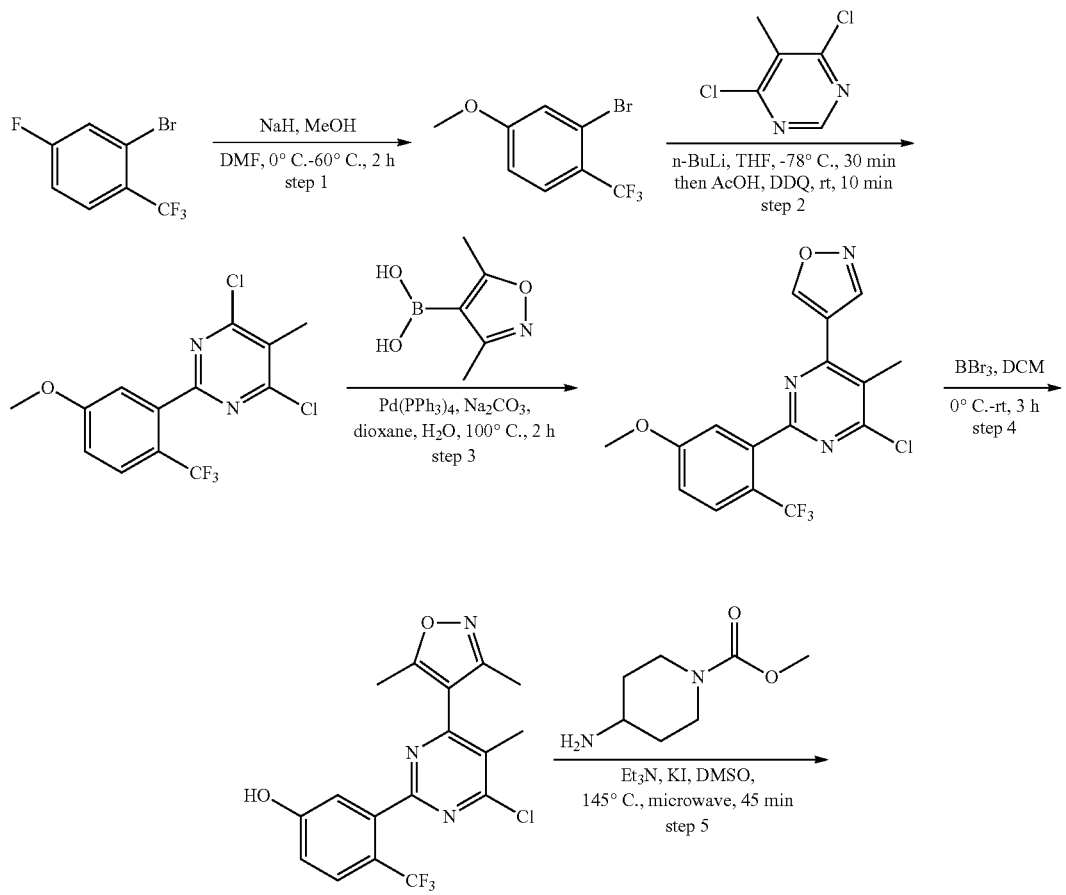

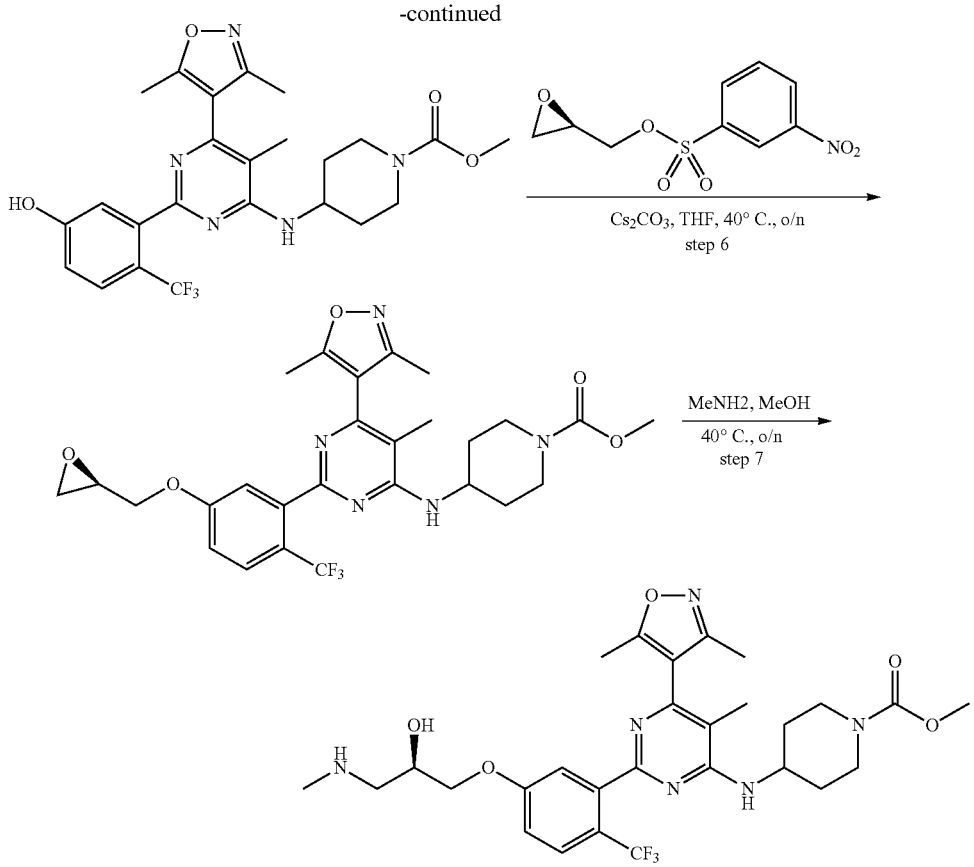

Step 1: Synthesis of 2-bromo-4-methoxy-1-(trifluoromethyl)benzene

To a suspension of NaH (60%, 6.0 g, 0.15 mol) in dry DMF (50 mL) stirred at 0° C. under nitrogen atmosphere, was added CH₃OH (6.0 mL, 0.15 mol) dropwise via syringe. After gas evolution ceased, the suspension was stirred at 0° C. for 20 minutes before 2-bromo-4-fluoro-1-(trifluoromethyl)benzene (6.0 mL, 0.043 mol) was added dropwise over 5 minutes. The reaction mixture was allowed to warm up to room temperature and then heated at 60° C. for 2 h. After being cooled down to room temperature the mixture was diluted with water (100 mL), extracted with EtOAc (100 mL×2), the combined organic layers were washed with water (100 mL×2) and brine (100 mL), dried over Na₂SO₄, filtered and concentrated. The residue was purified by chromatographic column on silicagel (petroleum ether/EtOAc=100/1 to 30/1) to give 2-bromo-4-methoxy-1-(trifluoromethyl)benzene as an oil (8.0 g, 73% yield). ¹HNMR (400 MHz, CD₃OD) δ ppm: 7.65 (d, J=8.4 Hz, 1H), 7.31 (d, J=2.0 Hz, 1H), 7.02 (dd, J=2.0 and 8.4 Hz, 1H), 3.86 (s, 3H).

Step 2: Synthesis of 4,6-dichloro-2-(5-methoxy-2-(trifluoromethyl)phenyl)-5-methylpyrimidine To a solution of 2-bromo-4-methoxy-1-(trifluoromethyl) benzene (5.0 g, 19.6 mmol) in dry THF (50 mL) stirred at −78° C. under nitrogen atmosphere, was added n-Butyl lithium (8.9 mL, 2.4 M in hexane, 21.4 mmol) over a period of 5 minutes, the mixture was stirred for another 10 minutes at the same temperature before 4,6-dichloro-5-methylpyrimidine (4.5 g, 27.9 mmol) in THF (5 mL) was added slowly over 5 minutes. The resulting mixture was stirred at −78° C. for 30 minutes, then quenched with HOAc (1.5 mL) and warmed to 0° C. slowly. DDQ (6.6 g, 29.1 mmol) was then added portion wise and the resulting mixture was stirred at 0° C. for 30 minutes, diluted with CH₂C₂ (100 mL), washed with 10% NaOH (50 mL×2) and brine (100 mL); the organic layer was dried over Na₂SO₄, filtered and concentrated. The residue was purified silica column chromatography with (petroleum ether/EtOAc=100/1 to 30/1) to render 4,6-dichloro-2-(5-methoxy-2-(trifluoromethyl) phenyl)-5-methylpyrimidine (1.0 g, 21% yield). ESI-LCMS (m/z): 337.0 [M+H]⁺.

Step 3: Synthesis of 4-(6-chloro-2-(5-methoxy-2-(trifluoromethyl)phenyl)-5-methylpyrimidin-4-yl)-3,5-dimethylisoxazole To a solution of 4,6-dichloro-2-(5-methoxy-2-(trifluoromethyl)phenyl)-5-methyl-pyrimidine (1.4 g, 4.1 mmol) in degassed dioxane and water (50 mL, 5/1) was added 3,5-dimethylisoxazol-4-ylboronic acid (831 mg, 5.9 mmol), Na₂CO₃ (1.2 g, 11.8 mmol) and Pd(PPh₃)₄ (335 mg, 0.29 mmol). The flask was evacuated and refilled with N₂ three times, then heated at 100° C. for 2 h. After being cooled down to room temperature, the mixture was diluted with water (50 mL) and extracted with EtOAc (40 mL×2). The combined organic layers were washed with brine (50 mL×2), dried over Na₂SO₄, filtered and concentrated. The residue was purified by preparative TLC (petroleum ether/EtOAc=5/1) to give 4-(6-chloro-2-(5-methoxy-2-(trifluoro methyl)phenyl)-5-methyl-pyrimidin-4-yl)-3,5-dimethyl-isoxazole (1.0 g, 60% yield). ESI-LCMS (m/z): 398.1 [M+H]+.

Step 4: Synthesis of 3-(4-chloro-6-(3,5-dimethyl-isoxazol-4-yl)-5-methylpyrimidin-2-yl)-4-(trifluoromethyl)phenol A solution of 4-(6-chloro-2-(5-methoxy-2-(trifluoromethyl)phenyl)-5-methyl-pyrimidin-4-yl)-3,5-dimethylisoxazole (700 mg, 1.7 mmol) in DCM (4 mL) stirred at 0° C. was treated with slow addition of BBr3 (1.5 mL, 16.5 mmol), and the mixture was further stirred at room temperature for 2 h, cooled down to 0° C. and quenched by slow addition of water (20 mL), extracted with EtOAc (20 mL×2), the combined organic layers were washed with aqueous NaHCO3 solution (20 mL) and brine (20 mL), dried over Na2SO4, filtered and concentrated. The residue was purified by preparative TLC (petroleum ether/EtOAc=5/1) to give 3-(4-chloro-6-(3,5-dimethylisoxazol-4-yl)-5-methylpyrimidin-2-yl)-4-(trifluoromethyl) phenol (220 mg, 32% yield). ESI-LCMS (m/z): 384.1 [M+H]+.

Step 5: Synthesis of methyl 4-(6-(3,5-dimethylisoxazol-4-yl)-2-(5-hydroxy-2-(trifluoromethyl)phenyl)-5-methylpyrimidin-4-ylamino)piperidine-1-carboxylate A reaction pressure vessel was charged with a mixture of 3-(4-chloro-6-(3, 5-dimethylisoxazol-4-yl)-5-methylpyrimidin-2-yl)-4-(trifluoromethyl)phenol (170 mg, 0.44 mmol); methyl 4-aminopiperidine-1-carboxylate HCl (200 mg, 1.03 mmol), TEA (0.5 mL, 3.5 mmol) and KI (145 mg, 0.88 mmol) in DMSO (2 mL), capped, placed in a microwave reactor and irradiated for 45 min. at external temperature of 145° C. After being cooled down to room temperature, the mixture was diluted with water (20 mL) and extracted with EtOAc (15 mL×2); the combined organic layers were washed with aqueous NH4Cl solution (20 mL) and brine (20 mL), dried over Na2SO4, filtered and concentrated. The residue was purified by preparative TLC (petroleum ether/EtOAc=2/1) to give methyl 4-(6-(3,5-dimethylisoxazol-4-yl)-2-(5-hydroxy-2-(trifluoromethyl)phenyl)-5-methylpyrimidin-4-ylamino)piperidine-1-carboxylate as a yellow solid (77 mg, 34% yield). ESI-LCMS (m/z): 505.8 [M+H]+.

Step 6: Synthesis of methyl 4-(6-(3, 5-dimethyl-isoxazol-4-yl)-5-methyl-2-(5-((R)-oxiran-2-yl-methoxy)-2-(trifluoromethyl)phenyl)pyrimidin-4-ylamino)piperidine-1-carboxylate To a solution of methyl 4-(6-(3,5-dimethylisoxazol-4-yl)-2-(5-hydroxy-2-(trifluoro-methyl)phenyl)-5-methylpyrimidin-4-ylamino)piperidine-1-carboxylate (77 mg, 0.15 mmol) and (R)-oxiran-2-ylmethyl 3-nitrobenzenesulfonate (73 mg, 0.3 mmol) in THF (10 mL) was added Cs2CO3 (98 mg, 0.3 mmol) and the mixture was stirred at 40° C. for 16 h, cooled down to room temperature, diluted with water (20 mL) and extracted with EtOAc (20 mL×2). The combined organic layers were washed with brine, dried over Na2SO4, filtered and concentrated to give methyl 4-(6-(3,5-dimethyl isoxazol-4-yl)-5-methyl-2-(5-((R)-oxiran-2-ylmethoxy)-2-(trifluoromethyl)phenyl) pyrimidin-4-ylamino)piperidine-1-carboxylate as a brown solid (83 mg, crude), which was used for the next step without further purification. ESI-LCMS (m/z): 561.9[M+H]+.

Step 7: Synthesis of methyl 4-(6-(3,5-dimethylisoxazol-4-yl)-2-(5-((R)-2-hydroxy-3-(methylamino) propoxy)-2-(trifluoromethyl)phenyl)-5-methylpyrimidin-4-yl-amino)piperidine-1-carboxylate A solution of 4-(6-(3,5-dimethylisoxazol-4-yl)-2-(5-hydroxy-2-(trifluoromethyl) phenyl)-5-methylpyrimidin-4-ylamino)piperidine-1-carboxylate (83 mg, crude from previous step) in 33% MeNH2 in MeOH (5 mL) was stirred at 35° C. for 16 h.; concentrated in vacuo and the resulting residue was purified by preparative HPLC to give methyl 4-(6-(3,5-dimethylisoxazol-4-yl)-2-(5-((R)-2-hydroxy-3-(methylamino) propoxy)-2-(trifluoro methyl)phenyl)-5-methylpyrimidin-4-ylamino)piperidine-1-carboxylate as a formic acid salt (36 mg, 37% yield for 2 steps). ESI-LCMS (m/z): 593.3 [M+H]+; 1HNMR (400 MHz, CD3OD) δ ppm: 8.56 (br s, 1H), 7.75 (d, J=9.2 Hz, 1H), 7.20 (br s, 2H), 4.50-4.35 (m, 1H), 4.30-4.10 (m, 4H), 3.70 (s, 3H), 3.30-3.10 (m, 2H), 3.00-2.85 (m, 2H), 2.74 (s, 3H), 2.35 (s, 3H), 2.21 (s, 3H), 2.08-1.98 (m, 6H), 1.65-1.50 (m, 2H).

Example 41. Preparation of (R)-1-(3-(4-(3,5-dimethylisoxazol-4-yl)-5-methyl-6-(5H-pyrrolo[3, 4-d]pyrimidin-6(7H)-yl)pyrimidin-2-yl)-4-(trifluoromethyl)phenoxy)-3-(methyl-amino)propan-2-ol

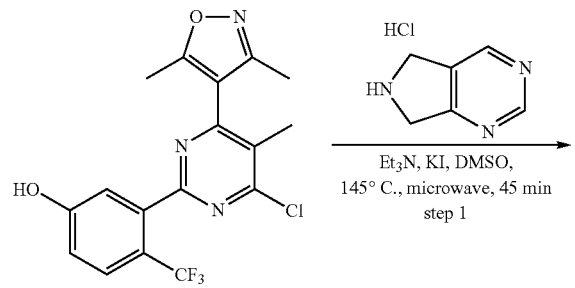

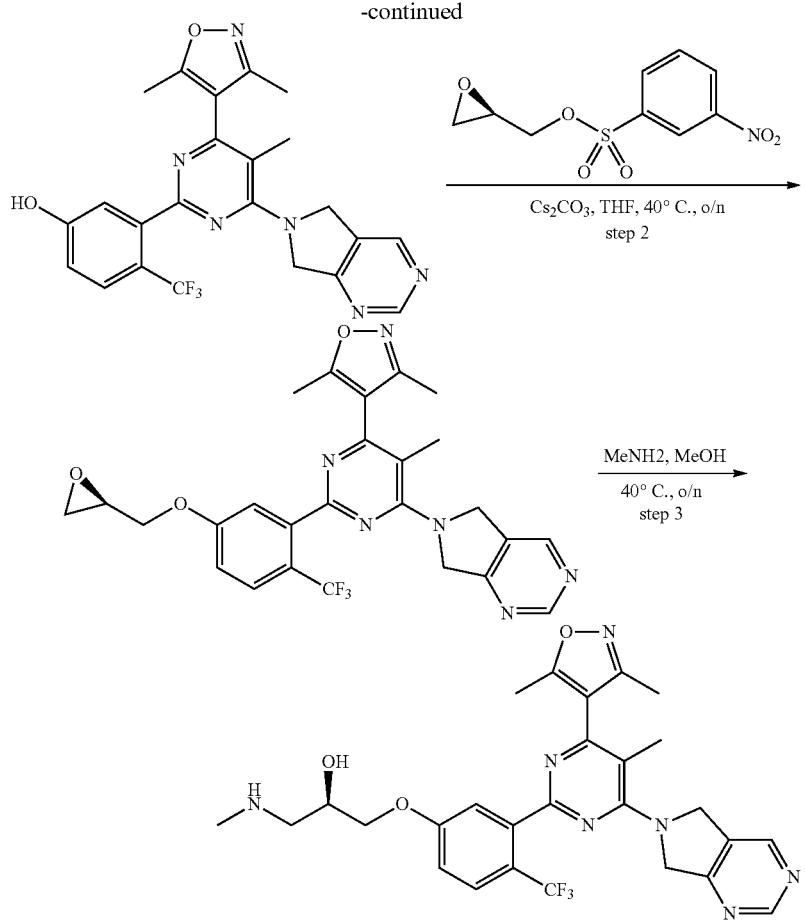

Step 1: Synthesis of 3-(4-(3, 5-dimethylisoxazol-4-yl)-5-methyl-6-(5H-pyrrolo[3, 4-d]pyrimidin-6(7H)-yl)pyrimidin-2-yl)-4-(trifluoromethyl)phenol A reaction pressure vessel was charged with a mixture of 3-(4-chloro-6-(3,5-dimethylisoxazol-4-yl)-5-methylpyrimidin-2-yl)-4-(trifluoromethyl)phenol (76 mg, 0.20 mmol); 6,7-dihydro-5H-pyrrolo [3,4-d]pyrimidine HCl (93 mg, 0.59 mmol), Et₃N (0.3 mL, 2.1 mmol) and KI (66 mg, 0.40 mmol) in DMSO (2 mL), capped, placed in a microwave reactor and irradiated for 45 min. at external temperature of 145° C. After being cooled down to room temperature, the mixture was diluted with water (20 mL) and extracted with EtOAc (15 mL×2). The combined organic layers were washed with brine (10 mL), dried over Na₂SO₄, filtered and concentrated. The residue was purified by preparative TLC (petroleum ether/EtOAc=5/1) to give 3-(4-(3,5-dimethyl-isoxazol-4-yl)-5-methyl-6-(5H-pyrrolo[3,4-d]pyrimidin-6 (7H)-yl) pyrimidin-2-yl)-4-(trifluoromethyl)phenol as a yellow solid (72 mg, 77% yield). ESI-LCMS (m/z): 469.2 [M+H]⁺.

Step 2: Synthesis of 3,5-dimethyl-4-(5-methyl-2-(5-((R)-oxiran-2-ylmethoxy)-2-(trifluoromethyl)phenyl)-6-(5H-pyrrolo[3,4-d]pyrimidin-6(7H)-yl)pyrimidin-4-yl)isoxazole A solution of 3-(4-(3,5-dimethylisoxazol-4-yl)-5-methyl-6-(5H-pyrrolo[3,4-d]pyrimidin-6(7H)-yl)pyrimidin-2-yl)-4-(trifluoro methyl)phenol (72 mg, 0.15 mmol) in THF (10 mL) was treated with (R)-(−)-Glycidyl nosylate (79 mg, 0.30 mmol) and Cs₂CO₃ (98 mg, 0.30 mmol), and the mixture was stirred at 40° C. for 16 h, diluted with EtOAc (20 mL), and consecutively washed with water (20 mL×2) and brine (20 mL). The organic phase was dried over Na₂SO₄, filtered and concentrated to give 3,5-dimethyl-4-(5-methyl-2-(5-((R)-oxiran-2-yl-methoxy)-2-(trifluoromethyl)phenyl)-6-(5H-pyrrolo[3,4-d]pyrimidin-6(7H)-yl) pyrimidin-4-yl)isoxazole as a brown solid (70 mg, crude), which was used for the next step without further purification. ESI-LCMS (m/z): 525.2 [M+H]⁺.

Step 3: Synthesis of (R)-1-(3-(4-(3,5-dimethylisoxazol-4-yl)-5-methyl-6-(5H-pyrrolo[3,4-d]pyrimidin-6(7H)-yl)pyrimidin-2-yl)-4-(trifluoromethyl)phenoxy)-3-(methylamino)propan-2-ol A solution of 3,5-dimethyl-4-(5-methyl-2-(5-((R)-oxiran-2-ylmethoxy)-2-(trifluoromethyl) phenyl)-6-(5H-pyrrolo[3, 4-d]pyrimidin-6(7H)-yl)pyrimidin-4-yl) isoxazole (70 mg, crude, from step 2) in 33% MeNH₂ in MeOH (5 mL) was stirred at 35° C. for 16 h, concentrated, and the resulting residue was purified by preparative HPLC to give (R)-1-(3-(4-(3,5-dimethylisoxazol-4-yl)-5-methyl-6-(5H-pyrrolo[3, 4-d] pyrimidin-6(7H)-yl)pyrimidin-2-yl)-4-(trifluoromethyl)phenoxy)-3-(methylamino)propan-2-ol as a white solid (10 mg, 11% yield for 2 steps). ESI-LCMS (m/z): 556.3[M+H]⁺; 1HNMR (400 MHz, CD₃OD) δ ppm: 9.11 (s, 1H), 8.81 (s, 1H), 7.75 (d, J=9.2 Hz, 1H), 7.26 (d, J=2.4 Hz, 2H), 7.20 (dd, J=2.0 and 9.2 Hz, 1H), 5.33 (s, 2H), 5.28 (s, 2H), 4.20-4.05 (m, 3H), 2.91-2.75 (m, 2H), 2.49 (s, 3H), 2.46 (s, 3H), 2.41 (s, 3H), 2.26 (s, 3H).
Example 42. Preparation of (R)-1-(4-chloro-3-(4-((2S, 4S)-1-cyclopropyl-2-methylpiperidin-4-ylamino)-6-(3,5-dimethylisoxazol-4-yl)-5-methylpyrimidin-2-yl)phenoxy)-3-(di-methyl amino)propan-2-ol
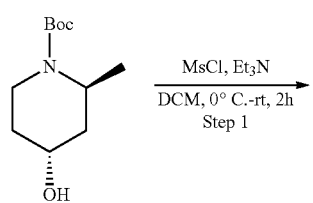
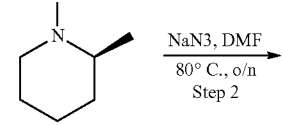
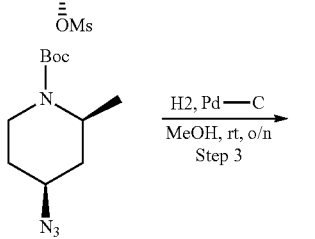
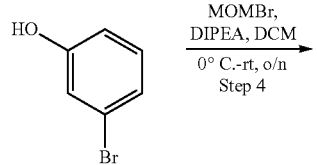
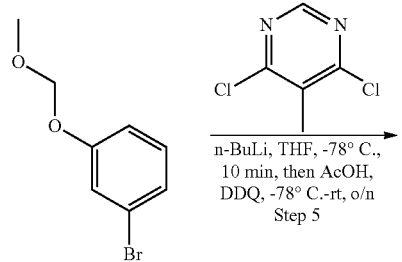
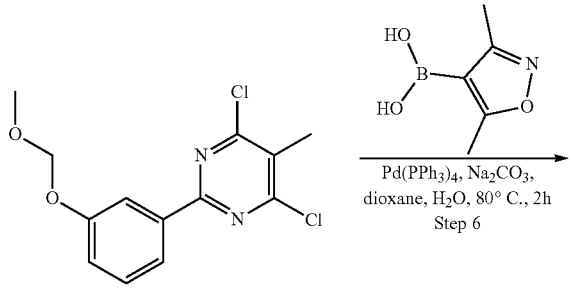
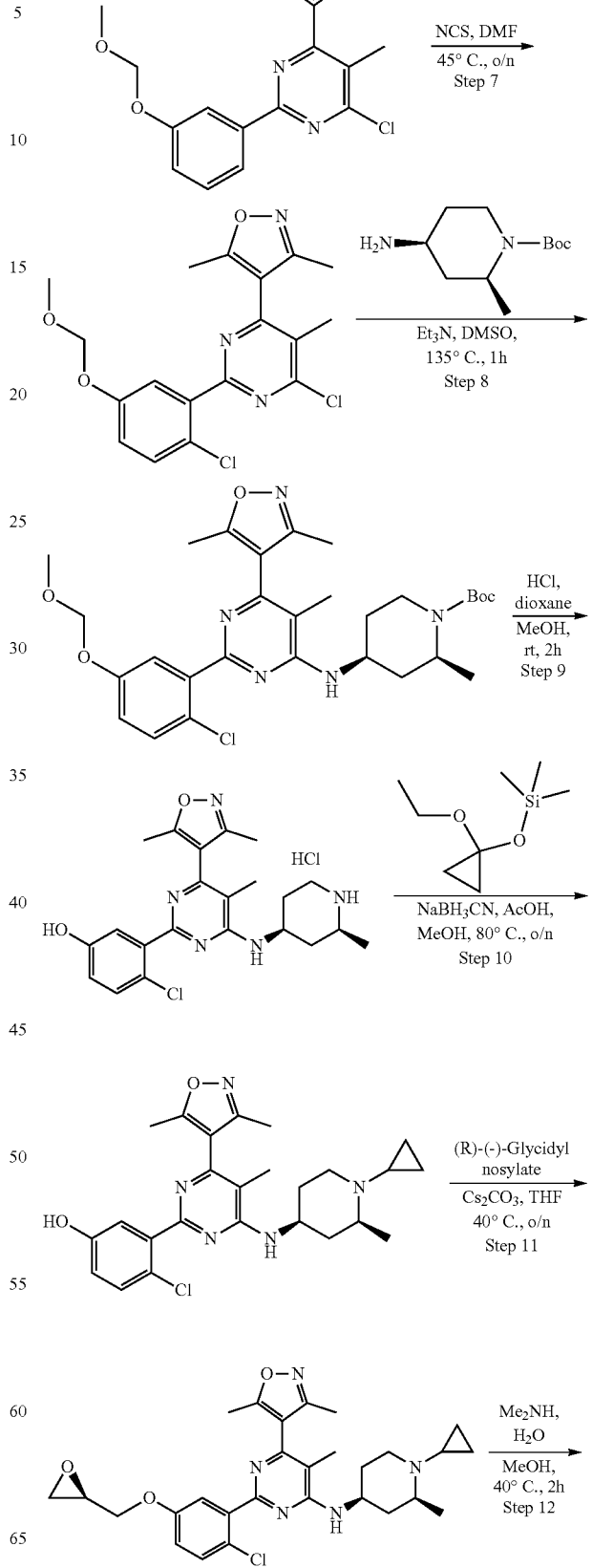

-continued

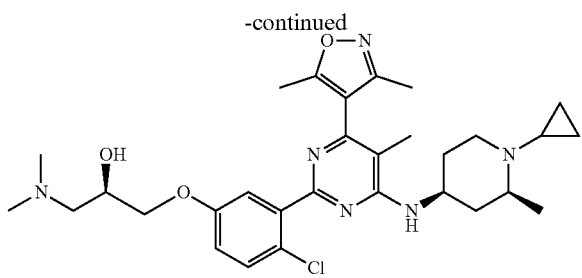

Step 1: Synthesis of (2S,4R)-tert-butyl 2-methyl-4-(methylsulfonyloxy)piperidine-1-carboxylate To a solution of (2S,4R)-tert-butyl 4-hydroxy-2-methylpiperidine-1-carboxylate (500 mg, 2.32 mmol) and $Et_3N$ (352 mg, 3.48 mmol) in DCM (15 mL) at 0° C. was added MsCl (318 mg, 2.78 mmol) dropwise, and the mixture was stirred to room temperature for 3 h. After the reaction was complete, water (30 mL) was added and the mixture was extracted by DCM (30 mL×2). The combined organic layers were washed with aqueous $NH_4Cl$ solution and brine, dried over $Na_2SO_4$, filtered and concentrated to give (2S,4R)-tert-butyl 2-methyl-4-(methylsulfonyloxy)piperidine-1-carboxylate, which was used for the next step without further purification. Assumed quantitative yield. ESI-LCMS (m/z): 238.1 [(M-56)+1]$^+$.

Step 2: Synthesis of (2S, 4S)-tert-butyl 4-azido-2-methylpiperidine-1-carboxylate To a solution of (2S,4R)-tert-butyl 2-methyl-4-(methylsulfonyloxy)piperidine-1-carboxylate (700 mg, crude from step 1) in DMF (5 mL) was added $NaN_3$ (300 mg, 4.6 mmol). The mixture was heated at 80° C. for 16 h., cooled down to room temperature, diluted with water (30 mL) and extracted with EtOAc (30 mL×2). The combined organic layers were washed with brine, dried over $Na_2SO_4$, filtered and concentrated to obtain (2S,4S)-tert-butyl 4-azido-2-methylpiperidine-1-carboxylate, which was used for the next step without further purification. Assumed quantitative yield. ESI-LCMS (m/z): 185.1 [(M-56)+1]$^+$.

Step 3: Synthesis of (2S,4S)-tert-butyl 4-amino-2-methylpiperidine-1-carboxylate To a solution of (2S,4S)-tert-butyl 4-azido-2-methylpiperidine-1-carboxylate (450 mg, crude from step 2) in MeOH (20 mL) was added 10% Pd—C (85 mg) and the mixture was stirred at room temperature for 16 h under $H_2$ atmosphere, filtered through a pad of Celite and the filtrate was concentrated to give (2S,4S)-tert-butyl 4-amino-2-methylpiperidine-1-carboxylate, which was used for the next step without further purification. Assumed quantitative yield. ESI-LCMS (m/z): 159.1 [(M-56)+1]$^+$.

Step 4: Synthesis of 1-bromo-3-(methoxymethoxy)benzene

A solution of 3-bromophenol (30 g, 0.17 mol) and DIPEA (33.6 g, 0.26 mol) in DCM (300 mL) stirred at 0° C. was treated with dropwise addition of methoxymethyl bromide (27.9 g, 225 mmol) and the reaction mixture was further stirred at room temperature for 16 h., washed with water (200 mL×2), aqueous $NH_4Cl$ solution (200 mL) and brine (200 mL). The organic layer was dried over $Na_2SO_4$, filtered and concentrated to render 1-bromo-3-(methoxy-methoxy) benzene (38 g) as a yellow oil. $^1$HNMR (400 MHz, $CDCl_3$) δ ppm: 7.28-7.22 (m, 2H), 7.20-7.17 (m, 1H), 7.06-7.02 (m, 1H), 5.21 (s, 2H), 3.37 (s, 3H).

Step 5: Synthesis of 4,6-dichloro-2-(3-(methoxymethoxy)phenyl)-5-methylpyrimidine To a solution of 1-bromo-3-(methoxymethoxy)benzene (20 g, 92.5 mmol) in dry THF (100 mL) stirred at −78° C. under $N_2$ atmosphere, was added n-butyl lithium (42 mL, 2.4 M in hexane, 101 mmol) over a period of 10 minutes, the mixture was stirred for another 10 minutes at −78° C. before a solution of 4,6-dichloro-5-methylpyrimidine (18 g, 111 mmol) in THF (20 mL) was added slowly over 10 minutes. The resulting mixture was stirred at same temperature for 30 minutes, then quenched with HOAc (20 mL) and warmed to 0° C. slowly. DDQ (30 g, 130 mmol) was then added portionwise and resulting mixture was stirred at for 0° C. for 30 minutes, diluted with $CH_2Cl_2$ (300 mL), washed with 10% NaOH (100 mL×2) and brine (100 mL). The organic layer was dried over $Na_2SO_4$, filtered, concentrated and the residue was purified chromatographic column on silicagel eluted with (petroleum ether/EtOAc=80/1) to afford the 4,6-dichloro-2-(3-(methoxymethoxy)phenyl)-5-methylpyrimidine (10.2 g, 37% yield) as a white solid. ESI-MS (m/z): 299.1 [M+1]$^+$.

Step 6: Synthesis of 4-(6-chloro-2-(3-(methoxymethoxy)phenyl)-5-methyl-pyrimidin-4-yl)-3,5-dimethylisoxazole To a solution of 4,6-dichloro-2-(3-(methoxymethoxy) phenyl)-5-methylpyrimidine (10 g, 33.5 mmol) and 3,5-dimethylisoxazol-4-ylboronic acid (4.72 g, 33.5 mmol) in degassed dioxane and $H_2O$ (3/1, 80 mL) was added $Pd(PPh_3)_4$ (1.9 g, 1.6 mmol) and $Na_2CO_3$ (10.6 g, 0.1 mol). The flask was evacuated and back-filled with dry $N_2$ three times, then heated at 80° C. for 2 h. After being cooled down to room temperature, the mixture was diluted with water (30 mL) and extracted with EtOAc (50 mL×2). The organic layers were combined, dried over $Na_2SO_4$, filtered and concentrated. The residue was purified by chromatographic column on silicagel (petroleum ether/EtOAc=30/1) to afford 4-(6-chloro-2-(3-(methoxymethoxy)phenyl)-5-methyl pyrimidin-4-yl)-3,5-dimethylisoxazole (4.7 g, 39% yield) as a white solid. ESI-MS (m/z): 360.1 [M+1]$^+$.

Step 7: Synthesis of 4-(6-chloro-2-(2-chloro-5-(methoxymethoxy)phenyl)-5-methylpyrimidin-4-yl)-3,5-dimethylisoxazole To a solution of 4-(6-chloro-2-(3-(methoxymethoxy)phenyl)-5-methylpyrimidin-4-yl)-3,5-dimethylisoxazole (5.0 g, 13.9 mmol) in DMF (50 mL) was added NCS (2.4 g, 18.1 mmol), and the mixture was stirred at 45° C. for 2 h. After being cooled down to room temperature, EtOAc (200 mL) was added, and the mixture was washed with water (100 mL×3), aqueous $Na_2SO_3$ solution (100 mL×1) and brine (200 mL). The organic phase was dried over $Na_2SO_4$, filtered and concentrated. The residue was purified by chromatographic column on silicagel (petroleum ether/EtOAc=20/1) to afford 4-(6-chloro-2-(2-chloro-5-(methoxymethoxy)phenyl)-5-methylpyrimidin-4-yl)-3,5-dimethylisoxazole (4.7 g, 87% yield) as a white solid. ESI-MS (m/z): 394.1 [M+1]$^+$.

Step 8: Synthesis of (2S,4S)-tert-butyl 4-(2-(2-chloro-5-(methoxymethoxy)phenyl)-6-(3,5-dimethylisoxazol-4-yl)-5-methylpyrimidin-4-ylamino)-2-methylpiperidine-1-carboxylate A reaction pressure vessel was charged with a mixture of 4-(6-chloro-2-(2-chloro-5-(methoxymethoxy)phenyl)-5-methyl-pyrimidin-4-yl)-3, 5-dimethylisoxazole (600 mg, 1.5 mmol), (2S,4S)-tert-butyl 4-amino-2-methyl piperidine-1-carboxylate (or any other suitably substituted primary or secondary amine, 2.3 mmol), $Et_3N$ (230 mg, 2.2 mmol) and DMSO (5 mL), capped, placed in a microwave reactor and irradiated for 60 min. at external temperature of 135° C. After being cooled down to room temperature, water (30 mL) was added and the mixture was extracted by EtOAc (30 mL×2). The combined organic layers were washed with brine, dried over $Na_2SO_4$, concentrated and the residue was purified by preparative TLC (petroleum ether/EtOAc=1/1) to obtain the (2S,4S)-tert-butyl 4-(2-(2-chloro-5-(methoxymethoxy)phenyl)-6-(3,5-dimethyl-isoxazol-4-yl)-5-methylpyrimidin-4-ylamino)-2-methylpiperidine-1-carboxylate (730 mg, 84% yield). ESI-LCMS (m/z): 571.8 $[M+1]^+$.

Step 9: Synthesis of 4-chloro-3-(4-(3,5-dimethyl-isoxazol-4-yl)-5-methyl-6-((2S,4S)-2-methylpiperidin-4-ylamino)pyrimidin-2-yl)phenol HCl To a solution of (2S,4S)-tert-butyl 4-(2-(2-chloro-5-(methoxymethoxy)phenyl)-6-(3,5-dimethylisoxazol-4-yl)-5-methylpyrimidin-4-ylamino)-2-methylpiperidine-1-carboxylate (730 mg, 1.2 mmol) in MeOH (5 mL) was added 4N HCl in dioxane (5 mL) and the mixture was stirred at room temperature for 2 h. and concentrated under vacuo to give 4-chloro-3-(4-(3,5-dimethylisoxazol-4-yl)-5-methyl-6-((2S,4S)-2-methylpiperidin-4-ylamino)pyrimidin-2-yl)phenol HCl salt (750 mg, crude, purity: 93% at 254 nm), which was used for the next step without further purification. ESI-LCMS (m/z): 427.9 $[M+1]^+$.

Step 10: Synthesis of 4-chloro-3-(4-((2S,4S)-1-cyclopropyl-2-methylpiperidin-4-ylamino)-6-(3,5-dimethylisoxazol-4-yl)-5-methylpyrimidin-2-yl)phenol To a solution of 4-chloro-3-(4-(3,5-dimethylisoxazol-4-yl)-5-methyl-6-((2S,4S)-2-methyl piperidin-4-ylamino)pyrimidin-2-yl)phenol HCl (400 mg crude from step 9) in MeOH (10 mL) was added (1-ethoxycyclopropoxy)trimethylsilane (450 mg, 2.5 mmol), AcOH (0.3 mL, 5.2 mmol) and $NaBH_3CN$ (164 mg, 2.5 mmol). The mixture was heated at 80° C. for 16 h., cooled down to room temperature and quenched with slow addition of aqueous $NaHCO_3$ solution (30 mL), then extracted with EtOAc (30 mL×3). The combined organic layers were washed with brine, dried over $Na_2SO_4$, filtered and concentrated. The residue was triturated with petroleum ether/EtOAc (4/1, 15 mL×2) to give 4-chloro-3-(4-((2S,4S)-1-cyclopropyl-2-methyl-piperidin-4-yl-amino)-6-(3,5-dimethylisoxazol-4-yl)-5-methylpyrimidin-2-yl)phenol (220 mg, 54%). ESI-LCMS (m/z): 467.8 $[M+1]^+$.

Step 11: Synthesis of 2-(2-chloro-5-((R)-oxiran-2-ylmethoxy)phenyl)-N-((2S,4S)-1-cyclopropyl-2-methylpiperidin-4-yl)-6-(3,5-dimethylisoxazol-4-yl)-5-methylpyrimidin-4-amine A solution of 4-chloro-3-(4-((2S,4S)-1-cyclopropyl-2-methyl-piperidin-4-yl-amino)-6-(3,5-dimethylisoxazol-4-yl)-5-methylpyrimidin-2-yl)phenol (110 mg, 0.23 mmol) in THF (10 mL) and (R)-oxiran-2-ylmethyl 3-nitrobenzenesulfonate (115 mg, 0.44 mmol) was treated with $Cs_2CO_3$ (153 mg, 0.47 mmol), and the mixture was heated at 40° C. for 16 h., diluted with water (30 mL) and the mixture was extracted with EtOAc (30 mL×2). The combined organic layers were washed with brine, dried over $Na_2SO_4$, filtered and concentrated to give 2-(2-chloro-5-((R)-oxiran-2-ylmethoxy) phenyl)-N-((2S,4S)-1-cyclopropyl-2-methylpiperidin-4-yl)-6-(3,5-dimethyl isoxazol-4-yl)-5-methylpyrimidin-4-amine (250 mg, crude), which was used for the next step without further purification. ESI-LCMS (m/z): 523.9 $[M+1]^+$.

Step 12: Synthesis of (R)-1-(4-chloro-3-(4-((2S,4S)-1-cyclopropyl-2-methyl-piperidin-4-ylamino)-6-(3, 5-dimethylisoxazol-4-yl)-5-methylpyrimidin-2-yl)phenoxy)-3-(dimethyl amino)propan-2-ol A solution of 2-(2-chloro-5-((R)-oxiran-2-ylmethoxy)phenyl)-N-((2S, 4S)-1-cyclo-propyl-2-methylpiperidin-4-yl)-6-(3,5-dimethylisoxazol-4-yl)-5-methylpyrimidin-4-amine (125 mg, crude from step 11) in MeOH (10 mL) was treated with 40 wt % dimethylamine solution in water (3 mL), and the reaction mixture was stirred at 40° C. for 2 h., the volatiles were then removed in vacuo and the resulting residue was purified by preparative HPLC to give (R)-1-(4-chloro-3-(4-((2S,4S)-1-cyclo-propyl-2-methylpiperidin-4-ylamino)-6-(3,5-dimethylisoxazol-4-yl)-5-methylpyrimidin-2-yl) phenoxy)-3-(dimethylamino)propan-2-ol as a white solid (47 mg, 71% yield). ESI-LCMS (m/z): 568.9 $[M+1]^+$; $^1$HNMR (400 MHz, $CD_3OD$) δ ppm: 7.40 (d, J=8.8 Hz, 1H), 7.21 (d, J=3.2 Hz, 1H), 7.06-7.02 (m, 1H), 4.35-4.23 (m, 1H), 4.15-4.08 (m, 1H), 4.07-4.01 (m, 1H), 3.99-3.94 (m, 1H), 3.20-3.12 (m, 1H), 2.60-2.40 (m, 2H), 2.37 (s, 3H), 2.35 (s, 6H), 2.23 (m, 3H), 2.12-2.03 (m, 2H), 2.01 (s, 3H), 1.72-1.57 (m, 2H), 1.50-1.35 (m, 1H), 1.29 (d, J=6.4 Hz, 2H), 0.75-0.60 (m, 2H), 0.56-0.47 (m, 1H), 0.40-0.30 (m, 1H).

Biological Assays

General Materials

S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates

Peptide representative of human histone H3 residues 16-30 was synthesized with an N-terminal linker-affinity tag motif and a C-terminal amide cap by $21^{st}$ Century Biochemicals. The peptide was purified by high-performance liquid chromatography (HPLC) to greater than 95% purity and confirmed by liquid chromatography mass spectrometry (LCMS). The sequence was Biot-Ahx-PRKQLATKAARK-SAP-amide and contained a monomethylated arginine at position 26 (SEQ ID NO.:1).

Molecular Biology

Human CARM1 (PRMT4) (NM_199141.1) transcript clone was amplified from an HEK 293 cDNA library, incorporating a flanking 5' sequence encoding a FLAG tag (MDYKDDDDK) (SEQ ID NO.:2) fused directly to Ala 2 of CARM1 and 3' sequence encoding a hexa His sequence (EGHHHHHH) (SEQ ID NO.:3) fused directly to Ser 608. The gene sequence encoding isoform1 containing a deletion of amino acids 539-561 was amplified subsequently and subcloned into pFastBacMam (Viva Biotech).

Protein Expression

Recombinant baculovirus were generated according to Bac-to-Bac kit instructions (Life Technologies). Protein over-expression was accomplished by infecting exponentially growing HEK 293F cell culture at $1.3 \times 10^6$ cell/ml with virus (MOI=10) in the presence of 8 mM sodium butyrate. Infections were carried out at 37° C. for 48 hours, harvested by centrifugation, and stored at -80° C. for purification.

Protein Purification

Expressed full-length human Flag- and His-tagged CARM1 protein was purified from cell paste by anti-flag M2 affinity chromatography with resin equilibrated with buffer containing 20 mM Tris, 150 mM NaC, 5% glycerol, pH 7.8. Column was washed with 500 mM NaCl in buffer A and Flag-CARM1-His was eluted with 200 ug/ml FLAG peptide in buffer A. Pooled fractions were dialyzed in 20 mM Tris, 150 mM NaCl, 5% glycerol and 1 mM DTT, pH 7.8. The purity of recovered protein was 94.

Predicted Translations

Flag-CARM1-His (SEQ ID NO.: 4)

MDYKDDDDKAAAAAAVGPGAGGAGSAVPGGAGPCATVSVFPGARLLTIGDA

NGEIQRHAEQQALRLEVRAGPDSAGIALYSHEDVCVFKCSVSRETECSRVG

KQSFIITLGCNSVLIQFATPNDFCSFYNILKTCRGHTLERSVFSERTEESS

AVQYFQFYGYLSQQQNMMQDYVRTGTYQRAILQNHTDFKDKIVLDVGCGSG

ILSFFAAQAGARKIYAVEASTMAQHAEVLVKSNNLTDRIVVIPGKVEEVSL

PEQVDIIISEPMGYMLFNERMLESYLHAKKYLKPSGNMFPTIGDVHLAPFT

DEQLYMEQFTKANFWYQPSFHGVDLSALRGAAVDEYFRQPVVDTFDIRILM

AKSVKYTVNFLEAKEGDLHRIEIPFKFHMLHSGLVHGLAFWFDVAFIGSIM

TVWLSTAPTEPLTHWYQVRCLFQSPLFAKAGDTLSGTCLLIANKRQSYDIS

IVAQVDQTGSKSSNLLDLKNPFFRYTGTTPSPPPGSHYTSPSENMWNTGST

YNLSSGMAVAGMPTAYDLSSVIASGSSVGHNNLIPLGSSGAQGSGGGSTSA

HYAVNSQFTMGGPAISMASPMSIPTNTMHYGSEGHHHHHH

General Procedure for CARM1 Enzyme Assays on Peptide Substrates

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of CARM1, was added to columns 11, 12, 23, 24, rows I-P for the minimum signal control. A cocktail (40 ul) containing the CARM1 enzyme was added by Multidrop Combi (Thermo-Fisher). The compounds were allowed to incubate with CARM1 for 30 min at room temperature, then a cocktail (10 ul) containing $^3$H-SAM and peptide was added to initiate the reaction (final volume=51 ul). The final concentrations of the components were as follows: CARM1 was 0.25 nM, $^3$H-SAM was 30 nM, peptide was 250 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

$$\% \text{ inhibition calculation } \% \ inh = 100 - \left(\frac{dpm_{cmpd} - dpm_{min}}{dpm_{max} - dpm_{min}}\right) \times 100$$

where dpm=disintegrations per minute, cmpd=signal in assay well, and min and max are the respective minimum and maximum signal controls.

$$\text{parameter } IC50 \text{ fit } Y = \text{Bottom} + \frac{(\text{Top} - \text{Bottom})}{\left(1 + \left(\frac{X}{IC_{50}}\right)^{\text{Hill Coefficient}}\right)}$$

where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

RKO Methylation Assay

RKO adherent cells were purchased from ATCC (American Type Culture Collection), Manassas, Va., USA. DMEM/Glutamax medium, penicillin-streptomycin, heat inactivated fetal bovine serum, 0.05% trypsin and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Asymmetric di-methyl PABP1 antibody was purchased from Cell Signaling Technology, Danvers, Mass., USA. Methanol was purchased from VWR, Franklin, Mass., USA. 10% Tween 20 was purchased from KPL, Inc., Gaithersburg, Md., USA. Paraformaldehyde (PFA) was purchased from EM Sciences. DRAQ5 was purchased from Biostatus Limited, Leicestershire, UK.

RKO adherent cells were maintained in growth medium (DMEM/Glutamax medium supplemented with 10% v/v heat inactivated fetal bovine serum and 100 units/mL penicillin-streptomycin) and cultured at 37° C. under 5% $CO_2$.

Cell treatment, In Cell Western (ICW) for detection of asymmetric di-methyl PABP1 and DNA content: RKO cells were seeded in assay medium at a concentration of 30,000 cells per mL to a poly-D-lysine coated 384 well culture plate (BD Biosciences 356697) with 50 μL per well. Compound (100 nL) from a 96-well source plate was added directly to 384 well cell plate. Plates were incubated at 37° C., 5% $CO_2$ for 48 hours. After two days of incubation, plates were brought to room temperature outside of the incubator for ten minutes and blotted on paper towels to remove cell media. Cells were fixed for 20 minutes at room temperature by adding 50 ul of 8% PFA followed by aspiration of supernatant with the Biotek EL406 plate washer. Cells were then permeabilized by addition of 50 μL of ice cold 100% methanol directly to each well and incubated for 30 min at room temperature. After 30 min, plates were transferred to a Biotek EL406 plate washer and washed 2 times with 100 µL per well of wash buffer (1×PBS). Next 60 µL per well of Odyssey blocking buffer (Odyssey Buffer with 0.1% Tween 20 (v/v)) were added to each plate and incubated 1 hour at room temperature. Blocking buffer was removed and 20 µL per well of primary antibody was added (asymmetric-methyl PABP1 diluted 1:400 in Odyssey buffer with 0.1% Tween 20 (v/v)) and plates were incubated overnight (16 hours) at 4° C. Plates were washed 5 times with 100 µL per well of wash buffer. Next 20 µL per well of secondary antibody was added (1:800 800CW goat anti-rabbit IgG (H+L) antibody, 1:2000 DRAQ5 in Odyssey buffer with 0.1% Tween 20 (v/v)) and incubated for 1 hour at room temperature. The plates were washed 5 times with 100 µL per well wash buffer then 2 times with 100 µL per well of water. Plates were allowed to dry at room temperature then imaged on the Licor Odyssey machine which measures integrated intensity at 700 nm and 800 nm wavelengths. Both 700 and 800 channels were scanned.

Calculations. First, the ratio for each well was determined by:

$$\left(\frac{\text{asymmetric di-methyl } PABP1 \text{ 800 nm value}}{DRAQ5 \text{ 700 nm value}}\right)$$

Each plate included fourteen control wells of DMSO only treatment (minimum inhibition) as well as fourteen control wells for maximum inhibition treated with 20 µM of a reference compound. The average of the ratio values for each control type was calculated and used to determine the percent activation for each test well in the plate. Reference compound was serially diluted three-fold in DMSO for a total of nine test concentrations, beginning at 20 µM.

Percent inhibition was determined and $IC_{50}$ curves were generated using triplicate wells per concentration of compound.

Percent Inhibition = 100 −

$$\left(\left(\frac{(\text{Minimum Inhibition Ratio}) - (\text{Individual Test Sample Ratio})}{(\text{Minimum Inhibition Ratio}) - (\text{Maximum Inhibition Ratio})}\right) * 100\right)$$

Human Myeloma Cell Line Proliferation Assay

Figure 1B:
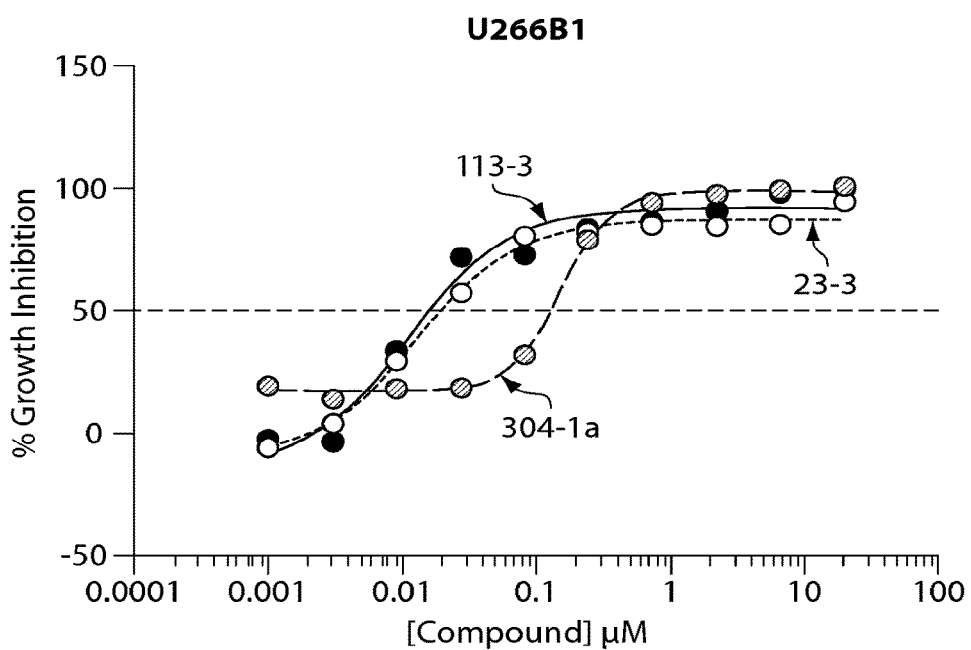

Human Multiple Myeloma cell lines NCI-H929 (FIG. 1A) and U266B1 (FIG. 1B) were treated with varying doses of 304-1a (medium grey data points), 23-3 (light grey data points), and 113-3 (black data points) in a 14-day proliferation assay. At the end of the experiment, total cell number was determined for each cell line for different doses of 304-1a, 23-3, and 113-3. As shown below, all compounds tested decreased the proliferation of these cell lines, at potencies consistent with that seen for the biochemical and cell-based (PABP1me2a) ICW (In Cell Western) assays.

TABLE 3

| Biochemical potencies | |
|---|---|
| # | Biochem $IC_{50}$ |
| 1-1 | A |
| 2-1 | A |
| 3-1 | A |
| 4-1 | E |
| 5-1 | D |
| 6-1 | B |
| 7-1 | B |
| 8-1 | B |
| 9-1 | A |
| 10-1 | A |
| 11-1 | A |
| 12-1 | B |
| 13-1 | A |
| 14-1 | A |
| 15-1 | A |
| 16-1 | B |
| 17-1 | C |
| 18-1 | A |
| 19-1 | A |
| 20-1 | A |
| 21-1 | B |
| 22-1 | A |
| 23-1 | B |
| 24-1 | A |
| 25-1 | A |
| 26-1 | A |
| 27-1 | B |
| 28-1 | B |
| 29-1 | A |
| 30-1 | B |
| 31-1 | B |
| 32-1 | A |
| 33-1 | A |
| 34-1 | A |
| 35-1 | B |
| 36-1 | A |
| 37-1 | A |
| 38-1 | B |
| 39-1 | B |
| 40-1 | B |
| 41-1 | A |
| 42-1 | A |
| 43-1 | B |
| 44-1 | B |
| 45-1 | A |
| 46-1 | A |
| 47-1 | B |
| 48-1 | A |
| 49-1 | A |
| 50-1 | A |
| 51-1 | B |
| 52-1 | B |
| 53-1 | A |
| 54-1 | B |
| 55-1 | A |
| 56-1 | A |
| 57-1 | A |
| 58-1 | B |
| 59-1 | A |
| 60-1 | A |
| 61-1 | C |
| 62-1 | A |
| 63-1 | B |
| 64-1 | A |
| 65-1 | B |
| 66-1 | B |
| 67-1 | B |
| 68-1 | B |
| 69-1 | B |
| 70-1 | A |
| 71-1 | A |
| 72-1 | B |
| 73-1 | B |
| 74-1 | B |
| 75-1 | B |
| 1-2 | B |
| 2-2 | A |
| 3-2 | B |
| 4-2 | A |
| 5-2 | A |
| 6-2 | A |

TABLE 3-continued

Biochemical potencies

| # | Biochem IC$_{50}$ |
|---|---|
| 7-2 | B |
| 8-2 | A |
| 9-2 | B |
| 10-2 | B |
| 11-2 | B |
| 12-2 | B |
| 13-2 | B |
| 14-2 | A |
| 15-2 | A |
| 16-2 | A |
| 1-1a | A |
| 2-1a | B |
| 3-1a | A |
| 4-1a | A |
| 5-1a | A |
| 6-1a | A |
| 7-1a | A |
| 8-1a | A |
| 9-1a | A |
| 10-1a | A |
| 11-1a | A |
| 12-1a | A |
| 13-1a | A |
| 14-1a | A |
| 15-1a | A |
| 16-1a | A |
| 17-1a | A |
| 18-1a | A |
| 19-1a | A |
| 20-1a | A |
| 21-1a | A |
| 22-1a | B |
| 23-1a | A |
| 24-1a | B |
| 25-1a | B |
| 26-1a | C |
| 27-1a | A |
| 28-1a | A |
| 29-1a | A |
| 30-1a | A |
| 31-1a | A |
| 32-1a | A |
| 33-1a | A |
| 34-1a | A |
| 35-1a | A |
| 36-1a | A |
| 37-1a | B |
| 38-1a | A |
| 39-1a | A |
| 40-1a | A |
| 41-1a | A |
| 42-1a | A |
| 43-1a | A |
| 44-1a | A |
| 45-1a | A |
| 46-1a | B |
| 47-1a | A |
| 48-1a | C |
| 49-1a | A |
| 50-1a | A |
| 51-1a | A |
| 52-1a | B |
| 53-1a | A |
| 54-1a | A |
| 55-1a | A |
| 56-1a | A |
| 57-1a | A |
| 58-1a | B |
| 59-1a | A |
| 60-1a | A |
| 61-1a | A |
| 62-1a | C |
| 63-1a | C |
| 64-1a | B |
| 65-1a | B |
| 66-1a | A |
| 67-1a | A |
| 68-1a | A |
| 69-1a | A |
| 70-1a | A |
| 71-1a | A |
| 72-1a | A |
| 73-1a | B |
| 74-1a | A |
| 75-1a | A |
| 76-1a | A |
| 77-1a | A |
| 78-1a | A |
| 79-1a | A |
| 80-1a | A |
| 81-1a | A |
| 82-1a | A |
| 83-1a | B |
| 84-1a | A |
| 85-1a | A |
| 86-1a | A |
| 87-1a | A |
| 88-1a | A |
| 89-1a | A |
| 90-1a | A |
| 91-1a | A |
| 92-1a | A |
| 93-1a | A |
| 94-1a | A |
| 95-1a | A |
| 96-1a | A |
| 97-1a | A |
| 98-1a | A |
| 99-1a | A |
| 100-1a | A |
| 101-1a | A |
| 102-1a | A |
| 103-1a | A |
| 104-1a | A |
| 105-1a | A |
| 106-1a | A |
| 107-1a | A |
| 108-1a | A |
| 109-1a | A |
| 110-1a | A |
| 111-1a | A |
| 112-1a | A |
| 113-1a | D |
| 114-1a | A |
| 115-1a | A |
| 116-1a | A |
| 117-1a | A |
| 118-1a | A |
| 119-1a | A |
| 120-1a | A |
| 121-1a | A |
| 122-1a | C |
| 123-1a | B |
| 124-1a | A |
| 125-1a | A |
| 126-1a | A |
| 127-1a | A |
| 128-1a | B |
| 129-1a | A |
| 130-1a | B |
| 131-1a | A |
| 132-1a | A |
| 133-1a | A |
| 134-1a | A |
| 135-1a | A |
| 136-1a | A |
| 137-1a | A |
| 138-1a | A |
| 139-1a | A |
| 140-1a | A |
| 141-1a | A |
| 142-1a | A |

TABLE 3-continued

Biochemical potencies

| # | Biochem $IC_{50}$ |
|---|---|
| 143-1a | A |
| 144-1a | A |
| 145-1a | A |
| 146-1a | A |
| 147-1a | A |
| 148-1a | A |
| 149-1a | A |
| 150-1a | A |
| 151-1a | A |
| 152-1a | A |
| 153-1a | A |
| 154-1a | A |
| 155-1a | A |
| 156-1a | A |
| 157-1a | A |
| 158-1a | B |
| 159-1a | A |
| 160-1a | A |
| 161-1a | A |
| 162-1a | A |
| 163-1a | A |
| 164-1a | A |
| 165-1a | A |
| 166-1a | A |
| 167-1a | A |
| 168-1a | A |
| 169-1a | A |
| 170-1a | A |
| 171-1a | A |
| 172-1a | A |
| 173-1a | A |
| 174-1a | A |
| 175-1a | A |
| 176-1a | A |
| 177-1a | A |
| 178-1a | A |
| 179-1a | A |
| 180-1a | B |
| 181-1a | A |
| 182-1a | A |
| 183-1a | A |
| 184-1a | A |
| 185-1a | A |
| 186-1a | A |
| 187-1a | A |
| 188-1a | A |
| 189-1a | A |
| 190-1a | A |
| 191-1a | A |
| 192-1a | A |
| 193-1a | A |
| 194-1a | A |
| 195-1a | A |
| 196-1a | A |
| 197-1a | A |
| 198-1a | A |
| 199-1a | A |
| 200-1a | A |
| 201-1a | A |
| 202-1a | A |
| 203-1a | A |
| 204-1a | A |
| 205-1a | A |
| 206-1a | A |
| 207-1a | A |
| 208-1a | A |
| 209-1a | A |
| 210-1a | A |
| 211-1a | A |
| 212-1a | A |
| 213-1a | B |
| 214-1a | B |
| 215-1a | A |
| 216-1a | A |
| 217-1a | A |
| 218-1a | A |
| 219-1a | A |
| 220-1a | A |
| 221-1a | A |
| 222-1a | B |
| 223-1a | C |
| 224-1a | A |
| 225-1a | A |
| 226-1a | A |
| 227-1a | A |
| 228-1a | A |
| 229-1a | A |
| 230-1a | A |
| 231-1a | A |
| 232-1a | A |
| 233-1a | A |
| 234-1a | A |
| 235-1a | A |
| 236-1a | A |
| 237-1a | A |
| 238-1a | A |
| 239-1a | A |
| 240-1a | A |
| 241-1a | A |
| 242-1a | A |
| 243-1a | A |
| 244-1a | A |
| 245-1a | A |
| 246-1a | A |
| 247-1a | A |
| 248-1a | A |
| 249-1a | A |
| 250-1a | A |
| 251-1a | A |
| 252-1a | A |
| 253-1a | A |
| 254-1a | A |
| 255-1a | A |
| 256-1a | A |
| 257-1a | A |
| 258-1a | A |
| 259-1a | A |
| 260-1a | A |
| 261-1a | A |
| 262-1a | A |
| 263-1a | A |
| 264-1a | A |
| 265-1a | A |
| 266-1a | A |
| 267-1a | A |
| 268-1a | A |
| 269-1a | A |
| 270-1a | A |
| 271-1a | A |
| 272-1a | A |
| 273-1a | A |
| 274-1a | A |
| 275-1a | A |
| 276-1a | A |
| 277-1a | A |
| 278-1a | A |
| 279-1a | A |
| 280-1a | A |
| 281-1a | A |
| 282-1a | A |
| 283-1a | A |
| 284-1a | A |
| 285-1a | A |
| 286-1a | A |
| 287-1a | A |
| 288-1a | A |
| 289-1a | A |
| 290-1a | A |
| 291-1a | A |
| 292-1a | A |
| 293-1a | A |
| 294-1a | A |

TABLE 3-continued

Biochemical potencies

| # | Biochem IC$_{50}$ |
|---|---|
| 295-1a | A |
| 296-1a | A |
| 297-1a | A |
| 298-1a | A |
| 299-1a | A |
| 300-1a | A |
| 301-1a | A |
| 302-1a | A |
| 303-1a | A |
| 304-1a | A |
| 305-1a | A |
| 306-1a | A |
| 307-1a | A |
| 308-1a | A |
| 309-1a | A |
| 310-1a | — |
| 311-1a | — |
| 312-1a | — |
| 313-1a | — |
| 314-1a | — |
| 315-1a | — |
| 316-1a | — |
| 317-1a | — |
| 318-1a | — |
| 319-1a | — |
| 320-1a | — |
| 321-1a | — |
| 322-1a | — |
| 323-1a | — |
| 324-1a | — |
| 325-1a | — |
| 326-1a | — |
| 327-1a | — |
| 328-1a | — |
| 329-1a | — |
| 330-1a | — |
| 331-1a | A |
| 332-1a | A |
| 333-1a | B |
| 334-1a | A |
| 335-1a | A |
| 336-1a | B |
| 337-1a | B |
| 338-1a | A |
| 339-1a | A |
| 340-1a | A |
| 341-1a | A |
| 346-1a | B |
| 347-1a | B |
| 348-1a | B |
| 349-1a | B |
| 350-1a | A |
| 351-1a | A |
| 352-1a | A |
| 353-1a | B |
| 354-1a | B |
| 355-1a | A |
| 356-1a | A |
| 357-1a | B |
| 358-1a | A |
| 359-1a | A |
| 360-1a | B |
| 361-1a | B |
| 362-1a | A |
| 363-1a | B |
| 364-1a | B |
| 365-1a | B |
| 366-1a | A |
| 367-1a | A |
| 368-1a | A |
| 369-1a | A |
| 370-1a | A |
| 371-1a | C |
| 372-1a | C |
| 373-1a | B |
| 374-1a | B |
| 375-1a | C |
| 376-1a | A |
| 377-1a | A |
| 378-1a | A |
| 379-1a | A |
| 380-1a | B |
| 381-1a | A |
| 382-1a | A |
| 383-1a | C |
| 384-1a | B |
| 385-1a | B |
| 386-1a | D |
| 387-1a | B |
| 388-1a | B |
| 389-1a | B |
| 390-1a | A |
| 391-1a | A |
| 392-1a | A |
| 393-1a | B |
| 394-1a | A |
| 395-1a | B |
| 396-1a | A |
| 397-1a | A |
| 398-1a | A |
| 399-1a | B |
| 400-1a | B |
| 401-1a | B |
| 402-1a | D |
| 403-1a | D |
| 404-1a | B |
| 405-1a | B |
| 406-1a | B |
| 407-1a | B |
| 408-1a | A |
| 409-1a | B |
| 410-1a | B |
| 412-1a | A |
| 413-1a | B |
| 414-1a | B |
| 415-1a | A |
| 416-1a | D |
| 418-1a | B |
| 419-1a | B |
| 420-1a | B |
| 421-1a | A |
| 422-1a | A |
| 423-1a | B |
| 424-1a | A |
| 425-1a | A |
| 426-1a | B |
| 427-1a | A |
| 428-1a | B |
| 429-1a | A |
| 430-1a | B |
| 431-1a | B |
| 432-1a | B |
| 433-1a | B |
| 434-1a | A |
| 435-1a | A |
| 436-1a | A |
| 437-1a | A |
| 438-1a | B |
| 439-1a | A |
| 440-1a | A |
| 441-1a | A |
| 442-1a | A |
| 443-1a | A |
| 445-1a | A |
| 446-1a | A |
| 447-1a | A |
| 448-1a | A |
| 449-1a | A |
| 450-1a | B |
| 451-1a | B |
| 452-1a | A |
| 453-1a | B |

TABLE 3-continued

Biochemical potencies

| # | Biochem IC$_{50}$ |
|---|---|
| 454-1a | A |
| 455-1a | A |
| 456-1a | A |
| 457-1a | A |
| 458-1a | A |
| 459-1a | B |
| 460-1a | B |
| 461-1a | A |
| 462-1a | A |
| 463-1a | A |
| 464-1a | A |
| 465-1a | A |
| 466-1a | A |
| 467-1a | A |
| 468-1a | A |
| 469-1a | A |
| 470-1a | A |
| 471-1a | A |
| 472-1a | B |
| 475-1a | A |
| 478-1a | — |
| 479-1a | — |
| 480-1a | — |
| 481-1a | — |
| 482-1a | A |
| 483-1a | A |
| 484-1a | A |
| 485-1a | A |
| 486-1a | A |
| 487-1a | A |
| 488-1a | A |
| 489-1a | A |
| 490-1a | A |
| 491-1a | A |
| 492-1a | A |
| 493-1a | A |
| 494-1a | B |
| 495-1a | A |
| 496-1a | A |
| 497-1a | B |
| 498-1a | A |
| 499-1a | A |
| 500-1a | A |
| 501-1a | A |
| 502-1a | A |
| 503-1a | A |
| 504-1a | A |
| 505-1a | A |
| 506-1a | A |
| 507-1a | A |
| 508-1a | A |
| 509-1a | B |
| 510-1a | A |
| 511-1a | A |
| 512-1a | A |
| 513-1a | A |
| 514-1a | A |
| 515-1a | B |
| 516-1a | A |
| 517-1a | A |
| 518-1a | B |
| 519-1a | A |
| 520-1a | B |
| 521-1a | A |
| 522-1a | A |
| 523-1a | B |
| 524-1a | A |
| 525-1a | A |
| 526-1a | A |
| 527-1a | B |
| 528-1a | A |
| 529-1a | A |
| 530-1a | B |
| 531-1a | A |
| 532-1a | B |
| 533-1a | B |
| 534-1a | B |
| 535-1a | B |
| 536-1a | A |
| 537-1a | A |
| 538-1a | A |
| 539-1a | B |
| 540-1a | B |
| 541-1a | A |
| 542-1a | A |
| 543-1a | A |
| 544-1a | A |
| 545-1a | B |
| 546-1a | B |
| 547-1a | B |
| 548-1a | A |
| 549-1a | A |
| 550-1a | B |
| 551-1a | B |
| 552-1a | B |
| 553-1a | B |
| 554-1a | B |
| 555-1a | B |
| 556-1a | B |
| 557-1a | B |
| 558-1a | A |
| 559-1a | A |
| 560-1a | A |
| 561-1a | A |
| 562-1a | A |
| 563-1a | A |
| 564-1a | A |
| 565-1a | A |
| 566-1a | A |
| 567-1a | A |
| 568-1a | A |
| 569-1a | A |
| 570-1a | A |
| 571-1a | A |
| 572-1a | A |
| 573-1a | A |
| 574-1a | A |
| 575-1a | A |
| 576-1a | A |
| 577-1a | A |
| 578-1a | A |
| 579-1a | A |
| 580-1a | A |
| 581-1a | A |
| 582-1a | B |
| 583-1a | B |
| 584-1a | B |
| 585-1a | B |
| 586-1a | B |
| 587-1a | B |
| 588-1a | B |
| 589-1a | B |
| 590-1a | B |
| 591-1a | B |
| 592-1a | B |
| 593-1a | B |
| 594-1a | B |
| 595-1a | B |
| 596-1a | B |
| 597-1a | B |
| 598-1a | B |
| 599-1a | B |
| 600-1a | B |
| 601-1a | B |
| 602-1a | B |
| 603-1a | C |
| 604-1a | C |
| 605-1a | C |
| 606-1a | C |
| 607-1a | D |
| 608-1a | D |
| 609-1a | A |

TABLE 3-continued

Biochemical potencies

| # | Biochem IC$_{50}$ |
|---|---|
| 610-1a | A |
| 611-1a | A |
| 612-1a | A |
| 613-1a | A |
| 614-1a | A |
| 615-1a | A |
| 616-1a | A |
| 617-1a | A |
| 618-1a | A |
| 619-1a | A |
| 620-1a | A |
| 621-1a | A |
| 622-1a | A |
| 623-1a | A |
| 624-1a | A |
| 625-1a | B |
| 626-1a | C |
| 627-1a | B |
| 628-1a | B |
| 629-1a | B |
| 630-1a | B |
| 631-1a | C |
| 632-1a | A |
| 635-1a | C |
| 636-1a | B |
| 637-1a | B |
| 638-1a | B |
| 639-1a | B |
| 640-1a | B |
| 641-1a | B |
| 642-1a | C |
| 643-1a | C |
| 644-1a | A |
| 645-1a | C |
| 646-1a | B |
| 647-1a | B |
| 648-1a | B |
| 649-1a | B |
| 650-1a | B |
| 651-1a | B |
| 652-1a | A |
| 653-1a | C |
| 654-1a | B |
| 655-1a | B |
| 656-1a | B |
| 657-1a | A |
| 658-1a | A |
| 659-1a | B |
| 660-1a | C |
| 661-1a | B |
| 662-1a | B |
| 663-1a | B |
| 664-1a | B |
| 665-1a | A |
| 666-1a | B |
| 667-1a | B |
| 668-1a | B |
| 669-1a | A |
| 670-1a | B |
| 671-1a | B |
| 672-1a | B |
| 673-1a | B |
| 674-1a | B |
| 675-1a | B |
| 676-1a | C |
| 677-1a | E |
| 678-1a | B |
| 679-1a | C |
| 680-1a | B |
| 681-1a | C |
| 682-1a | A |
| 683-1a | B |
| 684-1a | C |
| 685-1a | C |
| 686-1a | B |
| 687-1a | B |

TABLE 3-continued

Biochemical potencies

| # | Biochem IC$_{50}$ |
|---|---|
| 1-3 | A |
| 2-3 | A |
| 3-3 | A |
| 4-3 | A |
| 5-3 | A |
| 6-3 | A |
| 7-3 | A |
| 8-3 | A |
| 9-3 | A |
| 10-3 | A |
| 11-3 | A |
| 12-3 | A |
| 13-3 | A |
| 14-3 | A |
| 15-3 | A |
| 16-3 | A |
| 17-3 | A |
| 18-3 | A |
| 19-3 | A |
| 20-3 | A |
| 21-3 | A |
| 22-3 | A |
| 23-3 | A |
| 24-3 | A |
| 25-3 | A |
| 26-3 | A |
| 27-3 | A |
| 28-3 | A |
| 29-3 | A |
| 30-3 | A |
| 31-3 | A |
| 32-3 | A |
| 33-3 | A |
| 34-3 | A |
| 35-3 | A |
| 36-3 | A |
| 37-3 | A |
| 38-3 | A |
| 39-3 | A |
| 40-3 | A |
| 41-3 | A |
| 42-3 | A |
| 43-3 | A |
| 44-3 | A |
| 45-3 | A |
| 46-3 | A |
| 47-3 | A |
| 48-3 | A |
| 49-3 | A |
| 50-3 | B |
| 51-3 | B |
| 52-3 | B |
| 53-3 | A |
| 54-3 | A |
| 55-3 | A |
| 56-3 | A |
| 57-3 | A |
| 58-3 | A |
| 59-3 | A |
| 60-3 | A |
| 61-3 | A |
| 62-3 | A |
| 63-3 | A |
| 64-3 | A |
| 65-3 | A |
| 66-3 | A |
| 67-3 | A |
| 68-3 | A |
| 69-3 | A |
| 70-3 | A |
| 71-3 | A |
| 72-3 | A |
| 73-3 | A |
| 74-3 | A |
| 75-3 | A |
| 76-3 | A |

TABLE 3-continued

Biochemical potencies

| # | Biochem IC$_{50}$ |
|---|---|
| 77-3 | A |
| 78-3 | B |
| 79-3 | D |
| 80-3 | B |
| 81-3 | C |
| 82-3 | A |
| 83-3 | A |
| 84-3 | A |
| 85-3 | A |
| 86-3 | A |
| 87-3 | A |
| 88-3 | A |
| 89-3 | A |
| 90-3 | A |
| 91-3 | A |
| 92-3 | A |
| 93-3 | A |
| 94-3 | A |
| 95-3 | A |
| 96-3 | A |
| 97-3 | A |
| 98-3 | A |
| 99-3 | A |
| 100-3 | A |
| 101-3 | A |
| 102-3 | A |
| 103-3 | A |
| 104-3 | A |
| 105-3 | A |
| 106-3 | A |
| 107-3 | D |
| 108-3 | A |
| 109-3 | A |
| 110-3 | A |
| 111-3 | A |
| 112-3 | A |
| 113-3 | A |
| 114-3 | A |
| 115-3 | A |
| 116-3 | A |
| 117-3 | A |
| 118-3 | A |
| 119-3 | A |
| 120-3 | A |
| 121-3 | A |
| 122-3 | A |
| 123-3 | B |
| 124-3 | A |
| 125-3 | A |
| 126-3 | A |
| 127-3 | A |
| 128-3 | A |
| 129-3 | A |
| 130-3 | A |
| 131-3 | A |
| 132-3 | A |
| 133-3 | A |
| 134-3 | A |
| 135-3 | A |
| 136-3 | A |
| 137-3 | A |
| 138-3 | A |
| 139-3 | A |
| 140-3 | A |
| 141-3 | A |
| 142-3 | A |
| 143-3 | A |
| 144-3 | A |
| 145-3 | A |
| 146-3 | A |
| 147-3 | A |
| 148-3 | A |
| 149-3 | A |
| 150-3 | A |
| 151-3 | A |
| 152-3 | A |
| 153-3 | A |
| 154-3 | A |
| 155-3 | A |
| 156-3 | A |
| 157-3 | A |
| 158-3 | A |
| 159-3 | A |
| 160-3 | A |
| 161-3 | A |
| 162-3 | A |
| 163-3 | A |
| 164-3 | A |
| 165-3 | B |
| 166-3 | B |
| 167-3 | A |
| 168-3 | A |
| 169-3 | A |
| 170-3 | A |
| 171-3 | A |
| 172-3 | A |
| 173-3 | A |
| 174-3 | A |
| 175-3 | A |
| 176-3 | A |
| 177-3 | A |
| 178-3 | A |
| 179-3 | A |
| 180-3 | A |
| 181-3 | A |
| 182-3 | A |
| 183-3 | A |
| 184-3 | A |
| 185-3 | A |
| 186-3 | A |
| 187-3 | A |
| 188-3 | A |
| 189-3 | A |
| 190-3 | A |
| 191-3 | A |
| 192-3 | A |
| 193-3 | B |
| 194-3 | A |
| 195-3 | A |
| 196-3 | A |
| 197-3 | A |
| 198-3 | A |
| 199-3 | A |
| 200-3 | A |
| 201-3 | A |
| 202-3 | A |
| 203-3 | A |
| 204-3 | A |
| 205-3 | A |
| 206-3 | A |
| 207-3 | A |
| 208-3 | A |
| 209-3 | A |
| 210-3 | A |
| 211-3 | A |
| 212-3 | A |
| 213-3 | A |
| 214-3 | A |
| 215-3 | A |
| 216-3 | A |
| 217-3 | A |
| 218-3 | A |
| 219-3 | A |
| 220-3 | A |
| 221-3 | A |
| 222-3 | A |
| 223-3 | A |
| 224-3 | A |
| 225-3 | A |
| 226-3 | A |
| 227-3 | A |
| 228-3 | A |

TABLE 3-continued

Biochemical potencies

| # | Biochem IC$_{50}$ |
|---|---|
| 229-3 | A |
| 230-3 | A |
| 231-3 | A |
| 232-3 | A |
| 233-3 | A |
| 234-3 | A |
| 235-3 | A |
| 236-3 | A |
| 237-3 | A |
| 238-3 | A |
| 239-3 | A |
| 240-3 | A |
| 241-3 | A |
| 242-3 | A |
| 243-3 | A |
| 244-3 | A |
| 245-3 | A |
| 246-3 | A |
| 247-3 | A |
| 248-3 | A |
| 249-3 | A |
| 250-3 | A |
| 251-3 | A |
| 252-3 | A |
| 253-3 | A |
| 254-3 | A |
| 255-3 | A |
| 256-3 | A |
| 257-3 | A |
| 258-3 | A |
| 259-3 | A |
| 260-3 | A |
| 261-3 | A |
| 262-3 | B |
| 263-3 | A |
| 264-3 | A |
| 265-3 | A |
| 266-3 | A |
| 267-3 | A |
| 268-3 | A |
| 269-3 | A |
| 270-3 | A |
| 271-3 | — |
| 272-3 | A |
| 273-3 | A |
| 274-3 | A |
| 275-3 | A |
| 276-3 | A |
| 277-3 | A |
| 278-3 | A |
| 279-3 | A |
| 280-3 | A |
| 281-3 | A |
| 282-3 | A |
| 283-3 | A |
| 284-3 | A |
| 285-3 | A |
| 286-3 | A |
| 287-3 | A |
| 288-3 | A |
| 289-3 | A |
| 290-3 | A |
| 291-3 | A |
| 292-3 | A |
| 293-3 | A |
| 294-3 | A |
| 295-3 | A |
| 296-3 | A |
| 297-3 | A |

Classification codes for biochemical potencies:
A: IC$_{50}$ <0.1 uM
B: 0.1 uM ≤ IC$_{50}$ < 1 uM
C: 1 uM ≤ IC$_{50}$ < 3 uM
D: 3 uM ≤ IC$_{50}$ < 10 uM
E: 10 uM < IC$_{50}$

TABLE 4

Cellular potencies

| # | Cellular IC$_{50}$ |
|---|---|
| 3-1 | B |
| 26-1 | C |
| 33-1 | A |
| 40-1 | B |
| 41-1 | C |
| 51-1 | C |
| 52-1 | C |
| 70-1 | C |
| 1-1a | A |
| 2-1a | C |
| 3-1a | C |
| 4-1a | C |
| 5-1a | C |
| 6-1a | A |
| 7-1a | C |
| 8-1a | C |
| 9-1a | B |
| 10-1a | C |
| 11-1a | B |
| 12-1a | C |
| 13-1a | B |
| 14-1a | C |
| 15-1a | C |
| 16-1a | B |
| 17-1a | A |
| 18-1a | A |
| 19-1a | C |
| 20-1a | B |
| 21-1a | B |
| 22-1a | C |
| 23-1a | C |
| 24-1a | C |
| 25-1a | C |
| 26-1a | C |
| 27-1a | C |
| 28-1a | A |
| 29-1a | C |
| 30-1a | A |
| 31-1a | B |
| 32-1a | C |
| 33-1a | B |
| 34-1a | A |
| 35-1a | B |
| 36-1a | C |
| 37-1a | C |
| 38-1a | B |
| 39-1a | B |
| 40-1a | C |
| 41-1a | C |
| 42-1a | C |
| 43-1a | C |
| 44-1a | B |
| 45-1a | A |
| 46-1a | C |
| 47-1a | A |
| 48-1a | C |
| 49-1a | B |
| 50-1a | A |
| 51-1a | C |
| 52-1a | C |
| 53-1a | C |
| 54-1a | A |
| 55-1a | A |
| 56-1a | A |
| 57-1a | C |
| 58-1a | B |
| 59-1a | C |
| 60-1a | C |
| 61-1a | C |
| 62-1a | C |
| 63-1a | C |
| 64-1a | C |
| 65-1a | C |
| 66-1a | A |
| 67-1a | C |
| 68-1a | B |

TABLE 4-continued

Cellular potencies

| # | Cellular IC$_{50}$ |
|---|---|
| 69-1a | C |
| 70-1a | A |
| 71-1a | A |
| 72-1a | A |
| 73-1a | C |
| 74-1a | B |
| 75-1a | A |
| 76-1a | C |
| 77-1a | A |
| 78-1a | B |
| 79-1a | A |
| 80-1a | C |
| 81-1a | A |
| 82-1a | A |
| 83-1a | C |
| 84-1a | A |
| 85-1a | A |
| 86-1a | B |
| 87-1a | A |
| 88-1a | A |
| 89-1a | A |
| 90-1a | A |
| 91-1a | A |
| 92-1a | A |
| 93-1a | A |
| 94-1a | A |
| 95-1a | C |
| 96-1a | A |
| 97-1a | A |
| 98-1a | A |
| 99-1a | A |
| 100-1a | B |
| 101-1a | A |
| 102-1a | A |
| 103-1a | A |
| 104-1a | A |
| 105-1a | B |
| 106-1a | B |
| 107-1a | A |
| 108-1a | A |
| 109-1a | C |
| 110-1a | B |
| 111-1a | B |
| 112-1a | C |
| 113-1a | C |
| 114-1a | C |
| 115-1a | A |
| 116-1a | B |
| 117-1a | C |
| 118-1a | A |
| 119-1a | A |
| 120-1a | A |
| 121-1a | A |
| 122-1a | C |
| 123-1a | B |
| 124-1a | B |
| 125-1a | A |
| 126-1a | B |
| 127-1a | A |
| 128-1a | B |
| 129-1a | C |
| 130-1a | C |
| 131-1a | A |
| 132-1a | A |
| 133-1a | A |
| 134-1a | A |
| 135-1a | A |
| 136-1a | A |
| 137-1a | A |
| 139-1a | A |
| 140-1a | A |
| 141-1a | A |
| 142-1a | A |
| 143-1a | A |
| 144-1a | A |
| 145-1a | B |
| 146-1a | A |
| 147-1a | A |
| 148-1a | A |
| 149-1a | A |
| 150-1a | B |
| 151-1a | A |
| 152-1a | A |
| 153-1a | A |
| 154-1a | A |
| 155-1a | A |
| 156-1a | B |
| 157-1a | A |
| 158-1a | B |
| 159-1a | C |
| 160-1a | C |
| 161-1a | A |
| 162-1a | A |
| 163-1a | A |
| 164-1a | A |
| 165-1a | A |
| 166-1a | A |
| 167-1a | A |
| 168-1a | A |
| 169-1a | A |
| 170-1a | A |
| 171-1a | A |
| 172-1a | A |
| 173-1a | A |
| 174-1a | A |
| 175-1a | B |
| 176-1a | A |
| 177-1a | B |
| 178-1a | C |
| 179-1a | A |
| 180-1a | C |
| 181-1a | A |
| 182-1a | A |
| 183-1a | A |
| 184-1a | A |
| 185-1a | A |
| 186-1a | A |
| 187-1a | A |
| 188-1a | A |
| 189-1a | A |
| 190-1a | A |
| 191-1a | A |
| 192-1a | A |
| 193-1a | A |
| 194-1a | A |
| 195-1a | A |
| 196-1a | A |
| 197-1a | A |
| 198-1a | A |
| 199-1a | A |
| 200-1a | A |
| 201-1a | A |
| 202-1a | A |
| 203-1a | A |
| 204-1a | A |
| 205-1a | A |
| 206-1a | A |
| 207-1a | A |
| 208-1a | A |
| 209-1a | B |
| 210-1a | A |
| 211-1a | A |
| 212-1a | A |
| 213-1a | C |
| 214-1a | B |
| 215-1a | A |
| 216-1a | A |
| 217-1a | A |
| 218-1a | A |
| 219-1a | A |
| 220-1a | A |
| 221-1a | A |

TABLE 4-continued

Cellular potencies

| # | Cellular IC$_{50}$ |
|---|---|
| 222-1a | C |
| 223-1a | C |
| 224-1a | A |
| 225-1a | A |
| 226-1a | A |
| 227-1a | A |
| 228-1a | A |
| 229-1a | A |
| 230-1a | A |
| 231-1a | A |
| 232-1a | A |
| 233-1a | C |
| 234-1a | A |
| 235-1a | A |
| 236-1a | A |
| 237-1a | C |
| 238-1a | C |
| 239-1a | A |
| 240-1a | A |
| 241-1a | A |
| 242-1a | A |
| 243-1a | A |
| 244-1a | A |
| 245-1a | A |
| 246-1a | B |
| 247-1a | A |
| 248-1a | A |
| 249-1a | A |
| 250-1a | A |
| 251-1a | A |
| 252-1a | A |
| 253-1a | A |
| 254-1a | A |
| 255-1a | A |
| 256-1a | A |
| 257-1a | A |
| 258-1a | B |
| 259-1a | A |
| 260-1a | A |
| 261-1a | A |
| 262-1a | A |
| 263-1a | A |
| 264-1a | B |
| 265-1a | A |
| 266-1a | A |
| 267-1a | C |
| 268-1a | C |
| 269-1a | A |
| 270-1a | A |
| 271-1a | A |
| 273-1a | C |
| 274-1a | A |
| 275-1a | C |
| 276-1a | A |
| 277-1a | A |
| 278-1a | A |
| 279-1a | A |
| 280-1a | C |
| 281-1a | C |
| 282-1a | A |
| 283-1a | A |
| 284-1a | A |
| 285-1a | A |
| 286-1a | A |
| 287-1a | A |
| 288-1a | A |
| 289-1a | B |
| 290-1a | A |
| 291-1a | C |
| 292-1a | A |
| 293-1a | A |
| 294-1a | A |
| 295-1a | A |
| 296-1a | B |
| 297-1a | B |
| 298-1a | C |

TABLE 4-continued

Cellular potencies

| # | Cellular IC$_{50}$ |
|---|---|
| 299-1a | A |
| 660-1a | D |
| 661-1a | D |
| 662-1a | D |
| 663-1a | D |
| 664-1a | D |
| 665-1a | D |
| 666-1a | D |
| 667-1a | D |
| 668-1a | D |
| 669-1a | D |
| 670-1a | D |
| 671-1a | D |
| 672-1a | C |
| 673-1a | C |
| 674-1a | D |
| 675-1a | D |
| 676-1a | D |
| 677-1a | D |
| 678-1a | D |
| 679-1a | D |
| 680-1a | D |
| 681-1a | D |
| 682-1a | D |
| 683-1a | D |
| 684-1a | D |
| 685-1a | D |
| 686-1a | D |
| 687-1a | D |
| 1-3 | D |
| 2-3 | A |
| 3-3 | A |
| 4-3 | A |
| 5-3 | B |
| 6-3 | A |
| 7-3 | A |
| 8-3 | A |
| 9-3 | A |
| 10-3 | A |
| 11-3 | B |
| 12-3 | A |
| 13-3 | A |
| 14-3 | A |
| 15-3 | B |
| 16-3 | A |
| 17-3 | A |
| 18-3 | C |
| 19-3 | A |
| 20-3 | A |
| 21-3 | A |
| 22-3 | A |
| 23-3 | A |
| 24-3 | A |
| 25-3 | A |
| 26-3 | A |
| 27-3 | A |
| 28-3 | A |
| 29-3 | A |
| 30-3 | A |
| 31-3 | A |
| 32-3 | A |
| 33-3 | A |
| 34-3 | B |
| 35-3 | A |
| 36-3 | A |
| 37-3 | A |
| 38-3 | A |
| 39-3 | A |
| 40-3 | A |
| 41-3 | A |
| 42-3 | A |
| 43-3 | A |
| 44-3 | A |
| 45-3 | A |
| 46-3 | A |
| 47-3 | C |

TABLE 4-continued

Cellular potencies

| # | Cellular IC$_{50}$ |
|---|---|
| 48-3 | A |
| 49-3 | A |
| 50-3 | D |
| 51-3 | D |
| 52-3 | D |
| 53-3 | A |
| 54-3 | A |
| 55-3 | A |
| 56-3 | A |
| 57-3 | A |
| 58-3 | A |
| 59-3 | A |
| 60-3 | A |
| 61-3 | A |
| 62-3 | A |
| 63-3 | A |
| 64-3 | A |
| 65-3 | A |
| 66-3 | A |
| 67-3 | A |
| 68-3 | A |
| 69-3 | A |
| 70-3 | A |
| 71-3 | C |
| 72-3 | A |
| 73-3 | A |
| 74-3 | A |
| 75-3 | A |
| 76-3 | A |
| 77-3 | A |
| 78-3 | D |
| 79-3 | D |
| 80-3 | D |
| 81-3 | D |
| 82-3 | A |
| 83-3 | A |
| 84-3 | A |
| 85-3 | A |
| 86-3 | A |
| 87-3 | A |
| 88-3 | A |
| 89-3 | A |
| 90-3 | A |
| 91-3 | A |
| 92-3 | A |
| 93-3 | A |
| 94-3 | A |
| 95-3 | A |
| 96-3 | A |
| 97-3 | A |
| 98-3 | A |
| 99-3 | A |
| 100-3 | A |
| 101-3 | A |
| 102-3 | A |
| 103-3 | A |
| 104-3 | A |
| 105-3 | A |
| 106-3 | A |
| 107-3 | D |
| 108-3 | A |
| 109-3 | A |
| 110-3 | A |
| 111-3 | A |
| 112-3 | A |
| 113-3 | A |
| 114-3 | A |
| 115-3 | A |
| 116-3 | A |
| 117-3 | A |
| 118-3 | A |
| 119-3 | A |
| 120-3 | A |
| 121-3 | A |
| 122-3 | A |
| 123-3 | C |

TABLE 4-continued

Cellular potencies

| # | Cellular IC$_{50}$ |
|---|---|
| 124-3 | A |
| 125-3 | A |
| 126-3 | A |
| 127-3 | A |
| 128-3 | A |
| 129-3 | A |
| 130-3 | A |
| 131-3 | A |
| 132-3 | A |
| 133-3 | A |
| 134-3 | A |
| 135-3 | A |
| 136-3 | A |
| 137-3 | A |
| 138-3 | A |
| 139-3 | A |
| 140-3 | A |
| 141-3 | A |
| 142-3 | A |
| 143-3 | A |
| 144-3 | A |
| 145-3 | C |
| 146-3 | A |
| 147-3 | A |
| 148-3 | A |
| 149-3 | A |
| 150-3 | A |
| 300-1a | A |
| 301-1a | B |
| 302-1a | A |
| 303-1a | A |
| 304-1a | A |
| 305-1a | A |
| 306-1a | A |
| 307-1a | C |
| 308-1a | A |
| 309-1a | A |
| 310-1a | — |
| 311-1a | — |
| 312-1a | — |
| 313-1a | — |
| 314-1a | — |
| 315-1a | — |
| 316-1a | — |
| 317-1a | — |
| 318-1a | — |
| 319-1a | — |
| 320-1a | — |
| 321-1a | — |
| 322-1a | — |
| 323-1a | — |
| 324-1a | — |
| 325-1a | — |
| 326-1a | — |
| 327-1a | — |
| 328-1a | — |
| 329-1a | — |
| 330-1a | — |
| 331-1a | B |
| 332-1a | C |
| 333-1a | C |
| 334-1a | C |
| 335-1a | B |
| 336-1a | C |
| 337-1a | B |
| 338-1a | C |
| 339-1a | C |
| 340-1a | C |
| 341-1a | C |
| 346-1a | C |
| 347-1a | C |
| 348-1a | C |
| 349-1a | C |
| 350-1a | C |
| 351-1a | B |
| 352-1a | C |

TABLE 4-continued

Cellular potencies

| # | Cellular IC$_{50}$ |
|---|---|
| 353-1a | C |
| 354-1a | C |
| 355-1a | C |
| 356-1a | C |
| 357-1a | C |
| 358-1a | C |
| 359-1a | C |
| 360-1a | C |
| 361-1a | C |
| 364-1a | C |
| 365-1a | C |
| 366-1a | C |
| 367-1a | B |
| 368-1a | A |
| 369-1a | C |
| 370-1a | B |
| 371-1a | C |
| 372-1a | C |
| 373-1a | C |
| 374-1a | C |
| 375-1a | C |
| 376-1a | B |
| 377-1a | C |
| 378-1a | C |
| 379-1a | C |
| 380-1a | C |
| 382-1a | C |
| 383-1a | C |
| 384-1a | C |
| 385-1a | C |
| 386-1a | C |
| 387-1a | C |
| 388-1a | C |
| 389-1a | C |
| 390-1a | B |
| 391-1a | C |
| 392-1a | B |
| 393-1a | C |
| 394-1a | A |
| 395-1a | C |
| 396-1a | C |
| 397-1a | C |
| 398-1a | C |
| 399-1a | C |
| 400-1a | B |
| 401-1a | C |
| 402-1a | C |
| 403-1a | C |
| 404-1a | C |
| 405-1a | C |
| 406-1a | B |
| 407-1a | C |
| 408-1a | B |
| 409-1a | C |
| 410-1a | B |
| 411-1a | — |
| 412-1a | C |
| 413-1a | C |
| 414-1a | C |
| 415-1a | C |
| 416-1a | C |
| 417-1a | A |
| 418-1a | C |
| 419-1a | C |
| 420-1a | B |
| 421-1a | B |
| 422-1a | C |
| 423-1a | C |
| 424-1a | C |
| 425-1a | C |
| 426-1a | C |
| 427-1a | A |
| 428-1a | C |
| 429-1a | C |
| 430-1a | C |
| 431-1a | C |
| 432-1a | C |
| 433-1a | B |
| 434-1a | A |
| 435-1a | C |
| 436-1a | A |
| 437-1a | B |
| 438-1a | C |
| 439-1a | B |
| 440-1a | C |
| 441-1a | B |
| 442-1a | C |
| 443-1a | C |
| 445-1a | C |
| 446-1a | A |
| 447-1a | C |
| 448-1a | A |
| 449-1a | A |
| 450-1a | C |
| 451-1a | C |
| 452-1a | C |
| 453-1a | B |
| 454-1a | B |
| 455-1a | A |
| 456-1a | A |
| 457-1a | C |
| 458-1a | A |
| 459-1a | C |
| 460-1a | C |
| 461-1a | C |
| 462-1a | C |
| 463-1a | A |
| 464-1a | A |
| 465-1a | A |
| 466-1a | A |
| 467-1a | A |
| 468-1a | B |
| 469-1a | B |
| 470-1a | A |
| 471-1a | A |
| 472-1a | C |
| 475-1a | B |
| 478-1a | — |
| 479-1a | — |
| 480-1a | — |
| 481-1a | — |
| 482-1a | A |
| 483-1a | A |
| 484-1a | A |
| 485-1a | A |
| 486-1a | A |
| 487-1a | A |
| 488-1a | A |
| 489-1a | A |
| 490-1a | A |
| 491-1a | A |
| 492-1a | A |
| 493-1a | A |
| 494-1a | A |
| 495-1a | A |
| 496-1a | A |
| 497-1a | A |
| 498-1a | A |
| 499-1a | A |
| 500-1a | A |
| 501-1a | A |
| 502-1a | A |
| 503-1a | A |
| 504-1a | A |
| 505-1a | A |
| 506-1a | A |
| 507-1a | A |
| 508-1a | A |
| 509-1a | B |
| 510-1a | B |
| 511-1a | B |
| 512-1a | B |

TABLE 4-continued

Cellular potencies

| # | Cellular IC$_{50}$ |
|---|---|
| 513-1a | B |
| 514-1a | B |
| 515-1a | B |
| 516-1a | B |
| 517-1a | B |
| 518-1a | B |
| 519-1a | B |
| 520-1a | B |
| 521-1a | B |
| 522-1a | B |
| 523-1a | B |
| 524-1a | B |
| 525-1a | B |
| 526-1a | B |
| 527-1a | B |
| 528-1a | B |
| 529-1a | B |
| 530-1a | B |
| 531-1a | B |
| 532-1a | B |
| 533-1a | B |
| 534-1a | B |
| 535-1a | B |
| 536-1a | B |
| 537-1a | B |
| 538-1a | C |
| 539-1a | C |
| 540-1a | C |
| 541-1a | C |
| 542-1a | C |
| 543-1a | C |
| 544-1a | C |
| 545-1a | C |
| 546-1a | C |
| 547-1a | C |
| 548-1a | C |
| 549-1a | C |
| 550-1a | C |
| 551-1a | C |
| 552-1a | C |
| 553-1a | C |
| 554-1a | C |
| 555-1a | C |
| 556-1a | C |
| 557-1a | C |
| 558-1a | C |
| 559-1a | C |
| 560-1a | C |
| 561-1a | C |
| 562-1a | C |
| 563-1a | C |
| 564-1a | C |
| 565-1a | C |
| 566-1a | C |
| 567-1a | C |
| 568-1a | C |
| 569-1a | C |
| 570-1a | C |
| 571-1a | C |
| 572-1a | C |
| 573-1a | C |
| 574-1a | C |
| 575-1a | C |
| 576-1a | C |
| 577-1a | C |
| 578-1a | C |
| 579-1a | C |
| 580-1a | C |
| 581-1a | C |
| 582-1a | C |
| 583-1a | C |
| 584-1a | C |
| 585-1a | C |
| 586-1a | C |
| 587-1a | C |
| 588-1a | C |
| 589-1a | C |
| 590-1a | C |
| 591-1a | C |
| 592-1a | C |
| 593-1a | C |
| 594-1a | C |
| 595-1a | C |
| 596-1a | C |
| 597-1a | C |
| 598-1a | C |
| 599-1a | C |
| 600-1a | C |
| 601-1a | C |
| 602-1a | C |
| 603-1a | C |
| 604-1a | C |
| 605-1a | C |
| 606-1a | C |
| 607-1a | C |
| 608-1a | C |
| 609-1a | C |
| 610-1a | C |
| 611-1a | C |
| 612-1a | C |
| 613-1a | C |
| 614-1a | C |
| 615-1a | C |
| 616-1a | C |
| 617-1a | C |
| 618-1a | C |
| 619-1a | C |
| 620-1a | C |
| 621-1a | C |
| 622-1a | C |
| 623-1a | C |
| 624-1a | C |
| 625-1a | C |
| 626-1a | D |
| 627-1a | D |
| 628-1a | D |
| 629-1a | D |
| 630-1a | D |
| 631-1a | D |
| 632-1a | D |
| 635-1a | D |
| 636-1a | D |
| 637-1a | D |
| 638-1a | D |
| 639-1a | D |
| 640-1a | D |
| 641-1a | D |
| 642-1a | D |
| 643-1a | D |
| 644-1a | D |
| 645-1a | D |
| 646-1a | D |
| 647-1a | C |
| 648-1a | D |
| 649-1a | D |
| 650-1a | D |
| 651-1a | D |
| 652-1a | D |
| 653-1a | D |
| 654-1a | D |
| 655-1a | D |
| 656-1a | D |
| 657-1a | D |
| 658-1a | D |
| 659-1a | D |
| 151-3 | A |
| 152-3 | A |
| 153-3 | A |
| 154-3 | A |
| 155-3 | A |
| 156-3 | A |
| 157-3 | A |

TABLE 4-continued

Cellular potencies

| # | Cellular IC$_{50}$ |
|---|---|
| 158-3 | A |
| 159-3 | A |
| 160-3 | A |
| 161-3 | A |
| 162-3 | A |
| 163-3 | B |
| 164-3 | A |
| 165-3 | D |
| 166-3 | D |
| 167-3 | A |
| 168-3 | A |
| 169-3 | A |
| 170-3 | A |
| 171-3 | A |
| 172-3 | A |
| 173-3 | A |
| 174-3 | A |
| 175-3 | A |
| 176-3 | A |
| 177-3 | A |
| 178-3 | A |
| 179-3 | A |
| 180-3 | A |
| 181-3 | A |
| 182-3 | A |
| 183-3 | A |
| 184-3 | A |
| 185-3 | A |
| 186-3 | A |
| 187-3 | C |
| 188-3 | A |
| 189-3 | A |
| 190-3 | A |
| 191-3 | A |
| 192-3 | A |
| 193-3 | D |
| 194-3 | A |
| 195-3 | A |
| 196-3 | A |
| 197-3 | A |
| 198-3 | A |
| 199-3 | A |
| 200-3 | A |
| 201-3 | A |
| 202-3 | A |
| 203-3 | A |
| 204-3 | A |
| 205-3 | A |
| 206-3 | A |
| 207-3 | A |
| 208-3 | A |
| 209-3 | A |
| 210-3 | A |
| 211-3 | A |
| 212-3 | A |
| 213-3 | A |
| 214-3 | A |
| 215-3 | A |
| 216-3 | A |
| 217-3 | A |
| 218-3 | A |
| 219-3 | A |
| 220-3 | A |
| 221-3 | A |
| 222-3 | A |
| 223-3 | A |
| 224-3 | A |
| 225-3 | A |
| 226-3 | A |
| 227-3 | A |
| 228-3 | A |
| 229-3 | A |
| 230-3 | A |
| 231-3 | A |
| 232-3 | A |
| 233-3 | A |
| 234-3 | A |
| 235-3 | A |
| 236-3 | A |
| 237-3 | A |
| 238-3 | A |
| 239-3 | A |
| 240-3 | A |
| 241-3 | A |
| 242-3 | A |
| 243-3 | A |
| 244-3 | A |
| 245-3 | A |
| 246-3 | A |
| 247-3 | A |
| 248-3 | A |
| 249-3 | A |
| 250-3 | A |
| 251-3 | A |
| 252-3 | A |
| 253-3 | A |
| 254-3 | B |
| 255-3 | B |
| 256-3 | B |
| 257-3 | A |
| 258-3 | A |
| 259-3 | A |
| 260-3 | A |
| 261-3 | A |
| 262-3 | D |
| 263-3 | A |
| 264-3 | A |
| 265-3 | A |
| 266-3 | A |
| 267-3 | A |
| 268-3 | A |
| 269-3 | A |
| 270-3 | A |
| 271-3 | — |
| 272-3 | A |
| 273-3 | B |
| 274-3 | A |
| 275-3 | A |
| 276-3 | A |
| 277-3 | A |
| 278-3 | C |
| 279-3 | C |
| 280-3 | A |
| 281-3 | A |
| 282-3 | A |
| 283-3 | A |
| 284-3 | A |
| 285-3 | A |
| 286-3 | A |
| 287-3 | A |
| 288-3 | A |
| 289-3 | A |
| 290-3 | A |
| 291-3 | A |
| 292-3 | A |
| 293-3 | A |
| 294-3 | A |
| 295-3 | A |
| 296-3 | A |
| 297-3 | A |

Classification codes for cellular potencies:
A: IC$_{50}$ < 5 uM
B: 5 uM ≤ IC$_{50}$ < 10 uM
C: 10 uM ≤ IC$_{50}$ < 20 uM
D: ≥20 uM

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A compound which is:

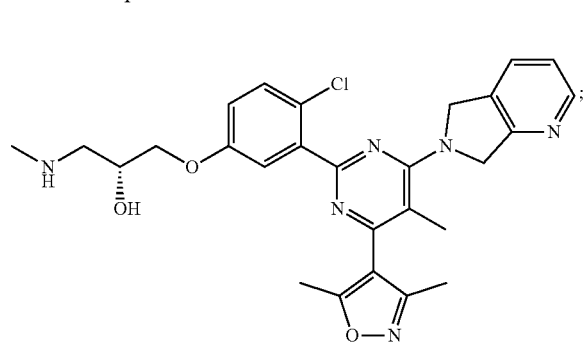

or a pharmaceutically acceptable salt thereof.

2. A compound which is:

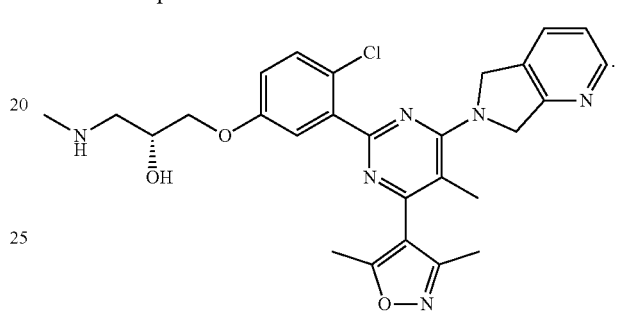

3. A pharmaceutical composition comprising the compound or pharmaceutically acceptable salt according to claim 1, and a pharmaceutically acceptable excipient.

4. A pharmaceutical composition comprising the compound according to claim 2, and a pharmaceutically acceptable excipient.

* * * * *